United States Patent
Tan et al.

(10) Patent No.: US 11,753,461 B2
(45) Date of Patent: Sep. 12, 2023

(54) OPTIMIZED FACTOR VIII GENES

(71) Applicant: Bioverativ Therapeutics Inc., Waltham, MA (US)

(72) Inventors: Siyuan Tan, Lexington, MA (US); Tongyao Liu, Lexington, MA (US)

(73) Assignee: BIOVERATIV THERAPEUTICS INC., Waltham, MA (US)

( * ) Notice: Subject to any disclaimer, the term of this patent is extended or adjusted under 35 U.S.C. 154(b) by 764 days.

(21) Appl. No.: 16/074,729

(22) PCT Filed: Jan. 31, 2017

(86) PCT No.: PCT/US2017/015879
§ 371 (c)(1),
(2) Date: Aug. 1, 2018

(87) PCT Pub. No.: WO2017/136358
PCT Pub. Date: Aug. 10, 2017

(65) Prior Publication Data
US 2019/0185543 A1  Jun. 20, 2019

Related U.S. Application Data

(60) Provisional application No. 62/409,739, filed on Oct. 18, 2016, provisional application No. 62/289,696, filed on Feb. 1, 2016.

(51) Int. Cl.
| | |
|---|---|
| C07H 21/04 | (2006.01) |
| C12N 15/00 | (2006.01) |
| C12N 15/63 | (2006.01) |
| A61K 31/70 | (2006.01) |
| C07K 14/755 | (2006.01) |
| A61K 48/00 | (2006.01) |
| C12N 15/86 | (2006.01) |
| A61P 7/04 | (2006.01) |
| C12N 7/00 | (2006.01) |
| A01K 67/00 | (2006.01) |
| A61K 38/00 | (2006.01) |

(52) U.S. Cl.
CPC .......... C07K 14/755 (2013.01); A61K 48/005 (2013.01); A61K 48/0016 (2013.01); A61P 7/04 (2018.01); C12N 7/00 (2013.01); C12N 15/86 (2013.01); A61K 38/00 (2013.01); C07K 2319/02 (2013.01); C07K 2319/30 (2013.01); C07K 2319/31 (2013.01); C12N 2740/15043 (2013.01); C12N 2740/16043 (2013.01); C12N 2800/22 (2013.01)

(58) Field of Classification Search
CPC .............. C07K 14/755; A61K 48/005; A61K 48/0016; C12N 15/86; C12N 2800/22; C12N 2740/16043; C12N 2740/15043
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis et al. | |
| 4,704,362 A | 11/1987 | Itakura et al. | |
| 4,800,159 A | 1/1989 | Mullis et al. | |
| 4,868,112 A | 9/1989 | Toole, Jr. | |
| 4,965,188 A | 10/1990 | Mullis et al. | |
| 5,112,950 A | 5/1992 | Meulien et al. | |
| 5,171,844 A | 12/1992 | Van Ooyen et al. | |
| 5,304,489 A | 4/1994 | Rosen | |
| 5,543,502 A | 8/1996 | Nordfang et al. | |
| 5,595,886 A | 1/1997 | Chapman et al. | |
| 5,610,278 A | 3/1997 | Nordfang et al. | |
| 5,648,260 A | 7/1997 | Winter et al. | |
| 5,658,570 A | 8/1997 | Newman et al. | |
| 5,712,122 A | 1/1998 | Boime et al. | |
| 5,736,137 A | 4/1998 | Anderson et al. | |
| 5,739,277 A | 4/1998 | Presta et al. | |
| 5,741,957 A | 4/1998 | Deboer et al. | |
| 5,789,203 A | 8/1998 | Chapman et al. | |
| 5,834,250 A | 11/1998 | Wells et al. | |
| 5,849,992 A | 12/1998 | Meade et al. | |
| 5,869,046 A | 2/1999 | Resta et al. | |
| 5,972,885 A | 10/1999 | Spira et al. | |
| 6,030,613 A | 2/2000 | Blumberg et al. | |
| 6,048,720 A | 4/2000 | Dalborg et al. | |

(Continued)

FOREIGN PATENT DOCUMENTS

| | | |
|---|---|---|
| CN | 104427995 A | 3/2015 |
| EA | 028309 B1 | 11/2017 |

(Continued)

OTHER PUBLICATIONS

Swystun et al. Gene therapy for coagulation disorders. Circ. Res. 118:1443-1452, (Year: 2016).*

(Continued)

*Primary Examiner* — Quang Nguyen

(74) *Attorney, Agent, or Firm* — LATHROP GPM LLP; James H. Velema; James V. DeGiulio

(57) ABSTRACT

The present disclosure provides codon optimized Factor VIII sequences, vectors, and host cells comprising codon optimized Factor VIII sequences, polypeptides encoded by codon optimized Factor VIII sequences, and methods of producing such polypeptides. The present disclosure also provides methods of treating bleeding disorders such as hemophilia comprising administering to the subject a codon optimized Factor VIII nucleic acid sequence or the polypeptide encoded thereby.

15 Claims, 44 Drawing Sheets

Specification includes a Sequence Listing.

(56) References Cited

U.S. PATENT DOCUMENTS

| | | | |
|---|---|---|---|
| 6,060,447 A | 5/2000 | Chapman et al. | |
| 6,086,875 A | 7/2000 | Blumberg et al. | |
| 6,096,871 A | 8/2000 | Presta et al. | |
| 6,121,022 A | 9/2000 | Presta et al. | |
| 6,159,730 A | 12/2000 | Reff | |
| 6,193,980 B1 | 2/2001 | Efstathiou et al. | |
| 6,194,551 B1 | 2/2001 | Idusogie et al. | |
| 6,207,455 B1 | 3/2001 | Chang | |
| 6,228,620 B1 | 5/2001 | Chapman et al. | |
| 6,242,195 B1 | 6/2001 | Idusogie et al. | |
| 6,251,632 B1 | 6/2001 | Lillicrap et al. | |
| 6,277,375 B1 | 8/2001 | Ward | |
| 6,316,226 B1 | 11/2001 | Van Ooyen et al. | |
| 6,346,513 B1 | 2/2002 | Van Ooyen et al. | |
| 6,413,777 B1 | 7/2002 | Reff et al. | |
| 6,458,563 B1 | 10/2002 | Lollar | |
| 6,485,726 B1 | 11/2002 | Blumberg et al. | |
| 6,528,624 B1 | 3/2003 | Idusogie et al. | |
| 6,531,298 B2 | 3/2003 | Stafford et al. | |
| 6,538,124 B1 | 3/2003 | Idusogie et al. | |
| 6,615,782 B1 | 9/2003 | Hendriksma et al. | |
| 6,696,245 B2 | 2/2004 | Winter et al. | |
| 6,737,056 B1 | 5/2004 | Presta | |
| 6,808,905 B2 | 10/2004 | McArthur et al. | |
| 6,818,439 B1 * | 11/2004 | Jolly et al. | |
| 6,821,505 B2 | 11/2004 | Ward | |
| 6,924,365 B1 | 8/2005 | Miller et al. | |
| 6,998,253 B1 | 2/2006 | Presta et al. | |
| 7,041,635 B2 | 5/2006 | Kim et al. | |
| 7,083,784 B2 | 8/2006 | Dall'Acqua et al. | |
| 7,179,903 B2 | 2/2007 | McArthur et al. | |
| 7,317,091 B2 | 1/2008 | Lazar et al. | |
| 7,404,956 B2 | 7/2008 | Peters et al. | |
| 7,745,179 B2 | 6/2010 | McArthur et al. | |
| 8,326,547 B2 | 12/2012 | Liu et al. | |
| 8,734,809 B2 | 5/2014 | Gao et al. | |
| 9,050,269 B2 | 6/2015 | Discher et al. | |
| 9,050,318 B2 | 6/2015 | Dumont et al. | |
| 9,061,059 B2 | 6/2015 | Chakraborty et al. | |
| 9,169,491 B2 | 10/2015 | Truran et al. | |
| 10,000,748 B2 | 6/2018 | Schüttrumpf et al. | |
| 10,058,624 B2 | 8/2018 | Doering et al. | |
| 10,125,357 B2 | 11/2018 | Seifried et al. | |
| 10,370,431 B2 | 8/2019 | Tan et al. | |
| 2003/0069395 A1 | 4/2003 | Sato et al. | |
| 2003/0077812 A1 | 4/2003 | McArthur et al. | |
| 2003/0109478 A1 | 6/2003 | Fewel et al. | |
| 2003/0235536 A1 | 12/2003 | Blumberg et al. | |
| 2004/0147436 A1 | 7/2004 | Kim et al. | |
| 2006/0003452 A1 | 1/2006 | Humeau et al. | |
| 2007/0231329 A1 | 10/2007 | Lazar et al. | |
| 2007/0237765 A1 | 10/2007 | Lazar et al. | |
| 2007/0237766 A1 | 10/2007 | Lazar et al. | |
| 2007/0237767 A1 | 10/2007 | Lazar et al. | |
| 2007/0243188 A1 | 10/2007 | Lazar et al. | |
| 2007/0248603 A1 | 10/2007 | Lazar et al. | |
| 2007/0286859 A1 | 12/2007 | Lazar et al. | |
| 2008/0004206 A1 | 1/2008 | Rosen et al. | |
| 2008/0057056 A1 | 3/2008 | Lazar et al. | |
| 2008/0076174 A1 | 3/2008 | Selden et al. | |
| 2008/0153156 A1 | 6/2008 | Gray | |
| 2008/0153751 A1 | 6/2008 | Rosen et al. | |
| 2008/0161243 A1 | 7/2008 | Rosen et al. | |
| 2008/0194481 A1 | 8/2008 | Rosen et al. | |
| 2008/0260738 A1 | 10/2008 | Moore et al. | |
| 2008/0261877 A1 | 10/2008 | Ballance et al. | |
| 2009/0017533 A1 | 1/2009 | Selden et al. | |
| 2009/0042283 A1 | 2/2009 | Selden et al. | |
| 2009/0087411 A1 | 4/2009 | Fares et al. | |
| 2010/0239554 A1 | 9/2010 | Schellenberger et al. | |
| 2010/0284971 A1 | 11/2010 | Samulski | |
| 2010/0292130 A1 | 11/2010 | Skerra et al. | |
| 2010/0323956 A1 | 12/2010 | Schellenberger et al. | |
| 2011/0046060 A1 | 2/2011 | Schellenberger et al. | |
| 2011/0046061 A1 | 2/2011 | Schellenberger et al. | |
| 2011/0077199 A1 | 3/2011 | Schellenberger et al. | |
| 2011/0172146 A1 | 7/2011 | Schellenberger et al. | |
| 2011/0244550 A1 | 10/2011 | Simioni | |
| 2012/0178691 A1 | 7/2012 | Schellenberger et al. | |
| 2013/0024960 A1 | 1/2013 | Nathwani et al. | |
| 2013/0052191 A1 | 2/2013 | Blein et al. | |
| 2013/0195801 A1 | 8/2013 | Gao et al. | |
| 2014/0010861 A1 | 1/2014 | Bancel et al. | |
| 2015/0023959 A1 | 1/2015 | Chhabra et al. | |
| 2015/0056696 A1 | 2/2015 | Fan et al. | |
| 2015/0158929 A1 | 6/2015 | Schellenberger et al. | |
| 2016/0304851 A1 | 10/2016 | Schüttrumpf et al. | |
| 2017/0073702 A1 | 3/2017 | Truran et al. | |
| 2017/0260516 A1 | 9/2017 | Tan et al. | |
| 2017/0326256 A1 | 11/2017 | Doering et al. | |
| 2019/0048362 A1 | 2/2019 | Kyostio-Moore et al. | |
| 2019/0314291 A1 | 10/2019 | Besin et al. | |
| 2020/0199626 A1 | 6/2020 | Liu et al. | |
| 2022/0033849 A1 | 2/2022 | Mayani et al. | |
| 2022/0090130 A1 | 3/2022 | Maghodia et al. | |

FOREIGN PATENT DOCUMENTS

| | | | |
|---|---|---|---|
| EP | 0295597 A2 | 12/1988 | |
| EP | 0295597 A3 | 5/1990 | |
| EP | 1395293 A1 | 3/2004 | |
| EP | 2173890 B1 | 3/2011 | |
| EP | 2829285 A1 | 1/2015 | |
| EP | 2881463 A1 | 6/2015 | |
| EP | 3160478 A1 | 5/2017 | |
| EP | 3377618 A1 | 9/2018 | |
| EP | 3411478 A1 | 12/2018 | |
| EP | 2956477 B1 | 11/2020 | |
| EP | 3746136 A1 | 12/2020 | |
| JP | 2015-509365 A | 3/2015 | |
| JP | 2017-525344 A | 9/2017 | |
| RU | 2500816 C1 | 12/2013 | |
| WO | WO 1987/004187 A1 | 7/1987 | |
| WO | WO 1988/000831 A1 | 2/1988 | |
| WO | WO 88/07089 A1 | 9/1988 | |
| WO | WO 1988/007089 A1 | 9/1988 | |
| WO | WO 91/09122 A1 | 6/1991 | |
| WO | WO 1991/009122 A1 | 6/1991 | |
| WO | WO 96/14339 A1 | 5/1996 | |
| WO | WO 1996/014339 A1 | 5/1996 | |
| WO | WO 97/12622 | 4/1997 | |
| WO | WO 1997/012622 A1 | 4/1997 | |
| WO | WO 98/05787 A1 | 2/1998 | |
| WO | WO 1998/005787 A1 | 2/1998 | |
| WO | WO 98/09657 A2 | 3/1998 | |
| WO | WO 1998/009657 A2 | 3/1998 | |
| WO | WO 98/17815 A1 | 4/1998 | |
| WO | WO 98/17816 A1 | 4/1998 | |
| WO | WO 1998/017815 A1 | 4/1998 | |
| WO | WO 1998/017816 A1 | 4/1998 | |
| WO | WO 98/18934 A1 | 5/1998 | |
| WO | WO 1998/018934 A1 | 5/1998 | |
| WO | WO 98/23289 A1 | 6/1998 | |
| WO | WO 1998/023289 A1 | 6/1998 | |
| WO | WO 99/31251 A1 | 6/1999 | |
| WO | WO 1999/031251 A1 | 6/1999 | |
| WO | WO 99/51642 A1 | 10/1999 | |
| WO | WO 1999/051642 A1 | 10/1999 | |
| WO | WO 99/58572 A1 | 11/1999 | |
| WO | WO 1999/058572 A1 | 11/1999 | |
| WO | WO 00/09560 A1 | 2/2000 | |
| WO | WO 2000/009560 A2 | 2/2000 | |
| WO | WO 00/20561 A1 | 4/2000 | |
| WO | WO 2000/020561 A1 | 4/2000 | |
| WO | WO 00/32767 A1 | 6/2000 | |
| WO | WO 2000/032767 A1 | 6/2000 | |
| WO | WO 2000/042072 A2 | 7/2000 | |
| WO | WO 2000/066759 A1 | 11/2000 | |
| WO | WO 02/44215 A2 | 6/2002 | |
| WO | WO 2002/044215 A2 | 6/2002 | |
| WO | WO 02/060919 A2 | 8/2002 | |
| WO | WO 2002/060919 A2 | 8/2002 | |
| WO | WO 2002/063025 A2 | 8/2002 | |
| WO | WO 2002/040544 A3 | 10/2002 | |

(56) References Cited

FOREIGN PATENT DOCUMENTS

| WO | WO 02/092134 | 11/2002 |
|---|---|---|
| WO | WO 2002/092134 A1 | 11/2002 |
| WO | WO 2003/020764 A2 | 3/2003 |
| WO | WO 03/042361 A2 | 5/2003 |
| WO | WO 03/042397 A2 | 5/2003 |
| WO | WO 2003/042361 A2 | 5/2003 |
| WO | WO 2003/042397 A2 | 5/2003 |
| WO | WO 03/052051 A2 | 6/2003 |
| WO | WO 2003/052051 A2 | 6/2003 |
| WO | WO 2003/057780 A1 | 7/2003 |
| WO | WO 03/074569 A2 | 9/2003 |
| WO | WO 03/077834 B2 | 9/2003 |
| WO | WO 2003/074569 A2 | 9/2003 |
| WO | WO 2003/077834 A2 | 9/2003 |
| WO | WO 2003/100053 A1 | 12/2003 |
| WO | WO 2004/016750 A2 | 2/2004 |
| WO | WO 2004/029207 A2 | 4/2004 |
| WO | WO 2004/035752 A2 | 4/2004 |
| WO | WO 2004/044859 A1 | 5/2004 |
| WO | WO 20044044859 A1 | 5/2004 |
| WO | WO 2004/063351 A2 | 7/2004 |
| WO | WO 2004/074455 A2 | 9/2004 |
| WO | WO 2004/094642 A2 | 11/2004 |
| WO | WO 2004/099249 A2 | 11/2004 |
| WO | WO 2005/013901 A2 | 2/2005 |
| WO | WO 2005/040217 A2 | 5/2005 |
| WO | WO 2005/052171 A2 | 6/2005 |
| WO | WO 2005/070963 A1 | 8/2005 |
| WO | WO 2005/077981 A2 | 8/2005 |
| WO | WO 2005070963 A1 | 8/2005 |
| WO | WO 2005/092925 A2 | 10/2005 |
| WO | WO 2005/123780 A2 | 12/2005 |
| WO | WO 2006/019447 A1 | 2/2006 |
| WO | WO 2006/047350 A2 | 5/2006 |
| WO | WO 2006/085967 A2 | 8/2006 |
| WO | WO 2007/000668 A2 | 1/2007 |
| WO | WO 2007/004670 A1 | 1/2007 |
| WO | WO 2007/021494 A2 | 2/2007 |
| WO | WO 2007/046703 A2 | 4/2007 |
| WO | WO 2007046703 A2 | 4/2007 |
| WO | WO 2007/148971 A2 | 12/2007 |
| WO | WO 2007/149406 A2 | 12/2007 |
| WO | WO 2007/149852 A2 | 12/2007 |
| WO | WO 2008/012543 A1 | 1/2008 |
| WO | WO 2008/033413 A2 | 3/2008 |
| WO | WO 2008/118507 A2 | 10/2008 |
| WO | WO 2008/143954 A2 | 11/2008 |
| WO | WO 2008143954 A2 | 11/2008 |
| WO | WO 2008/155134 A1 | 12/2008 |
| WO | WO 2009/051717 A2 | 4/2009 |
| WO | WO 2009/058322 A1 | 5/2009 |
| WO | WO 2009/075772 A1 | 6/2009 |
| WO | WO 2009/130198 A2 | 10/2009 |
| WO | WO 2009/137254 A2 | 11/2009 |
| WO | WO 2009/140015 A2 | 11/2009 |
| WO | WO 2010/029178 A1 | 3/2010 |
| WO | WO 2010/055413 A1 | 5/2010 |
| WO | WO 2010/0091122 A1 | 8/2010 |
| WO | WO 2010/091122 A1 | 8/2010 |
| WO | WO 2010/115866 A1 | 10/2010 |
| WO | WO 2010/125471 A2 | 11/2010 |
| WO | WO 2010/140148 A1 | 12/2010 |
| WO | WO 2010/144502 A2 | 12/2010 |
| WO | WO 2010/144508 A1 | 12/2010 |
| WO | WO 2011/004361 A2 | 1/2011 |
| WO | WO 2011/005968 A1 | 1/2011 |
| WO | WO 2011/028228 A1 | 3/2011 |
| WO | WO 2011/028229 A1 | 3/2011 |
| WO | WO 2011/028344 A2 | 3/2011 |
| WO | WO 2011/033105 A1 | 3/2011 |
| WO | WO 2011/069164 A2 | 6/2011 |
| WO | WO 2012/006623 A1 | 1/2012 |
| WO | WO 2012/006624 A2 | 1/2012 |
| WO | WO 2012/006633 A1 | 1/2012 |
| WO | WO 2012/006635 A1 | 1/2012 |
| WO | WO 2012/170289 A1 | 12/2012 |
| WO | WO 2013/009627 A2 | 1/2013 |
| WO | WO 2013/093760 A2 | 6/2013 |
| WO | WO 2013/122617 A1 | 8/2013 |
| WO | WO 2013/123457 A1 | 8/2013 |
| WO | WO 2013123457 A1 | 8/2013 |
| WO | WO 2014/011819 A2 | 1/2014 |
| WO | WO 2014/127215 A1 | 8/2014 |
| WO | WO 2015/023891 A2 | 2/2015 |
| WO | WO 2015/086406 A2 | 6/2015 |
| WO | WO 2015/106052 A1 | 7/2015 |
| WO | WO 2015106052 A1 | 7/2015 |
| WO | WO 2016/004113 A1 | 1/2016 |
| WO | WO 2016/009326 A1 | 1/2016 |
| WO | WO 2016/168728 A2 | 10/2016 |
| WO | WO 2017/024060 A1 | 2/2017 |
| WO | WO 2017/087861 A1 | 5/2017 |
| WO | WO 2017/136358 A1 | 8/2017 |
| WO | WO 2019/152692 A1 | 8/2019 |
| WO | WO 2020/113197 A1 | 6/2020 |
| WO | WO 2021/067389 A1 | 4/2021 |

OTHER PUBLICATIONS

Lange et al. Overexpresslon or factor VIII alter AAV delivery is transiently associated with cellular stress in hemophilia A mice. Molecular Therapy—Methods & Clinical Development 3, 16064; doi:10.1038/mtm.2016.64, 8 pages; (Year: 2016).*

Armour et al. (1999) "Recombinant human IgG molecules lacking Fcy receptor I binding and monocyte triggering activities," Eur. J. Immunol., 29: 2613-2624.

Amendola et al. (2005) "Coordinate dual-gene transgenesis by lentiviral vector carrying synthetic bidriectional promoters," Nature Biotechnology, 23(1):108-116.

Burmeister et al. (1994) "Crystal structure of the complex of rat neonatal Fc receptor with Fc," Nature, 372(24):379-383.

Capon et al. (1989) "Designing CD4 immunoadhesins for AIDS therapy," Nature, 337, 525-531.

Cameron et al. (1997) "The Canine Factor VIII cDNA and 5' Flanking Sequence," Thromb. Haemost., 79(2):317-322.

Chen et al. (2005) "MicroRNAs as regulators of mammalian hematopoiesis," Seminars in Immunology, 17:155-165.

Chiorini et al. (1999) "Cloning and Characterization of Adeno-Associated Virus Type5," Journal of Virology, 73(2):1309-1319.

Chiorini et al. (1997) "Cloning of Adeno-Associated Virus Type 4 (AAV4) and Generation of Recombinant AAV4 Particles," Journal of Virology, 71(9):6823-6833.

Costa et al. (1986) "Transcriptional Control of the Mouse Prealbumin (Transthyretin) Gene: Both Promoter Sequences and a Distinct Enhancer are Cell Specific," Molecular and Cellular Biology, 6(12):4697-4708.

Dalkara et al. (2013) "In vivo-directed evolution of a new adeno-associated virus for therapeutic outer retinal gene delivery from the vitreous," Sci. Transl. Med., 5(189):189ra76, 12 pages.

Dennis et al. (2002) "Albumin binding as a general strategy for improving the pharmacokinetics of proteins," The Journal of Biological Chemistry, 277(38):35035-35043.

Eaton et al. (1986) "Construction and Characterization of an Active Factor VIII Variant Lacking the Central One-Third of the Molecule," Biochemistry, 25 (26): 8343-8347.

Ellman et al. (1991) "Biosynthetic Method for Introducing Unnatural Amino Acids Site-Specifically into Proteins," Methods in Enzymology, 202 (15): 301-336.

Fallaux et al. (1996) "The Human Clotting Factor VIII cDNA Contains an Autonomously Replicating Sequence Consensus- and Matrix Attachment Region-Like Sequence That Binds a Nuclear Factor, Represses Heterologous Gene Expression, and Mediates the Transcriptional Effects of Sodium Butyrate," Molecular and Cellular Biology, 16 (8): 4264-4272.

Figueiredo et al. (1995) "cis-Acting elements and transcription factors involved in the promoter activity of the human factor VII gene," The Journal of Biological Chemistry, 270(20):11828-11838.

(56) References Cited

OTHER PUBLICATIONS

Friend et al. (1999) "Phase I Study of an Engineered Aglycosylated Humanized CD3 Antibody in Renal Transplant Rejection," Transplantation, 68 (11): 1632-1637.
Gaspar et al. (2012) "EuGene: maximizing synthetic gene design for heterologous expression," Bioinformatics, 28(20):2683-2684.
GenBank Accession No. AF043303.1.
GenBank Accession No. AF085716.1.
GenBank Accession No. AY661265.1.
GenBank Accession No. J01901.1.
GenBank Accession No. U89790.1.
Ho et al. (1989) "Site-directed mutagenesis by overlap extension using the polymerase chain reaction," Elsevier Science Pub. B.V. (Biomed. Div.), Gene, 77: 51-59.
Hoeben et al. (1990) "Expression of Functional Factor VIII in Primary Human Skin Fibroblasts after Retrovirus-mediated Gene Transfer," J. Biol. Chem., 265 (13): 7318-7323.
Hoeben et al. (1995) "Expression of the Blood-Clotting Factor-VIII cDNA is Repressed by a Transcriptional Silencer Located in Its Coding Region," Blood, 85 (9): 2447-2454.
Holt et al. (2008) "Anti-serum albumin domain antibodies for extending the half-lives of short lived drugs," Protein Engineering, Design and Selection, 21(5):283-288.
Horton et al. (1993) "Gene Splicing by Overlap Extension," Methods in Enzymology, 217 (17):270-279.
International Search Report for International Application No. PCT/US2017/015879, dated Apr. 5, 2017.
International Preliminary Report on Patentability and Written Opinion for International Application No. PCT/US2017/015879, dated Aug. 7, 2018.
Israel et al. (1997) "Expression of the neonatal Fc receptor, FcRn, on human intestinal epithelial cells," Immunology 92: 69-74.
Kobayashi et al. (2002) "FcRn-mediated transcytosis of immunoglobulin G in human renal proximal tubular epithelial cells," Am J Physiol Renal Physiol 282: F358-F365.
Koeberl et al. (1995) "Sequences Within the Coding Regions of Clotting Factor VIII and CFTR Block Transcriptional Elongation," Human Gene Threapy 6: 469-479.
Konig et al. (1998) "Use of an albumin-binding domain for the selective immobilisation of recombinant capture antibody fragments on ELISA plates," Journal of Immunological Methods, 218:73-83.
Kotterman et al. (2014) "Engineering adeno-associated viruses for clinical gene therapy," Nat. Rev. Genet., 15(7):445-451.
Kraulis et al. (1996) "The serum albumin-binding domain of streptococcal protein G is a three-helical bundle: a heteronuclear NMR study," FEBS Letters, 378:190-194.
Kudla et al. (2006) "High Guanine and Cytosine Content Increases mRNA Levels in Mammalian Cells," PloS Biol, e180.
Larrick et al. (1989) "Rapid Cloning of Rearranged Immunoglobulin Genes From Human Hybridoma Cells Using Mixed Primers and the Polymerase Chain Reaction," Biochem. and Biophys. Res. Comm. 160 (3): 1250-1256.
Lenting et al. (2007) "Clearance mechanisms of von Willebrand factor and factor," Journal of Thrombosis and Haemostasis, 5:1353-1360.
Lenting et al. (1998) "The Life Cycle of Coagulation Factor VIII in View of Its Structure and Function," Blood, 92(11):3983-3996.
Linhult et al. (2002) "Mutational analysis of the interaction between albumin-binding domain from streptococcal protein G and human serum albumin," Protein Science, 11:206-213.
Lynch et al. (1993) "Sequences in the Coding Region of Clotting Factor VIII Act as Dominant Inhibitors of RNA Accumulation and Protein Production," Human Gene Therapy 4: 259-272.
Manco-Johnson et al. (2007) "Prophylaxis versus Episodic Treatment to Prevent Joint Disease in Boys with Severe Hemophilia," N. Engl. J. Med. 357 (6): 535-44.
Mannucci et al. (2001) "The Hemophilias—From Royal Genes to Gene Therapy," N. Engl. J. Med. 344 (23): 1773-1779.
Meulien et al. (1988) "A new recombinant procoagulant protein derived from the cDNA encoding human factor VIII," Protein Engineering 2 (4): 301-306.
Mount et al. (2002) "Sustained phenotypic correction of hemophilia B dogs with a factor IX null mutation by liver-directed gene therapy," Blood, 99(8):2670-2676.
Morfini et al. (2003) "Pharmacokinetics of factor VIII and factor IX," Haemophilia, 9 (Suppl. 1): 94-100.
Nakamura et al. (2000) "Codon usage tabulated from international DNA sequence databases: status for the year 2000," Nucleic Acids Research, 28 (1): 292.
Narita et al. (1998) "The low-density lipoprotein receptor-related protein (LRP) mediates clearance of coagulation factor Xa in Vivo," Blood, 91(2):555-560.
NCBI Reference Sequence No. NM_000552.4.
Noren et al. (1989) "A General Method for Site-Specific Incorporation of Unnatural Amino Acids into Proteins," Science, 244: 182-188.
Peyvandi et al. (2006) "Genetic diagnosis of haemophilia and other inherited bleeding disorders," Haemophilia, 12:82-89.
Rodriguez-Merchan (2010) "Musculoskeletal Complications of Hemophilia," HSS Journal 6:37-42.
Roovers et al. (2007) "Efficient inhibition of EGFR signalling and of tumour growth by antagonistic anti-EGFR Nanobodies," Cacer Immunol Immunother, 56:303-317.
Rouet et al. (1995) "Hierarchy and positive/negative interplays of the hepatocyte nuclear factors HNF-1,-3 and -4 in the liver-specific enhancer for the human α-1-microglobulin/bikunin precursor," Nucleic Acids Research, 23(3):395-404.
Rouet et al. (1998) "An array of binding sites for hepatocyte nuclear factor of 4 of high and low affinities modulates the liver-specific enhancer for the human α1-microglobulin/bikunin precursor," Biochem. J., 334:577-584.
Rouet et al. (1992) "A potent enhancer made of clustered liver-specific elements in the transcription control sequences of human α1-Microglobulin/bikunin," The Journal of Biological Chemistry, 267(29):20765-20773.
Ruberti et al. (1994) "The use of the RACE method to clone hybridoma cDNA when V region primers fail," Journal of Immunological Methods, 173: 33-39.
Routledge et al. (1995) "The Effect of Aglycosylation on the Immunogenicity of a Humanized Therapeutic CD3 Monoclonal Antibody," Transplantation, 60 (8): 847-853.
Rutledge et al. (1998) "Infectious Clones and Vectors Derived from Adeno-Associated Virus (AAV) Serotypes Other Than AAV Type 2," Journal of Virology, 72(1):309-319.
Sarver et al. (1987) "Stabel Expression of Recombinant Factor VIII Molecules Using a Bovine Papillomavirus Vector," DNA, 6 (6): 553-564.
Sharp et al. (1987) "The codon adaptation index—a measure of directional synonymous codon usage bias, and its potential applications," Nucleic Acids Research, 15 (3): 1281-1295.
Shields et al. (2001) "High Resolution Mapping of the Binding Site on Human IgG1 for FcγRI, FcγRII, FcγRIII, and FcRn and Design of IgG1 Variants with Improved Binding to the FcγR," J. Biol. Chem., 276 (9) 6591-6604.
Story et al. (1994) "A Major Histocompatibility Complex Class I-like Fc Receptor Cloned from Human Placenta: Possible Role in Transfer of Immunoglobulin G from Mother to Fetus," J. Exp. Med., Brief Definitive Report, 180: 2377-2381.
Srivastava et al. (1983) "Nucleotide Sequence and Organization of the Adeno-Associated Virus 2 Genome," Journal of Virology, 45(2):555-564.
Toole et al. (1986) "A large region (=95 kDa) of human factor VIII is dispensable for in vitro procoagulant activity," Proc. Natl. Acad. Sci. USA, 83: 5939-5942.
Torres-Torronteras et al. (2014) "Gene Therapy Using a Liver-targeted AAV Vector Restores Nucleoside and Nucleotide Homeostasis in a Murine Model of MNGIE," Molecular Therapy, 22(5):901-907.
Trüssel et al. (2009) "New Strategy for the Extension of the Serum Half-Life of Antibody Fragments," Bioconjugate Chem., 20:2286-2292.

(56) References Cited

OTHER PUBLICATIONS

Vigna et al. (2004) "Efficient Tet-Dependent Expression of Human Factor IX in Vivo by a New Self-Regulating Lentiviral Vector," Molecular Therapy, 11(5):763-775.
White et al. (1997) "A multicenter study of recombinant factor VIII (Recombinate) in previously treated patients with haemophilia," Thrombosis and Heamostasis, 4:660-667.
Wu et al. (2000) "Mutational Analysis of the Adeno-Associated Virus Type 2 (AAV2) Capsid Gene and Construction of AAV2 Vectors with Altered Tropism," Journal of Virology, 74(18):8635-8647.
Cao et al., "Factor VIII Accelerates Proteolytic Cleavage of Von Willebrand Factor by ADAMTS13", PNAS May 27, 2008, 105(21): 7416-7421.
Lind et al., "Novel Forms of B-domain-deleted Recombinant Factor VIII molecules Construction and Biochemical Characterization", Eur Journ Biochem., Aug. 15, 1995, 232: 19-27.
Sandberg et al., "Structural and Functional Characterization of B-Domain Deleted Recombinant Factor VIII", Seminars in Hematology, Apr. 2001, 38(2), Suppl 4: 4-12.
Strohl, "Fusion Proteins for Half-Life Extension of Biologies as a Strategy to Make Biobetters", BioDrugs, 2015, 29: 215-239.
Vehar et al., "Structure of Human Factor VIII", Nature, Nov. 22, 1984; 312(5992): 337-342.
Ward et al., "Codon Optimization of Human Factor VIII cDNAs Leads to High-Level Expression", Blood, Jan. 20, 2011, 117(3): 798-807.
Amendola, et al., "Coordinate Dual-Gene Transgenesis by Lentiviral Vectors Carrying Synthetic Bidirectional Promoters", Nature Biotechnology, vol. 23, No. 1, pp. 108-116, 2005.
Armour, et al., "Recombinant Human IgG Molecules Lacking Fc gamma Receptor I Binding and Monocyte Triggering Activities", European Journal of Immunology, vol. 29, No. 8, pp. 2613-2624, Aug. 1, 1999.
Burmeister, et al., "Crystal Structure of the Complex of Rat Neonatal Fc Receptor with Fc", Nature, vol. 372, No. 6504, pp. 379-383, Nov. 24, 1994.
Cameron, et al., "The Canine Factor VIII cDNA and 5' Flanking Sequence", Journal of Thrombosis and Haemostasis, vol. 79, No. 2, pp. 317-322, Feb. 1998.
Capon, et al., "Designing CD4 Immunoadhesins for AIDS Therapy", Nature, vol. 337, No. 6207, pp. 525-531, Feb. 1989.
Chen, et al., "MicroRNAs as Regulators of Mammalian Hematopoiesis", Seminars in Immunology, vol. 17, No. 2, pp. 155-165, Apr. 1, 2005.
Chiorini, et al., "Cloning and Characterization of Adeno-Associated Virus Type 5", Journal of Virology, vol. 73, No. 2, pp. 1309-1319, 1999.
Chiorini, et al., "Cloning of Adeno-Associated Virus Type 4 (AAV4) and Generation of Recombinant AAV4 Particles", Journal of Virology, vol. 71, No. 9, pp. 6823-6833, 1997.
Costa, et al., "Transcriptional Control of the Mouse Prealbumin (Transthyretin) Gene: Both Promoter Sequences and a Distinct Enhancer are Cell Specific", Molecular and Cellular Biology, vol. 6, No. 12, pp. 4697-4708, Jan. 1, 1986.
Dalkara, et al., "In Vivo-Directed Evolution of a New Adeno-Associated Virus for Therapeutic Outer Retinal Gene Delivery From the Vitreous", Science Translational Medicine vol. 5, No. 189, pp. 1-12, Jan. 2013.
Dennis, et al., "Albumin Binding as a General Strategy for Improving the Pharmacokinetics of Proteins", Journal of Biological Chemistry, vol. 277, No. 38, pp. 35035-35043, Sep. 20, 2009.
Eaton, et al., "Construction and Characterization of an Active Factor VIII Variant Lacking the Central One-Third of the Molecule", Biochemistry, vol. 25, No. 26, pp. 8343-8347, Dec. 1986.
Ellman, et al., "Biosynthetic Method for Introducing Unnatural Amino Acids Site-Specifically Into Proteins", Methods In Enzymology. vol. 202, Academic Press, pp. 301-336, 1991.
Fallaux, et al., "The Human Clotting Factor VIII cDNA Contains an Autonomously Replicating Sequence Consensus- and Matrix Attachment Region-Like Sequence That Binds a Nuclear Factor, Represses Heterologous Gene Expression, and Mediates the Transcriptional Effects of Sodium", Molecular and Cellular Biology, vol. 16, No. 8, pp. 4264-4272, Aug. 1996.
Figueiredo, et al., "Cis-Acting Elements and Transcription Factors Involved in the Promoter Activity of the Human Factor VIII Gene", Journal of Biological Chemistry, vol. 270, No. 20, pp. 11828-11838, May 19, 1995.
Friend, et al., "Phase I Study of an Engineered Aglycosylated Humanized Cd3 Antibody in Renal Transplant Rejection1", Transplantation, vol. 68, Issue 11, pp. 1632-1637, Dec. 15, 1999.
Gaspar, et al., "EuGene: Maximizing Synthetic Gene Design for Heterologous Expression", Bioinformatics, vol. 28, No. 20, pp. 2683-2684, Oct. 15, 2012.
Genbank, Adena-associated Virus 2, Complete Genome, Accession J01901.1, Accessed at http://www.ncbi.nlm.nih.gov/nuccore/J01901, 3 Pages, 1993.
Genbank, Adeno-associated Virus 2, Complete Genome, GenBank Accession AF043303.1, Retrieved from: <<https://www.ncbi.nlm.nih.gov/nuccore/AF043303.1>>, 4 Pages, 2012.
Genbank, Adeno-associated Virus 4, Complete Genome, Accession U89790.1, Retrieved from: <<http://www.ncbi.nlm.nih.gov/nuccore/U89790>>, 2 Pages, Aug. 27, 1997.
Genbank, Adeno-associated Virus 5 DNA Binding trs Helicase (Rep22) and Capsid Protein, GenBank Accession AF085716.1, Retrieved from: <<https://www.ncbi.nlm.nih.gov/nuccore/AF085716.1>>, 2 Pages, Feb. 9, 1999.
Genbank, *Homo sapiens* von Willebrand Factor (VWF), mRNA, NCBI Reference Sequence: NM_000552.4, Retrieved from: <<https://www.ncbi.nlm.nih.gov/nuccore/NM_000552.4>>, 15 Pages, Apr. 28, 2016.
Genbank, Synthetic Construct Hepatocyte-Restricted Expression Cassette, GenBank Accession No. AY661265.1, Retrieved From:<<https://www.ncbi.nlm.nih.gov/nuccore/AY661265>>, 2 Pages, Sep. 29, 2009.
Ho, et al., "Site-Directed Mutagenesis by Overlap Extension Using the Polymerase Chain Reaction", Gene, vol. 77, No. 1, pp. 51-59, Apr. 15, 1989.
Hoeben, et al., "Expression of Functional Factor VIII in Primary Human Skin Fibroblasts After Retrovirus-Mediated Gene Transfer", Journal of Biological Chemistry, vol. 265, No. 13, pp. 7318-7323, May 1990.
Holt, et al., "Anti-Serum Albumin Domain Antibodies for Extending the Half-Lives of Short Lived Drugs", Protein Engineering, Design and Selection, vol. 21, No. 5, pp. 283-288, May 1, 2008.
Horton, et al., "Gene Splicing by Overlap Extension", Methods in Enzymology, vol. 217, pp. 270-279, Apr. 1, 1994.
International Preliminary Examination Report Received for PCT Application No. PCT/US2017/015879, dated Aug. 7, 2018, 10 Pages.
International Search Report & Written Opinion Received for PCT Application No. PCT/US2017/015879, dated Apr. 5, 2017, 12 Pages.
Israel, et al., "Expression of the Neonatal Fc Receptor, FcRn, on Human Intestinal Epithelial Cells", Immunology, vol. 92, No. 1, pp. 69-74, Sep. 1997.
Kobayashi, et al., "FcRn-Mediated Transcytosis of Immunoglobulin G in Human Renal Proximal Tubular Epithelial Cells", American Journal of Physiology-Renal Physiology, vol. 282, No. 2, pp. F358-F365, Feb. 2002.
Koeberl, et al., "Sequences Within the Coding Regions of Clotting Factor VIII and CFTR Block Transcriptional Elongation", Human Gene Therapy, vol. 6, No. 4, pp. 469-479, Apr. 1995.
Konig, et al., "Use of an Albumin-Binding Domain for the Selective Immobilisation of Recombinant Capture Antibody Fragments on ELISA Plates", Journal of Immunological Methods, vol. 218, No. 1-2, pp. 73-83, Sep. 1, 1998.
Kotterman, et al., "Engineering Adeno-Associated Viruses for Clinical Gene Therapy", Nature Reviews Genetics, vol. 15, No. 7, pp. 455-451, 2014.
Kraulis, et al., "The Serum Albumin-Binding Domain of Streptococcal Protein G is a Three-Helical Bundle: A Heteronuclear NMR Study", FEBS Letters, vol. 378, Issue 2, pp. 190-194, Jan. 8, 1996.

(56) References Cited

OTHER PUBLICATIONS

Kudla, et al., "High Guanine and Cytosine Content Increases Mrna Levels in Mammalian Cells", PLoS Biology, vol. 4, No. 6, pp. e180, 2006.
Lange, et al., "Overexpression of Factor VIII After AAV Delivery is Transiently Associated With Cellular Stress in Hemophilia A Mice", Molecular Therapy-Methods & Clinical Development, vol. 3, No. 16064, pp. 1-8, 2016.
Larrick, et al., "Rapid Cloning of Rearranged Immunoglobulin Genes from Human Hybridoma Cells using Mixed Primers and the Polymerase Chain Reaction", Biochemical and Biophysical Research Communications, vol. 160, No. 3, pp. 1250-1256, May 15, 1989.
Lenting, et al., "Clearance Mechanisms of von Willebrand Factor and Factor VIII", Journal of Thrombosis and Haemostasis, vol. 5, No. 7, pp. 1353-1360, Jul. 1, 2007.
Lenting, et al., "The Life Cycle of Coagulation Factor VIII in View of its Structure and Function", Blood, vol. 92, No. 11, pp. 3983-3996, Dec. 1, 1998.
Linhult, et al., "Mutational Analysis of the Interaction Between Albumin-Binding Domain From Streptococcal Protein G and Human Serum Albumin", Protein Science, vol. 11, No. 2, pp. 206-213, Feb. 1, 2002.
Lynch, et al., "Sequences in the Coding Region of Clotting Factor VIII Act as Dominant Inhibitors of RNA Accumulation and Protein Production", Human Gene Therapy, vol. 4, No. 3, pp. 259-272, Mar. 19, 2018.
Manco-Johnson, et al., "Prophylaxis Versus Episodic Treatment to Prevent Joint Disease in Boys With Severe Hemophilia", The New England Journal of Medicine, vol. 357, No. 6, pp. 535-544, Aug. 9, 2007.
Mannucci, et al., "The Hemophilias—From Royal Genes to Gene Therapy", New England Journal of Medicine, vol. 344, No. 23, pp. 1773-1779, Jun. 1, 2001.
Meulien, et al., "A New Recombinant Procoagulant Protein Derived from the Cdna Encoding Human Factor VIII", Protein Engineering, Design and Selection, vol. 2, No. 4, pp. 301-306, Oct. 1988.
Morfini, M, "Pharmacokinetics of Factor VIII and Factor IX", Haemophilia, vol. 9, No. 1, pp. 94-99, May 1, 2003.
Mount, et al., "Sustained Phenotypic Correction of Hemophilia B Dogs With a Factor IX Null Mutation by Liver-Directed Gene Therapy", Blood, vol. 99, No. 8, pp. 2670-2676, Apr. 15, 2002.
Nakamura, et al., "Codon Usage Tabulated From International DNA Sequence Databases: Status for the Year 2000", Nucleic Acids Research, vol. 28, No. 1, p. 292, 2000.
Narita, et al., "The Low-Density Lipoprotein Receptor-Related Protein (LRP) Mediates Clearance of Coagulation Factor Xa In Vivo", Blood, vol. 91, No. 2, pp. 555-560, Jan. 15, 1998.
Noren, et al., "A General Method for Site-Specific Incorporation of Unnatural Amino Acids Into Proteins", Science, vol. 244, No. 4901, pp. 182-188, Apr. 14, 1989.
Peyvandi, et al., "Genetic Diagnosis of Haemophilia and Other Inherited Bleeding Disorders", Haemophilia, vol. 12, Suppl 3, pp. 82-89, Jul. 1, 2006.
Rodriguez-Merchan, "Management of Musculoskeletal Complications of Hemophilia", Seminars in Thrombosis and Hemostasis, vol. 29, No. 1, pp. 87-96, 2003.
Roovers, et al., "Efficient Inhibition of EGFR Signaling and of Tumour Growth by Antagonistic Anti-EFGR Nanobodies", Cancer Immunology, Immunotherapy, vol. 56, No. 3, pp. 303-317, Mar. 1, 2007.
Rouet, et al., "A Potent Enhancer Made of Clustered Liver-Specific Elements in the Transcription Control Sequences of Human Alpha 1-Microglobulin/Bikunin Gene", Journal of Biological Chemistry, vol. 267, No. 29, pp. 20765-20773, Jan. 1, 1992.
Rouet, et al., "An Array of Binding Sites for Hepatocyte Nuclear Factor 4 of High and Low Affinities Modulates the Liver-Specific Enhancer for the Human α1-Microglobulin/Bikunin Precursor", Biochemical Journal, vol. 334, No. 3, pp. 577-584, Jan. 1, 1998.
Rouet, et al., "Hierarchy and Positive/Negative Interplays of the Hepatocyte Nuclear Factors HNF-1, -3 and -4 in the Liver-Specific Enhancer for the Human α-1-Microglobulin/Bikunin Precursor", Nucleic Acids Research, vol. 23, No. 3, pp. 395-404, Jan. 1, 1995.
Routledge, et al., "The Effect of Aglycosylation on the Immunogenicity of a Humanized Therapeutic CD3 Monoclonal Antibody", Transplantation, vol. 60, No. 8, pp. 847-853, Oct. 1, 1995.
Ruberti, et al., "The Use of the RACE Method to Clone Hybridoma cDNA When V Region Primers Fail", Journal of Immunological Methods, vol. 173, No. 1, pp. 33-39, Jul. 12, 1994.
Rutledge, et al., "Infectious Clones and Vectors Derived From Adeno-Associated Virus (AAV) Serotypes Other Than AAV Type 2", Journal of Virology, vol. 72, No. 1, pp. 309-319, 1998.
Sarver, et al., "Stable Expression of Recombinant Factor VIII Molecules Using a Bovine Papillomavirus Vector", DNA, vol. 6, No. 6, pp. 553-564, Dec. 1, 1987.
Sharp, et al., "The Codon Adaptation Index—A Measure of Directional Synonymous Codon Usage Bias, and Its Potential Applications", Nucleic Acids Research vol. 15, No. 3, pp. 1281-1295, 1987.
Shields, et al., "High Resolution Mapping of the Binding Site on Human IgG1 for Fc Gamma RI, Fc Gamma RII, Fc Gamma RIII, and FcRn and Design of IgG1 Variants with Improved Binding to the Fc Gamma R", Journal of Biological Chemistry, vol. 276, No. 9, pp. 6591-6604, Mar. 2, 2001.
Srivastava, et al., "Nucleotide Sequence and Organization of the Adeno-Associated Virus 2 Genome", Journal of Virology, vol. 45, No. 2, pp. 555-564, 1983.
Story, et al., "A Major Histocompatibility Complex Class I-like Fc Receptor Cloned from Human Placenta: Possible Role in Transfer of Immunoglobulin G from Mother to Fetus", Journal of Experimental Medicine, vol. 180, No. 6, pp. 2377-2381, Dec. 1, 1994.
Swystun, et al., "Gene Therapy for Coagulation Disorders", Circulation Research, vol. 118, No. 9, pp. 1443-1452, Apr. 29, 2016.
Toole, et al., "A Large Region (Approximately Equal to 95 kDa) of Human Factor VIII is Dispensable for In Vitro Procoagulant Activity", Proceedings of the National Academy of Sciences, vol. 83, No. 16, pp. 5939-5942, Aug. 1, 1986.
Torres-Torronteras, et al., "Gene Therapy Using a Liver-Targeted AAV Vector Restores Nucleoside and Nucleotide Homeostasis in a Murine Model of MNGIE", Molecular Therapy, vol. 22, No. 5, pp. 901-907, 2014.
Trussel, et al., "New Strategy for the Extension of the Serum Half-Life of Antibody Fragments", Bioconjugate Chemistry, vol. 20, No. 12, pp. 2286-2292, Dec. 1, 2009.
Vigna, et al., "Efficient Tet-Dependent Expression of Human Factor IX In Vivo by a New Self-Regulating Lentiviral Vector", Molecular Therapy, vol. 11, No. 5, pp. 763-775, Jan. 1, 2005.
White et al., "A Multicenter Study of Recombinant Factor VIII (Recombinate) in Previously Treated Patients With Hemophilia A. The Recombinate Previously Treated Patient Study Group", Thrombosis and Haemostasis, vol. 77, No. 4, pp. 660-667, Apr. 1, 1997.
Defensive Opposition regarding European Patent No. EP2956477 filed by Bioverative Therapeutics Inc., dated Mar. 11, 2022, including Main Request and Auxiliary Requests 1, 1a, 2a, 3a, 3, 4, 5, 5a, 6a, 6, 7, 7a, 8, 9a, 9, 10a, 10, 11a, 11, 12, 13a, 13, 14, 14a, 15a, and 15.
Comparison of in vivo FVIII activity after expression with codon optimised FVIII (SEQ ID: 1) and non-optimised FVIII (SEQ ID: 3).
Comparison of codon usage frequency in SEQ ID No. 1 and SEQ ID: 3 of the Patent and SEQ ID: 5 of D2 (WO 2011/005968 A1, submitted with IDS dated Sep. 7, 2021).
Akkina, et al., High-efficiency Gene Transfer into CD34+ Cells with a Human Immunodeficiency Virus Type 1-based Retroviral Vector Pseudotyped With Vesicular Stomatitis Virus Envelope Glycoprotein G, Journal of Virology, vol. 70, No. 4, pp. 2581-2585, Apr. 1996.
Andersson, et al., "Purification and Characterization of Human Factor IX", Thrombosis Research, vol. 7, Issue 3, pp. 451-459. (Sep. 1975).
Baekelandt et al., "Optimized lentiviral vector production and purification procedure prevents immune response after transduction of mouse brain Laboratory for Experimental", Jun. 2003, 10: 1933-1940.

(56) References Cited

OTHER PUBLICATIONS

Baldassarre, et al., "Production of Transgenic Goats By Pronuclear Microinjection Of In Vitro Produced Zygotes Derived From Oocytes Recovered By Laparoscopy", Theriogenology, vol. 59, Issues 3-4, pp. 831-839, Feb. 2003.
Benhar, et al., "Cloning, Expression and Characterization Of The Fv Fragments Of The Anti-Carbohydrate mAbs BI and B5 As Single-Chain Immunotoxins", Protein Engineering, Design and Selection, vol. 7, No. 12, pp. 1509-1515, Dec. 1994.
Biochemistry, 1990, Section 6-3 Chemical Evolution, pp. 126-129, John Wiley and Sons.
Bril et al. (2006) "Tolerance to factor VIII in a transgenic mouse expressing human factor VIII cDNA carrying an Arg$^{593}$ to Cys substitution", Thromb. Haemost. 95(2): 341-347.
Brinster, et al., "Expression of A Microinjected Immunoglobulin Gene In The Spleen Of Transgenic Mice", Nature, vol. 306, No. 5941, pp. 332-336, 1983.
Brinster, et al., "Factors Affecting the Efficiency Of Introducing Foreign DNA Into Mice By Microinjecting Eggs", Proceedings of the National Academy of Sciences of the United States of America, vol. 82, No. 13, pp. 4438-4442, Jul. 1, 1985.
Brown, et al., Endogenous microRNA Regulation Suppresses Transgene Expression in Hematopoietic Lineages and Enables Stable Gene Transfer, Nature Medicine, vol. 12, No. 5, pp. 585-591, May 1, 2006.
Brown et al., "Endogenous microRNA can be broadly exploited to regulate transgene expression according to tissue, lineage and differentiation state", Nat. Biotechnol., Dec. 2007, 25(12): 1457-1467.
Brown, et al., "A microRNA-Regulated Lentiviral Vector Mediates Stable Correction of Hemophilia B Mice", Blood, vol. 110, No. 13, pp. 4144-4152, Dec. 15, 2007.
Brown, et al., "Production of Recombinant H1 Parvovirus Stocks Devoid of Replication-Competent Viruses", Human Gene Therapy, vol. 13, No. 18, pp. 2135-2145, Dec. 10, 2002.
Burgess-Brown et al., "Codon Optimization Can Improve Expression Of Human Genes In *Escherichia Coli*: A Multi-Gene Study", Protein Expression and Purification, 2008, vol. 59, No. 1, pp. 94-102.
Cantore et al., "Hyperfunctional Coagulation Factor IX Improves The Efficacy Of Gene Therapy In Hemophilic Mice", Blood, 2012, vol. 120, No. 23, pp. 4517-4520.
Cantore et al., "Liver-Directed Gene Therapy for Hemophilia B with Immune Stealth Lentiviral Vectors", Gene Therapy and Transfer: Gene Therapy for Hemophilia and Improving Lentiviral Vectors, Dec. 7, 2017 Blood, 130(Suppl. 1): 605.
Cleland et al., "A novel long-acting human growth hormone fusion protein (vrs-317): enhanced in vivo potency and half-life", Journal of Pharmaceutical Sciences, 2012, 101(8): 2744-2754.
Codon Optimization for Increased Protein Expression, downloaded Mar. 26, 2018 from GenScript, OptimumGene—Codon Optimization.
Codon Usage Database, Retrieved from http://www.kazusa.or.jp/codon/, 2013, 1 page.
Coffin, et al., "The Interaction of Retroviruses and Their Hosts", Retroviruses, Cold Spring Harbor Laboratory Press, pp. 758-763, 1997.
Cutler et al., "The Identification and Classification Of 41 Novel Mutations In The Factor VIII Gene (F8c)", Human Mutation, Mar. 2002, vol. 19, No. 3, pp. 274-278.
Database Geneseq, "Human Codon-Optimized Clotting Factor IX (hFIX) Gene, Seq ID No. 2", XP002776590, retrieved from EBI accession No. GSN: BBB41169 Database accession No. BBB41169, Feb. 27, 2014.
Dellgren, et al., "Cell Surface Expression Level Variation between Two Common Human Leukocyte Antigen Alleles, HLA-A2 and HLA-B8, Is Dependent on the Structure of the C Terminal Part of the Alpha 2 and the Alpha 3 Domains", PLOS One, vol. 10, No. 8, e0135385, pp. 1-15, Aug. 25, 2010.

Ding et al., "Multivalent Antiviral XTEN-Peptide Conjugates with Long in Vivo Half-Life and Enhanced Solubility", Bioconjugate Chemistry, 2014, 25(7): 1351-1359.
Dull, et al., "A Third-Generation Lentivirus Vector with a Conditional Packaging System", Journal of Virology, vol. 72, No. 11, pp. 8463-8471, Nov. 1998.
Ensembl, Gene: B2M ENSG00000166710, Beta-2-Microglobulin, obtained from url: http://uswest.ensembl.org/Homo_sapiens/Gene/Summary?g=ENSG00000166710;r=15:44711477-44718877;mobileredirect=no.
Fathallah, et al., Effects of Hypertonic Buffer Composition on Lymph Node Uptake and Bioavailability of Rituximab, After Subcutaneous Administration, Biopharmaceutics & Drug Disposition, vol. 36, No. 2, pp. 115-125, Mar. 2015.
Genbank Database, "Transferrin Precursor [Homo sapiens]", GenBank Accession No. AAA61140.1, Jan. 14, 1995, 1 page, Retrieved from: << http://www.ncbi.nlm.nih.gov/protein/AAA61140.1>>.
Genbank, "Homo sapiens von Willebrand factor (VWF), mRNA," Accession No. NM_000552.3, Accessed At http://www.ncbi.nlm.nih.gov/nuccore/NM_000552.
Genbank, "Von Willebrand Factor Preproprotein [homo Sapiens]," Accession No. NP000543.2, Accessed at http://www.ncbi.nlm.nih.gov/protein/NP_000543.
Genbank, "Homo Sapiens Transferrin (TF), mRNA", GenBank Accession No. XM002793, May 13, 2002, 2 pages, Retrieved from: <<https://www.ncbi.nlm.nih.gov/nuccore/XM_002793.7?report=genbank>>.
Genbank, "Homo Sapiens Transferrin (TF), mRNA", GenBank Accession No. XM039845, Jul. 16, 2001, 2 pages, Retrieved From: <<https://www.ncbi.nlm.nih.gov/nuccore/XM_039845.1?report=genbank>>.
Genbank, "Homo Sapiens Transferrin (TF), mRNA", GenBank Accession No. XM039847, Jul. 16, 2001, 2 pages, Retrieved From <<https://www.ncbi.nlm.nih.gov/nuccore/XM_039847.1?report=genbank>>.
Genbank, "Homo Sapiens Transferrin (TF), Transcript Variant 1, mRNA", GenBank Accession No. NM001063, Sep. 3, 2009, 5 pages, Retrieved from: <<http://www.ncbi.nlm.nih.gov/nuccore/NM_001063>>.
Genbank, "Human Transferrin mRNA, Complete cds", GenBank Accession No. M12530, Jan. 14, 1995, 2 pages, Retrieved From: <<http://www.ncbi.nlm.nih.gov/nuccore/M12530>>.
Genbank, "Transferrin [Human, Liver, mRNA, 2347 nt]", GenBank Accession No. S95936, May 7, 1993, 2 pages, Retrieved From: <<http://www.ncbi.nlm.nih.gov/nuccore/S95936>>.
Generation Bio, "Generation Bio Announces Two Non-Viral Gene Therapy Milestone Achievements: Target Levels of Factor VIII Expression in Hemophilia A Mice and Translation of Expression from Mice to Non-Human Primates", Jan. 4, 2021, obtained from url: <https://www.globenewswire.com/en/news-release/2021/01/04/2152472/0/en/Generation-Bio-Announces-Two-Non-Viral-Gene-Therapy-Milestone-Achievements-Target-Levels-of-Factor-VIII-Expression-in-Hemophilia-A-Mice-and-Translation-of-Expression-from-Mice-to-N.html>.
Giangrande, Paul, "Haemophilia B: Christmas Disease", Expert Opinion On Pharmacotherapy, vol. 6, No. 9, pp. 1517-1524. (2005).
Graf, M., et al., "Concerted Action of Multiple Cis-acting Sequences Is Required for Rev Dependence of Late Human Immunodeficiency Virus Type 1 Gene Expression," Journal of Virology 74(22):10822-10826, American Society for Microbiology, United States (2000).
Higashikawa, et al., Kinetic Analyses of Stability of Simple and Complex Retroviral Vectors, Virology, vol. 280, No. 1, pp. 124-131, 2001.
Holt, et al., "Domain Antibodies: Proteins for therapy", Trends in Biotechnology, vol. 21, Issue 11, pp. 484-490, Nov. 2003.
Ill, et al., (1997) "Optimization Of The Human Factor VIII Complementary DNA Expression Plasmid For Gene Therapy Of Hemophilia A", Blood Coagulation & Fibrinolysis: An International Journal In Haemostasis And Thrombosis, vol. 8, pp. S23-S30.
International Preliminary Report on Patentability for PCT International Patent Application No. PCT/US2019/016122, dated Aug. 4, 2020.

(56) References Cited

OTHER PUBLICATIONS

International Search Report & Written Opinion for PCT International Patent Application No. PCT/US2019/016122, dated Mar. 21, 2019.
International Search Report & Written Opinion for PCT International Patent Application No. PCT/US2020/053463, dated Feb. 4, 2021.
International Search Report & Written Opinion for PCT International Patent Application No. PCT/US2021/038871, dated Nov. 24, 2021.
International Search Report and Written Opinion for PCT International Patent Application No. PCT/US2019/064711, dated Jun. 23, 2020.
International Search Report and Written Opinion for PCT International Application No. PCT/US2015/038678, dated Dec. 8, 2015.
International Search Report and Written Opinion for PCT International Patent Application No. PCT/US2014/016441, dated May 23, 2014.
Johnston et al., "Generation of an optimized lentiviral vector encoding a high-expression factor VIII transgene for gene therapy of hemophilia A", Gene Therapy, Jun. 2013, 20(6):607-615.
Kasuda et al., "Establishment Of Embryonic Stem Cells Secreting Human Factor VIII For Cell-Based Treatment Of Hemophilia A", Journal of Thrombosis and Haemostasis, Aug. 2008, vol. 6, No. 8, pp. 1352-1359.
Kimchi-Sarfaty et al., "A" Silent" Polymorphism In The Mdr1 Gene Changes Substrate Specificity", Science, 2007, vol. 315, No. 5811, pp. 525-528.
Klimatcheva, et al., "Lentiviral Vectors and Gene Therapy", Frontiers in Bioscience, vol. 4, pp. 481-496, Jun. 1, 1999.
Langner, K-D., et al., "Synthesis of Biologically Active Deletion Mutants of Human Factor VIII:C," Behring Institute Mitteilungen 82:16-25, Behringwerke AG, Germany (1988).
Le Bras et al., "Shielded vectors improve liver gene therapy", Lab Animal, 2019, 48: 238.
Liu et al., "Codon Optimization Improves Factor IX Expression In Hemophilia B Mice By More Than 15-Fold", Human Gene Therapy, Oct. 2015, vol. 26, No. 10, Page A2.
Malassagne, et al. (Apr. 14, 2003) "Hypodermin A, A New Inhibitor of Human Complement for the Prevention of Xenogeneic Hyperacute Rejection", Xenotransplantation, vol. 10, Issue 3, pp. 267-277.
Maunder et al., "Enhancing titres of therapeutic viral vectors using the transgene repression in vector production (TRiP) system", Nature Communications, Mar. 2017, 8(1).
McCue et al., "Application of a novel affinity adsorbent for the capture and purification of recombinant Factor VIII compounds", J. Chroma., Nov. 6, 2009, 1216(45): 7824-7830.
McKnight, et al. (Sep. 1983) "Expression of The Chicken Transferrin Gene in Transgenic Mice", Cell, vol. 34, Issue 2, pp. 335-341.
Miao et al., "Bioengineering of Coagulation Factor VIII for Improved Secretion", Blood, May 1, 2004, vol. 103, No. 9, pp. 3412-3419.
Milani et al., "Phagocytosis-shielded lentiviral vectors improve liver gene therapy in nonhuman primates", Sci Transl Med., May 22, 2019, 11(493): eaav7325.
Milani, et al., "Genome Editing For Scalable Production of Alloantigen-Free Lentiviral Vectors for In Vivo Gene Therapy", EMBO Molecular Medicine, Aug. 23, 2017, 9(11): 1558-1573.
Muller, et al. (Aug. 2007) "Recombinant Bispecific Antibodies for Cellular Cancer Immunotherapy", Current opinion in molecular therapeutics, vol. 9, No. 4, pp. 319-326.
Nair et al., "Computationally Designed Liver-Specific Transcriptional Modules And Hyperactive Factor IX Improve Hepatic Gene Therapy", Blood, 2014, vol. 123, No. 20, pp. 3195-3199.
Nair et al., "Computationaly Designed Liver-Specific Transcriptional Modules and Hyperactive Factor IX Improve Hepatic Gene Therapy ERRATA 2007", Blood, Mar. 19, 2015, vol. 125, No. 12.
Nayak, et al., "Progress and Prospects: Immune Responses to Viral Vectors", Gene Therapy, Nov. 12, 2009, 17: 295-304.
NCBI, "Beta-2-Microglobin [Homo sapiens]", GenBank Accession No. ABB01003.1, 2 Pages. 2005.
Neumann, et al., "Gene Transfer Into Mouse Lyoma Cells By Electroporation In High Electric Fields", The EMBO Journal, vol. 1, No. 7, pp. 841-845. (Jul. 1, 1982).
Otto-Wilhelm et al., "Production of lentiviral vectors", Molecular Therapy—Methods & Clinical Development, Jan. 2016, 3: 1-14.
Partial European Search Report for European Patent Application No. 15814881.7, dated Jan. 12, 2018, 6 pages.
Pipe et al., "Functional Factor VIII Made With Von Willebrand Factor At High Levels In Transgenic Milk", Journal of Thrombosis and Haemostasis, Nov. 2011, vol. 9, No. 11, pp. 2235-2242.
Podust, "Extension of In Vivo Half-Life of Biologically Active Molecules by XTEN Protein Polymers", Journal of Controlled Release, Oct. 28, 2016, 240(6): 52-66.
Ritchie, et al. (Dec. 6, 1984) "Allelic Exclusion and Control of Endogenous Immunoglobulin Gene Rearrangement in κ Transgenic Mice", Nature, vol. 312, No. 5994, pp. 517-520.
Robl, et al. (Jan. 1, 2003) "Artificial Chromosome Vectors and Expression of Complex Proteins in Transgenic Animals", Theriogenology, vol. 59, Issue 1, pp. 107-113.
Ruther et al., "Easy Identification of cDNA Clones," The EMBO Journal 2(10):1791-1794, IRL Press Ltd, England (1983).
Schlapschy, et al., "Fusion of A Recombinant Antibody Fragment with A Homo-Amino-Acid Polymer: Effects On Biophysical Properties And Prolonged Plasma Half-Life", Protein Engineering, Design and Selection, vol. 20, No. 6, pp. 273-284, Jun. 1, 2007.
Sebastian et al., "Treatment of malignant pleural effusion with the trifunctional antibody catumaxomab (Removab) (anti-EpCAM x Anti-CD3): results of a phase 1/2 study", Journal of Immunotherapy, 2009, 32(2): 195-202.
Simioni, et al. (Oct. 22, 2009) "X-Linked Thrombophilia with a Mutant Factor IX (Factor IX Padua)", The New England Journal of Medicine, vol. 361, No. 17, pp. 1671-1675.
Sosale, et al., "Marker of Self CD47 on Lentiviral Vectors Decreases Macrophage-Mediated Clearance and Increases Delivery to SIRPA-Expressing Lung Carcinoma Tumors", Molecular Therapy-Methods & Clinical Development, vol. 3, No. 16080, 13 Pages, Jan. 1, 2016.
Summons to Attend Oral Proceedings for European Patent Application No. 14751254.5, dated Nov. 9, 2022.
Supplementary European Search Report for European Patent Application No. 15814881.7, dated Apr. 13, 2015, 7 pages.
Suwanmanee et al., "Integration-Deficient Lentiviral Vectors Expressing Codon-Optimized R338L Human FIX Restore Normal Hemostasis In Hemophilia B Mice", Molecular Therapy, 2014, vol. 22, No. 3, pp. 567-574.
Third party observations against European Application No. 15814881.7, dated Oct. 2, 2020, 107 pages.
Wagner, et al. (Oct. 1, 1981) "Microinjection of a Rabbit Beta-Globin Gene into Zygotes and Its Subsequent Expression in Adult Mice and Their Offspring", Proceedings of the National Academy of Sciences of the United States of America, vol. 78, No. 10, pp. 6376-6380.
Ward, et al., "The Effector Functions Of Immunoglobulins: Implications For Therapy", Therapeutic immunology, vol. 2, No. 2, pp. 77-94. (Apr. 1995).
Wigler, et al., "Biochemical Transfer of Single-Copy Eucaryotic Genes using Total Cellular DNA as Donor", Cell, vol. 14, No. 3, pp. 725-731. (Jul. 1978).
Zhang et al., "An EpCAM/CD3 bispecific antibody efficiently eliminates hepatocellular carcinoma cells with limited galectin-1 expression", Cancer Immunology, Immunotherapy, 2014, 63(2): 121-132.
Zufferey, et al., "Multiply Attenuated Lentiviral Vector Achieves Efficient Gene Delivery In Vivo", Nature Biotechnology, vol. 15, No. 9, pp. 871-875, Sep. 1, 1997.

* cited by examiner

FIG. 1A: coFVIII-3 – SEQ ID NO: 1

```
ATGCAGATCGAACTGAGCACCTGCTTCTTTCTGTGCCTGCTGAGGTTTTGCTTTAGCGCCACCAGGAGATACTATCTGGGCGC
CGTGGAACTGAGCTGGGACTATATGCAGTCTGATCTGGGCGAACTGCCAGTGGATGCCAGGTTTCCCCCAGAGTGCCCAAAA
GCTTTCCCTTTAATACCAGCGTGGTGTATAAGAAAACCCTGTTTGTGGAATTCACTGATCATCTGTTTAATATCGCCAAGCCC
AGGCCCCCCTGGATGGGCCTGCTGGGCCCCACCATCCAGGCCGAAGTGTATGATACCGTGGTCATCACCCTGAAAAACATGGC
CAGCCATCCAGTGAGCCTGCATGCTGTGGGCGTCTCCTATTGGAAAGCCTCTGAAGGCGCCGAGTATGATGATCAGACCAGCC
AGAGGGAAAAAGAAGATGATAAAGTCTTTCCTGGGGGCAGCCATACCTATGTCTGGCAGGTCCTGAAAGAAAATGGCCCCATG
GCCAGCGATCCCCTGTGCCTGACCTATAGCTATCTGAGCCATGTGGACCTGGTGAAGGATCTGAACAGCGGCCTGATTGGGGC
CCTGCTGGTGTGCAGGGAAGGCAGCCTGGCCAAAGAAAAACCCAGACCCTGCATAAGTTTATCCTGCTGTTTGCCGTGTTTG
ATGAAGGCAAAAGCTGGCATTCTGAAACCAAAAACAGCCTGATGCAGGACAGGGATGCCGCCTCTGCCAGGGCCTGGCCCAAA
ATGCATACCGTGAATGGCTATGTGAATAGGAGCCTGCCTGGCCTGATTGGCTGCCACAGGAAAGCGTGTATTGGCATGTGAT
CGGCATGGGCACCACCCCCGAAGTGCATAGCATCTTTCTGGAAGGCCATACCTTCCTGGTCAGGAACCACAGGCAGGCCAGCC
TGGAAATCAGCCCCATCACCTTCCTGACCGCCCAGACCCTGCTGATGGATCTGGGCAGTTTCTGCTGTTTTGCCACATCTCC
AGCCATCAGCATGATGGCATGGAAGCCTATGTGAAAGTCGATAGCTGCCCCGAAGAACCCAGCTGAGGATGAAAAACAATGA
AGAAGCCGAAGACTATGATGATGATCTGACTGATTCTGAAATGGATGTGGTCAGGTTTGATGATGATAATAGCCCCAGCTTTA
TCCAGATCAGGAGCGTGGCCAAAAAACATCCCAAGACCTGGGTGCATTATATCGCTGCTGAGGAAGAAGATTGGGACTATGCC
CCCCTGGTGCTGGCCCCTGATGATAGGAGCTATAAAAGCCAGTATCTGAACAATGGCCCCCAGAGGATTGGCAGGAAGTATAA
AAAAGTCAGGTTTATGGCCTACACTGATGAAACCTTCAAGACCAGGGAAGCCATCCAGCATGAGTCTGGCATCCTGGGCCCCC
TGCTGTATGGCGAAGTGGGGGACACCCTGCTGATCATCTTTAAAAATCAGGCCAGCAGGCCCTATAATATCTATCCCCATGGC
ATCACTGATGTGAGGCCCCTGTACAGCAGGAGGCTGCCCAAAGGCGTGAAACATCTGAAAGATTTTCCCATCCTGCCTGGCGA
AATCTTTAAGTATAAATGGACTGTGACTGTGGAAGATGGCCCCACCAAAAGCGATCCCAGGTGCCTGACCAGGTATTATTCCA
GCTTTGTGAATATGGAACGCGATCTGGCCTCTGGCCTGATTGGCCCCCTGCTGATCTGCTATAAAGAGTCTGTGGACCAGAGG
GGCAATCAGATCATGAGCGATAAAAGGAATGTCATCCTGTTCTCTGTCTTTGATGAGAATAGGAGCTGGTACCTGACCGAAAA
CATCCAGAGGTTTCTGCCCAATCCCGCCGGCGTGCAGCTGGAAGATCCCGAGTTTCAGGCCAGCAATATCATGCATAGCATCA
ATGGCTATGTCTTTGATAGCCTGCAGCTGAGCGTGTGCCTGCATGAGGTGGCCTATTGGTATATCCTGAGCATCGGCGCCCAG
ACCGATTTTCTGAGCGTGTTTTCTCTGGCTATACCTTTAAACATAAAATGGTGTATGAGGACACCCTGACCCTGTTTCCCTT
CTCTGGCGAAACCGTGTTTATGAGCATGGAAAATCCCGGCCTGTGGATCCTGGGCTGCCACAACAGCGATTTCAGGAACAGGG
GCATGACTGCCCTGCTGAAAGTCTCCAGCTGCGATAAAAACACTGGGGACTATTATGAGGACAGCTATGAGGACATCAGCGCC
TATCTGCTGAGCAAGAACAATGCCATCGAACCCAGGAGCTTTAGCCAGAATCCCCCAGTGCTGAAAAGGCATCAGAGGGAAAT
CACCAGGACCACCCTGCAGTCTGATCAGGAAGAAATCGACTATGATGATACCATCAGCGTGGAAATGAAGAAAGAAGATTTTG
ATATCTATGATGAAGATGAAAATCAGAGCCCCAGGAGCTTTCAGAAGAAACCAGGCATTACTTCATCGCTGCTGTGGAAAGG
CTGTGGGACTATGGCATGTCCAGCAGCCCCATGTGCTGAGGAACAGGGCCCAGTCTGGCAGCGTGCCCCAGTTTAAAAAGT
CGTGTTTCAGGAGTTTACCGATGGCAGCTTTACCCAGCCCCTGTATAGGGCGAACTGAATGAACATCTGGGCCTGCTGGGCC
CCTACATCAGGGCCGAAGTGGAAGATAATATCATGGTGACCTTCAGGAACCAGGCCAGCAGGCCCTACAGCTTTTATTCCAGC
CTGATCAGCTATGAGGAAGATCAGAGGCAGGGGGCTGAGCCCAGGAAAAACTTTGTGAAACCCAATGAAACCAAGACCTACTT
TTGGAAAGTCCAGCATCATATGGCCCCCACCAAGGATGAATTTGATTGCAAAGCCTGGGCCTACTTCTCTGATGTGGACCTGG
AAAAAGATGTGCATAGCGGCCTGATTGGCCCCCTGCTGGTGTGCCACACCAATACCCTGAACCCTGCCCATGGCAGGCAGGTG
ACTGTGCAGGAGTTTGCCCTGTTCTTTACCATCTTTGATGAAACCAAAAGCTGGTACTTCACCGAAAACATGGAAAGGAACTG
CAGGGCCCCCTGCAACATCCAGATGGAAGATCCCACCTTTAAAGAAATTATAGGTTCCATGCCATCAATGGCTATATCATGG
ATACCCTGCCTGGCCTGGTCATGGCCCAGGACCAGAGGATCAGGTGGTATCTGCTGAGCATGGGCAGCAATGAAAACATCCAT
AGCATCCATTTCTCTGGCCATGTCTTTACCGTCAGGAAAAAGAAGAGTATAAAATGGCCCTGTATAATCTGTACCCTGGGGT
GTTTGAAACCGTGGAAATGCTGCCCAGCAAAGCCGGCATCTGGAGGGTGGAATGCCTGATTGGCGAACATCTGCATGCTGGCA
TGAGCACCCTGTTTCTGGTGTATAGCAATAAGTGCCAGACCCCCCTGGGCATGGCCTCTGGCCATATCAGGGATTTTCAGATC
ACTGCCTCTGGCCAGTATGGCCAGTGGGCCCCCAAACTGGCCAGGCTGCATTATTCCGGAAGCATCAATGCCTGGAGCACCAA
AGAACCCTTTAGCTGGATCAAAGTCGATCTGCTGGCCCCCATGATCATCCATGGCATCAAGACCCAGGGGCCAGGCAGAAAT
TTTCCAGCCTGTACATCAGCCAGTTTATCATCATGTATAGCCTGGATGGCAAAAATGGCAGACCTATAGGGGCAATAGCACC
GGCACCCTGATGGTGTTCTTTGGCAATGTGGACAGCAGCGGCATCAAACATAATATCTTTAATCCCCCATCATCGCCAGGTA
TATCAGGCTGCATCCCACCCATTATAGCATCAGGAGCACCCTGAGGATGGAACTGATGGGCTGCGATCTGAACAGCTGCAGCA
TGCCCCTGGGCATGGAAAGCAAAGCCATCAGCGATGCCCAGATCACTGCCTCCAGCTACTTCACTAATATGTTTGCCACCTGG
AGCCCCAGCAAAGCCAGGCTGCATCTGCAGGGCAGGAGCAATGCCTGGAGGCCCCAGGTCAACAATCCCAAAGAATGGCTGCA
GGTCGATTTTCAGAAAACCATGAAAGTCACTGGGGTGACCACCCAGGGGGTGAAAAGCCTGCTGACCAGCATGTATGTGAAAG
AGTTTCTGATCTCCAGCAGCCAGGATGGCCATCAGTGGACCCTGTTCTTTCAGAATGGCAAAGTCAAGTCTTTCAGGGCAAT
CAGGACAGCTTTACCCCTGTGGTGAATAGCCTGGATCCCCCCTGCTGACCAGGTATCTGAGGATCCATCCCCAGAGCTGGGT
GCATCAGATCGCCCTGAGGATGGAAGTGCTGGGCTGCGAAGCCCAGGACCTGTACTGA
```

FIG. 1B: coFVIII-4 – SEQ ID NO: 2

```
ATGCAGATCGAGCTGAGCACGTGCTTCTTCCTGTGCCTGCTGAGGTTCTGCTTCAGCGCCACCAGGAGGTACTACCTGGGCGC
CGTGGAGCTGAGCTGGGACTACATGCAGAGCGACCTGGGCGAGCTGCCCGTGGACGCCAGGTTCCCCCCCAGGGTGCCCAAGA
GCTTCCCCTTCAACACGAGCGTGGTGTACAAGAAGACCCTGTTCGTGGAGTTCACCGACCATCTGTTCAATATCGCCAAGCCC
AGGCCCCCTGGATGGGGCTGCTGGGGCCCACGATCCAGGCCGAGGTGTACGACACCGTGGTCATCACCCTGAAGAACATGGC
CAGCCACCCCGTGAGCCTGCACGCCGTGGGCGTGAGCTACTGGAAGGCCAGCGAGGGCGCCGAGTACGACGACCAGACCAGCC
AGAGGGAGAAGGAGGACGACAAGGTGTTCCCCGGCGGCAGCCACACCTACGTGTGGCAGGTGCTGAAGGAGAATGGGCCCATG
GCCAGCGACCCCCTGTGCCTGACCTACTCTTACCTGAGCCACGTGGATCTGGTGAAGGACCTGAACAGCGGCCTGATCGGCGC
CCTGCTGGTGTGCAGGGAGGGCAGCCTGGCCAAGGAGAAGACCCAGACCCTGCACAAGTTCATCCTGCTGTTCGCCGTGTTCG
ACGAGGGCAAGAGCTGGCACAGCGAGACCAAGAACAGCCTGATGCAGGATAGGGACGCCGCCAGCGCCAGGGCCTGGCCCAAG
ATGCACACCGTGAACGGCTACGTGAACAGGTCTCTGCCCGGCCTGATCGGCTGCCACAGGAAGAGCGTGTACTGGCACGTGAT
CGGCATGGGGACCACCCCCGAGGTGCACAGCATCTTCCTGGAGGGCCACACGTTCCTGGTGAGGAATCACAGGCAGGCCAGCC
TGGAGATCAGCCCGATCACCTTCCTGACCGCCCAGACCCTGCTGATGGACCTGGGGCAGTTCCTGCTGTTCTGCCATATCAGC
TCTCACCAGCACGACGGCATGGAGGCCTACGTGAAGGTGGATAGCTGCCCCGAGGAGCCCCAGCTGAGGATGAAGAACAACGA
GGAGGCCGAGGACTACGACGACGACCTGACCGACAGCGAGATGGACGTGGTGAGGTTCGACGACGACAATAGCCCGAGCTTCA
TCCAGATCAGGAGCGTGGCCAAGAAGCACCCCAAGACCTGGGTGCATTACATCGCCGCCGAGGAGGAGGATTGGGACTACGCC
CCCCTGGTGCTGGCCCCCGACGACAGGTCTTACAAGAGCCAGTACCTGAACAACGGGCCCCAGAGGATCGGCAGGAAGTACAA
GAAGGTGAGGTTCATGGCCTACACCGACGAGACCTTCAAGACCAGGGAGGCGATCCAGCACGAGAGCGGGATCCTGGGGCCCC
TGCTGTACGGCGAGGTGGGCGACACGCTGCTGATCATCTTCAAGAACCAGGCCAGCAGGCCGTACAATATCTACCCCCACGGG
ATCACCGACGTGAGGCCCCTGTACTCTAGGAGGCTGCCCAAGGGCGTGAAGCACCTGAAGGACTTCCCCATCCTGCCCGGCGA
GATCTTCAAGTACAAGTGGACCGTGACCGTGGAGGACGGGCCCACGAAGAGCGACCCCAGGTGCCTGACCAGGTACTACAGCT
CTTTCGTGAACATGGAGAGGGACCTGGCCAGCGGCCTGATCGGGCCCCTGCTGATCTGCTACAAGGAGAGCGTGGATCAGAGG
GGCAACCAGATCATGAGCGACAAGAGGAACGTGATCCTGTTCAGCGTGTTCGACGAGAATAGGTCTTGGTACCTGACCGAGAA
TATCCAGAGGTTCCTGCCCAACCCCGCCGGCGTGCAGCTGGAGGATCCCGAGTTCCAGGCCAGCAACATCATGCACAGCATCA
ACGGCTACGTGTTCGACAGCCTGCAGCTGAGCGTGTGCCTGCACGAGGTGGCCTACTGGTACATCCTGAGCATCGGCGCCCAG
ACCGACTTCCTGAGCGTGTTCTTCAGCGGCTACACCTTCAAGCACAAGATGGTGTACGAGGATACCCTGACCCTGTTCCCCTT
CAGCGGCGAGACCGTGTTCATGAGCATGGAGAACCCCGGCCTGTGGATCCTGGGCTGCCATAACTCCGACTTCAGGAATAGGG
GCATGACCGCCCTGCTGAAGGTGAGCTCTTGCGACAAGAACACCGGCGACTACTACGAGGATAGCTACGAGGATATCAGCGCC
TACCTGCTGAGCAAGAACAACGCCATCGAGCCCAGGTCTTTCAGCCAGAACCCCCCGTGCTGAAGAGGCACCAGAGGGAGAT
CACCAGGACGACCCTGCAGAGCGACCAGGAGGAGATCGACTACGACGACACGATCAGCGTGGAGATGAAGAAGGAGGATTTCG
ACATCTACGACGAGGACGAGAATCAGAGCCCCAGGTCTTTCCAGAAGAAGACCAGGCATTACTTCATCGCCGCCGTGGAGAGG
CTGTGGGACTACGGCATGAGCAGCTCTCCCCACGTGCTGAGGAATAGGGCCCAGAGCGGCAGCGTGCCCCAGTTCAAGAAGGT
GGTGTTCCAGGAGTTCACCGACGGCAGCTTCACCCAGCCCCTGTACAGGGGCGAGCTGAACGAGCACCTGGGCCTGCTGGGGC
CCTACATCAGGGCCGAGGTGGAGGATAACATCATGGTGACCTTCAGGAATCAGGCCAGCAGGCCCTATAGCTTCTATAGCTCT
CTGATCAGCTACGAGGAGGATCAGAGGCAGGGCGCCGAGCCCAGGAAGAACTTCGTGAAGCCCAACGAGACCAAGACCTACTT
CTGGAAGGTGCAGCACCACATGGCCCCCACGAAGGACGAGTTCGACTGCAAGGCCTGGGCCTACTTCAGCGACGTGGATCTGG
AGAAGGACGTGCACAGCGGCCTGATCGGCCCCCTGCTGGTGTGCCACACCAACACCCTGAACCCCGCCCACGGCAGGCAGGTG
ACCGTGCAGGAGTTCGCCCTGTTCTTCACCATCTTCGACGAGACCAAGAGCTGGTACTTCACCGAGAATATGGAGAGGAATTG
CAGGGCCCCCTGCAATATCCAGATGGAGGACCCGACCTTCAAGGAGAATTACAGGTTCCACGCCATCAACGGCTACATCATGG
ACACGCTGCCCGGCCTGGTCATGGCCCAGGATCAGAGGATCAGGTGGTATCTGCTGAGCATGGGGAGCAACGAGAATATCCAC
AGCATCCACTTCAGCGGCCACGTGTTCACCGTGAGGAAGAAGGAGGAGTACAAGATGGCCCTGTACAATCTGTACCCCGGCGT
GTTCGAGACCGTGGAGATGCTGCCCAGCAAGGCCGGGATCTGGAGGGTGGAGTGCCTGATCGGCGAGCACCTGCACGCCGGCA
TGAGCACGCTGTTCCTGGTGTACTCTAACAAGTGCCAGACCCCCTGGGGATGGCCAGCGGCCACATCAGGGACTTCCAGATC
ACCGCCAGCGGCCAGTACGGCCAGTGGGCCCCCAAGCTGGCCAGGCTGCACTATTCCGGAAGCATCAACGCCTGGAGCACGAA
GGAGCCCTTCAGCTGGATCAAGGTGGATCTGCTGGCCCCCATGATCATCCACGGGATCAAGACCCAGGGCGCCAGGCAGAAGT
TCAGCTCTCTGTATATCAGCCAGTTCATCATCATGTACTCTCTGGACGGCAAGAAGTGGCAGACCTACAGGGGCAACAGCACC
GGCACGCTGATGGTGTTCTTCGGCAACGTGGACTCTAGCGGGATCAAGCACAATATCTTCAACCCCCCCATCATCGCCAGGTA
CATCAGGCTGCACCCCACCCATTACTCTATCAGGTCTACCCTGAGGATGGAGCTGATGGGCTGCGACCTGAACAGCTGCAGCA
TGCCCCTGGGGATGGAGAGCAAGGCCATCAGCGACGCCCAGATCACCGCCAGCTCTTACTTCACCAACATGTTCGCCACCTGG
AGCCCGAGCAAGGCCAGGCTGCACCTGCAGGGCAGGTCTAACGCCTGGAGGCCCCAGGTGAACAACCCCAAGGAGTGGCTGCA
GGTGGATTTCCAGAAGACCATGAAGGTGACCGGCGTGACCACGCAGGGCGTGAAGAGCCTGCTGACCAGCATGTACGTGAAGG
AGTTCCTGATCAGCTCTAGCCAGGACGGCCACCAGTGGACCCTGTTCTTCCAGAACGGCAAGGTGAAGGTGTTCCAGGGCAAC
CAGGATAGCTTCACCCCCGTGGTGAACAGCCTGGACCCCCCCTGCTGACCAGGTATCTGAGGATCCACCCCAGAGCTGGGT
GCACCAGATCGCCCTGAGGATGGAGGTGCTGGGCTGCGAGGCCCAGGATCTGTATTGA
```

FIG. 1C: coFVIII-5 – SEQ ID NO: 70

```
ATGCAAATCGAACTGAGCACCTGTTTCTTCCTCTGCCTGCTGAGATTCTGTTTCTCCGCGACCCGCCGATACTACCTGGGAGCAGTGG
AGCTCTCCTGGGATTACATGCAGAGCGACCTTGGGGAGCTGCCCGTGGATGCCAGGTTCCCTCCCCGGGTGCCAAAGTCGTTTCCGTT
CAACACCTCCGTGGTGTACAAGAAAACTCTGTTCGTGGAGTTCACCGACCACCTGTTCAATATCGCCAAGCCCAGACCTCCCTGGATG
GGGCTGTTGGGACCTACCATCCAAGCGGAGGTGTACGACACTGTGGTCATCACTCTGAAGAACATGGCCTCGCATCCCGTGTCCCTGC
ACGCCGTGGGAGTGTCTTACTGGAAAGCGTCCGAGGGGCCGAATACGACGACCAGACCTCGCAGAGAGAAAAGGAAGATGACAAGGT
GTTCCCAGGAGGATCGCACACCTACGTGTGGCAAGTGTTGAAGGAGAACGGCCCAATGGCCTCCGACCCGCTGTGCCTGACCTACTCG
TACCTGTCCCACGTGGACCTCGTGAAGGACCTCAACTCGGGACTGATTGGAGCCCTGCTGGTCTGCAGGGAAGGCTCACTGGCGAAAG
AAAAGACTCAGACCTTGCACAAGTTCATTCTGCTGTTCGCTGTGTTCGACGAGGGGAAGTCGTGGCACAGCGAGACTAAGAACTCCCT
GATGCAAGATAGAGATGCCGCCTCCGCCCGGGCCTGGCCTAAGATGCACACCGTGAACGGTTACGTGAACCGCTCCCTCCCTGGCCTG
ATTGGATGCCACCGGAAGTCCGTGTACTGGACGTGATCGGGATGGGGACCACCCCCGAGGTGCACAGCATCTTCCTGGAAGGTCACA
CATTTCTCGTGCGCAACCACCGGCAGGCCTCCCTGGAAATCAGCCCCATTACCTTCCTCACTGCCCAGACTCTGCTGATGGACCTGGG
ACAGTTCCTGCTGTTCTGCCATATCTCCTCCCACCAACATGACGGAATGGAGGCATACGTGAAGGTCGATTCCTGCCCTGAGGAACCC
CAGCTCCGCATGAAGAACAATGAGGAAGCCGAGGACTACGACGACGACCTGACGGATAGCGAGATGGATGTGGTCCGGTTCGATGACG
ATAACAGCCCTTCCTTCATCCAAATTCGCTCGGTGGCAAAGAAGCACCCCAAGACCTGGGTGCATTACATTGCGGCGGAAGAAGAGGA
CTGGGATTATGCCCCGCTTGTCCTCGCTCCTGACGACCGGAGCTACAAGAGCCAGTACCTGAACAACGGTCCACAGAGGATCGGTAGA
AAGTACAAGAAGGTCCGCTTCATGGCCTATACCGACGAAACCTTCAAAACTAGAGAGGCCATCCAACACGAATCCGGCATCCTGGGCC
CGCTCTTGTACGGAGAAGTCGGCGACACCCTTCTCATTATCTTCAAGAACCAGGCTTCCCGGCCGTACAACATCTATCCGCATGGGAT
CACTGACGTGCGCCCACTGTACTCGCGGCGCCTGCCCAAGGGTGTCAAACACCTGAAGGATTTTCCGATCCTTCCGGGAGAAATCTTC
AAGTACAAGTGGACCGTGACCGTGGAAGATGGCCCAACTAAGTCTGACCCTAGATGCCTCACCCGCTACTACTCATCCTTCGTCAACA
TGGAGCGCGACCTGGCCAGCGGACTGATCGGCCCGCTGCTGATTTGCTACAAGGAATCAGTGGACCAACGGGGAAACCAGATCATGTC
GGATAAGAGGAACGTCATCCTCTTCTCCGTGTTTGACGAAAACCGGTCGTGGTACCTGACTGAAAACATCCAGCGGTTCCTCCCCAAC
CCCGCGGGCGTGCAGCTGGAAGATCCTGAGTTTCAGGCATCAAACATCATGCACTCCATTAACGGCTACGTGTTCGATTCGCTGCAGC
TGAGCGTGTGTCTGCACGAAGTGGCCTACTGGTACATCCTGTCCATTGGTGCCCAGACTGACTTCCTGTCCGTGTTTTTCTCCGGCTA
CACGTTCAAGCACAAGATGGTGTACGAGGACACCCTGACCCTCTTCCCTTTTTCCGGCGAAACTGTGTTTATGAGCATGGAGAATCCC
GGCCTGTGGATCTTGGGCTGCCACAACAGCGACTTCCGTAACAGAGGAATGACTGCGCTGCTCAAGGTGTCCAGCTGCGACAAGAACA
CCGGAGACTATTATGAGGACTCATACGAGGACATCTCCGCCTACCTCCTGTCCAAGAATAACGCCATTGAACCTCGGAGCTTCAGCCA
GAACCCACCCGTGCTTAAGAGACATCAACGGGAGATCACTAGGACCACCCTGCAGTCAGACCAGGAGGAAATCGACTACGATGACACC
ATCTCGGTCGAGATGAAGAAGGAGGACTTTGACATCTACGACGAAGATGAAAACCAGAGCCCGAGGTCGTTCCAAAAGAAAACCCGCC
ACTACTTTATTGCTGCTGTCGAGCGGCTGTGGGACTACGGAATGTCGTCCTCGCCGCACGTGCTCCGCAACCGAGCCCAGAGCGGCTC
GGTGCCGCAATTCAAGAAGGTCGTGTTCCAGGAGTTCACTGACGGGAGCTTCACTCAGCCTTTGTACCGGGGAGAACTCAATGAACAT
CTCGGCCTCCTCGGACCTTACATCAGAGCAGAAGTGGAAGATAACATCATGGTCACTTTCCGTAACCAAGCCAGCCGCCCGTACTCGT
TCTACTCCTCCCTCATTTCTTACGAAGAGGACCAGCGGCAGGGCGCAGAACGCGCAAGAACTTCGTGAAGCCCAACGAAACCAAGAC
CTACTTCTGGAAAGTGCAGCATCATATGGCCCCGACTAAGGACGAGTTTGACTGCAAAGCCTGGGCCTACTTCTCCGATGTGGACTTG
GAGAAGGACGTCCACTCCGGCCTCATCGGTCCCCTGCTCGTGTGCCATACCAATACCCTGAACCCCGCACACGGTCGCCAGGTCACCG
TGCAGGAGTTCGCTCTGTTCTTCACTATCTTCGACGAAACTAAGTCCTGGTACTTCACCGAGAACATGGAGAGGAACTGCAGAGCCCC
CTGTAACATCCAGATGGAGGACCCGACGTTCAAGGAAAACTACCGGTTCCACGCCATTAACGGATACATCATGGATACGCTGCCGGGT
CTTGTGATGGCCCAGGATCAACGGATCAGATGGTACTTATTGTCGATGGGCAGCAACGAGAACATCCACTCTATTCACTTCTCCGGTC
ATGTGTTCACTGTGCGGAAGAAGGAAGAGTACAAGATGGCCCTGTACAACCTTATCCCGGAGTGTTCGAAACTGTGGAAATGCTGCC
GTCGAAGGCCGGCATTTGGCGCGTGGAGTGTTTGATTGGAGAACATCTCCATGCGGGATGTCAACCCTGTTCCTGGTGTATAGCAAC
AAGTGCCAGACTCCGCTTGGGATGCGTCAGGACACATTAGGGATTTCCAGATCACTGCGTCCGGCCAGTACGGCCAATGGGCCCCTA
AGCTGGCCCGCCTGCATTACTCCGGATCCATTAACGCCTGGTCAACCAAGGAGCCATTCTCCTGGATCAAGGTGGACCTTCTGGCCCC
CATGATTATCCACGGAATTAAGACCCAGGGGGCCCGGCAGAAGTTCTCCTCACTGTACATCAGCCAGTTCATAATCATGTACTCCCTG
GACGGAAAGAAGTGGCAAACCTACAGGGGGAACAGCACCGGCACACTGATGGTCTTTTTCGGAAATGTGGACTCCTCCGGGATTAAGC
ATAACATCTTCAACCCTCCGATTATCGCTCGGTACATTAGACTTCACCCTACCCACTACAGCATTCGCTCCACCCTGCGGATGGAACT
GATGGGCTGCGATCTGAACTCGTGCAGCATGCCGTTGGGAATGGAGTCCAAAGCAATTTCCGACGCGCAGATCACCGCCTCGTCCTAC
TTTACCAACATGTTCGCCACGTGGTCACCGTCCAAGGCCCGGCTGCACCTCCAGGGAAGATCCAACGCATGGCGGCCACAGGTCAACA
ACCCTAAGGAGTGGCTCCAGGTGGACTTCCAGAAAACCATGAAGGTCACCGGAGTCACAACCCAGGGAGTGAAGTCGCTGCTGACTTC
TATGTACGTCAAGGAGTTCCTGATCTCCAGCAGCCAGGACGGGCACCAGTGGACCCTGTTCTTCCAAAATGGAAAGGTCAAGGTGTTT
CAGGGCAATCAGGATTCATTCACCCCGGTGGTGAACTCCCTTGATCCACCCCTCCTGACCCGCTACCTTCGCATCCACCCACAGTCCT
GGGTGCACCAGATCGCGCTGAGGATGGAGGTCCTGGGATGCGAAGCCCAGGACCTGTACTGA
```

FIG. 1D : coFVIII-6 – SEQ ID NO: 71

```
ATGCAGATTGAGCTGTCCACTTGTTTCTTCCTGTGCCTCCTGCGCTTCTGTTTCTCCGCCACTCGCCGGTACTACCTTGGAGCCGTGG
AGCTTTCATGGGACTACATGCAGAGCGACCTGGGCGAACTCCCCGTGGATGCCAGATTCCCCCCCGCGTGCCAAAGTCCTTCCCCTT
TAACACCTCCGTGGTGTACAAGAAAACCCTCTTTGTCGAGTTCACTGACCACCTGTTCAACATCGCCAAGCGCGCCCACCTTGGATG
GGCCTCCTGGGACCGACCATTCAAGCTGAAGTGTACGACACCGTGGTGATCACCCTGAAGAACATGGCGTCCCACCCCGTGTCCCTGC
ATGCGGTCGGAGTGTCCTACTGGAAGGCCTCCGAAGGAGCTGAGTACGACGACCAGACTAGCCAGCGGGAAAAGGAGGACGATAAAGT
GTTCCCGGGCGGCTCGCATACTTACGTGTGGCAAGTCCTGAAGGAAAACGGACCTATGGCATCCGATCCTCTGTGCCTGACTTACTCC
TACCTTTCCCATGTGGACCTCGTGAAGGACCTGAACAGCGGGCTGATTGGTGCACTTCTCGTGTGCCGCGAAGGTTCGCTCGCTAAGG
AAAAGACCCAGACCCTCCATAAGTTCATCCTTTTGTTCGCTGTGTTCGATGAAGGAAAGTCATGGCATTCCGAAACTAAGAACTCGCT
GATGCAGGACCGGGATGCCGCCTCAGCCCGCGCCTGGCCTAAAATGCATACAGTCAACGGATACGTGAATCGGTCACTGCCCGGGCTC
ATCGGTTGTCACAGAAAGTCCGTGTACTGGCACGTCATCGGCATGGGCACTACGCCTGAAGTGCACTCCATCTTCCTGGAAGGGCACA
CCTTCCTCGTGCGCAACCACCGCCAGGCCTCTCTGGAAATCTCCCCGATTACCTTTCTGACCGCCCAGACTCTGCTCATGGACCTGGG
GCAGTTCCTTCTCTTCTGCCACATCTCCAGCCATCAGCACGACGGAATGGAGGCCTACGTGAAGGTGGACTCATGCCCGGAAGAACCT
CAGTTGCGGATGAAGAACAACGAGGAGGCCGAGGACTATGACGACGATTTGACTGACTCCGAGATGGACGTCGTGCGGTTCGATGACG
ACAACAGCCCCAGCTTCATCCAGATTCGCAGCGTGGCCAAGAAGCACCCCAAAACCTGGGTGCACTACATCGCGGCCGAGGAAGAAGA
TTGGGACTACGCCCCGTTGGTGCTGGCACCCGATGACCGGTCGTACAAGTCCCAGTATCTGAACAATGGTCCGCAGCGGATTGGCAGA
AAGTACAAGAAAGTGCGGTTCATGGCGTACACTGACGAAACGTTTAAGACCCGGGAGGCCATTCAACATGAGAGCGGCATTCTGGGAC
CACTGCTGTACGGAGAGGTCGGCGATACCCTGCTCATCATCTTCAAAAACCAGGCCTCCCGGCCTTACAACATCTACCCTCACGGAAT
CACCGACGTGCGGCCACTCTACTCGCGGCGCCTGCCGAAGGGCGTCAAGCACCTGAAAGACTTCCCTATCCTGCCGGGCGAAATCTTC
AAGTATAAGTGGACCGTCACCGTGGAGGACGGGCCCACCAAGAGCGATCCTAGGTGTCTGACTCGGTACTACTCCAGCTTCGTGAACA
TGGAACGGGACCTGGCATCGGGACTCATTGGACCGCTGCTGATCTGCTACAAAGAGTCGGTGGATCAACGCGGCAACCAGATCATGTC
CGACAAGCGCAACGTGATCCTGTTCTCCGTGTTTGATGAAAACAGATCCTGGTACCTCACTGAAAACATCCAGAGGTTCCTCCCAAAC
CCCGCAGGAGTGCAACTGGAGGACCCTGAGTTTCAGGCCTCGAATATCATGCACTCGATTAACGGTTACGTGTTCGACTCGCTGCAGC
TGAGCGTGTGCCTCCATGAAGTCGCTTACTGGTACATTCTGTCCATCGGCGCCCAGACTGACTTCCTGAGCGTGTTCTTTTCCGGTTA
CACCTTTAAGCACAAGATGGTGTACGAAGATACCCTGACCCTGTTCCCTTTCTCCGGCGAAACGGTGTTCATGTCGATGGAGAACCCG
GGTCTGTGGATTCTGGGATGCCACAACAGCGACTTTCGGAACCGCGGAATGACTGCCCTGCTGAAGGTGTCCTCATGCGACAAGAACA
CCGGAGACTACTACGAGGACTCCTACGAGGATATCTCAGCCTACCTCCTGTCCAAGAACAACGCGATCGAGCCGCGCAGCTTCAGCCA
GAACCCGCCTGTGCTGAAGAGGCACCAGCGAGAAATTACCCGGACCACCCTCCAATCGGATCAGGAGGAAATCGACTACGACGACACC
ATCTCGGTGGAAATGAAGAAGGAAGATTTCGATATCTACGACGAGGACGAAAATCAGTCCCCTCGCTCATTCCAAAAGAAAACTAGAC
ACTACTTTATCGCCGCGGTGGAAAGACTGTGGGACTATGGAATGTCATCCAGCCCTCACGTCCTTCGGAACCGGGCCCAGAGCGGATC
GGTGCCTCAGTTCAAGAAAGTGGTGTTCCAGGAGTTCACCGACGGCAGCTTCACCCAGCCGCTGTACCGGGGAGAACTGAACGAACAC
CTGGGCCTGCTCGGTCCCTACATCCGCGCGGAAGTGGAGGATAACATCATGGTGACCTTCCGTAACCAAGCATCCAGACCTTACTCCT
TCTATTCCTCCCTGATCTCATACGAGGAGGACCAGCGCCAAGGCGCCGAGCCCCGCAAGAACTTCGTCAAGCCCAACGAGACTAAGAC
CTACTTCTGGAAGGTCCAACACCATATGGCCCCGACCAAGGATGAGTTTGACTGCAAGGCCTGGGCCTACTTCTCCGACGTGGACCTT
GAGAAGGATGTCCATTCCGGCCTGATCGGGCCGCTGCTCGTGTGTCACACCAACACCCTGAACCCAGCGCATGGACGCCAGGTCACCG
TCCAGGAGTTTGCTCTGTTCTTCACCATTTTTGACGAAACTAAGTCCTGGTACTTCACCGAGAATATGGAGCGAAACTGTAGAGCGCC
CTGCAATATCCAGATGGAAGATCCGACTTTCAAGGAGAACTATAGATTCCACGCCATCAACGGGTACATCATGGATACTCTGCCGGGG
CTGGTCATGGCCCAGGATCAGAGGATTCGGTGGTACTTGCTGTCAATGGGATCGAACGAAAACATTCACTCCATTCACTTCTCCGGTC
ACGTGTTCACTGTGCGCAAGAAGGAGGAGTACAAGATGGCGCTGTACAATCTGTACCCCGGGGTGTTCGAAACTGTGGAGATGCTGCC
GTCCAAGGCCGGCATCTGGAGAGTGGAGTGCCTGATCGGAGAGCACCTCCACGCGGGGATGTCCACCCTCTTCCTGGTGTACTCGAAT
AAGTGCCAGACCCCGCTGGGCATGGCCTCGGGCCACATCAGAGACTTCCAGATCACAGCAAGCGGACAATACGGCCAATGGGCGCCGA
AGCTGGCCGCCTTGCACTACTCCGGATCGATCAACGCATGGTCCACCAAGGAACCGTTCTCGTGGATTAAGGTGGACCTCCTGGCCCC
TATGATTATCCACGGAATTAAGACCCAGGGCGCCAGGCAGAAGTTCTCCTCCCTGTACATCTCGCAATTCATCATCATGTACAGCCTG
GACGGGAAGAAGTGGCAGACTTACAGGGGAAACTCCACCGGCACCCTGATGGTCTTTTTCGGCAACGTGGATTCCTCCGGCATTAAGC
ACAACATCTTCAACCCCACCGATCATAGCCAGATATATTAGGCTCCACCCCACTCACTACTCAATCCGCTCAACTCTTCGGATGGAACT
CATGGGTGCGACCTGAACTCCTGCTCCATGCCGTTGGGGATGGAATCAAAGGCTATTAGCGACGCCCAGATCACCGCGAGCTCCTAC
TTCACTAACATGTTCGCCACCTGGAGCCCCTCCAAGGCCAGGCTGCACTTGCAGGGACGGTCAAATGCCTGGCGGCCGCAAGTGAACA
ATCCGAAGGAATGGCTTCAAGTGGATTTCCAAAAGACCATGAAAGTGACCGGAGTCACCACCCAGGGAGTGAAGTCCCTTCTGACCTC
GATGTATGTGAAGGAGTTCCTGATTAGCAGCAGCCAGGACGGGCACCAGTGGACCCTGTTCTTCCAAAACGGAAAGGTCAAGGTGTTC
CAGGGGAACCAGGACTCGTTCACACCCGTGGTGAACTCCCTGGACCCCCCACTGCTGACGCGGTACTTGAGGATTCATCCTCAGTCCT
GGGTCCATCAGATTGCATTGCGAATGGAAGTCCTGGGCTGCGAGGCCCAGGACCTGTACTGA
```

FIG. 1E: coFVIII-52 – SEQ ID NO: 3

```
ATGCAAATCGAACTGAGCACCTGTTTCTTCCTCTGCCTGCTGAGATTCTGTTTCTCCGCGACCCGCCGATACTACCTGGGAGC
AGTGGAGCTCTCCTGGGATTACATGCAGAGCGACCTTGGGGAGCTGCCCGTGGATGCCAGGTTCCCTCCCCGGGTGCCAAAGT
CGTTTCCGTTCAACACCTCCGTGGTGTACAAGAAAACTCTGTTCGTGGAGTTCACCGACCACCTGTTCAATATCGCCAAGCCC
AGACCTCCCTGGATGGGGCTGTTGGGACCTACCATCCAAGCGGAGGTGTACGACACTGTGGTCATCACTCTGAAGAACATGGC
CTCGCATCCCGTGTCCCTGCACGCCGTGGGAGTGTCTTACTGGAAAGCGTCCGAGGGGCCGAATACGACGACCAGACCTCGC
AGAGAGAAAGGAAGATGACAAGGTGTTCCCAGGAGGATCGCACACCTACGTGTGGCAAGTGTTGAAGGAGAACGGCCCAATG
GCCTCCGACCCGCTGTGCCTGACCTACTCGTACCTGTCCCACGTGGACCTCGTGAAGGACCTCAACTCGGGACTGATTGGAGC
CCTGCTGGTCTGCAGGGAAGGCTCACTGGCGAAAGAAAAGACTCAGACCTTGCACAAGTTCATTCTGCTGTTCGCTGTGTTCG
ACGAGGGGAAGTCGTGGCACAGCGAGACTAAGAACTCCCTGATGCAAGATAGAGATGCCGCCTCCGCCCGGGCCTGGCCTAAG
ATGCACACCGTGAACGGTTACGTGAACCGCTCCCTCCCTGGCCTGATTGGATGCCACCGGAAGTCCGTGTACTGGCACGTGAT
CGGGATGGGGACCACCCCCGAGGTGCACAGCATCTTCCTGGAAGGTCACACATTTCTCGTGCGCAACCACCGGCAGGCCTCCC
TGGAAATCAGCCCCATTACCTTCCTCACTGCCCAGACTCTGCTGATGGACCTGGGACAGTTCCTGCTGTTCTGCCATATCTCC
TCCCACCAACATGACGGAATGGAGGCATACGTGAAGGTCGATTCCTGCCCTGAGGAACCCAGCTCCGCATGAAGAACAATGA
GGAAGCCGAGGACTACGACGACGACCTGACGGATAGCGAGATGGATGTGGTCCGGTTCGATGACGATAACAGCCCTTCCTTCA
TCCAAATTCGCTCGGTGGCAAAGAAGCACCCCAAGACCTGGGTGCATTACATTGCGGCGGAAGAAGAGGACTGGGATTATGCC
CCGCTTGTCCTCGCTCCTGACGACCGGAGCTACAAGAGCCAGTACCTGAACAACGGTCCACAGAGGATCGGTAGAAAGTACAA
GAAGGTCCGCTTCATGGCCTATACCGACGAAACCTTCAAAACTAGAGAGGCCATCCAACACGAATCCGGCATCCTGGGCCCGC
TCTTGTACGGAGAAGTCGGCGACACCCTTCTCATTATCTTCAAGAACCAGGCTTCCCGGCCGTACAACATCTATCCGCATGGG
ATCACTGACGTGCGCCCACTGTACTCGCGGCGCCTGCCCAAGGGTGTCAAACACCTGAAGGATTTTCCGATCCTTCCGGGAGA
AATCTTCAAGTACAAGTGGACCGTGACCGTGGAAGATGGCCCAACTAAGTCTGACCCTAGATGCCTCACCCGCTACTACTCAT
CCTTCGTCAACATGGAGCGCGACCTGGCCAGCGGACTGATCGGCCCGCTGCTGATTTGCTACAAGGAATCAGTGGACCAACGG
GGAAACCAGATCATGTCGGATAAGAGGAACGTCATCCTCTTCTCCGTGTTTGACGAAAACCGGTCGTGGTACCTGACCGAGAA
CATCCAGAGGTTCCTGCCCAACCCTGCTGGGGTGCAGCTGGAGGACCCCGAGTTCCAGGCCAGCAACATCATGCACAGCATCA
ATGGCTACGTGTTCGACAGCCTGCAGCTGAGCGTGTGCCTGCACGAGGTGGCCTACTGGTACATCCTGAGCATCGGCGCCCAG
ACCGACTTCCTGAGCGTGTTCTTCTCTGGCTACACCTTCAAGCACAAGATGGTGTATGAGGACACCCTGACCCTGTTCCCCTT
CAGCGGGGAGACTGTCTTCATGAGCATGGAGAACCCTGGCCTGTGGATCCTGGGCTGCCACAACAGCGACTTCAGGAACAGGG
GCATGACTGCCCTGCTGAAAGTCTCCAGCTGTGACAAGAACACCGGGGACTACTACGAGGACAGCTACGAGGACATCAGCGCC
TACCTGCTGAGCAAGAACAATGCCATCGAGCCCAGGAGCTTCTCTCAGAACCCCCCAGTGCTGAAGAGGCACCAGAGGGAGAT
CACCAGGACCACCCTGCAGTCTGACCAGGAGGAGATCGACTATGATGACACCATCAGCGTGGAGATGAAGAAGGAGGACTTCG
ACATCTACGACGAGGACGAGAACCAGAGCCCCAGGAGCTTCCAGAAGAAGACCAGGCACTACTTCATTGCTGCTGTGGAGAGG
CTGTGGGACTATGGCATGTCCAGCAGCCCCATGTGCTGAGGAACAGGGCCCAGTCTGGCAGCGTGCCCCAGTTCAAGAAAGT
CGTGTTCCAGGAGTTCACCGACGGCAGCTTCACCCAGCCCCTGTACAGAGGGGAGCTGAACGAGCACCTGGGCCTGCTGGGCC
CCTACATCAGGGCCGAGGTGGAGGACAACATCATGGTGACCTTCAGGAACCAGGCCAGCAGGCCCTACAGCTTCTACAGCAGC
CTGATCAGCTACGAGGAGGACCAGAGGCAGGGGCTGAGCCCAGGAAGAACTTTGTGAAGCCCAATGAAACCAAGACCTACTT
CTGGAAGGTGCAGCACCACATGGCCCCCACCAAGGACGAGTTCGACTGCAAGGCCTGGGCCTACTTCTCTGACGTGGACCTGG
AGAAGGACGTGCACTCTGGCCTGATTGGCCCCCTGCTGGTGTGCCACACCAACACCCTGAACCCTGCCCATGGCAGGCAGGTG
ACTGTGCAGGAGTTCGCCCTGTTCTTCACCATCTTCGATGAAACCAAGAGCTGGTACTTCACTGAGAACATGGAGAGGAACTG
CAGGGCCCCCTGCAACATCCAGATGGAGGACCCCACCTTCAAGGAGAACTACAGGTTCCATGCCATCAATGGCTACATCATGG
ACACCCTGCCTGGCCTGGTCATGGCCCAGGACCAGAGGATCAGGTGGTATCTGCTGAGCATGGGCAGCAACGAGAACATCCAC
AGCATCCACTTCTCTGGCCACGTGTTCACTGTGAGGAAGAAGGAGGAGTACAAGATGGCCCTGTACAACCTGTACCCTGGGGT
GTTCGAAACCGTGGAGATGCTGCCCAGCAAGGCCGGCATCTGGAGGGTGGAGTGCCTGATTGGGGAGCACCTGCACGCCGGCA
TGAGCACCCTGTTCCTGGTGTACAGCAACAAGTGCCAGACCCCCCTGGGCATGGCCTCTGGCCACATCAGGGACTTCCAGATC
ACTGCCTCTGGCCAGTACGGCCAGTGGGCCCCCAAGCTGGCCAGGCTGCACTACTCCGGAAGCATCAATGCCTGGAGCACCAA
GGAGCCCTTCAGCTGGATCAAAGTGGACCTGCTGGCCCCCATGATCATCCACGGCATCAAGACCCAGGGGCCAGGCAGAAGT
TCTCCAGCCTGTACATCAGCCAGTTCATCATCATGTACAGCCTGGACGGCAAGAAGTGGCAGACCTACAGGGGCAACAGCACC
GGCACCCTGATGGTGTTCTTCGGCAACGTGGACAGCAGCGGCATCAAGCACAACATCTTCAACCCCCCCATCATCGCCAGATA
CATCAGGCTGCACCCCACCCACTACAGCATCAGGAGCACCCTGAGGATGGAGCTGATGGGCTGTGACCTGAACAGCTGCAGCA
TGCCCCTGGGCATGGAGAGCAAGGCCATCTCTGACGCCCAGATCACTGCCTCCAGCTACTTCACCAACATGTTTGCCACCTGG
AGCCCCAGCAAGGCCAGGCTGCACCTGCAGGGCAGGAGCAATGCCTGGAGGCCCCAGGTCAACAACCCCAAGGAGTGGCTGCA
GGTGGACTTCCAGAAGACCATGAAGGTGACTGGGGTGACCACCCAGGGGGTGAAGAGCCTGCTGACCAGCATGTACGTGAAGG
AGTTCCTGATCTCCAGCAGCCAGGACGGCCACCAGTGGACCCTGTTCTTCCAGAATGGCAAGGTGAAGGTGTTCCAGGGCAAC
CAGGACAGCTTCACCCCTGTGGTCAACAGCCTGGACCCCCCCTGCTGACCAGATACCTGAGGATCCACCCCCAGAGCTGGGT
GCACCAGATCGCCCTGAGGATGGAGGTGCTGGGCTGTGAGGCCCAGGACCTGTACTGA
```

Solid underline = coFVIII-52-NT58 (SEQ ID NO: 7)
Dashed underline = coFVIII-52-CT (SEQ ID NO: 8)

FIG. 1F: coFVIII-62 – SEQ ID NO: 4

ATGCAGATTGAGCTGTCCACTTGTTTCTTCCTGTGCCTCCTGCGCTTCTGTTTCTCCG<u>CCACTCGCCGGTACTACCTTGGAGC
CGTGGAGCTTTCATGGGACTACATGCAGAGCGACCTGGGCGAACTCCCCGTGGATGCCAGATTCCCCCCCGCGTGCCAAAGT
CCTTCCCCTTTAACACCTCCGTGGTGTACAAGAAAACCCTCTTTGTCGAGTTCACTGACCACCTGTTCAACATCGCCAAGCCG
CGCCCACCTTGGATGGGCCTCCTGGGACCGACCATTCAAGCTGAAGTGTACGACACCGTGGTGATCACCCTGAAGAACATGGC
GTCCCACCCCGTGTCCCTGCATGCGGTCGGAGTGTCCTACTGGAAGGCCTCCGAAGGAGCTGAGTACGACGACCAGACTAGCC
AGCGGGAAAAGGAGGACGATAAAGTGTTCCCGGGCGGCTCGCATACTTACGTGTGGCAAGTCCTGAAGGAAAACGGACCTATG
GCATCCGATCCTCTGTGCCTGACTTACTCCTACCTTTCCCATGTGGACCTCGTGAAGGACCTGAACAGCGGGCTGATTGGTGC
ACTTCTCGTGTGCCGCGAAGGTTCGCTCGCTAAGGAAAAGACCCAGACCCTCCATAAGTTCATCCTTTTGTTCGCTGTGTTCG
ATGAAGGAAAGTCATGGCATTCCGAAACTAAGAACTCGCTGATGCAGGACGGGATGCCGCCTCAGCCCGCGCCTGGCCTAAA
ATGCATACAGTCAACGGATACGTGAATCGGTCACTGCCCGGGCTCATCGGTTGTCACAGAAAGTCCGTGTACTGGCACGTCAT
CGGCATGGGCACTACGCCTGAAGTGCACTCCATCTTCCTGGAAGGGCACACCTTCCTCGTGCGCAACCACCGCCAGGCCTCTC
TGGAAATCTCCCCGATTACCTTTCTGACCGCCCAGACTCTGCTCATGGACCTGGGGCAGTTCCTTCTCTTCTGCCACATCTCC
AGCCATCAGCACGACGGAATGGAGGCCTACGTGAAGGTGGACTCATGCCCGGAAGAACCTCAGTTGCGGATGAAGAACAACGA
GGAGGCCGAGGACTATGACGACGATTTGACTGACTCCGAGATGGACGTCGTGCGGTTCGATGACGACAACAGCCCCAGCTTCA
TCCAGATTCGCAGCGTGGCCAAGAAGCACCCCAAAACCTGGGTGCACTACATCGCGGCCGAGGAAGAAGATTGGGACTACGCC
CCGTTGGTGCTGGCACCCGATGACCGGTCGTACAAGTCCCAGTATCTGAACAATGGTCCGCAGCGGATTGGCAGAAAGTACAA
GAAAGTGCGGTTCATGGCGTACACTGACGAAACGTTTAAGACCCGGGAGGCCATTCAACATGAGAGCGGCATTCTGGGACCAC
TGCTGTACGGAGAGGTCGGCGATACCCTGCTCATCATCTTCAAAAACCAGGCCTCCCGGCCTTACAACATCTACCCTCACGGA
ATCACCGACGTGCGGCCACTCTACTCGCGGCGCCTGCCGAAGGGCGTCAAGCACCTGAAAGACTTCCCTATCCTGCCGGGCGA
AATCTTCAAGTATAAGTGGACCGTCACCGTGGAGGACGGGCCCACCAAGAGCGATCCTAGGTGTCTGACTCGGTACTACTCCA
GCTTCGTGAACATGGAACGGGACCTGGCATCGGGACTCATTGGACCGCTGCTGATCTGCTACAAGAGTCGGTGGATCAACGC
GGCAACCAGATCATGTCCGACAAGCGCAACGTGATCCTGTTCTCCGTG</u>**TTTGATGAAAACAGATCCTGGTACCTGACCGAGAA
CATCCAGAGGTTCCTGCCCAACCCTGCTGGGGTGCAGCTGGAGGACCCCGAGTTCCAGGCCAGCAACATCATGCACAGCATCA
ATGGCTACGTGTTCGACAGCCTGCAGCTGAGCGTGTGCCTGCACGAGGTGGCCTACTGGTACATCCTGAGCATCGGCGCCCAG
ACCGACTTCCTGAGCGTGTTCTTCTCTGGCTACACCTTCAAGCACAAGATGGTGTATGAGGACACCCTGACCCTGTTCCCCTT
CAGCGGGGAGACTGTCTTCATGAGCATGGAGAACCCTGGCCTGTGGATCCTGGGCTGCCACAACAGCGACTTCAGGAACAGGG
GCATGACTGCCCTGCTGAAAGTCTCCAGCTGTGACAAGAACACCGGGGACTACTACGAGGACAGCTACGAGGACATCAGCGCC
TACCTGCTGAGCAAGAACAATGCCATCGAGCCCAGGAGCTTCTCTCAGAACCCCCCAGTGCTGAAGAGGCACCAGAGGGAGAT
CACCAGGACCACCCTGCAGTCTGACCAGGAGGAGATCGACTATGATGACACCATCAGCGTGGAGATGAAGAAGGAGGACTTCG
ACATCTACGACGAGGACGAGAACCAGAGCCCCAGGAGCTTCCAGAAGAAGACCAGGCACTACTTCATTGCTGCTGTGGAGAGG
CTGTGGGACTATGGCATGTCCAGCAGCCCCCATGTGCTGAGGAACAGGGCCCAGTCTGGCAGCGTGCCCCAGTTCAAGAAAGT
CGTGTTCCAGGAGTTCACCGACGGCAGCTTCACCCAGCCCCTGTACAGAGGGGAGCTGAACGAGCACCTGGGCCTGCTGGGCC
CCTACATCAGGGCCGAGGTGGAGGACAACATCATGGTGACCTTCAGGAACCAGGCCAGCAGGCCCTACAGCTTCTACAGCAGC
CTGATCAGCTACGAGGAGGACCAGAGGCAGGGGCTGAGCCCAGGAAGAACTTTGTGAAGCCCAATGAAACCAAGACCTACTT
CTGGAAGGTGCAGCACCACATGGCCCCCACCAAGGACGAGTTCGACTGCAAGGCCTGGGCCTACTTCTCTGACGTGGACCTGG
AGAAGGACGTGCACTCTGGCCTGATTGGCCCCCTGCTGGTGTGCCACACCAACACCCTGAACCCTGCCCATGGCAGGCAGGTG
ACTGTGCAGGAGTTCGCCCTGTTCTTCACCATCTTCGATGAAACCAAGAGCTGGTACTTCACTGAGAACATGGAGAGGAACTG
CAGGGCCCCCTGCAACATCCAGATGGAGGACCCCACCTTCAAGGAGAACTACAGGTTCCATGCCATCAATGGCTACATCATGG
ACACCCTGCCTGGCCTGGTCATGGCCCAGGACCAGAGGATCAGGTGGTATCTGCTGAGCATGGGCAGCAACGAGAACATCCAC
AGCATCCACTTCTCTGGCCACGTGTTCACTGTGAGGAAGAAGGAGGAGTACAAGATGGCCCTGTACAACCTGTACCCTGGGGT
GTTCGAAACCGTGGAGATGCTGCCCAGCAAGGCCGGCATCTGGAGGGTGGAGTGCCTGATTGGGGAGCACCTGCACGCCGGCA
TGAGCACCCTGTTCCTGGTGTACAGCAACAAGTGCCAGACCCCCCTGGGCATGGCCTCTGGCCACATCAGGGACTTCCAGATC
ACTGCCTCTGGCCAGTACGGCCAGTGGGCCCCCAAGCTGGCCAGGCTGCACTACTCCGGAAGCATCAATGCCTGGAGCACCAA
GGAGCCCTTCAGCTGGATCAAAGTGGACCTGCTGGCCCCCATGATCATCCACGGCATCAAGACCCAGGGGCCAGGCAGAAGT
TCTCCAGCCTGTACATCAGCCAGTTCATCATCATGTACAGCCTGGACGGCAAGAAGTGGCAGACCTACAGGGGCAACAGCACC
GGCACCCTGATGGTGTTCTTCGGCAACGTGGACAGCAGCGGCATCAAGCACAACATCTTCAACCCCCCCATCATCGCCAGATA
CATCAGGCTGCACCCCACCCACTACAGCATCAGGAGCACCCTGAGGATGGAGCTGATGGGCTGTGACCTGAACAGCTGCAGCA
TGCCCCTGGGCATGGAGAGCAAGGCCATCTCTGACGCCCAGATCACTGCCTCCAGCTACTTCACCAACATGTTTGCCACCTGG
AGCCCCAGCAAGGCCAGGCTGCACCTGCAGGGCAGGAGCAATGCCTGGAGGCCCCAGGTCAACAACCCCAAGGAGTGGCTGCA
GGTGGACTTCCAGAAGACCATGAAGGTGACTGGGGTGACCACCCAGGGGGTGAAGAGCCTGCTGACCAGCATGTACGTGAAGG
AGTTCCTGATCTCCAGCAGCCAGGACGGCCACCAGTGGACCCTGTTCTTCCAGAATGGCAAGGTGAAGGTGTTCCAGGGCAAC
CAGGACAGCTTCACCCCTGTGGTCAACAGCCTGGACCCCCCCCTGCTGACCAGATACCTGAGGATCCACCCCCAGAGCTGGGT
GCACCAGATCGCCCTGAGGATGGAGGTGCTGGGCTGTGAGGCCCAGGACCTGTACTGA**

Solid underline = coFVIII-62-NT58 (SEQ ID NO: 9)
Dashed underline = coFVIII-62-CT (SEQ ID NO: 10)

FIG. 1G: coFVIII-25 – SEQ ID NO: 5

```
ATGCAGATTGAGCTGAGCACCTGCTTCTTCCTGTGCCTGCTGAGGTTCTGCTTCTCTGCCACCAGGAGATACTACCTGGGCGC
CGTGGAGCTGAGCTGGGACTACATGCAGTCTGACCTGGGCGAGCTGCCAGTGGACGCCAGGTTCCCCCCCAGAGTGCCCAAGA
GCTTCCCCTTCAACACCAGCGTGGTGTACAAGAAGACCCTGTTCGTGGAGTTCACTGACCACCTGTTCAACATCGCCAAGCCC
AGGCCCCCCTGGATGGGCCTGCTGGGCCCCACCATCCAGGCCGAGGTGTACGACACCGTGGTCATCACCCTGAAGAACATGGC
CAGCCACCCCGTCTCCCTGCACGCCGTGGGGGTGAGCTACTGGAAGGCCTCTGAGGGCGCCGAGTACGACGACCAGACCAGCC
AGAGGGAGAAGGAGGACGACAAGGTGTTCCCTGGGGGCAGCCACACCTACGTGTGGCAGGTCCTGAAGGAGAACGGCCCCATG
GCCTCTGACCCCTGTGCCTGACCTACAGCTACCTGAGCCACGTGGACCTGGTGAAGGACCTGAACTCTGGCCTGATTGGGGC
CCTGCTGGTGTGCAGGGAGGGCAGCCTGGCCAAGGAGAAGACCCAGACCCTGCACAAGTTCATCCTGCTGTTCGCCGTGTTCG
ACGAGGGCAAGAGCTGGCACTCTGAAACCAAGAACAGCCTGATGCAGGACAGGGACGCCGCCTCTGCCAGGGCCTGGCCCAAG
ATGCACACCGTCAACGGCTACGTCAACAGGAGCCTGCCTGGCCTGATTGGCTGCCACAGGAAGAGCGTGTACTGGCATGTGAT
CGGCATGGGCACCACCCCTGAGGTGCACAGCATCTTCCTGGAGGGCCACACCTTCCTGGTCAGGAACCACAGGCAGGCCAGCC
TGGAGATCAGCCCCATCACCTTCCTGACCGCCCAGACCCTGCTGATGGACCTGGGCCAGTTCCTGCTGTTCTGCCACATCTCC
AGCCACCAGCACGACGGCATGGAGGCCTACGTGAAAGTGGACAGCTGCCCTGAGGAGCCCCAGCTGAGGATGAAGAACAACGA
GGAGGCCGAGGACTATGATGACGACCTGACCGACAGCGAGATGGACGTGGTCAGGTTCGACGACGACAACAGCCCCAGCTTCA
TCCAGATCAGGAGCGTGGCCAAGAAGCACCCCAAGACCTGGGTGCACTACATCGCTGCTGAGGAGGAGGACTGGGACTATGCC
CCCCTGGTGCTGGCCCCTGATGACAGGAGCTACAAGAGCCAGTACCTGAACAATGGCCCCCAGAGGATTGGCAGGAAGTACAA
GAAAGTCAGGTTCATGGCCTACACTGATGAAACCTTCAAGACCAGGGAGGCCATCCAGCATGAGTCTGGCATCCTGGGCCCCC
TGCTGTACGGGGAGGTGGGGGACACCCTGCTGATCATCTTCAAGAACCAGGCCAGCAGGCCCTACAACATCTACCCCCATGGC
ATCACCGACGTGAGGCCCCTGTACAGCAGGAGGCTGCCTAAGGGGGTGAAGCACCTGAAAGACTTCCCCATCCTGCCTGGGGA
GATCTTCAAGTACAAGTGGACTGTGACTGTGGAGGACGGCCCCACCAAGAGCGACCCCAGGTGCCTGACCAGATACTACAGCA
GCTTCGTCAACATGGAGAGGGACCTGGCCTCTGGCCTGATTGGCCCCCTGCTGATCTGCTACAAGGAGTCTGTGGACCAGAGG
GGCAACCAGATCATGAGCGACAAGAGGAACGTGATCCTGTTCTCTGTC**TTCGACGAGAACAGGAGCTGGTACCTGACTGAAAA
CATCCAGCGGTTCCTCCCCAACCCGCGGGCGTGCAGCTGGAAGATCCTGAGTTTCAGGCATCAAACATCATGCACTCCATTA
ACGGCTACGTGTTCGATTCGCTGCAGCTGAGCGTGTGTCTGCACGAAGTGGCCTACTGGTACATCCTGTCCATTGGTGCCCAG
ACTGACTTCCTGTCCGTGTTTTTCTCCGGCTACACGTTCAAGCACAAGATGGTGTACGAGGACACCCTGACCCTCTTCCCTTT
TTCCGGCGAAACTGTGTTTATGAGCATGGAGAATCCGGCCTGTGGATCTTGGGCTGCCACAACAGCGACTTCCGTAACAGAG
GAATGACTGCGCTGCTCAAGGTGTCCAGCTGCGACAAGAACACCGGAGACTATTATGAGGACTCATACGAGGACATCTCCGCC
TACCTCCTGTCCAAGAATAACGCCATTGAACCTCGGAGCTTCAGCCAGAACCCACCCGTGCTTAAGAGACATCAACGGGAGAT
CACTAGGACCACCCTGCAGTCAGACCAGGAGGAAATCGACTACGATGACACCATCTCGGTCGAGATGAAGAAGGAGGACTTTG
ACATCTACGACGAAGATGAAAACCAGAGCCCGAGGTCGTTCCAAAAGAAAACCCGCCACTACTTTATTGCTGCTGTCGAGCGG
CTGTGGGACTACGGAATGTCGTCCTCGCCGACGTGCTCCGCAACCGAGCCCAGAGCGGCTCGGTGCCGCAATTCAAGAAGGT
CGTGTTCCAGGAGTTCACTGACGGGAGCTTCACTCAGCCTTTGTACCGGGAGAACTCAATGAACATCTCGGCCTCCTCGGAC
CTTACATCAGAGCAGAAGTGGAAGATAACATCATGGTCACTTTCCGTAACCAAGCCAGCCGCCCGTACTCGTTCTACTCCTCC
CTCATTTCTTACGAAGAGGACCAGCGGCAGGGCGCAGAACCGCGCAAGAACTTCGTGAAGCCCAACGAAACCAAGACCTACTT
CTGGAAAGTGCAGCATCATATGGCCCCGACTAAGGACGAGTTTGACTGCAAAGCCTGGGCCTACTTCTCCGATGTGGACTTGG
AGAAGGACGTCCACTCCGGCCTCATCGGTCCCCTGCTCGTGTGCCATACCAATACCCTGAACCCCGCACACGGTCGCCAGGTC
ACCGTGCAGGAGTTCGCTCTGTTCTTCACTATCTTCGACGAAACTAAGTCCTGGTACTTCACCGAGAACATGGAGAGGAACTG
CAGAGCCCCCTGTAACATCCAGATGGAGGACCCGACGTTCAAGGAAAACTACCGGTTCCACGCCATTAACGGATACATCATGG
ATACGCTGCCGGGTCTTGTGATGGCCCAGGATCAACGGATCAGATGGTACTTATTGTCGATGGGCAGCAACGAGAACATCCAC
TCTATTCACTTCTCCGGTCATGTGTTCACTGTCGGGAAGAAGGAAGAGTACAAGATGGCCCTGTACAACCTTTATCCCGGAGT
GTTCGAAACTGTGGAAATGCTGCCGTCGAAGGCCGGCATTTGGCGCGTGGAGTGTTTGATTGGAGAACATCTCCATGCGGGGA
TGTCAACCCTGTTCCTGGTGTATAGCAACAAGTGCCAGACTCCGCTTGGGATGGCGTCAGGACACATTAGGGATTTCCAGATC
ACTGCGTCCGGCCAGTACGGCCAATGGGCCCCTAAGCTGGCCCGCCTGCATTACTCCGGATCCATTAACGCCTGGTCAACCAA
GGAGCCATTCTCCTGGATCAAGGTGGACCTTCTGGCCCCCATGATTATCCACGGAATTAAGACCCAGGGGCCCGGCAGAAGT
TCTCCTCACTGTACATCAGCCAGTTCATAATCATGTACTCCCTGGACGGAAAGAAGTGGCAAACCTACAGGGGGAACAGCACC
GGCACACTGATGGTCTTTTTCGGAAATGTGGACTCCTCCGGGATTAAGCATAACATCTTCAACCCTCCGATTATCGCTCGGTA
CATTAGACTTCACCCTACCCACTACAGCATTCGCTCCACCCTGCGGATGGAACTGATGGGCTGCGATCTGAACTCGTGCAGCA
TGCCGTTGGGAATGGAGTCCAAAGCAATTTCCGACGCGCAGATCACCGCCTCGTCCTACTTTACCAACATGTTCGCCACGTGG
TCACCGTCCAAGGCCCGGCTGCACCTCCAGGGAAGATCCAACGCATGGCGGCCACAGGTCAACAACCCTAAGGAGTGGCTCCA
GGTGGACTTCCAGAAAACCATGAAGGTCACCGGAGTCACAACCCAGGGAGTGAAGTCGCTGCTGACTTCTATGTACGTCAAGG
AGTTCCTGATCTCCAGCAGCCAGGACGGGCACCAGTGGACCCTGTTCTTCCAAAATGGAAAGGTCAAGGTGTTTCAGGGCAAT
CAGGATTCATTCACCCCGGTGGTGAACTCCCTTGATCCACCCCTCCTGACCCGCTACCTTCGCATCCACCCACAGTCCTGGGT
GCACCAGATCGCGCTGAGGATGGAGGTCCTGGGATGCGAAGCCCAGGACCTGTACTGA**
```

Solid underline = coFVIII-25-NT58 (SEQ ID NO: 11)
Dashed underline = coFVIII-25-CT (SEQ ID NO: 12)

FIG. 1H: coFVIII-26 – SEQ ID NO: 6

ATGCAGATTGAGCTGAGCACCTGCTTCTTCCTGTGCCTGCTGAGGTTCTGCTTCTCT<u>GCCACCAGGAGATACTACCTGGGCGC
CGTGGAGCTGAGCTGGGACTACATGCAGTCTGACCTGGGCGAGCTGCCAGTGGACGCCAGGTTCCCCCCCAGAGTGCCCAAGA
GCTTCCCCTTCAACACCAGCGTGGTGTACAAGAAGACCCTGTTCGTGGAGTTCACTGACCACCTGTTCAACATCGCCAAGCCC
AGGCCCCCCTGGATGGGCCTGCTGGGCCCCACCATCCAGGCCGAGGTGTACGACACCGTGGTCATCACCCTGAAGAACATGGC
CAGCCACCCCGTCTCCCTGCACGCCGTGGGGGTGAGCTACTGGAAGGCCTCTGAGGGCGCCGAGTACGACGACCAGACCAGCC
AGAGGGAGAAGGAGGACGACAAGGTGTTCCCTGGGGGCAGCCACACCTACGTGTGGCAGGTCCTGAAGGAGAACGGCCCCATG
GCCTCTGACCCCCTGTGCCTGACCTACAGCTACCTGAGCCACGTGGACCTGGTGAAGGACCTGAACTCTGGCCTGATTGGGGC
CCTGCTGGTGTGCAGGGAGGGCAGCCTGGCCAAGGAGAAGACCCAGACCCTGCACAAGTTCATCCTGCTGTTCGCCGTGTTCG
ACGAGGGCAAGAGCTGGCACTCTGAAACCAAGAACAGCCTGATGCAGGACAGGGACGCCGCCTCTGCCAGGGCCTGGCCCAAG
ATGCACACCGTCAACGGCTACGTCAACAGGAGCCTGCCTGGCCTGATTGGCTGCCACAGGAAGAGCGTGTACTGGCATGTGAT
CGGCATGGGCACCACCCCTGAGGTGCACAGCATCTTCCTGGAGGGCCACACCTTCCTGGTCAGGAACCACAGGCAGGCCAGCC
TGGAGATCAGCCCCATCACCTTCCTGACCGCCCAGACCCTGCTGATGGACCTGGGCCAGTTCCTGCTGTTCTGCCACATCTCC
AGCCACCAGCACGACGGCATGGAGGCCTACGTGAAAGTGGACAGCTGCCCTGAGGAGCCCAGCTGAGGATGAAGAACAACGA
GGAGGCCGAGGACTATGATGACGACCTGACCGACAGCGAGATGGACGTGGTCAGGTTCGACGACGACAACAGCCCCAGCTTCA
TCCAGATCAGGAGCGTGGCCAAGAAGCACCCCAAGACCTGGGTGCACTACATCGCTGCTGAGGAGGAGGACTGGGACTATGCC
CCCCTGGTGCTGGCCCCTGATGACAGGAGCTACAAGAGCCAGTACCTGAACAATGGCCCCCAGAGGATTGGCAGGAAGTACAA
GAAAGTCAGGTTCATGGCCTACACTGATGAAACCTTCAAGACCAGGGAGGCCATCCAGCATGAGTCTGGCATCCTGGGCCCCC
TGCTGTACGGGGAGGTGGGGGACACCCTGCTGATCATCTTCAAGAACCAGGCCAGCAGGCCCTACAACATCTACCCCCATGGC
ATCACCGACGTGAGGCCCCTGTACAGCAGGAGGCTGCCTAAGGGGGTGAAGCACCTGAAAGACTTCCCCATCCTGCCTGGGGA
GATCTTCAAGTACAAGTGGACTGTGACTGTGGAGGACGGCCCCACCAAGAGCGACCCCAGGTGCCTGACCAGATACTACAGCA
GCTTCGTCAACATGGAGAGGGACCTGGCCTCTGGCCTGATTGGCCCCTGCTGATCTGCTACAAGGAGTCTGTGGACCAGAGG
GGCAACCAGATCATGAGCGACAAGAGGAACGTGATCCTGTTCTCTGTC</u>**TTCGACGAGAACAGGAGCTGGTACCTCACTGAAAA
CATCCAGAGGTTCCTCCCAAACCCCGCAGGAGTGCAACTGGAGGACCCTGAGTTTCAGGCCTCGAATATCATGCACTCGATTA
ACGGTTACGTGTTCGACTCGCTGCAGCTGAGCGTGTGCCTCCATGAAGTCGCTTACTGGTACATTCTGTCCATCGGCGCCCAG
ACTGACTTCCTGAGCGTGTTCTTTTCCGGTTACACCTTTAAGCACAAGATGGTGTACGAAGATACCCTGACCCTGTTCCCTTT
CTCCGGCGAAACGGTGTTCATGTCGATGGAGAACCCGGGTCTGTGGATTCTGGGATGCCACAACAGCGACTTTCGGAACCGCG
GAATGACTGCCCTGCTGAAGGTGTCCTCATGCGACAAGAACACCGGAGACTACTACGAGGACTCCTACGAGGATATCTCAGCC
TACCTCCTGTCCAAGAACAACGCGATCGAGCCGCGCAGCTTCAGCCAGAACCCGCCTGTGCTGAAGAGGCACCAGCGAGAAAT
TACCCGGACCACCCTCCAATCGGATCAGGAGGAAATCGACTACGACGACACCATCTCGGTGGAAATGAAGAAGGAAGATTTCG
ATATCTACGACGAGGACGAAAATCAGTCCCCTCGCTCATTCCAAAAGAAAACTAGACACTACTTTATCGCCGCGGTGGAAAGA
CTGTGGGACTATGGAATGTCATCCAGCCCTCACGTCCTTCGGAACCGGGCCCAGAGCGGATCGGTGCCTCAGTTCAAGAAAGT
GGTGTTCCAGGAGTTCACCGACGGCAGCTTCACCCAGCCGCTGTACCGGGGAGAACTGAACGAACACCTGGGCCTGCTCGGTC
CCTACATCCGCGCGGAAGTGGAGGATAACATCATGGTGACCTTCCGTAACCAAGCATCCAGACCTTACTCCTTCTATTCCTCC
CTGATCTCATACGAGGAGGACCAGCGCCAAGGCGCCGAGCCCCGCAAGAACTTCGTCAAGCCCAACGAGACTAAGACCTACTT
CTGGAAGGTCCAACACCATATGGCCCCGACCAAGGATGAGTTTGACTGCAAGGCCTGGGCCTACTTCTCCGACGTGGACCTTG
AGAAGGATGTCCATTCCGGCCTGATCGGCCGCTGCTCGTGTGTCACACCAACACCCTGAACCCAGCGCATGGACGCCAGGTC
ACCGTCCAGGAGTTTGCTCTGTTCTTCACCATTTTTGACGAAACTAAGTCCTGGTACTTCACCGAGAATATGGAGCGAAACTG
TAGAGCGCCCTGCAATATCCAGATGGAAGATCCGACTTTCAAGGAGAACTATAGATTCCACGCCATCAACGGGTACATCATGG
ATACTCTGCCGGGGCTGGTCATGGCCCAGGATCAGAGGATTCGGTGGTACTTGCTGTCAATGGGATCGAACGAAAACATTCAC
TCCATTCACTTCTCCGGTCACGTGTTCACTGTGCGCAAGAAGGAGGAGTACAAGATGGCGCTGTACAATCTGTACCCCGGGGT
GTTCGAAACTGTGGAGATGCTGCCGTCCAAGGCCGGCATCTGGAGAGTGGAGTGCCTGATCGGAGAGCACCTCCACGCGGGGA
TGTCCACCCTCTTCCTGGTGTACTCGAATAAGTGCCAGACCCCGCTGGGCATGGCCTCGGGCCACATCAGAGACTTCCAGATC
ACAGCAAGCGGACAATACGGCCAATGGGCGCCGAAGCTGGCCCGCTTGCACTACTCCGGATCGATCAACGCATGGTCCACCAA
GGAACCGTTCTCGTGGATTAAGGTGGACCTCCTGGCCCCTATGATTATCCACGGAATTAAGACCCAGGGCGCCAGGCAGAAGT
TCTCCTCCCTGTACATCTCGCAATTCATCATCATGTACAGCCTGGACGGGAAGAAGTGGCAGACTTACAGGGGAAACTCCACC
GGCACCCTGATGGTCTTTTTCGGCAACGTGGATTCCTCCGGCATTAAGCACAACATCTTCAACCCACCGATCATAGCCAGATA
TATTAGGCTCCACCCCACTCACTACTCAATCCGCTCAACTCTTCGGATGGAACTCATGGGTGCGACCTGAACTCCTGCTCCA
TGCCGTTGGGGATGGAATCAAAGGCTATTAGCGACGCCAGATCACCGCGAGCTCCTACTTCACTAACATGTTCGCCACCTGG
AGCCCCTCCAAGGCCAGGCTGCACTTGCAGGGACGGTCAAATGCCTGGCGGCCGCAAGTGAACAATCCGAAGGAATGGCTTCA
AGTGGATTTCCAAAAGACCATGAAAGTGACCGGAGTCACCACCCAGGGAGTGAAGTCCCTTCTGACCTCGATGTATGTGAAGG
AGTTCCTGATTAGCAGCAGCCAGGACGGGCACCAGTGGACCCTGTTCTTCCAAAACGGAAAGGTCAAGGTGTTCCAGGGGAAC
CAGGACTCGTTCACACCCGTGGTGAACTCCCTGGACCCCCCACTGCTGACGCGGTACTTGAGGATTCATCCTCAGTCCTGGGT
CCATCAGATTGCATTGCGAATGGAAGTCCTGGGCTGCGAGGCCCAGGACCTGTACTGA**

<u>Solid underline</u> = coFVIII-26-NT58 (SEQ ID NO: 13)
<u>Dashed underline</u>= coFVIII-26-CT (SEQ ID NO: 14)

FIG. 1I: BDD-FVIII (non-optimized; "parental"), Nucleotide Sequence (SEQ ID NO: 16)

ATGCAAATAGAGCTCTCCACCTGCTTCTTTCTGTGCCTTTTGCGATTCTGCTTTAGTGCCACCAGAAGATACTACCTGGGTGCAGTG
GAACTGTCATGGGACTATATGCAAAGTGATCTCGGTGAGCTGCCTGTGGACGCAAGATTTCCTCCTAGAGTGCCAAAATCTTTTCC
ATTCAACACCTCAGTCGTGTACAAAAAGACTCTGTTTGTAGAATTCACGGATCACCTTTTCAACATCGCTAAGCCAAGGCCACCCT
GGATGGGTCTGCTAGGTCCTACCATCCAGGCTGAGGTTTATGATACAGTGGTCATTACACTTAAGAACATGGCTTCCCATCCTGTC
AGTCTTCATGCTGTTGGTGTATCCTACTGGAAAGCTTCTGAGGGAGCTGAATATGATGATCAGACCAGTCAAAGGGAGAAAGAA
GATGATAAAGTCTTCCCTGGTGGAAGCCATACATATGTCTGGCAGGTCCTGAAAGAGAATGGTCCAATGGCCTCTGACCCACTGT
GCCTTACCTACTCATATCTTTCTCATGTGGACCTGGTAAAAGACTTGAATTCAGGCCTCATTGGAGCCCTACTAGTATGTAGAGAA
GGGAGTCTGGCCAAGGAAAAGACACAGACCTTGCACAAATTTATACTACTTTTTGCTGTATTTGATGAAGGGAAAAGTTGGCACT
CAGAAACAAAGAACTCCTTGATGCAGGATAGGGATGCTGCATCTGCTCGGGCCTGGCCTAAAATGCACACAGTCAATGGTTATGT
AAACAGGTCTCTGCCAGGTCTGATTGGATGCCACAGGAAATCAGTCTATTGGCATGTGATTGGAATGGGCACCACTCCTGAAGTG
CACTCAATATTCCTCGAAGGTCACACATTTCTTGTGAGGAACCATCGCCAGGCGTCCTTGGAAATCTCGCCAATAACTTTCCTTACT
GCTCAAACACTCTTGATGGACCTTGGACAGTTTCTACTGTTTTGTCATATCTCTTCCCACCAACATGATGGCATGGAAGCTTATGTC
AAAGTAGACAGCTGTCCAGAGGAACCCCAACTACGAATGAAAAATAATGAAGAAGCGGAAGACTATGATGATGATCTTACTGAT
TCTGAAATGGATGTGGTCAGGTTTGATGATGACAACTCTCCTTCCTTTATCCAAATTCGCTCAGTTGCCAAGAAGCATCCTAAAACT
TGGGTACATTACATTGCTGCTGAAGAGGAGGACTGGGACTATGCTCCCTTAGTCCTCGCCCCCGATGACAGAAGTTATAAAAGTC
AATATTTGAACAATGGCCCTCAGCGGATTGGTAGGAAGTACAAAAAAGTCCGATTTATGGCATACACAGATGAAACCTTTAAGAC
TCGTGAAGCTATTCAGCATGAATCAGGAATCTTGGGACCTTTACTTTATGGGGAAGTTGGAGACACACTGTTGATTATATTTAAGA
ATCAAGCAAGCAGACCCATATAACATCTACCCTCACGGAATCACTGATGTCCGTCCTTTGTATTCAAGGAGATTACCAAAAGGTGTA
AAACATTTGAAGGATTTTCCAATTCTGCCAGGAGAAATATTCAAATATAAATGGACAGTGACTGTAGAAGATGGGCCAACTAAAT
CAGATCCTCGGTGCCTGACCCGCTATTACTCTAGTTTCGTTAATATGGAGAGAGATCTAGCTTCAGGACTCATTGGCCCTCTCCTCA
TCTGCTACAAAGAATCTGTAGATCAAAGAGGAAACCAGATAATGTCAGACAAGAGGAATGTCATCCTGTTTTCTGTATTTGATGA
GAACCGAAGCTGGTACCTCACAGAGAATATACAACGCTTTCTCCCCAATCCAGCTGGAGTGCAGCTTGAGGATCCAGAGTTCCAA
GCCTCCAACATCATGCACAGCATCAATGGCTATGTTTTTGATAGTTTGCAGTTGTCAGTTTGTTTGCATGAGGTGGCATACTGGTA
CATTCTAAGCATTGGAGCACAGACTGACTTCCTTTCTGTCTTCTTCTCTGGATATACCTTCAAACACAAAATGGTCTATGAAGACAC
ACTCACCCTATTCCCATTCTCAGGAGAAACTGTCTTCATGTCGATGGAAAACCCAGGTCTATGGATTCTGGGGTGCCACAACTCAG
ACTTTCGGAACAGAGGCATGACCGCCTTACTGAAGGTTTCTAGTTGTGACAAGAACACTGGTGATTATTACGAGGACAGTTATGA
AGATATTTCAGCATACTTGCTGAGTAAAAACAATGCCATTGAACCAAGAAGCTTCTCTCAAAACCCACCAGTCTTGAAACGCCATC
AACGGGAAATAACTCGTACTACTCTTCAGTCAGATCAAGAGGAAATTGACTATGATGATACCATATCAGTTGAAATGAAGAAGGA
AGATTTTGACATTTATGATGAGGATGAAAATCAGAGCCCCCGCAGCTTTCAAAAGAAAACACGACACTATTTTATTGCTGCAGTGG
AGAGGCTCTGGGATTATGGGATGAGTAGCTCCCCACATGTTCTAAGAAACAGGGCTCAGAGTGGCAGTGTCCCTCAGTTCAAGA
AAGTTGTTTTCCAGGAATTTACTGATGGCTCCTTTACTCAGCCCTTATACCGTGGAGAACTAAATGAACATTTGGGACTCCTGGGG
CCATATATAAGAGCAGAAGTTGAAGATAATATCATGGTAACTTTCAGAAATCAGGCCTCTCGTCCCTATTCCTTCTATTCTAGCCTT
ATTTCTTATGAGGAAGATCAGAGGCAAGGAGCAGAACCTAGAAAAAACTTTGTCAAGCCTAATGAAACCAAAACTTACTTTTGGA
AAGTGCAACATCATATGGCACCCACTAAAGATGAGTTTGACTGCAAAGCCTGGGCTTATTTCTCTGATGTTGACCTGGAAAAAGAT
GTGCACTCAGGCCTGATTGGACCCCTTCTGGTCTGCCACACTAACACACTGAACCCTGCTCATGGGAGACAAGTGACAGTACAGG
AATTTGCTCTGTTTTTCACCATCTTTGATGAGACCAAAAGCTGGTACTTCACTGAAAAATATGGAAAGAAACTGCAGGGCTCCCTGC
AATATCCAGATGGAAGATCCCACTTTTAAAGAGAATTATCGCTTCCATGCAATAATGGCTACATAATGGATACACTACCTGGCTT
AGTAATGGCTCAGGATCAAAGGATTCGATGGTATCTGCTCAGCATGGGCAGCAATGAAAACATCCATTCTATTCATTTCAGTGGA
CATGTGTTCACTGTACGAAAAAAAGAGGAGTATAAAATGGCACTGTACAATCTCTATCCAGGTGTTTTTGAGACAGTGGAAATGT
TACCATCCAAAGCTGGAATTTGGCGGGTGGAATGCCTTATTGGCGAGCATCTACATGCTGGGATGAGCACACTTTTTCTGGTGTA
CAGCAATAAGTGTCAGACTCCCCTGGGAATGGCTTCTGGACACATTAGAGATTTTCAGATTACAGCTTCAGGACAATATGGACAG
TGGGCCCCAAAGCTGGCCAGACTTCATTATTCCGGATCAATCAATGCCTGGAGCACCAAGGAGCCCTTTTCTTGGATCAAGGTGG
ATCTGTTGGCACCAATGATTATTCACGGCATCAAGACCCAGGGTGCCCGTCAGAAGTTCTCCAGCCTCTACATCTCTCAGTTTATCA
TCATGTATAGTCTTGATGGGAAGAAGTGGCAGACTTATCGAGGAAATTCCACTGGAACCTTAATGGTCTTCTTTGGCAATGTGGAT
TCATCTGGGATAAAACACAATATTTTTAACCCTCCAATTATTGCTCGATACATCCGTTTGCACCCAACTCATTATAGCATTCGCAGC
ACTCTTCGCATGGAGTTGATGGCTGTGATTTAAATAGTTGCAGCATGCCATTGGGAATGGAGAGTAAAGCAATATCAGATGCAC
AGATTACTGCTTCATCCTACTTTACCAATATGTTTGCCACCTGGTCTCCTTCAAAAGCTCGACTTCACCTCCAAGGGAGGAGTAATG
CCTGGAGACCTCAGGTGAATAATCCAAAAGAGTGGCTGCAAGTGGACTTCCAGAAGACAATGAAAGTCACAGGAGTAACTACTC
AGGGAGTAAAATCTCTGCTTACCAGCATGTATGTGAAGGAGTTCCTCATCTCCAGCAGTCAAGATGGCCATCAGTGGACTCTCTTT
TTTCAGAATGGCAAAGTAAAGGTTTTTCAGGGAAATCAAGACTCCTTCACACCTGTGGTGAACTCTCTAGACCCACCGTTACTGAC
TCGCTACCTTCGAATTCACCCCCAGAGTTGGGTGCACCAGATTGCCCTGAGGATGGAGGTTCTGGGCTGCGAGGCACAGGACCTC
TAC

*BDD-FVIII = B Domain-Deleted FVIII

FIG. 1J: BDD-FVIII (non-optimized; "parental"), Amino Acid Sequence (SEQ ID NO: 17)

ATRRYYLGAVELSWDYMQSDLGELPVDARFPPRVPKSFPFNTSVVYKKTLFVEFTDHLFNIAKPRPPWMGLLGPTIQAEVYDTVVITLK
NMASHPVSLHAVGVSYWKASEGAEYDDQTSQREKEDDKVFPGGSHTYVWQVLKENGPMASDPLCLTYSYLSHVDLVKDLNSGLIGA
LLVCREGSLAKEKTQTLHKFILLFAVFDEGKSWHSETKNSLMQDRDAASARAWPKMHTVNGYVNRSLPGLIGCHRKSVYWHVIGMGT
TPEVHSIFLEGHTFLVRNHRQASLEISPITFLTAQTLLMDLGQFLLFCHISSHQHDGMEAYVKVDSCPEEPQLRMKNNEEAEDYDDDLT
DSEMDVVRFDDDNSPSFIQIRSVAKKHPKTWVHYIAAEEEDWDYAPLVLAPDDRSYKSQYLNNGPQRIGRKYKKVRFMAYTDETFKTR
EAIQHESGILGPLLYGEVGDTLLIIFKNQASRPYNIYPHGITDVRPLYSRRLPKGVKHLKDFPILPGEIFKYKWTVTVEDGPTKSDPRCLTRYY
SSFVNMERDLASGLIGPLLICYKESVDQRGNQIMSDKRNVILFSVFDENRSWYLTENIQRFLPNPAGVQLEDPEFQASNIMHSINGYVF
DSLQLSVCLHEVAYWYILSIGAQTDFLSVFFSGYTFKHKMVYEDTLTLFPFSGETVFMSMENPGLWILGCHNSDFRNRGMTALLKVSSC
DKNTGDYYEDSYEDISAYLLSKNNAIEPRSFSQNPPVLKRHQREITRTTLQSDQEEIDYDDTISVEMKKEDFDIYDEDENQSPRSFQKKTR
HYFIAAVERLWDYGMSSSPHVLRNRAQSGSVPQFKKVVFQEFTDGSFTQPLYRGELNEHLGLLGPYIRAEVEDNIMVTFRNQASRPYSF
YSSLISYEEDQRQGAEPRKNFVKPNETKTYFWKVQHHMAPTKDEFDCKAWAYFSDVDLEKDVHSGLIGPLLVCHTNTLNPAHGRQVT
VQEFALFFTIFDETKSWYFTENMERNCRAPCNIQMEDPTFKENYRFHAINGYIMDTLPGLVMAQDQRIRWYLLSMGSNENIHSIHFSG
HVFTVRKKEEYKMALYNLYPGVFETVEMLPSKAGIWRVECLIGEHLHAGMSTLFLVYSNKCQTPLGMASGHIRDFQITASGQYGQWA
PKLARLHYSGSINAWSTKEPFSWIKVDLLAPMIIHGIKTQGARQKFSSLYISQFIIMYSLDGKKWQTYRGNSTGTLMVFFGNVDSSGIKH
NIFNPPIIARYIRLHPTHYSIRSTLRMELMGCDLNSCSMPLGMESKAISDAQITASSYFTNMFATWSPSKARLHLQGRSNAWRPQVNNP
KEWLQVDFQKTMKVTGVTTQGVKSLLTSMYVKEFLISSSQDGHQWTLFFQNGKVKVFQGNQDSFTPVVNSLDPPLLTRYLRIHPQSW
VHQIALRMEVLGCEAQDLY

*BDD-FVIII = B Domain-Deleted FVIII

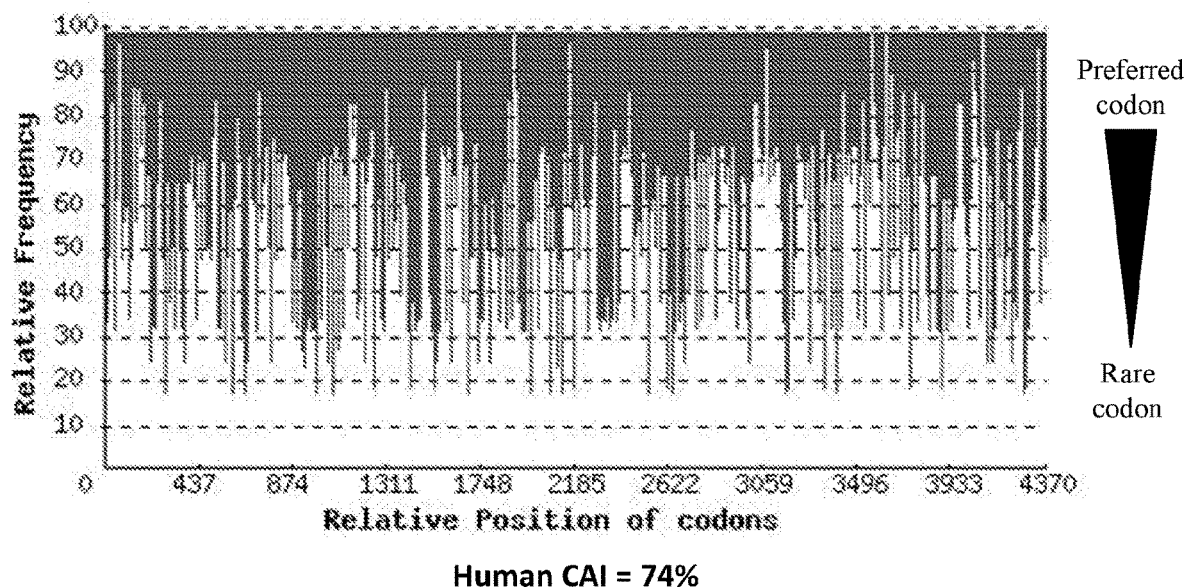
FIG. 2A – Non-Optimized BDD FVIII
Human CAI = 74%
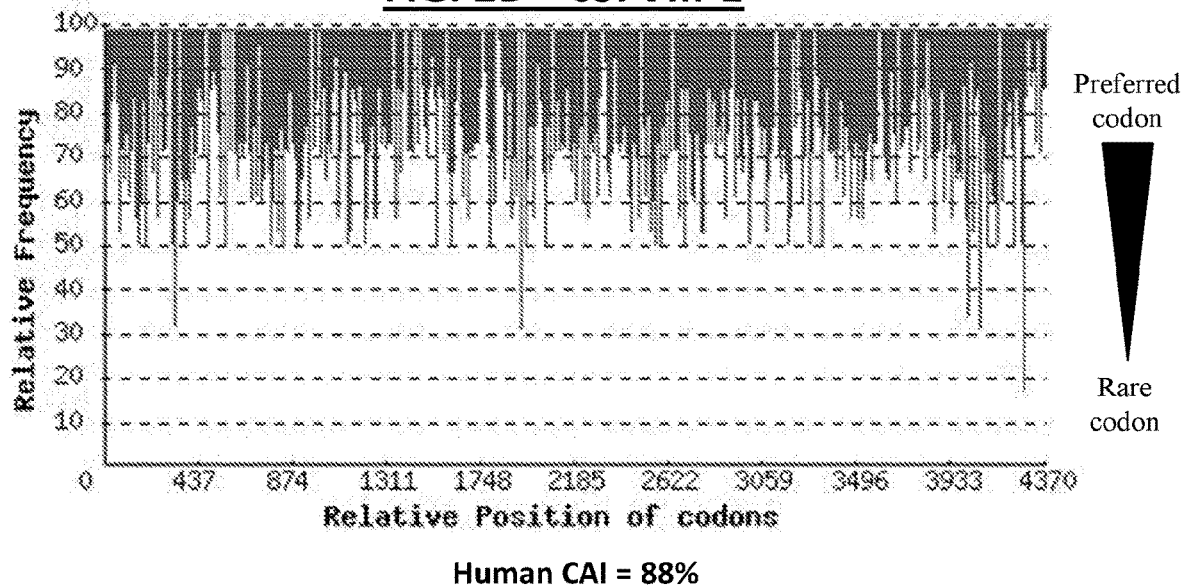
FIG. 2B – coFVIII-1
Human CAI = 88%
BDD FVIII = B Domain-Deleted FVIII

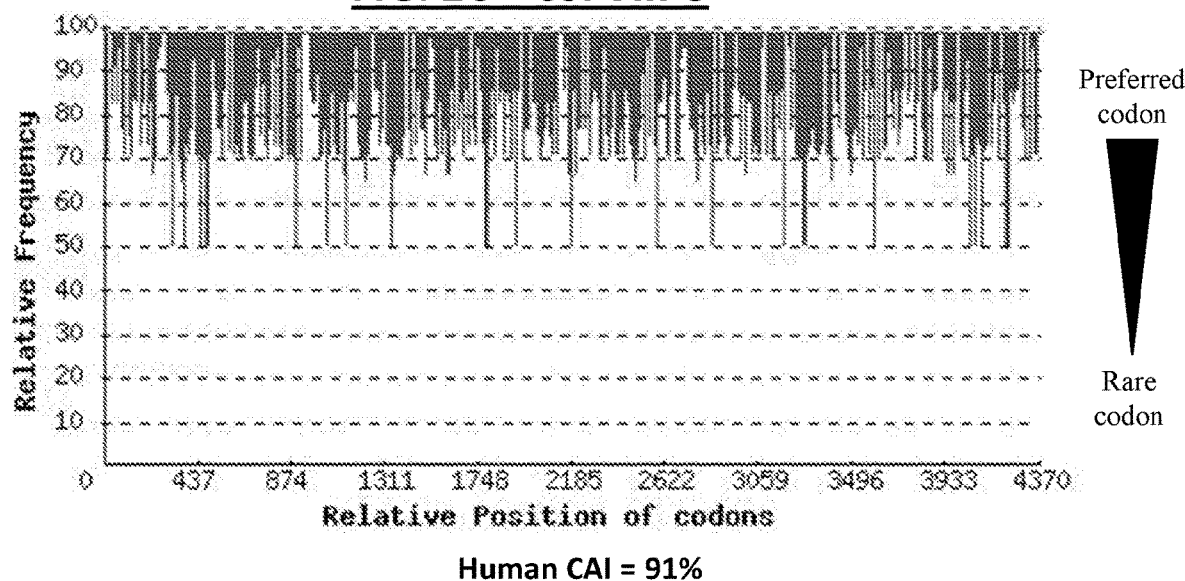
FIG. 2C – coFVIII-3
Human CAI = 91%
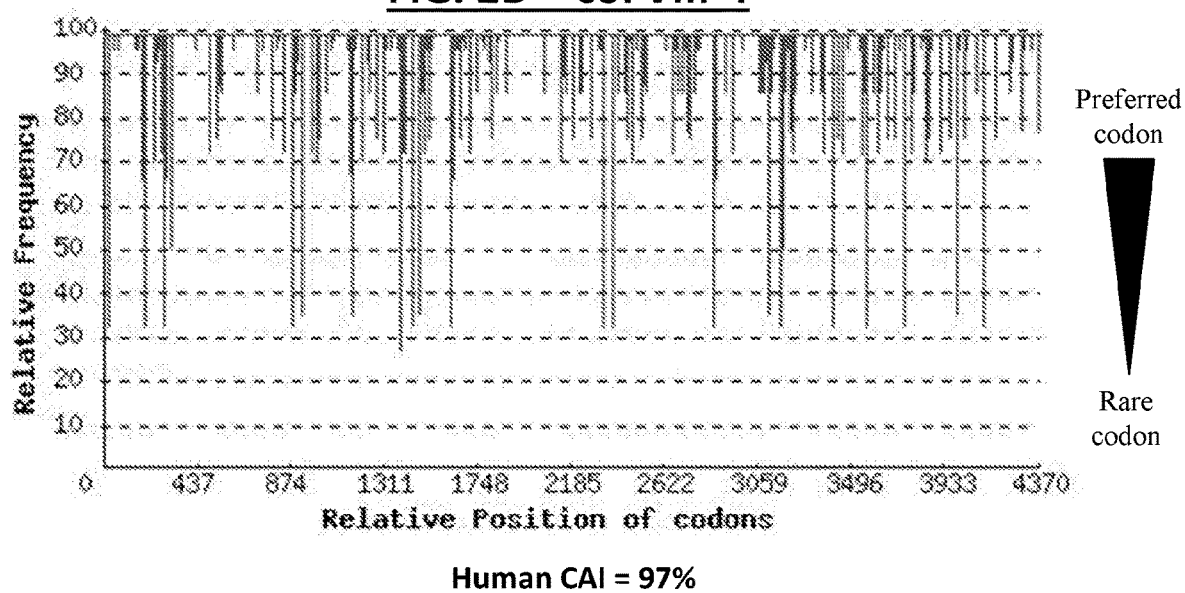
FIG. 2D – coFVIII-4
Human CAI = 97%

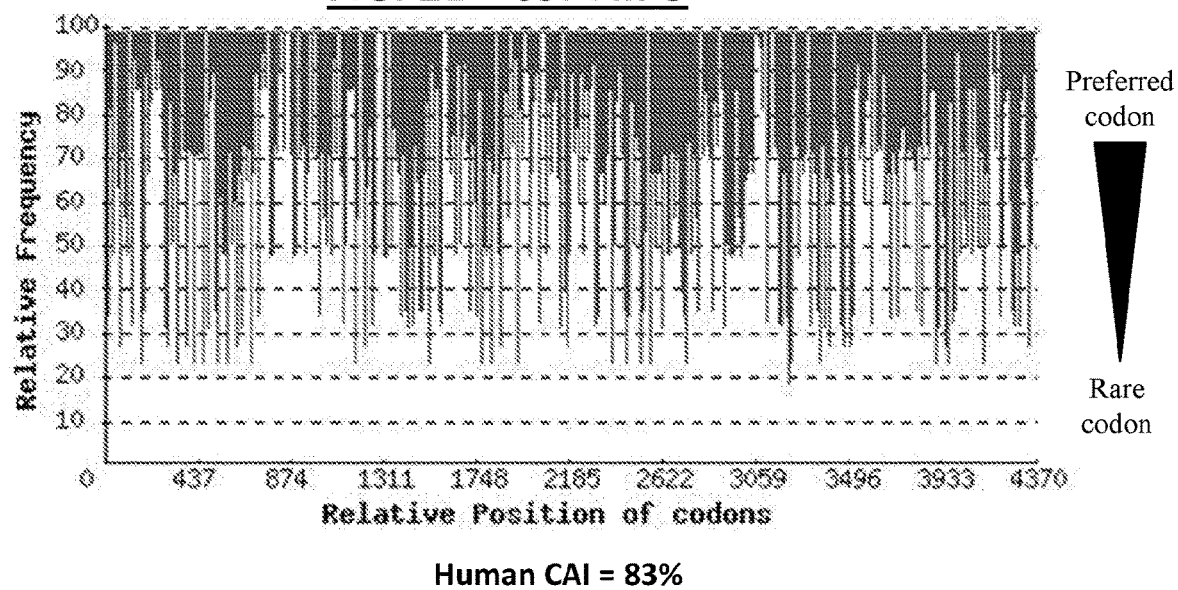
FIG. 2E – coFVIII-5
Human CAI = 83%
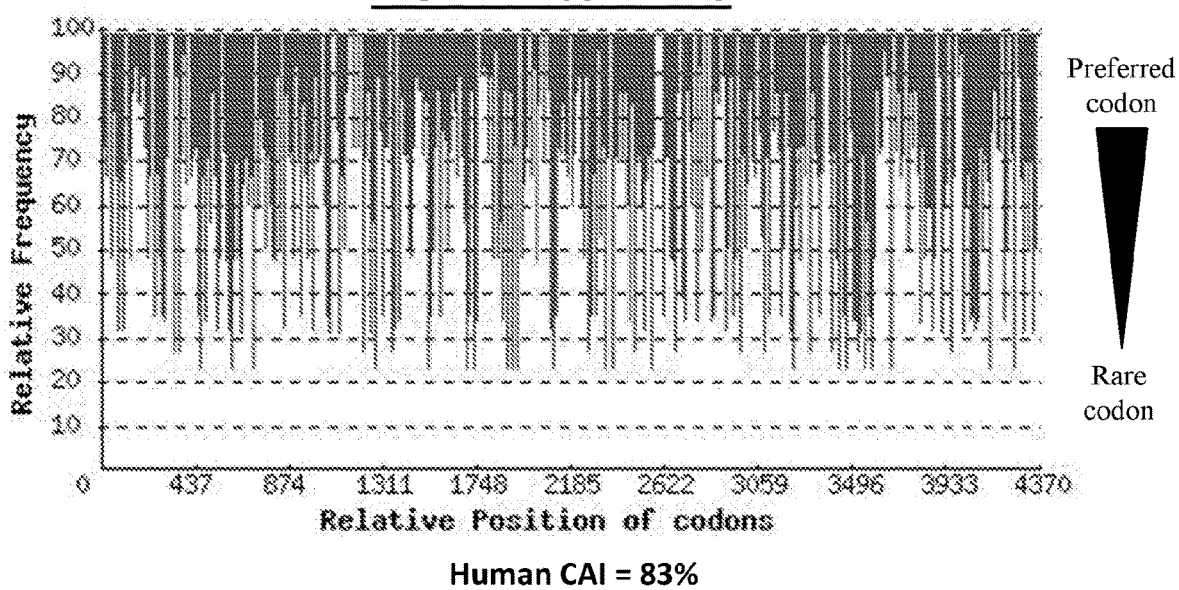
FIG. 2F – coFVIII-6
Human CAI = 83%

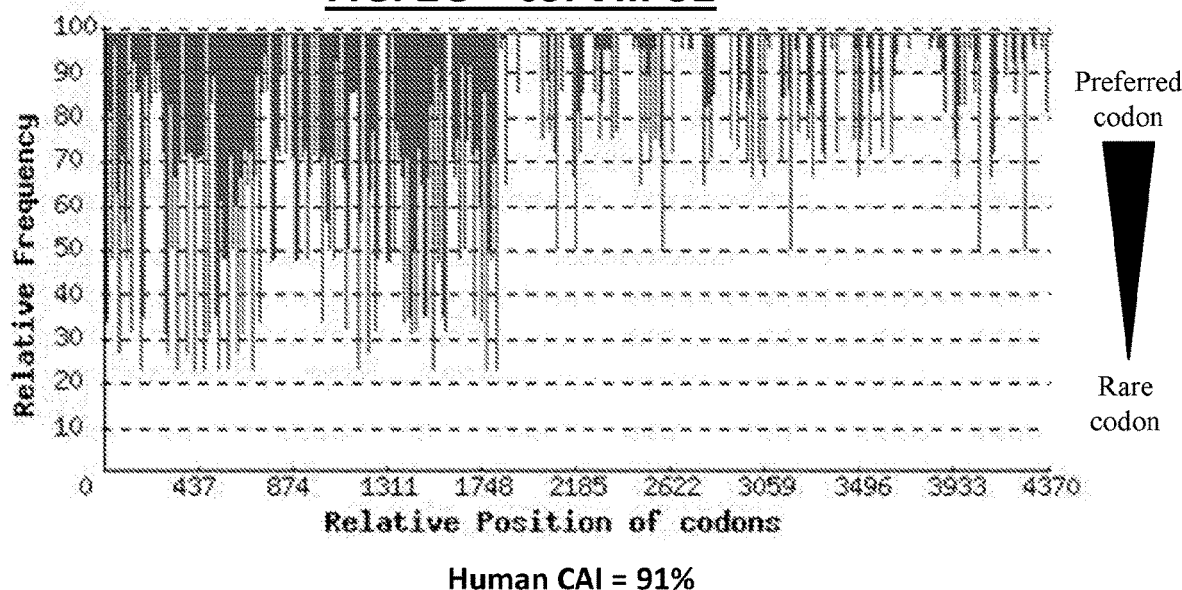
FIG. 2G – coFVIII-52
Human CAI = 91%
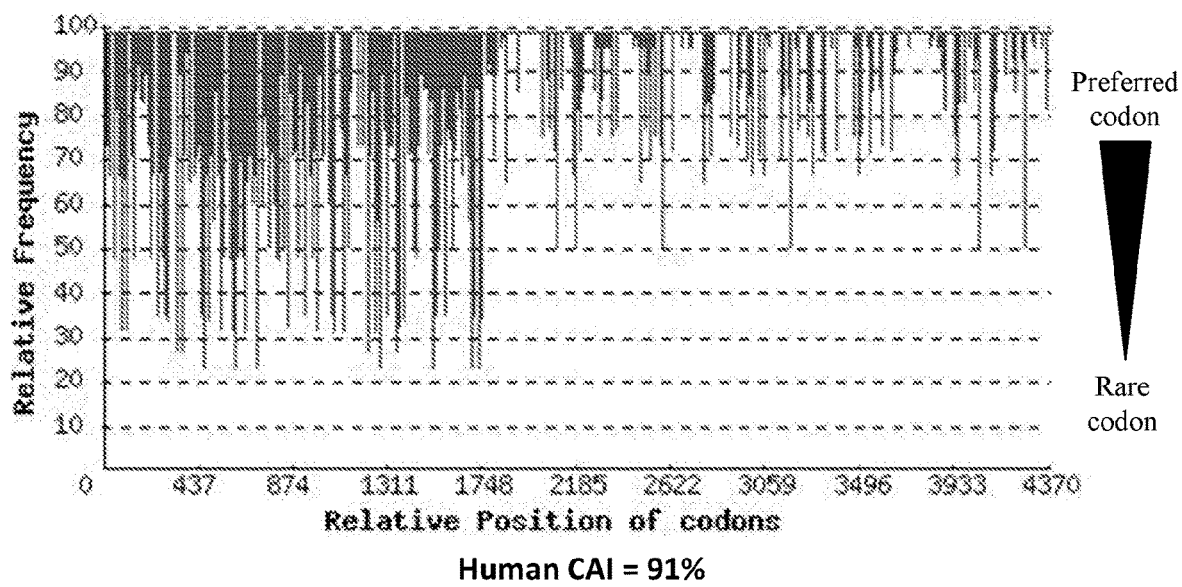
FIG. 2H – coFVIII-62
Human CAI = 91%

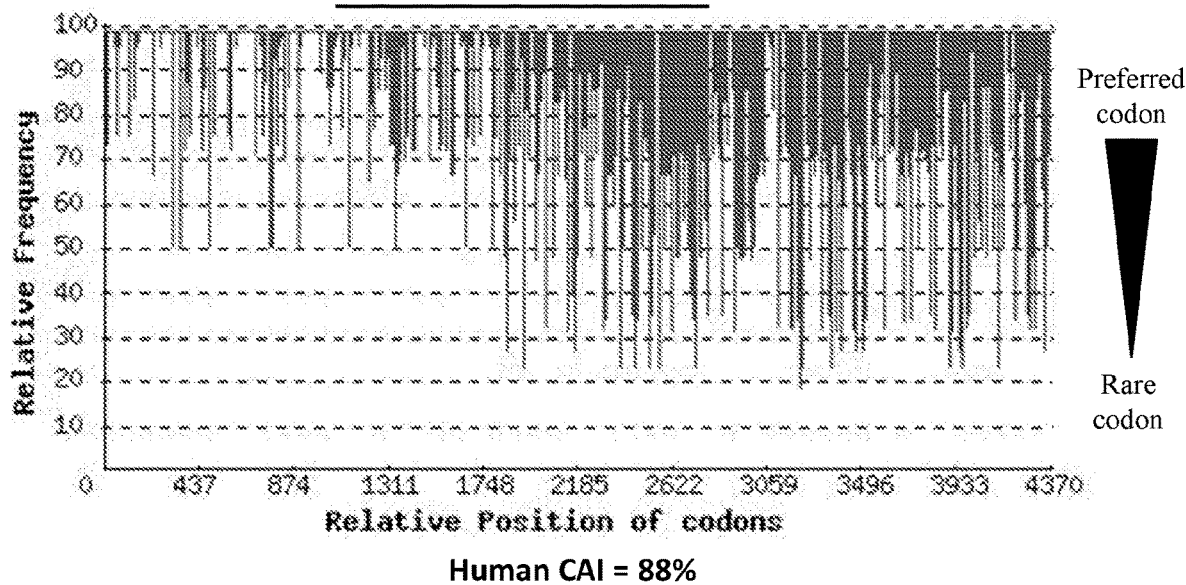
FIG. 2I – coFVIII-25
Human CAI = 88%
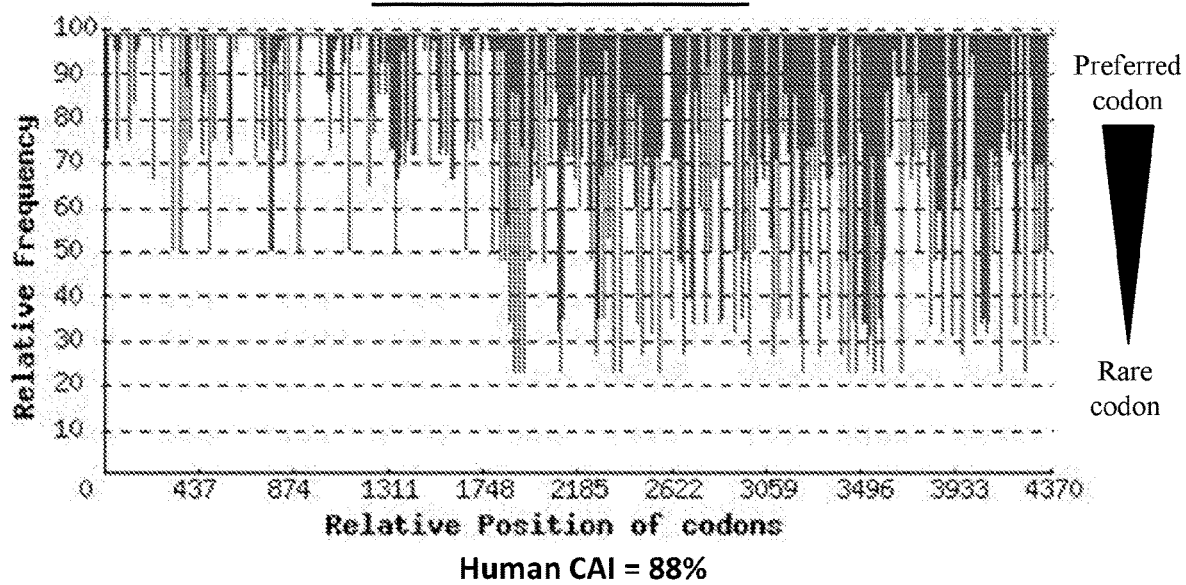
FIG. 2J – coFVIII-26
Human CAI = 88%

FIG. 3: Plasmid Maps of Codon Optimized FVIII Expression Plasmids
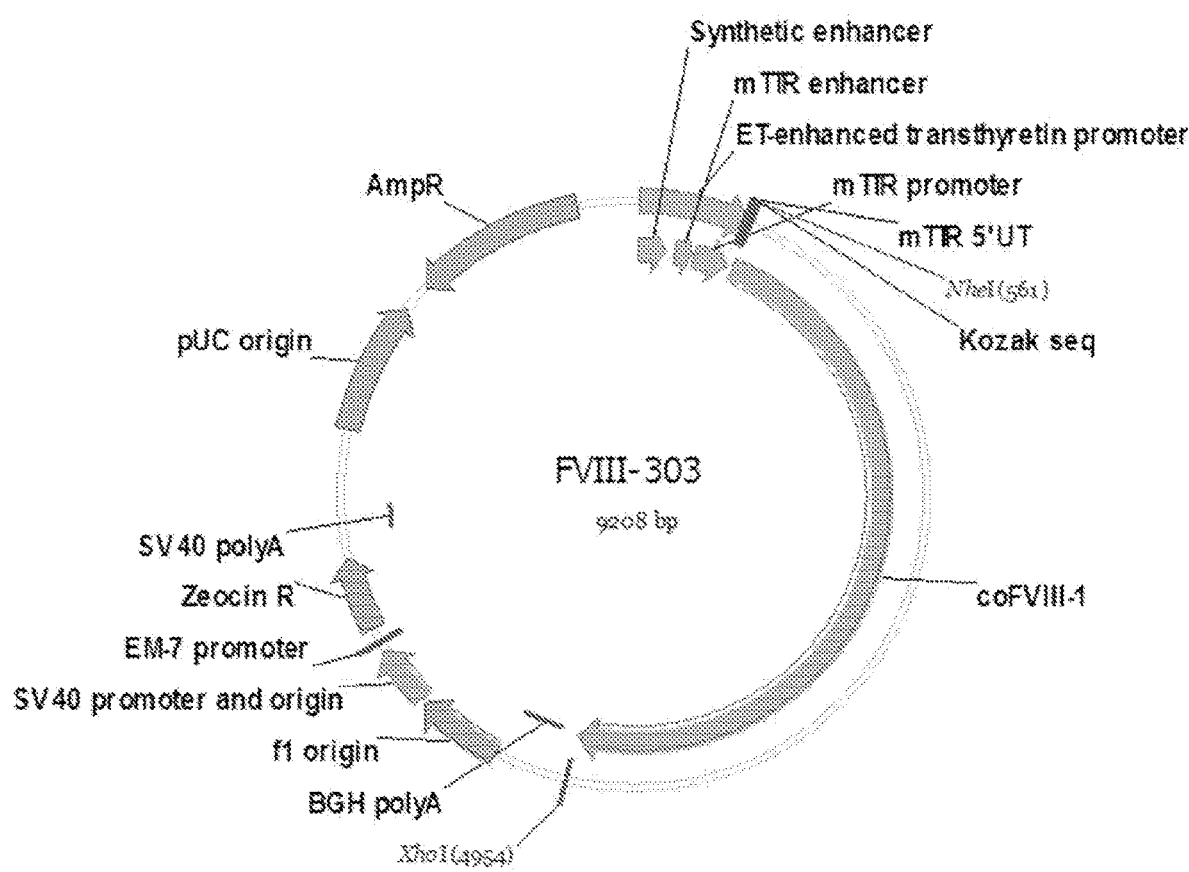

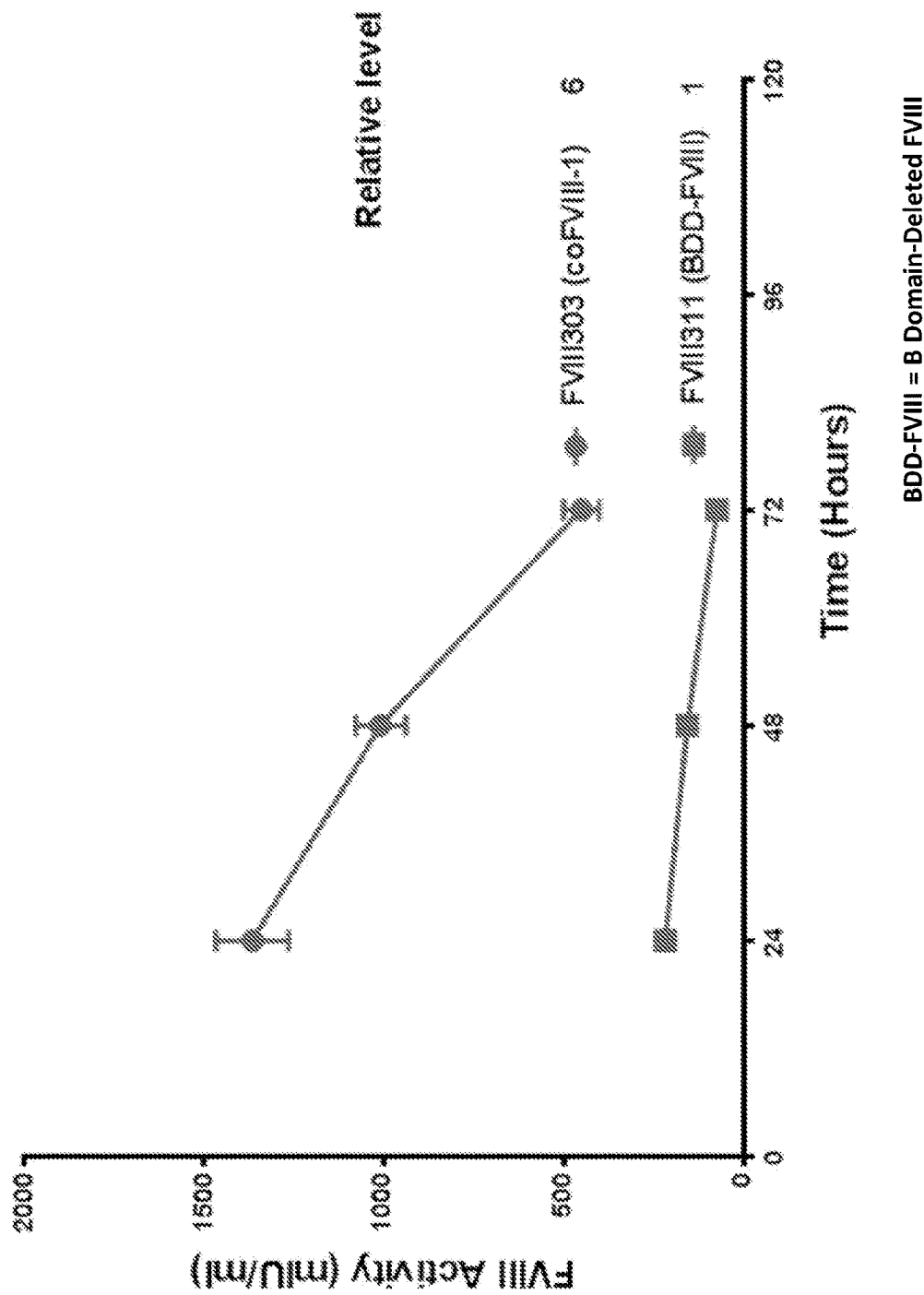
FIG. 4: FVIII Activity in HemA Mice

FIG. 5: Plasmid Maps of Codon Optimized FVIII Expression Plasmids
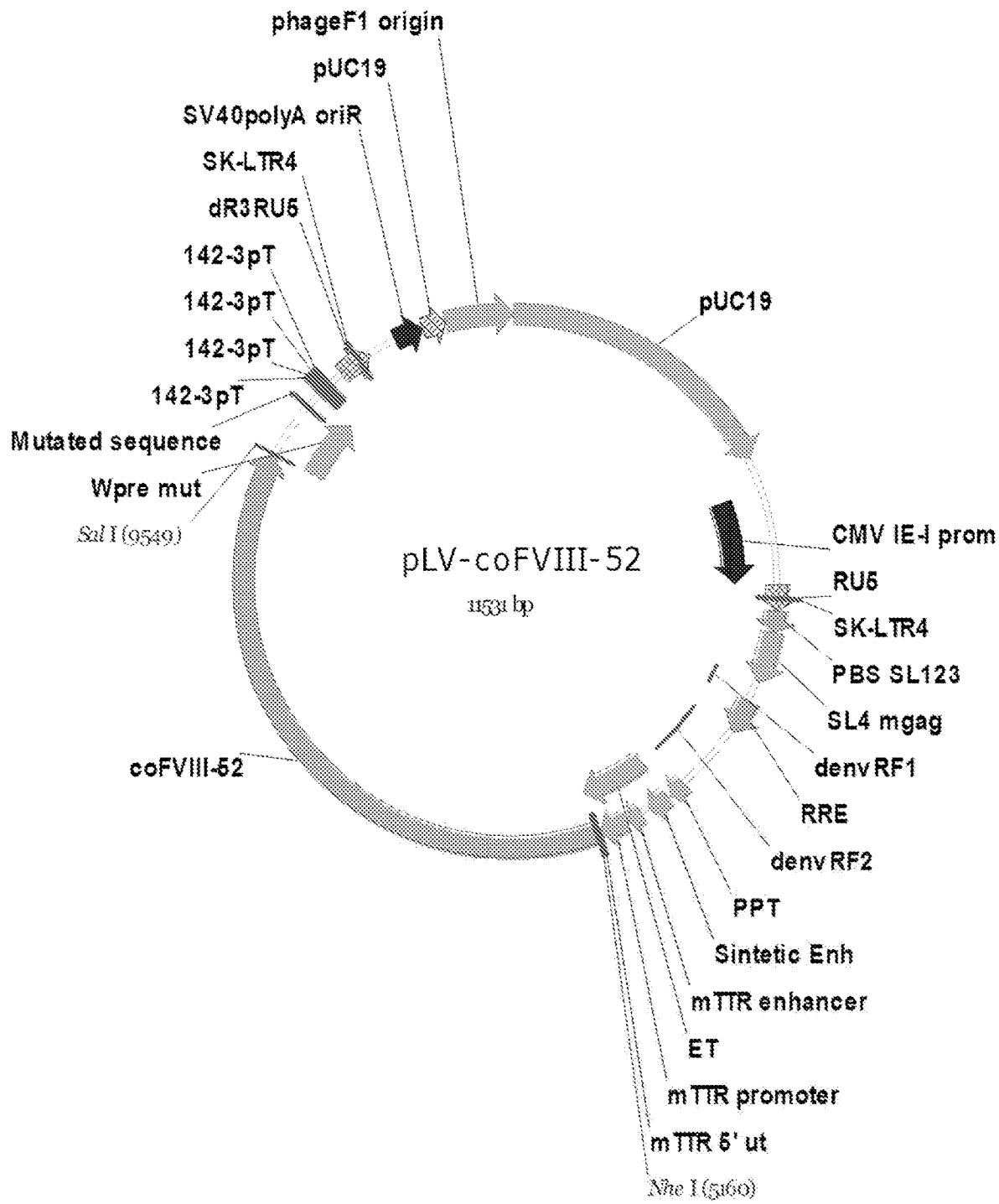

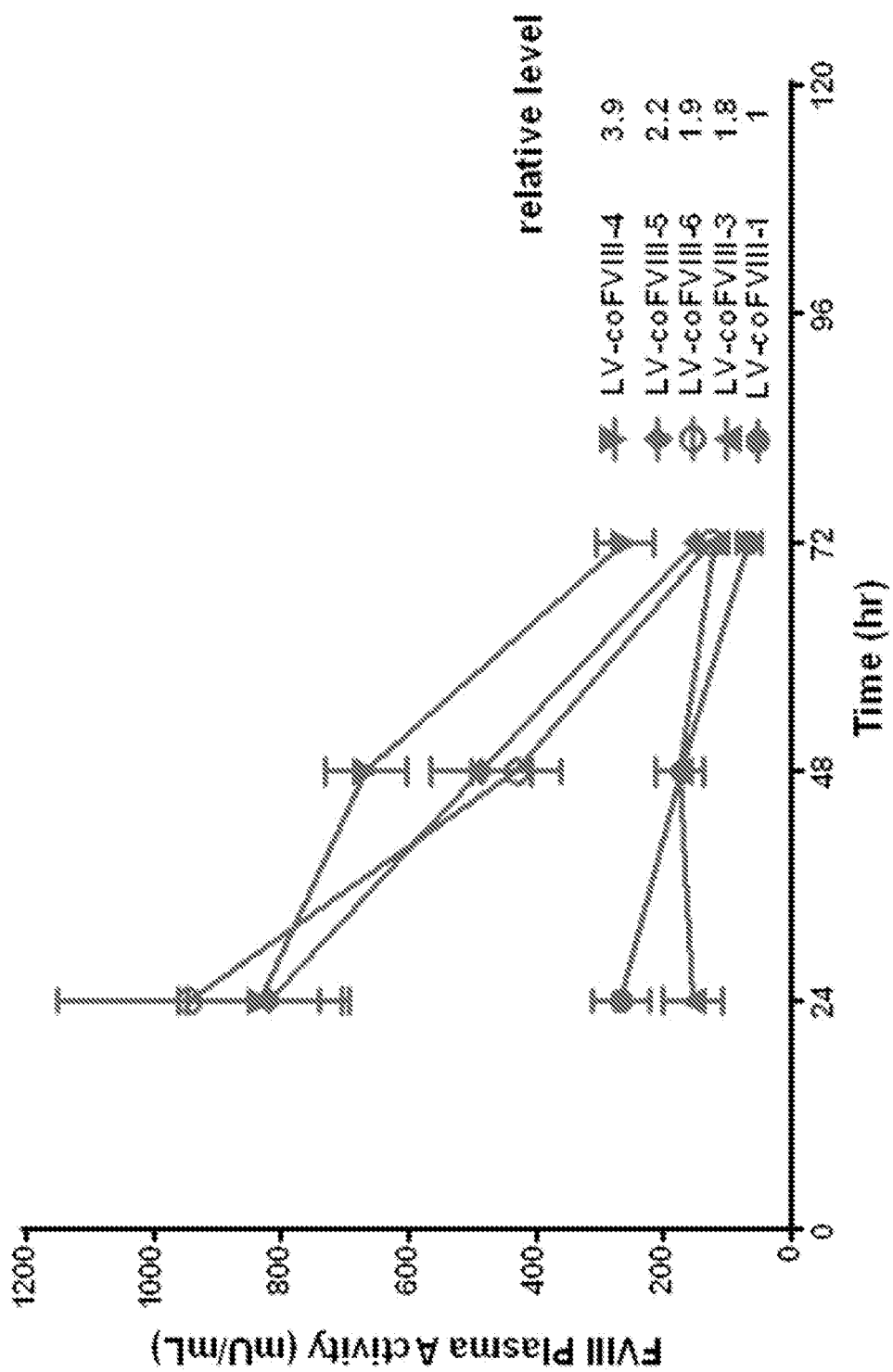
FIG. 6A: coFVIII-3, coFVIII-4, coFVIII-5, and coFVIII-6 relative to coFVIII-1

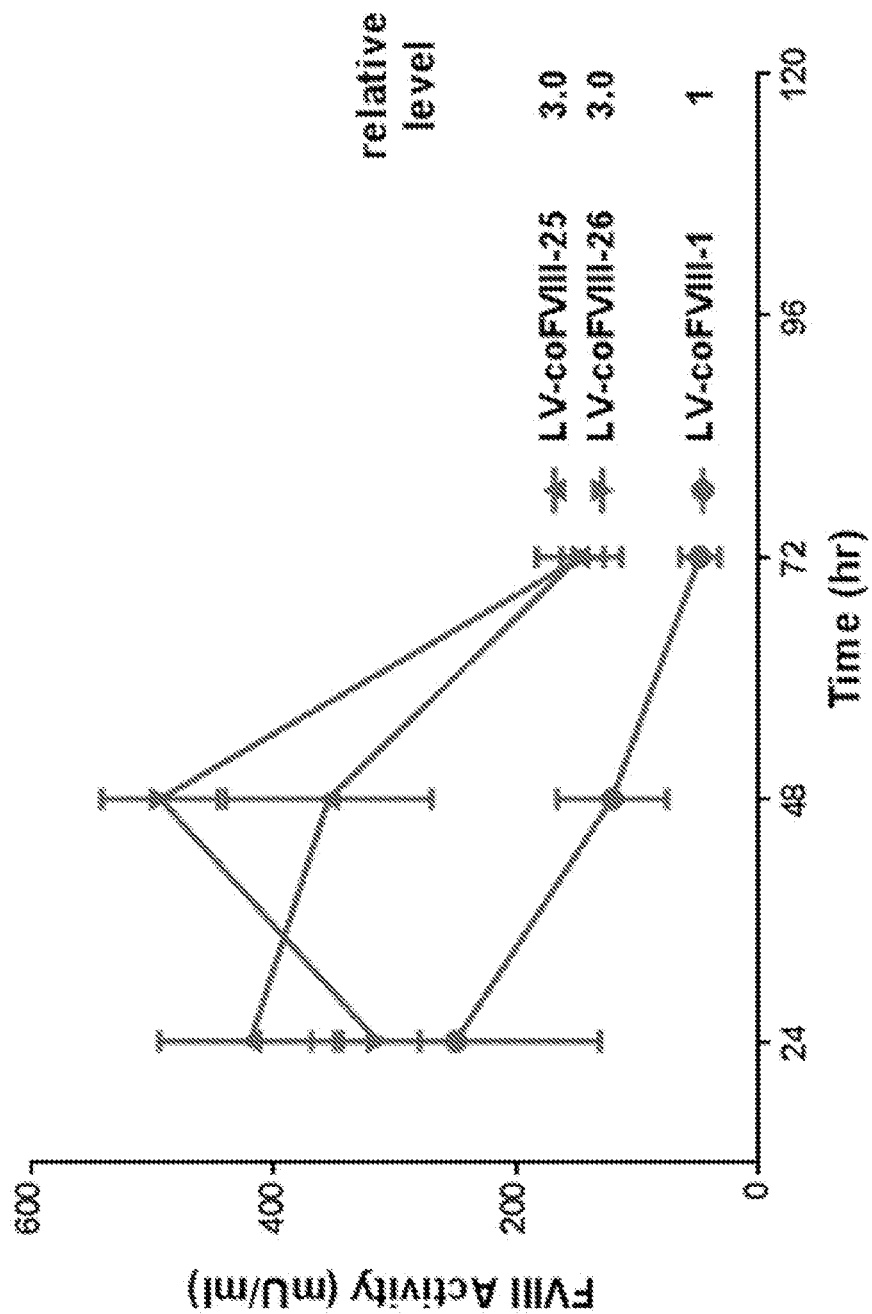

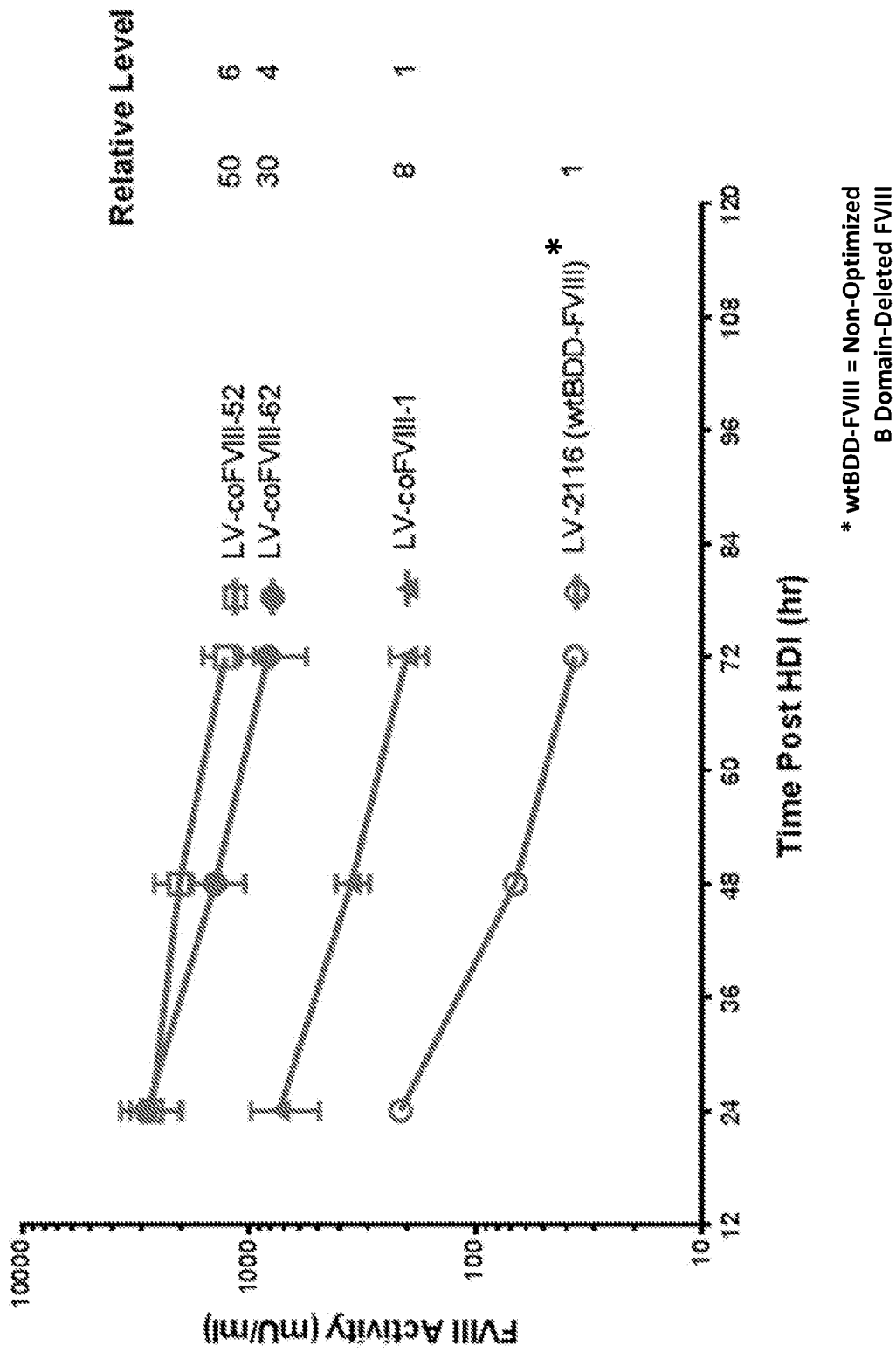

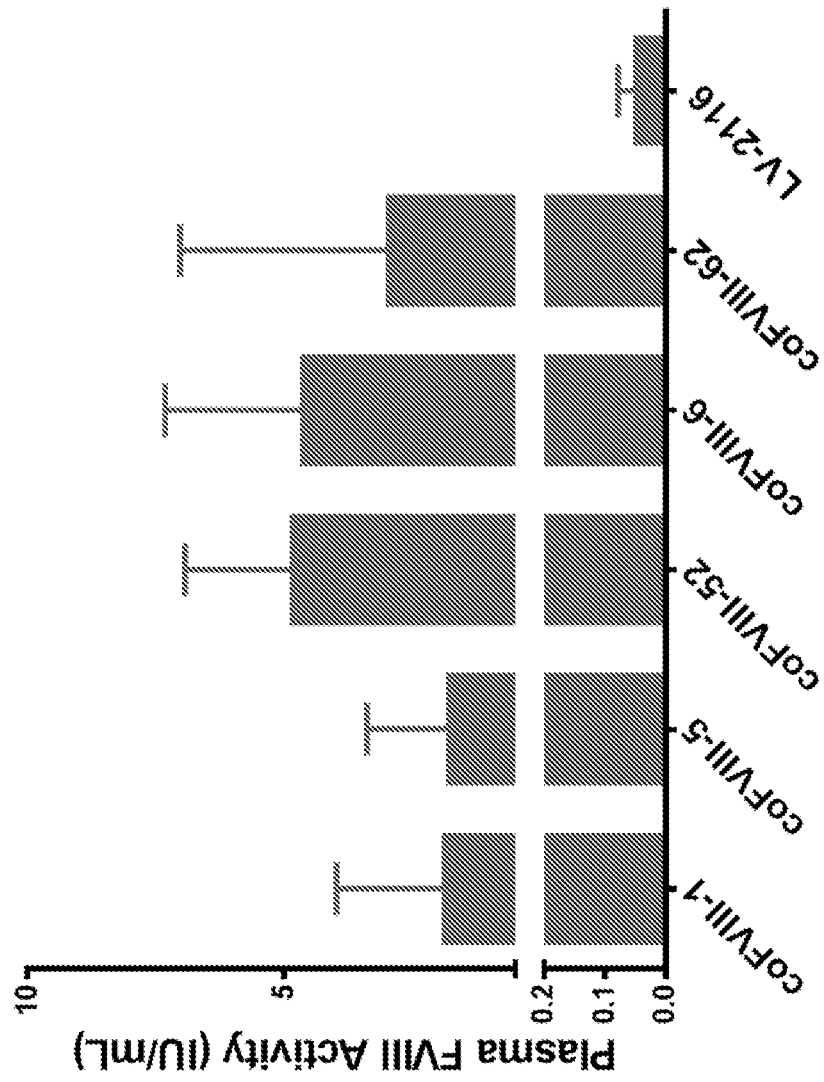
FIG. 7: Lentiviral Vector Mediated FVIII Activity in HemA Mice

FIG. 8A: coFVIII-52-XTEN – SEQ ID NO: 19

```
ATGCAAATCGAACTGAGCACCTGTTTCTTCCTCTGCCTGCTGAGATTCTGTTTCTCCGCGACCCGCCGATACTACCTGGGAGCAGTGG
AGCTCTCCTGGGATTACATGCAGAGCGACCTTGGGGAGCTGCCCGTGGATGCCAGGTTCCCTCCCCGGGTGCCAAAGTCGTTTCCGTT
CAACACCTCCGTGGTGTACAAGAAAACTCTGTTCGTGGAGTTCACCGACCACCTGTTCAATATCGCCAAGCCCAGACCTCCCTGGATG
GGGCTGTTGGGACCTACCATCCAAGCGGAGGTGTACGACACTGTGGTCATCACTCTGAAGAACATGGCCTCGCATCCCGTGTCCCTGC
ACGCCGTGGGAGTGTCTTACTGGAAAGCGTCCGAGGGGGCCGAATACGACGACCAGACCTCGCAGAGAGAAAAGGAAGATGACAAGGT
GTTCCCAGGAGGATCGCACACCTACGTGTGGCAAGTGTTGAAGGAGAACGGCCCAATGGCCTCCGACCCGCTGTGCCTGACCTACTCG
TACCTGTCCCACGTGGACCTCGTGAAGGACCTCAACTCGGGACTGATTGGAGCCCTGCTGGTCTGCAGGGAAGGCTCACTGGCGAAAG
AAAAGACTCAGACCTTGCACAAGTTCATTCTGCTGTTCGCTGTGTTCGACGAGGGGAAGTCGTGGCACAGCGAGACTAAGAACTCCCT
GATGCAAGATAGAGATGCCGCCTCCGCCCGGGCCTGGCCTAAGATGCACACCGTGAACGGTTACGTGAACCGCTCCCTCCCTGGCCTG
ATTGGATGCCACCGGAAGTCCGTGTACTGGACGTGATCGGGATGGGGACCACCCCCGAGGTGCACAGCATCTTCCTGGAAGGTCACA
CATTTCTCGTGCGCAACCACCGGCAGGCCTCCCTGGAAATCAGCCCCATTACCTTCCTCACTGCCCAGACTCTGCTGATGGACCTGGG
ACAGTTCCTGCTGTTCTGCCATATCTCCTCCCACCAACATGACGGAATGGAGGCATACGTGAAGGTCGATTCCTGCCCTGAGGAACCC
CAGCTCCGCATGAAGAACAATGAGGAAGCCGAGGACTACGACGACGACCTGACGGATAGCGAGATGGATGTGGTCCGGTTCGATGACG
ATAACAGCCCTTCCTTCATCCAAATTCGCTCGGTGGCAAAGAAGCACCCCAAGACCTGGGTGCATTACATTGCGGCGGAAGAAGAGGA
CTGGGATTATGCCCCGCTTGTCCTCGCTCCTGACGACCGGAGCTACAAGAGCCAGTACCTGAACAACGGTCCACAGAGGATCGGTAGA
AAGTACAAGAAGGTCCGCTTCATGGCCTATACCGACGAAACCTTCAAAACTAGAGAGGCCATCCAACACGAATCCGGCATCCTGGGCC
CGCTCTTGTACGGAGAAGTCGGCGACACCCTTCTCATTATCTTCAAGAACCAGGCTTCCCGGCCGTACAACATCTATCCGCATGGGAT
CACTGACGTGCGCCCACTGTACTCGCGGCGCCTGCCCAAGGGTGTCAAACACCTGAAGGATTTTCCGATCCTTCCGGGAGAAATCTTC
AAGTACAAGTGGACCGTGACCGTGGAAGATGGCCCAACTAAGTCTGACCCTAGATGCCTCACCCGCTACTACTCATCCTTCGTCAACA
TGGAGCGCGACCTGGCCAGCGGACTGATCGGCCCGCTGCTGATTTGCTACAAGGAATCAGTGGACCAACGGGGAAACCAGATCATGTC
GGATAAGAGGAACGTCATCCTCTTCTCCGTGTTTGACGAAAACCGGTCGTGGTACCTGACCGAGAACATCCAGAGGTTCCTGCCCAAC
CCTGCTGGGGTGCAGCTGGAGGACCCCGAGTTCCAGGCCAGCAACATCATGCACAGCATCAATGGCTACGTGTTCGACAGCCTGCAGC
TGAGCGTGTGCCTGCACGAGGTGGCCTACTGGTACATCCTGAGCATCGGCGCCCAGACCGACTTCCTGAGCGTGTTCTTCTCTGGCTA
CACCTTCAAGCACAAGATGGTGTATGAGGACACCCTGACCCTGTTCCCCTTCAGCGGGGAGACTGTCTTCATGAGCATGGAGAACCCT
GGCCTGTGGATCCTGGGCTGCCACAACAGCGACTTCAGGAACAGGGGCATGACTGCCCTGCTGAAAGTCTCCAGCTGTGACAAGAACA
CCGGGGACTACTACGAGGACAGCTACGAGGACATCAGCGCCTACCTGCTGAGCAAGAACAATGCCATCGAGCCCAGGAGCTTCTCTCA
GAACGGCGCGCCAACATCAGAGAGCGCCACCCCTGAAAGTGGTCCCGGGAGCGAGCCAGCCACATCTGGGTCGGAAACGCCAGGCACA
AGTGAGTCTGCAACTCCCGAGTCCGGACCTGGCTCCGAGCCTGCCACTAGCGGCTCCGAGACTCCGGGAACTTCCGAGAGCGCTACAC
CAGAAAGCGGACCCGGAACCAGTACCGAACCTAGCGAGGGCTCTGCTCCGGGCAGCCCAGCCGGCTCTCCTACATCCACGGAGGAGGG
CACTTCCGAATCCGCCACCCCGGAGTCAGGGCCAGGATCTGAACCCGCTACCTCAGGCAGTGAGACGCCAGGAACGAGCGAGTCCGCT
ACACCGGAGAGTGGGCCAGGGAGCCCTGCTGGATCTCCTACGTCCACTGAGGAAGGGTCACCAGCGGGCTCGCCCACCAGCACTGAAG
AAGGTGCCTCGAGCCCCCAGTGCTGAAGAGGCACCAGAGGGAGATCACCAGGACCACCCTGCAGTCTGACCAGGAGGAGATCGACTA
TGATGACACCATCAGCGTGGAGATGAAGAAGGAGGACTTCGACATCTACGACGAGGACGAGAACCAGAGCCCCAGGAGCTTCCAGAAG
AAGACCAGGCACTACTTCATTGCTGCTGTGGAGAGGCTGTGGGACTATGGCATGTCCAGCAGCCCCATGTGCTGAGGAACAGGGCCC
AGTCTGGCAGCGTGCCCCAGTTCAAGAAAGTCGTGTTCCAGGAGTTCACCGACGGCAGCTTCACCCAGCCCCTGTACAGAGGGGAGCT
GAACGAGCACCTGGGCCTGCTGGGCCCCTACATCAGGGCCGAGGTGGAGGACAACATCATGGTGACCTTCAGGAACCAGGCCAGCAGG
CCCTACAGCTTCTACAGCAGCCTGATCAGCTACGAGGAGGACCAGAGGCAGGGGCTGAGCCCAGGAAGAACTTTGTGAAGCCCAATG
AAACCAAGACCTACTTCTGGAAGGTGCAGCACCACATGGCCCCCACCAAGGACGAGTTCGACTGCAAGGCCTGGGCCTACTTCTCTGA
CGTGGACCTGGAGAAGGACGTGCACTCTGGCCTGATTGGCCCCTGCTGGTGTGCCACACCAACACCCTGAACCCTGCCCATGGCAGG
CAGGTGACTGTGCAGGAGTTCGCCCTGTTCTTCACCATCTTCGATGAAACCAAGAGCTGGTACTTCACTGAGAACATGGAGAGGAACT
GCAGGGCCCCCTGCAACATCCAGATGGAGGACCCCACCTTCAAGGAGAACTACAGGTTCCATGCCATCAATGGCTACATCATGGACAC
CCTGCCTGGCCTGGTCATGGCCCAGGACCAGAGGATCAGGTGGTATCTGCTGAGCATGGGCAGCAACGAGAACATCCACAGCATCCAC
TTCTCTGGCCACGTGTTCACTGTGAGGAAGAAGGAGGAGTACAAGATGGCCCTGTACAACCTGTACCCTGGGGTGTTCGAAACCGTGG
AGATGCTGCCCAGCAAGGCCGGCATCTGGAGGGTGGAGTGCCTGATTGGGGAGCACCTGCACGCCGGCATGAGCACCCTGTTCCTGGT
GTACAGCAACAAGTGCCAGACCCCCCTGGGCATGGCCTCTGGCCACATCAGGGACTTCCAGATCACTGCCTCTGGCCAGTACGGCCAG
TGGGCCCCCAAGCTGGCCAGGCTGCACTACTCCGGAAGCATCAATGCCTGGAGCACCAAGGAGCCCTTCAGCTGGATCAAAGTGGACC
TGCTGGCCCCCATGATCATCCACGGCATCAAGACCCAGGGGGCCAGGCAGAAGTTCTCCAGCCTGTACATCAGCCAGTTCATCATCAT
GTACAGCCTGGACGGCAAGAAGTGGCAGACCTACAGGGGCAACAGCACCGGCACCCTGATGGTGTTCTTCGGCAACGTGGACAGCAGC
GGCATCAAGCACAACATCTTCAACCCCCCATCATCGCCAGATACATCAGGCTGCACCCCACCCACTACAGCATCAGGAGCACCCTGA
GGATGGAGCTGATGGGCTGTGACCTGAACAGCTGCAGCATGCCCCTGGGCATGGAGAGCAAGGCCATCTCTGACGCCCAGATCACTGC
CTCCAGCTACTTCACCAACATGTTTGCCACCTGGAGCCCCAGCAAGGCCAGGCTGCACCTGCAGGGCAGGAGCAATGCCTGGAGGCCC
CAGGTCAACAACCCCAAGGAGTGGCTGCAGGTGGACTTCCAGAAGACCATGAAGGTGACTGGGGTGACCACCCAGGGGGTGAAGAGCC
TGCTGACCAGCATGTACGTGAAGGAGTTCCTGATCTCCAGCAGCCAGGACGGCCACCAGTGGACCCTGTTCTTCCAGAATGGCAAGGT
GAAGGTGTTCCAGGGCAACCAGGACAGCTTCACCCCTGTGGTCAACAGCCTGGACCCCCCCCTGCTGACCAGATACCTGAGGATCCAC
CCCCAGAGCTGGGTGCACCAGATCGCCCTGAGGATGGAGGTGCTGGGCTGTGAGGCCCAGGACCTGTACTGA
```

Underlined = XTEN nucleotide sequence (SEQ ID NO: 18)

FIG. 8B: coFVIII-1-XTEN – SEQ ID NO: 20

ATGCAGATTGAGCTGTCTACTTGCTTTTTCCTGTGCCTGCTGAGGTTTTGCTTTTCCGCTACACGAAGGTATTATCTGGGGGCTGTGG
AACTGTCTTGGGATTACATGCAGAGTGACCTGGGAGAGCTGCCAGTGGACGCAAGGTTTCCCCCTAGAGTCCCTAAGTCATTCCCCTT
CAACACTAGCGTGGTCTACAAGAAAACACTGTTCGTGGAGTTTACTGATCACCTGTTCAACATCGCAAAGCCTAGGCCACCCTGGATG
GGACTGCTGGGGCCAACAATCCAGGCCGAGGTGTACGACACCGTGGTCATTACACTTAAGAACATGGCCTCACACCCCGTGAGCCTGC
ATGCTGTGGGCGTCAGCTACTGGAAGGCTTCCGAAGGAGCAGAGTATGACGATCAGACTTCCCAGAGAGAAAAAGAGGACGATAAGGT
GTTTCCTGGCGGATCTCATACCTACGTGTGGCAGGTCCTGAAAGAGAATGGCCCTATGGCCTCCGACCCTCTGTGCCTGACCTACTCT
TATCTGAGTCACGTGGACCTGGTCAAGGATCTGAACAGCGGCCTGATCGGAGCCCTGCTGGTGTGCAGGGAAGGAAGCCTGGCTAAGG
AGAAAACCCAGACACTGCATAAGTTCATTCTGCTGTTCGCCGTGTTTGACGAAGGGAAATCATGGCACAGCGAGACAAAGAATAGTCT
GATGCAGGACAGGGATGCCGCTTCAGCCAGAGCTTGGCCCAAAATGCACACTGTGAACGGCTACGTCAATCGCTCACTGCCTGGGCTG
ATCGGCTGCCACCGAAAGAGCGTGTATTGGCATGTCATCGGGATGGGCACCACACCTGAAGTGCACTCCATTTTCCTGGAGGGACATA
CCTTTCTGGTCCGCAACCACCGACAGGCTTCCCTGGAGATCTCTCCAATTACCTTCCTGACAGCACAGACTCTGCTGATGGACCTGGG
GCAGTTCCTGCTGTTTTGCCACATCAGCTCCCACCAGCATGATGGCATGGAGGCTTACGTGAAAGTGGACTCTTGTCCCGAGGAACCT
CAGCTGCGGATGAAGAACAATGAGGAAGCAGAAGACTATGACGATGACCTGACCGACTCCGAGATGGATGTGGTCCGATTCGATGACG
ATAACAGCCCCTCCTTTATCCAGATTAGATCTGTGGCCAAGAAACACCCTAAGACATGGGTCCATTACATCGCAGCCGAGGAAGAGGA
CTGGGATTATGCACCACTGGTGCTGGCACCAGACGATCGCTCCTACAAATCTCAGTATCTGAACAATGGGCACAGAGGATTGGCAGA
AAGTACAAGAAAGTGCGGTTCATGGCATATACCGATGAGACCTTCAAGACTCGCGAAGCCATCCAGCACGAGAGCGGCATCCTGGGAC
CACTGCTGTACGGAGAAGTGGGAGACACCCTGCTGATCATTTTCAAGAACCAGGCCAGCCGGCCTTACAATATCTATCCACATGGGAT
TACAGATGTGCGCCCTCTGTACAGCAGGAGACTGCCAAAGGGCGTCAAACACCTGAAGGACTTCCCAATCCTGCCCGGAGAAATCTTC
AAGTACAAGTGGACTGTCACCGTCGAGGATGGCCCCACTAAGAGCGACCCTCGGTGCCTGACCCGCTACTATTCTAGTTTCGTGAATA
TGGAAAGAGATCTGGCAAGCGGACTGATCGGACCACTGCTGATTTGTTACAAAGAGAGCGTGGATCAGAGAGGCAACCAGATCATGTC
CGACAAGCGGAATGTGATTCTGTTCAGTGTCTTTGACGAAAACAGGTCATGGTACCTGACCGAGAACATCCAGAGATTCCTGCCTAAT
CCAGCTGGGGTGCAGCTGGAAGATCCTGAGTTTCAGGCATCTAACATCATGCATAGTATTAATGGCTACGTGTTCGACAGTTTGCAGC
TGAGCGTGTGCCTGCACGAGGTCGCTTACTGGTATATCCTGAGCATTGGGGCACAGACAGATTTCCTGAGCGTGTTCTTTTCCGGCTA
CACTTTTAAGCATAAAATGGTCTATGAGGACACACTGACTCTGTTCCCCTTCAGCGGCGAAACCGTGTTTATGAGCATGGAGAATCCC
GGACTGTGGATTCTGGGGTGCCACAACAGCGATTTCAGAAATCGCGGAATGACTGCCCTGCTGAAAGTGTCAAGCTGTGACAAGAACA
CCGGGGACTACTATGAAGATTCATACGAGGACATCAGCGCATATCTGCTGTCCAAAAACAATGCCATTGAACCCGGTCTTTTAGTCA
GAATGGCGCGCCAACATCAGAGAGCGCCACCCCTGAAAGTGGTCCCGGGAGCGAGCCAGCCACATCTGGGTCGGAAACGCCAGGCACA
<u>AGTGAGTCTGCAACTCCCGAGTCCGGACCTGGCTCCGAGCCTGCCACTAGCGGCTCCGAGACTCCGGGAACTTCCGAGAGCGCTACAC</u>
<u>CAGAAAGCGGACCCGGAACCAGTACCGAACCTAGCGAGGGCTCTGCTCCGGGCAGCCCAGCCGGCTCTCCTACATCCACGGAGGAGGG</u>
<u>CACTTCCGAATCCGCCACCCCGGAGTCAGGGCCAGGATCTGAACCCGCTACCTCAGGCAGTGAGACGCCAGGAACGAGCGAGTCCGCT</u>
<u>ACACCGGAGAGTGGGCCAGGGAGCCCTGCTGGATCTCCTACGTCCACTGAGGAAGGGTCACCAGCGGGCTCGCCCACCAGCACTGAAG</u>
<u>AAGGTGCCTCGAGCCCTCCAGTGCTGAAGCGGCACCAGCGCGAGATCACCCGCACTACCCTGCAGAGTGATCAGGAAGAGATCGACTA</u>
CGACGATACAATTTCTGTGGAAATGAAGAAAGAGGACTTCGATATCTATGACGAAGATGAGAACCAGAGTCCTCGATCATTCCAGAAG
AAAACCAGGCATTACTTTATTGCCGCAGTGGAGCGGCTGTGGGATTATGGCATGTCCTCTAGTCCTCACGTGCTGCGAAATAGGGCCC
AGTCAGGAAGCGTCCCACAGTTCAAGAAAGTGGTCTTCCAGGAGTTTACAGACGGGTCCTTTACTCAGCCACTGTACAGGGGCGAACT
GAACGAGCACCTGGGACTGCTGGGGCCCTATATCAGAGCAGAAGTGGAGGATAACATTATGGTCACCTTCAGAAATCAGGCCTCTCGG
CCTTACAGTTTTTATTCAAGCCTGATCTCTTACGAAGAGGACCAGCGACAGGGAGCTGAACCACGAAAAACTTCGTGAAGCCTAATG
AGACCAAAACATACTTTTGGAAGGTGCAGCACCATATGGCCCCAACAAAAGACGAGTTCGATTGCAAGGCATGGGCCTATTTTTCTGA
CGTGGATCTGGAGAAGGACGTGCACAGTGGCCTGATTGGCCCACTGCTGGTGTGCCATACTAACACCCTGAATCCAGCCCACGGCCGG
CAGGTCACTGTCCAGGAGTTCGCTCTGTTCTTTACCATCTTTGATGAGACAAAGAGCTGGTACTTCACCGAAAACATGGAGCGAAATT
GCAGGGCTCCATGTAACATTCAGATGGAAGACCCCACATTCAAGGAGAACTACCGCTTTCATGCTATCAATGGATACATCATGGATAC
TCTGCCCGGGCTGGTCATGGCACAGGACCAGAGAATCCGGTGGTATCTGCTGAGCATGGGCAGCAACGAGAATATCCACTCAATTCAT
TTCAGCGGGCACGTGTTTACTGTCAGGAAGAAAGAAGAGTACAAGATGGCCCTGTACAACCTGTATCCCGGCGTGTTCGAAACCGTCG
AGATGCTGCCTAGCAAGGCCGGAATCTGGAGAGTGGAATGCCTGATTGGAGAGCACCTGCATGCTGGGATGTCTACCCTGTTTCTGGT
GTACAGTAATAAGTGTCAGACACCCCTGGGAATGGCATCCGGGCATATCAGGGATTTCCAGATTACCGCATCTGGACAGTACGGACAG
TGGGCACCTAAGCTGGCTAGACTGCACTATTCCGGATCTATCAACGCTTGGTCCACAAAAGAGCCTTTCTCTTGGATTAAGGTGGACC
TGCTGGCCCCAATGATCATTCATGGCATCAAAACTCAGGGAGCTCGGCAGAAGTTCTCCTCTCTGTACATCTCACAGTTTATCATCAT
GTACAGCCTGGATGGGAAGAAATGGCAGACATACCGCGGCAATAGCACAGGAACTCTGATGGTGTTCTTTGGCAACGTGGACAGCAGC
GGAATCAAGCACAACATTTTCAATCCCCCTATCATTGCTAGATACATCCGGCTGCACCCAACCCATTATTCTATTCGAAGTACACTGA
GGATGGAACTGATGGGATGCGATCTGAACAGTTGTTCAATGCCCCTGGGGATGGAGTCCAAGGCAATCTCTGACGCCCAGATTACCGC
CAGCTCCTACTTCACTAATATGTTTGCTACCTGGAGCCCTTCCAAAGCAAGACTGCACCTGCAAGGCCGCAGCAACGCATGGCGACCA
CAGGTGAACAATCCCAAGGAGTGGTTGCAGGTCGATTTTCAGAAAACTATGAAGGTGACCGGGGTCACAACTCAGGGCGTGAAAAGTC
TGCTGACCTCAATGTACGTCAAGGAGTTCCTGATCTCTAGTTCACAGGACGGACATCAGTGGACACTGTTCTTTCAGAACGGGAAGGT
GAAAGTCTTCCAGGGCAATCAGGATTCCTTTACACCTGTGGTCAACAGTCTAGACCCTCCACTGCTGACCAGATACCTGAGAATCCAC
CCTCAGTCCTGGGTGCACCAGATTGCCCTGAGAATGGAAGTGCTGGGATGCGAGGCCCAGGATCTGTACTGA

Underlined = XTEN nucleotide sequence (SEQ ID NO: 18)

FIG. 8C: coFVIII-6-XTEN – SEQ ID NO: 72

ATGCAGATTGAGCTGTCCACTTGTTTCTTCCTGTGCCTCCTGCGCTTCTGTTTCTCCGCCACTCGCCGGTACTACCTTGGAGCCGTGG
AGCTTTCATGGGACTACATGCAGAGCGACCTGGGCGAACTCCCCGTGGATGCCAGATTCCCCCCCGCGTGCCAAAGTCCTTCCCCTT
TAACACCTCCGTGGTGTACAAGAAAACCCTCTTTGTCGAGTTCACTGACCACCTGTTCAACATCGCCAAGCCGCGCCCACCTTGGATG
GGCCTCCTGGGACCGACCATTCAAGCTGAAGTGTACGACACCGTGGTGATCACCCTGAAGAACATGGCGTCCCACCCCGTGTCCCTGC
ATGCGGTCGGAGTGTCCTACTGGAAGGCCTCCGAAGGAGCTGAGTACGACGACCAGACTAGCCAGCGGGAAAAGGAGGACGATAAAGT
GTTCCCGGGCGGCTCGCATACTTACGTGTGGCAAGTCCTGAAGGAAAACGGACCTATGGCATCCGATCCTCTGTGCCTGACTTACTCC
TACCTTTCCCATGTGGACCTCGTGAAGGACCTGAACAGCGGGCTGATTGGTGCACTTCTCGTGTGCCGCGAAGGTTCGCTCGCTAAGG
AAAAGACCCAGACCCTCCATAAGTTCATCCTTTTGTTCGCTGTGTTCGATGAAGGAAAGTCATGGCATTCCGAAACTAAGAACTCGCT
GATGCAGGACCGGGATGCCGCCTCAGCCCGCGCCTGGCCTAAAATGCATACAGTCAACGGATACGTGAATCGGTCACTGCCCGGGCTC
ATCGGTTGTCACAGAAAGTCCGTGTACTGGACGTCATCGGCATGGGCACTACGCCTGAAGTGCACTCCATCTTCCTGGAAGGGCACA
CCTTCCTCGTGCGCAACCACCGCCAGGCCTCTCTGGAAATCTCCCCGATTACCTTTCTGACCGCCCAGACTCTGCTCATGGACCTGGG
GCAGTTCCTTCTCTTCTGCCACATCTCCAGCCATCAGCACGACGGAATGGAGGCCTACGTGAAGGTGGACTCATGCCCGGAAGAACCT
CAGTTGCGGATGAAGAACAACGAGGAGGCCGAGGACTATGACGACGATTTGACTGACTCCGAGATGGACGTCGTGCGGTTCGATGACG
ACAACAGCCCCAGCTTCATCCAGATTCGCAGCGTGGCCAAGAAGCACCCCAAAACCTGGGTGCACTACATCGCGGCCGAGGAAGAAGA
TTGGGACTACGCCCCGTTGGTGCTGGCACCCGATGACCGGTCGTACAAGTCCCAGTATCTGAACAATGGTCCGCAGCGGATTGGCAGA
AAGTACAAGAAAGTGCGGTTCATGGCGTACACTGACGAAACGTTTAAGACCCGGGAGGCCATTCAACATGAGAGCGGCATTCTGGGAC
CACTGCTGTACGGAGAGGTCGGCGATACCCTGCTCATCATCTTCAAAAACCAGGCCTCCCGGCCTTACAACATCTACCCTCACGGAAT
CACCGACGTGCGGCCACTCTACTCGCGGCGCCTGCCGAAGGGCGTCAAGCACCTGAAAGACTTCCCTATCCTGCCGGGCGAAATCTTC
AAGTATAAGTGGACCGTCACCGTGGAGGACGGGCCCACCAAGAGCGATCCTAGGTGTCTGACTCGGTACTACTCCAGCTTCGTGAACA
TGGAACGGGACCTGGCATCGGGACTCATTGGACCGCTGCTGATCTGCTACAAAGAGTCGGTGGATCAACGCGGCAACCAGATCATGTC
CGACAAGCGCAACGTGATCCTGTTCTCCGTGTTTGATGAAACAGATCCTGGTACCTCACTGAAAACATCCAGAGGTTCCTCCCAAAC
CCCGCAGGAGTGCAACTGGAGGACCCTGAGTTTCAGGCCTCGAATATCATGCACTCGATTAACGGTTACGTGTTCGACTCGCTGCAGC
TGAGCGTGTGCCTCCATGAAGTCGCTTACTGGTACATTCTGTCCATCGGCGCCCAGACTGACTTCCTGAGCGTGTTCTTTTCCGGTTA
CACCTTTAAGCACAAGATGGTGTACGAAGATACCCTGACCCTGTTCCCTTTCTCCGGCGAAACGGTGTTCATGTCGATGGAGAACCCG
GGTCTGTGGATTCTGGGATGCCACAACAGCGACTTTCGGAACCGCGGAATGACTGCCCTGCTGAAGGTGTCCTCATGCGACAAGAACA
CCGGAGACTACTACGAGGACTCCTACGAGGATATCTCAGCCTACCTCCTGTCCAAGAACAACGCGATCGAGCCGCGCAGCTTCAGCCA
GAACGGCGCGCCAACATCAGAGAGCGCCACCCCTGAAAGTGGTCCCGGGAGCGAGCCAGCCACATCTGGGTCGGAAACGCCAGGCACA
AGTGAGTCTGCAACTCCCGAGTCCGGACCTGGCTCCGAGCCTGCCACTAGCGGCTCCGAGACTCCGGGAACTTCCGAGAGCGCTACAC
CAGAAAGCGGACCCGGAACCAGTACCGAACCTAGCGAGGGCTCTGCTCCGGGCAGCCCAGCCGGCTCTCCTACATCCACGGAGGAGGG
CACTTCCGAATCCGCCACCCCGGAGTCAGGGCCAGGATCTGAACCCGCTACCTCAGGCAGTGAGACGCCAGGAACGAGCGAGTCCGCT
ACACCGGAGAGTGGGCCAGGGAGCCCTGCTGGATCTCCTACGTCCACTGAGGAAGGGTCACCAGCGGGCTCGCCCACCAGCACTGAAG
AAGGTGCCTCGAGCCCGCCTGTGCTGAAGAGGCACCAGCGAGAAATTACCCGGACCACCCTCCAATCGGATCAGGAGGAAATCGACTA
CGACGACACCATCTCGGTGGAAATGAAGAAGGAAGATTTCGATATCTACGACGAGGACGAAAATCAGTCCCCTCGCTCATTCCAAAAG
AAAACTAGACACTACTTTATCGCCGCGGTGGAAAGACTGTGGGACTATGGAATGTCATCCAGCCCTCACGTCCTTCGGAACCGGGCCC
AGAGCGGATCGGTGCCTCAGTTCAAGAAAGTGGTGTTCCAGGAGTTCACCGACGGCAGCTTCACCCAGCCGCTGTACCGGGGAGAACT
GAACGAACACCTGGGCCTGCTCGGTCCCTACATCCGCGCGAAGTGGAGGATAACATCATGGTGACCTTCCGTAACCAAGCATCCAGA
CCTTACTCCTTCTATTCCTCCCTGATCTCATACGAGGAGGACCAGCGCCAAGGCGCCGAGCCCCGCAAGAACTTCGTCAAGCCCAACG
AGACTAAGACCTACTTCTGGAAGGTCCAACACCATATGGCCCCGACCAAGGATGAGTTTGACTGCAAGGCCTGGGCCTACTTCTCCGA
CGTGGACCTTGAGAAGGATGTCCATTCCGGCCTGATCGGGCCGCTGCTCGTGTGTCACACCAACACCCTGAACCCAGCGCATGGACGC
CAGGTCACCGTCCAGGAGTTTGCTCTGTTCTTCACCATTTTTGACGAAACTAAGTCCTGGTACTTCACCGAGAATATGGAGCGAAACT
GTAGAGCGCCCTGCAATATCCAGATGGAAGATCCGACTTTCAAGGAGAACTATAGATTCCACGCCATCAACGGGTACATCATGGATAC
TCTGCCGGGGCTGGTCATGGCCCAGGATCAGAGGATTCGGTGGTACTTGCTGTCAATGGGATCGAACGAAAACATTCACTCCATTCAC
TTCTCCGGTCACGTGTTCACTGTGCGCAAGAAGGAGGAGTACAAGATGGCGCTGTACAATCTGTACCCCGGGGTGTTCGAAACTGTGG
AGATGCTGCCGTCCAAGGCCGGCATCTGGAGAGTGGAGTGCCTGATCGGAGAGCACCTCCACGCGGGGATGTCCACCCTCTTCCTGGT
GTACTCGAATAAGTGCCAGACCCCGCTGGGCATGGCCTCGGGCCACATCAGAGACTTCCAGATCACAGCAAGCGGACAATACGGCCAA
TGGGCGCCGAAGCTGGCCCGCTTGCACTACTCCGGATCGATCAACGCATGGTCCACCAAGGAACCGTTCTCGTGGATTAAGGTGGACC
TCCTGGCCCCTATGATTATCCACGGAATTAAGACCCAGGGCGCCAGGCAGAAGTTCTCCTCCCTGTACATCTCGCAATTCATCATCAT
GTACAGCCTGGACGGGAAGAAGTGGCAGACTTACAGGGGAAACTCCACCGGCACCCTGATGGTCTTTTTCGGCAACGTGGATTCCTCC
GGCATTAAGCACAACATCTTCAACCCACCGATCATAGCCAGATATATTAGGCTCCACCCCACTCACTACTCAATCCGCTCAACTCTTC
GGATGGAACTCATGGGGTGCGACCTGAACTCCTGCTCCATGCCGTTGGGGATGGAATCAAAGGCTATTAGCGACGCCCAGATCACCGC
GAGCTCCTACTTCACTAACATGTTCGCCACCTGGAGCCCCTCCAAGGCCAGGCTGCACTTGCAGGGACGGTCAAATGCCTGGCGGCCG
CAAGTGAACAATCCGAAGGAATGGCTTCAAGTGGATTTCCAAAAGACCATGAAAGTGACCGGAGTCACCACCCAGGGAGTGAAGTCCC
TTCTGACCTCGATGTATGTGAAGGAGTTCCTGATTAGCAGCAGCCAGGACGGGCACCAGTGGACCCTGTTCTTCCAAAACGGAAAGGT
CAAGGTGTTCCAGGGGAACCAGGACTCGTTCACACCCGTGGTGAACTCCCTGGACCCCCCACTGCTGACGCGGTACTTGAGGATTCAT
CCTCAGTCCTGGGTCCATCAGATTGCATTGCGAATGGAAGTCCTGGGCTGCGAGGCCCAGGACCTGTACTGA

Underlined = XTEN nucleotide sequence (SEQ ID NO: 18)

FIG. 9: Plasmid Map of pLV-coFVIII-52-XTEN
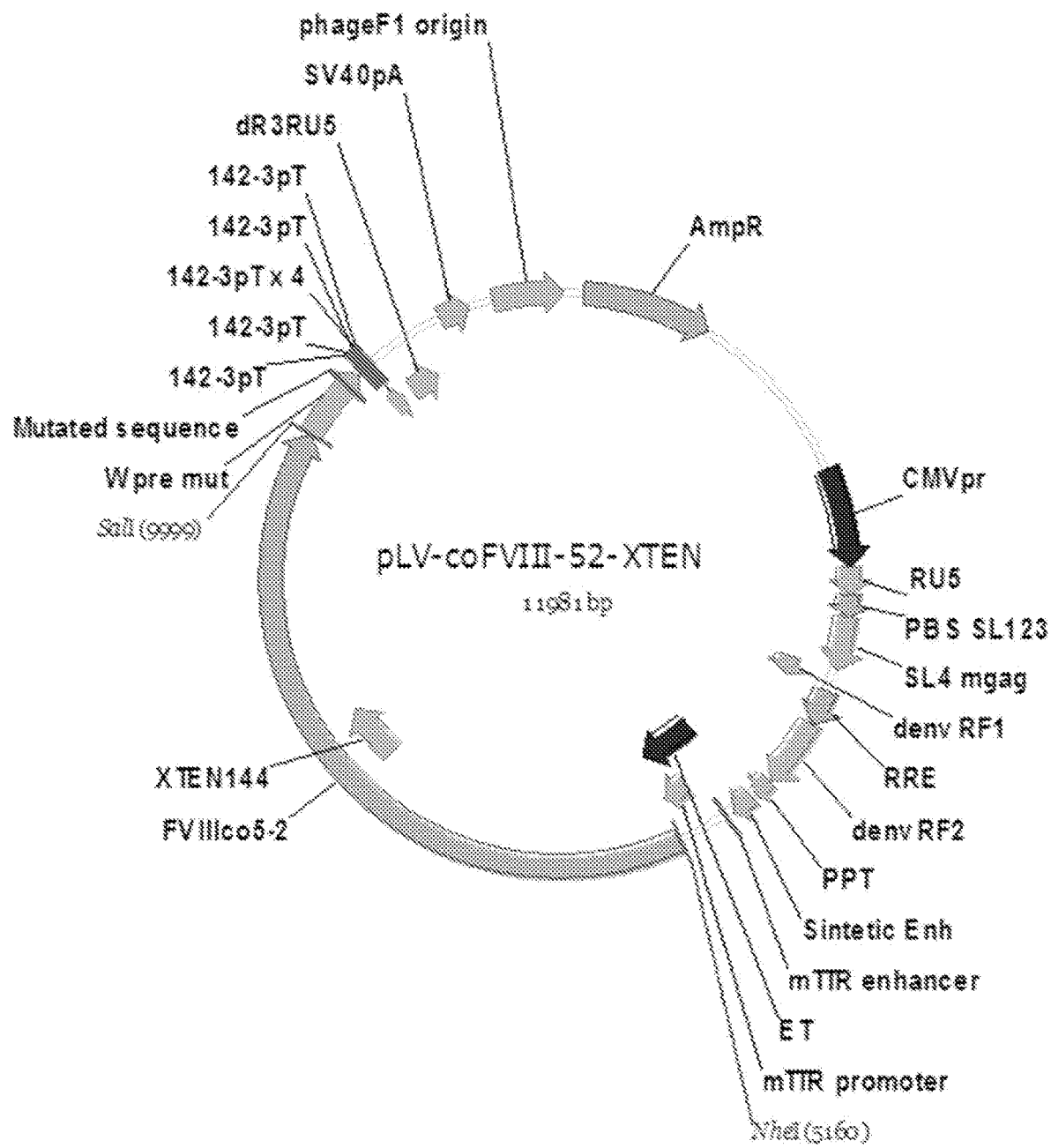

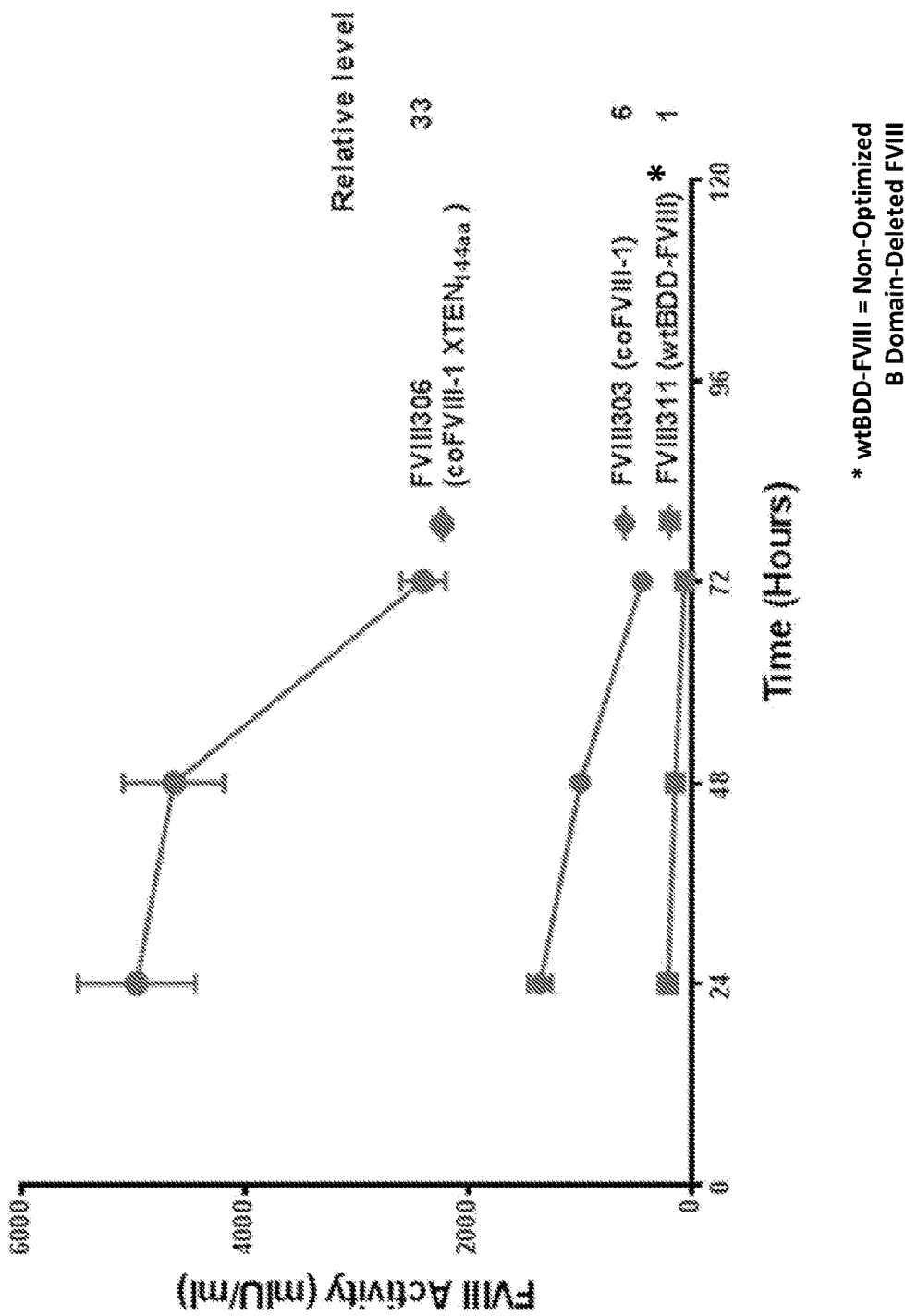

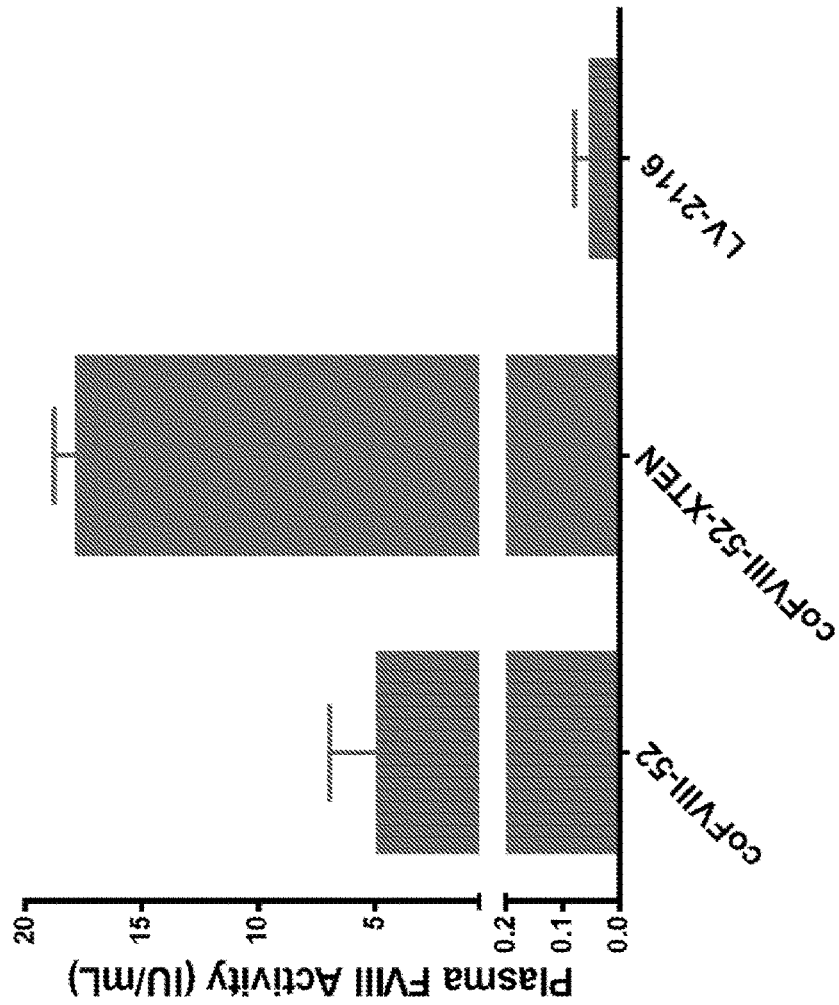
FIG. 10B: FVIII Activity in HemA Mice 21 days Post Lentiviral Injection

FIG. 11A: Full-Length Mature Human Factor VIII, Amino Acid Sequence (SEQ ID NO: 15)

ATRRYYLGAVELSWDYMQSDLGELPVDARFPPRVPKSFPFNTSVVYKKTLFVEFTDHLFNIAKPRPPWMGLLGPTIQAEVYDTVVITLK
NMASHPVSLHAVGVSYWKASEGAEYDDQTSQREKEDDKVFPGGSHTYVWQVLKENGPMASDPLCLTYSYLSHVDLVKDLNSGLIGA
LLVCREGSLAKEKTQTLHKFILLFAVFDEGKSWHSETKNSLMQDRDAASARAWPKMHTVNGYVNRSLPGLIGCHRKSVYWHVIGMGT
TPEVHSIFLEGHTFLVRNHRQASLEISPITFLTAQTLLMDLGQFLLFCHISSHQHDGMEAYVKVDSCPEEPQLRMKNNEEAEDYDDDLT
DSEMDVVRFDDDNSPSFIQIRSVAKKHPKTWVHYIAAEEEDWDYAPLVLAPDDRSYKSQYLNNGPQRIGRKYKKVRFMAYTDETFKTR
EAIQHESGILGPLLYGEVGDTLLIFKNQASRPYNIYPHGITDVRPLYSRRLPKGVKHLKDFPILPGEIFKYKWTVTVEDGPTKSDPRCLTRYY
SSFVNMERDLASGLIGPLLICYKESVDQRGNQIMSDKRNVILFSVFDENRSWYLTENIQRFLPNPAGVQLEDPEFQASNIMHSINGYVF
DSLQLSVCLHEVAYWYILSIGAQTDFLSVFFSGYTFKHKMVYEDTLTLFPFSGETVFMSMENPGLWILGCHNSDFRNRGMTALLKVSSC
DKNTGDYYEDSYEDISAYLLSKNNAIEPRSFSQNSRHPSTRQKQFNATTIPENDIEKTDPWFAHRTPMPKIQNVSSSDLLMLLRQSPTPH
GLSLSDLQEAKYETFSDDPSPGAIDSNNSLSEMTHFRPQLHHSGDMVFTPESGLQLRLNEKLGTTAATELKKLDFKVSSTSNNLISTIPSD
NLAAGTDNTSSLGPPSMPVHYDSQLDTTLFGKKSSPLTESGGPLSLSEENNDSKLLESGLMNSQESSWGKNVSSTESGRLFKGKRAHGP
ALLTKDNALFKVSISLLKTNKTSNNSATNRKTHIDGPSLLIENSPSVWQNILESDTEFKKVTPLIHDRMLMDKNATALRLNHMSNKTTSS
KNMEMVQQKKEGPIPPDAQNPDMSFFKMLFLPESARWIQRTHGKNSLNSGQGPSPKQLVSLGPEKSVEGQNFLSEKNKVVVGKGEF
TKDVGLKEMVFPSSRNLFLTNLDNLHENNTHNQEKKIQEEIEKKETLIQENVVLPQIHTVTGTKNFMKNLFLLSTRQNVEGSYDGAYAP
VLQDFRSLNDSTNRTKKHTAHFSKKGEEENLEGLGNQTKQIVEKYACTTRISPNTSQQNFVTQRSKRALKQFRLPLEETELEKRIIVDDTS
TQWSKNMKHLTPSTLTQIDYNEKEKGAITQSPLSDCLTRSHSIPQANRSPLPIAKVSSFPSIRPIYLTRVLFQDNSSHLPAASYRKKDSGVQ
ESSHFLQGAKKNNLSLAILTLEMTGDQREVGSLGTSATNSVTYKKVENTVLPKPDLPKTSGKVELLPKVHIYQKDLFPTETSNGSPGHLDL
VEGSLLQGTEGAIKWNEANRPGKVPFLRVATESSAKTPSKLLDPLAWDNHYGTQIPKEEWKSQEKSPEKTAFKKKDTILSLNACESNHAI
AAINEGQNKPEIEVTWAKQGRTERLCSQNPPVLKRHQREITRTTLQSDQEEIDYDDTISVEMKKEDFDIYDEDENQSPRSFQKKTRHYFI
AAVERLWDYGMSSSPHVLRNRAQSGSVPQFKKVVFQEFTDGSFTQPLYRGELNEHLGLLGPYIRAEVEDNIMVTFRNQASRPYSFYSSL
ISYEEDQRQGAEPRKNFVKPNETKTYFWKVQHHMAPTKDEFDCKAWAYFSDVDLEKDVHSGLIGPLLVCHTNTLNPAHGRQVTVQE
FALFFTIFDETKSWYFTENMERNCRAPCNIQMEDPTFKENYRFHAINGYIMDTLPGLVMAQDQRIRWYLLSMGSNENIHSIHFSGHVF
TVRKKEEYKMALYNLYPGVFETVEMLPSKAGIWRVECLIGEHLHAGMSTLFLVYSNKCQTPLGMASGHIRDFQITASGQYGQWAPKLA
RLHYSGSINAWSTKEPFSWIKVDLLAPMIIHGIKTQGARQKFSSLYISQFIIMYSLDGKKWQTYRGNSTGTLMVFFGNVDSSGIKHNIFN
PPIIARYIRLHPTHYSIRSTLRMELMGCDLNSCSMPLGMESKAISDAQITASSYFTNMFATWSPSKARLHLQGRSNAWRPQVNNPKEW
LQVDFQKTMKVTGVTTQGVKSLLTSMYVKEFLISSSQDGHQWTLFFQNGKVKVFQGNQDSFTPVVNSLDPPLLTRYLRIHPQSWVHQ
IALRMEVLGCEAQDLY

FIG. 11B: Full length von Willebrand Factor, Amino Acid Sequence (SEQ ID NO: 44)

ATRRYYLGAVELSWDYMQSDLGELPVDARFPPRVPKSFPFNTSVVYKKTLFVEFTDHLFNIAKPRPPWMGLLGPTIQAEVYDTVVITLK
NMASHPVSLHAVGVSYWKASEGAEYDDQTSQREKEDDKVFPGGSHTYVWQVLKENGPMASDPLCLTYSYLSHVDLVKDLNSGLIGA
LLVCREGSLAKEKTQTLHKFILLFAVFDEGKSWHSETKNSLMQDRDAASARAWPKMHTVNGYVNRSLPGLIGCHRKSVYWHVIGMGT
TPEVHSIFLEGHTFLVRNHRQASLEISPITFLTAQTLLMDLGQFLLFCHISSHQHDGMEAYVKVDSCPEEPQLRMKNNEEAEDYDDDLT
DSEMDVVRFDDDNSPSFIQIRSVAKKHPKTWVHYIAAEEEDWDYAPLVLAPDDRSYKSQYLNNGPQRIGRKYKKVRFMAYTDETFKTR
EAIQHESGILGPLLYGEVGDTLLIIFKNQASRPYNIYPHGITDVRPLYSRRLPKGVKHLKDFPILPGEIFKYKWTVTVEDGPTKSDPRCLTRYY
SSFVNMERDLASGLIGPLLICYKESVDQRGNQIMSDKRNVILFSVFDENRSWYLTENIQRFLPNPAGVQLEDPEFQASNIMHSINGYVF
DSLQLSVCLHEVAYWYILSIGAQTDFLSVFFSGYTFKHKMVYEDTLTLFPFSGETVFMSMENPGLWILGCHNSDFRNRGMTALLKVSSC
DKNTGDYYEDSYEDISAYLLSKNNAIEPRSFSQNSRHPSTRQKQFNATTIPENDIEKTDPWFAHRTPMPKIQNVSSSDLLMLLRQSPTPH
GLSLSDLQEAKYETFSDDPSPGAIDSNNSLSEMTHFRPQLHHSGDMVFTPESGLQLRLNEKLGTTAATELKKLDFKVSSTSNNLISTIPSD
NLAAGTDNTSSLGPPSMPVHYDSQLDTTLFGKKSSPLTESGGPLSLSEENNDSKLLESGLMNSQESSWGKNVSSTESGRLFKGKRAHGP
ALLTKDNALFKVSISLLKTNKTSNNSATNRKTHIDGPSLLIENSPSVWQNILESDTEFKKVTPLIHDRMLMDKNATALRLNHMSNKTTSS
KNMEMVQQKKEGPIPPDAQNPDMSFFKMLFLPESARWIQRTHGKNSLNSGQGPSPKQLVSLGPEKSVEGQNFLSEKNKVVVGKGEF
TKDVGLKEMVFPSSRNLFLTNLDNLHENNTHNQEKKIQEEIEKKETLIQENVVLPQIHTVTGTKNFMKNLFLLSTRQNVEGSYDGAYAP
VLQDFRSLNDSTNRTKKHTAHFSKKGEEENLEGLGNQTKQIVEKYACTTRISPNTSQQNFVTQRSKRALKQFRLPLEETELEKRIIVDDTS
TQWSKNMKHLTPSTLTQIDYNEKEKGAITQSPLSDCLTRSHSIPQANRSPLPIAKVSSFPSIRPIYLTRVLFQDNSSHLPAASYRKKDSGVQ
ESSHFLQGAKKNNLSLAILTLEMTGDQREVGSLGTSATNSVTYKKVENTVLPKPDLPKTSGKVELLPKVHIYQKDLFPTETSNGSPGHLDL
VEGSLLQGTEGAIKWNEANRPGKVPFLRVATESSAKTPSKLLDPLAWDNHYGTQIPKEEWKSQEKSPEKTAFKKKDTILSLNACESNHAI
AAINEGQNKPEIEVTWAKQGRTERLCSQNPPVLKRHQREITRTTLQSDQEEIDYDDTISVEMKKEDFDIYDEDENQSPRSFQKKTRHYFI
AAVERLWDYGMSSSPHVLRNRAQSGSVPQFKKVVFQEFTDGSFTQPLYRGELNEHLGLLGPYIRAEVEDNIMVTFRNQASRPYSFYSSL
ISYEEDQRQGAEPRKNFVKPNETKTYFWKVQHHMAPTKDEFDCKAWAYFSDVDLEKDVHSGLIGPLLVCHTNTLNPAHGRQVTVQE
FALFFTIFDETKSWYFTENMERNCRAPCNIQMEDPTFKENYRFHAINGYIMDTLPGLVMAQDQRIRWYLLSMGSNENIHSIHFSGHVF
TVRKKEEYKMALYNLYPGVFETVEMLPSKAGIWRVECLIGEHLHAGMSTLFLVYSNKCQTPLGMASGHIRDFQITASGQYGQWAPKLA
RLHYSGSINAWSTKEPFSWIKVDLLAPMIIHGIKTQGARQKFSSLYISQFIIMYSLDGKKWQTYRGNSTGTLMVFFGNVDSSGIKHNIFN
PPIIARYIRLHPTHYSIRSTLRMELMGCDLNSCSMPLGMESKAISDAQITASSYFTNMFATWSPSKARLHLQGRSNAWRPQVNNPKEW
LQVDFQKTMKVTGVTTQGVKSLLTSMYVKEFLISSSQDGHQWTLFFQNGKVKVFQGNQDSFTPVVNSLDPPLLTRYLRIHPQSWVHQ
IALRMEVLGCEAQDLY

(X is any natural amino acid)

FIG. 11C: XTEN AE42-4, protein sequence (SEQ ID NO: 46)

GAPGSPAGSPTSTEEGTSESATPESGPGSEPATSGSETPASS

FIG. 11D: XTEN AE42-4, DNA sequence (SEQ ID NO: 47)

GGCGCGCCAGGTTCTCCTGCTGGCTCCCCCACCTCAACAGAAGAGGGGACAAGCGAAAGCGCTACGCCTGAGAGTGGCCCTGGCT
CTGAGCCAGCCACCTCCGGCTCTGAAACCCCTGCCTCGAGC

FIG. 11E: XTEN AE144-2A, protein sequence (SEQ ID NO: 48)

TSTEPSEGSAPGSPAGSPTSTEEGTSTEPSEGSAPGTSTEPSEGSAPGTSESATPESGPGTSTEPSEGSAPGTSESATPESGPGSEPATSGSE
TPGTSTEPSEGSAPGTSTEPSEGSAPGTSESATPESGPGTSESATPESGPG

FIG. 11F: XTEN AE144-2A, DNA sequence (SEQ ID NO: 49)

GGCGCGCCAACCAGTACGGAGCCGTCCGAGGGGAGCGCACCAGGAAGCCCGGCTGGGAGCCCGACTTCTACCGAAGAGGGTACA
TCTACCGAACCAAGTGAAGGTTCAGCACCAGGCACCTCAACAGAACCCTCTGAGGGCTCGGCGCCTGGTACAAGTGAGTCCGCCAC
CCCAGAATCCGGGCCTGGGACAAGCACAGAACCTTCGGAAGGGAGTGCCCCTGGAACATCCGAATCGGCAACCCCAGAATCAGGG
CCAGGATCTGAGCCCGCGACTTCGGGCTCCGAGACGCCTGGGACATCCACCGAGCCCTCCGAAGGATCAGCCCCAGGCACCAGCA
CGGAGCCCTCTGAGGGAAGCGCACCTGGTACCAGCGAAAGCGCAACTCCCGAATCAGGTCCCGGTACGAGCGAGTCGGCGACCCC
GGAGAGCGGGCCAGGTGCCTCGAGC

FIG. 11G: XTEN AE144-3B, protein sequence (SEQ ID NO: 50 )

SPAGSPTSTEEGTSESATPESGPGSEPATSGSETPGTSESATPESGPGTSTEPSEGSAPGTSTEPSEGSAPGTSTEPSEGSAPGTSTEPSEGS
APGTSTEPSEGSAPGTSTEPSEGSAPGSPAGSPTSTEEGTSTEPSEGSAPG

FIG. 11H: XTEN AE144-3B, DNA sequence (SEQ ID NO: 51)

GGCGCGCCAAGTCCCGCTGGAAGCCCAACTAGCACCGAAGAGGGGACCTCAGAGTCCGCCACCCCCGAGTCCGGCCCTGGCTCTG
AGCCTGCCACTAGCGGCTCCGAGACTCCTGGCACATCCGAAAGCGCTACACCCGAGAGTGGACCCGGCACCTCTACCGAGCCCAGT
GAGGGCTCCGCCCCTGGAACAAGCACCGAGCCCAGCGAAGGCAGCGCCCCAGGGACCTCCACAGAGCCCAGTGAAGGCAGTGCT
CCTGGCACCAGCACCGAACCAAGCGAGGGCTCTGCACCCGGGACCTCCACCGAGCCAAGCGAAGGCTCTGCCCCTGGCACTTCCA
CCGAGCCCAGCGAAGGCAGCGCCCCTGGGAGCCCCGCTGGCTCTCCCACCAGCACTGAGGAGGGCACATCTACCGAACCAAGTGA
AGGCTCTGCACCAGGTGCCTCGAGC

FIG. 11I: XTEN AE144-4A, protein sequence (SEQ ID NO: 52)

TSESATPESGPGSEPATSGSETPGTSESATPESGPGSEPATSGSETPGTSESATPESGPGTSTEPSEGSAPGTSESATPESGPGSPAGSPTST
EEGSPAGSPTSTEEGSPAGSPTSTEEGTSESATPESGPGTSTEPSEGSAPG

FIG. 11J: XTEN AE144-4A, DNA sequence (SEQ ID NO: 53)

GGCGCGCCAACGTCCGAAAGTGCTACCCCTGAGTCAGGCCCTGGTAGTGAGCCTGCCACAAGCGGAAGCGAAACTCCGGGGACCT
CAGAGTCTGCCACTCCCGAATCGGGGCCAGGCTCTGAACCGGCCACTTCAGGGAGCGAAACACCAGGAACATCGGAGAGCGCTAC
CCCGGAGAGCGGGCCAGGAACTAGTACTGAGCCTAGCGAGGGAAGTGCACCTGGTACAAGCGAGTCCGCCACACCCGAGTCTGG
CCCTGGCTCTCCAGCGGGCTCACCCACGAGCACTGAAGAGGGCTCTCCCGCTGGCAGCCCAACGTCGACAGAAGAAGGATCACCA
GCAGGCTCCCCCACATCAACAGAGGAGGGTACATCAGAATCTGCTACTCCCGAGAGTGGACCCGGTACCTCCACTGAGCCCAGCG
AGGGGAGTGCACCAGGTGCCTCGAGC

FIG. 11K: XTEN AE144-5A, protein sequence (SEQ ID NO: 54)

TSESATPESGPGSEPATSGSETPGTSESATPESGPGSEPATSGSETPGTSESATPESGPGTSTEPSEGSAPGSPAGSPTSTEEGTSESATPESGP
GSEPATSGSETPGTSESATPESGPGSPAGSPTSTEEGSPAGSPTSTEEG

FIG. 11L: XTEN AE144-5A, DNA sequence (SEQ ID NO: 55)

GGCGCGCCAACATCAGAGAGCGCCACCCCTGAAAGTGGTCCCGGGAGCGAGCCAGCCACATCTGGGTCGGAAACGCCAGGCACAA
GTGAGTCTGCAACTCCCGAGTCCGGACCTGGCTCCGAGCCTGCCACTAGCGGCTCCGAGACTCCGGGAACTTCCGAGAGCGCTACAC
CAGAAAGCGGACCCGGAACCAGTACCGAACCTAGCGAGGGCTCTGCTCCGGGCAGCCCAGCCGGCTCTCCTACATCCACGGAGGAG
GGCACTTCCGAATCCGCCACCCCGGAGTCAGGGCCAGGATCTGAACCCGCTACCTCAGGCAGTGAGACGCCAGGAACGAGCGAGTC
CGCTACACCGGAGAGTGGGCCAGGGAGCCCTGCTGGATCTCCTACGTCCACTGAGGAAGGGTCACCAGCGGGCTCGCCCACCAGCA
CTGAAGAAGGTGCCTCGAGC

FIG. 11M: XTEN AE144-6B, protein sequence (SEQ ID NO: 56)

TSTEPSEGSAPGTSESATPESGPGTSESATPESGPGTSESATPESGPGSEPATSGSETPGSEPATSGSETPGSPAGSPTSTEEGTSTEPSEGSAP
GTSTEPSEGSAPGSEPATSGSETPGTSESATPESGPGTSTEPSEGSAPG

FIG. 11N: XTEN AE144-6B, DNA sequence (SEQ ID NO: 57)

GGCGCGCCAACATCTACCGAGCCTTCCGAAGGCTCTGCCCCTGGGACCTCAGAATCTGCAACCCCTGAAAGCGGCCCTGGAACCTCC
GAAAGTGCCACTCCCGAGAGCGGCCCAGGGACAAGCGAGTCAGCAACCCCTGAGTCTGGACCCGGCAGCGAGCCTGCAACCTCTGG
CTCAGAGACTCCCGGCTCAGAACCCGCTACCTCAGGCTCCGAGACACCCGGCTCTCCTGCTGGGAGTCCCACTTCCACCGAGGAAGG
AACATCCACTGAGCCTAGTGAGGGCTCTGCCCCTGGAACCAGCACAGAGCCAAGTGAGGGCAGTGCACCAGGATCCGAGCCAGCAA
CCAGCGGGTCCGAGACTCCCGGGACCTCTGAGTCTGCCACCCCAGAGAGCGGACCCGGCACTTCAACCGAGCCCTCCGAAGGATCA
GCACCAGGTGCCTCGAGC

FIG. 11O: XTEN AG144-1, protein sequence (SEQ ID NO: 58)

PGSSPSASTGTGPGSSPSASTGTGPGTPGSGTASSSPGSSTPSGATGSPGSSPSASTGTGPGASPGTSSTGSPGTPGSGTASSSPGSSTPSGA
TGSPGTPGSGTASSSPGASPGTSSTGSPGASPGTSSTGSPGTPGSGTASSS

FIG. 11P: XTEN AG144-1, DNA sequence (SEQ ID NO: 59)

GGCGCGCCACCCGGGTCGTCCCCGTCGGCGTCCACCGGAACAGGGCCAGGGTCATCCCCGTCAGCGTCGACTGGGACGGGACCCGG
GACACCCGGTTCGGGGACTGCATCCTCCTCGCCTGGTTCGTCCACCCCGTCAGGAGCCACGGGTTCGCCGGGAAGCAGCCCAAGCGC
ATCCACTGGTACAGGGCCTGGGGCTTCACCGGGTACTTCATCCACGGGGTCACCGGGAACGCCCGGATCGGGGACGGCTTCCTCATC
ACCAGGATCGTCAACACCCTCGGGCGCAACGGGCAGCCCCGGAACCCCTGGTTCGGGTACGGCGTCGTCGAGCCCCGGTGCGAGCC
CGGGAACAAGCTCGACAGGATCGCCTGGGCGTCACCCGGCACGTCGAGCACAGGCAGCCCCGGAACCCCTGGATCGGGAACCGC
GTCGTCAAGCGCCTCGAGC

FIG. 11Q: XTEN AG144-A, protein sequence (SEQ ID NO: 60)

GASPGTSSTGSPGSSPSASTGTGPGSSPSASTGTGPGTPGSGTASSSPGSSTPSGATGSPGSSPSASTGTGPGASPGTSSTGSPGTPGSGTAS
SSPGSSTPSGATGSPGTPGSGTASSSPGASPGTSSTGSPGASPGTSSTGSP

FIG. 11R: XTEN AG144-A, DNA sequence (SEQ ID NO: 61)

GGCGCGCCAGGTGCCTCGCCGGGAACATCATCAACTGGTTCACCCGGGTCATCCCCCTCGGCCTCAACCGGGACGGGTCCCGGCTCA
TCCCCCAGCGCCAGCACTGGAACAGGTCCTGGCACTCCTGGTTCCGGTACGGCATCGTCATCCCCGGGAAGCTCAACACCGTCCGGA
GCGACAGGATCACCTGGCTCGTCACCTTCGGCGTCAACTGGAACGGGGCCAGGGGCCTCACCCGGAACGTCCTCGACTGGGTCGCCT
GGTACGCCGGGATCAGGAACGGCCTCATCCTCGCCTGGGTCCTCAACGCCCTCGGGTGCGACTGGTTCGCCGGGAACTCCTGGCTCG
GGGACGGCCTCGTCGTCGCCTGGGGCATCACCGGGGACGAGCTCCACGGGGTCCCCTGGAGCGTCACCGGGGACCTCCTCGACAGG
TAGCCCGGCCTCGAGC

FIG. 11S: XTEN AG144-B, protein sequence (SEQ ID NO: 62)

GTPGSGTASSSPGSSTPSGATGSPGASPGTSSTGSPGTPGSGTASSSPGSSTPSGATGSPGSSPSASTGTGPGSSPSASTGTGPGSSTPSGAT
GSPGSSTPSGATGSPGASPGTSSTGSPGASPGTSSTGSPGASPGTSSTGSP

FIG. 11T: XTEN AG144-B, DNA sequence (SEQ ID NO: 63)

GGCGCGCCAGGTACACCGGGCAGCGGCACGGCTTCGTCGTCACCCGGCTCGTCCACACCGTCGGGAGCTACGGGAAGCCCAGGAGC
GTCACCGGGAACGTCGTCAACGGGGTCACCGGGTACGCCAGGTAGCGGCACGGCCAGCAGCTCGCCAGGTTCATCGACCCCGTCGG
GAGCGACTGGGTCGCCCGGATCAAGCCCGTCAGCTTCCACTGGAACAGGACCCGGGTCGTCGCCGTCAGCCTCAACGGGGACAGGA
CCTGGTTCATCGACGCCGTCAGGGGCGACAGGCTCGCCCGGATCGTCAACACCCTCGGGGGCAACGGGGAGCCCTGGTGCGTCGCC
TGGAACCCTCATCCACCGGAAGCCCGGGGGCCTCGCCGGGTACGAGCTCCACGGGATCGCCCGGAGCGTCCCCCGGAACTTCAAGCA
CAGGGAGCCCTGCCTCGAGC

FIG. 11U: XTEN AG144-C, protein sequence (SEQ ID NO: 64)

GTPGSGTASSSPGASPGTSSTGSPGASPGTSSTGSPGASPGTSSTGSPGSSPSASTGTGPGTPGSGTASSSPGASPGTSSTGSPGASPGTSST
GSPGASPGTSSTGSPGSSTPSGATGSPGSSTPSGATGSPGASPGTSSTGSP

FIG. 11V: XTEN AG144-C, DNA sequence (SEQ ID NO: 65)

GGCGCGCCAGGTACACCCGGATCGGGTACAGCGTCATCGAGCCCCGGTGCGTCACCTGGTACGTCGAGCACGGGGTCGCCAGGGGC
GTCCCCTGGGACGTCCTCAACAGGCTCGCCCGGTGCGTCACCCGGCACGTCGTCCACGGGTTCACCTGGTAGCTCCCCTTCCGCGTCC
ACTGGCACCGGGCCTGGAACTCCGGGGAGCGGCACAGCGAGCTCGTCGCCGGGAGCATCGCCTGGGACATCGAGCACCGGGTCGC
CAGGAGCATCGCCCGGAACATCCAGCACAGGAAGCCCCGGCGCGTCGCCCGGGACATCAAGCACAGGTTCCCCGGGATCGAGCACG
CCGTCCGGAGCCACTGGATCACCAGGGAGCTCGACACCTTCCGGCGCAACGGGATCGCCCGGAGCCAGCCCGGGTACGTCAAGCAC
TGGCTCCCCTGCCTCGAGC

FIG. 11W: XTEN AG144-F, protein sequence (SEQ ID NO: 66)

GSSPSASTGTGPGSSPSASTGTGPGASPGTSSTGSPGASPGTSSTGSPGSSTPSGATGSPGSSPSASTGTGPGASPGTSSTGSPGSSPSASTG
TGPGTPGSGTASSSPGSSTPSGATGSPGSSTPSGATGSPGASPGTSSTGSP

FIG. 11X: XTEN AG144-F, DNA sequence (SEQ ID NO: 67)

GGCGCGCCAGGCTCCAGCCCCTCCGCGAGCACGGGAACCGGACCAGGTTCGTCACCCTCAGCATCAACGGGGACGGGACCGGGGG
CGTCACCAGGAACGTCCTCCACCGGCTCGCCGGGTGCATCACCCGGAACGTCATCGACCGGATCGCCAGGGAGCTCGACGCCATCAG
GCGCAACAGGATCACCTGGCTCAAGCCCTAGCGCGTCAACCGGCACGGGTCGGGTGCCTCCCCTGGCACGTCCAGCACCGGATCAC
CCGGATCGAGCCCATCCGCCTCAACCGGAACCGGACCCGGTACACCAGGGTCGGGAACAGCCTCCTCGTCACCAGGCTCCTCAACCC
CCTCGGGAGCCACGGGTTCGCCCGGTTCGTCAACGCCTTCCGGAGCAACTGGTAGCCCCGGAGCATCGCCAGGAACTTCGAGCACG
GGGTCGCCCGCCTCGAGC

FIG. 11Y: ET Promoter, DNA sequence (SEQ ID NO: 69)

CTCGAGGTCAATTCACGCGAGTTAATAATTACCAGCGCGGGCCAAATAAATAATCCGCGAGGGGCAGGTGACGTTTGCCCAGCGCGC
GCTGGTAATTATTAACCTCGCGAATATTGATTCGAGGCCGCGATTGCCGCAATCGCGAGGGGCAGGTGACCTTTGCCCAGCGCGCGT
TCGCCCCGCCCCGGACGGTATCGATAAGCTTAGGAGCTTGGGCTGCAGGTCGAGGGCACTGGAGGATGTTGAGTAAGATGGAAAA
CTACTGATGACCCTTGCAGAGACAGAGTATTAGGACATGTTTGAACAGGGGCCGGGCGATCAGCAGGTAGCTCTAGAGGATCCCCGT
CTGTCTGCACATTTCGTAGAGCGAGTGTTCCGATACTCTAATCTCCCTAGGCAAGGTTCATATTTGTGTAGGTTACTTATTCTCCTTTTG
TTGACTAAGTCAATAATCAGAATCAGCAGGTTTGGAGTCAGCTTGGCAGGGATCAGCAGCCTGGGTTGGAAGGAGGGGGTATAAAA
GCCCCTTCACCAGGAGAAGCCGTCACACAGATCCACAAGCTCCTGCCACCATGG

FIG. 11Z: coFVIII-1 – DNA Sequence (SEQ ID NO: 68)

ATGCAGATTGAGCTGTCTACTTGCTTTTTCCTGTGCCTGCTGAGGTTTTGCTTTTCCGCTACACGAAGGTATTATCTGGGGGCTGTGGA
ACTGTCTTGGGATTACATGCAGAGTGACCTGGGAGAGCTGCCAGTGGACGCAAGGTTTCCCCCTAGAGTCCCTAAGTCATTCCCCTTC
AACACTAGCGTGGTCTACAAGAAAACACTGTTCGTGGAGTTTACTGATCACCTGTTCAACATCGCAAAGCCTAGGCCACCCTGGATGG
GACTGCTGGGGCCAACAATCCAGGCCGAGGTGTACGACACCGTGGTCATTACACTTAAGAACATGGCCTCACACCCCGTGAGCCTGC
ATGCTGTGGGCGTCAGCTACTGGAAGGCTTCCGAAGGAGCAGAGTATGACGATCAGACTTCCCAGAGAGAAAAAGAGGACGATAAG
GTGTTTCCTGGCGGATCTCATACCTACGTGTGGCAGGTCCTGAAAGAGAATGGCCCTATGGCCTCCGACCCTCTGTGCCTGACCTACT
CTTATCTGAGTCACGTGGACCTGGTCAAGGATCTGAACAGCGGCCTGATCGGAGCCCTGCTGGTGTGCAGGGAAGGAAGCCTGGCTA
AGGAGAAAACCCAGACACTGCATAAGTTCATTCTGCTGTTCGCCGTGTTTGACGAAGGGAAATCATGGCACAGCGAGACAAAGAATA
GTCTGATGCAGGACAGGGATGCCGCTTCAGCCAGAGCTTGGCCCAAAATGCACACTGTGAACGGCTACGTCAATCGCTCACTGCCTG
GGCTGATCGGCTGCCACCGAAAGAGCGTGTATTGGCATGTCATCGGGATGGGCACCACACCTGAAGTGCACTCCATTTTCCTGGAGG
ACATACCTTTCTGGTCCGCAACCACCGACAGGCTTCCCTGGAGATCTCTCCAATTACCTTCCTGACAGCACAGACTCTGCTGATGGAC
CTGGGGCAGTTCCTGCTGTTTTGCCACATCAGCTCCCACCAGCATGATGGCATGGAGGCTTACGTGAAAGTGGACTCTTGTCCCGAGG
AACCTCAGCTGCGGATGAAGAACAATGAGGAAGCAGAAGACTATGACGATGACCTGACCGACTCCGAGATGGATGTGGTCCGATTC
GATGACGATAACAGCCCCTCCTTTATCCAGATTAGATCTGTGGCCAAGAAACACCCTAAGACATGGGTCCATTACATCGCAGCCGAGG
AAGAGGACTGGGATTATGCACCACTGGTGCTGGCACCAGACGATCGCTCCTACAAATCTCAGTATCTGAACAATGGGCCACAGAGGA
TTGGCAGAAAGTACAAGAAAGTGCGGTTCATGGCATATACCGATGAGACCTTCAAGACTCGCGAAGCCATCCAGCACGAGAGCGGCA
TCCTGGGACCACTGCTGTACGGAGAAGTGGGAGACACCCTGCTGATCATTTTCAAGAACCAGGCCAGCCGGCCTTACAATATCTATCC
ACATGGGATTACAGATGTGCGCCCTCTGTACAGCAGGAGACTGCCAAAGGGCGTCAAACACCTGAAGGACTTCCCAATCCTGCCCGG
AGAAATCTTCAAGTACAAGTGGACTGTCACCGTCGAGGATGGCCCCACTAAGAGCGACCCTCGGTGCCTGACCCGCTACTATTCTAGT
TTCGTGAATATGGAAAGAGATCTGGCAAGCGGACTGATCGGACCACTGCTGATTTGTTACAAAGAGAGCGTGGATCAGAGAGGCAAC
CAGATCATGTCCGACAAGCGGAATGTGATTCTGTTCAGTGTCTTTGACGAAAACAGGTCATGGTACCTGACCGAGAACATCCAGAGAT
TCCTGCCTAATCCAGCTGGGGTGCAGCTGGAAGATCCTGAGTTTCAGGCATCTAACATCATGCATAGTATTAATGGCTACGTGTTCGA
CAGTTTGCAGCTGAGCGTGTGCCTGCACGAGGTCGCTTACTGGTATATCCTGAGCATTGGGGCACAGACAGATTTCCTGAGCGTGTTC
TTTTCCGGCTACACTTTTAAGCATAAAATGGTCTATGAGGACACACTGACTCTGTTCCCCTTCAGCGGCGAAACCGTGTTTATGAGCAT
GGAGAATCCCGGACTGTGGATTCTGGGGTGCCACAACAGCGATTTCAGAAATCGCGGAATGACTGCCCTGCTGAAAGTGTCAAGCTG
TGACAAGAACACCGGGGACTACTATGAAGATTCATACGAGGACATCAGCGCATATCTGCTGTCCAAAAACAATGCCATTGAACCCCG
GTCTTTTAGTCAGAATCCTCCAGTGCTGAAGAGGCACCAGAGGGAGATCACCCGCACTACCCTGCAGAGTGATCAGGAAGAGATCGA
CTACGACGATACAATTTCTGTGGAAATGAAGAAAGAGGACTTCGATATCTATGACGAAGATGAGAACCAGAGTCCTCGATCATTCCAG
AAGAAAACCAGGCATTACTTTATTGCCGCAGTGGAGCGGCTGTGGGATTATGGCATGTCCTCTAGTCCTCACGTGCTGCGAAATAGG
GCCCAGTCAGGAAGCGTCCCACAGTTCAAGAAAGTGGTCTTCCAGGAGTTTACAGACGGGTCCTTTACTCAGCCACTGTACAGGGGC
GAACTGAACGAGCACCTGGGACTGCTGGGGCCCTATATCAGAGCAGAAGTGGAGGATAACATTATGGTCACCTTCAGAAATCAGGCC
TCTCGGCCTTACAGTTTTTATTCAAGCCTGATCTCTTACGAAGAGGACCAGCGACAGGGAGCTGAACCACGAAAAAACTTCGTGAAGC
CTAATGAGACCAAAACATACTTTTGGAAGGTGCAGCACCATATGGCCCCAACAAAAGACGAGTTCGATTGCAAGGCATGGGCCTATTT
TTCTGACGTGGATCTGGAGAAGGACGTGCACAGTGGCCTGATTGGCCCACTGCTGGTGTGCCATACTAACACCCTGAATCCAGCCCAC
GGCCGGCAGGTCACTGTCCAGGAGTTCGCTCTGTTCTTTACCATCTTTGATGAGACAAAGAGCTGGTACTTCACCGAAAACATGGAGC
GAAATTGCAGGGCTCCATGTAACATTCAGATGGAAGACCCCACATTCAAGGAGAACTACCGCTTTCATGCTATCAATGGATACATCAT
GGATACTCTGCCCGGGCTGGTCATGGCACAGGACCAGAGAATCCGGTGGTATCTGCTGAGCATGGGCAGCAACGAGAATATCCACTC
AATTCATTTCAGCGGGCACGTGTTTACTGTCAGGAAGAAAGAAGAGTACAAGATGGCCCTGTACAACCTGTATCCCGGCGTGTTCGAA
ACCGTCGAGATGCTGCCTAGCAAGGCCGGAATCTGGAGAGTGGAATGCCTGATTGGAGAGCACCTGCATGCTGGGATGTCTACCCTG
TTTCTGGTGTACAGTAATAAGTGTCAGACACCCCTGGGAATGGCATCCGGGCATATCAGGGATTTCCAGATTACCGCATCTGGACAGT
ACGGACAGTGGGCACCTAAGCTGGCTAGACTGCACTATTCCGGATCTATCAACGCTTGGTCCACAAAAGAGCCTTTCTCTTGGATTAA
GGTGGACCTGCTGGCCCCAATGATCATTCATGGCATCAAAACTCAGGGAGCTCGGCAGAAGTTCTCCTCTCTGTACATCTCACAGTTTA
TCATCATGTACAGCCTGGATGGGAAGAAATGGCAGACATACCGCGGCAATAGCACAGGAACTCTGATGGTGTTCTTTGGCAACGTGG
ACAGCAGCGGAATCAAGCACAACATTTTCAATCCCCCTATCATTGCTAGATACATCCGGCTGCACCCAACCCATTATTCTATTCGAAGT
ACACTGAGGATGGAACTGATGGGATGCGATCTGAACAGTTGTTCAATGCCCCTGGGGATGGAGTCCAAGGCAATCTCTGACGCCCAG
ATTACCGCCAGCTCCTACTTCACTAATATGTTTGCTACCTGGAGCCCTTCCAAAGCAAGACTGCACCTGCAAGGCCGCAGCAACGCATG
GCGACCACAGGTGAACAATCCCAAGGAGTGGTTGCAGGTCGATTTTCAGAAAACTATGAAGGTGACCGGGGTCACAACTCAGGGCG
TGAAAAGTCTGCTGACCTCAATGTACGTCAAGGAGTTCCTGATCTCTAGTTCACAGGACGGACATCAGTGGACACTGTTCTTTCAGAA
CGGGAAGGTGAAAGTCTTCCAGGGCAATCAGGATTCCTTTACACCTGTGGTCAACAGTCTAGACCCTCCACTGCTGACCAGATACCTG
AGAATCCACCCTCAGTCCTGGGTGCACCAGATTGCCCTGAGAATGGAAGTGCTGGGATGCGAGGCCCAGGATCTGTACTGA

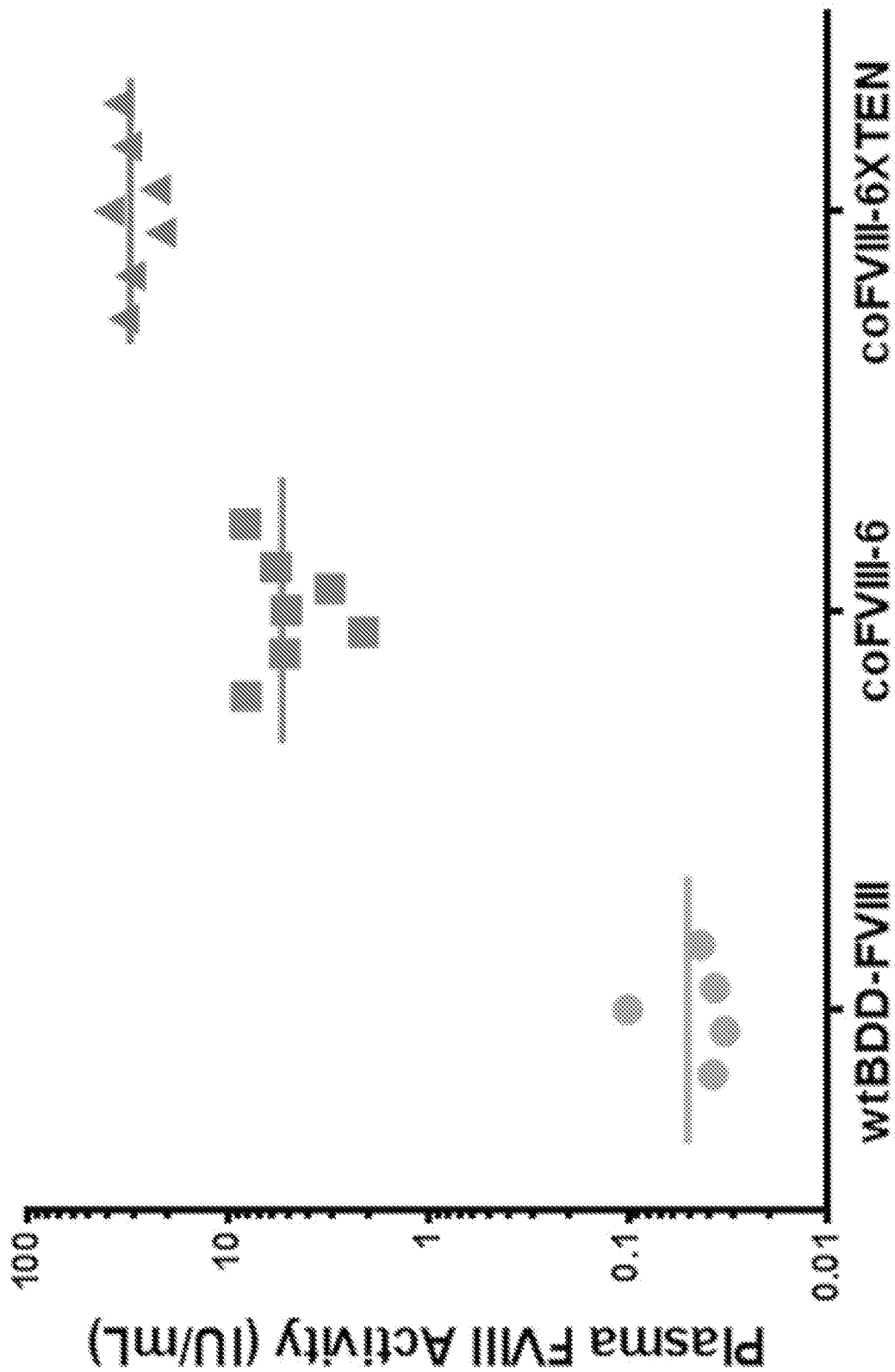
FIG. 12A: IV Injection of HemA Mice with LV-FVIII

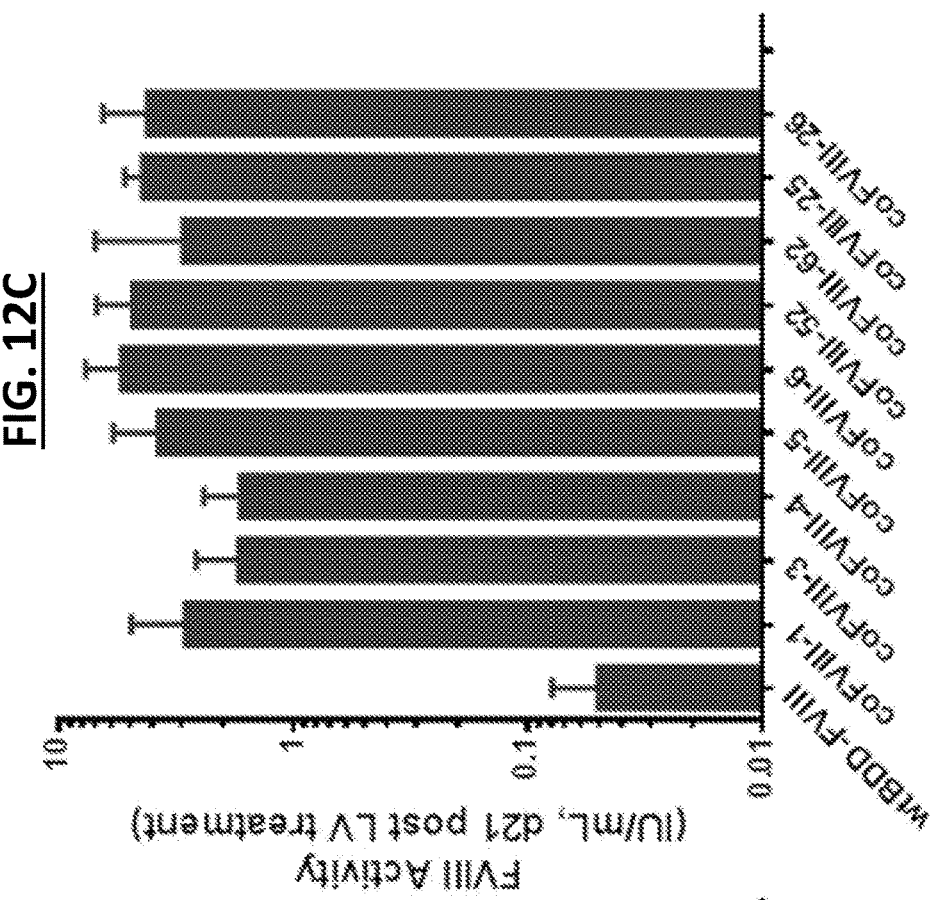
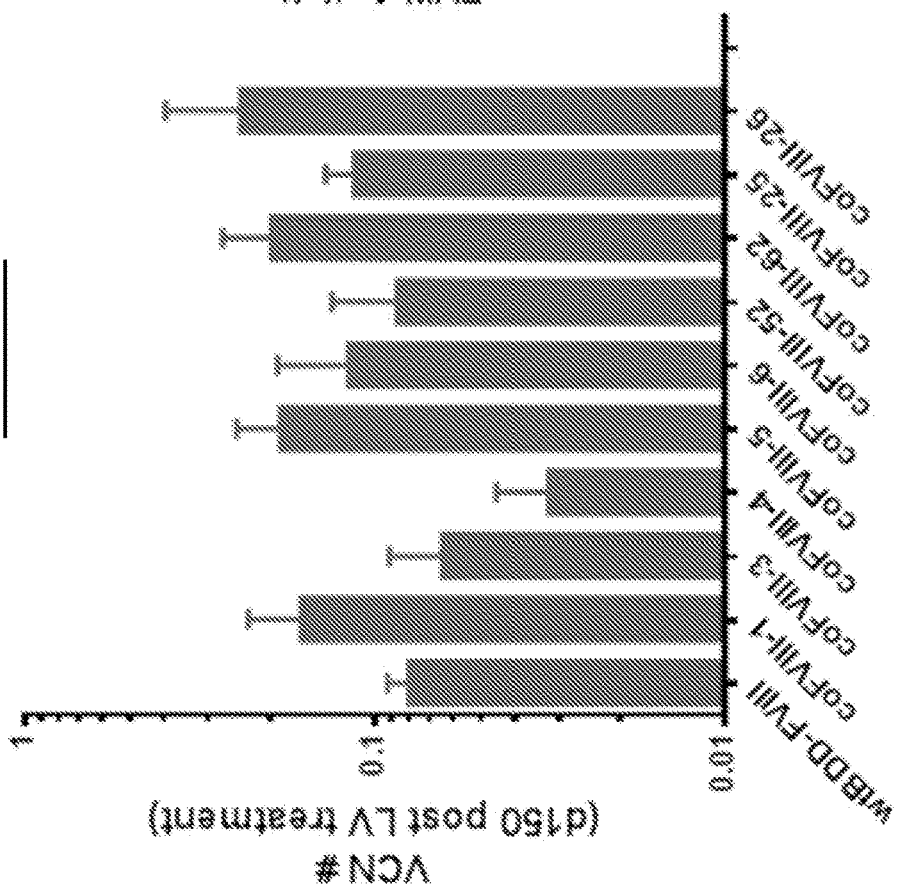

coFVIII-5 coFVIII-5

| Parameter | Parameter description | Normal range |
|---|---|---|
| CT (sec) | clotting time | 120-480 |
| CFT (sec) | clot formation time | 60-240 |
| α(°) | alpha angle | 27-60 |
| A5 (mm) | amplitude 5 min after CT | na |
| A20 (mm) | amplitude 20 min after CT | na |
| MCF (mm) | maximum clot firmness | 40-60 |

OPTIMIZED FACTOR VIII GENES

CROSS-REFERENCE TO RELATED APPLICATIONS

This application is a 35 U.S.C. § 371 filing of International Patent Application No. PCT/US2017/015879, filed Jan. 31, 2017, which claims priority to U.S. Provisional Patent Application Ser. Nos. 62/409,739, filed Oct. 18, 2016, and 62/289,696, filed Feb. 1, 2016, the entire disclosures of which are hereby incorporated herein by reference.

REFERENCE TO SEQUENCE LISTING SUBMITTED ELECTRONICALLY

The content of the electronically submitted sequence listing in ASCII text file (Name: 4159_4690002_ST25.txt; Size: 204,234 bytes; and Date of Creation: Jul. 31, 2018) was originally submitted in the International Application No. PCT/US2017/015879 and is incorporated herein by reference in its entirety.

BACKGROUND OF THE DISCLOSURE

The blood coagulation pathway, in part, involves the formation of an enzymatic complex of Factor VIIIa (FVIIIa) and Factor IXa (FIXa) (Xase complex) on the surface of platelets. FIXa is a serine protease with relatively weak catalytic activity without its cofactor FVIIIa. The Xase complex cleaves Factor X (FX) into Factor Xa (FXa), which in turn interacts with Factor Va (FVa) to cleave prothrombin and generate thrombin. Hemophilia A is a bleeding disorder caused by mutations and/or deletions in the FVIII (FVIII) gene resulting in a deficiency of FVIII activity (Peyvandi et al. 2006). In some cases, patients have reduced levels of FVIII due to the presence of FVIII inhibitors, such as anti-FVIII antibodies.

Hemophilia A is characterized by spontaneous hemorrhage and excessive bleeding. Over time, the repeated bleeding into muscles and joints, which often begins in early childhood, results in hemophilic arthropathy and irreversible joint damage. This damage is progressive and can lead to severely limited mobility of joints, muscle atrophy and chronic pain (Rodriguez-Merchan, E. C., *Semin. Thromb. Hemost.* 29:87-96 (2003), which is herein incorporated by reference in its entirety).

The disease can be treated by replacement therapy targeting restoration of FVIII activity to 1 to 5% of normal levels to prevent spontaneous bleeding (see, e.g., Mannucci, P. M., et al., *N. Engl. J. Med.* 344:1773-9 (2001), herein incorporated by reference in its entirety). There are plasma-derived and recombinant FVIII products available to treat bleeding episodes on-demand or to prevent bleeding episodes from occurring by treating prophylactically. Based on the half-life of these products (10-12 hr) (White G. C., et al., *Thromb. Haemost.* 77:660-7 (1997); Morfini, M., *Haemophilia* 9 (suppl 1):94-99; discussion 100 (2003)), treatment regimens require frequent intravenous administration, commonly two to three times weekly for prophylaxis and one to three times daily for on-demand treatment (Manco-Johnson, M. J., et al., *N. Engl. J. Med.* 357:535-544 (2007)), each of which is incorporated herein by reference in its entirety. Such frequent administration is inconvenient and costly.

A major impediment in providing a low-cost recombinant FVIII protein to patients is the high cost of commercial production. FVIII protein expresses poorly in heterologous expression systems, two to three orders of magnitude lower than similarly sized proteins. (Lynch et al., *Hum. Gene. Ther.;* 4:259-72 (1993). The poor expression of FVIII is due in part to the presence of cis-acting elements in the FVIII coding sequence that inhibit FVIII expression, such as transcriptional silencer elements (Hoeben et al., *Blood* 85:2447-2454 (1995)), matrix attachment-like sequences (MARs) (Fallux et al., *Mol. Cell. Biol.* 16:4264-4272 (1996)), and transcriptional elongation inhibitory elements (Koeberl et al., *Hum. Gene. Ther.;* 6:469-479 (1995)).

Advances in our understanding of the biology of FVIII expression has led to the development of more potent FVIII variants. For instance, biochemical studies demonstrated that the FVIII B-domain was dispensable for FVIII cofactor activity. Deletion of the B-domain resulted in a 17-fold increase in mRNA levels over full-length wild-type FVIII and a 30% increase in secreted protein. (Toole et al., *Proc Natl Acad Sci USA* 83:5939-42 (1986)). This led to the development of B domain-deleted (BDD) FVIII protein concentrate, which is now widely used in the clinic. Recent studies, however, indicate that full length and BDD hFVIII misfold in the ER lumen, resulting in activation of the unfolded protein response (UPR) and apoptosis of murine hepatocytes.

Thus, there exists a need in the art for FVIII sequences that express efficiently in heterologous systems.

SUMMARY OF THE DISCLOSURE

Disclosed are codon optimized nucleic acid molecules encoding a polypeptide with FVIII activity. In one aspect, the disclosure provides an isolated nucleic acid molecule comprising a nucleotide sequence which comprises a first nucleic acid sequence encoding an N-terminal portion of a Factor VIII (FVIII) polypeptide and a second nucleic acid sequence encoding a C-terminal portion of a FVIII polypeptide; wherein the first nucleic acid sequence has at least 85%, at least 90%, at least 95%, at least 96%, at least 97%, at least 98%, or at least 99% sequence identity to (i) nucleotides 58-2277 and 2320-1791 of SEQ ID NO: 3 or (ii) nucleotides 58-2277 and 2320-1791 of SEQ ID NO: 4; and wherein the N-terminal portion and the C-terminal portion together have a FVIII polypeptide activity.

The disclosure also provides an isolated nucleic acid molecule comprising a nucleotide sequence which comprises a first nucleic acid sequence encoding an N-terminal portion of a FVIII polypeptide and a second nucleic acid sequence encoding a C-terminal portion of a FVIII polypeptide; wherein the second nucleic acid sequence has at least 85%, at least 90%, at least 95%, at least 96%, at least 97%, at least 98%, or at least 99% sequence identity to (i) nucleotides 1792-2277 and 2320-4374 of SEQ ID NO: 5 or (ii) 1792-2277 and 2320-4374 of SEQ ID NO: 6; and wherein the N-terminal portion and the C-terminal portion together have a FVIII polypeptide activity.

In some embodiments, the disclosure provides an isolated nucleic acid molecule comprising a nucleotide sequence encoding a polypeptide with FVIII activity, wherein the nucleotide sequence comprises a nucleic acid sequence having at least 91%, at least 95%, at least 96%, at least 97%, at least 98%, or at least 99% sequence identity to nucleotides 58-2277 and 2320-4374 of SEQ ID NO: 1. In other embodiments, the disclosure provides an isolated nucleic acid molecule comprising a nucleotide sequence encoding a polypeptide with FVIII activity, wherein the nucleotide sequence comprises a nucleic acid sequence having at least about 94%, at least about 95%, at least 96%, at least 97%, at least 98%, or at least 99% sequence identity to nucleotides 58-2277 and 2320-4374 of SEQ ID NO: 2. In one embodiment, the disclosure provides an isolated nucleic acid molecule comprising a nucleotide sequence encoding a polypeptide with FVIII activity, wherein the nucleotide sequence comprises a nucleic acid sequence having at least 85%, at least 86%, at least 87%, at least 88%, at least 89%, at least 90%, at least 91%, at least 95%, at least 96%, at least 97%, at least 98%, or at least 99% sequence identity to nucleotides 58-2277 and 2320-4374 of SEQ ID NO: 70. In another embodiment, the disclosure provides an isolated nucleic acid molecule comprising a nucleotide sequence encoding a polypeptide with FVIII activity, wherein the nucleotide sequence comprises a nucleic acid sequence having at least 85%, at least 86%, at least 87%, at least 88%, at least 89%, at least 90%, at least 91%, at least 95%, at least 96%, at least 97%, at least 98%, or at least 99% sequence identity to nucleotides 58-2277 and 2320-4374 of SEQ ID NO: 71.

In some embodiments, the disclosure provides an isolated nucleic acid molecule comprising a nucleotide sequence encoding a polypeptide with FVIII activity, wherein the nucleotide sequence comprises a nucleic acid sequence having at least about 92%, at least about 93%, at least about 94%, at least about 95%, at least 96%, at least 97%, at least 98% or at least 99% sequence identity to nucleotides 58-2277 and 2320-4374 of SEQ ID NO: 3.

In some embodiments, the disclosure provides an isolated nucleic acid molecule comprising a nucleotide sequence encoding a polypeptide with FVIII activity, wherein the nucleotide sequence comprises a nucleic acid sequence having at least about 91%, at least about 92%, at least about 93%, at least about 94%, at least about 95%, at least 96%, at least 97%, at least 98% or at least 99% sequence identity to nucleotides 58-2277 and 2320-4374 of SEQ ID NO: 4.

In some embodiments, the disclosure provides an isolated nucleic acid molecule comprising a nucleotide sequence encoding a polypeptide with FVIII activity, wherein the nucleotide sequence comprises a nucleic acid sequence having at least 89%, at least 90%, at least 91%, at least 92%, at least 93%, at least 94%, at least 95%, at least 96%, at least 97%, at least 98%, or at least 99% sequence identity to nucleotides 58-2277 and 2320-4374 of SEQ ID NO: 5.

In some embodiments, the disclosure provides an isolated nucleic acid molecule comprising a nucleotide sequence encoding a polypeptide with FVIII activity, wherein the nucleotide sequence comprises a nucleic acid sequence having at least 89%, at least 90%, at least 91%, at least 92%, at least 93%, at least 94%, at least 95%, at least 96%, at least 97%, at least 98%, or at least 99% sequence identity to nucleotides 58-2277 and 2320-4374 of SEQ ID NO: 6.

In some embodiments, the disclosure provides a method of increasing expression of a polypeptide with FVIII activity in a subject comprising administering an isolated nucleic acid molecule or a vector disclosed herein to a subject in need thereof, wherein the expression of the polypeptide is increased relative to a reference nucleic acid molecule comprising SEQ ID NO: 16 or the vector comprising the reference nucleic acid molecule.

In some embodiments, the disclosure provides a method of treating a bleeding disorder comprising: administering to a subject in need thereof a nucleic acid molecule, a vector, or a polypeptide disclosed herein.

EMBODIMENTS

E1. An isolated nucleic acid molecule comprising a nucleotide sequence which comprises a first nucleic acid sequence encoding an N-terminal portion of a Factor VIII (FVIII) polypeptide and a second nucleic acid sequence encoding a C-terminal portion of a FVIII polypeptide; wherein the first nucleic acid sequence has at least 85%, at least 90%, at least 95%, at least 96%, at least 97%, at least 98%, or at least 99% sequence identity to (i) nucleotides 58-2277 and 2320-1791 of SEQ ID NO: 3 or (ii) nucleotides 58-2277 and 2320-1791 of SEQ ID NO: 4; and wherein the N-terminal portion and the C-terminal portion together have a FVIII polypeptide activity.

E2. The isolated nucleic acid molecule of E1, wherein the first nucleotide sequence comprises nucleotides 58-1791 of SEQ ID NO: 3 or nucleotides 58-1791 of SEQ ID NO: 4.

E3. The isolated nucleic acid molecule of E1 or E2, wherein the second nucleotide sequence has at least 60%, at least 70%, at least 80%, at least 90%, at least 95%, at least 96%, at least 97%, at least 98%, or at least 99% sequence identity to nucleotides 1792-2277 and 2320-4374 of SEQ ID NO: 3 or 1792-2277 and 2320-4374 of SEQ ID NO: 4.

E4. The isolated nucleic acid molecule of E1 or E2, wherein the second nucleotide sequence comprises nucleotides 1792-2277 and 2320-4374 of SEQ ID NO: 3 or 1792-2277 and 2320-4374 of SEQ ID NO: 4.

E5. An isolated nucleic acid molecule comprising a nucleotide sequence which comprises a first nucleic acid sequence encoding an N-terminal portion of a FVIII polypeptide and a second nucleic acid sequence encoding a C-terminal portion of a FVIII polypeptide; wherein the second nucleic acid sequence has at least 85%, at least 90%, at least 95%, at least 96%, at least 97%, at least 98%, or at least 99% sequence identity to (i) nucleotides 1792-2277 and 2320-4374 of SEQ ID NO: 5 or (ii) 1792-2277 and 2320-4374 of SEQ ID NO: 6; and wherein the N-terminal portion and the C-terminal portion together have a FVIII polypeptide activity.

E6. The isolated nucleic acid molecule of E5, wherein the second nucleic acid sequence comprises nucleotides 1792-2277 and 2320-4374 of SEQ ID NO: 5 or 1792-2277 and 2320-4374 of SEQ ID NO: 6.

E7. The isolated nucleic acid molecule of E5 or E6, wherein the first nucleic acid sequence has at least 60%, at least 70%, at least 80%, at least 90%, at least 95%, at least 96%, at least 97%, at least 98%, or at least 99% sequence identity to nucleotides 58-1791 of SEQ ID NO: 5 or nucleotides 58-1791 of SEQ ID NO: 6.

E8. The isolated nucleic acid molecule of E5 or E6, wherein the first nucleic acid sequence comprises nucleotides 58-1791 of SEQ ID NO: 5 or nucleotides 58-1791 of SEQ ID NO: 6.

E9. An isolated nucleic acid molecule comprising a nucleotide sequence encoding a polypeptide with FVIII activity, wherein the nucleotide sequence comprises a nucleic acid sequence having at least 91%, at least 95%, at least 96%, at least 97%, at least 98%, or at least 99% sequence identity to nucleotides 58-2277 and 2320-4374 of SEQ ID NO: 1.

E10. The isolated nucleic acid molecule of E9, wherein the nucleotide sequence comprises nucleotides 58-2277 and 2320-4374 of SEQ ID NO: 1.

E11. An isolated nucleic acid molecule comprising a nucleotide sequence encoding a polypeptide with FVIII activity, wherein the nucleotide sequence comprises a nucleic acid sequence having at least about 94%, at least about 95%, at least 96%, at least 97%, at least 98%, or at least 99% sequence identity to nucleotides 58-2277 and 2320-4374 of SEQ ID NO: 2.

E12. The isolated nucleic acid molecule of E10, wherein the nucleotide sequence comprises nucleotides 58-2277 and 2320-4374 of SEQ ID NO: 2.

E13. An isolated nucleic acid molecule comprising a nucleotide sequence encoding a polypeptide with FVIII activity, wherein the nucleotide sequence comprises a nucleic acid sequence having at least 85%, at least 86%, at least 87%, at least 88%, at least 89%, at least 90%, at least 91%, at least 95%, at least 96%, at least 97%, at least 98%, or at least 99% sequence identity to nucleotides 58-2277 and 2320-4374 of SEQ ID NO: 70.

E14. The isolated nucleic acid molecule of E13, wherein the nucleotide sequence comprises nucleotides 58-2277 and 2320-4374 of SEQ ID NO: 70.

E15. An isolated nucleic acid molecule comprising a nucleotide sequence encoding a polypeptide with FVIII activity, wherein the nucleotide sequence comprises a nucleic acid sequence having at least 85%, at least 86%, at least 87%, at least 88%, at least 89%, at least 90%, at least 91%, at least 95%, at least 96%, at least 97%, at least 98%, or at least 99% sequence identity to nucleotides 58-2277 and 2320-4374 of SEQ ID NO: 71.

E16. The isolated nucleic acid molecule of E15, wherein the nucleotide sequence comprises nucleotides 58-2277 and 2320-4374 of SEQ ID NO: 71.

E17. An isolated nucleic acid molecule comprising a nucleotide sequence encoding a polypeptide with FVIII activity, wherein the nucleotide sequence comprises a nucleic acid sequence having at least about 92%, at least about 93%, at least about 94%, at least about 95%, at least 96%, at least 97%, at least 98% or at least 99% sequence identity to nucleotides 58-2277 and 2320-4374 of SEQ ID NO: 3.

E18. The isolated nucleic acid molecule of E17, wherein the nucleotide sequence comprises nucleotides 58-2277 and 2320-4374 of SEQ ID NO: 3.

E19. An isolated nucleic acid molecule comprising a nucleotide sequence encoding a polypeptide with FVIII activity, wherein the nucleotide sequence comprises a nucleic acid sequence having at least about 91%, at least about 92%, at least about 93%, at least about 94%, at least about 95%, at least 96%, at least 97%, at least 98% or at least 99% sequence identity to nucleotides 58-2277 and 2320-4374 of SEQ ID NO: 4.

E20. The isolated nucleic acid molecule of E19, wherein the nucleotide sequence comprises nucleotides 58-2277 and 2320-4374 of SEQ ID NO: 4.

E21. An isolated nucleic acid molecule comprising a nucleotide sequence encoding a polypeptide with FVIII activity, wherein the nucleotide sequence comprises a nucleic acid sequence having at least 89%, at least 90%, at least 91%, at least 92%, at least 93%, at least 94%, at least 95%, at least 96%, at least 97%, at least 98%, or at least 99% sequence identity to nucleotides 58-2277 and 2320-4374 of SEQ ID NO: 5.

E22. The isolated nucleic acid molecule of E21, wherein the nucleotide sequence comprises nucleotides 58-2277 and 2320-4374 of SEQ ID NO: 5.

E23. An isolated nucleic acid molecule comprising a nucleotide sequence encoding a polypeptide with FVIII activity, wherein the nucleotide sequence comprises a nucleic acid sequence having at least 89%, at least 90%, at least 91%, at least 92%, at least 93%, at least 94%, at least 95%, at least 96%, at least 97%, at least 98%, or at least 99% sequence identity to nucleotides 58-2277 and 2320-4374 of SEQ ID NO: 6.

E24. The isolated nucleic acid molecule of E23, wherein the nucleotide sequence comprises nucleotides 58-2277 and 2320-4374 of SEQ ID NO: 6.

E25. The isolated nucleic acid molecule of any one of E1 to E24, wherein the nucleotide sequence further comprises a nucleic acid sequence encoding a signal peptide.

E26. The isolated nucleic acid molecule of E25, wherein the signal peptide is a FVIII signal peptide.

E27. The isolated nucleic acid molecule of E25 or E26, wherein the nucleic acid sequence encoding a signal peptide is codon optimized.

E28. The isolated nucleic acid molecule of any one of E25 to E27, wherein the nucleic acid sequence encoding a signal peptide has at least 60%, at least 70%, at least 80%, at least 90%, at least 95%, at least 96%, at least 97%, at least 98%, at least 99%, or 100% sequence identity to (i) nucleotides 1 to 57 of SEQ ID NO: 1; (ii) nucleotides 1 to 57 of SEQ ID NO: 2; (iii) nucleotides 1 to 57 of SEQ ID NO: 3; (iv) nucleotides 1 to 57 of SEQ ID NO: 4; (v) nucleotides 1 to 57 of SEQ ID NO: 5; (vi) nucleotides 1 to 57 of SEQ ID NO: 6; (vii) nucleotides 1 to 57 of SEQ ID NO: 70; (viii) nucleotides 1 to 57 of SEQ ID NO: 71; or (ix) nucleotides 1 to 57 of SEQ ID NO: 68.

E29. The isolated nucleic acid molecule of any one of E1 to E28, wherein the nucleic acid molecule comprises one or more property selected from the group consisting of:
  (a) the human codon adaptation index the nucleic acid molecule or a portion thereof is increased relative to SEQ ID NO: 16;
  (b) the frequency of optimal codons of the nucleotide sequence or a portion thereof is increased relative to SEQ ID NO:16;
  (c) the nucleotide sequence or a portion thereof contains a higher percentage of G/C nucleotides compared to the percentage of G/C nucleotides in SEQ ID NO: 16;
  (d) the relative synonymous codon usage of the nucleotide sequence or a portion thereof is increased relative to SEQ ID NO: 16;
  (e) the effective number of codons of the nucleotide sequence or a portion thereof is reduced relative SEQ ID NO: 16;
  (f) the nucleotide sequence contains fewer MARS/ARS sequences (SEQ ID NOs: 21 and 22) relative to SEQ ID NO: 16;
  (g) the nucleotide sequence contains fewer destabilizing elements (SEQ ID NOs: 23 and 24) relative to SEQ ID NO: 16; and
  (h) any combination thereof.

E30. The isolated nucleic acid molecule of any one of E1 to E29 further comprising a heterologous nucleotide sequence.

E31. The isolated nucleic acid molecule of E30, wherein the heterologous nucleotide sequence encodes a heterologous amino acid sequence that is a half-life extender.

E32. The isolated nucleic acid molecule of E30 or E31, wherein the heterologous amino acid sequence is an immunoglobulin constant region or a portion thereof, transferrin, albumin, or a PAS sequence.

E33. The isolated nucleic acid molecule of E30 or E31, wherein the heterologous amino acid sequence is an Fc region.

E34. The isolated nucleic acid molecule of any one of E30 to E33, wherein the heterologous amino acid sequence is linked to the N-terminus or the C-terminus of the amino acid sequence encoded by the nucleotide sequence or inserted between two amino acids in the amino acid sequence encoded by the nucleotide sequence.

E35. The isolated nucleic acid molecule of E34, wherein the heterologous amino acid sequence is inserted between two amino acids at one or more insertion site selected from Table 3.

E36. The isolated nucleic acid molecule of any one of E30 to E35, which encodes a monomer-dimer hybrid molecule comprising FVIII.

E37. The isolated nucleic acid molecule of any one of E1 to E36, wherein the FVIII polypeptide is a full length FVIII or a B domain deleted FVIII.

E38. The isolated nucleic acid molecule of any one of any one of E1 to E37, operably linked to at least one transcription control sequence.

E39. A vector comprising the nucleic acid molecule of any one of E1 to E38.

E40. The vector of E39, wherein the vector is a viral vector.

E41. A host cell comprising the nucleic acid molecule of any one of E1 to E32 or the vector of E39 or E40.

E42. The host cell of E41, wherein the host cell is selected from the group consisting of: a CHO cell, a HEK293 cell, a BHK21 cell, a PER.C6 cell, a NS0 cell, and a CAP cell.

E43. A polypeptide encoded by the nucleic acid molecule of any one of E1 to E37 or the vector of E39 or 40 or produced by the host cell of E41 or E42.

E44. A method of producing a polypeptide with FVIII activity, comprising: culturing the host cell of E41 or E42 under conditions whereby a polypeptide with FVIII activity is produced; and, recovering the polypeptide with FVIII activity.

E45. The method of E44, wherein the expression of the polypeptide with FVIII activity is increased relative to a host cell cultured under the same conditions comprising a reference nucleotide sequence comprising SEQ ID NO: 16.

E46. A method of increasing expression of a polypeptide with FVIII activity in a subject comprising administering the isolated nucleic acid molecule of any one of E1 to E38 or the vector of E39 or E40 to a subject in need thereof, wherein the expression of the polypeptide is increased relative to a reference nucleic acid molecule comprising SEQ ID NO: 16 or the vector comprising the reference nucleic acid molecule.

E47. A method of increasing expression of a polypeptide with FVIII activity comprising culturing the host cell of E41 or E42 under conditions whereby a polypeptide with FVIII activity is expressed by the nucleic acid molecule, wherein the expression of the polypeptide with FVIII activity is increased relative to a host cell cultured under the same conditions comprising a reference nucleic acid sequence comprising SEQ ID NO: 16.

E48. The method of any one of E44 to E47, wherein the expression of the FVIII polypeptide is increased by at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 20-fold, at least about 25-fold, at least about 30-fold, at least about 35-fold, at least about 40-fold, at least about 50-fold, at least about 60-fold, at least about 70-fold, at least about 80-fold, at least about 90-fold, or at least about 100-fold.

E49. A method of improving yield of a polypeptide with FVIII activity comprising culturing the host cell of E41 or E42 under conditions whereby a polypeptide with FVIII activity is produced by the nucleic acid molecule, wherein the yield of polypeptide with FVIII activity is increased relative to a host cell cultured under the same conditions comprising a reference nucleic acid sequence comprising SEQ ID NO: 16.

E50. A method of treating a bleeding disorder comprising: administering to a subject in need thereof a nucleic acid molecule of any one of E1 to E38, the vector of E39 or E40, or the polypeptide of E43.

E51. The method of E50, wherein the bleeding disorder is characterized by a deficiency in FVIII.

E52. The method of E50, wherein the bleeding disorder is hemophilia.

E53. The method of E50, wherein the bleeding disorder is hemophilia A.

E54. The method of any one of E50 to E53, wherein plasma FVIII activity at 24 hours post administration is increased relative to a subject administered a reference nucleic acid molecule comprising SEQ ID NO: 16, a vector comprising the reference nucleic acid molecule, or a polypeptide encoded by the reference nucleic acid molecule.

E55. The method of E54, wherein the plasma FVIII activity is increased by at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 20-fold, at least about 25-fold, at least about 30-fold, at least about 35-fold, at least about 40-fold, at least about 50-fold, at least about 60-fold, at least about 70-fold, at least about 80-fold, at least about 90-fold, or at least about 100-fold.

E56. The vector of E39 or 40, wherein the vector is a lentiviral vector.

E57. The vector of any one of E39, E40, and E56 further comprising a tissue specific promoter, a tissue specific enhancer, or both a tissue specific promoter and a tissue specific enhancer.

E58. The vector of E57, wherein the tissue specific promoter and/or the tissue specific enhancer selectively enhances expression of the transgene in liver cells.

E59. The vector of E57 or E58, wherein the tissue specific promoter comprises a promoter sequence selected from the group consisting of a mouse thyretin promoter (mTTR), an endogenous human factor VIII promoter (F8), human alpha-1-antitrypsin promoter (hAAT), human albumin minimal promoter, and mouse albumin promoter.

E60. The vector of any one of E57 to E59, wherein the tissue specific promoter comprises mTTR promoter.

E61. A method of treating a bleeding disorder comprising: administering to a subject in need thereof the vector of any one of E56 to E60.

BRIEF DESCRIPTION OF THE DRAWINGS

FIGS. 1A-1J provide the codon optimized nucleotide sequences encoding B domain-deleted Factor VIII (SEQ ID NO: 17). FIG. 1A shows the nucleotide sequence of coFVIII-3 (SEQ ID NO:1). FIG. 1B shows the nucleotide sequence of coFVIII-4 (SEQ ID NO: 2). FIG. 1C shows the nucleotide sequence of coFVIII-5 (SEQ ID NO: 70). FIG. 1D shows the nucleotide sequence of coFVIII-6 (SEQ ID NO: 71). FIG. 1E shows the nucleotide sequence of coFVIII-52 (SEQ ID NO: 3). FIG. 1F shows the nucleotide sequence of coFVIII-62 (SEQ ID NO: 4). FIG. 1G shows the nucleotide sequence of coFVIII-25 (SEQ ID NO: 5). FIG. 1H shows the nucleotide sequence of coFVIII-26 (SEQ ID NO: 6). FIGS. 1I and 1J show the nucleotide and amino acid sequences, respectively, of B domain-deleted (BDD-FVIII) (SEQ ID NOs: 16 and 17, respectively).

FIGS. 2A-2J show codon usage bias adjustments in the codon optimized nucleotide sequences encoding BDD-FVIII. FIG. 2A shows the relative frequency of codons in the wild-type nucleotide sequence (before codon optimization) encoding BDD-FVIII, e.g., non-optimized BDD-FVIII. The human codon adaptation index (CAI) of the non-optimized BDD-FVIII sequence is 74%. FIG. 2B shows the relative frequency of codons in the coFVIII-1 variant sequence, which has a human CAI of 88%. FIG. 2C shows the relative frequency of codons in the coFVIII-3 variant sequence, which has a human CAI of 91%. FIG. 2D shows the relative frequency of codons in the coFVIII-4 variant sequence, which has a human CAI of 97%. FIG. 2E shows the relative frequency of codons in the coFVIII-5 variant sequence, which has a human CAI of 83%. FIG. 2F shows the relative frequency of codons in the coFVIII-6 variant sequence, which has a human CAI of 83%. FIG. 2G shows the relative frequency of codons in the coFVIII-52 variant sequence, which has a human CAI of 91%. FIG. 2H shows the relative frequency of codons in the coFVIII-62 variant sequence, which has a human CAI of 91%. FIG. 2I shows the relative frequency of codons in the coFVIII-25 variant sequence, which has a human CAI of 88%. FIG. 2J shows the relative frequency of codons in the coFVIII-26 variant sequence, which has a human CAI of 88%.

FIG. 3 provides a plasmid map of FVIII-303, which comprises coFVIII-1 in a pcDNA3 backbone under the control of the ET-enhanced transthyretin promoter, which is positioned upstream of the coFVIII-1 translation start site and which comprises a synthetic enhancer, an mTIR enhancer, and an mTIR promoter.

FIG. 4 shows a graphical representation of FVIII plasma activity in HemA mice following hydrodynamic injection of 5 µg FVIII-303 (coFVIII-1; circles) or 5 µg FVIII-311 (BDD-FVIII; squares). FVIII plasma activity was determined by a FVIII specific chromogenic assay at 24, 48, and 72 hours post-injection. The relative activity levels at 72 hours, normalized to the expression level of FVIII-311, are shown.

FIG. 5 shows a plasmid map of pLV-coFVIII-52, which comprises coFVIII-52 in a lentiviral plasmid under the control of an ET promoter, which is positioned upstream of the coFVIII-52 translation start site and which comprises a synthetic enhancer, an mTTR enhancer, and an mTTR promoter.

FIGS. 6A-6C show graphical representations of FVIII plasma activity in HemA mice following hydrodynamic injection of various FVIII encoding nucleotides. FVIII plasma activity was determined by a FVIII specific chromogenic assay at 24, 48, and 72 hours post-injection. FIG. 6A shows FVIII plasma activity in HemA mice following hydrodynamic injection of 5 µg LV-coFVIII-1 (filled circles), 5 µg LV-coFVIII-3 (triangles), 5 µg LV-coFVIII-4 (inverted triangles), 5 µg LV-coFVIII-5 (diamonds), or 5 µg LV-coFVIII-6 (open circles). FIG. 6B shows FVIII plasma activity in HemA mice following hydrodynamic injection of 5 µg LV-coFVIII-1 (circles), 5 µg LV-coFVIII-25 (triangles), or 5 µg LV-coFVIII-26 (inverted triangles). FIG. 6C shows FVIII plasma activity in HemA mice following hydrodynamic injection of 20 µg LV-2116 (non-codon optimized (WT) BDD-FVIII nucleotide sequence; open circles), 20 µg LV-coFVIII-1 (triangles), 20 µg LV-coFVIII-52 (squares), or 20 µg LV-coFVIII-62 (filled circles). The relative activity levels at 72 hours are shown for each plasmid, normalized to the expression levels of LV-coFVIII-1 (FIGS. 6A, 6B, and 6C) and/or LV-2116 (FIG. 6C), as indicated.

FIG. 7 shows plasma FVIII activity in HemA mice 24 days after injection with 1E8 TU/mouse lentiviral vector comprising coFVIII-1, coFVIII-5, coFVIII-52, coFVIII-6, or coFVIII-62 as compared with the LV-2116 (BDD-FVIII) control, and as measured by a FVIII-specific chromogenic assay. Error bars indicate standard deviations.

FIGS. 8A-8C provide the various codon optimized nucleotide sequences encoding BDD-FVIII fused to an XTEN. FIG. 8A shows the nucleotide sequence of coFVIII-52-XTEN (SEQ ID NO: 19), wherein a nucleotide sequence encoding an XTEN having 144 amino acids ("XTEN$_{144}$"; SEQ ID NO: 18; underlined) is inserted within the coFVIII-52 nucleotide sequence. FIG. 8B shows the nucleotide sequence of coFVIII-1-XTEN (SEQ ID NO: 20), wherein a nucleotide sequence encoding an XTEN having 144 amino acid ("XTEN$_{144}$"; SEQ ID NO: 18; underlined) is inserted within the coFVIII-1 nucleotide sequence. FIG. 8C shows the nucleotide sequence of coFVIII-6-XTEN (SEQ ID NO: 72), wherein a nucleotide sequence encoding an XTEN having 144 amino acid ("XTEN$_{144}$"; SEQ ID NO: 18; underlined) is inserted within the coFVIII-6 nucleotide sequence (e.g., amino acid residue 745 corresponding to mature FVIII sequence).

FIG. 9 provides a plasmid map of pLV-coFVIII-52-XTEN, which comprises coFVIII-52-XTEN in a lentiviral vector under the control of the ET promoter. Lentiviral vectors comprising each of the remaining codon optimized nucleic acid molecules encoding a polypeptide with FVIII activity, as described herein, were constructed in the same manner as pLV-coFVIII-52-XTEN, in which the same XTEN sequence was inserted to replace the B-domain of FVIII.

FIGS. 10A and 10B show FVIII activity in HemA mice following injection with plasmid DNA (FIG. 10A) or lentiviral vector (FIG. 10B) comprising the various codon optimized nucleotide sequences encoding BDD-FVIII. FIG. 10A shows a graphical representation of FVIII plasma activity in HemA mice following hydrodynamic injection with 5 µg FVIII-311 (non-codon optimized, BDD-FVIII encoding nucleotide sequence; squares), 5 µg FVIII-303 (coFVIII-1; small circles), or FVIII-306 (coFVIII-1-XTEN$_{144}$; large circles). The relative activity at 72 hours, normalized to FVIII-311, is shown for each plasmid. FIG. 10B shows plasma FVIII activity in HemA mice 21 days after injection with 1E8 TU/mouse of lentiviral vector comprising coFVIII-52 or coFVIII-52-XTEN as compared with the LV-2116 (BDD-FVIII) control, and as measured by a FVIII-specific chromogenic assay. Error bars indicate standard deviations.

FIG. 11A shows the amino acid sequence of full-length mature human factor VIII. FIG. 11B shows the amino acid sequence of full length human von Willebrand Factor (SEQ ID NO: 44). FIGS. 11C and 11D show the amino acid and nucleotide sequences, respectively, of an XTEN polypeptide having 42 amino acids (XTEN AE42-4; SEQ ID NOs: 46 and 47, respectively). The amino acid sequences of various XTEN polypeptides having 144 amino acids are shown in FIGS. 11E, 11G, 11I, 11K, 11M, 11O, 11Q, 11S, 11U, and 11W (SEQ ID NOs: 48, 50, 52, 54, 56, 58, 60, 62, 64, and 66, respectively), and the corresponding nucleotide sequences are shown in FIGS. 11F, 11H, 11J, 11L, 11N, 11P, 11R, 11T, 11V, and 11X (SEQ ID NOs. 49, 51, 53, 55, 57, 59, 61, 63, 65, and 67, respectively). FIG. 11Y shows the nucleotide sequence of an ET promoter (SEQ ID NO: 69). FIG. 11Z shows the nucleotide sequence for coFVIII-1

(SEQ ID NO: 68) (see International Publication No. WO 2014/127215, SEQ ID NO: 1).

FIG. 12A is a graphic representation of FVIII plasma activity (IU/mL) in 14-day-old HemA mice following IV administration of about 1.5 E10 TU/kg LV-wtBDD-FVIII (circles), LV-coFVIII-6 (squares), or LV-coFVIII-6XTEN (triangles). FIG. 12B is a graphic representation of vector copy number (VCN) 150 days after treatment of 14-day-old HemA mice administered by IV about 1.5 E10 TU/kg of lentiviral vectors expressing wtBDD-FVIII, coFVIII-1, coFVIII-3, coFVIII-4, coFVIII-5, coFVIII-6, coFVIII-52, coFVIII-62, coFVIII-25, or coFVIII-26. FIG. 12C is a graphic representation of FVIII plasma activity (IU/mL) 21 days after treatment of 14-day-old HemA mice administered by IV about 1.5 E10 TU/kg of lentiviral vectors expressing wtBDD-FVIII, coFVIII-1, coFVIII-3, coFVIII-4, coFVIII-5, coFVIII-6, coFVIII-52, coFVIII-62, coFVIII-25, or coFVIII-26.

Figure 13B:
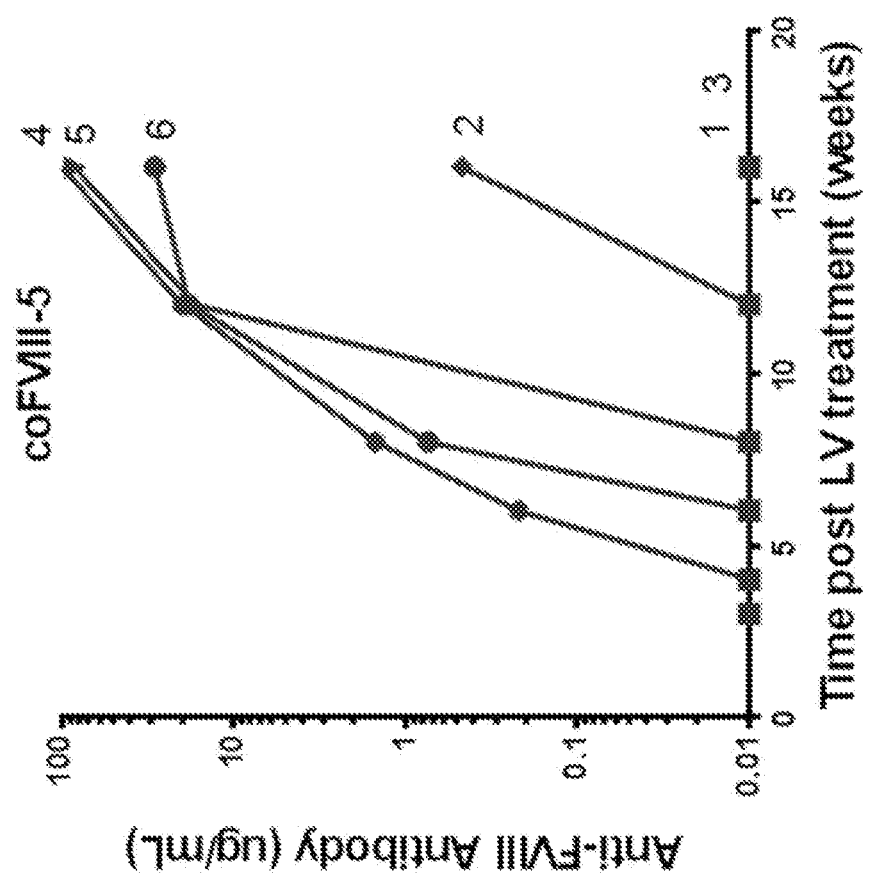
Figure 13A:
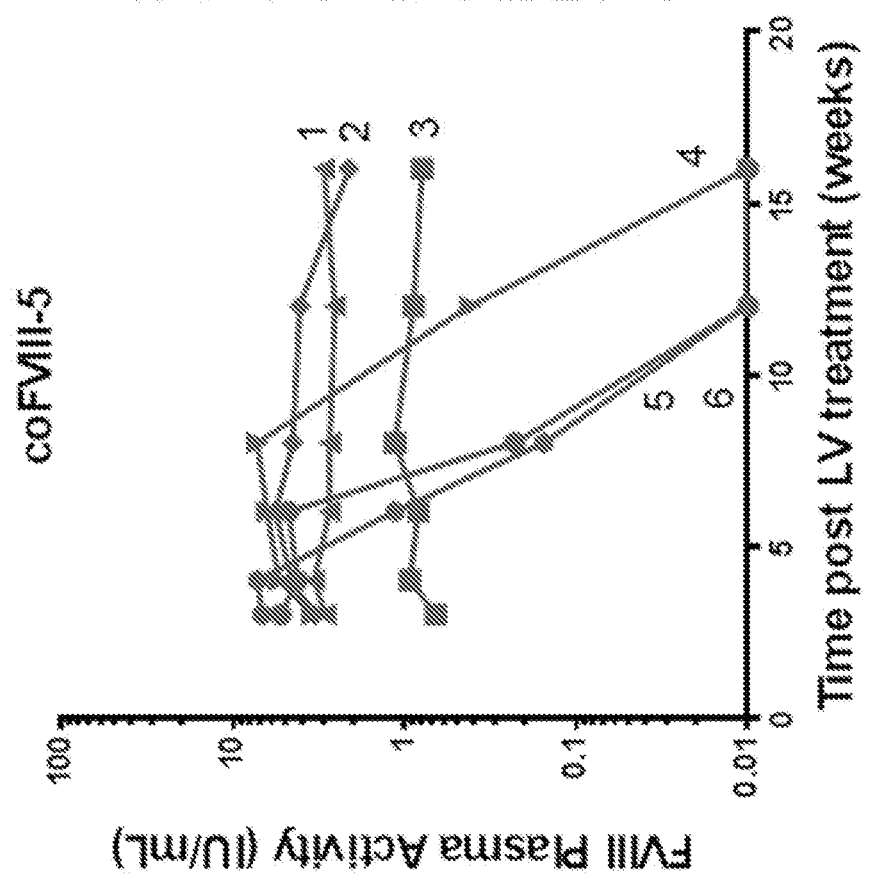

FIGS. 13A and 13B are graphic representations that illustrate the FVIII plasma activity levels (FIG. 13A) and anti-FVIII antibody levels (FIG. 13B) in five HemA mice treated with a lentivirus expressing the coFVIII-5 variant. Fourteen-day-old HemA littermates were administered approximately 1.5 E10 TU/kg of a lentivirus expressing the coFVIII-5 variant by intravenous injection. Each mouse is designated by a number (i.e., 1, 2, 3, 4, and 5; FIGS. 13A and 13B).

Figure 14:
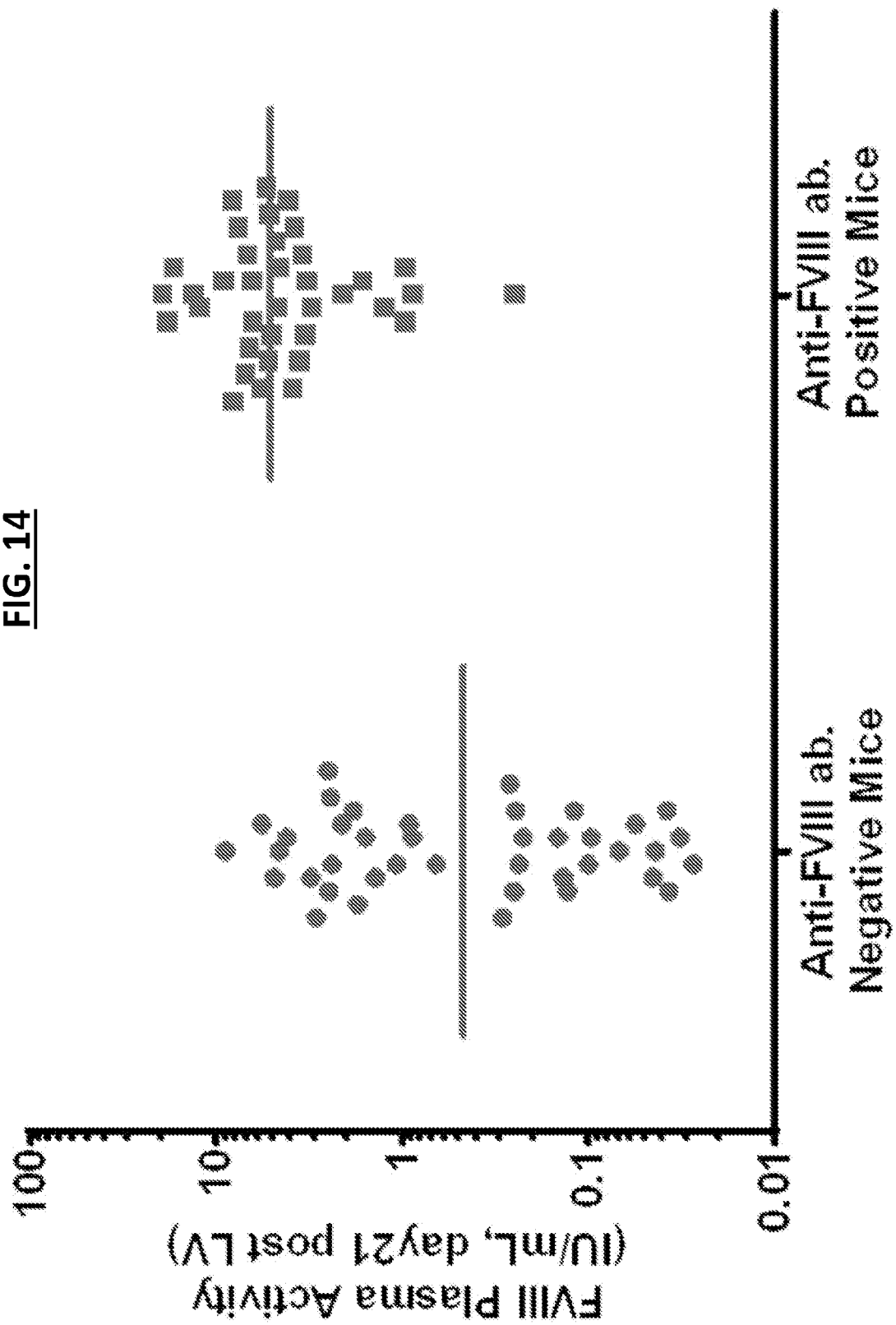

FIG. 14 is a graphic representation of the correlation between LV-FVIII expression level, as evidenced by FVIII plasma activity at 21 days post lentiviral treatment, and the presence of anti-FVIII antibodies. Each data point corresponds to a single HemA mouse. Each mouse received a 1.5 E10 TU/kg dose by intravenous injection of a lentivirus expressing one of the coFVIII variants disclosed herein. Horizontal lines indicate the average FVIII plasma activity.

Figure 15:
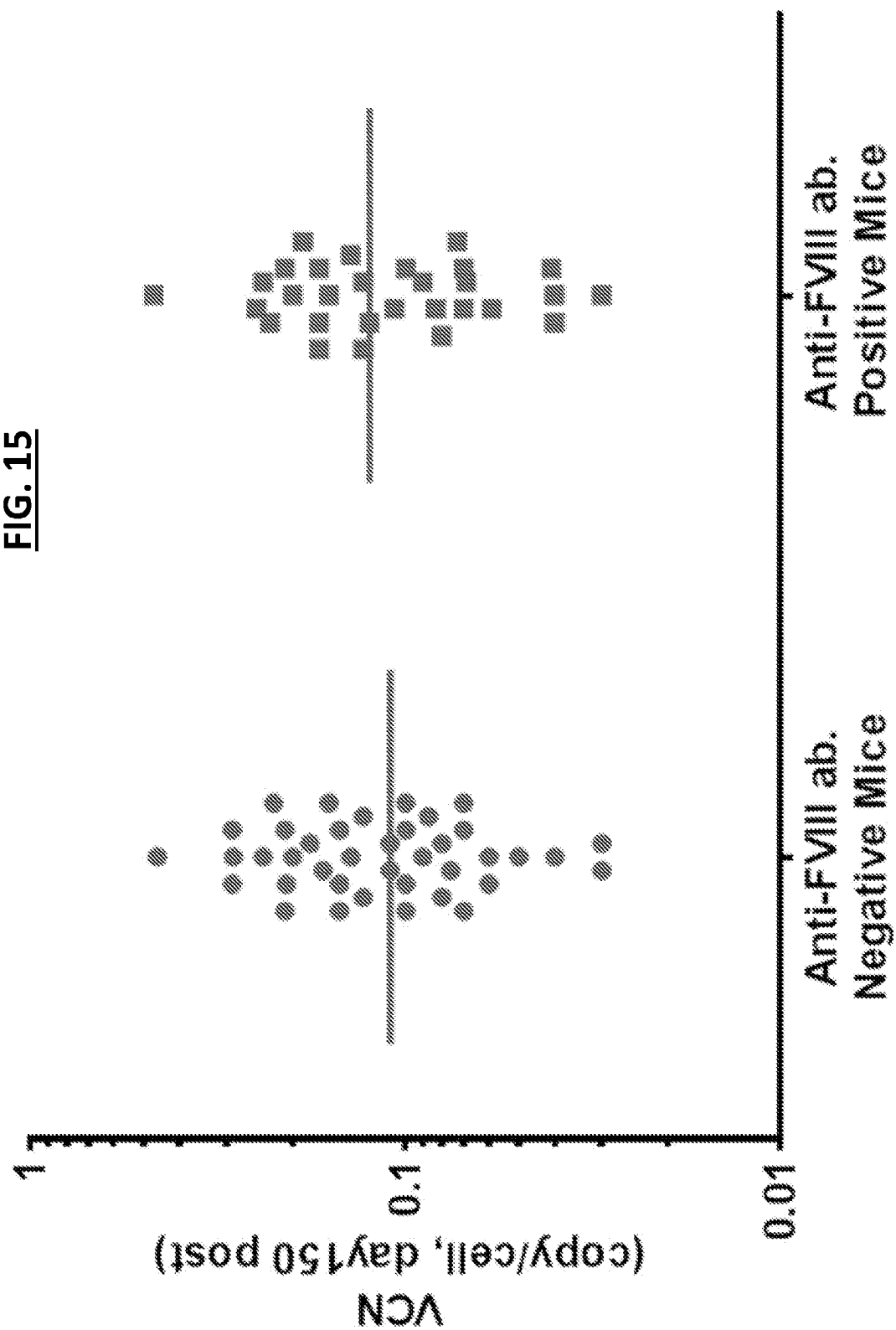

FIG. 15 is a graphic representation of the correlation between vector copy number (VCN) per cell at 150 days post lentiviral treatment and the presence of anti-FVIII antibodies. Each data point corresponds to a single HemA mouse. Each mouse received a 1.5 E10 TU/kg dose by intravenous injection of a lentivirus expressing one of the coFVIII variants disclosed herein. Horizontal lines indicate the average VCN.

Figure 16A:
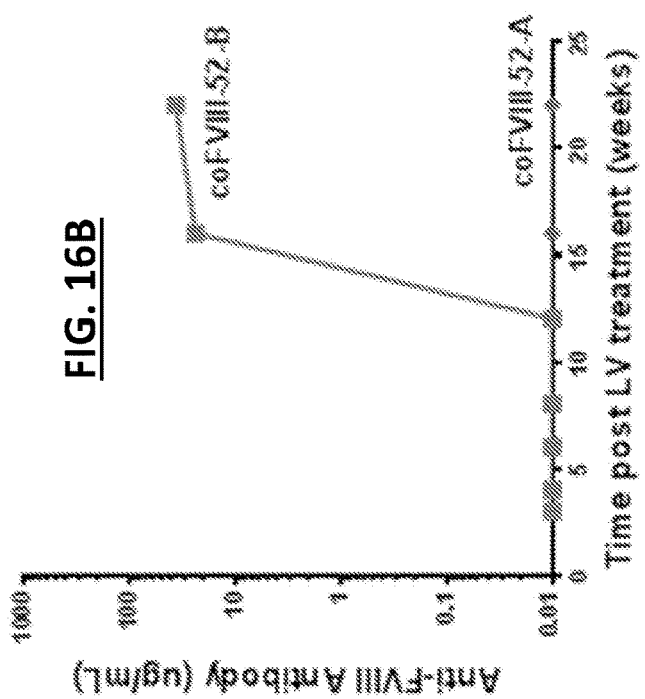
Figure 16B:
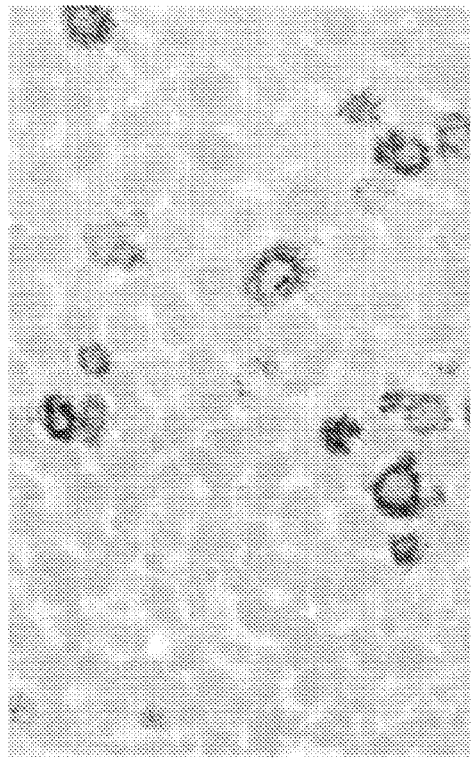
Figure 16C:
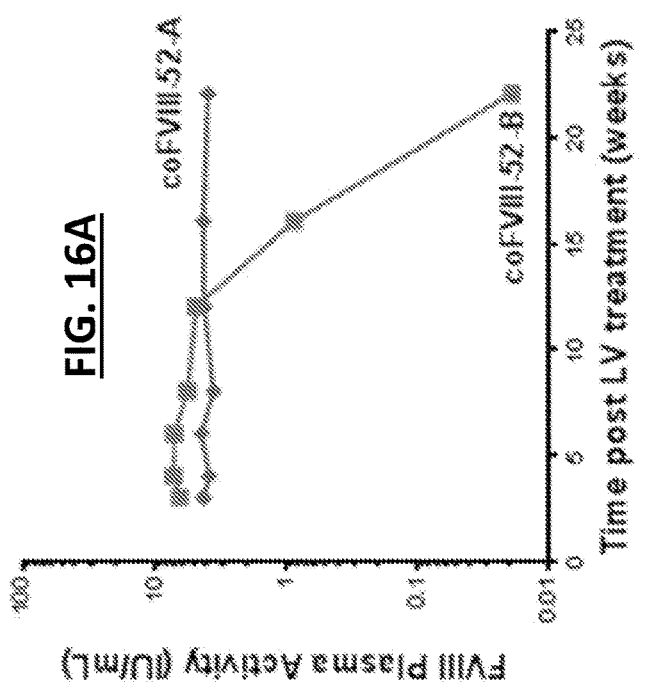
Figure 16D:
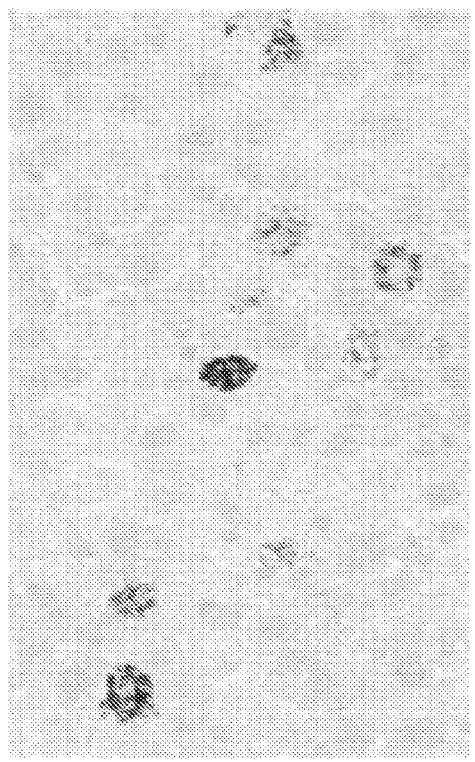

FIGS. 16A and 16B are graphic representations that illustrate the FVIII plasma activity levels (FIG. 16A) and anti-FVIII antibody levels (FIG. 16B) in two HemA mice (coFVIII-52-A and coFVIII-52-B) treated with a lentivirus expressing the coFVIII-52 variant. Fourteen-day-old HemA littermates were administered approximately 1.5 E10 TU/kg of a lentivirus expressing the coFVIII-52 variant by intravenous injection. FIGS. 16C and 16D are images showing RNA in situ hybridization staining for FVIII expression (dark staining) in liver tissue collected from the coFVIII-52-A (FIG. 16C) and coFVIII-52-B (FIG. 16D) mice of FIGS. 16A and 16B.

Figure 17:
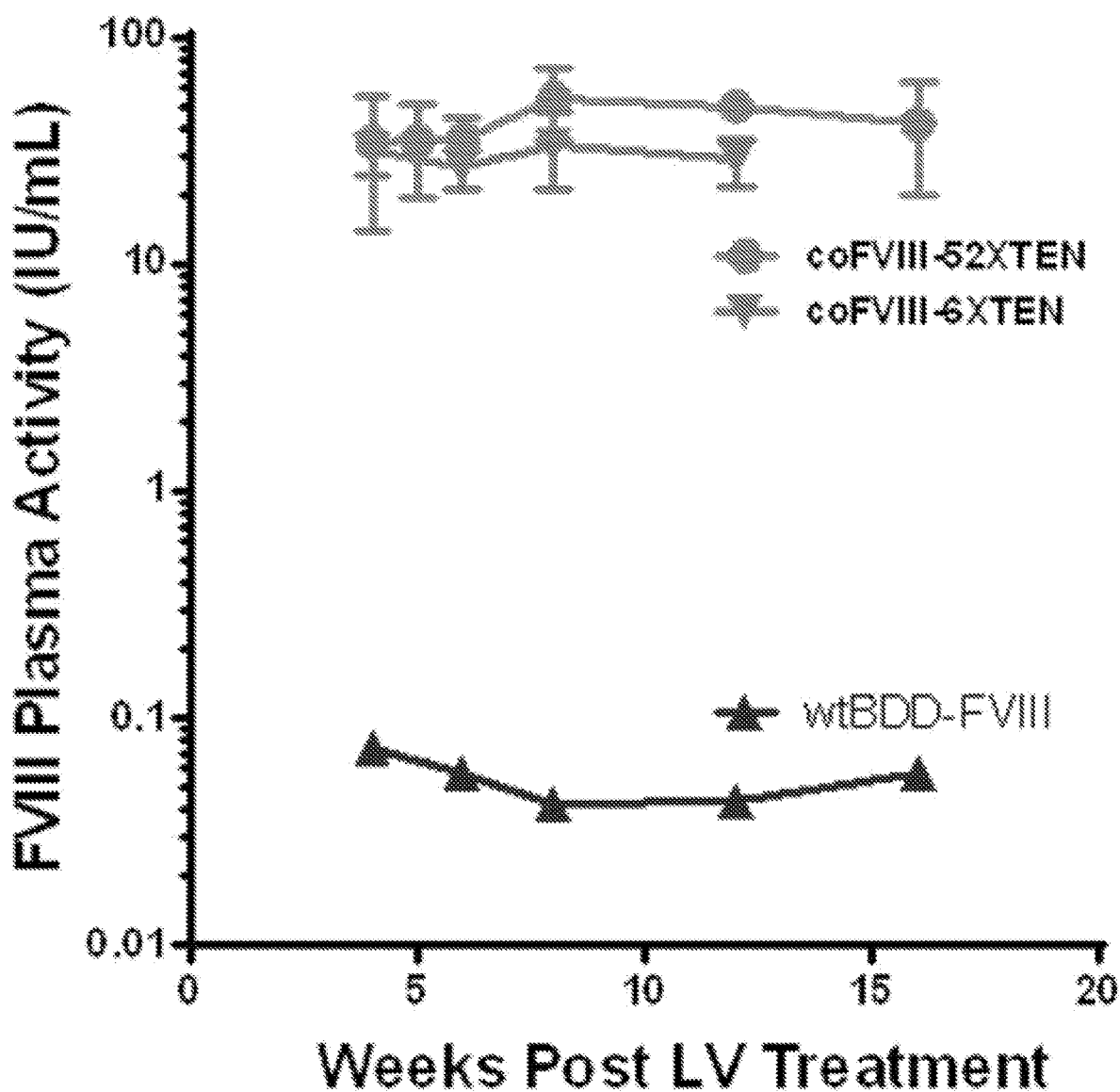

FIG. 17 is a graphic representation that shows long-term FVIII expression in HemA neonate mice treated with a lentivirus expressing a wild-type B domain deleted FVIII (wtBDD-FVIII; triangles), coFVIII-52XTEN (circles), or coFVIII-6XTEN (inverted triangle) variant. Neonatal HemA mice were administered by intravenous injection approximately 1.5 A10 TU/kg of a lentivirus expressing wtBDD-FVIII, coFVIII-52XTEN, or coFVIII-6XTEN. FVIII plasma activity was measured over approximately 16 weeks.

Figure 18:
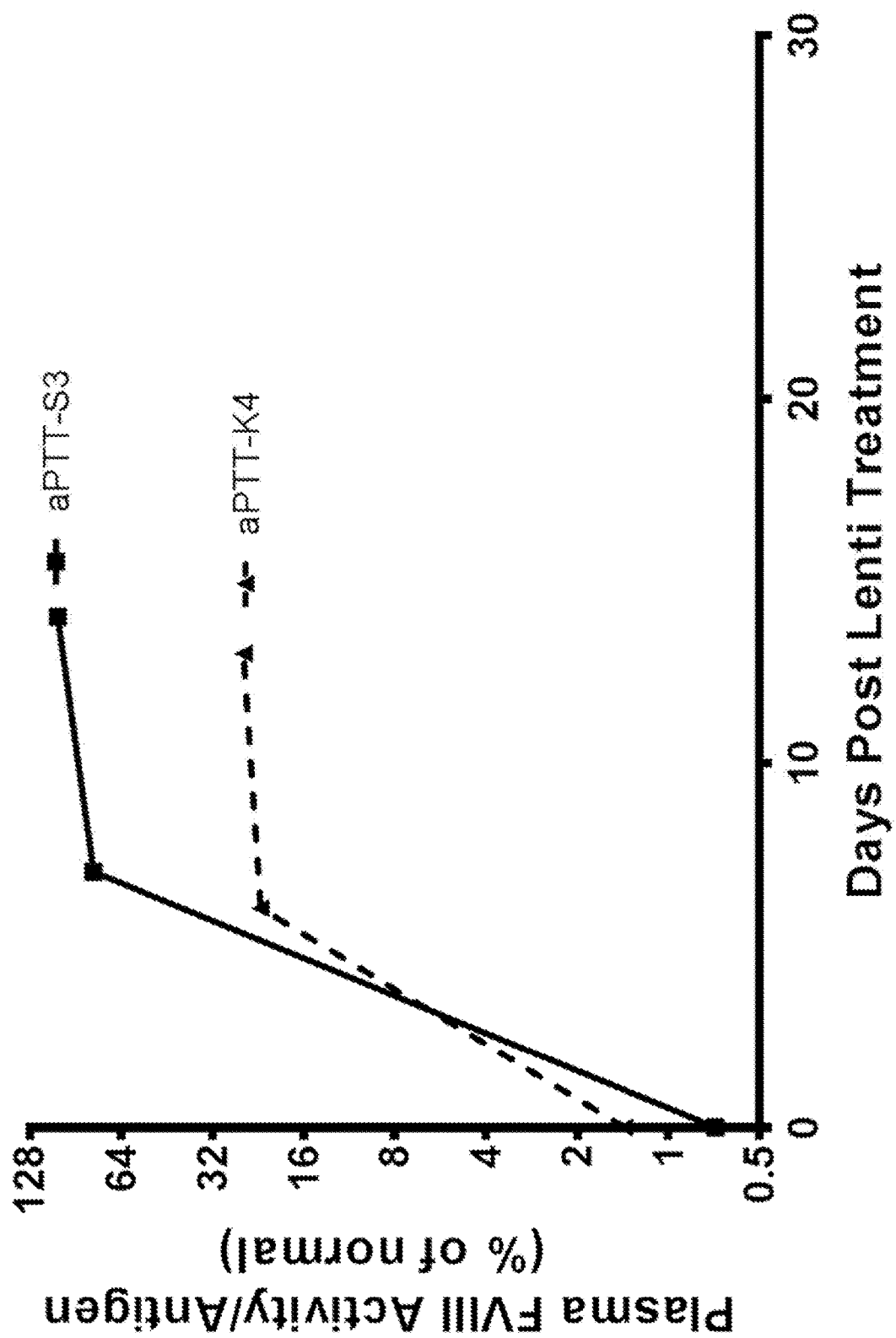

FIG. 18 is a graphic representation of the circulating FVIII level in HemA dog neonates (S3 or K4) after administration of $1.3 \times 10^9$ transducing units/kg lentiviral vector comprising a nucleotide encoding Factor VIII fused to XTEN (SEQ ID NO: 72; LV-coFVIII-6-XTEN). Squares connected by a solid line represent aPTT-S3 samples, and triangles connected by a dashed line represent aPTT-K4 samples. The y-axis shows the plasma FVIII activity as the percent of normal, wherein normal human FVIII activity is 100%. The x-axis shows the days post-lentivirus treatment, wherein lentivirus treatment is administered at day 0.

Figure 19A:
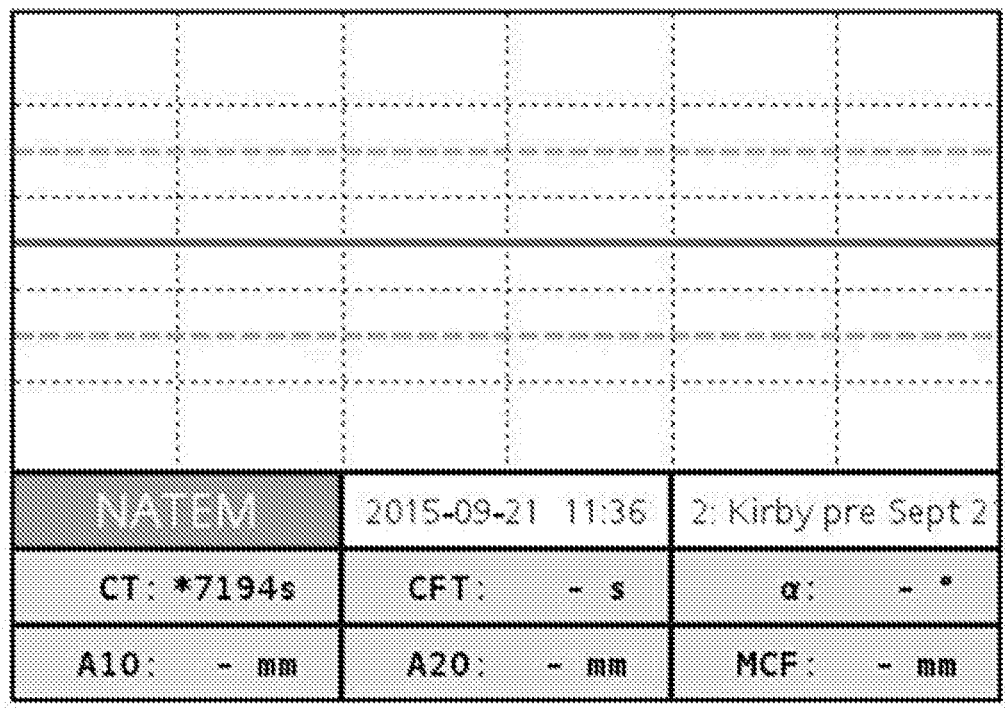
Figure 19B:
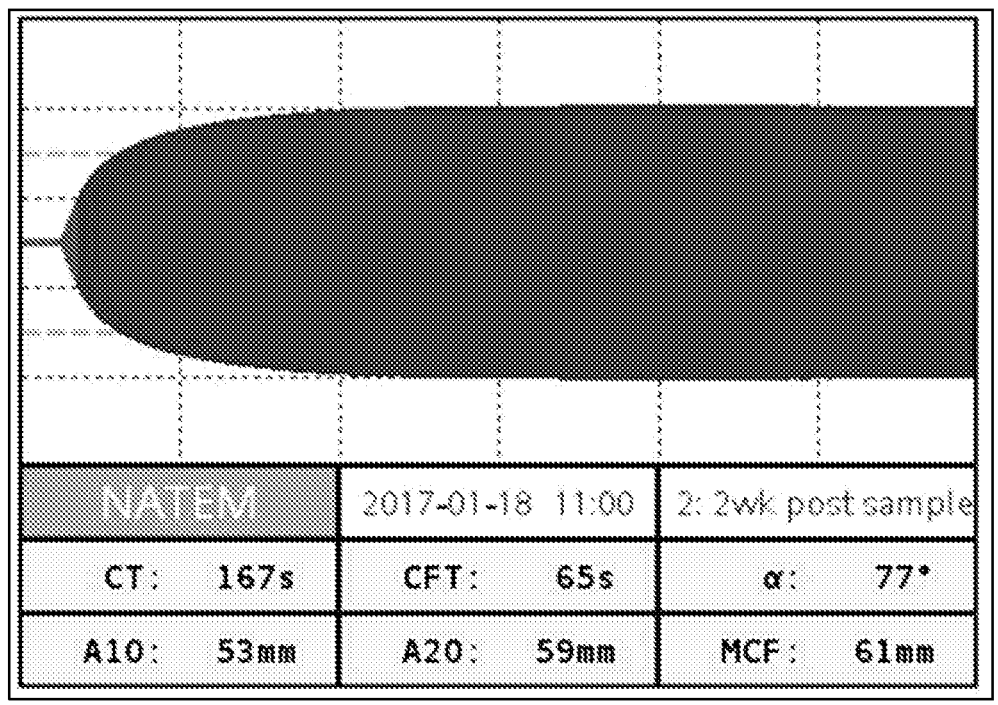
Figures 19C, 19D:
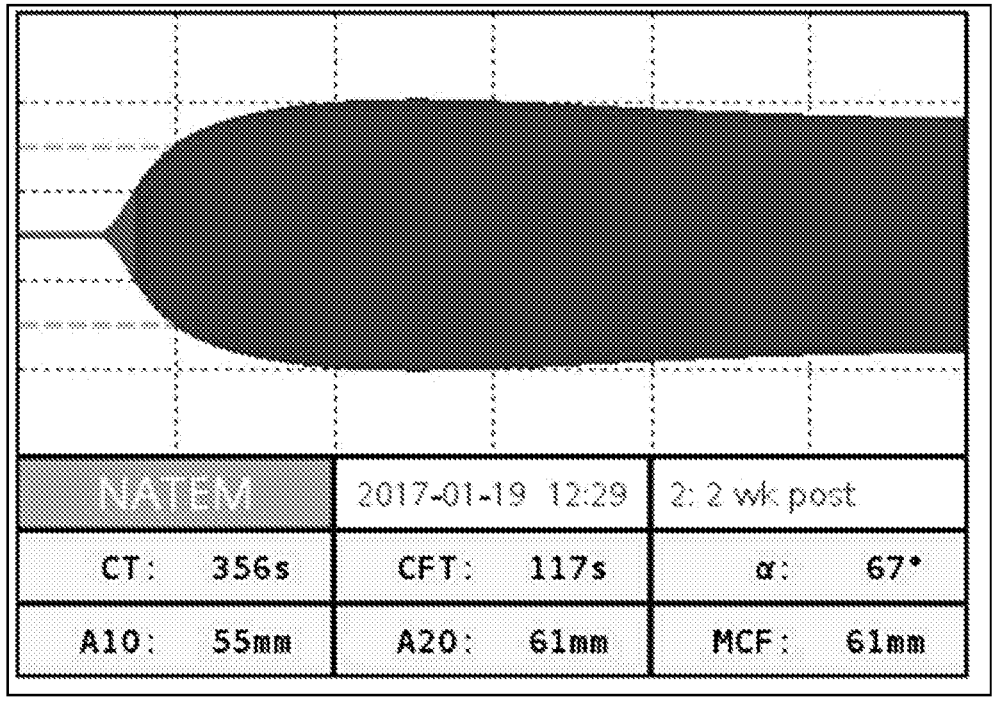

FIGS. 19A-19C are graphical representations of whole blood hemostasis as monitored by rotational thromboelastometry (ROTEM) assay for a naïve HemA dog (FIG. 19A), dog S3 at 2 weeks post-lentivirus treatment (FIG. 19B), and dog K4 at 2 weeks post-lentivirus treatment (FIG. 19C). Clotting time (CT) is shown as seconds (s), clot formation time (CFT) is shown as seconds (s), alpha angle (α) is shown as degrees (°), amplitude 5 minutes after CT (A5) is shown as millimeters (mm), amplitude 20 minutes after CT (A20) is shown as millimeters (mm), and maximum clot firmness (MCF) is shown as millimeters (mm) for each of FIGS. 19A-19C. FIG. 19D is a table summarizing the normal range for each of the parameters CT, CFT, a, A5, A2, and MCF displayed in FIGS. 19A-19C.

DETAILED DESCRIPTION OF THE DISCLOSURE

The present disclosure describes codon-optimized genes encoding polypeptides with Factor VIII (FVIII) activity. The present disclosure is directed to codon optimized nucleic acid molecules encoding polypeptides with Factor VIII activity, vectors and host cells comprising optimized nucleic acid molecules, polypeptides encoded by optimized nucleic acid molecules, and methods of producing such polypeptides. The present disclosure is also directed to methods of treating bleeding disorders such as hemophilia comprising administering to the subject an optimized Factor VIII nucleic acid sequence, a vector comprising the optimized nucleic acid sequence, or the polypeptide encoded thereby. The present disclosure meets an important need in the art by providing optimized Factor VIII sequences that demonstrate increased expression in host cells, improved yield of Factor VIII protein in methods to produce recombinant Factor VIII, and potentially result in greater therapeutic efficacy when used in gene therapy methods. In certain embodiments, the disclosure describes an isolated nucleic acid molecule comprising a nucleotide sequence which has sequence homology to a nucleotide sequence selected from SEQ ID NOs: 1-14, 70, and 71.

Exemplary constructs of the disclosure are illustrated in the accompanying Figures and sequence listing. In order to provide a clear understanding of the specification and claims, the following definitions are provided below.

I. Definitions

It is to be noted that the term "a" or "an" entity refers to one or more of that entity: for example, "a nucleotide sequence" is understood to represent one or more nucleotide sequences. As such, the terms "a" (or "an"), "one or more," and "at least one" can be used interchangeably herein.

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

The term "isolated" for the purposes of the present disclosure designates a biological material (cell, polypeptide, polynucleotide, or a fragment, variant, or derivative thereof) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated." No particular level of purification is required. Recombinantly produced polypeptides and proteins expressed in host cells are considered isolated for the purpose of the disclosure, as are native or recombinant polypeptides which have been separated, fractionated, or partially or substantially purified by any suitable technique.

"Nucleic acids," "nucleic acid molecules," "oligonucleotide," and "polynucleotide" are used interchangeably and refer to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, supercoiled DNA and chromosomes. In discussing the structure of particular double-stranded DNA molecules, sequences can be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation. DNA includes, but is not limited to, cDNA, genomic DNA, plasmid DNA, synthetic DNA, and semi-synthetic DNA. A "nucleic acid composition" of the disclosure comprises one or more nucleic acids as described herein.

As used herein, a "coding region" or "coding sequence" is a portion of polynucleotide which consists of codons translatable into amino acids. Although a "stop codon" (TAG, TGA, or TAA) is typically not translated into an amino acid, it can be considered to be part of a coding region, but any flanking sequences, for example promoters, ribosome binding sites, transcriptional terminators, introns, and the like, are not part of a coding region. The boundaries of a coding region are typically determined by a start codon at the 5' terminus, encoding the amino terminus of the resultant polypeptide, and a translation stop codon at the 3' terminus, encoding the carboxyl terminus of the resulting polypeptide. Two or more coding regions can be present in a single polynucleotide construct, e.g., on a single vector, or in separate polynucleotide constructs, e.g., on separate (different) vectors. It follows, then, that a single vector can contain just a single coding region, or comprise two or more coding regions.

Certain proteins secreted by mammalian cells are associated with a secretory signal peptide which is cleaved from the mature protein once export of the growing protein chain across the rough endoplasmic reticulum has been initiated. Those of ordinary skill in the art are aware that signal peptides are generally fused to the N-terminus of the polypeptide, and are cleaved from the complete or "full-length" polypeptide to produce a secreted or "mature" form of the polypeptide. In certain embodiments, a native signal peptide or a functional derivative of that sequence that retains the ability to direct the secretion of the polypeptide that is operably associated with it. Alternatively, a heterologous mammalian signal peptide, e.g., a human tissue plasminogen activator (TPA) or mouse β-glucuronidase signal peptide, or a functional derivative thereof, can be used.

The term "downstream" refers to a nucleotide sequence that is located 3' to a reference nucleotide sequence. In certain embodiments, downstream nucleotide sequences relate to sequences that follow the starting point of transcription. For example, the translation initiation codon of a gene is located downstream of the start site of transcription.

The term "upstream" refers to a nucleotide sequence that is located 5' to a reference nucleotide sequence. In certain embodiments, upstream nucleotide sequences relate to sequences that are located on the 5' side of a coding region or starting point of transcription. For example, most promoters are located upstream of the start site of transcription.

As used herein, the term "gene regulatory region" or "regulatory region" refers to nucleotide sequences located upstream (5' non-coding sequences), within, or downstream (3' non-coding sequences) of a coding region, and which influence the transcription, RNA processing, stability, or translation of the associated coding region. Regulatory regions can include promoters, translation leader sequences, introns, polyadenylation recognition sequences, RNA processing sites, effector binding sites and stem-loop structures. If a coding region is intended for expression in a eukaryotic cell, a polyadenylation signal and transcription termination sequence will usually be located 3' to the coding sequence.

A polynucleotide which encodes a gene product, e.g., a polypeptide, can include a promoter and/or other expression (e.g., transcription or translation) control elements operably associated with one or more coding regions. In an operable association a coding region for a gene product, e.g., a polypeptide, is associated with one or more regulatory regions in such a way as to place expression of the gene product under the influence or control of the regulatory region(s). For example, a coding region and a promoter are "operably associated" if induction of promoter function results in the transcription of mRNA encoding the gene product encoded by the coding region, and if the nature of the linkage between the promoter and the coding region does not interfere with the ability of the promoter to direct the expression of the gene product or interfere with the ability of the DNA template to be transcribed. Other expression control elements, besides a promoter, for example enhancers, operators, repressors, and transcription termination signals, can also be operably associated with a coding region to direct gene product expression.

"Transcriptional control sequences" refer to DNA regulatory sequences, such as promoters, enhancers, terminators, and the like, that provide for the expression of a coding sequence in a host cell. A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

The term "expression" as used herein refers to a process by which a polynucleotide produces a gene product, for example, an RNA or a polypeptide. It includes without limitation transcription of the polynucleotide into messenger RNA (mRNA), transfer RNA (tRNA), small hairpin RNA (shRNA), small interfering RNA (siRNA) or any other RNA product, and the translation of an mRNA into a polypeptide. Expression produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation or splicing, or polypeptides with post translational modifications, e.g., methylation, glycosylation, the addition of lipids, association with other protein subunits, or proteolytic cleavage. The term "yield," as used herein, refers to the amount of a polypeptide produced by the expression of a gene.

A "vector" refers to any vehicle for the cloning of and/or transfer of a nucleic acid into a host cell. A vector can be a replicon to which another nucleic acid segment can be attached so as to bring about the replication of the attached segment. A "replicon" refers to any genetic element (e.g., plasmid, phage, cosmid, chromosome, virus) that functions as an autonomous unit of replication in vivo, i.e., capable of replication under its own control. The term "vector" includes both viral and nonviral vehicles for introducing the nucleic acid into a cell in vitro, ex vivo or in vivo. A large number of vectors are known and used in the art including, for example, plasmids, modified eukaryotic viruses, or modified bacterial viruses. Insertion of a polynucleotide into a suitable vector can be accomplished by ligating the appropriate polynucleotide fragments into a chosen vector that has complementary cohesive termini.

Vectors can be engineered to encode selectable markers or reporters that provide for the selection or identification of cells that have incorporated the vector. Expression of selectable markers or reporters allows identification and/or selection of host cells that incorporate and express other coding regions contained on the vector. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like. Examples of reporters known and used in the art include: luciferase (Luc), green fluorescent protein (GFP), chloramphenicol acetyltransferase (CAT), β-galactosidase (LacZ), β-glucuronidase (Gus), and the like. Selectable markers can also be considered to be reporters.

The term "selectable marker" refers to an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term "reporter gene" refers to a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), chloramphenicol acetyltransferase (CAT), β-galactosidase (LacZ), β-glucuronidase (Gus), and the like. Selectable marker genes can also be considered reporter genes.

"Promoter" and "promoter sequence" are used interchangeably and refer to a DNA sequence capable of controlling the expression of a coding sequence or functional RNA. In general, a coding sequence is located 3' to a promoter sequence. Promoters can be derived in their entirety from a native gene, or be composed of different elements derived from different promoters found in nature, or even comprise synthetic DNA segments. It is understood by those skilled in the art that different promoters can direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." It is further recognized that since in most cases the exact boundaries of regulatory sequences have not been completely defined, DNA fragments of different lengths can have identical promoter activity.

The promoter sequence is typically bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease Si), as well as protein binding domains (consensus sequences) responsible for the binding of RNA polymerase.

The terms "restriction endonuclease" and "restriction enzyme" are used interchangeably and refer to an enzyme that binds and cuts within a specific nucleotide sequence within double stranded DNA.

The term "plasmid" refers to an extra-chromosomal element often carrying a gene that is not part of the central metabolism of the cell, and usually in the form of circular double-stranded DNA molecules. Such elements can be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

Eukaryotic viral vectors that can be used include, but are not limited to, adenovirus vectors, retrovirus vectors, adeno-associated virus vectors, poxvirus, e.g., vaccinia virus vectors, baculovirus vectors, or herpesvirus vectors. Non-viral vectors include plasmids, liposomes, electrically charged lipids (cytofectins), DNA-protein complexes, and biopolymers.

A "cloning vector" refers to a "replicon," which is a unit length of a nucleic acid that replicates sequentially and which comprises an origin of replication, such as a plasmid, phage or cosmid, to which another nucleic acid segment can be attached so as to bring about the replication of the attached segment. Certain cloning vectors are capable of replication in one cell type, e.g., bacteria and expression in another, e.g., eukaryotic cells. Cloning vectors typically comprise one or more sequences that can be used for selection of cells comprising the vector and/or one or more multiple cloning sites for insertion of nucleic acid sequences of interest.

The term "expression vector" refers to a vehicle designed to enable the expression of an inserted nucleic acid sequence following insertion into a host cell. The inserted nucleic acid sequence is placed in operable association with regulatory regions as described above.

Vectors are introduced into host cells by methods well known in the art, e.g., transfection, electroporation, microinjection, transduction, cell fusion, DEAE dextran, calcium phosphate precipitation, lipofection (lysosome fusion), use of a gene gun, or a DNA vector transporter.

"Culture," "to culture" and "culturing," as used herein, means to incubate cells under in vitro conditions that allow for cell growth or division or to maintain cells in a living state. "Cultured cells," as used herein, means cells that are propagated in vitro.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide can be derived from a natural biological source or produced recombinant technology, but is not necessarily translated from a designated nucleic acid sequence. It can be generated in any manner, including by chemical synthesis.

The term "amino acid" includes alanine (Ala or A); arginine (Arg or R); asparagine (Asn or N); aspartic acid (Asp or D); cysteine (Cys or C); glutamine (Gln or Q); glutamic acid (Glu or E); glycine (Gly or G); histidine (His or H); isoleucine (Ile or I): leucine (Leu or L); lysine (Lys or K); methionine (Met or M); phenylalanine (Phe or F); proline (Pro or P); serine (Ser or S); threonine (Thr or T); tryptophan (Trp or W); tyrosine (Tyr or Y); and valine (Val or V). Non-traditional amino acids are also within the scope of the disclosure and include norleucine, ornithine, norvaline, homoserine, and other amino acid residue analogues such as those described in Ellman et al. Meth. Enzym. 202:301-336 (1991). To generate such non-naturally occurring amino acid residues, the procedures of Noren et al. Science 244:182 (1989) and Ellman et al., supra, can be used. Briefly, these procedures involve chemically activating a suppressor tRNA with a non-naturally occurring amino acid residue followed by in vitro transcription and translation of the RNA. Introduction of the non-traditional amino acid can also be achieved using peptide chemistries known in the art. As used herein, the term "polar amino acid" includes amino acids that have net zero charge, but have non-zero partial charges in different portions of their side chains (e.g., M, F, W, S, Y, N, Q, C). These amino acids can participate in hydrophobic interactions and electrostatic interactions. As used herein, the term "charged amino acid" includes amino acids that can have non-zero net charge on their side chains (e.g., R, K, H, E, D). These amino acids can participate in hydrophobic interactions and electrostatic interactions.

Also included in the present disclosure are fragments or variants of polypeptides, and any combination thereof. The term "fragment" or "variant" when referring to polypeptide binding domains or binding molecules of the present disclosure include any polypeptides which retain at least some of the properties (e.g., FcRn binding affinity for an FcRn binding domain or Fc variant, coagulation activity for an FVIII variant, or FVIII binding activity for the VWF fragment) of the reference polypeptide. Fragments of polypeptides include proteolytic fragments, as well as deletion fragments, in addition to specific antibody fragments discussed elsewhere herein, but do not include the naturally occurring full-length polypeptide (or mature polypeptide). Variants of polypeptide binding domains or binding molecules of the present disclosure include fragments as described above, and also polypeptides with altered amino acid sequences due to amino acid substitutions, deletions, or insertions. Variants can be naturally or non-naturally occurring. Non-naturally occurring variants can be produced using art-known mutagenesis techniques. Variant polypeptides can comprise conservative or non-conservative amino acid substitutions, deletions or additions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another embodiment, a string of amino acids can be conservatively replaced with a structurally similar string that differs in order and/or composition of side chain family members.

The term "percent identity" as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case can be, as determined by the match between strings of such sequences. "Identity" can be readily calculated by known methods, including but not limited to those described in: Computational Molecular Biology (Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, New York (1991). Preferred methods to determine identity are designed to give the best match between the sequences tested. Methods to determine identity are codified in publicly available computer programs. Sequence alignments and percent identity calculations can be performed using sequence analysis software such as the Megalign program of the LASERGENE bioinformatics computing suite (DNASTAR Inc., Madison, Wis.), the GCG suite of programs (Wisconsin Package Version 9.0, Genetics Computer Group (GCG), Madison, Wis.), BLASTP, BLASTN, BLASTX (Altschul et al., *J. Mol. Biol.* 215:403 (1990)), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized. For the purposes of determining percent identity between an optimized BDD FVIII sequence of the disclosure and a reference sequence, only nucleotides in the reference sequence corresponding to nucleotides in the optimized BDD FVIII sequence of the disclosure are used to calculate percent identity. For example, when comparing a full length FVIII nucleotide sequence containing the B domain to an optimized B domain deleted (BDD) FVIII nucleotide sequence of the disclosure, the portion of the alignment including the A1, A2, A3, C1, and C2 domain will be used to calculate percent identity. The nucleotides in the portion of the full length FVIII sequence encoding the B domain (which will result in a large "gap" in the alignment) will not be counted as a mismatch. In addition, in determining percent identity between an optimized BDD FVIII sequence of the disclosure, or a designated portion thereof (e.g., nucleotides 58-2277 and 2320-4374 of SEQ ID NO:3), and a reference sequence, percent identity will be calculated by aligning dividing the number of matched nucleotides by the total number of nucleotides in the complete sequence of the optimized BDD-FVIII sequence, or a designated portion thereof, as recited herein.

As used herein, "nucleotides corresponding to nucleotides in the optimized BDD FVIII sequence of the disclosure" are identified by alignment of the optimized BDD FVIII sequence of the disclosure to maximize the identity to the reference FVIII sequence. The number used to identify an equivalent amino acid in a reference FVIII sequence is based on the number used to identify the corresponding amino acid in the optimized BDD FVIII sequence of the disclosure.

A "fusion" or "chimeric" protein comprises a first amino acid sequence linked to a second amino acid sequence with which it is not naturally linked in nature. The amino acid sequences which normally exist in separate proteins can be brought together in the fusion polypeptide, or the amino acid sequences which normally exist in the same protein can be placed in a new arrangement in the fusion polypeptide, e.g., fusion of a Factor VIII domain of the disclosure with an Ig Fc domain. A fusion protein is created, for example, by chemical synthesis, or by creating and translating a polynucleotide in which the peptide regions are encoded in the desired relationship. A chimeric protein can further comprises a second amino acid sequence associated with the first amino acid sequence by a covalent, non-peptide bond or a non-covalent bond.

As used herein, the term "insertion site" refers to a position in a FVIII polypeptide, or fragment, variant, or derivative thereof, which is immediately upstream of the position at which a heterologous moiety can be inserted. An "insertion site" is specified as a number, the number being the number of the amino acid in mature native FVIII (SEQ ID NO: 15; FIG. 11A) to which the insertion site corresponds, which is immediately N-terminal to the position of the insertion. For example, the phrase "a3 comprises a heterologous moiety at an insertion site which corresponds to amino acid 1656 of SEQ ID NO: 15" indicates that the heterologous moiety is located between two amino acids corresponding to amino acid 1656 and amino acid 1657 of SEQ ID NO: 15.

The phrase "immediately downstream of an amino acid" as used herein refers to position right next to the terminal carboxyl group of the amino acid. Similarly, the phrase "immediately upstream of an amino acid" refers to the position right next to the terminal amine group of the amino acid.

The terms "inserted," "is inserted," "inserted into" or grammatically related terms, as used herein refers to the position of a heterologous moiety in a recombinant FVIII polypeptide, relative to the analogous position in native mature human FVIII. As used herein the terms refer to the characteristics of the recombinant FVIII polypeptide relative to native mature human FVIII, and do not indicate, imply or infer any methods or process by which the recombinant FVIII polypeptide was made.

As used herein, the term "half-life" refers to a biological half-life of a particular polypeptide in vivo. Half-life can be represented by the time required for half the quantity administered to a subject to be cleared from the circulation and/or other tissues in the animal. When a clearance curve of a given polypeptide is constructed as a function of time, the curve is usually biphasic with a rapid α-phase and longer β-phase. The α-phase typically represents an equilibration of the administered Fc polypeptide between the intra- and extra-vascular space and is, in part, determined by the size of the polypeptide. The β-phase typically represents the catabolism of the polypeptide in the intravascular space. In some embodiments, FVIII and chimeric proteins comprising FVIII are monophasic, and thus do not have an alpha phase, but just the single beta phase. Therefore, in certain embodiments, the term half-life as used herein refers to the half-life of the polypeptide in the β-phase.

The term "linked" as used herein refers to a first amino acid sequence or nucleotide sequence covalently or non-covalently joined to a second amino acid sequence or nucleotide sequence, respectively. The first amino acid or nucleotide sequence can be directly joined or juxtaposed to the second amino acid or nucleotide sequence or alternatively an intervening sequence can covalently join the first sequence to the second sequence. The term "linked" means not only a fusion of a first amino acid sequence to a second amino acid sequence at the C-terminus or the N-terminus, but also includes insertion of the whole first amino acid sequence (or the second amino acid sequence) into any two amino acids in the second amino acid sequence (or the first amino acid sequence, respectively). In one embodiment, the first amino acid sequence can be linked to a second amino acid sequence by a peptide bond or a linker. The first nucleotide sequence can be linked to a second nucleotide sequence by a phosphodiester bond or a linker. The linker can be a peptide or a polypeptide (for polypeptide chains) or a nucleotide or a nucleotide chain (for nucleotide chains) or any chemical moiety (for both polypeptide and polynucleotide chains). The term "linked" is also indicated by a hyphen (-).

As used herein the term "associated with" refers to a covalent or non-covalent bond formed between a first amino acid chain and a second amino acid chain. In one embodiment, the term "associated with" means a covalent, non-peptide bond or a non-covalent bond. This association can be indicated by a colon, i.e., (:). In another embodiment, it means a covalent bond except a peptide bond. For example, the amino acid cysteine comprises a thiol group that can form a disulfide bond or bridge with a thiol group on a second cysteine residue. In most naturally occurring IgG molecules, the CH1 and CL regions are associated by a disulfide bond and the two heavy chains are associated by two disulfide bonds at positions corresponding to 239 and 242 using the Kabat numbering system (position 226 or 229, EU numbering system). Examples of covalent bonds include, but are not limited to, a peptide bond, a metal bond, a hydrogen bond, a disulfide bond, a sigma bond, a pi bond, a delta bond, a glycosidic bond, an agnostic bond, a bent bond, a dipolar bond, a Pi backbond, a double bond, a triple bond, a quadruple bond, a quintuple bond, a sextuple bond, conjugation, hyperconjugation, aromaticity, hapticity, or antibonding. Non-limiting examples of non-covalent bond include an ionic bond (e.g., cation-pi bond or salt bond), a metal bond, an hydrogen bond (e.g., dihydrogen bond, dihydrogen complex, low-barrier hydrogen bond, or symmetric hydrogen bond), van der Walls force, London dispersion force, a mechanical bond, a halogen bond, aurophilicity, intercalation, stacking, entropic force, or chemical polarity.

The term "monomer-dimer hybrid" used herein refers to a chimeric protein comprising a first polypeptide chain and a second polypeptide chain, which are associated with each other by a disulfide bond, wherein the first chain comprises a clotting factor, e.g., Factor VIII, and a first Fc region and the second chain comprises, consists essentially of, or consists of a second Fc region without the clotting factor. The monomer-dimer hybrid construct thus is a hybrid comprising a monomer aspect having only one clotting factor and a dimer aspect having two Fc regions.

Hemostasis, as used herein, means the stopping or slowing of bleeding or hemorrhage; or the stopping or slowing of blood flow through a blood vessel or body part.

Hemostatic disorder, as used herein, means a genetically inherited or acquired condition characterized by a tendency to hemorrhage, either spontaneously or as a result of trauma, due to an impaired ability or inability to form a fibrin clot. Examples of such disorders include the hemophilias. The three main forms are hemophilia A (factor VIII deficiency), hemophilia B (factor IX deficiency or "Christmas disease") and hemophilia C (factor XI deficiency, mild bleeding tendency). Other hemostatic disorders include, e.g., von Willebrand disease, Factor XI deficiency (PTA deficiency), Factor XII deficiency, deficiencies or structural abnormalities in fibrinogen, prothrombin, Factor V, Factor VII, Factor X or factor XIII, Bernard-Soulier syndrome, which is a defect or deficiency in GPIb. GPIb, the receptor for vWF, can be defective and lead to lack of primary clot formation (primary hemostasis) and increased bleeding tendency), and thrombasthenia of Glanzman and Naegeli (Glanzmann thrombasthenia). In liver failure (acute and chronic forms), there is insufficient production of coagulation factors by the liver; this can increase bleeding risk.

The isolated nucleic acid molecules, isolated polypeptides, or vectors comprising the isolated nucleic acid molecule of the disclosure can be used prophylactically. As used herein the term "prophylactic treatment" refers to the administration of a molecule prior to a bleeding episode. In one embodiment, the subject in need of a general hemostatic agent is undergoing, or is about to undergo, surgery. A polynucleotide, polypeptide, or vector of the disclosure can be administered prior to or after surgery as a prophylactic. The polynucleotide, polypeptide, or vector of the disclosure can be administered during or after surgery to control an acute bleeding episode. The surgery can include, but is not limited to, liver transplantation, liver resection, dental procedures, or stem cell transplantation.

The isolated nucleic acid molecules, isolated polypeptides, or vectors of the disclosure are also used for on-demand treatment. The term "on-demand treatment" refers to the administration of an isolated nucleic acid molecule, isolated polypeptide, or vector in response to symptoms of a bleeding episode or before an activity that can cause bleeding. In one aspect, the on-demand treatment can be given to a subject when bleeding starts, such as after an injury, or when bleeding is expected, such as before surgery. In another aspect, the on-demand treatment can be given prior to activities that increase the risk of bleeding, such as contact sports.

As used herein the term "acute bleeding" refers to a bleeding episode regardless of the underlying cause. For example, a subject can have trauma, uremia, a hereditary bleeding disorder (e.g., factor VII deficiency) a platelet disorder, or resistance owing to the development of antibodies to clotting factors.

Treat, treatment, treating, as used herein refers to, e.g., the reduction in severity of a disease or condition; the reduction in the duration of a disease course; the amelioration of one or more symptoms associated with a disease or condition; the provision of beneficial effects to a subject with a disease or condition, without necessarily curing the disease or condition, or the prophylaxis of one or more symptoms associated with a disease or condition. In one embodiment, the term "treating" or "treatment" means maintaining a FVIII trough level at least about 1 IU/dL, 2 IU/dL, 3 IU/dL, 4 IU/dL, 5 IU/dL, 6 IU/dL, 7 IU/dL, 8 IU/dL, 9 IU/dL, 10 IU/dL, 11 IU/dL, 12 IU/dL, 13 IU/dL, 14 IU/dL, 15 IU/dL, 16 IU/dL, 17 IU/dL, 18 IU/dL, 19 IU/dL, or 20 IU/dL in a subject by administering an isolated nucleic acid molecule, isolated polypeptide or vector of the disclosure. In another embodiment, treating or treatment means maintaining a FVIII trough level between about 1 and about 20 IU/dL, about 2 and about 20 IU/dL, about 3 and about 20 IU/dL, about 4 and about 20 IU/dL, about 5 and about 20 IU/dL, about 6 and about 20 IU/dL, about 7 and about 20 IU/dL, about 8 and about 20 IU/dL, about 9 and about 20 IU/dL, or about 10 and about 20 IU/dL. Treatment or treating of a disease or condition can also include maintaining FVIII activity in a subject at a level comparable to at least about 1%, 2%, 3%, 4%, 5%, 6%, 7%, 8%, 9%, 10%, 11%, 12%, 13%, 14%, 15%, 16%, 17%, 18%, 19%, or 20% of the FVIII activity in a non-hemophiliac subject. The minimum trough level required for treatment can be measured by one or more known methods and can be adjusted (increased or decreased) for each person.

"Administering," as used herein, means to give a pharmaceutically acceptable Factor VIII-encoding nucleic acid molecule, Factor VIII polypeptide, or vector comprising a Factor VIII-encoding nucleic acid molecule of the disclosure to a subject via a pharmaceutically acceptable route. Routes of administration can be intravenous, e.g., intravenous injection and intravenous infusion. Additional routes of administration include, e.g., subcutaneous, intramuscular, oral, nasal, and pulmonary administration. The nucleic acid molecules, polypeptides, and vectors can be administered as part of a pharmaceutical composition comprising at least one excipient.

As used herein, the phrase "subject in need thereof" includes subjects, such as mammalian subjects, that would benefit from administration of a nucleic acid molecule, a polypeptide, or vector of the disclosure, e.g., to improve hemostasis. In one embodiment, the subjects include, but are not limited to, individuals with hemophilia. In another embodiment, the subjects include, but are not limited to, the individuals who have developed a FVIII inhibitor and thus are in need of a bypass therapy. The subject can be an adult or a minor (e.g., under 12 years old).

As used herein, the term "clotting factor," refers to molecules, or analogs thereof, naturally occurring or recombinantly produced which prevent or decrease the duration of a bleeding episode in a subject. In other words, it means molecules having pro-clotting activity, i.e., are responsible for the conversion of fibrinogen into a mesh of insoluble fibrin causing the blood to coagulate or clot. An "activatable clotting factor" is a clotting factor in an inactive form (e.g., in its zymogen form) that is capable of being converted to an active form.

Clotting activity, as used herein, means the ability to participate in a cascade of biochemical reactions that culminates in the formation of a fibrin clot and/or reduces the severity, duration or frequency of hemorrhage or bleeding episode.

As used herein the terms "heterologous" or "exogenous" refer to such molecules that are not normally found in a given context, e.g., in a cell or in a polypeptide. For example, an exogenous or heterologous molecule can be introduced into a cell and are only present after manipulation of the cell, e.g., by transfection or other forms of genetic engineering or a heterologous amino acid sequence can be present in a protein in which it is not naturally found.

As used herein, the term "heterologous nucleotide sequence" refers to a nucleotide sequence that does not naturally occur with a given polynucleotide sequence. In one embodiment, the heterologous nucleotide sequence encodes a polypeptide capable of extending the half-life of FVIII. In another embodiment, the heterologous nucleotide sequence encodes a polypeptide that increases the hydrodynamic radius of FVIII. In other embodiments, the heterologous nucleotide sequence encodes a polypeptide that improves one or more pharmacokinetic properties of FVIII without significantly affecting its biological activity or function (e.g., its procoagulant activity). In some embodiments, FVIII is linked or connected to the polypeptide encoded by the heterologous nucleotide sequence by a linker. Non-limiting examples of polypeptide moieties encoded by heterologous nucleotide sequences include an immunoglobulin constant region or a portion thereof, albumin or a fragment thereof, an albumin-binding moiety, a transferrin, the PAS polypeptides of U.S. Pat Application No. 20100292130, a HAP sequence, transferrin or a fragment thereof, the C-terminal peptide (CTP) of the 13 subunit of human chorionic gonadotropin, albumin-binding small molecule, an XTEN sequence, FcRn binding moieties (e.g., complete Fc regions or portions thereof which bind to FcRn), single chain Fc regions (ScFc regions, e.g., as described in US 2008/0260738, WO 2008/012543, or WO 2008/1439545), polyglycine linkers, polyserine linkers, peptides and short polypeptides of 6-40 amino acids of two types of amino acids selected from glycine (G), alanine (A), serine (S), threonine (T), glutamate (E) and proline (P) with varying degrees of secondary structure from less than 50% to greater than 50%, amongst others, or two or more combinations thereof. In some embodiments, the polypeptide encoded by the heterologous nucleotide sequence is linked to a non-polypeptide moiety. Non-limiting examples of the non-polypeptide moieties include polyethylene glycol (PEG), albumin-binding small molecules, polysialic acid, hydroxyethyl starch (HES), a derivative thereof, or any combinations thereof.

As used herein, the term "Fc region" is defined as the portion of a polypeptide which corresponds to the Fc region of native Ig, i.e., as formed by the dimeric association of the respective Fc domains of its two heavy chains. A native Fc region forms a homodimer with another Fc region. In contrast, the term "genetically-fused Fc region" or "single-chain Fc region" (scFc region), as used herein, refers to a synthetic dimeric Fc region comprised of Fc domains genetically linked within a single polypeptide chain (i.e., encoded in a single contiguous genetic sequence).

In one embodiment, the "Fc region" refers to the portion of a single Ig heavy chain beginning in the hinge region just upstream of the papain cleavage site (i.e. residue 216 in IgG, taking the first residue of heavy chain constant region to be 114) and ending at the C-terminus of the antibody. Accordingly, a complete Fc domain comprises at least a hinge domain, a CH2 domain, and a CH3 domain.

The Fc region of an Ig constant region, depending on the Ig isotype can include the CH2, CH3, and CH4 domains, as well as the hinge region. Chimeric proteins comprising an Fc region of an Ig bestow several desirable properties on a chimeric protein including increased stability, increased serum half-life (see Capon et al., 1989, Nature 337:525) as well as binding to Fc receptors such as the neonatal Fc receptor (FcRn) (U.S. Pat. Nos. 6,086,875, 6,485,726, 6,030,613; WO 03/077834; US2003-0235536A1), which are incorporated herein by reference in their entireties.

A "reference nucleotide sequence," when used herein as a comparison to a nucleotide sequence of the disclosure, is a polynucleotide sequence essentially identical to the nucleotide sequence of the disclosure except that the portions corresponding to FVIII sequence are not optimized. For example, the reference nucleotide sequence for a nucleic acid molecule consisting of the codon optimized BDD FVIII of SEQ ID NO: 1 and a heterologous nucleotide sequence that encodes a single chain Fc region linked to SEQ ID NO: 1 at its 3' end is a nucleic acid molecule consisting of the original (or "parent") BDD FVIII of SEQ ID NO: 16 (FIG. 1I) and the identical heterologous nucleotide sequence that encodes a single chain Fc region linked to SEQ ID NO: 16 at its 3' end.

A "codon adaptation index," as used herein, refers to a measure of codon usage bias. A codon adaptation index (CAI) measures the deviation of a given protein coding gene sequence with respect to a reference set of genes (Sharp P M and Li W H, *Nucleic Acids Res.* 15(3):1281-95 (1987)). CAI is calculated by determining the geometric mean of the weight associated to each codon over the length of the gene sequence (measured in codons):

$$CAI = \exp\left(1/L\sum_{l=1}^{L}\ln(w_1(l))\right), \quad (I)$$

For each amino acid, the weight of each of its codons, in CAI, is computed as the ratio between the observed frequency of the codon (fi) and the frequency of the synonymous codon (fj) for that amino acid:

Formula 2:

$$w_i = \frac{f_i}{\max(f_j)} \quad ij \in [\text{synonymous codons for amino acid}] \quad (II)$$

As used herein, the term "optimized," with regard to nucleotide sequences, refers to a polynucleotide sequence that encodes a polypeptide, wherein the polynucleotide sequence has been mutated to enhance a property of that polynucleotide sequence. In some embodiments, the optimization is done to increase transcription levels, increase translation levels, increase steady-state mRNA levels, increase or decrease the binding of regulatory proteins such as general transcription factors, increase or decrease splicing, or increase the yield of the polypeptide produced by the polynucleotide sequence. Examples of changes that can be made to a polynucleotide sequence to optimize it include codon optimization, G/C content optimization, removal of repeat sequences, removal of AT rich elements, removal of cryptic splice sites, removal of cis-acting elements that repress transcription or translation, adding or removing poly-T or poly-A sequences, adding sequences around the transcription start site that enhance transcription, such as Kozak consensus sequences, removal of sequences that could form stem loop structures, removal of destabilizing sequences, and two or more combinations thereof.

Polynucleotide Sequence Encoding FVIII Protein

In some embodiments, the present disclosure is directed to codon optimized nucleic acid molecules encoding a polypeptide with FVIII activity. In some embodiments, the polynucleotide encodes a full-length FVIII polypeptide. In other embodiments, the nucleic acid molecule encodes a B domain-deleted (BDD) FVIII polypeptide, wherein all or a portion of the B domain of FVIII is deleted. In one particular embodiment, the nucleic acid molecule encodes a polypeptide comprising an amino acid sequence having at least about 80%, at least about 85%, at least about 86%, at least about 87%, at least about 88%, at least about 89%, at least about 90%, at least about 95%, at least about 96%, at least about 97%, at least about 98%, or at least about 99% sequence identity to SEQ ID NO: 17 (FIG. 1J) or a fragment thereof. In one embodiment, the nucleic acid molecule encodes a polypeptide having the amino acid sequence of SEQ ID NO: 17 or a fragment thereof.

In some embodiments, the nucleic acid molecule of the disclosure encodes a FVIII polypeptide comprising a signal peptide or a fragment thereof. In other embodiments, the nucleic acid molecule encodes a FVIII polypeptide which lacks a signal peptide. In some embodiments, the signal peptide comprises amino acids 1-19 of SEQ ID NO: 17.

In some embodiments, the present disclosure provides an isolated nucleic acid molecule comprising a nucleotide sequence which comprises a first nucleic acid sequence encoding an N-terminal portion of a FVIII polypeptide and a second nucleic acid sequence encoding a C-terminal portion of a FVIII polypeptide; wherein the first nucleic acid sequence has at least 85%, at least 90%, at least 95%, at least 96%, at least 97%, at least 98%, or at least 99% sequence identity to (i) nucleotides 58-1791 of SEQ ID NO: 3 or (ii) nucleotides 58-1791 of SEQ ID NO: 4; and wherein the N-terminal portion and the C-terminal portion together have a FVIII polypeptide activity. In one particular embodiment, the first nucleic acid sequence has at least 85%, at least 90%, at least 95%, at least 96%, at least 97%, at least 98%, or at least 99% sequence identity to nucleotides 58-1791 of SEQ ID NO: 3. In another embodiment, the first nucleic acid sequence has at least 85%, at least 90%, at least 95%, at least 96%, at least 97%, at least 98%, or at least 99% sequence identity to nucleotides 58-1791 of SEQ ID NO: 4. In other embodiments, the first nucleotide sequence comprises nucleotides 58-1791 of SEQ ID NO: 3 or nucleotides 58-1791 of SEQ ID NO: 4.

In other embodiments, the present disclosure provides an isolated nucleic acid molecule comprising a nucleotide sequence which comprises a first nucleic acid sequence encoding an N-terminal portion of a FVIII polypeptide and a second nucleic acid sequence encoding a C-terminal portion of a FVIII polypeptide; wherein the first nucleic acid sequence has at least 85%, at least 90%, at least 95%, at least 96%, at least 97%, at least 98%, or at least 99% sequence identity to (i) nucleotides 1-1791 of SEQ ID NO: 3 or (ii) nucleotides 1-1791 of SEQ ID NO: 4; and wherein the N-terminal portion and the C-terminal portion together have a FVIII polypeptide activity. In one embodiment, the first nucleotide sequence comprises nucleotides 1-1791 of SEQ ID NO: 3 or nucleotides 1-1791 of SEQ ID NO: 4. In another embodiment, the second nucleotide sequence has at least 60%, at least 70%, at least 80%, at least 90%, at least 95%, at least 96%, at least 97%, at least 98%, or at least 99% sequence identity to nucleotides 1792-4374 of SEQ ID NO: 3 or 1792-4374 of SEQ ID NO: 4. In one particular embodiment, the second nucleotide sequence comprises nucleotides 1792-4374 of SEQ ID NO: 3 or 1792-4374 of SEQ ID NO: 4. In still another embodiment, the second nucleotide sequence has at least 60%, at least 70%, at least 80%, at least 90%, at least 95%, at least 96%, at least 97%, at least 98%, or at least 99% sequence identity to nucleotides 1792-2277 and 2320-4374 of SEQ ID NO: 3 or 1792-2277 and 2320-4374 of SEQ ID NO: 4 (i.e., nucleotides 1792-4374 of SEQ ID NO: 3 or 1792-4374 of SEQ ID NO: 4 without the nucleotides encoding the B domain or B domain fragment). In one particular embodiment, the second nucleotide sequence comprises nucleotides 1792-2277 and 2320-4374 of SEQ ID NO: 3 or 1792-2277 and 2320-4374 of SEQ ID NO: 4 (i.e., nucleotides 1792-4374 of SEQ ID NO: 3 or 1792-4374 of SEQ ID NO: 4 without the nucleotides encoding the B domain or B domain fragment).

In some embodiments, the present disclosure provides an isolated nucleic acid molecule comprising a nucleotide sequence which comprises a first nucleic acid sequence encoding an N-terminal portion of a FVIII polypeptide and a second nucleic acid sequence encoding a C-terminal portion of a FVIII polypeptide; wherein the second nucleic acid sequence has at least 85%, at least 90%, at least 95%, at least 96%, at least 97%, at least 98%, or at least 99% sequence identity to (i) nucleotides 1792-4374 of SEQ ID NO: 5 or (ii) 1792-4374 of SEQ ID NO: 6; and wherein the N-terminal portion and the C-terminal portion together have a FVIII polypeptide activity. In certain embodiments, the second nucleic acid sequence has at least 85%, at least 90%, at least 95%, at least 96%, at least 97%, at least 98%, or at least 99% sequence identity to nucleotides 1792-4374 of SEQ ID NO: 5. In other embodiments, the second nucleic acid sequence has at least 85%, at least 90%, at least 95%, at least 96%, at least 97%, at least 98%, or at least 99% sequence identity to nucleotides 1792-4374 of SEQ ID NO: 6. In one particular embodiment, the second nucleic acid sequence comprises nucleotides 1792-4374 of SEQ ID NO: 5 or 1792-4374 of SEQ ID NO: 6. In some embodiments, the first nucleic acid sequence linked to the second nucleic acid sequence listed above has at least 60%, at least 70%, at least 80%, at least 90%, at least 95%, at least 96%, at least 97%, at least 98%, or at least 99% sequence identity to nucleotides 58-1791 of SEQ ID NO: 5 or nucleotides 58-1791 of SEQ ID NO: 6. In other embodiments, the first nucleic acid sequence linked to the second nucleic acid sequence listed above has at least 60%, at least 70%, at least 80%, at least 90%, at least 95%, at least 96%, at least 97%, at least 98%, or at least 99% sequence identity to nucleotides 1-1791 of SEQ ID NO: 5 or nucleotides 1-1791 of SEQ ID NO: 6.

In other embodiments, the present disclosure provides an isolated nucleic acid molecule comprising a nucleotide sequence which comprises a first nucleic acid sequence encoding an N-terminal portion of a FVIII polypeptide and a second nucleic acid sequence encoding a C-terminal portion of a FVIII polypeptide; wherein the second nucleic acid sequence has at least 85%, at least 90%, at least 95%, at least 96%, at least 97%, at least 98%, or at least 99% sequence identity to (i) nucleotides 1792-2277 and 2320-4374 of SEQ ID NO: 5 (i.e., nucleotides 1792-4374 of SEQ ID NO: 5 without the nucleotides encoding the B domain or B domain fragment) or (ii) 1792-2277 and 2320-4374 of SEQ ID NO: 6 (i.e., nucleotides 1792-4374 of SEQ ID NO: 6 without the nucleotides encoding the B domain or B domain fragment); and wherein the N-terminal portion and the C-terminal portion together have a FVIII polypeptide activity. In certain embodiments, the second nucleic acid sequence has at least 85%, at least 90%, at least 95%, at least 96%, at least 97%, at least 98%, or at least 99% sequence identity to nucleotides 1792-2277 and 2320-4374 of SEQ ID NO: 5 (i.e., nucleotides 1792-4374 of SEQ ID NO: 5 without the nucleotides encoding the B domain or B domain fragment). In other embodiments, the second nucleic acid sequence has at least 85%, at least 90%, at least 95%, at least 96%, at least 97%, at least 98%, or at least 99% sequence identity to nucleotides 1792-2277 and 2320-4374 of SEQ ID NO: 6 (i.e., nucleotides 1792-4374 of SEQ ID NO: 6 without the nucleotides encoding the B domain or B domain fragment). In one particular embodiment, the second nucleic acid sequence comprises nucleotides 1792-2277 and 2320-4374 of SEQ ID NO: 5 or 1792-2277 and 2320-4374 of SEQ ID NO: 6 (i.e., nucleotides 1792-4374 of SEQ ID NO: 5 or 1792-4374 of SEQ ID NO: 6 without the nucleotides encoding the B domain or B domain fragment). In some embodiments, the first nucleic acid sequence linked to the second nucleic acid sequence listed above has at least 60%, at least 70%, at least 80%, at least 90%, at least 95%, at least 96%, at least 97%, at least 98%, or at least 99% sequence identity to nucleotides 58-1791 of SEQ ID NO: 5 or nucleotides 58-1791 of SEQ ID NO: 6. In other embodiments, the first nucleic acid sequence linked to the second nucleic acid sequence listed above has at least 60%, at least 70%, at least 80%, at least 90%, at least 95%, at least 96%, at least 97%, at least 98%, or at least 99% sequence identity to nucleotides 1-1791 of SEQ ID NO: 5 or nucleotides 1-1791 of SEQ ID NO: 6.

In some embodiments, the present disclosure provides an isolated nucleic acid molecule comprising a nucleotide sequence which comprises a first nucleic acid sequence encoding an N-terminal portion of a FVIII polypeptide and a second nucleic acid sequence encoding a C-terminal portion of a FVIII polypeptide; wherein the first nucleic acid sequence has at least 90%, at least 95%, at least 96%, at least 97%, at least 98%, or at least 99% sequence identity to (i) nucleotides 58-1791 of SEQ ID NO: 1, (ii) nucleotides 58-1791 of SEQ ID NO: 2, (iii) nucleotides 58-1791 of SEQ ID NO: 70, or (iv) nucleotides 58-1791 of SEQ ID NO: 71; and wherein the N-terminal portion and the C-terminal portion together have a FVIII polypeptide activity. In other embodiments, the first nucleotide sequence comprises nucleotides 58-1791 of SEQ ID NO: 1, nucleotides 58-1791 of SEQ ID NO: 2, (iii) nucleotides 58-1791 of SEQ ID NO: 70, or (iv) nucleotides 58-1791 of SEQ ID NO: 71.

In other embodiments, the present disclosure provides an isolated nucleic acid molecule comprising a nucleotide sequence which comprises a first nucleic acid sequence encoding an N-terminal portion of a FVIII polypeptide and a second nucleic acid sequence encoding a C-terminal portion of a FVIII polypeptide; wherein the first nucleic acid sequence has at least 90%, at least 95%, at least 96%, at least 97%, at least 98%, or at least 99% sequence identity to (i) nucleotides 1-1791 of SEQ ID NO: 1, (ii) nucleotides 1-1791 of SEQ ID NO: 2, (iii) nucleotides 1-1791 of SEQ ID NO: 70, or (iv) nucleotides 1-1791 of SEQ ID NO: 71; and wherein the N-terminal portion and the C-terminal portion together have a FVIII polypeptide activity. In one embodiment, the first nucleotide sequence comprises nucleotides 1-1791 of SEQ ID NO: 1, nucleotides 1-1791 of SEQ ID NO: 2, (iii) nucleotides 1-1791 of SEQ ID NO: 70, or (iv) nucleotides 1-1791 of SEQ ID NO: 71. In another embodiment, the second nucleotide sequence linked to the first nucleotide sequence has at least 60%, at least 70%, at least 80%, at least 90%, at least 95%, at least 96%, at least 97%, at least 98%, or at least 99% sequence identity to nucleotides 1792-4374 of SEQ ID NO: 1, 1792-4374 of SEQ ID NO: 2, (iii) nucleotides 1792-4374 of SEQ ID NO: 70, or (iv) nucleotides 1792-4374 of SEQ ID NO: 71. In one particular embodiment, the second nucleotide sequence linked to the first nucleotide sequence comprises (i) nucleotides 1792-4374 of SEQ ID NO: 1, (ii) nucleotides 1792-4374 of SEQ ID NO: 2, (iii) nucleotides 1792-4374 of SEQ ID NO: 70, or (iv) nucleotides 1792-4374 of SEQ ID NO: 71. In other embodiments, the second nucleotide sequence linked to the first nucleotide sequence has at least 60%, at least 70%, at least 80%, at least 90%, at least 95%, at least 96%, at least 97%, at least 98%, or at least 99% sequence identity to (i) nucleotides 1792-2277 and 2320-4374 of SEQ ID NO: 1, (ii) nucleotides 1792-2277 and 2320-4374 of SEQ ID NO: 2, (iii) nucleotides 1792-2277 and 2320-4374 of SEQ ID NO: 70, or (iv) nucleotides 1792-2277 and 2320-4374 of SEQ ID NO: 71. In one embodiment, the second nucleotide sequence comprises (i) nucleotides 1792-2277 and 2320-4374 of SEQ ID NO: 1, (ii) nucleotides 1792-2277 and 2320-4374 of SEQ ID NO: 2, (iii) nucleotides 1792-2277 and 2320-4374 of SEQ ID NO: 70, or (iv) nucleotides 1792-2277 and 2320-4374 of SEQ ID NO: 71.

In another embodiment, the present disclosure provides an isolated nucleic acid molecule comprising a nucleotide sequence which comprises a first nucleic acid sequence encoding an N-terminal portion of a FVIII polypeptide and a second nucleic acid sequence encoding a C-terminal portion of a FVIII polypeptide; wherein the second nucleic acid sequence has at least 90%, at least 95%, at least 96%, at least 97%, at least 98%, or at least 99% sequence identity to (i) nucleotides 1792-4374 of SEQ ID NO: 1, (ii) nucleotides 1792-4374 of SEQ ID NO: 2, (iii) nucleotides 1792-4374 of SEQ ID NO: 70, or (iv) nucleotides 1792-4374 of SEQ ID NO: 71; and wherein the N-terminal portion and the C-terminal portion together have a FVIII polypeptide activity. In one particular embodiment, the second nucleic acid sequence comprises (i) nucleotides 1792-4374 of SEQ ID NO: 1, (ii) nucleotides 1792-4374 of SEQ ID NO: 2, (iii) nucleotides 1792-4374 of SEQ ID NO: 70, or (iv) nucleotides 1792-4374 of SEQ ID NO: 71. In some embodiments, the present disclosure provides an isolated nucleic acid molecule comprising a nucleotide sequence which comprises a first nucleic acid sequence encoding an N-terminal portion of a FVIII polypeptide and a second nucleic acid sequence encoding a C-terminal portion of a FVIII polypeptide; wherein the second nucleic acid sequence has at least 90%, at least 95%, at least 96%, at least 97%, at least 98%, or at least 99% sequence identity to (i) nucleotides 1792-2277 and 2320-4374 of SEQ ID NO: 1, (ii) nucleotides 1792-2277 and 2320-4374 of SEQ ID NO: 2, (iii) nucleotides 1792-2277 and 2320-4374 of SEQ ID NO: 70, or (iv) nucleotides 1792-2277 and 2320-4374 of SEQ ID NO: 71 (i.e., nucleotides 1792-4374 of SEQ ID NO: 1, nucleotides 1792-4374 of SEQ ID NO: 2, nucleotides 1792-4374 of SEQ ID NO: 70, or nucleotides 1792-4374 of SEQ ID NO: 71 without the nucleotides encoding the B domain or B domain fragment); and wherein the N-terminal portion and the C-terminal portion together have a FVIII polypeptide activity. In one embodiment, the second nucleic acid sequence comprises (i) nucleotides 1792-2277 and 2320-4374 of SEQ ID NO: 1, (ii) nucleotides 1792-2277 and 2320-4374 of SEQ ID NO: 2, (iii) nucleotides 1792-2277 and 2320-4374 of SEQ ID NO: 70, or (iv) nucleotides 1792-2277 and 2320-4374 of SEQ ID NO: 71 (i.e., nucleotides 1792-4374 of SEQ ID NO: 1, nucleotides 1792-4374 of SEQ ID NO: 2, nucleotides 1792-4374 of SEQ ID NO: 70, or nucleotides 1792-4374 of SEQ ID NO: 71 without the nucleotides encoding the B domain or B domain fragment).

In some embodiments, the present disclosure provides an isolated nucleic acid molecule comprising a nucleotide sequence encoding a polypeptide with FVIII activity, wherein the nucleotide sequence comprises a nucleic acid sequence having at least 90%, at least 91%, at least 92%, at least 93%, at least 94%, at least 95%, at least 96%, at least 97%, at least 98%, or at least 99% sequence identity to nucleotides 58 to 4374 of SEQ ID NO: 1. In other embodiments, the nucleotide sequence comprises a nucleic acid sequence having at least 90%, at least 91%, at least 92%, at least 93%, at least 94%, at least 95%, at least 96%, at least 97%, at least 98%, or at least 99% sequence identity to nucleotides 58-2277 and 2320-4374 of SEQ ID NO: 1 (i.e., nucleotides 58-4374 of SEQ ID NO: 1 without the nucleotides encoding the B domain or B domain fragment). In other embodiments, the nucleic acid sequence has at least 90%, at least 91%, at least 92%, at least 93%, at least 94%, at least 95%, at least 96%, at least 97%, at least 98%, or at least 99% sequence identity to SEQ ID NO: 1. In other embodiments, the nucleotide sequence comprises nucleotides 58-2277 and 2320-4374 of SEQ ID NO: 1 (i.e., nucleotides 58-4374 of SEQ ID NO: 1 without the nucleotides encoding the B domain or B domain fragment) or nucleotides 58 to 4374 of SEQ ID NO: 1. In still other embodiments, the nucleotide sequence comprises nucleotides 1-2277 and 2320-4374 of SEQ ID NO: 1 (i.e., nucleotides 1-4374 of SEQ ID NO: 1 without the nucleotides encoding the B domain or B domain fragment) or nucleotides 1 to 4374 of SEQ ID NO: 1.

In some embodiments, the present disclosure provides an isolated nucleic acid molecule comprising a nucleotide sequence encoding a polypeptide with FVIII activity, wherein the nucleotide sequence comprises a nucleic acid sequence having at least 94%, at least 95%, at least 96%, at least 97%, at least 98%, or at least 99% sequence identity to nucleotides 58 to 4374 of SEQ ID NO: 2. In other embodiments, the nucleotide sequence comprises a nucleic acid sequence having at least 94%, at least 95%, at least 96%, at least 97%, at least 98%, or at least 99% sequence identity to nucleotides 58-2277 and 2320-4374 of SEQ ID NO: 2. In other embodiments, the nucleic acid sequence has at least 94%, at least 95%, at least 96%, at least 97%, at least 98%, or at least 99% sequence identity to SEQ ID NO: 2. In other embodiments, the nucleotide sequence comprises nucleotides 58-2277 and 2320-4374 of SEQ ID NO: 2 (i.e., nucleotides 58-4374 of SEQ ID NO: 2 without the nucleotides encoding the B domain or B domain fragment) or nucleotides 58 to 4374 of SEQ ID NO: 2. In still other embodiments, the nucleotide sequence comprises nucleotides 1-2277 and 2320-4374 of SEQ ID NO: 2 (i.e., nucleotides 1-4374 of SEQ ID NO: 2 without the nucleotides encoding the B domain or B domain fragment) or nucleotides 1 to 4374 of SEQ ID NO: 2.

In some embodiments, the present disclosure provides an isolated nucleic acid molecule comprising a nucleotide sequence encoding a polypeptide with FVIII activity, wherein the nucleotide sequence comprises a nucleic acid sequence having at least 85%, at least 86%, at least 87%, at least 88%, at least 89%, at least 90%, at least 91%, at least 95%, at least 96%, at least 97%, at least 98%, or at least 99% sequence identity to nucleotides 58 to 4374 of SEQ ID NO: 70. In other embodiments, the nucleotide sequence comprises a nucleic acid sequence having at least 85%, at least 86%, at least 87%, at least 88%, at least 89%, at least 90%, at least 91%, at least 95%, at least 96%, at least 97%, at least 98%, or at least 99% sequence identity to nucleotides 58-2277 and 2320-4374 of SEQ ID NO: 70 (i.e., nucleotides 58-4374 of SEQ ID NO: 70 without the nucleotides encoding the B domain or B domain fragment). In other embodiments, the nucleic acid sequence has at least 85%, at least 86%, at least 87%, at least 88%, at least 89%, at least 90%, at least 91%, at least 95%, at least 96%, at least 97%, at least 98%, or at least 99% sequence identity to SEQ ID NO: 70. In other embodiments, the nucleotide sequence comprises nucleotides 58-2277 and 2320-4374 of SEQ ID NO: 70 (i.e., nucleotides 58-4374 of SEQ ID NO: 70 without the nucleotides encoding the B domain or B domain fragment) or nucleotides 58 to 4374 of SEQ ID NO: 70. In still other embodiments, the nucleotide sequence comprises nucleotides 1-2277 and 2320-4374 of SEQ ID NO: 70 (i.e., nucleotides 1-4374 of SEQ ID NO: 70 without the nucleotides encoding the B domain or B domain fragment) or nucleotides 1 to 4374 of SEQ ID NO: 70.

In some embodiments, the present disclosure provides an isolated nucleic acid molecule comprising a nucleotide sequence encoding a polypeptide with FVIII activity, wherein the nucleotide sequence comprises a nucleic acid sequence having at least 85%, at least 86%, at least 87%, at least 88%, at least 89%, at least 90%, at least 91%, at least 95%, at least 96%, at least 97%, at least 98%, or at least 99% sequence identity to nucleotides 58 to 4374 of SEQ ID NO:

71. In other embodiments, the nucleotide sequence comprises a nucleic acid sequence having at least 85%, at least 86%, at least 87%, at least 88%, at least 89%, at least 90%, at least 91%, at least 95%, at least 96%, at least 97%, at least 98%, or at least 99% sequence identity to nucleotides 58-2277 and 2320-4374 of SEQ ID NO: 71 (i.e., nucleotides 58-4374 of SEQ ID NO: 71 without the nucleotides encoding the B domain or B domain fragment). In other embodiments, the nucleic acid sequence has at least 85%, at least 86%, at least 87%, at least 88%, at least 89%, at least 90%, at least 91%, at least 95%, at least 96%, at least 97%, at least 98%, or at least 99% sequence identity to SEQ ID NO: 71. In other embodiments, the nucleotide sequence comprises nucleotides 58-2277 and 2320-4374 of SEQ ID NO: 71 (i.e., nucleotides 58-4374 of SEQ ID NO: 71 without the nucleotides encoding the B domain or B domain fragment) or nucleotides 58 to 4374 of SEQ ID NO: 71. In still other embodiments, the nucleotide sequence comprises nucleotides 1-2277 and 2320-4374 of SEQ ID NO: 71 (i.e., nucleotides 1-4374 of SEQ ID NO: 71 without the nucleotides encoding the B domain or B domain fragment) or nucleotides 1 to 4374 of SEQ ID NO: 71.

In some embodiments, the present disclosure provides an isolated nucleic acid molecule comprising a nucleotide sequence encoding a polypeptide with FVIII activity, wherein the nucleotide sequence comprises a nucleic acid sequence having at least 92%, at least 93%, at least 94%, at least 95%, at least 96%, at least 97%, at least 98%, or at least 99% sequence identity to nucleotides 58 to 4374 of SEQ ID NO: 3. In other embodiments, the nucleotide sequence comprises a nucleic acid sequence having at least 92%, at least 93%, at least 94%, at least 95%, at least 96%, at least 97%, at least 98%, or at least 99% sequence identity to nucleotides 58-2277 and 2320-4374 of SEQ ID NO: 3 (i.e., nucleotides 58-4374 of SEQ ID NO: 3 without the nucleotides encoding the B domain or B domain fragment). In certain embodiments, the nucleic acid sequence has at least 92%, at least 93%, at least 94%, at least 95%, at least 96%, at least 97%, at least 98%, or at least 99% sequence identity to SEQ ID NO: 3. In some embodiments, the nucleotide sequence comprises nucleotides 58-2277 and 2320-4374 of SEQ ID NO: 3 (i.e., nucleotides 58-4374 of SEQ ID NO: 3 without the nucleotides encoding the B domain or B domain fragment) or nucleotides 58 to 4374 of SEQ ID NO: 3. In still other embodiments, the nucleotide sequence comprises nucleotides 58-2277 and 2320-4374 of SEQ ID NO: 3 (i.e., nucleotides 1-4374 of SEQ ID NO: 3 without the nucleotides encoding the B domain or B domain fragment) or nucleotides 1 to 4374 of SEQ ID NO: 3.

In some embodiments, the present disclosure provides an isolated nucleic acid molecule comprising a nucleotide sequence encoding a polypeptide with FVIII activity, wherein the nucleotide sequence comprises a nucleic acid sequence having at least 91%, at least 92%, at least 93%, at least 94%, at least 95%, at least 96%, at least 97%, at least 98%, or at least 99% sequence identity to nucleotides 58 to 4374 of SEQ ID NO: 4. In other embodiments, the nucleotide sequence comprises a nucleic acid sequence having at least 91%, at least 92%, at least 93%, at least 94%, at least 95%, at least 96%, at least 97%, at least 98%, or at least 99% sequence identity to nucleotides 58-2277 and 2320-4374 of SEQ ID NO: 4 (i.e., nucleotides 58-4374 of SEQ ID NO: 4 without the nucleotides encoding the B domain or B domain fragment). In other embodiments, the nucleic acid sequence has at least 91%, at least 92%, at least 93%, at least 94%, at least 95%, at least 96%, at least 97%, at least 98%, or at least 99% sequence identity to SEQ ID NO: 4. In other embodiments, the nucleotide sequence comprises nucleotides 58-2277 and 2320-4374 of SEQ ID NO: 4 (i.e., nucleotides 58-4374 of SEQ ID NO: 4 without the nucleotides encoding the B domain or B domain fragment) or nucleotides 58 to 4374 of SEQ ID NO: 4. In still other embodiments, the nucleotide sequence comprises nucleotides 1-2277 and 2320-4374 of SEQ ID NO: 4 (i.e., nucleotides 1-4374 of SEQ ID NO: 4 without the nucleotides encoding the B domain or B domain fragment) or nucleotides 1 to 4374 of SEQ ID NO: 4.

In some embodiments, the present disclosure provides an isolated nucleic acid molecule comprising a nucleotide sequence encoding a polypeptide with FVIII activity, wherein the nucleotide sequence comprises a nucleic acid sequence having at least 89%, at least 90%, at least 91%, at least 92%, at least 93%, at least 94%, at least 95%, at least 96%, at least 97%, at least 98%, or at least 99% sequence identity to nucleotides 58 to 4374 of SEQ ID NO: 5. In other embodiments, the nucleotide sequence comprises a nucleic acid sequence having at least 89%, at least 90%, at least 91%, at least 92%, at least 93%, at least 94%, at least 95%, at least 96%, at least 97%, at least 98%, or at least 99% sequence identity to nucleotides 58-2277 and 2320-4374 of SEQ ID NO: 5 (i.e., nucleotides 58-4374 of SEQ ID NO: 5 without the nucleotides encoding the B domain or B domain fragment). In certain embodiments, the nucleic acid sequence has at least 89%, at least 90%, at least 91%, at least 92%, at least 93%, at least 94%, at least 95%, at least 96%, at least 97%, at least 98%, or at least 99% sequence identity to SEQ ID NO: 5. In some embodiments, the nucleotide sequence comprises nucleotides 58-2277 and 2320-4374 of SEQ ID NO: 5 (i.e., nucleotides 58-4374 of SEQ ID NO: 5 without the nucleotides encoding the B domain or B domain fragment) or nucleotides 58 to 4374 of SEQ ID NO: 5. In still other embodiments, the nucleotide sequence comprises nucleotides 1-2277 and 2320-4374 of SEQ ID NO: 5 (i.e., nucleotides 1-4374 of SEQ ID NO: 5 without the nucleotides encoding the B domain or B domain fragment) or nucleotides 1 to 4374 of SEQ ID NO: 5.

In some embodiments, the present disclosure provides an isolated nucleic acid molecule comprising a nucleotide sequence encoding a polypeptide with FVIII activity, wherein the nucleotide sequence comprises a nucleic acid sequence having at least 89%, at least 90%, at least 91%, at least 92%, at least 93%, at least 94%, at least 95%, at least 96%, at least 97%, at least 98%, or at least 99% sequence identity to nucleotides 58 to 4374 of SEQ ID NO: 6. In other embodiments, the nucleotide sequence comprises a nucleic acid sequence having at least 89%, at least 90%, at least 91%, at least 92%, at least 93%, at least 94%, at least 95%, at least 96%, at least 97%, at least 98%, or at least 99% sequence identity to nucleotides 58-2277 and 2320-4374 of SEQ ID NO: 6 (i.e., nucleotides 58-4374 of SEQ ID NO: 6 without the nucleotides encoding the B domain or B domain fragment). In certain embodiments, the nucleic acid sequence has at least 89%, at least 90%, at least 91%, at least 92%, at least 93%, at least 94%, at least 95%, at least 96%, at least 97%, at least 98%, or at least 99% sequence identity to SEQ ID NO: 6. In some embodiments, the nucleotide sequence comprises nucleotides 58-2277 and 2320-4374 of SEQ ID NO: 6 (i.e., nucleotides 58-4374 of SEQ ID NO: 6 without the nucleotides encoding the B domain or B domain fragment) or nucleotides 58 to 4374 of SEQ ID NO: 6. In still other embodiments, the nucleotide sequence comprises nucleotides 1-2277 and 2320-4374 of SEQ ID NO: 6 (i.e., nucleotides 1-4374 of SEQ ID NO: 6 without the nucleotides encoding the B domain or B domain fragment) or nucleotides 1 to 4374 of SEQ ID NO: 6.

In some embodiments, the nucleotide sequence comprises a nucleic acid sequence encoding a signal peptide. In certain embodiments, the signal peptide is a FVIII signal peptide. In some embodiments, the nucleic acid sequence encoding a signal peptide is codon optimized. In one particular embodiment, the nucleic acid sequence encoding a signal peptide has at least 60%, at least 70%, at least 80%, at least 90%, at least 95%, at least 96%, at least 97%, at least 98%, at least 99%, or 100% sequence identity to (i) nucleotides 1 to 57 of SEQ ID NO: 1; (ii) nucleotides 1 to 57 of SEQ ID NO: 2; (iii) nucleotides 1 to 57 of SEQ ID NO: 3; (iv) nucleotides 1 to 57 of SEQ ID NO: 4; (v) nucleotides 1 to 57 of SEQ ID NO: 5; (vi) nucleotides 1 to 57 of SEQ ID NO: 6; (vii) nucleotides 1 to 57 of SEQ ID NO: 70; (viii) nucleotides 1 to 57 of SEQ ID NO: 71; or (ix) nucleotides 1 to 57 of SEQ ID NO: 68.

SEQ ID NOs: 1-6, 70, and 71 are optimized versions of SEQ ID NO: 16, the starting or "parental" or "wild-type" FVIII nucleotide sequence. SEQ ID NO: 16 encodes a B domain-deleted human FVIII. While SEQ ID NOs: 1-6, 70, and 71 are derived from a specific B domain-deleted form of FVIII (SEQ ID NO: 16), it is to be understood that the present disclosure is also directed to optimized versions of nucleic acids encoding other versions of FVIII. For example, other versions of FVIII can include full length FVIII, other B-domain deletions of FVIII (described below), or other fragments of FVIII that retain FVIII activity.

"A polypeptide with FVIII activity" as used herein means a functional FVIII polypeptide in its normal role in coagulation, unless otherwise specified. The term a polypeptide with FVIII activity includes a functional fragment, variant, analog, or derivative thereof that retains the function of full-length wild-type Factor VIII in the coagulation pathway. "A polypeptide with FVIII activity" is used interchangeably with FVIII protein, FVIII polypeptide, or FVIII. Examples of FVIII functions include, but are not limited to, an ability to activate coagulation, an ability to act as a cofactor for factor IX, or an ability to form a tenase complex with factor IX in the presence of $Ca^{2+}$ and phospholipids, which then converts Factor X to the activated form Xa. In one embodiment, a polypeptide having FVIII activity comprises two polypeptide chains, the first chain having the FVIII heavy chain and the second chain having the FVIII light chain. In another embodiment, the polypeptide having FVIII activity is single chain FVIII. Single chain FVIII can contain one or more mutation or substitutions at amino acid residue 1645 and/or 1648 corresponding to mature FVIII sequence. See International Application No. PCT/US2012/045784, incorporated herein by reference in its entirety. The FVIII protein can be the human, porcine, canine, rat, or murine FVIII protein. In addition, comparisons between FVIII from humans and other species have identified conserved residues that are likely to be required for function (Cameron et al., Thromb. Haemost. 79:317-22 (1998); U.S. Pat. No. 6,251,632).

The "B domain" of FVIII, as used herein, is the same as the B domain known in the art that is defined by internal amino acid sequence identity and sites of proteolytic cleavage by thrombin, e.g., residues Ser741-Arg1648 of full length human FVIII. The other human FVIII domains are defined by the following amino acid residues: A1, residues Ala1-Arg372; A2, residues Ser373-Arg740; A3, residues Ser1690-Ile2032; C1, residues Arg2033-Asn2172; C2, residues Ser2173-Tyr2332. The A3-C1-C2 sequence includes residues Ser1690-Tyr2332. The remaining sequence, residues Glu1649-Arg1689, is usually referred to as the FVIII light chain activation peptide. The locations of the boundaries for all of the domains, including the B domains, for porcine, mouse and canine FVIII are also known in the art. An example of a BDD FVIII is REFACTO® recombinant BDD FVIII (Wyeth Pharmaceuticals, Inc.).

A "B domain deleted FVIII" can have the full or partial deletions disclosed in U.S. Pat. Nos. 6,316,226, 6,346,513, 7,041,635, 5,789,203, 6,060,447, 5,595,886, 6,228,620, 5,972,885, 6,048,720, 5,543,502, 5,610,278, 5,171,844, 5,112,950, 4,868,112, and 6,458,563, each of which is incorporated herein by reference in its entirety. In some embodiments, a B domain deleted FVIII sequence of the present disclosure comprises any one of the deletions disclosed at col. 4, line 4 to col. 5, line 28 and examples 1-5 of U.S. Pat. No. 6,316,226 (also in U.S. Pat. No. 6,346,513). In some embodiments, a B domain deleted FVIII of the present disclosure has a deletion disclosed at col. 2, lines 26-51 and examples 5-8 of U.S. Pat. No. 5,789,203 (also U.S. Pat. Nos. 6,060,447, 5,595,886, and 6,228,620). In some embodiments, a B domain deleted FVIII has a deletion described in col. 1, lines 25 to col. 2, line 40 of U.S. Pat. No. 5,972,885; col. 6, lines 1-22 and example 1 of U.S. Pat. No. 6,048,720; col. 2, lines 17-46 of U.S. Pat. No. 5,543,502; col. 4, line 22 to col. 5, line 36 of U.S. Pat. No. 5,171,844; col. 2, lines 55-68, FIG. 2, and example 1 of U.S. Pat. No. 5,112,950; col. 2, line 2 to col. 19, line 21 and table 2 of U.S. Pat. No. 4,868,112; col. 2, line 1 to col. 3, line 19, col. 3, line 40 to col. 4, line 67, col. 7, line 43 to col. 8, line 26, and col. 11, line 5 to col. 13, line 39 of U.S. Pat. No. 7,041,635; or col. 4, lines 25-53, of U.S. Pat. No. 6,458,563. In some embodiments, a B domain deleted FVIII has a deletion of most of the B domain, but still contains amino-terminal sequences of the B domain that are essential for in vivo proteolytic processing of the primary translation product into two polypeptide chain, as disclosed in WO 91/09122, which is incorporated herein by reference in its entirety. In some embodiments, a B domain deleted FVIII is constructed with a deletion of amino acids 747-1638, i.e., virtually a complete deletion of the B domain. Hoeben R. C., et al. J. Biol. Chem. 265 (13): 7318-7323 (1990), incorporated herein by reference in its entirety. A B domain deleted FVIII can also contain a deletion of amino acids 771-1666 or amino acids 868-1562 of FVIII. Meulien P., et al. Protein Eng. 2(4): 301-6 (1988), incorporated herein by reference in its entirety. Additional B domain deletions that are part of the disclosure include, e.g., deletion of amino acids 982 through 1562 or 760 through 1639 (Toole et al., Proc. Natl. Acad. Sci. U.S.A. (1986) 83, 5939-5942)), 797 through 1562 (Eaton, et al. Biochemistry (1986) 25:8343-8347)), 741 through 1646 (Kaufman (PCT published application No. WO 87/04187)), 747-1560 (Sarver, et al., DNA (1987) 6:553-564)), 741 through 1648 (Pasek (PCT application No. 88/00831)), 816 through 1598 or 741 through 1689 (Lagner (Behring Inst. Mitt. (1988) No 82:16-25, EP 295597)), each of which is incorporated herein by reference in its entirety. Each of the foregoing deletions can be made in any FVIII sequence.

A number of functional FVIII molecules, including B-domain deletions, are disclosed in the following patents U.S. Pat. Nos. 6,316,226 and 6,346,513, both assigned to Baxter; U.S. Pat. No. 7,041,635 assigned to In2Gen; U.S. Pat. Nos. 5,789,203, 6,060,447, 5,595,886, and 6,228,620 assigned to Chiron; U.S. Pat. Nos. 5,972,885 and 6,048,720 assigned to Biovitrum, U.S. Pat. Nos. 5,543,502 and 5,610,278 assigned to Novo Nordisk; U.S. Pat. No. 5,171,844 assigned to Immuno Ag; U.S. Pat. No. 5,112,950 assigned to Transgene S.A.; U.S. Pat. No. 4,868,112 assigned to Genetics Institute, each of which is incorporated herein by reference in its entirety.

Codon Optimization

In one embodiment, the present disclosure provides an isolated nucleic acid molecule comprising a nucleotide sequence that encodes a polypeptide with FVIII activity, wherein the nucleic acid sequence has been codon optimized. In another embodiment, the starting nucleic acid sequence that encodes a polypeptide with FVIII activity and that is subject to codon optimization is SEQ ID NO: 16. In some embodiments, the sequence that encodes a polypeptide with FVIII activity is codon optimized for human expression. In other embodiments, the sequence that encodes a polypeptide with FVIII activity is codon optimized for murine expression. SEQ ID NOs: 1-6, 70, and 71 are codon optimized versions of SEQ ID NO: 16, optimized for human expression.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Such optimization includes replacing at least one, or more than one, or a significant number, of codons with one or more codons that are more frequently used in the genes of that organism.

Deviations in the nucleotide sequence that comprises the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

Many organisms display a bias for use of particular codons to code for insertion of a particular amino acid in a growing peptide chain. Codon preference, or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, the relative frequencies of codon usage have been calculated. Codon usage tables are available, for example, at the "Codon Usage Database" available at www.kazusa.or.jp/codon/ (visited Jun. 18, 2012). See Nakamura, Y., et al. Nucl. Acids Res. 28:292 (2000).

Randomly assigning codons at an optimized frequency to encode a given polypeptide sequence can be done manually by calculating codon frequencies for each amino acid, and then assigning the codons to the polypeptide sequence randomly. Additionally, various algorithms and computer software programs can be used to calculate an optimal sequence.

In some embodiments, the nucleic acid molecule comprises one or more properties: (a) the nucleic acid molecule or a portion thereof has an increased the human codon adaptation index relative to SEQ ID NO: 16; (b) the nucleotide sequence or a portion thereof has an increased frequency of optimal codons relative to SEQ ID NO:16; (c) the nucleotide sequence or a portion thereof contains a higher percentage of G/C nucleotides compared to the percentage of G/C nucleotides in SEQ ID NO: 16; (d) the nucleotide sequence or a portion thereof has an increased relative synonymous codon usage relative to SEQ ID NO: 16; (e) the nucleotide sequence or a portion thereof is a reduced effective number of codons relative SEQ ID NO: 16; (f) the nucleotide sequence contains fewer MARS/ARS sequences (SEQ ID NOs: 21 and 22) relative to SEQ ID NO: 16; (g) the nucleotide sequence contains fewer destabilizing ele-

TABLE 1

The Standard Genetic Code

|   | T | C | A | G |
|---|---|---|---|---|
| T | TTT Phe (F)<br>TTC"<br>TTA Leu (L)<br>TTG" | TCT Ser (S)<br>TCC"<br>TCA"<br>TCG" | TAT Tyr (Y)<br>TAC"<br>TAA Stop<br>TAG Stop | TGT Cys (C)<br>TGC<br>TGA Stop<br>TGG Trp (W) |
| C | CTT Leu (L)<br>CTC"<br>CTA"<br>CTG" | CCT Pro (P)<br>CCC"<br>CCA"<br>CCG" | CAT His (H)<br>CAC"<br>CAA Gln (Q)<br>CAG" | CGT Arg (R)<br>CGC"<br>CGA"<br>CGG" |
| A | ATT Ile (I)<br>ATC"<br>ATA"<br>ATG Met (M) | ACT Thr (T)<br>ACC"<br>ACA"<br>ACG" | AAT Asn (N)<br>AAC"<br>AAA Lys (K)<br>AAG" | AGT Ser (S)<br>AGC"<br>AGA Arg (R)<br>AGG" |
| G | GTT Val (V)<br>GTC"<br>GTA"<br>GTG" | GCT Ala (A)<br>GCC"<br>GCA"<br>GCG" | GAT Asp (D)<br>GAC"<br>GAA Glu (E)<br>GAG" | GGT Gly (G)<br>GGC"<br>GGA"<br>GGG" | ments (SEQ ID NOs: 23 and 24) relative to SEQ ID NO: 16; (i) the nucleotide sequence does not contain a poly-T sequence, (j) the nucleotide sequence does not contain a poly-A sequence; or (k) any combination thereof. In some embodiments, the nucleic acid molecules contains at least two, at least three, at least four, at least five, at least six, at least seven, at least eight, at least nine, or ten characteristics of (a) to (j).

Codon Adaptation Index

In one embodiment, the present disclosure provides an isolated nucleic acid molecule comprising a nucleotide sequence described herein that encodes a polypeptide with FVIII activity, wherein the human codon adaptation index is increased relative to SEQ ID NO: 16. For example, the nucleotide sequence can have a human codon adaptation index that is at least about 0.75 (75%), at least about 0.76 (76%), at least about 0.77 (77%), at least about 0.78 (78%), at least about 0.79 (79%), at least about 0.80 (80%), at least about 0.81 (81%), at least about 0.82 (82%), at least about 0.83 (83%), at least about 0.84 (84%), at least about 0.85 (85%), at least about 0.86 (86%), at least about 0.87 (87%), at least about 0.88 (88%), at least about 0.89 (89%), at least about 0.90 (90%), at least about 0.91 (91%), at least about 0.92 (92%), at least about 0.93 (93%), at least about 0.94 (94%), at least about 0.95 (95%), at least about 0.96 (96%), at least about 0.97 (97%), at least about 0.98 (98%), or at least about 0.99 (99%). In some embodiments, the nucleotide sequence has a human codon adaptation index that is at least about 0.88 (88%). In other embodiments, the nucleotide sequence has a human codon adaptation index that is at least about 0.91 (91%). In other embodiments, the nucleotide sequence has a human codon adaptation index that is at least about 0.91 (97%).

In one particular embodiment, the present disclosure provides an isolated nucleic acid molecule comprising a nucleotide sequence which comprises a first nucleic acid sequence encoding an N-terminal portion of a FVIII polypeptide and a second nucleic acid sequence encoding a C-terminal portion of a FVIII polypeptide; wherein the first nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-1791 of SEQ ID NO: 3; (ii) nucleotides 1-1791 of SEQ ID NO: 3; (iii) nucleotides 58-1791 of SEQ ID NO: 4; or (iv) nucleotides 1-1791 of SEQ ID NO: 4; wherein the N-terminal portion and the C-terminal portion together have a FVIII polypeptide activity; and wherein the human codon adaptation index of the nucleotide sequence is increased relative to SEQ ID NO: 16. In some embodiments, the nucleotide sequence has a human codon adaptation index that is at least about 0.75 (75%), at least about 0.76 (76%), at least about 0.77 (77%), at least about 0.78 (78%), at least about 0.79 (79%), at least about 0.80 (80%), at least about 0.81 (81%), at least about 0.82 (82%), at least about 0.83 (83%), at least about 0.84 (84%), at least about 0.85 (85%), at least about 0.86 (86%), at least about 0.87 (87%), at least about 0.88 (88%), at least about 0.89 (89%), at least about 0.90 (90%), or at least about 0.91 (91%). In one particular the nucleotide sequence has a human codon adaptation index that is at least about 0.88 (88%). In another embodiment, the nucleotide sequence has a human codon adaptation index that is at least about 0.91 (91%).

In another embodiment, the present disclosure provides an isolated nucleic acid molecule comprising a nucleotide sequence which comprises a first nucleic acid sequence encoding an N-terminal portion of a FVIII polypeptide and a second nucleic acid sequence encoding a C-terminal portion of a FVIII polypeptide; wherein the second nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 1792-2277 and 2320-4374 of SEQ ID NO: 5 or (ii) 1792-2277 and 2320-4374 of SEQ ID NO: 6; wherein the N-terminal portion and the C-terminal portion together have a FVIII polypeptide activity; and wherein the human codon adaptation index of the nucleotide sequence is increased relative to SEQ ID NO: 16. In some embodiments, the nucleotide sequence has a human codon adaptation index that is at least about 0.75 (75%), at least about 0.76 (76%), at least about 0.77 (77%), at least about 0.78 (78%), at least about 0.79 (79%), at least about 0.80 (80%), at least about 0.81 (81%), at least about 0.82 (82%), at least about 0.83 (83%), at least about 0.84 (84%), at least about 0.85 (85%), at least about 0.86 (86%), at least about 0.87 (87%), or at least about 0.88 (88%). In one particular the nucleotide sequence has a human codon adaptation index that is at least about 0.83 (83%). In another embodiment, the nucleotide sequence has a human codon adaptation index that is at least about 0.88 (88%).

In other embodiments, the present disclosure provides an isolated nucleic acid molecule comprising a nucleotide sequence encoding a polypeptide with FVIII activity, wherein the nucleotide sequence comprises a nucleic acid sequence having at least about 80%, at least about 85%, at least about 89%, at least about 90%, at least about 91%, at least about 92%, at least about 93%, at least about 94%, at least about 95%, at least about 96%, at least about 97%, at least about 98%, or at least about 99% sequence identity to nucleotides 58-2277 and 2320-4374 of an amino acid sequence selected from SEQ ID NOs: 1, 2, 3, 4, 5, 6, 70, and 71 (i.e., nucleotides 58-4374 of SEQ ID NO: 1, 2, 3, 4, 5, 6, 70, or 71 without the nucleotides encoding the B domain or B domain fragment); and wherein the human codon adaptation index of the nucleotide sequence is increased relative to SEQ ID NO: 16. In some embodiments, the nucleotide sequence has a human codon adaptation index that is at least about 0.75 (75%), at least about 0.76 (76%), at least about 0.77 (77%), at least about 0.78 (78%), at least about 0.79 (79%), at least about 0.80 (80%), at least about 0.81 (81%), at least about 0.82 (82%), at least about 0.83 (83%), at least about 0.84 (84%), at least about 0.85 (85%), at least about 0.86 (86%), at least about 0.87 (87%), or at least about 0.88 (88%). In one particular the nucleotide sequence has a human codon adaptation index that is at least about 0.75 (75%). In another embodiment, the nucleotide sequence has a human codon adaptation index that is at least about 0.83 (83%). In another embodiment, the nucleotide sequence has a human codon adaptation index that is at least about 0.88 (88%). In another embodiment, the nucleotide sequence has a human codon adaptation index that is at least about 0.91 (91%). In another embodiment, the nucleotide sequence has a human codon adaptation index that is at least about 0.97 (97%).

In some embodiments, the isolated nucleic acid molecule of the present disclosure has an increased frequency of optimal codons (FOP) relative to SEQ ID NO: 16. In certain embodiments, the FOP of the isolated nucleic acid molecule is at least about 40, at least about 45, at least about 50, at least about 55, at least about 60, at least about 64, at least about 65, at least about 70, at least about 75, at least about 79, at least about 80, at least about 85, or at least about 90.

In other embodiments, the isolated nucleic acid molecule of the present disclosure has an increased relative synonymous codon usage (RCSU) relative to SEQ ID NO: 16. In some embodiments, the RCSU of the isolated nucleic acid molecule is greater than 1.5. In other embodiments, the RCSU of the isolated nucleic acid molecule is greater than 2.0. In certain embodiments, the RCSU of the isolated nucleic acid molecule is at least about 1.5, at least about 1.6, at least about 1.7, at least about 1.8, at least about 1.9, at least about 2.0, at least about 2.1, at least about 2.2, at least about 2.3, at least about 2.4, at least about 2.5, at least about 2.6, or at least about 2.7.

In still other embodiments, the isolated nucleic acid molecule of the present disclosure has a decreased effective number of codons relative to SEQ ID NO: 16. In some embodiments, the isolated nucleic acid molecule has an effective number of codons of less than about 50, less than about 45, less than about 40, less than about 35, less than about 30, or less than about 25. In one particular embodiment, the isolated nucleic acid molecule has an effective number of codons of about 40, about 35, about 30, about 25, or about 20.

G/C Content Optimization

In some embodiments, the present disclosure provides an isolated nucleic acid molecule comprising a nucleotide sequence described herein that encodes a polypeptide with FVIII activity, wherein the nucleotide sequence contains a higher percentage of G/C nucleotides compared to the percentage of G/C nucleotides in SEQ ID NO: 16. In other embodiments, the nucleotide sequence that encodes a polypeptide with FVIII activity has a G/C content that is at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, or at least about 60%.

In one particular embodiment, the present disclosure provides an isolated nucleic acid molecule comprising a nucleotide sequence which comprises a first nucleic acid sequence encoding an N-terminal portion of a FVIII polypeptide and a second nucleic acid sequence encoding a C-terminal portion of a FVIII polypeptide; wherein the first nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-1791 of SEQ ID NO: 3; (ii) nucleotides 1-1791 of SEQ ID NO: 3; (iii) nucleotides 58-1791 of SEQ ID NO: 4; or (iv) nucleotides 1-1791 of SEQ ID NO: 4; wherein the N-terminal portion and the C-terminal portion together have a FVIII polypeptide activity; and wherein the nucleotide sequence contains a higher percentage of G/C nucleotides compared to the percentage of G/C nucleotides in SEQ ID NO: 16. In some embodiments, the nucleotide sequence that encodes a polypeptide with FVIII activity has a G/C content that is at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, or at least about 58%. In one particular embodiment, the nucleotide sequence that encodes a polypeptide with FVIII activity has a G/C content that is at least about 58%.

In another embodiment, the present disclosure provides an isolated nucleic acid molecule comprising a nucleotide sequence which comprises a first nucleic acid sequence encoding an N-terminal portion of a FVIII polypeptide and a second nucleic acid sequence encoding a C-terminal portion of a FVIII polypeptide; wherein the second nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 1792-4374 of SEQ ID NO: 5; (ii) nucleotides 1792-4374 of SEQ ID NO: 6; (iii) nucleotides 1792-2277 and 2320-4374 of SEQ ID NO: 5 (i.e., nucleotides 1792-4374 of SEQ ID NO: 5 without the nucleotides encoding the B domain or B domain fragment), or (iv) 1792-2277 and 2320-4374 of SEQ ID NO: 6 (i.e., nucleotides 1792-4374 of SEQ ID NO: 6 without the nucleotides encoding the B domain or B domain fragment); wherein the N-terminal portion and the C-terminal portion together have a FVIII polypeptide activity; and wherein the nucleotide sequence contains a higher percentage of G/C nucleotides compared to the percentage of G/C nucleotides in SEQ ID NO: 16. In other embodiments, the nucleotide sequence that encodes a polypeptide with FVIII activity has a G/C content that is at least about 45%, at least about 46%, at least about 47%, at least about 48%, at least about 49%, at least about 50%, at least about 51%, at least about 52%, at least about 53%, at least about 54%, at least about 55%, at least about 56%, or at least about 57%. In one particular embodiment, the nucleotide sequence that encodes a polypeptide with FVIII activity has a G/C content that is at least about 52%. In another embodiment, the nucleotide sequence that encodes a polypeptide with FVIII activity has a G/C content that is at least about 55%. In another embodiment, the nucleotide sequence that encodes a polypeptide with FVIII activity has a G/C content that is at least about 57%.

In other embodiments, the present disclosure provides an isolated nucleic acid molecule comprising a nucleotide sequence encoding a polypeptide with FVIII activity, wherein the nucleotide sequence comprises a nucleic acid sequence having at least about 80%, at least about 85%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-4374 or (ii) nucleotides 58-2277 and 2320-4374 of an amino acid sequence selected from SEQ ID NOs: 1, 2, 3, 4, 5, 6, 70, and 71 (i.e., nucleotides 58-4374 of SEQ ID NO: 1, 2, 3, 4, 5, 6, 70, or 71 without the nucleotides encoding the B domain or B domain fragment); and wherein the nucleotide sequence contains a higher percentage of G/C nucleotides compared to the percentage of G/C nucleotides in SEQ ID NO: 16. In other embodiments, the nucleotide sequence that encodes a polypeptide with FVIII activity has a G/C content that is at least about 45%. In one particular embodiment, the nucleotide sequence that encodes a polypeptide with FVIII activity has a G/C content that is at least about 52%. In another embodiment, the nucleotide sequence that encodes a polypeptide with FVIII activity has a G/C content that is at least about 55%. In another embodiment, the nucleotide sequence that encodes a polypeptide with FVIII activity has a G/C content that is at least about 57%. In another embodiment, the nucleotide sequence that encodes a polypeptide with FVIII activity has a G/C content that is at least about 58%. In still another embodiment, the nucleotide sequence that encodes a polypeptide with FVIII activity has a G/C content that is at least about 60%.

"G/C content" (or guanine-cytosine content), or "percentage of G/C nucleotides," refers to the percentage of nitrogenous bases in a DNA molecule that are either guanine or cytosine. G/C content can be calculated using the following formula:

$$\frac{G+C}{A+T+G+C} \times 100 \quad \text{(III)}$$

Human genes are highly heterogeneous in their G/C content, with some genes having a G/C content as low as 20%, and other genes having a G/C content as high as 95%. In general, G/C rich genes are more highly expressed. In fact, it has been demonstrated that increasing the G/C content of a gene can lead to increased expression of the gene, due mostly to an increase in transcription and higher steady state mRNA levels. See Kudla et al., PLoS Biol., 4(6): e180 (2006).

Matrix Attachment Region-Like Sequences

In some embodiments, the present disclosure provides an isolated nucleic acid molecule comprising a nucleotide sequence described herein that encodes a polypeptide with FVIII activity, wherein the nucleotide sequence contains fewer MARS/ARS sequences relative to SEQ ID NO: 16. In other embodiments, the nucleotide sequence that encodes a polypeptide with FVIII activity contains at most 6, at most 5, at most 4, at most 3, or at most 2 MARS/ARS sequences. In other embodiments, the nucleotide sequence that encodes a polypeptide with FVIII activity contains at most 1 MARS/ARS sequence. In yet other embodiments, the nucleotide sequence that encodes a polypeptide with FVIII activity does not contain a MARS/ARS sequence.

In one particular embodiment, the present disclosure provides an isolated nucleic acid molecule comprising a nucleotide sequence which comprises a first nucleic acid sequence encoding an N-terminal portion of a FVIII polypeptide and a second nucleic acid sequence encoding a C-terminal portion of a FVIII polypeptide; wherein the first nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-1791 of SEQ ID NO: 3; (ii) nucleotides 1-1791 of SEQ ID NO: 3; (iii) nucleotides 58-1791 of SEQ ID NO: 4; or (iv) nucleotides 1-1791 of SEQ ID NO: 4; wherein the N-terminal portion and the C-terminal portion together have a FVIII polypeptide activity; and wherein the nucleotide sequence contains fewer MARS/ARS sequences relative to SEQ ID NO: 16. In other embodiments, the nucleotide sequence that encodes a polypeptide with FVIII activity contains at most 6, at most 5, at most 4, at most 3, or at most 2 MARS/ARS sequences. In other embodiments, the nucleotide sequence that encodes a polypeptide with FVIII activity contains at most 1 MARS/ARS sequence. In yet other embodiments, the nucleotide sequence that encodes a polypeptide with FVIII activity does not contain a MARS/ARS sequence.

In another embodiment, the present disclosure provides an isolated nucleic acid molecule comprising a nucleotide sequence which comprises a first nucleic acid sequence encoding an N-terminal portion of a FVIII polypeptide and a second nucleic acid sequence encoding a C-terminal portion of a FVIII polypeptide; wherein the second nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 1792-4374 of SEQ ID NO: 5; (ii) nucleotides 1792-4374 of SEQ ID NO: 6; (iii) nucleotides 1792-2277 and 2320-4374 of SEQ ID NO: 5 (i.e., nucleotides 1792-4374 of SEQ ID NO: 5 without the nucleotides encoding the B domain or B domain fragment); or (iv) nucleotides 1792-2277 and 2320-4374 of SEQ ID NO: 6 (i.e., nucleotides 1792-4374 of SEQ ID NO: 6 without the nucleotides encoding the B domain or B domain fragment); wherein the N-terminal portion and the C-terminal portion together have a FVIII polypeptide activity; and wherein the nucleotide sequence contains fewer MARS/ARS sequences relative to SEQ ID NO: 16. In other embodiments, the nucleotide sequence that encodes a polypeptide with FVIII activity contains at most 6, at most 5, at most 4, at most 3, or at most 2 MARS/ARS sequences. In other embodiments, the nucleotide sequence that encodes a polypeptide with FVIII activity contains at most 1 MARS/ARS sequence. In yet other embodiments, the nucleotide sequence that encodes a polypeptide with FVIII activity does not contain a MARS/ARS sequence.

In other embodiments, the present disclosure provides an isolated nucleic acid molecule comprising a nucleotide sequence encoding a polypeptide with FVIII activity, wherein the nucleotide sequence comprises a nucleic acid sequence having at least about 80%, at least about 85%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-4374 of SEQ ID NOs: 1, 2, 3, 4, 5, 6, 70, or 71 or (ii) nucleotides 58-2277 and 2320-4374 of SEQ ID NOs: 1, 2, 3, 4, 5, 6, 70, or 71 (i.e., nucleotides 58-4374 of SEQ ID NO: 1, 2, 3, 4, 5, 6, 70, or 71 without the nucleotides encoding the B domain or B domain fragment); and wherein the nucleotide sequence contains fewer MARS/ARS sequences relative to SEQ ID NO: 16. In other embodiments, the nucleotide sequence that encodes a polypeptide with FVIII activity contains at most 6, at most 5, at most 4, at most 3, or at most 2 MARS/ARS sequences. In other embodiments, the nucleotide sequence that encodes a polypeptide with FVIII activity contains at most 1 MARS/ARS sequence. In yet other embodiments, the nucleotide sequence that encodes a polypeptide with FVIII activity does not contain a MARS/ARS sequence.

AT-rich elements in the human FVIII nucleotide sequence that share sequence similarity with *Saccharomyces cerevisiae* autonomously replicating sequences (ARSs) and nuclear-matrix attachment regions (MARs) have been identified. (Fallux et al., *Mol. Cell. Biol.* 16:4264-4272 (1996). One of these elements has been demonstrated to bind nuclear factors in vitro and to repress the expression of a chloramphenicol acetyltransferase (CAT) reporter gene. Id. It has been hypothesized that these sequences can contribute to the transcriptional repression of the human FVIII gene. Thus, in one embodiment, all MAR/ARS sequences are abolished in the FVIII gene of the present disclosure. There are four MAR/ARS ATATTT sequences (SEQ ID NO: 21) and three MAR/ARS AAATAT sequences (SEQ ID NO: 22) in the parental FVIII sequence (SEQ ID NO: 16). All of these sites were mutated to destroy the MAR/ARS sequences in the optimized FVIII sequences (SEQ ID NOs: 1-6). The location of each of these elements, and the sequence of the corresponding nucleotides in the optimized sequences are shown in Table 2, below.

TABLE 2

Summary of Changes to Repressive Elements

| Location of Element | Starting BDD FVIII Sequence (SEQ ID NO: 16) | SEQ ID NO: 1 | SEQ ID NO: 2 | SEQ ID NO: 3 | SEQ ID NO: 4 | SEQ ID NO: 5 | SEQ ID NO: 6 | SEQ ID NO: 70 | SEQ ID NO: 71 |
|---|---|---|---|---|---|---|---|---|---|
| \multicolumn Destabilizing Sequences ||||||||||
| 639 | ATTTA | GTTTA | GTTCA | GTTCA | GTTCA | GTTCA | GTTCA | GTTCA | GTTCA |
| 1338 | ATTTA | GTTTA | GTTCA | CTTCA | GTTCA | GTTCA | GTTCA | CTTCA | GTTCA |
| 1449 | ATTTA | CITTA | CTTCA | CTTCA | CTTCA | CTTCA | CTTCA | CTTCA | CTTCA |
| 1590 | TAAAT | TAAAT | CAAGT | CAAGT | TAAGT | CAAGT | CAAGT | CAAGT | TAAGT |
| 1623 | TAAAT | CAAAA | GAAGA | CTAAG | CAAGA | CAAGA | CAAGA | TAAGT | CAAGA |
| 2410 | ATTTA | ATCTA | ATCTA | ATCTA | ATCTA | ATCTA | ATCTA | ATCTA | ATCTA |
| 2586 | ATTTA | GTTTA | GTTCA | GTTCA | GTTCA | GTTCA | GTTCA | GTTCA | GTTCA |
| 2630 | TAAAT | TGAAT | TGAAC | TGAAC | TGAAC | TCAAT | TGAAC | TCAAT | TGAAC |
| 3884 | ATTTA | ATCTG | ACCTG | ACCTG | ACCTG | ATCTG | ACCTG | ATCTG | ACCTG |
| 3887 | TAAAT | TGAAC | TGAAC | TGAAC | TGAAC | TGAAC | TGAAC | TGAAC | TGAAC |
| Potential Promoter Binding Sites |||||||||| 
| 641 | TTATA | TTATC | TCATC | TCATT | TCATC | TCATC | TCATC | TCATT | TCATC |
| 1275 | TATAA | CTATA | TTACA | CTACA | GTACA | CTACA | CTACA | CTACA | GTACA |
| 1276 | TTATA | TATAA | TACAA | TACAA | TACAA | TACAA | TACAA | TACAA | TACAA |
| 1445 | TTATA | TCATC | TCATC | TTATC | TCATC | TCATC | TCATC | TTATC | TCATC |
| 1474 | TATAA | TATAA | TACAA | TACAA | TACAA | TACAA | TACAA | TACAA | TACAA |
| 1588 | TATAA | TATAA | TACAA | TACAA | TATAA | TACAA | TACAA | TACAA | TATAA |
| 2614 | TTATA | CTGTA | CTGTA | CTGTA | CTGTA | TTGTA | CTGTA | TTGTA | CTGTA |
| 2661 | TATAA | CATCA | CATCA | CATCA | CATCA | CATCA | CATCC | CATCA | CATCC |
| 3286 | TATAA | TATAA | TACAA | TACAA | TACAA | TACAA | TACAA | TACAA | TACAA |
| 3840 | TTATA | TTATA | TTACT | CTACA | CTACA | CTACA | CTACT | CTACA | CTACT |
| Matrix Attachment-Like Sequences (MARS/ARS) ||||||||||
| 1287 | ATATTT | GTATCT | GTACCT | GTACCT | GTATCT | GTACCT | GTACCT | GTACCT | GTATCT |
| 1447 | ATATTT | ATCTTT | ATCTTC | ATCTTC | ATCTTC | ATCTTC | ATCTTC | ATCTTC | ATCTTC |
| 1577 | AAATAT | AAATCT | AGATCT | AAATCT | AAATCT | AGATCT | AGATCT | AAATCT | AAATCT |
| 1585 | AAATAT | AAGTAT | AAGTAC | AAGTAC | AAGTAT | AAGTAC | AAGTAC | AAGTAC | AAGTAT |
| 2231 | ATATTT | ACATCA | ATATCA | ACATCA | ACATCA | ACATCA | ATATCT | ACATCT | ATATCT |
| 3054 | AAATAT | AAACAT | GAATAT | GAACAT | GAACAT | GAACAT | GAATAT | GAACAT | GAATAT |
| 3788 | ATATTT | ATATCT | ATATCT | ACATCT | ACATCT | ACATCT | ACATCT | ACATCT | ACATCT |

TABLE 2-continued

Summary of Changes to Repressive Elements

| Location of Element | Starting BDD FVIII Sequence (SEQ ID NO: 16) | Optimized BDD FVIII Sequence | | | | | | | |
|---|---|---|---|---|---|---|---|---|---|
| | | SEQ ID NO: 1 | SEQ ID NO: 2 | SEQ ID NO: 3 | SEQ ID NO: 4 | SEQ ID NO: 5 | SEQ ID NO: 6 | SEQ ID NO: 70 | SEQ ID NO: 71 |
| AU Rich Sequence Elements (AREs) | | | | | | | | | |
| 2468 | 1. ATTTTATT | ACTTCATC | ACTTCATC | ACTTCATT | ACTTCATT | ACTTTATT | ACTTTATC | ACTTTATT | ACTTTATC |
| 3790 | 2. ATTTTTAA | ATCTTTAA | ATCTTCAA | ATCTTCAA | ATCTTCAA | ATCTTCAA | ATCTTCAA | ATCTTCAA | ATCTTCAA |
| Poly A/Poly T Sequences | | | | | | | | | |
| 3273 | AAAAAAA | GAAAAAA | GAAGAAG | GAAGAAG | GAAGAAG | GAAGAAG | CAAGAAG | GAAGAAG | CAAGAAG |
| 4195 | TTTTTT | TTCTTT | TTCTTC | TTCTTC | TTCTTC | TTCTTC | TTCTTC | TTCTTCC | TTCTTCC |
| Splice Sites | | | | | | | | | |
| 2203 | GGTGAT | GGGGAC | GGCGAC | GGGGAC | GGGGAC | GGAGAC | GGAGAC | GGAGAC | GGAGAC |

Destabilizing Sequences

In some embodiments, the present disclosure provides an isolated nucleic acid molecule comprising a nucleotide sequence described herein that encodes a polypeptide with FVIII activity, wherein the nucleotide sequence contains fewer destabilizing elements relative to SEQ ID NO: 16. In other embodiments, the nucleotide sequence that encodes a polypeptide with FVIII activity contains at most 9, at most 8, at most 7, at most 6, or at most 5 destabilizing elements. In other embodiments, the nucleotide sequence that encodes a polypeptide with FVIII activity contains at most 4, at most 3, at most 2, or at most 1 destabilizing elements. In yet other embodiments, the nucleotide sequence that encodes a polypeptide with FVIII activity does not contain a destabilizing element.

In one particular embodiment, the present disclosure provides an isolated nucleic acid molecule comprising a nucleotide sequence which comprises a first nucleic acid sequence encoding an N-terminal portion of a FVIII polypeptide and a second nucleic acid sequence encoding a C-terminal portion of a FVIII polypeptide; wherein the first nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-1791 of SEQ ID NO: 3; (ii) nucleotides 1-1791 of SEQ ID NO: 3; (iii) nucleotides 58-1791 of SEQ ID NO: 4; or (iv) nucleotides 1-1791 of SEQ ID NO: 4; wherein the N-terminal portion and the C-terminal portion together have a FVIII polypeptide activity; and wherein the nucleotide sequence contains fewer destabilizing elements relative to SEQ ID NO: 16. In other embodiments, the nucleotide sequence that encodes a polypeptide with FVIII activity contains at most 9, at most 8, at most 7, at most 6, or at most 5 destabilizing elements. In other embodiments, the nucleotide sequence that encodes a polypeptide with FVIII activity contains at most 4, at most 3, at most 2, or at most 1 destabilizing elements. In yet other embodiments, the nucleotide sequence that encodes a polypeptide with FVIII activity does not contain a destabilizing element.

In another embodiment, the present disclosure provides an isolated nucleic acid molecule comprising a nucleotide sequence which comprises a first nucleic acid sequence encoding an N-terminal portion of a FVIII polypeptide and a second nucleic acid sequence encoding a C-terminal portion of a FVIII polypeptide; wherein the second nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 1792-4374 of SEQ ID NO: 5; (ii) nucleotides 1792-4374 of SEQ ID NO: 6; (iii) nucleotides 1792-2277 and 2320-4374 of SEQ ID NO: 5 (i.e., nucleotides 1792-4374 of SEQ ID NO: 5 without the nucleotides encoding the B domain or B domain fragment); or (iv) nucleotides 1792-2277 and 2320-4374 of SEQ ID NO: 6 (i.e., nucleotides 1792-4374 of SEQ ID NO: 6 without the nucleotides encoding the B domain or B domain fragment); wherein the N-terminal portion and the C-terminal portion together have a FVIII polypeptide activity; and wherein the nucleotide sequence contains fewer destabilizing elements relative to SEQ ID NO: 16. In other embodiments, the nucleotide sequence that encodes a polypeptide with FVIII activity contains at most 9, at most 8, at most 7, at most 6, or at most 5 destabilizing elements. In other embodiments, the nucleotide sequence that encodes a polypeptide with FVIII activity contains at most 4, at most 3, at most 2, or at most 1 destabilizing elements. In yet other embodiments, the nucleotide sequence that encodes a polypeptide with FVIII activity does not contain a destabilizing element.

In other embodiments, the present disclosure provides an isolated nucleic acid molecule comprising a nucleotide sequence encoding a polypeptide with FVIII activity, wherein the nucleotide sequence comprises a nucleic acid sequence having at least about 80%, at least about 85%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-4374 of an amino acid sequence selected from SEQ ID NOs: 1, 2, 3, 4, 5, 6, 70, and 71 or (ii) nucleotides 58-2277 and 2320-4374 of an amino acid sequence selected from SEQ ID NOs: 1, 2, 3, 4, 5, 6, 70, and 71 (i.e., nucleotides 58-4374 of SEQ ID NO: 1, 2, 3, 4, 5, 6, 70, or 71 without the nucleotides encoding the B domain or B domain fragment); and wherein the nucleotide sequence contains fewer destabilizing elements relative to SEQ ID NO: 16. In other embodiments, the nucleotide sequence that encodes a polypeptide with FVIII activity contains at most 9, at most 8, at most 7, at most 6, or at most 5 destabilizing elements. In other embodiments, the nucleotide sequence that encodes a polypeptide with FVIII activity contains at most 4, at most 3, at most 2, or at most 1 destabilizing elements. In yet other embodiments, the nucleotide sequence that encodes a polypeptide with FVIII activity does not contain a destabilizing element.

There are ten destabilizing elements in the parental FVIII sequence (SEQ ID NO: 16): six ATTTA sequences (SEQ ID NO: 23) and four TAAAT sequences (SEQ ID NO: 24). In one embodiment, sequences of these sites were mutated to destroy the destabilizing elements in optimized FVIII SEQ ID NOs: 1-6, 70, and 71. The location of each of these elements, and the sequence of the corresponding nucleotides in the optimized sequences are shown in Table 2.

Potential Promoter Binding Sites

In some embodiments, the present disclosure provides an isolated nucleic acid molecule comprising a nucleotide sequence described herein that encodes a polypeptide with FVIII activity, wherein the nucleotide sequence contains fewer potential promoter binding sites relative to SEQ ID NO: 16. In other embodiments, the nucleotide sequence that encodes a polypeptide with FVIII activity contains at most 9, at most 8, at most 7, at most 6, or at most 5 potential promoter binding sites. In other embodiments, the nucleotide sequence that encodes a polypeptide with FVIII activity contains at most 4, at most 3, at most 2, or at most 1 potential promoter binding sites. In yet other embodiments, the nucleotide sequence that encodes a polypeptide with FVIII activity does not contain a potential promoter binding site.

In one particular embodiment, the present disclosure provides an isolated nucleic acid molecule comprising a nucleotide sequence which comprises a first nucleic acid sequence encoding an N-terminal portion of a FVIII polypeptide and a second nucleic acid sequence encoding a C-terminal portion of a FVIII polypeptide; wherein the first nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-1791 of SEQ ID NO: 3; (ii) nucleotides 1-1791 of SEQ ID NO: 3; (iii) nucleotides 58-1791 of SEQ ID NO: 4; or (iv) nucleotides 1-1791 of SEQ ID NO: 4; wherein the N-terminal portion and the C-terminal portion together have a FVIII polypeptide activity; and wherein the nucleotide sequence contains fewer potential promoter binding sites relative to SEQ ID NO: 16. In other embodiments, the nucleotide sequence that encodes a polypeptide with FVIII activity contains at most 9, at most 8, at most 7, at most 6, or at most 5 potential promoter binding sites. In other embodiments, the nucleotide sequence that encodes a polypeptide with FVIII activity contains at most 4, at most 3, at most 2, or at most 1 potential promoter binding sites. In yet other embodiments, the nucleotide sequence that encodes a polypeptide with FVIII activity does not contain a potential promoter binding site.

In another embodiment, the present disclosure provides an isolated nucleic acid molecule comprising a nucleotide sequence which comprises a first nucleic acid sequence encoding an N-terminal portion of a FVIII polypeptide and a second nucleic acid sequence encoding a C-terminal portion of a FVIII polypeptide; wherein the second nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 1792-4374 of SEQ ID NO: 5; (ii) nucleotides 1792-4374 of SEQ ID NO: 6; (iii) nucleotides 1792-2277 and 2320-4374 of SEQ ID NO: 5 (i.e., nucleotides 1792-4374 of SEQ ID NO: 5 without the nucleotides encoding the B domain or B domain fragment); or (iv) nucleotides 1792-2277 and 2320-4374 of SEQ ID NO: 6 (i.e., nucleotides 1792-4374 of SEQ ID NO: 6 without the nucleotides encoding the B domain or B domain fragment); wherein the N-terminal portion and the C-terminal portion together have a FVIII polypeptide activity; and wherein the nucleotide sequence contains fewer potential promoter binding sites relative to SEQ ID NO: 16. In other embodiments, the nucleotide sequence that encodes a polypeptide with FVIII activity contains at most 9, at most 8, at most 7, at most 6, or at most 5 potential promoter binding sites. In other embodiments, the nucleotide sequence that encodes a polypeptide with FVIII activity contains at most 4, at most 3, at most 2, or at most 1 potential promoter binding sites. In yet other embodiments, the nucleotide sequence that encodes a polypeptide with FVIII activity does not contain a potential promoter binding site.

In other embodiments, the present disclosure provides an isolated nucleic acid molecule comprising a nucleotide sequence encoding a polypeptide with FVIII activity, wherein the nucleotide sequence comprises a nucleic acid sequence having at least about 80%, at least about 85%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-4374 of an amino acid sequence selected from SEQ ID NOs: 1, 2, 3, 4, 5, 6, 70, and 71 or (ii) nucleotides 58-2277 and 2320-4374 of an amino acid sequence selected from SEQ ID NOs: 1, 2, 3, 4, 5, 6, 70, and 71 (i.e., nucleotides 58-4374 of SEQ ID NO: 1, 2, 3, 4, 5, 6, 70, or 71 without the nucleotides encoding the B domain or B domain fragment); and wherein the nucleotide sequence contains fewer potential promoter binding sites relative to SEQ ID NO: 16. In other embodiments, the nucleotide sequence that encodes a polypeptide with FVIII activity contains at most 9, at most 8, at most 7, at most 6, or at most 5 potential promoter binding sites. In other embodiments, the nucleotide sequence that encodes a polypeptide with FVIII activity contains at most 4, at most 3, at most 2, or at most 1 potential promoter binding sites. In yet other embodiments, the nucleotide sequence that encodes a polypeptide with FVIII activity does not contain a potential promoter binding site.

TATA boxes are regulatory sequences often found in the promoter regions of eukaryotes. They serve as the binding site of TATA binding protein (TBP), a general transcription factor. TATA boxes usually comprise the sequence TATAA (SEQ ID NO: 28) or a close variant. TATA boxes within a coding sequence, however, can inhibit the translation of full-length protein. There are ten potential promoter binding sequences in the wild type BDD FVIII sequence (SEQ ID NO: 16): five TATAA sequences (SEQ ID NO: 28) and five TTATA sequences (SEQ ID NO: 29). In some embodiments, at least 1, at least 2, at least 3, or at least 4 of the promoter binding sites are abolished in the FVIII genes of the present disclosure. In some embodiments, at least 5 of the promoter binding sites are abolished in the FVIII genes of the present disclosure. In other embodiments, at least 6, at least 7, or at least 8 of the promoter binding sites are abolished in the FVIII genes of the present disclosure. In one embodiment, at least 9 of the promoter binging sites are abolished in the FVIII genes of the present disclosure. In one particular embodiment, all promoter binding sites are abolished in the FVIII genes of the present disclosure. The location of each potential promoter binding site and the sequence of the corresponding nucleotides in the optimized sequences are shown in Table 2.

Other Cis Acting Negative Regulatory Elements

In addition to the MAR/ARS sequences, destabilizing elements, and potential promoter sites described above, several additional potentially inhibitory sequences can be identified in the wild type BDD FVIII sequence (SEQ ID NO: 16). Two AU rich sequence elements (AREs) can be identified (ATTTTATT (SEQ ID NOs: 30); and ATTTTTAA (SEQ ID NO: 31), along with a poly-A site (AAAAAAA; SEQ ID NO: 26), a poly-T site (TTTTTT; SEQ ID NO: 25), and a splice site (GGTGAT; SEQ ID NO: 27) in the non-optimized BDD FVIII sequence. One or more of these elements can be removed from the optimized FVIII sequences. The location of each of these sites and the sequence of the corresponding nucleotides in the optimized sequences are shown in Table 2.

In certain embodiments, the present disclosure provides an isolated nucleic acid molecule comprising a nucleotide sequence which comprises a first nucleic acid sequence encoding an N-terminal portion of a FVIII polypeptide and a second nucleic acid sequence encoding a C-terminal portion of a FVIII polypeptide; wherein the first nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-1791 of SEQ ID NO: 3; (ii) nucleotides 1-1791 of SEQ ID NO: 3; (iii) nucleotides 58-1791 of SEQ ID NO: 4; or (iv) nucleotides 1-1791 of SEQ ID NO: 4; wherein the N-terminal portion and the C-terminal portion together have a FVIII polypeptide activity; and wherein the nucleotide sequence does not contain one or more cis-acting negative regulatory elements, for example, a splice site, a poly-T sequence, a poly-A sequence, an ARE sequence, or any combinations thereof.

In another embodiment, the present disclosure provides an isolated nucleic acid molecule comprising a nucleotide sequence which comprises a first nucleic acid sequence encoding an N-terminal portion of a FVIII polypeptide and a second nucleic acid sequence encoding a C-terminal portion of a FVIII polypeptide; wherein the second nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 1792-4374 of SEQ ID NO: 5; (ii) nucleotides 1792-4374 of SEQ ID NO: 6; (iii) nucleotides 1792-2277 and 2320-4374 of SEQ ID NO: 5 (i.e., nucleotides 1792-4374 of SEQ ID NO: 5 without the nucleotides encoding the B domain or B domain fragment); or (iv) nucleotides 1792-2277 and 2320-4374 of SEQ ID NO: 6 (i.e., nucleotides 1792-4374 of SEQ ID NO: 6 without the nucleotides encoding the B domain or B domain fragment); wherein the N-terminal portion and the C-terminal portion together have a FVIII polypeptide activity; and wherein the nucleotide sequence does not contain one or more cis-acting negative regulatory elements, for example, a splice site, a poly-T sequence, a poly-A sequence, an ARE sequence, or any combinations thereof.

In other embodiments, the present disclosure provides an isolated nucleic acid molecule comprising a nucleotide sequence encoding a polypeptide with FVIII activity, wherein the nucleotide sequence comprises a nucleic acid sequence having at least about 80%, at least about 85%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-4374 of an amino acid sequence selected from SEQ ID NOs: 1, 2, 3, 4, 5, 6, 70, and 71 or (ii) nucleotides 58-2277 and 2320-4374 of an amino acid sequence selected from SEQ ID NOs: 1, 2, 3, 4, 5, 6, 70, and 71 (i.e., nucleotides 58-4374 of SEQ ID NO: 1, 2, 3, 4, 5, 6, 70, or 71 without the nucleotides encoding the B domain or B domain fragment); and wherein the nucleotide sequence does not contain one or more cis-acting negative regulatory elements, for example, a splice site, a poly-T sequence, a poly-A sequence, an ARE sequence, or any combinations thereof.

In some embodiments, the present disclosure provides an isolated nucleic acid molecule comprising a nucleotide sequence which comprises a first nucleic acid sequence encoding an N-terminal portion of a FVIII polypeptide and a second nucleic acid sequence encoding a C-terminal portion of a FVIII polypeptide; wherein the first nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-1791 of SEQ ID NO: 3; (ii) nucleotides 1-1791 of SEQ ID NO: 3; (iii) nucleotides 58-1791 of SEQ ID NO: 4; or (iv) nucleotides 1-1791 of SEQ ID NO: 4; wherein the N-terminal portion and the C-terminal portion together have a FVIII polypeptide activity; and wherein the nucleotide sequence does not contain the splice site GGTGAT (SEQ ID NO: 27). In some embodiments, the present disclosure provides an isolated nucleic acid molecule comprising a nucleotide sequence which comprises a first nucleic acid sequence encoding an N-terminal portion of a FVIII polypeptide and a second nucleic acid sequence encoding a C-terminal portion of a FVIII polypeptide; wherein the first nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-1791 of SEQ ID NO: 3; (ii) nucleotides 1-1791 of SEQ ID NO: 3; (iii) nucleotides 58-1791 of SEQ ID NO: 4; or (iv) nucleotides 1-1791 of SEQ ID NO: 4; wherein the N-terminal portion and the C-terminal portion together have a FVIII polypeptide activity; and wherein the nucleotide sequence does not contain a poly-T sequence (SEQ ID NO: 25). In some embodiments, the present disclosure provides an isolated nucleic acid molecule comprising a nucleotide sequence which comprises a first nucleic acid sequence encoding an N-terminal portion of a FVIII polypeptide and a second nucleic acid sequence encoding a C-terminal portion of a FVIII polypeptide; wherein the first nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-1791 of SEQ ID NO: 3; (ii) nucleotides 1-1791 of SEQ ID NO: 3; (iii) nucleotides 58-1791 of SEQ ID NO: 4; or (iv) nucleotides 1-1791 of SEQ ID NO: 4; wherein the N-terminal portion and the C-terminal portion together have a FVIII polypeptide activity; and wherein the nucleotide sequence does not contain a poly-A sequence (SEQ ID NO: 26). In some embodiments, the present disclosure provides an isolated nucleic acid molecule comprising a nucleotide sequence which comprises a first nucleic acid sequence encoding an N-terminal portion of a FVIII polypeptide and a second nucleic acid sequence encoding a C-terminal portion of a FVIII polypeptide; wherein the first nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-1791 of SEQ ID NO: 3; (ii) nucleotides 1-1791 of SEQ ID NO: 3; (iii) nucleotides 58-1791 of SEQ ID NO: 4; or (iv) nucleotides 1-1791 of SEQ ID NO: 4; wherein the N-terminal portion and the C-terminal portion together have a FVIII polypeptide activity; and wherein the nucleotide sequence does not contain an ARE element (SEQ ID NO: 30 or SEQ ID NO: 31).

In some embodiments, the present disclosure provides an isolated nucleic acid molecule comprising a nucleotide sequence encoding a polypeptide with FVIII activity, wherein the nucleotide sequence comprises a nucleic acid sequence having at least about 80%, at least about 85%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-4374 of an amino acid sequence selected from SEQ ID NOs: 1, 2, 3, 4, 5, 6, 70, and 71 or (ii) nucleotides 58-2277 and 2320-4374 of an amino acid sequence selected from SEQ ID NOs: 1, 2, 3, 4, 5, 6, 70, and 71 (i.e., nucleotides 58-4374 of SEQ ID NO: 1, 2, 3, 4, 5, 6, 70, or 71 without the nucleotides encoding the B domain or B domain fragment); and wherein the nucleotide sequence does not contain the splice site GGTGAT (SEQ ID NO: 27). In some embodiments, the present disclosure provides an isolated nucleic acid molecule comprising a nucleotide sequence encoding a polypeptide with FVIII activity, wherein the nucleotide sequence comprises a nucleic acid sequence having at least about 80%, at least about 85%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-4374 of an amino acid sequence selected from SEQ ID NOs: 1, 2, 3, 4, 5, 6, 70, and 71 or (ii) nucleotides 58-2277 and 2320-4374 of an amino acid sequence selected from SEQ ID NOs: 1, 2, 3, 4, 5, 6, 70, and 71 (i.e., nucleotides 58-4374 of SEQ ID NO: 1, 2, 3, 4, 5, 6, 70, or 71 without the nucleotides encoding the B domain or B domain fragment); and wherein the nucleotide sequence does not contain a poly-T sequence (SEQ ID NO: 25). In some embodiments, the present disclosure provides an isolated nucleic acid molecule comprising a nucleotide sequence encoding a polypeptide with FVIII activity, wherein the nucleotide sequence comprises a nucleic acid sequence having at least about 80%, at least about 85%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-4374 of an amino acid sequence selected from SEQ ID NOs: 1, 2, 3, 4, 5, 6, 70, and 71 or (ii) nucleotides 58-2277 and 2320-4374 of an amino acid sequence selected from SEQ ID NOs: 1, 2, 3, 4, 5, 6, 70, and 71 (i.e., nucleotides 58-4374 of SEQ ID NO: 1, 2, 3, 4, 5, 6, 70, or 71 without the nucleotides encoding the B domain or B domain fragment); and wherein the nucleotide sequence does not contain a poly-A sequence (SEQ ID NO: 26). In some embodiments, the present disclosure provides an isolated nucleic acid molecule comprising a nucleotide sequence encoding a polypeptide with FVIII activity, wherein the nucleotide sequence comprises a nucleic acid sequence having at least about 80%, at least about 85%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-4374 of an amino acid sequence selected from SEQ ID NOs: 1, 2, 3, 4, 5, 6, 70, and 71 or (ii) nucleotides 58-2277 and 2320-4374 of an amino acid sequence selected from SEQ ID NOs: 1, 2, 3, 4, 5, 6, 70, and 71 (i.e., nucleotides 58-4374 of SEQ ID NO: 1, 2, 3, 4, 5, 6, 70, or 71 without the nucleotides encoding the B domain or B domain fragment); and wherein the nucleotide sequence does not contain an ARE element (SEQ ID NO: 30 or SEQ ID NO: 31).

In other embodiments, an optimized FVIII sequence of the disclosure does not comprise one or more of antiviral motifs, stem-loop structures, and repeat sequences.

In still other embodiments, the nucleotides surrounding the transcription start site are changed to a kozak consensus sequence (GCCGCCACCATGC (SEQ ID NO: 32), wherein the underlined nucleotides are the start codon). In other embodiments, restriction sites can be added or removed to facilitate the cloning process.

Heterologous Nucleotide Sequences

In some embodiments, the isolated nucleic acid molecules of the disclosure further comprise a heterologous nucleotide sequence. In some embodiments, the isolated nucleic acid molecules of the disclosure further comprise at least one heterologous nucleotide sequence. The heterologous nucleotide sequence can be linked with the optimized BDD-FVIII nucleotide sequences of the disclosure at the 5' end, at the 3' end, or inserted into the middle of the optimized BDD-FVIII nucleotide sequence. Thus, in some embodiments, the heterologous amino acid sequence encoded by the heterologous nucleotide sequence is linked to the N-terminus or the C-terminus of the FVIII amino acid sequence encoded by the nucleotide sequence or inserted between two amino acids in the FVIII amino acid sequence. In some embodiments, the heterologous amino acid sequence can be inserted between two amino acids at one or more insertion site selected from Table 3. In some embodiments, the heterologous amino acid sequence can be inserted within the FVIII polypeptide encoded by the nucleic acid molecule of the disclosure at any site disclosed in International Publication No. WO 2013/123457 A1, WO 2015/106052 A1 or U.S. Publication No. 2015/0158929 A1, which are herein incorporated by reference in their entirety.

In some embodiments, the heterologous amino acid sequence encoded by the heterologous nucleotide sequence is inserted within the B domain or a fragment thereof. In some embodiments, the heterologous amino acid sequence is inserted within the FVIII immediately downstream of an amino acid corresponding to amino acid 745 of mature human FVIII (SEQ ID NO:15). In one particular embodiment, the FVIII comprises a deletion of amino acids 746-1646, corresponding to mature human FVIII (SEQ ID NO:15), and the heterologous amino acid sequence encoded by the heterologous nucleotide sequence is inserted immediately downstream of amino acid 745, corresponding to mature human FVIII (SEQ ID NO:15).

TABLE 3

Heterologous Moiety Insertion Sites

| Insertion Site | Domain |
|---|---|
| 3 | A1 |
| 18 | A1 |
| 22 | A1 |
| 26 | A1 |
| 40 | A1 |
| 60 | A1 |
| 65 | A1 |
| 81 | A1 |
| 116 | A1 |
| 119 | A1 |
| 130 | A1 |
| 188 | A1 |
| 211 | A1 |
| 216 | A1 |
| 220 | A1 |
| 224 | A1 |
| 230 | A1 |
| 333 | A1 |
| 336 | A1 |
| 339 | A1 |
| 375 | A2 |
| 378 | A2 |
| 399 | A2 |
| 403 | A2 |
| 409 | A2 |
| 416 | A2 |
| 442 | A2 |
| 487 | A2 |
| 490 | A2 |
| 494 | A2 |
| 500 | A2 |
| 518 | A2 |
| 599 | A2 |
| 603 | A2 |
| 713 | A2 |
| 745 | B |
| 1656 | a3 region |
| 1711 | A3 |
| 1720 | A3 |
| 1725 | A3 |
| 1749 | A3 |
| 1796 | A3 |
| 1802 | A3 |

TABLE 3-continued

Heterologous Moiety Insertion Sites

| Insertion Site | Domain |
|---|---|
| 1827 | A3 |
| 1861 | A3 |
| 1896 | A3 |
| 1900 | A3 |
| 1904 | A3 |
| 1905 | A3 |
| 1910 | A3 |
| 1937 | A3 |
| 2019 | A3 |
| 2068 | C1 |
| 2111 | C1 |
| 2120 | C1 |
| 2171 | C2 |
| 2188 | C2 |
| 2227 | C2 |
| 2332 | CT |

Note:
Insertion sites indicate the amino acid position corresponding to an amino acid position of mature human FVIII (SEQ ID NO: 15).

In other embodiments, the isolated nucleic acid molecules of the disclosure further comprise two, three, four, five, six, seven, or eight heterologous nucleotide sequences. In some embodiments, all the heterologous nucleotide sequences are identical. In some embodiments, at least one heterologous nucleotide sequence is different from the other heterologous nucleotide sequences. In some embodiments, the disclosure can comprise two, three, four, five, six, or more than seven heterologous nucleotide sequences in tandem.

In some embodiments, the heterologous nucleotide sequence encodes an amino acid sequence. In some embodiments, the amino acid sequence encoded by the heterologous nucleotide sequence is a heterologous moiety that can increase the half-life (a "half-life extender") of a FVIII molecule.

In some embodiments, the heterologous moiety is a peptide or a polypeptide with either unstructured or structured characteristics that are associated with the prolongation of in vivo half-life when incorporated in a protein of the disclosure. Non-limiting examples include albumin, albumin fragments, Fc fragments of immunoglobulins, the C-terminal peptide (CTP) of the β subunit of human chorionic gonadotropin, a HAP sequence, an XTEN sequence, a transferrin or a fragment thereof, a PAS polypeptide, polyglycine linkers, polyserine linkers, albumin-binding moieties, or any fragments, derivatives, variants, or combinations of these polypeptides. In one particular embodiment, the heterologous amino acid sequence is an immunoglobulin constant region or a portion thereof, transferrin, albumin, or a PAS sequence. In some aspects, a heterologous moiety includes von Willebrand factor or a fragment thereof. In other related aspects a heterologous moiety can include an attachment site (e.g., a cysteine amino acid) for a non-polypeptide moiety such as polyethylene glycol (PEG), hydroxyethyl starch (HES), polysialic acid, or any derivatives, variants, or combinations of these elements. In some aspects, a heterologous moiety comprises a cysteine amino acid that functions as an attachment site for a non-polypeptide moiety such as polyethylene glycol (PEG), hydroxyethyl starch (HES), polysialic acid, or any derivatives, variants, or combinations of these elements.

In one specific embodiment, a first heterologous nucleotide sequence encodes a first heterologous moiety that is a half-life extending molecule which is known in the art, and a second heterologous nucleotide sequence encodes a second heterologous moiety that can also be a half-life extending molecule which is known in the art. In certain embodiments, the first heterologous moiety (e.g., a first Fc moiety) and the second heterologous moiety (e.g., a second Fc moiety) are associated with each other to form a dimer. In one embodiment, the second heterologous moiety is a second Fc moiety, wherein the second Fc moiety is linked to or associated with the first heterologous moiety, e.g., the first Fc moiety. For example, the second heterologous moiety (e.g., the second Fc moiety) can be linked to the first heterologous moiety (e.g., the first Fc moiety) by a linker or associated with the first heterologous moiety by a covalent or non-covalent bond.

In some embodiments, the heterologous moiety is a polypeptide comprising, consisting essentially of, or consisting of at least about 10, at least about 100, at least about 200, at least about 300, at least about 400, at least about 500, at least about 600, at least about 700, at least about 800, at least about 900, at least about 1000, at least about 1100, at least about 1200, at least about 1300, at least about 1400, at least about 1500, at least about 1600, at least about 1700, at least about 1800, at least about 1900, at least about 2000, at least about 2500, at least about 3000, or at least about 4000 amino acids. In other embodiments, the heterologous moiety is a polypeptide comprising, consisting essentially of, or consisting of about 100 to about 200 amino acids, about 200 to about 300 amino acids, about 300 to about 400 amino acids, about 400 to about 500 amino acids, about 500 to about 600 amino acids, about 600 to about 700 amino acids, about 700 to about 800 amino acids, about 800 to about 900 amino acids, or about 900 to about 1000 amino acids.

In certain embodiments, a heterologous moiety improves one or more pharmacokinetic properties of the FVIII protein without significantly affecting its biological activity or function.

In certain embodiments, a heterologous moiety increases the in vivo and/or in vitro half-life of the FVIII protein of the disclosure. In other embodiments, a heterologous moiety facilitates visualization or localization of the FVIII protein of the disclosure or a fragment thereof (e.g., a fragment comprising a heterologous moiety after proteolytic cleavage of the FVIII protein). Visualization and/or location of the FVIII protein of the disclosure or a fragment thereof can be in vivo, in vitro, ex vivo, or combinations thereof.

In other embodiments, a heterologous moiety increases stability of the FVIII protein of the disclosure or a fragment thereof (e.g., a fragment comprising a heterologous moiety after proteolytic cleavage of the FVIII protein). As used herein, the term "stability" refers to an art-recognized measure of the maintenance of one or more physical properties of the FVIII protein in response to an environmental condition (e.g., an elevated or lowered temperature). In certain aspects, the physical property can be the maintenance of the covalent structure of the FVIII protein (e.g., the absence of proteolytic cleavage, unwanted oxidation or deamidation). In other aspects, the physical property can also be the presence of the FVIII protein in a properly folded state (e.g., the absence of soluble or insoluble aggregates or precipitates). In one aspect, the stability of the FVIII protein is measured by assaying a biophysical property of the FVIII protein, for example thermal stability, pH unfolding profile, stable removal of glycosylation, solubility, biochemical function (e.g., ability to bind to a protein, receptor or ligand), etc., and/or combinations thereof. In another aspect, biochemical function is demonstrated by the binding affinity of the interaction. In one aspect, a measure of protein stability is thermal stability, i.e., resistance to thermal challenge. Stability can be measured using methods known in the art, such as, HPLC (high performance liquid chromatography), SEC (size exclusion chromatography), DLS (dynamic light scattering), etc. Methods to measure thermal stability include, but are not limited to differential scanning calorimetry (DSC), differential scanning fluorimetry (DSF), circular dichroism (CD), and thermal challenge assay.

In certain aspects, a FVIII protein encoded by the nucleic acid molecule of the disclosure comprises at least one half-life extender, i.e., a heterologous moiety which increases the in vivo half-life of the FVIII protein with respect to the in vivo half-life of the corresponding FVIII protein lacking such heterologous moiety. In vivo half-life of a FVIII protein can be determined by any methods known to those of skill in the art, e.g., activity assays (chromogenic assay or one stage clotting aPTT assay), ELISA, ROTEM™, etc.

In some embodiments, the presence of one or more half-life extenders results in the half-life of the FVIII protein to be increased compared to the half-life of the corresponding protein lacking such one or more half-life extenders. The half-life of the FVIII protein comprising a half-life extender is at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than the in vivo half-life of the corresponding FVIII protein lacking such half-life extender.

In one embodiment, the half-life of the FVIII protein comprising a half-life extender is about 1.5-fold to about 20-fold, about 1.5 fold to about 15 fold, or about 1.5 fold to about 10 fold longer than the in vivo half-life of the corresponding protein lacking such half-life extender. In another embodiment, the half-life of FVIII protein comprising a half-life extender is extended about 2-fold to about 10-fold, about 2-fold to about 9-fold, about 2-fold to about 8-fold, about 2-fold to about 7-fold, about 2-fold to about 6-fold, about 2-fold to about 5-fold, about 2-fold to about 4-fold, about 2-fold to about 3-fold, about 2.5-fold to about 10-fold, about 2.5-fold to about 9-fold, about 2.5-fold to about 8-fold, about 2.5-fold to about 7-fold, about 2.5-fold to about 6-fold, about 2.5-fold to about 5-fold, about 2.5-fold to about 4-fold, about 2.5-fold to about 3-fold, about 3-fold to about 10-fold, about 3-fold to about 9-fold, about 3-fold to about 8-fold, about 3-fold to about 7-fold, about 3-fold to about 6-fold, about 3-fold to about 5-fold, about 3-fold to about 4-fold, about 4-fold to about 6 fold, about 5-fold to about 7-fold, or about 6-fold to about 8 fold as compared to the in vivo half-life of the corresponding protein lacking such half-life extender.

In other embodiments, the half-life of the FVIII protein comprising a half-life extender is at least about 17 hours, at least about 18 hours, at least about 19 hours, at least about 20 hours, at least about 21 hours, at least about 22 hours, at least about 23 hours, at least about 24 hours, at least about 25 hours, at least about 26 hours, at least about 27 hours, at least about 28 hours, at least about 29 hours, at least about 30 hours, at least about 31 hours, at least about 32 hours, at least about 33 hours, at least about 34 hours, at least about 35 hours, at least about 36 hours, at least about 48 hours, at least about 60 hours, at least about 72 hours, at least about 84 hours, at least about 96 hours, or at least about 108 hours.

In still other embodiments, the half-life of the FVIII protein comprising a half-life extender is about 15 hours to about two weeks, about 16 hours to about one week, about 17 hours to about one week, about 18 hours to about one week, about 19 hours to about one week, about 20 hours to about one week, about 21 hours to about one week, about 22 hours to about one week, about 23 hours to about one week, about 24 hours to about one week, about 36 hours to about one week, about 48 hours to about one week, about 60 hours to about one week, about 24 hours to about six days, about 24 hours to about five days, about 24 hours to about four days, about 24 hours to about three days, or about 24 hours to about two days.

In some embodiments, the average half-life per subject of the FVIII protein comprising a half-life extender is about 15 hours, about 16 hours, about 17 hours, about 18 hours, about 19 hours, about 20 hours, about 21 hours, about 22 hours, about 23 hours, about 24 hours (1 day), about 25 hours, about 26 hours, about 27 hours, about 28 hours, about 29 hours, about 30 hours, about 31 hours, about 32 hours, about 33 hours, about 34 hours, about 35 hours, about 36 hours, about 40 hours, about 44 hours, about 48 hours (2 days), about 54 hours, about 60 hours, about 72 hours (3 days), about 84 hours, about 96 hours (4 days), about 108 hours, about 120 hours (5 days), about six days, about seven days (one week), about eight days, about nine days, about 10 days, about 11 days, about 12 days, about 13 days, or about 14 days.

One or more half-life extenders can be fused to C-terminus or N-terminus of FVIII or inserted within FVIII.

1. An Immunoglobulin Constant Region or a Portion Thereof

In another aspect, a heterologous moiety comprises one or more immunoglobulin constant regions or portions thereof (e.g., an Fc region). In one embodiment, an isolated nucleic acid molecule of the disclosure further comprises a heterologous nucleic acid sequence that encodes an immunoglobulin constant region or a portion thereof. In some embodiments, the immunoglobulin constant region or portion thereof is an Fc region.

An immunoglobulin constant region is comprised of domains denoted CH (constant heavy) domains (CH1, CH2, etc.). Depending on the isotype, (i.e. IgG, IgM, IgA IgD, or IgE), the constant region can be comprised of three or four CH domains. Some isotypes (e.g. IgG) constant regions also contain a hinge region. See Janeway et al. 2001, *Immunobiology*, Garland Publishing, N.Y., N.Y.

An immunoglobulin constant region or a portion thereof for producing the FVIII protein of the present disclosure can be obtained from a number of different sources. In one embodiment, an immunoglobulin constant region or a portion thereof is derived from a human immunoglobulin. It is understood, however, that the immunoglobulin constant region or a portion thereof can be derived from an immunoglobulin of another mammalian species, including for example, a rodent (e.g., a mouse, rat, rabbit, guinea pig) or non-human primate (e.g., chimpanzee, macaque) species. Moreover, the immunoglobulin constant region or a portion thereof can be derived from any immunoglobulin class, including IgM, IgG, IgD, IgA and IgE, and any immunoglobulin isotype, including IgG1, IgG2, IgG3 and IgG4. In one embodiment, the human isotype IgG1 is used.

A variety of the immunoglobulin constant region gene sequences (e.g., human constant region gene sequences) are available in the form of publicly accessible deposits. Constant region domains sequence can be selected having a particular effector function (or lacking a particular effector function) or with a particular modification to reduce immunogenicity. Many sequences of antibodies and antibody-encoding genes have been published and suitable Ig constant region sequences (e.g., hinge, CH2, and/or CH3 sequences, or portions thereof) can be derived from these sequences using art recognized techniques. The genetic material obtained using any of the foregoing methods can then be altered or synthesized to obtain polypeptides of the present disclosure. It will further be appreciated that the scope of this disclosure encompasses alleles, variants and mutations of constant region DNA sequences.

The sequences of the immunoglobulin constant region or a portion thereof can be cloned, e.g., using the polymerase chain reaction and primers which are selected to amplify the domain of interest. To clone a sequence of the immunoglobulin constant region or a portion thereof from an antibody, mRNA can be isolated from hybridoma, spleen, or lymph cells, reverse transcribed into DNA, and antibody genes amplified by PCR. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, Calif. (1990); Ho et al. 1989. Gene 77:51; Horton et al. 1993. *Methods Enzymol.* 217:270). PCR can be initiated by consensus constant region primers or by more specific primers based on the published heavy and light chain DNA and amino acid sequences. PCR also can be used to isolate DNA clones encoding the antibody light and heavy chains. In this case the libraries can be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. *Protein Engineering* 7:1509); rapid amplification of cDNA ends (Ruberti, F. et al. 1994. *J. Immunol. Methods* 173:33); antibody leader sequences (Larrick et al. 1989 *Biochem. Biophys. Res. Commun.* 160:1250). The cloning of antibody sequences is further described in Newman et al., U.S. Pat. No. 5,658,570, filed Jan. 25, 1995, which is incorporated by reference herein.

An immunoglobulin constant region used herein can include all domains and the hinge region or portions thereof. In one embodiment, the immunoglobulin constant region or a portion thereof comprises CH2 domain, CH3 domain, and a hinge region, i.e., an Fc region or an FcRn binding partner.

As used herein, the term "Fc region" is defined as the portion of a polypeptide which corresponds to the Fc region of native Ig, i.e., as formed by the dimeric association of the respective Fc domains of its two heavy chains. A native Fc region forms a homodimer with another Fc region. In contrast, the term "genetically-fused Fc region" or "single-chain Fc region" (scFc region), as used herein, refers to a synthetic dimeric Fc region comprised of Fc domains genetically linked within a single polypeptide chain (i.e., encoded in a single contiguous genetic sequence). See International Publication No. WO 2012/006635, incorporated herein by reference in its entirety.

In one embodiment, the "Fc region" refers to the portion of a single Ig heavy chain beginning in the hinge region just upstream of the papain cleavage site (i.e. residue 216 in IgG, taking the first residue of heavy chain constant region to be 114) and ending at the C-terminus of the antibody. Accordingly, a complete Fc region comprises at least a hinge domain, a CH2 domain, and a CH3 domain.

An immunoglobulin constant region or a portion thereof can be an FcRn binding partner. FcRn is active in adult epithelial tissues and expressed in the lumen of the intestines, pulmonary airways, nasal surfaces, vaginal surfaces, colon and rectal surfaces (U.S. Pat. No. 6,485,726). An FcRn binding partner is a portion of an immunoglobulin that binds to FcRn.

The FcRn receptor has been isolated from several mammalian species including humans. The sequences of the human FcRn, monkey FcRn, rat FcRn, and mouse FcRn are known (Story et al. 1994, J. Exp. Med. 180:2377). The FcRn receptor binds IgG (but not other immunoglobulin classes such as IgA, IgM, IgD, and IgE) at relatively low pH, actively transports the IgG transcellularly in a luminal to serosal direction, and then releases the IgG at relatively higher pH found in the interstitial fluids. It is expressed in adult epithelial tissue (U.S. Pat. Nos. 6,485,726, 6,030,613, 6,086,875; WO 03/077834; US2003-0235536A1) including lung and intestinal epithelium (Israel et al. 1997, Immunology 92:69) renal proximal tubular epithelium (Kobayashi et al. 2002, Am. J. Physiol. Renal Physiol. 282:F358) as well as nasal epithelium, vaginal surfaces, and biliary tree surfaces.

FcRn binding partners useful in the present disclosure encompass molecules that can be specifically bound by the FcRn receptor including whole IgG, the Fc fragment of IgG, and other fragments that include the complete binding region of the FcRn receptor. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The FcRn binding partners include whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of immunoglobulins or immunoglobulin fragments, or regions, are all based on Kabat et al. 1991, Sequences of Proteins of Immunological Interest, U.S. Department of Public Health, Bethesda, Md.

Fc regions or FcRn binding partners bound to FcRn can be effectively shuttled across epithelial barriers by FcRn, thus providing a non-invasive means to systemically administer a desired therapeutic molecule. Additionally, fusion proteins comprising an Fc region or an FcRn binding partner are endocytosed by cells expressing the FcRn. But instead of being marked for degradation, these fusion proteins are recycled out into circulation again, thus increasing the in vivo half-life of these proteins. In certain embodiments, the portions of immunoglobulin constant regions are an Fc region or an FcRn binding partner that typically associates, via disulfide bonds and other non-specific interactions, with another Fc region or another FcRn binding partner to form dimers and higher order multimers.

Two FcRn receptors can bind a single Fc molecule. Crystallographic data suggest that each FcRn molecule binds a single polypeptide of the Fc homodimer. In one embodiment, linking the FcRn binding partner, e.g., an Fc fragment of an IgG, to a biologically active molecule provides a means of delivering the biologically active molecule orally, buccally, sublingually, rectally, vaginally, as an aerosol administered nasally or via a pulmonary route, or via an ocular route. In another embodiment, the FVIII protein can be administered invasively, e.g., subcutaneously, intravenously.

An FcRn binding partner region is a molecule or portion thereof that can be specifically bound by the FcRn receptor with consequent active transport by the FcRn receptor of the Fc region. Specifically bound refers to two molecules forming a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the affinity constant KA is higher than $10^6$ $M^{-1}$, or higher than $10^8$ $M^{-1}$. If necessary, non-specific binding can be reduced without substantially affecting specific binding by varying the binding conditions. The appropriate binding conditions such as concentration of the molecules, ionic strength of the solution, temperature, time allowed for binding, concentration of a blocking agent (e.g., serum albumin, milk casein), etc., can be optimized by a skilled artisan using routine techniques.

In certain embodiments, a FVIII protein encoded by the nucleic acid molecule of the disclosure comprises one or more truncated Fc regions that are nonetheless sufficient to confer Fc receptor (FcR) binding properties to the Fc region. For example, the portion of an Fc region that binds to FcRn (i.e., the FcRn binding portion) comprises from about amino acids 282-438 of IgG1, EU numbering (with the primary contact sites being amino acids 248, 250-257, 272, 285, 288, 290-291, 308-311, and 314 of the CH2 domain and amino acid residues 385-387, 428, and 433-436 of the CH3 domain. Thus, an Fc region of the disclosure can comprise or consist of an FcRn binding portion. FcRn binding portions can be derived from heavy chains of any isotype, including IgG1, IgG2, IgG3 and IgG4. In one embodiment, an FcRn binding portion from an antibody of the human isotype IgG1 is used. In another embodiment, an FcRn binding portion from an antibody of the human isotype IgG4 is used.

The Fc region can be obtained from a number of different sources. In one embodiment, an Fc region of the polypeptide is derived from a human immunoglobulin. It is understood, however, that an Fc moiety can be derived from an immunoglobulin of another mammalian species, including for example, a rodent (e.g., a mouse, rat, rabbit, guinea pig) or non-human primate (e.g., chimpanzee, macaque) species. Moreover, the polypeptide of the Fc domains or portions thereof can be derived from any immunoglobulin class, including IgM, IgG, IgD, IgA and IgE, and any immunoglobulin isotype, including IgG1, IgG2, IgG3 and IgG4. In another embodiment, the human isotype IgG1 is used.

In certain embodiments, the Fc variant confers a change in at least one effector function imparted by an Fc moiety comprising said wild-type Fc domain (e.g., an improvement or reduction in the ability of the Fc region to bind to Fc receptors (e.g. FcγRI, FcγRII, or FcγRII) or complement proteins (e.g. C1q), or to trigger antibody-dependent cytotoxicity (ADCC), phagocytosis, or complement-dependent cytotoxicity (CDCC)). In other embodiments, the Fc variant provides an engineered cysteine residue.

The Fc region of the disclosure can employ art-recognized Fc variants which are known to impart a change (e.g., an enhancement or reduction) in effector function and/or FcR or FcRn binding. Specifically, an Fc region of the disclosure can include, for example, a change (e.g., a substitution) at one or more of the amino acid positions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO004/029207A2, WO04/035752A2, WO04/063351A2, WO004/

074455A2, WO004/099249A2, WO05/040217A2, WO04/044859, WO05/070963A1, WO05/077981A2, WO005/092925A2, WO05/123780A2, WO06/019447A1, WO06/047350A2, and WO06/085967A2; US Patent Publication Nos. US2007/0231329, US2007/0231329, US2007/0237765, US2007/0237766, US2007/0237767, US2007/0243188, US20070248603, US20070286859, US20080057056; or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; 7,083,784; 7,404,956, and 7,317,091, each of which is incorporated by reference herein. In one embodiment, the specific change (e.g., the specific substitution of one or more amino acids disclosed in the art) can be made at one or more of the disclosed amino acid positions. In another embodiment, a different change at one or more of the disclosed amino acid positions (e.g., the different substitution of one or more amino acid position disclosed in the art) can be made.

The Fc region or FcRn binding partner of IgG can be modified according to well recognized procedures such as site directed mutagenesis and the like to yield modified IgG or Fc fragments or portions thereof that will be bound by FcRn. Such modifications include modifications remote from the FcRn contact sites as well as modifications within the contact sites that preserve or even enhance binding to the FcRn. For example, the following single amino acid residues in human IgG1 Fc (Fc γ1) can be substituted without significant loss of Fc binding affinity for FcRn: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, P331A, E333A, K334A, T335A, S337A, K338A, K340A, Q342A, R344A, E345A, Q347A, R355A, E356A, M358A, T359A, K360A, N361A, Q362A, Y373A, S375A, D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wild type proline substituted by alanine at position number 238. As an example, a specific embodiment incorporates the N297A mutation, removing a highly conserved N-glycosylation site. In addition to alanine other amino acids can be substituted for the wild type amino acids at the positions specified above. Mutations can be introduced singly into Fc giving rise to more than one hundred Fc regions distinct from the native Fc. Additionally, combinations of two, three, or more of these individual mutations can be introduced together, giving rise to hundreds more Fc regions.

Certain of the above mutations can confer new functionality upon the Fc region or FcRn binding partner. For example, one embodiment incorporates N297A, removing a highly conserved N-glycosylation site. The effect of this mutation is to reduce immunogenicity, thereby enhancing circulating half-life of the Fc region, and to render the Fc region incapable of binding to FcγRI, FcγRIIA, FcγRIIB, and FcγRIIIA, without compromising affinity for FcRn (Routledge et al. 1995, Transplantation 60:847; Friend et al. 1999, Transplantation 68:1632; Shields et al. 1995, J. Biol. Chem. 276:6591). As a further example of new functionality arising from mutations described above affinity for FcRn can be increased beyond that of wild type in some instances. This increased affinity can reflect an increased "on" rate, a decreased "off" rate or both an increased "on" rate and a decreased "off" rate. Examples of mutations believed to impart an increased affinity for FcRn include, but not limited to, T256A, T307A, E380A, and N434A (Shields et al. 2001, J. Biol. Chem. 276:6591).

Additionally, at least three human Fc gamma receptors appear to recognize a binding site on IgG within the lower hinge region, generally amino acids 234-237. Therefore, another example of new functionality and potential decreased immunogenicity can arise from mutations of this region, as for example by replacing amino acids 233-236 of human IgG1 "ELLG" (SEQ ID NO: 45) to the corresponding sequence from IgG2 "PVA" (with one amino acid deletion). It has been shown that FcγRI, FcγRII, and FcγRIII, which mediate various effector functions will not bind to IgG1 when such mutations have been introduced. Ward and Ghetie 1995, Therapeutic Immunology 2:77 and Armour et al. 1999, Eur. J. Immunol. 29:2613.

In another embodiment, the immunoglobulin constant region or a portion thereof comprises an amino acid sequence in the hinge region or a portion thereof that forms one or more disulfide bonds with a second immunoglobulin constant region or a portion thereof. The second immunoglobulin constant region or a portion thereof can be linked to a second polypeptide, bringing the FVIII protein and the second polypeptide together. In some embodiments, the second polypeptide is an enhancer moiety. As used herein, the term "enhancer moiety" refers to a molecule, fragment thereof or a component of a polypeptide which is capable of enhancing the procoagulant activity of FVIII. The enhancer moiety can be a cofactor, such as soluble tissue factor (sTF), or a procoagulant peptide. Thus, upon activation of FVIII, the enhancer moiety is available to enhance FVIII activity.

In certain embodiments, a FVIII protein encoded by a nucleic acid molecule of the disclosure comprises an amino acid substitution to an immunoglobulin constant region or a portion thereof (e.g., Fc variants), which alters the antigen-independent effector functions of the Ig constant region, in particular the circulating half-life of the protein.

2. scFc Regions

In another aspect, a heterologous moiety comprises a scFc (single chain Fc) region. In one embodiment, an isolated nucleic acid molecule of the disclosure further comprises a heterologous nucleic acid sequence that encodes a scFc region. The scFc region comprises at least two immunoglobulin constant regions or portions thereof (e.g., Fc moieties or domains (e.g., 2, 3, 4, 5, 6, or more Fc moieties or domains)) within the same linear polypeptide chain that are capable of folding (e.g., intramolecularly or intermolecularly folding) to form one functional scFc region which is linked by an Fc peptide linker. For example, in one embodiment, a polypeptide of the disclosure is capable of binding, via its scFc region, to at least one Fc receptor (e.g., an FcRn, an FcγR receptor (e.g., FcγRIII), or a complement protein (e.g., C1q)) in order to improve half-life or trigger an immune effector function (e.g., antibody-dependent cytotoxicity (ADCC), phagocytosis, or complement-dependent cytotoxicity (CDCC) and/or to improve manufacturability).

3. CTP

In another aspect, a heterologous moiety comprises one C-terminal peptide (CTP) of the β subunit of human chorionic gonadotropin or fragment, variant, or derivative thereof. One or more CTP peptides inserted into a recombinant protein is known to increase the in vivo half-life of that protein. See, e.g., U.S. Pat. No. 5,712,122, incorporated by reference herein in its entirety.

Exemplary CTP peptides include DPRFQDSSSSKAPPPSLPSPSRLPGPSDTPIL (SEQ ID NO: 33) or SSSSKAPPPSLPSPSRLPGPSDTPILPQ (SEQ ID NO: 34). See, e.g., U.S. Patent Application Publication No. US 2009/0087411 A1, incorporated by reference.

4. XTEN Sequence

In some embodiments, a heterologous moiety comprises one or more XTEN sequences, fragments, variants, or derivatives thereof. As used here "XTEN sequence" refers to extended length polypeptides with non-naturally occurring, substantially non-repetitive sequences that are composed mainly of small hydrophilic amino acids, with the sequence having a low degree or no secondary or tertiary structure under physiologic conditions. As a heterologous moiety, XTENs can serve as a half-life extension moiety. In addition, XTEN can provide desirable properties including but are not limited to enhanced pharmacokinetic parameters and solubility characteristics.

The incorporation of a heterologous moiety comprising an XTEN sequence into a protein of the disclosure can confer to the protein one or more of the following advantageous properties: conformational flexibility, enhanced aqueous solubility, high degree of protease resistance, low immunogenicity, low binding to mammalian receptors, or increased hydrodynamic (or Stokes) radii.

In certain aspects, an XTEN sequence can increase pharmacokinetic properties such as longer in vivo half-life or increased area under the curve (AUC), so that a protein of the disclosure stays in vivo and has procoagulant activity for an increased period of time compared to a protein with the same but without the XTEN heterologous moiety.

In some embodiments, the XTEN sequence useful for the disclosure is a peptide or a polypeptide having greater than about 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, or 2000 amino acid residues. In certain embodiments, XTEN is a peptide or a polypeptide having greater than about 20 to about 3000 amino acid residues, greater than 30 to about 2500 residues, greater than 40 to about 2000 residues, greater than 50 to about 1500 residues, greater than 60 to about 1000 residues, greater than 70 to about 900 residues, greater than 80 to about 800 residues, greater than 90 to about 700 residues, greater than 100 to about 600 residues, greater than 110 to about 500 residues, or greater than 120 to about 400 residues. In one particular embodiment, the XTEN comprises an amino acid sequence of longer than 42 amino acids and shorter than 144 amino acids in length.

The XTEN sequence of the disclosure can comprise one or more sequence motif of 5 to 14 (e.g., 9 to 14) amino acid residues or an amino acid sequence at least 80%, 90%, 91%, 92%, 93%, 94%, 95%, 96%, 97%, 98%, or 99% identical to the sequence motif, wherein the motif comprises, consists essentially of, or consists of 4 to 6 types of amino acids (e.g., 5 amino acids) selected from the group consisting of glycine (G), alanine (A), serine (S), threonine (T), glutamate (E) and proline (P). See US 2010-0239554 A1.

In some embodiments, the XTEN comprises non-overlapping sequence motifs in which about 80%, or at least about 85%, or at least about 90%, or about 91%, or about 92%, or about 93%, or about 94%, or about 95%, or about 96%, or about 97%, or about 98%, or about 99% or about 100% of the sequence consists of multiple units of non-overlapping sequences selected from a single motif family selected from Table 4, resulting in a family sequence. As used herein, "family" means that the XTEN has motifs selected only from a single motif category from Table 4; i.e., AD, AE, AF, AG, AM, AQ, BC, or BD XTEN, and that any other amino acids in the XTEN not from a family motif are selected to achieve a needed property, such as to permit incorporation of a restriction site by the encoding nucleotides, incorporation of a cleavage sequence, or to achieve a better linkage to FVIII. In some embodiments of XTEN families, an XTEN sequence comprises multiple units of non-overlapping sequence motifs of the AD motif family, or of the AE motif family, or of the AF motif family, or of the AG motif family, or of the AM motif family, or of the AQ motif family, or of the BC family, or of the BD family, with the resulting XTEN exhibiting the range of homology described above. In other embodiments, the XTEN comprises multiple units of motif sequences from two or more of the motif families of Table 2A. These sequences can be selected to achieve desired physical/chemical characteristics, including such properties as net charge, hydrophilicity, lack of secondary structure, or lack of repetitiveness that are conferred by the amino acid composition of the motifs, described more fully below. In the embodiments hereinabove described in this paragraph, the motifs incorporated into the XTEN can be selected and assembled using the methods described herein to achieve an XTEN of about 36 to about 3000 amino acid residues.

TABLE 4

XTEN Sequence Motifs of 12 Amino Acids and Motif Families

| Motif Family* | MOTIF SEQUENCE | SEQ ID NO: |
|---|---|---|
| AD | GESPGGSSGSES | 73 |
| AD | GSEGSSGPGESS | 74 |
| AD | GSSESGSSEGGP | 75 |
| AD | GSGGEPSESGSS | 76 |
| AE, AM | GSPAGSPTSTEE | 77 |
| AE, AM, AQ | GSEPATSGSETP | 78 |
| AE, AM, AQ | GTSESATPESGP | 79 |
| AE, AM, AQ | GTSTEPSEGSAP | 80 |
| AF, AM | GSTSESPSGTAP | 81 |
| AF, AM | GTSTPESGSASP | 82 |
| AF, AM | GTSPSGESSTAP | 83 |
| AF, AM | GSTSSTAESPGP | 84 |
| AG, AM | GTPGSGTASSSP | 85 |
| AG, AM | GSSTPSGATGSP | 86 |
| AG, AM | GSSPSASTGTGP | 87 |
| AG, AM | GASPGTSSTGSP | 88 |
| AQ | GEPAGSPTSTSE | 89 |
| AQ | GTGEPSSTPASE | 90 |
| AQ | GSGPSTESAPTE | 91 |
| AQ | GSETPSGPSETA | 92 |
| AQ | GPSETSTSEPGA | 93 |
| AQ | GSPSEPTEGTSA | 94 |

TABLE 4-continued

XTEN Sequence Motifs of 12 Amino Acids and Motif Families

| Motif Family* | MOTIF SEQUENCE | SEQ ID NO: |
|---|---|---|
| BC | GSGASEPTSTEP | 95 |
| BC | GSEPATSGTEPS | 96 |
| BC | GTSEPSTSEPGA | 97 |
| BC | GTSTEPSEPGSA | 98 |
| BD | GSTAGSETSTEA | 99 |
| BD | GSETATSGSETA | 100 |
| BD | GTSESATSESGA | 101 |
| BD | GTSTEASEGSAS | 102 |

*Denotes individual motif sequences that, when used together in various permutations, results in a "family sequence"

Examples of XTEN sequences that can be used as heterologous moieties in chimeric proteins of the disclosure are disclosed, e.g., in U.S. Patent Publication Nos. 2010/0239554 A1, 2010/0323956 A1, 2011/0046060 A1, 2011/0046061 A1, 2011/0077199 A1, or 2011/0172146 A1, or International Patent Publication Nos. WO 2010091122 A1, WO 2010144502 A2, WO 2010144508 A1, WO 2011028228 A1, WO 2011028229 A1, or WO 2011028344 A2, each of which is incorporated by reference herein in its entirety.

XTEN can have varying lengths for insertion into or linkage to FVIII. In one embodiment, the length of the XTEN sequence(s) is chosen based on the property or function to be achieved in the fusion protein. Depending on the intended property or function, XTEN can be short or intermediate length sequence or longer sequence that can serve as carriers. In certain embodiments, the XTEN includes short segments of about 6 to about 99 amino acid residues, intermediate lengths of about 100 to about 399 amino acid residues, and longer lengths of about 400 to about 1000 and up to about 3000 amino acid residues. Thus, the XTEN inserted into or linked to FVIII can have lengths of about 6, about 12, about 36, about 40, about 42, about 72, about 96, about 144, about 288, about 400, about 500, about 576, about 600, about 700, about 800, about 864, about 900, about 1000, about 1500, about 2000, about 2500, or up to about 3000 amino acid residues in length. In other embodiments, the XTEN sequences is about 6 to about 50, about 50 to about 100, about 100 to 150, about 150 to 250, about 250 to 400, about 400 to about 500, about 500 to about 900, about 900 to 1500, about 1500 to 2000, or about 2000 to about 3000 amino acid residues in length. The precise length of an XTEN inserted into or linked to FVIII can vary without adversely affecting the activity of the FVIII. In one embodiment, one or more of the XTENs used herein have 42 amino acids, 72 amino acids, 144 amino acids, 288 amino acids, 576 amino acids, or 864 amino acids in length and can be selected from one or more of the XTEN family sequences; i.e., AD, AE, AF, AG, AM, AQ, BC or BD.

In some embodiments, the XTEN sequence used in the disclosure is at least 60%, 70%, 80%, 85%, 90%, 91%, 92%, 93%, 94%, 95%, 96%, 97%, 98%, 99%, or 100% identical to a sequence selected from the group consisting of AE42, AG42, AE48, AM48, AE72, AG72, AE108, AG108, AE144, AF144, AG144, AE180, AG180, AE216, AG216, AE252, AG252, AE288, AG288, AE324, AG324, AE360, AG360, AE396, AG396, AE432, AG432, AE468, AG468, AE504, AG504, AF504, AE540, AG540, AF540, AD576, AE576, AF576, AG576, AE612, AG612, AE624, AE648, AG648, AG684, AE720, AG720, AE756, AG756, AE792, AG792, AE828, AG828, AD836, AE864, AF864, AG864, AM875, AE912, AM923, AM1318, BC864, BD864, AE948, AE1044, AE1140, AE1236, AE1332, AE1428, AE1524, AE1620, AE1716, AE1812, AE1908, AE2004A, AG948, AG1044, AG1140, AG1236, AG1332, AG1428, AG1524, AG1620, AG1716, AG1812, AG1908, AG2004, and any combination thereof. See US 2010-0239554 A1. In one particular embodiment, the XTEN comprises AE42, AE72, AE144, AE288, AE576, AE864, AG 42, AG72, AG144, AG288, AG576, AG864, or any combination thereof.

Exemplary XTEN sequences that can be used as heterologous moieties in chimeric protein of the disclosure include XTEN AE42-4 (SEQ ID NO: 46, encoded by SEQ ID NO: 47; FIGS. 11C and 11D, respectively), XTEN 144-2A (SEQ ID NO: 48, encoded by SEQ ID NO: 49; FIGS. 11E and 11F, respectively), XTEN A144-3B (SEQ ID NO: 50, encoded by SEQ ID NO: 51; FIGS. 11G and 11H, respectively), XTEN AE144-4A (SEQ ID NO: 52, encoded by SEQ ID NO: 53; FIGS. 11I and 11J, respectively), XTEN AE144-5A (SEQ ID NO: 54, encoded by SEQ ID NO: 55; FIGS. 11K and 11L, respectively), XTEN AE144-6B (SEQ ID NO: 56, encoded by SEQ ID NO: 57; FIGS. 11M and 11N, respectively), XTEN AG144-1 (SEQ ID NO: 58, encoded by SEQ ID NO: 59; FIGS. 11O and 11P, respectively), XTEN AG144-A (SEQ ID NO: 60, encoded by SEQ ID NO: 61; FIGS. 11Q and 11R, respectively), XTEN AG144-B (SEQ ID NO: 62, encoded by SEQ ID NO: 63; FIGS. 11S and 11T, respectively), XTEN AG144-C (SEQ ID NO: 64, encoded by SEQ ID NO: 65; FIGS. 11U and 11V, respectively), and XTEN AG144-F (SEQ ID NO: 66, encoded by SEQ ID NO: 67; FIGS. 11W and 11X, respectively). In one particular embodiment, the XTEN is encoded by SEQ ID NO:18.

In some embodiments, less than 100% of amino acids of an XTEN are selected from glycine (G), alanine (A), serine (S), threonine (T), glutamate (E) and proline (P), or less than 100% of the sequence consists of the sequence motifs from Table 2A or an XTEN sequence provided herein. In such embodiments, the remaining amino acid residues of the XTEN are selected from any of the other 14 natural L-amino acids, but can be preferentially selected from hydrophilic amino acids such that the XTEN sequence contains at least about 90%, 91%, 92%, 93%, 94%, 95%, 96%, 97%, 98%, or at least about 99% hydrophilic amino acids. The content of hydrophobic amino acids in the XTEN utilized in the conjugation constructs can be less than 5%, or less than 2%, or less than 1% hydrophobic amino acid content. Hydrophobic residues that are less favored in construction of XTEN include tryptophan, phenylalanine, tyrosine, leucine, isoleucine, valine, and methionine. Additionally, XTEN sequences can contain less than 5% or less than 4% or less than 3% or less than 2% or less than 1% or none of the following amino acids: methionine (for example, to avoid oxidation), or asparagine and glutamine (to avoid desamidation).

The one or more XTEN sequences can be inserted at the C-terminus or at the N-terminus of the amino acid sequence encoded by the nucleotide sequence or inserted between two amino acids in the amino acid sequence encoded by the nucleotide sequence. For example, the XTEN can be inserted between two amino acids at one or more insertion site selected from Table 3. Examples of sites within FVIII that are permissible for XTEN insertion can be found in, e.g., International Publication No. WO 2013/123457 A1 or U.S. Publication No. 2015/0158929 A1, which are herein incorporated by reference in their entirety.

5. Albumin or Fragment, Derivative, or Variant Thereof

In some embodiments, a heterologous moiety comprises albumin or a functional fragment thereof. Human serum albumin (HSA, or HA), a protein of 609 amino acids in its full-length form, is responsible for a significant proportion of the osmotic pressure of serum and also functions as a carrier of endogenous and exogenous ligands. The term "albumin" as used herein includes full-length albumin or a functional fragment, variant, derivative, or analog thereof. Examples of albumin or the fragments or variants thereof are disclosed in US Pat. Publ. Nos. 2008/0194481A1, 2008/0004206 A1, 2008/0161243 A1, 2008/0261877 A1, or 2008/0153751 A1 or PCT Appl. Publ. Nos. 2008/033413 A2, 2009/058322 A1, or 2007/021494 A2, which are incorporated herein by reference in their entireties.

In one embodiment, the FVIII protein encoded by a nucleic acid molecule of the disclosure comprises albumin, a fragment, or a variant thereof which is further linked to a second heterologous moiety selected from the group consisting of an immunoglobulin constant region or portion thereof (e.g., an Fc region), a PAS sequence, HES, and PEG.

6. Albumin-Binding Moiety

In certain embodiments, the heterologous moiety is an albumin-binding moiety, which comprises an albumin-binding peptide, a bacterial albumin-binding domain, an albumin-binding antibody fragment, or any combinations thereof.

For example, the albumin-binding protein can be a bacterial albumin-binding protein, an antibody or an antibody fragment including domain antibodies (see U.S. Pat. No. 6,696,245). An albumin-binding protein, for example, can be a bacterial albumin-binding domain, such as the one of streptococcal protein G (Konig, T. and Skerra, A. (1998) *J. Immunol. Methods* 218, 73-83). Other examples of albumin-binding peptides that can be used as conjugation partner are, for instance, those having a Cys-$Xaa_1$-$Xaa_2$-$Xaa_3$-$Xaa_4$-Cys consensus sequence, wherein $Xaa_1$ is Asp, Asn, Ser, Thr, or Trp; $Xaa_2$ is Asn, Gin, H is, Ile, Leu, or Lys; $Xaa_3$ is Ala, Asp, Phe, Trp, or Tyr; and $Xaa_4$ is Asp, Gly, Leu, Phe, Ser, or Thr as described in US patent application 2003/0069395 or Dennis et al. (Dennis et al. (2002) *J. Biol. Chem.* 277, 35035-35043).

Domain 3 from streptococcal protein G, as disclosed by Kraulis et al., FEBS Lett. 378:190-194 (1996) and Linhult et al., Protein Sci. 11:206-213 (2002) is an example of a bacterial albumin-binding domain. Examples of albumin-binding peptides include a series of peptides having the core sequence DICLPRWGCLW (SEQ ID NO: 35). See, e.g., Dennis et al., *J. Biol. Chem.* 2002, 277: 35035-35043 (2002). Examples of albumin-binding antibody fragments are disclosed in Muller and Kontermann, Curr. Opin. Mol. Ther. 9:319-326 (2007); Roovers et al., Cancer Immunol. Immunother. 56:303-317 (2007), and Holt et al., Prot. Eng. Design Sci., 21:283-288 (2008), which are incorporated herein by reference in their entireties. An example of such albumin-binding moiety is 2-(3-maleimidopropanamido)-6-(4-(4-iodophenyl)butanamido) hexanoate ("Albu" tag) as disclosed by Trussel et al., Bioconjugate Chem. 20:2286-2292 (2009).

Fatty acids, in particular long chain fatty acids (LCFA) and long chain fatty acid-like albumin-binding compounds can be used to extend the in vivo half-life of FVIII proteins of the disclosure. An example of a LCFA-like albumin-binding compound is 16-(I-(3-(9-(((2,5-dioxopyrrolidin-1-yloxy) carbonyloxy)-methyl)-7-sulfo-9H-fluoren-2-ylamino)-3-oxopropyl)-2,5-dioxopyrrolidin-3-ylthio) hexadecanoic acid (see, e.g., WO 2010/140148).

7. PAS Sequence

In other embodiments, the heterologous moiety is a PAS sequence. A PAS sequence, as used herein, means an amino acid sequence comprising mainly alanine and serine residues or comprising mainly alanine, serine, and proline residues, the amino acid sequence forming random coil conformation under physiological conditions. Accordingly, the PAS sequence is a building block, an amino acid polymer, or a sequence cassette comprising, consisting essentially of, or consisting of alanine, serine, and proline which can be used as a part of the heterologous moiety in the chimeric protein. Yet, the skilled person is aware that an amino acid polymer also can form random coil conformation when residues other than alanine, serine, and proline are added as a minor constituent in the PAS sequence. The term "minor constituent" as used herein means that amino acids other than alanine, serine, and proline can be added in the PAS sequence to a certain degree, e.g., up to about 12%, i.e., about 12 of 100 amino acids of the PAS sequence, up to about 10%, i.e. about 10 of 100 amino acids of the PAS sequence, up to about 9%, i.e., about 9 of 100 amino acids, up to about 8%, i.e., about 8 of 100 amino acids, about 6%, i.e., about 6 of 100 amino acids, about 5%, i.e., about 5 of 100 amino acids, about 4%, i.e., about 4 of 100 amino acids, about 3%, i.e., about 3 of 100 amino acids, about 2%, i.e., about 2 of 100 amino acids, about 1%, i.e., about 1 of 100 of the amino acids. The amino acids different from alanine, serine and proline can be selected from the group consisting of Arg, Asn, Asp, Cys, Gin, Glu, Gly, His, Ile, Leu, Lys, Met, Phe, Thr, Trp, Tyr, and Val.

Under physiological conditions, the PAS sequence stretch forms a random coil conformation and thereby can mediate an increased in vivo and/or in vitro stability to the FVIII protein. Since the random coil domain does not adopt a stable structure or function by itself, the biological activity mediated by the FVIII protein is essentially preserved. In other embodiments, the PAS sequences that form random coil domain are biologically inert, especially with respect to proteolysis in blood plasma, immunogenicity, isoelectric point/electrostatic behaviour, binding to cell surface receptors or internalisation, but are still biodegradable, which provides clear advantages over synthetic polymers such as PEG.

Non-limiting examples of the PAS sequences forming random coil conformation comprise an amino acid sequence selected from the group consisting of ASPAAPA-PASPAAPAPSAPA (SEQ ID NO: 36), AAPASPAPAAP-SAPAPAAPS (SEQ ID NO: 37), APSSPSP-SAPSSPSPASPSS (SEQ ID NO: 38), APSSPSPSAPSSPSPASPS (SEQ ID NO: 39), SSP-SAPSPSSPASPSPSSPA (SEQ ID NO: 40), AASPAAPSAP-PAAASPAAPSAPPA (SEQ ID NO: 41) and ASAAAPAAASAAASAPSAAA (SEQ ID NO: 42) or any combinations thereof. Additional examples of PAS sequences are known from, e.g., US Pat. Publ. No. 2010/0292130 A1 and PCT Appl. Publ. No. WO 2008/155134 A1.

8. HAP Sequence

In certain embodiments, the heterologous moiety is a glycine-rich homo-amino-acid polymer (HAP). The HAP sequence can comprise a repetitive sequence of glycine, which has at least 50 amino acids, at least 100 amino acids, 120 amino acids, 140 amino acids, 160 amino acids, 180 amino acids, 200 amino acids, 250 amino acids, 300 amino acids, 350 amino acids, 400 amino acids, 450 amino acids, or 500 amino acids in length. In one embodiment, the HAP sequence is capable of extending half-life of a moiety fused to or linked to the HAP sequence. Non-limiting examples of the HAP sequence includes, but are not limited to (Gly)$_n$, (Gly$_4$Ser)$_n$, or S(Gly$_4$Ser)$_n$, wherein n is 1, 2, 3, 4, 5, 6, 7, 8, 9, 10, 11, 12, 13, 14, 15, 16, 17, 18, 19, or 20. In one embodiment, n is 20, 21, 22, 23, 24, 25, 26, 26, 28, 29, 30, 31, 32, 33, 34, 35, 36, 37, 38, 39, or 40. In another embodiment, n is 50, 60, 70, 80, 90, 100, 110, 120, 130, 140, 150, 160, 170, 180, 190, or 200.

9. Transferrin or Fragment Thereof

In certain embodiments, the heterologous moiety is transferrin or a fragment thereof. Any transferrin can be used to make the FVIII proteins of the disclosure. As an example, wild-type human TF (TF) is a 679 amino acid protein, of approximately 75 KDa (not accounting for glycosylation), with two main domains, N (about 330 amino acids) and C (about 340 amino acids), which appear to originate from a gene duplication. See GenBank accession numbers NM001063, XM002793, M12530, XM039845, XM 039847 and S95936 (www.ncbi.nlm.nih.gov/), all of which are herein incorporated by reference in their entirety. Transferrin comprises two domains, N domain and C domain. N domain comprises two subdomains, N1 domain and N2 domain, and C domain comprises two subdomains, C1 domain and C2 domain.

In one embodiment, the transferrin heterologous moiety includes a transferrin splice variant. In one example, a transferrin splice variant can be a splice variant of human transferrin, e.g., Genbank Accession AAA61140. In another embodiment, the transferrin portion of the chimeric protein includes one or more domains of the transferrin sequence, e.g., N domain, C domain, N1 domain, N2 domain, C1 domain, C2 domain or any combinations thereof.

10. Clearance Receptors

In certain embodiments, the heterologous moiety is a clearance receptor, fragment, variant, or derivative thereof. LRP1 is a 600 kDa integral membrane protein that is implicated in the receptor-mediate clearance of a variety of proteins, such as Factor X. See, e.g., Narita et al., *Blood* 91:555-560 (1998).

11. Von Willebrand Factor or Fragments Thereof

In certain embodiments, the heterologous moiety is von Willebrand Factor (VWF) or one or more fragments thereof.

VWF (also known as F8VWF) is a large multimeric glycoprotein present in blood plasma and produced constitutively in endothelium (in the Weibel-Palade bodies), megakaryocytes (α-granules of platelets), and subendothelian connective tissue. The basic VWF monomer is a 2813 amino acid protein. Every monomer contains a number of specific domains with a specific function, the D' and D3 domains (which together bind to Factor VIII), the A1 domain (which binds to platelet GPIb-receptor, heparin, and/or possibly collagen), the A3 domain (which binds to collagen), the C1 domain (in which the RGD domain binds to platelet integrin αIIbβ3 when this is activated), and the "cysteine knot" domain at the C-terminal end of the protein (which VWF shares with platelet-derived growth factor (PDGF), transforming growth factor-β (TGFβ) and β-human chorionic gonadotropin (βHCG)).

The 2813 monomer amino acid sequence for human VWF is reported as Accession Number NP000543.2 in Genbank. The nucleotide sequence encoding the human VWF is reported as Accession Number NM000552.3 in Genbank. SEQ ID NO: 44 (FIG. 11B) is the amino acid sequence encoded by SEQ ID NO: 43. The D' domain includes amino acids 764 to 866 of SEQ ID NO: 44. The D3 domain includes amino acids 867 to 1240 of SEQ ID NO: 44.

In plasma, 95-98% of FVIII circulates in a tight non-covalent complex with full-length VWF. The formation of this complex is important for the maintenance of appropriate plasma levels of FVIIII in vivo. Lenting et al., *Blood.* 92(11): 3983-96 (1998); Lenting et al., *J. Thromb. Haemost.* 5(7): 1353-60 (2007). When FVIII is activated due to proteolysis at positions 372 and 740 in the heavy chain and at position 1689 in the light chain, the VWF bound to FVIII is removed from the activated FVIII.

In certain embodiments, the heterologous moiety is full length von Willebrand Factor. In other embodiments, the heterologous moiety is a von Willebrand Factor fragment. As used herein, the term "VWF fragment" or "VWF fragments" used herein means any VWF fragments that interact with FVIII and retain at least one or more properties that are normally provided to FVIII by full-length VWF, e.g., preventing premature activation to FVIIIa, preventing premature proteolysis, preventing association with phospholipid membranes that could lead to premature clearance, preventing binding to FVIII clearance receptors that can bind naked FVIII but not VWF-bound FVIII, and/or stabilizing the FVIII heavy chain and light chain interactions. In a specific embodiment, the heterologous moiety is a (VWF) fragment comprising a D' domain and a D3 domain of VWF. The VWF fragment comprising the D' domain and the D3 domain can further comprise a VWF domain selected from the group consisting of an A1 domain, an A2 domain, an A3 domain, a D1 domain, a D2 domain, a D4 domain, a B1 domain, a B2 domain, a B3 domain, a C1 domain, a C2 domain, a CK domain, one or more fragments thereof, and any combinations thereof. Additional examples of the polypeptide having FVIII activity fused to the VWF fragment are disclosed in U.S. provisional patent application No. 61/667, 901, filed Jul. 3, 2012, and U.S. Publication No. 2015/0023959 A1, which are both incorporated herein by reference in its entirety.

12. Linker Moieties

In certain embodiments, the heterologous moiety is a peptide linker.

As used herein, the terms "peptide linkers" or "linker moieties" refer to a peptide or polypeptide sequence (e.g., a synthetic peptide or polypeptide sequence) which connects two domains in a linear amino acid sequence of a polypeptide chain.

In some embodiments, heterologous nucleotide sequences encoding peptide linkers can be inserted between the optimized FVIII polynucleotide sequences of the disclosure and a heterologous nucleotide sequence encoding, for example, one of the heterologous moieties described above, such as albumin. Peptide linkers can provide flexibility to the chimeric polypeptide molecule. Linkers are not typically cleaved, however such cleavage can be desirable. In one embodiment, these linkers are not removed during processing.

A type of linker which can be present in a chimeric protein of the disclosure is a protease cleavable linker which comprises a cleavage site (i.e., a protease cleavage site substrate, e.g., a factor XIa, Xa, or thrombin cleavage site) and which can include additional linkers on either the N-terminal of C-terminal or both sides of the cleavage site. These cleavable linkers when incorporated into a construct of the disclosure result in a chimeric molecule having a heterologous cleavage site.

In one embodiment, an FVIII polypeptide encoded by a nucleic acid molecule of the instant disclosure comprises two or more Fc domains or moieties linked via a cscFc linker to form an Fc region comprised in a single polypeptide chain. The cscFc linker is flanked by at least one intracellular processing site, i.e., a site cleaved by an intracellular enzyme. Cleavage of the polypeptide at the at least one intracellular processing site results in a polypeptide which comprises at least two polypeptide chains.

Other peptide linkers can optionally be used in a construct of the disclosure, e.g., to connect an FVIII protein to an Fc region. Some exemplary linkers that can be used in connection with the disclosure include, e.g., polypeptides comprising GlySer amino acids described in more detail below.

In one embodiment, the peptide linker is synthetic, i.e., non-naturally occurring. In one embodiment, a peptide linker includes peptides (or polypeptides) (which can or cannot be naturally occurring) which comprise an amino acid sequence that links or genetically fuses a first linear sequence of amino acids to a second linear sequence of amino acids to which it is not naturally linked or genetically fused in nature. For example, in one embodiment the peptide linker can comprise non-naturally occurring polypeptides which are modified forms of naturally occurring polypeptides (e.g., comprising a mutation such as an addition, substitution or deletion). In another embodiment, the peptide linker can comprise non-naturally occurring amino acids. In another embodiment, the peptide linker can comprise naturally occurring amino acids occurring in a linear sequence that does not occur in nature. In still another embodiment, the peptide linker can comprise a naturally occurring polypeptide sequence.

For example, in certain embodiments, a peptide linker can be used to fuse identical Fc moieties, thereby forming a homodimeric scFc region. In other embodiments, a peptide linker can be used to fuse different Fc moieties (e.g. a wild-type Fc moiety and an Fc moiety variant), thereby forming a heterodimeric scFc region.

In another embodiment, a peptide linker comprises or consists of a gly-ser linker. In one embodiment, a scFc or cscFc linker comprises at least a portion of an immunoglobulin hinge and a gly-ser linker. As used herein, the term "gly-ser linker" refers to a peptide that consists of glycine and serine residues. In certain embodiments, said gly-ser linker can be inserted between two other sequences of the peptide linker. In other embodiments, a gly-ser linker is attached at one or both ends of another sequence of the peptide linker. In yet other embodiments, two or more gly-ser linker are incorporated in series in a peptide linker. In one embodiment, a peptide linker of the disclosure comprises at least a portion of an upper hinge region (e.g., derived from an IgG1, IgG2, IgG3, or IgG4 molecule), at least a portion of a middle hinge region (e.g., derived from an IgG1, IgG2, IgG3, or IgG4 molecule) and a series of gly/ser amino acid residues.

Peptide linkers of the disclosure are at least one amino acid in length and can be of varying lengths. In one embodiment, a peptide linker of the disclosure is from about 1 to about 50 amino acids in length. As used in this context, the term "about" indicates +/−two amino acid residues. Since linker length must be a positive integer, the length of from about 1 to about 50 amino acids in length, means a length of from 1-3 to 48-52 amino acids in length. In another embodiment, a peptide linker of the disclosure is from about 10 to about 20 amino acids in length. In another embodiment, a peptide linker of the disclosure is from about 15 to about 50 amino acids in length. In another embodiment, a peptide linker of the disclosure is from about 20 to about 45 amino acids in length. In another embodiment, a peptide linker of the disclosure is from about 15 to about 35 or about 20 to about 30 amino acids in length. In another embodiment, a peptide linker of the disclosure is from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 500, 1000, or 2000 amino acids in length. In one embodiment, a peptide linker of the disclosure is 20 or 30 amino acids in length.

In some embodiments, the peptide linker can comprise at least two, at least three, at least four, at least five, at least 10, at least 20, at least 30, at least 40, at least 50, at least 60, at least 70, at least 80, at least 90, or at least 100 amino acids. In other embodiments, the peptide linker can comprise at least 200, at least 300, at least 400, at least 500, at least 600, at least 700, at least 800, at least 900, or at least 1,000 amino acids. In some embodiments, the peptide linker can comprise at least about 10, 20, 30, 40, 50, 60, 70, 80, 90, 100, 150, 200, 300, 400, 500, 600, 700, 800, 900, 1000, 1100, 1200, 1300, 1400, 1500, 1600, 1700, 1800, 1900, or 2000 amino acids. The peptide linker can comprise 1-5 amino acids, 1-10 amino acids, 1-20 amino acids, 10-50 amino acids, 50-100 amino acids, 100-200 amino acids, 200-300 amino acids, 300-400 amino acids, 400-500 amino acids, 500-600 amino acids, 600-700 amino acids, 700-800 amino acids, 800-900 amino acids, or 900-1000 amino acids.

Peptide linkers can be introduced into polypeptide sequences using techniques known in the art. Modifications can be confirmed by DNA sequence analysis. Plasmid DNA can be used to transform host cells for stable production of the polypeptides produced.

Monomer-Dimer Hybrids

In some embodiments, the isolated nucleic acid molecules of the disclosure which further comprise a heterologous nucleotide sequence encode a monomer-dimer hybrid molecule comprising FVIII.

The term "monomer-dimer hybrid" used herein refers to a chimeric protein comprising a first polypeptide chain and a second polypeptide chain, which are associated with each other by a disulfide bond, wherein the first chain comprises Factor VIII and a first Fc region and the second chain comprises, consists essentially of, or consists of a second Fc region without the FVIII. The monomer-dimer hybrid construct thus is a hybrid comprising a monomer aspect having only one clotting factor and a dimer aspect having two Fc regions.

Expression Control Element

In some embodiments, the nucleic acid molecule or vector of the disclosure further comprises at least one expression control sequence. A expression control sequences as used herein is any regulatory nucleotide sequence, such as a promoter sequence or promoter-enhancer combination, which facilitates the efficient transcription and translation of the coding nucleic acid to which it is operably linked. For example, the isolated nucleic acid molecule of the disclosure can be operably linked to at least one transcription control sequence. The gene expression control sequence can, for example, be a mammalian or viral promoter, such as a constitutive or inducible promoter. Constitutive mammalian promoters include, but are not limited to, the promoters for the following genes: hypoxanthine phosphoribosyl transferase (HPRT), adenosine deaminase, pyruvate kinase, beta-actin promoter, and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus, and other retroviruses, and the thymidine kinase promoter of herpes simplex virus. Other constitutive promoters are known to those of ordinary skill in the art. The promoters useful as gene expression sequences of the disclosure also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In one embodiment, the disclosure includes expression of a transgene under the control of a tissue specific promoter and/or enhancer. In another embodiment, the promoter or other expression control sequence selectively enhances expression of the transgene in liver cells. Examples of liver specific promoters include, but are not limited to, a mouse thyretin promoter (mTTR), an endogenous human factor VIII promoter (F8), human alpha-1-antitrypsin promoter (hAAT), human albumin minimal promoter, and mouse albumin promoter. In a particular embodiment, the promoter comprises a mTTR promoter. The mTTR promoter is described in R. H. Costa et al., 1986, Mol. Cell. Biol. 6:4697. The F8 promoter is described in Figueiredo and Brownlee, 1995, J. Biol. Chem. 270:11828-11838.

Expression levels can be further enhanced to achieve therapeutic efficacy using one or more enhancers. One or more enhancers can be provided either alone or together with one or more promoter elements. Typically, the expression control sequence comprises a plurality of enhancer elements and a tissue specific promoter. In one embodiment, an enhancer comprises one or more copies of the α-1-microglobulin/bikunin enhancer (Rouet et al., 1992, J. Biol. Chem. 267:20765-20773; Rouet et al., 1995, Nucleic Acids Res. 23:395-404; Rouet et al., 1998, Biochem. J. 334:577-584; III et al., 1997, Blood Coagulation Fibrinolysis 8:S23-S30). In another embodiment, an enhancer is derived from liver specific transcription factor binding sites, such as EBP, DBP, HNF1, HNF3, HNF4, HNF6, with Enh1, comprising HNF1, (sense)-HNF3, (sense)-HNF4, (antisense)-HNF1, (antisense)-HNF6, (sense)-EBP, (antisense)-HNF4 (antisense).

In a particular example, a promoter useful for the disclosure comprises SEQ ID NO: 69 (i.e., ET promoter; FIG. 11Y), which is also known as GenBank No. AY661265. See also Vigna et al., Molecular Therapy 11(5):763 (2005). Examples of other suitable vectors and gene regulatory elements are described in WO 02/092134, EP1395293, or U.S. Pat. Nos. 6,808,905, 7,745,179, or 7,179,903, which are incorporated by reference herein in their entireties.

In general, the expression control sequences shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined coding nucleic acid. The gene expression sequences optionally include enhancer sequences or upstream activator sequences as desired.

Vectors Systems

Some embodiments of the present disclosure are directed to vectors comprising one or more codon optimized nucleic acid molecules encoding a polypeptide with FVIII activity described herein, host cells comprising the vectors, and methods of treating a bleeding disorder using the vectors. The present disclosure meets an important need in the art by providing a vector comprising an optimized FVIII sequence that demonstrates increased expression in a subject and potentially result in greater therapeutic efficacy when used in gene therapy methods.

In some embodiments, the present disclosure provides a vector comprising an isolated nucleic acid molecule comprising a nucleotide sequence which comprises a first nucleic acid sequence encoding an N-terminal portion of a FVII) polypeptide and a second nucleic acid sequence encoding a C-terminal portion of a FVIII polypeptide; wherein the first nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-1791 of SEQ ID NO: 3 or (ii) nucleotides 58-1791 of SEQ ID NO: 4; and wherein the N-terminal portion and the C-terminal portion together have a FVIII polypeptide activity. In other embodiments, the nucleic acid molecule comprises a nucleotide sequence which comprises a first nucleic acid sequence encoding an N-terminal portion of a FVIII polypeptide and a second nucleic acid sequence encoding a C-terminal portion of a FVIII polypeptide; wherein the second nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 1792-4374 of SEQ ID NO: 5; (ii) nucleotides 1792-4374 of SEQ ID NO: 6; (iii) nucleotides 1792-2277 and 2320-4374 of SEQ ID NO: 5; or (iv) nucleotides 1792-2277 and 2320-4374 of SEQ ID NO: 6; and wherein the N-terminal portion and the C-terminal portion together have a FVIII polypeptide activity.

In some embodiments, the present disclosure provides a vector comprising an isolated nucleic acid molecule comprising a nucleotide sequence encoding a polypeptide with FVIII activity, wherein the nucleotide sequence comprises a nucleic acid sequence having at least about 91%, at least about 92%, at least about 93%, at least about 94%, at least about 95%, at least about 96%, at least about 97%, at least about 98%, or at least about 99% sequence identity to (i) nucleotides 58-4374 of SEQ ID NO: 1 or (ii) nucleotides 58-2277 and 2320-4374 of SEQ ID NO: 1 and is operably linked to a promoter, a target sequence, or both. In other embodiments, the nucleic acid sequence comprises (i) nucleotides 58-4374 of SEQ ID NO: 1 or (ii) nucleotides 58-2277 and 2320-4374 of SEQ ID NO: 1.

In some embodiments, the present disclosure provides a vector comprising an isolated nucleic acid molecule comprising a nucleotide sequence encoding a polypeptide with FVIII activity, wherein the nucleotide sequence comprises a nucleic acid sequence having at least about 94%, at least about 95%, at least about 96%, at least about 97%, at least about 98%, or at least about 99% sequence identity to (i) nucleotides 58-4374 of SEQ ID NO: 2 or (ii) nucleotides 58-2277 and 2320-4374 of SEQ ID NO: 2 and is operably linked to a promoter, a target sequence, or both. In other embodiments, the nucleic acid sequence comprises (i) nucleotides 58-4374 of SEQ ID NO: 2 or (ii) nucleotides 58-2277 and 2320-4374 of SEQ ID NO: 2.

In some embodiments, the present disclosure provides a vector comprising an isolated nucleic acid molecule comprising a nucleotide sequence encoding a polypeptide with FVIII activity, wherein the nucleotide sequence comprises a nucleic acid sequence having at least 85%, at least 86%, at least 87%, at least 88%, at least 89%, at least 90%, at least 91%, at least 95%, at least 96%, at least 97%, at least 98%, or at least 99% sequence identity to (i) nucleotides 58-4374 of SEQ ID NO: 70 or (ii) nucleotides 58-2277 and 2320-4374 of SEQ ID NO: 70 and is operably linked to a promoter, a target sequence, or both. In other embodiments, the nucleic acid sequence comprises (i) nucleotides 58-4374 of SEQ ID NO: 70 or (ii) nucleotides 58-2277 and 2320-4374 of SEQ ID NO: 70.

In some embodiments, the present disclosure provides a vector comprising an isolated nucleic acid molecule comprising a nucleotide sequence encoding a polypeptide with FVIII activity, wherein the nucleotide sequence comprises a nucleic acid sequence having at least 85%, at least 86%, at least 87%, at least 88%, at least 89%, at least 90%, at least 91%, at least 95%, at least 96%, at least 97%, at least 98%, or at least 99% sequence identity to (i) nucleotides 58-4374 of SEQ ID NO: 71 or (ii) nucleotides 58-2277 and 2320-4374 of SEQ ID NO: 71 and is operably linked to a promoter, a target sequence, or both. In other embodiments, the nucleic acid sequence comprises (i) nucleotides 58-4374 of SEQ ID NO: 71 or (ii) nucleotides 58-2277 and 2320-4374 of SEQ ID NO: 71.

In some embodiments, the present disclosure provides a vector comprising an isolated nucleic acid molecule comprising a nucleotide sequence encoding a polypeptide with FVIII activity, wherein the nucleotide sequence comprises a nucleic acid sequence having at least about 92%, at least about 93%, at least about 94%, at least about 95%, at least about 96%, at least about 97%, at least about 98%, or at least about 99% sequence identity (i) nucleotides 58-4374 of SEQ ID NO: 3 or (ii) nucleotides 58-2277 and 2320-4374 of SEQ ID NO: 3 and is operably linked to a promoter, a target sequence, or both. In other embodiments, the nucleic acid sequence comprises (i) nucleotides 58-4374 of SEQ ID NO: 3 or (ii) nucleotides 58-2277 and 2320-4374 of SEQ ID NO: 3.

In some embodiments, the present disclosure provides a vector comprising an isolated nucleic acid molecule comprising a nucleotide sequence encoding a polypeptide with FVIII activity, wherein the nucleotide sequence comprises a nucleic acid sequence at least about 91%, at least about 92%, at least about 93%, at least about 94%, at least about 95%, at least about 96%, at least about 97%, at least about 98%, or at least about 99% sequence identity to (i) nucleotides 58-4374 of SEQ ID NO: 4 or (ii) nucleotides 58-2277 and 2320-4374 of SEQ ID NO: 4 and is operably linked to a promoter, a target sequence, or both. In other embodiments, the nucleic acid sequence comprises (i) nucleotides 58-4374 of SEQ ID NO: 4 or (ii) nucleotides 58-2277 and 2320-4374 of SEQ ID NO: 4.

In some embodiments, the present disclosure provides a vector comprising an isolated nucleic acid molecule comprising a nucleotide sequence encoding a polypeptide with FVIII activity, wherein the nucleotide sequence comprises a nucleic acid sequence having at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-4374 of SEQ ID NO: 5 or (ii) nucleotides 58-2277 and 2320-4374 of SEQ ID NO: 5 and is operably linked to a promoter, a target sequence, or both. In other embodiments, the nucleic acid sequence comprises (i) nucleotides 58-4374 of SEQ ID NO: 5 or (ii) nucleotides 58-2277 and 2320-4374 of SEQ ID NO: 5.

In some embodiments, the present disclosure provides a vector comprising an isolated nucleic acid molecule comprising a nucleotide sequence encoding a polypeptide with FVIII activity, wherein the nucleotide sequence comprises a nucleic acid sequence having at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-4374 of SEQ ID NO: 6 or (ii) nucleotides 58-2277 and 2320-4374 of SEQ ID NO: 6 and is operably linked to a promoter, a target sequence, or both. In other embodiments, the nucleic acid sequence comprises (i) nucleotides 58-4374 of SEQ ID NO: 6 or (ii) nucleotides 58-2277 and 2320-4374 of SEQ ID NO: 6.

Suitable vectors for the disclosure include expression vectors, viral vectors, and plasmid vectors. In one embodiment, the vector is a viral vector.

As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

Expression vectors of the disclosure will include optimized polynucleotides encoding the BDD FVIII protein described herein. In one embodiment, the optimized coding sequences for the BDD FVIII protein is operably linked to an expression control sequence. As used herein, two nucleic acid sequences are operably linked when they are covalently linked in such a way as to permit each component nucleic acid sequence to retain its functionality. A coding sequence and a gene expression control sequence are said to be operably linked when they are covalently linked in such a way as to place the expression or transcription and/or translation of the coding sequence under the influence or control of the gene expression control sequence. Two DNA sequences are said to be operably linked if induction of a promoter in the 5' gene expression sequence results in the transcription of the coding sequence and if the nature of the linkage between the two DNA sequences does not (1) result in the introduction of a frame-shift mutation, (2) interfere with the ability of the promoter region to direct the transcription of the coding sequence, or (3) interfere with the ability of the corresponding RNA transcript to be translated into a protein. Thus, a gene expression sequence would be operably linked to a coding nucleic acid sequence if the gene expression sequence were capable of effecting transcription of that coding nucleic acid sequence such that the resulting transcript is translated into the desired protein or polypeptide.

Viral vectors include, but are not limited to, nucleic acid sequences from the following viruses: retrovirus, such as Moloney murine leukemia virus, Harvey murine sarcoma virus, murine mammary tumor virus, and Rous sarcoma virus; lentivirus; adenovirus; adeno-associated virus; SV40-type viruses; polyomaviruses; Epstein-Barr viruses; papilloma viruses; herpes virus; vaccinia virus; polio virus; and RNA virus such as a retrovirus. One can readily employ other vectors well-known in the art. Certain viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., Gene Transfer and Expression, A Laboratory Manual, W.H. Freeman Co., New York (1990) and Murry, E. J., Methods in Molecular Biology, Vol. 7, Humana Press, Inc., Cliffton, N.J. (1991).

In one embodiment, the virus is an adeno-associated virus, a double-stranded DNA virus. The adeno-associated virus can be engineered to be replication-deficient and is capable of infecting a wide range of cell types and species. It further has advantages such as heat and lipid solvent stability; high transduction frequencies in cells of diverse lineages, including hematopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In another embodiment, the viral vector is an adeno-associated virus (AAV) that has been manipulated to carry a polynucleotide encoding a FVIII protein as disclosed herein. General methods for obtaining recombinant AAVs (rAAVs) have been disclosed. See, for example, U.S. Pat. No. 8,734, 809, 2013/0195801 as well as the references cited therein. In some embodiments, a rAAV vector comprises one or more AAV inverted terminal repeats (ITRs) and a transgene of interest (e.g., an optimized FVIII polynucleotide sequence). In certain embodiments, the methods of making rAAV involve culturing a desired host cell which contains a nucleic acid sequence encoding an AAV capsid protein or fragment thereof; a functional rep gene; a rAAV vector composed of, AAV inverted terminal repeats (ITRs) and a transgene of interest; and sufficient helper functions to permit packaging of the recombinant AAV vector into the AAV capsid proteins. Materials and methods for performing these and related procedures have been disclosed, for example, in U.S. Pat. No. 8,734,809, 2013/0195801, PCT/US1997/015692, PCT/US2002/033692, PCT/US2002/033630, WO2007/148971, WO00/20561, WO03/042361, and WO2007/04670.

One or more of different AAV vector sequences derived from nearly any serotype can be used in accord with the present disclosure. Choice of a particular AAV vector sequence will be guided by known parameters such as tropism of interest, required vector yields, etc. Generally, the AAV serotypes have genomic sequences of significant homology at the amino acid and the nucleic acid levels, provide a related set of genetic functions, produce virions which are related, and replicate and assemble similarly. For the genomic sequence of the various AAV serotypes and an overview of the genomic similarities see, e.g., GenBank Accession number U89790; GenBank Accession number J01901; GenBank Accession number AF043303; GenBank Accession number AF085716; Chlorini et al. (1997, J. Vir. 71: 6823-33); Srivastava et al. (1983, J. Vir. 45:555-64); Chlorini et al. (1999, J. Vir. 73:1309-1319); Rutledge et al. (1998, J. Vir. 72:309-319); and Wu et al. (2000, J. Vir. 74: 8635-47). AAV serotypes 1, 2, 3, 4 and 5 are an illustrative source of AAV nucleotide sequences for use in the context of the present disclosure. AAV6, AAV7, AAV8 or AAV9 or newly developed AAV-like particles obtained by e.g. capsid shuffling techniques and AAV capsid libraries, or from newly designed, developed or evolved ITR's are also suitable for certain disclosure applications. See Dalkara, D et al. (2013), Sci. Transl. Med. 5(189): 189ra76; Kotterman, M A Nat. Rev. Genet. (2014) 15(7):455.

In certain embodiments however, AAV vectors with significant tropism to the liver and related tissues will be of interest for expressing the FVIII proteins disclosed herein. Non-limiting examples include AAV serotypes 1, 2, 6 and 8. See, e.g., Torres-Torranteras et al. (2014) 22: 901 and references cited therein.

In other embodiments, the vector is derived from lentivirus. In certain embodiments, the vector is a vector of a recombinant lentivirus capable of infecting non-dividing cells.

The lentiviral genome and the proviral DNA typically have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNA's. The LTR contains all other cis-acting sequences necessary for viral replication. Lentiviruses have additional genes including vif, vpr, tat, rev, vpu, nef and vpx (in HIV-I, HIV-2 and/or SIV).

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA.

However, the resulting mutant remains capable of directing the synthesis of all virion proteins. The disclosure provides a method of producing a recombinant lentivirus capable of infecting a non-dividing cell comprising transfecting a suitable host cell with two or more vectors carrying the packaging functions, namely gag, pol and env, as well as rev and tat. As will be disclosed herein below, vectors lacking a functional tat gene are desirable for certain applications. Thus, for example, a first vector can provide a nucleic acid encoding a viral gag and a viral pol and another vector can provide a nucleic acid encoding a viral env to produce a packaging cell. Introducing a vector providing a heterologous gene, herein identified as a transfer vector, into that packaging cell yields a producer cell which releases infectious viral particles carrying the foreign gene of interest.

According to the above-indicated configuration of vectors and foreign genes, the second vector can provide a nucleic acid encoding a viral envelope (env) gene. The env gene can be derived from nearly any suitable virus, including retroviruses. In some embodiments, the env protein is an amphotropic envelope protein which allows transduction of cells of human and other species.

Examples of retroviral-derived env genes include, but are not limited to: Moloney murine leukemia virus (MoMuLV or MMLV), Harvey murine sarcoma virus (HaMuSV or HSV), murine mammary tumor virus (MuMTV or MMTV), gibbon ape leukemia virus (GaLV or GALV), human immunodeficiency virus (HIV) and Rous sarcoma virus (RSV). Other env genes such as Vesicular stomatitis virus (VSV) protein G (VSV G), that of hepatitis viruses and of influenza also can be used.

The vector providing the viral env nucleic acid sequence is associated operably with regulatory sequences described elsewhere herein.

In certain embodiments, the vector includes a lentiviral vector in which the HIV virulence genes env, vif, vpr, vpu and nef were deleted without compromising the ability of the vector to transduce non-dividing cells.

In some embodiments, the vector includes a lentiviral vector which comprises a deletion of the U3 region of the 3' LTR. The deletion of the U3 region can be the complete deletion or a partial deletion.

In some embodiments, the lentiviral vector of the disclosure comprising the FVIII nucleotide sequence described herein can be transfected in a cell with (a) a first nucleotide sequence comprising a gag, a pol, or gag and pol genes and (b) a second nucleotide sequence comprising a heterologous env gene; wherein the lentiviral vector lacks a functional tat gene. In other embodiments, the cell is further transfected with a fourth nucleotide sequence comprising a rev gene. In certain embodiments, the lentiviral vector lacks functional genes selected from vif, vpr, vpu, vpx and nef, or a combination thereof.

In certain embodiments, a lentiviral vector comprises one or more nucleotide sequences encoding a gag protein, a Rev-response element, a central polypurine track (cPPT), or any combination thereof.

Examples of the lentiviral vectors are disclosed in WO9931251, WO9712622, WO9817815, WO9817816, and WO9818934, which are incorporated herein by reference in their entireties.

Other vectors include plasmid vectors. Plasmid vectors have been extensively described in the art and are well-known to those of skill in the art. See, e.g., Sambrook et al., Molecular Cloning: A Laboratory Manual, Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operably encoded within the plasmid. Some commonly used plasmids available from commercial suppliers include pBR322, pUC18, pUC19, various pcDNA plasmids, pRC/CMV, various pCMV plasmids, pSV40, and pBlueScript. Additional examples of specific plasmids include pcDNA3.1, catalog number V79020; pcDNA3.1/hygro, catalog number V87020; pcDNA4/myc-His, catalog number V86320; and pBudCE4.1, catalog number V53220, all from Invitrogen (Carlsbad, Calif.). Other plasmids are well-known to those of ordinary skill in the art. Additionally, plasmids can be custom designed using standard molecular biology techniques to remove and/or add specific fragments of DNA.

Tissue Specific Expression

In certain embodiments, it will be useful to include within the vector one or more miRNA target sequences which, for example, are operably linked to the optimized FVIII transgene. Thus, the disclosure also provides at least one miRNA sequence target operably linked to the optimized FVIII nucleotide sequence or otherwise inserted within a vector. More than one copy of a miRNA target sequence included in the vector can increase the effectiveness of the system. Also included are different miRNA target sequences. For example, vectors which express more than one transgene can have the transgene under control of more than one miRNA target sequence, which can be the same or different. The miRNA target sequences can be in tandem, but other arrangements are also included. The transgene expression cassette, containing miRNA target sequences, can also be inserted within the vector in antisense orientation. Antisense orientation can be useful in the production of viral particles to avoid expression of gene products which can otherwise be toxic to the producer cells. In other embodiments, the vector comprises 1, 2, 3, 4, 5, 6, 7 or 8 copies of the same or different miRNA target sequence. However in certain other embodiments, the vector will not include any miRNA target sequence. Choice of whether or not to include an miRNA target sequence (and how many) will be guided by known parameters such as the intended tissue target, the level of expression required, etc.

In one embodiment, the target sequence is an miR-223 target which has been reported to block expression most effectively in myeloid committed progenitors and at least partially in the more primitive HSPC. miR-223 target can block expression in differentiated myeloid cells including granulocytes, monocytes, macrophages, myeloid dendritic cells. miR-223 target can also be suitable for gene therapy applications relying on robust transgene expression in the lymphoid or erythroid lineage. miR-223 target can also block expression very effectively in human HSC.

In another embodiment, the target sequence is an miR142 target (tccataaagt aggaaacact aca (SEQ ID NO: 43)). In one embodiment, the vector comprises 4 copies of miR-142 target sequences. In certain embodiments, the complementary sequence of hematopoietic-specific microRNAs, such as miR-142 (142T), is incorporated into the 3' untranslated region of a vector, e.g., lentiviral vectors (LV), making the transgene-encoding transcript susceptible to miRNA-mediated down-regulation. By this method, transgene expression can be prevented in hematopoietic-lineage antigen presenting cells (APC), while being maintained in non-hematopoietic cells (Brown et al., Nat Med 2006). This strategy can imposes a stringent post-transcriptional control on transgene expression and thus enables stable delivery and long-term expression of transgenes. In some embodiments, miR-142 regulation prevents immune-mediated clearance of transduced cells and/or induce antigen-specific Regulatory T cells (T regs) and mediate robust immunological tolerance to the transgene-encoded antigen.

In some embodiments, the target sequence is an miR181 target. Chen C-Z and Lodish H, Seminars in Immunology (2005) 17(2):155-165 discloses miR-181, a miRNA specifically expressed in B cells within mouse bone marrow (Chen and Lodish, 2005). It also discloses that some human miRNAs are linked to leukemias.

The target sequence can be fully or partially complementary to the miRNA. The term "fully complementary" means that the target sequence has a nucleic acid sequence which is 100% complementary to the sequence of the miRNA which recognizes it. The term "partially complementary" means that the target sequence is only in part complementary to the sequence of the miRNA which recognizes it, whereby the partially complementary sequence is still recognized by the miRNA. In other words, a partially complementary target sequence in the context of the present disclosure is effective in recognizing the corresponding miRNA and effecting prevention or reduction of transgene expression in cells expressing that miRNA. Examples of the miRNA target sequences are described at WO2007/000668, WO2004/094642, WO2010/055413, or WO2010/125471, which are incorporated herein by reference in their entireties.

Host Cells

The disclosure also provides a host cell comprising a nucleic acid molecule or vector of the disclosure. As used herein, the term "transformation" shall be used in a broad sense to refer to the introduction of DNA into a recipient host cell that changes the genotype and consequently results in a change in the recipient cell.

"Host cells" refers to cells that have been transformed with vectors constructed using recombinant DNA techniques and encoding at least one heterologous gene. The host cells of the present disclosure are preferably of mammalian origin; most preferably of human or mouse origin. Those skilled in the art are credited with ability to preferentially determine particular host cell lines which are best suited for their purpose. Exemplary host cell lines include, but are not limited to, CHO, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-1clBPT (bovine endothelial cells), RAJI (human lymphocyte), PER.C6®, NS0, CAP, BHK21, and HEK 293 (human kidney). In one particular embodiment, the host cell is selected from the group consisting of: a CHO cell, a HEK293 cell, a BHK21 cell, a PER.C6® cell, a NS0 cell, and a CAP cell. Host cell lines are typically available from commercial services, the American Tissue Culture Collection, or from published literature.

Introduction of the isolated nucleic acid molecules or vectors of the disclosure into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Chapter 24.2, pp. 470-472 Vectors, Rodriguez and Denhardt, Eds. (Butterworths, Boston, Mass. 1988). Most preferably, plasmid introduction into the host is via electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or flourescence-activated cell sorter analysis (FACS), immunohistochemistry and the like.

Host cells comprising the isolated nucleic acid molecules or vectors of the disclosure are grown in an appropriate growth medium. As used herein, the term "appropriate growth medium" means a medium containing nutrients required for the growth of cells. Nutrients required for cell growth can include a carbon source, a nitrogen source, essential amino acids, vitamins, minerals, and growth factors. Optionally, the media can contain one or more selection factors. Optionally the media can contain bovine calf serum or fetal calf serum (FCS). In one embodiment, the media contains substantially no IgG. The growth medium will generally select for cells containing the DNA construct by, for example, drug selection or deficiency in an essential nutrient which is complemented by the selectable marker on the DNA construct or co-transfected with the DNA construct. Cultured mammalian cells are generally grown in commercially available serum-containing or serum-free media (e.g., MEM, DMEM, DMEM/F12). In one embodiment, the medium is CDoptiCHO (Invitrogen, Carlsbad, Calif.). In another embodiment, the medium is CD17 (Invitrogen, Carlsbad, Calif.). Selection of a medium appropriate for the particular cell line used is within the level of those ordinary skilled in the art.

Preparation of Polypeptides

The disclosure also provides a polypeptide encoded by a nucleic acid molecule of the disclosure. In other embodiments, the polypeptide of the disclosure is encoded by a vector comprising the isolated nucleic molecules of the disclosure. In yet other embodiments, the polypeptide of the disclosure is produced by a host cell comprising the isolated nucleic molecules of the disclosure.

In other embodiments, the disclosure also provides a method of producing a polypeptide with FVIII activity, comprising culturing a host cell of the disclosure under conditions whereby a polypeptide with FVIII activity is produced, and recovering the polypeptide with FVIII activity. In some embodiments, the expression of the polypeptide with FVIII activity is increased relative to a host cell cultured under the same conditions but comprising a reference nucleotide sequence comprising SEQ ID NO: 16, the parental FVIII gene sequence.

In other embodiments, the disclosure provides a method of increasing the expression of a polypeptide with FVIII activity comprising culturing a host cell of the disclosure under conditions whereby a polypeptide with FVIII activity is expressed by the nucleic acid molecule, wherein the expression of the polypeptide with FVIII activity is increased relative to a host cell cultured under the same conditions comprising a reference nucleic acid molecule comprising SEQ ID NO: 16.

In other embodiments, the disclosure provides a method of improving yield of a polypeptide with FVIII activity comprising culturing a host cell under conditions whereby a polypeptide with FVIII activity is produced by the nucleic acid molecule, wherein the yield of polypeptide with FVIII activity is increased relative to a host cell cultured under the same conditions comprising a reference nucleic acid sequence comprising SEQ ID NO: 16.

In other embodiments, the disclosure provides a method of improving yield of a polypeptide with FVIII activity comprising culturing a host cell comprising a nucleotide sequence encoding the polypeptide, wherein the codon adaptation index of a 3' portion of the nucleotide sequence is increased relative to a 5' portion of the nucleotide sequence; wherein the yield of the polypeptide with FVIII activity is increased relative to a host cell cultured under the same conditions comprising a reference nucleic acid sequence comprising SEQ ID NO: 16. In some embodiments, the codon adaptation index of the 5' portion of the nucleotide sequence is increased, decreased, or unchanged relative to the codon optimization index of SEQ ID NO: 16.

In other embodiments, the disclosure provides a method of improving yield of a polypeptide with FVIII activity comprising culturing a host cell comprising a nucleotide sequence encoding the polypeptide, wherein the codon adaptation index of a 5' portion of the nucleotide sequence is increased relative to a 3' portion of the nucleotide sequence; wherein the yield of polypeptide with FVIII activity is increased relative to a host cell cultured under the same conditions comprising a reference nucleic acid sequence comprising SEQ ID NO: 16. In some embodiments, the codon adaptation index of the 3' portion of the nucleotide sequence is increased, decreased, or unchanged relative to the codon optimization index of SEQ ID NO: 16.

In other embodiments, the disclosure provides a method of improving yield of a polypeptide with FVIII activity comprising culturing a host cell comprising a nucleotide sequence encoding the polypeptide, wherein the codon adaptation index of a portion of the nucleotide encoding a C-terminal portion of the polypeptide is increased relative to a portion of the nucleotide encoding an N-terminal portion of the polypeptide; wherein the yield of polypeptide with FVIII activity is increased relative to a host cell cultured under the same conditions comprising a reference nucleic acid sequence comprising SEQ ID NO: 16. In some embodiments, the codon adaptation index of the portion of the nucleotide encoding the N-terminal portion of the polypeptide is increased, decreased, or unchanged relative to the codon optimization index of SEQ ID NO: 16.

In other embodiments, the disclosure provides a method of improving yield of a polypeptide with FVIII activity comprising culturing a host cell comprising a nucleotide sequence encoding the polypeptide, wherein the codon adaptation index of a portion of the nucleotide encoding a N-terminal portion of the polypeptide is increased relative to a portion of the nucleotide encoding an C-terminal portion of the polypeptide; wherein the yield of polypeptide with FVIII activity is increased relative to a host cell cultured under the same conditions comprising a reference nucleic acid sequence comprising SEQ ID NO: 16. In some embodiments, the codon adaptation index of the portion of the nucleotide encoding the C-terminal portion of the polypeptide is increased, decreased, or unchanged relative to the codon optimization index of SEQ ID NO: 16.

In certain embodiments of improving yield of a polypeptide with FVIII activity, the 5' portion of the nucleotide sequence, when properly aligned, corresponds with about nucleotides 1-1791 of SEQ ID NO: 1, nucleotides 58-1791 of SEQ ID NO: 1, or a fragment thereof. In other embodiments, a polypeptide encoded by the 5' portion of the nucleotide, when properly aligned, corresponds with about amino acids 1-497 of SEQ ID NO: 17, amino acids 20-497 of SEQ ID NO: 17, or a fragment thereof. In certain embodiments, the portion of the nucleotide sequence encoding the N-terminal portion of the polypeptide, when properly aligned, corresponds with about nucleotides 1-1791 of SEQ ID NO: 1, nucleotides 58-1791 of SEQ ID NO: 1, or a fragment thereof. In some embodiments, the 3' portion of the nucleotide sequence, when properly aligned, corresponds with about nucleotides 1792-4374 of SEQ ID NO: 1 or a fragment thereof. In other embodiments, a polypeptide encoded by the 3' portion of the nucleotide, when properly aligned, corresponds with about amino acids 498-1458 of SEQ ID NO: 17, or a fragment thereof. In certain embodiments, the portion of the nucleotide sequence encoding the C-terminal portion of the polypeptide, when properly aligned, corresponds with about nucleotides 1792-4374 of SEQ ID NO: 1 or a fragment thereof In some embodiments, the expression of the FVIII polypeptide is increased by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 20-fold, at least about 25-fold, at least about 30-fold, at least about 35-fold, at least about 40-fold, at least about 50-fold, at least about 60-fold, at least about 70-fold, at least about 80-fold, at least about 90-fold, at least about 100-fold, at least about 150-fold, or at least about 200-fold relative to a host cell cultured under the same conditions comprising a reference nucleic acid sequence comprising SEQ ID NO: 16.

A variety of methods are available for recombinantly producing a FVIII protein from the optimized nucleic acid molecule of the disclosure. A polynucleotide of the desired sequence can be produced by de novo solid-phase DNA synthesis or by PCR mutagenesis of an earlier prepared polynucleotide. Oligonucleotide-mediated mutagenesis is one method for preparing a substitution, insertion, deletion, or alteration (e.g., altered codon) in a nucleotide sequence. For example, the starting DNA is altered by hybridizing an oligonucleotide encoding the desired mutation to a single-stranded DNA template. After hybridization, a DNA polymerase is used to synthesize an entire second complementary strand of the template that incorporates the oligonucleotide primer. In one embodiment, genetic engineering, e.g., primer-based PCR mutagenesis, is sufficient to incorporate an alteration, as defined herein, for producing a polynucleotide of the disclosure.

For recombinant protein production, an optimized polynucleotide sequence of the disclosure encoding the FVIII protein is inserted into an appropriate expression vehicle, i.e., a vector which contains the necessary elements for the transcription and translation of the inserted coding sequence, or in the case of an RNA viral vector, the necessary elements for replication and translation.

The polynucleotide sequence of the disclosure is inserted into the vector in proper reading frame. The expression vector is then transfected into a suitable target cell which will express the polypeptide. Transfection techniques known in the art include, but are not limited to, calcium phosphate precipitation (Wigler et al. 1978, *Cell* 14: 725) and electroporation (Neumann et al. 1982, *EMBO, J.* 1: 841). A variety of host-expression vector systems can be utilized to express the FVIII proteins described herein in eukaryotic cells. In one embodiment, the eukaryotic cell is an animal cell, including mammalian cells (e.g. HEK293 cells, PER.C6®, CHO, BHK, Cos, HeLa cells). A polynucleotide sequence of the disclosure can also code for a signal sequence that will permit the FVIII protein to be secreted. One skilled in the art will understand that while the FVIII protein is translated the signal sequence is cleaved by the cell to form the mature protein. Various signal sequences are known in the art, e.g., native factor VII signal sequence, native factor IX signal sequence and the mouse IgK light chain signal sequence. Alternatively, where a signal sequence is not included the FVIII protein can be recovered by lysing the cells.

The FVIII protein of the disclosure can be synthesized in a transgenic animal, such as a rodent, goat, sheep, pig, or cow. The term "transgenic animals" refers to non-human animals that have incorporated a foreign gene into their genome. Because this gene is present in germline tissues, it is passed from parent to offspring. Exogenous genes are introduced into single-celled embryos (Brinster et al. 1985, Proc. Natl. Acad. Sci. USA 82:4438). Methods of producing transgenic animals are known in the art including transgenics that produce immunoglobulin molecules (Wagner et al. 1981, Proc. Natl. Acad. Sci. USA 78: 6376; McKnight et al. 1983, Cell 34: 335; Brinster et al. 1983, Nature 306: 332;

Ritchie et al. 1984, Nature 312: 517; Baldassarre et al. 2003, Theriogenology 59: 831; Robl et al. 2003, Theriogenology 59: 107; Malassagne et al. 2003, Xenotransplantation 10 (3): 267).

The expression vectors can encode for tags that permit for easy purification or identification of the recombinantly produced protein. Examples include, but are not limited to, vector pUR278 (Ruther et al. 1983, EMBO J. 2: 1791) in which the FVIII protein described herein coding sequence can be ligated into the vector in frame with the lac Z coding region so that a hybrid protein is produced; pGEX vectors can be used to express proteins with a glutathione S-transferase (GST) tag. These proteins are usually soluble and can easily be purified from cells by adsorption to glutathione-agarose beads followed by elution in the presence of free glutathione. The vectors include cleavage sites (e.g., Pre-Cission Protease (Pharmacia, Peapack, N.J.)) for easy removal of the tag after purification.

For the purposes of this disclosure, numerous expression vector systems can be employed. These expression vectors are typically replicable in the host organisms either as episomes or as an integral part of the host chromosomal DNA. Expression vectors can include expression control sequences including, but not limited to, promoters (e.g., naturally-associated or heterologous promoters), enhancers, signal sequences, splice signals, enhancer elements, and transcription termination sequences. Preferably, the expression control sequences are eukaryotic promoter systems in vectors capable of transforming or transfecting eukaryotic host cells. Expression vectors can also utilize DNA elements which are derived from animal viruses such as bovine papilloma virus, polyoma virus, adenovirus, vaccinia virus, baculovirus, retroviruses (RSV, MMTV or MOMLV), cytomegalovirus (CMV), or SV40 virus. Others involve the use of polycistronic systems with internal ribosome binding sites.

Commonly, expression vectors contain selection markers (e.g., ampicillin-resistance, hygromycin-resistance, tetracycline resistance or neomycin resistance) to permit detection of those cells transformed with the desired DNA sequences (see, e.g., Itakura et al., U.S. Pat. No. 4,704,362). Cells which have integrated the DNA into their chromosomes can be selected by introducing one or more markers which allow selection of transfected host cells. The marker can provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation.

An example of a vector useful for expressing an optimized FVIII sequence is NEOSPLA (U.S. Pat. No. 6,159,730). This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression of antibodies upon incorporation of variable and constant region genes, transfection in cells, followed by selection in G418 containing medium and methotrexate amplification. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other embodiments the polypeptides of the disclosure of the instant disclosure can be expressed using polycistronic constructs. In these expression systems, multiple gene products of interest such as multiple polypeptides of multimer binding protein can be produced from a single polycistronic construct. These systems advantageously use an internal ribosome entry site (IRES) to provide relatively high levels of polypeptides in eukaryotic host cells. Compatible IRES sequences are disclosed in U.S. Pat. No. 6,193,980 which is also incorporated herein.

More generally, once the vector or DNA sequence encoding a polypeptide has been prepared, the expression vector can be introduced into an appropriate host cell. That is, the host cells can be transformed. Introduction of the plasmid into the host cell can be accomplished by various techniques well known to those of skill in the art, as discussed above. The transformed cells are grown under conditions appropriate to the production of the FVIII polypeptide, and assayed for FVIII polypeptide synthesis. Exemplary assay techniques include enzyme-linked immunosorbent assay (ELISA), radioimmunoassay (RIA), or fluorescence-activated cell sorter analysis (FACS), immunohistochemistry and the like.

In descriptions of processes for isolation of polypeptides from recombinant hosts, the terms "cell" and "cell culture" are used interchangeably to denote the source of polypeptide unless it is clearly specified otherwise. In other words, recovery of polypeptide from the "cells" can mean either from spun down whole cells, or from the cell culture containing both the medium and the suspended cells.

The host cell line used for protein expression is preferably of mammalian origin; most preferably of human or mouse origin, as the isolated nucleic acids of the disclosure have been optimized for expression in human cells. Exemplary host cell lines have been described above. In one embodiment of the method to produce a polypeptide with FVIII activity, the host cell is a HEK293 cell. In another embodiment of the method to produce a polypeptide with FVIII activity, the host cell is a CHO cell.

Genes encoding the polypeptides of the disclosure can also be expressed in non-mammalian cells such as bacteria or yeast or plant cells. In this regard it will be appreciated that various unicellular non-mammalian microorganisms such as bacteria can also be transformed; i.e., those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis*; *Pneumococcus*; *Streptococcus*, and *Haemophilus influenzae*. It will further be appreciated that, when expressed in bacteria, the polypeptides typically become part of inclusion bodies. The polypeptides must be isolated, purified and then assembled into functional molecules.

Alternatively, optimized nucleotide sequences of the disclosure can be incorporated in transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for polypeptides in operable linkage with a promoter and enhancer from a mammary gland specific gene, such as casein or beta lactoglobulin.

In vitro production allows scale-up to give large amounts of the desired polypeptides. Techniques for mammalian cell cultivation under tissue culture conditions are known in the art and include homogeneous suspension culture, e.g., in an airlift reactor or in a continuous stirrer reactor, or immobilized or entrapped cell culture, e.g., in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein. An affinity tag sequence (e.g. a His(6) tag) can optionally be attached or included within the polypeptide sequence to facilitate downstream purification.

Once expressed, the FVIII protein can be purified according to standard procedures of the art, including ammonium sulfate precipitation, affinity column chromatography, HPLC purification, gel electrophoresis and the like (see generally Scopes, Protein Purification (Springer-Verlag, N.Y., (1982)). Substantially pure proteins of at least about 90 to 95% homogeneity are preferred, and 98 to 99% or more homogeneity most preferred, for pharmaceutical uses.

Pharmaceutical Composition

Compositions containing an isolated nucleic acid molecule, a polypeptide having FVIII activity encoded by the nucleic acid molecule, a vector, or a host cell of the present disclosure can contain a suitable pharmaceutically acceptable carrier. For example, they can contain excipients and/or auxiliaries that facilitate processing of the active compounds into preparations designed for delivery to the site of action.

The pharmaceutical composition can be formulated for parenteral administration (i.e. intravenous, subcutaneous, or intramuscular) by bolus injection. Formulations for injection can be presented in unit dosage form, e.g., in ampoules or in multidose containers with an added preservative. The compositions can take such forms as suspensions, solutions, or emulsions in oily or aqueous vehicles, and contain formulatory agents such as suspending, stabilizing and/or dispersing agents. Alternatively, the active ingredient can be in powder form for constitution with a suitable vehicle, e.g., pyrogen free water.

Suitable formulations for parenteral administration also include aqueous solutions of the active compounds in water-soluble form, for example, water-soluble salts. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides. Aqueous injection suspensions can contain substances, which increase the viscosity of the suspension, including, for example, sodium carboxymethyl cellulose, sorbitol and dextran. Optionally, the suspension can also contain stabilizers. Liposomes also can be used to encapsulate the molecules of the disclosure for delivery into cells or interstitial spaces. Exemplary pharmaceutically acceptable carriers are physiologically compatible solvents, dispersion media, coatings, antibacterial and antifungal agents, isotonic and absorption delaying agents, water, saline, phosphate buffered saline, dextrose, glycerol, ethanol and the like. In some embodiments, the composition comprises isotonic agents, for example, sugars, polyalcohols such as mannitol, sorbitol, or sodium chloride. In other embodiments, the compositions comprise pharmaceutically acceptable substances such as wetting agents or minor amounts of auxiliary substances such as wetting or emulsifying agents, preservatives or buffers, which enhance the shelf life or effectiveness of the active ingredients.

Compositions of the disclosure can be in a variety of forms, including, for example, liquid (e.g., injectable and infusible solutions), dispersions, suspensions, semi-solid and solid dosage forms. The preferred form depends on the mode of administration and therapeutic application.

The composition can be formulated as a solution, micro emulsion, dispersion, liposome, or other ordered structure suitable to high drug concentration. Sterile injectable solutions can be prepared by incorporating the active ingredient in the required amount in an appropriate solvent with one or a combination of ingredients enumerated above, as required, followed by filtered sterilization. Generally, dispersions are prepared by incorporating the active ingredient into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The active ingredient can be formulated with a controlled-release formulation or device. Examples of such formulations and devices include implants, transdermal patches, and microencapsulated delivery systems. Biodegradable, biocompatible polymers can be used, for example, ethylene vinyl acetate, polyanhydrides, polyglycolic acid, collagen, polyorthoesters, and polylactic acid. Methods for the preparation of such formulations and devices are known in the art. See, e.g., Sustained and Controlled Release Drug Delivery Systems, J. R. Robinson, ed., Marcel Dekker, Inc., New York, 1978.

Injectable depot formulations can be made by forming microencapsulated matrices of the drug in biodegradable polymers such as polylactide-polyglycolide. Depending on the ratio of drug to polymer, and the nature of the polymer employed, the rate of drug release can be controlled. Other exemplary biodegradable polymers are polyorthoesters and polyanhydrides. Depot injectable formulations also can be prepared by entrapping the drug in liposomes or microemulsions.

Supplementary active compounds can be incorporated into the compositions. In one embodiment, the chimeric protein of the disclosure is formulated with another clotting factor, or a variant, fragment, analogue, or derivative thereof. For example, the clotting factor includes, but is not limited to, factor V, factor VII, factor VIII, factor IX, factor X, factor XI, factor XII, factor XIII, prothrombin, fibrinogen, von Willebrand factor or recombinant soluble tissue factor (rsTF) or activated forms of any of the preceding. The clotting factor of hemostatic agent can also include antifibrinolytic drugs, e.g., epsilon-amino-caproic acid, tranexamic acid.

Dosage regimens can be adjusted to provide the optimum desired response. For example, a single bolus can be administered, several divided doses can be administered over time, or the dose can be proportionally reduced or increased as indicated by the exigencies of the therapeutic situation. It is advantageous to formulate parenteral compositions in dosage unit form for ease of administration and uniformity of dosage. See, e.g., Remington's Pharmaceutical Sciences (Mack Pub. Co., Easton, Pa. 1980).

In addition to the active compound, the liquid dosage form can contain inert ingredients such as water, ethyl alcohol, ethyl carbonate, ethyl acetate, benzyl alcohol, benzyl benzoate, propylene glycol, 1,3-butylene glycol, dimethylformamide, oils, glycerol, tetrahydrofurfuryl alcohol, polyethylene glycols, and fatty acid esters of sorbitan.

Non-limiting examples of suitable pharmaceutical carriers are also described in Remington's Pharmaceutical Sciences by E. W. Martin. Some examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain pH buffering reagents, and wetting or emulsifying agents.

For oral administration, the pharmaceutical composition can take the form of tablets or capsules prepared by conventional means. The composition can also be prepared as a liquid for example a syrup or a suspension. The liquid can include suspending agents (e.g., sorbitol syrup, cellulose derivatives or hydrogenated edible fats), emulsifying agents (lecithin or acacia), non-aqueous vehicles (e.g., almond oil, oily esters, ethyl alcohol, or fractionated vegetable oils), and preservatives (e.g., methyl or propyl-p-hydroxybenzoates or sorbic acid). The preparations can also include flavoring, coloring and sweetening agents. Alternatively, the composition can be presented as a dry product for constitution with water or another suitable vehicle.

For buccal administration, the composition can take the form of tablets or lozenges according to conventional protocols.

For administration by inhalation, the compounds for use according to the present disclosure are conveniently delivered in the form of a nebulized aerosol with or without excipients or in the form of an aerosol spray from a pressurized pack or nebulizer, with optionally a propellant, e.g., dichlorodifluoromethane, trichlorofluoromethane, dichlorotetrafluoromethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The pharmaceutical composition can also be formulated for rectal administration as a suppository or retention enema, e.g., containing conventional suppository bases such as cocoa butter or other glycerides.

In one embodiment, a pharmaceutical composition comprises a polypeptide having Factor VIII activity, an optimized nucleic acid molecule encoding the polypeptide having Factor VIII activity, the vector comprising the nucleic acid molecule, or the host cell comprising the vector, and a pharmaceutically acceptable carrier. In some embodiments, the composition is administered by a route selected from the group consisting of topical administration, intraocular administration, parenteral administration, intrathecal administration, subdural administration and oral administration. The parenteral administration can be intravenous or subcutaneous administration.

In other embodiments, the composition is used to treat a bleeding disease or condition in a subject in need thereof. The bleeding disease or condition is selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, bleeding in the illiopsoas sheath and any combinations thereof. In still other embodiments, the subject is scheduled to undergo a surgery. In yet other embodiments, the treatment is prophylactic or on-demand.

Methods of Treatment

The disclosure provides a method of treating a bleeding disorder comprising administering to a subject in need thereof a nucleic acid molecule, vector, or polypeptide of the disclosure. In some embodiments, the bleeding disorder is characterized by a deficiency in FVIII. In some embodiments, the bleeding disorder is hemophilia. In some embodiments, the bleeding disorder is hemophilia A. In some embodiments of the method of treating a bleeding disorder, plasma FVIII activity at 24 hours post administration is increased relative to a subject administered a reference nucleic acid molecule comprising SEQ ID NO: 16, a vector comprising the reference nucleic acid molecule, or a polypeptide encoded by the reference nucleic acid molecule.

In some embodiments, plasma FVIII activity is increased at about 6 hours, at about 12 hours, at about 18 hours, at about 24 hours, at about 36 hours, at about 48 hours, at about 3 days, at about 4 days, at about 5 days, at about 6 days, at about 7 days, at about 8 days, at about 9 days, at about 10 days, at about 11 days, at about 12 days, at about 13 days, at about 14 days, at about 15 days, at about 16 days, at about 17 days, at about 18 days, at about 19 days, at about 20 days, at about 21 days, at about 22 days, at about 23 days, at about 24 days, at about 25 days, at about 26 days, at about 27 days, or at about 28 days post administration relative to a subject administered a reference nucleic acid molecule comprising SEQ ID NO: 16, a viral vector comprising the reference nucleic acid molecule, or a polypeptide encoded by the reference nucleic acid molecule. In certain embodiments, plasma FVIII activity is increased at about 24 hours post administration relative to a subject administered a reference nucleic acid molecule comprising SEQ ID NO: 16, a viral vector comprising the reference nucleic acid molecule, or a polypeptide encoded by the reference nucleic acid molecule. In another embodiment, plasma FVIII activity is increased at about 21 days post administration relative to a subject administered a reference nucleic acid molecule comprising SEQ ID NO: 16, a viral vector comprising the reference nucleic acid molecule, or a polypeptide encoded by the reference nucleic acid molecule.

In some embodiments, plasma FVIII activity post administration is increased by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 20-fold, at least about 25-fold, at least about 30-fold, at least about 35-fold, at least about 40-fold, at least about 50-fold, at least about 60-fold, at least about 70-fold, at least about 80-fold, at least about 90-fold, at least about 100-fold, at least about 150-fold, at least about 200-fold, at least about 250-fold, at least about 300-fold, at least about 350-fold, at least about 400-fold, at least about 450-fold, or at least about 500-fold relative to a subject administered a reference nucleic acid molecule comprising SEQ ID NO: 16, a viral vector comprising the reference nucleic acid molecule, or a polypeptide encoded by the reference nucleic acid molecule. In some embodiments, plasma FVIII activity post administration is increased by at least about 150%, at least about 200%, at least about 250%, at least about 300%, at least about 350%, at least about 400%, at least about 450%, at least about 500%, at least about 550%, at least about 600%, at least about 650%, at least about 700%, at least about 750%, at least about 800%, at least about 850%, at least about 900%, at least about 950%, at least about 1000%, at least about 1500%, at least about 2000%, at least about 2500%, at least about 3000%, at least about 3500%, at least about 4000%, at least about 4500%, at least about 5000%, at least about 5500%, at least about 6000%, at least about 7000%, at least about 8000%, at least about 9000%, at least about 10,000% relative to physiologically normal circulating FVIII levels. In one embodiment, the plasma FVIII activity post administration is increased by at least about 3000 to about 5000% relative to physiologically normal circulating FVIII levels. In some embodiments, at 24 hours post administration of a plasmid comprising a codon-optimized gene encoding polypeptides with Factor VIII (FVIII) activity described herein, or at 21 days post administration of a lentiviral or AAV vector comprising a codon-optimized gene encoding polypeptides with Factor VIII (FVIII) activity described herein, plasma FVIII activity is increased by at least about 6-fold relative to a subject administered a reference nucleic acid molecule comprising SEQ ID NO: 16, a vector comprising the reference nucleic acid molecule, or a polypeptide encoded by the reference nucleic acid molecule. In some embodiments, at 24 hours post administration of a plasmid comprising a codon-optimized gene encoding polypeptides with Factor VIII (FVIII) activity described herein, or at 21 days post administration of a lentiviral or AAV vector comprising a codon-optimized gene encoding polypeptides with Factor VIII (FVIII) activity described herein, plasma FVIII activity is increased by at least about 10-fold relative to a subject administered a reference nucleic acid molecule comprising SEQ ID NO: 16, a vector comprising the reference nucleic acid molecule, or a polypeptide encoded by the reference nucleic acid molecule. In some embodiments, at 24 hours post administration of a plasmid comprising a codon-optimized gene encoding polypeptides with Factor VIII (FVIII) activity described herein, or at 21 days post administration of a lentiviral or AAV vector comprising a codon-optimized gene encoding polypeptides with Factor VIII (FVIII) activity described herein, plasma FVIII activity is increased by at least about 23-fold relative to a subject administered a reference nucleic acid molecule comprising SEQ ID NO: 16, a vector comprising the reference nucleic acid molecule, or a polypeptide encoded by the reference nucleic acid molecule. In some embodiments, at 24 hours post administration of a plasmid comprising a codon-optimized gene encoding polypeptides with Factor VIII (FVIII) activity described herein, or at 21 days post administration of a lentiviral or AAV vector comprising a codon-optimized gene encoding polypeptides with Factor VIII (FVIII) activity described herein, plasma FVIII activity is increased by at least about 18-fold relative to a subject administered a reference nucleic acid molecule comprising SEQ ID NO: 16, a vector comprising the reference nucleic acid molecule, or a polypeptide encoded by the reference nucleic acid molecule. In some embodiments, at 24 hours post administration of a plasmid comprising a codon-optimized gene encoding polypeptides with Factor VIII (FVIII) activity described herein, or at 21 days post administration of a lentiviral or AAV vector comprising a codon-optimized gene encoding polypeptides with Factor VIII (FVIII) activity described herein, plasma FVIII activity is increased by at least about 30-fold relative to a subject administered a reference nucleic acid molecule comprising SEQ ID NO: 16, a vector comprising the reference nucleic acid molecule, or a polypeptide encoded by the reference nucleic acid molecule. In some embodiments, at 24 hours post administration of a plasmid comprising a codon-optimized gene encoding polypeptides with Factor VIII (FVIII) activity described herein, or at 21 days post administration of a lentiviral or AAV vector comprising a codon-optimized gene encoding polypeptides with Factor VIII (FVIII) activity described herein, plasma FVIII activity is increased by at least about 50-fold relative to a subject administered a reference nucleic acid molecule comprising SEQ ID NO: 16, a vector comprising the reference nucleic acid molecule, or a polypeptide encoded by the reference nucleic acid molecule. In some embodiments, at 24 hours post administration of a plasmid comprising a codon-optimized gene encoding polypeptides with Factor VIII (FVIII) activity described herein, or at 21 days post administration of a lentiviral or AAV vector comprising a codon-optimized gene encoding polypeptides with Factor VIII (FVIII) activity described herein, plasma FVIII activity is increased by at least about 100-fold relative to a subject administered a reference nucleic acid molecule comprising SEQ ID NO: 16, a vector comprising the reference nucleic acid molecule, or a polypeptide encoded by the reference nucleic acid molecule.

The disclosure also relates to a method of treating, ameliorating, or preventing a hemostatic disorder in a subject comprising administering a therapeutically effective amount of an isolated nucleic acid molecule of the disclosure or a polypeptide having FVIII activity encoded by the nucleic acid molecule of the disclosure. The treatment, amelioration, and prevention by the isolated nucleic acid molecule or the encoded polypeptide can be a bypass therapy. The subject receiving bypass therapy can have already developed an inhibitor to a clotting factor, e.g., FVIII, or is subject to developing a clotting factor inhibitor.

The nucleic acid molecules, vectors, or polypeptides of the disclosure treat or prevent a hemostatic disorder by promoting the formation of a fibrin clot. The polypeptide having FVIII activity encoded by the nucleic acid molecule of the disclosure can activate a member of a coagulation cascade. The clotting factor can be a participant in the extrinsic pathway, the intrinsic pathway or both.

The nucleic acid molecules, vectors, or polypeptides of the disclosure can be used to treat hemostatic disorders known to be treatable with FVIII. The hemostatic disorders that can be treated using methods of the disclosure include, but are not limited to, hemophilia A, hemophilia B, von Willebrand's disease, Factor XI deficiency (PTA deficiency), Factor XII deficiency, as well as deficiencies or structural abnormalities in fibrinogen, prothrombin, Factor V, Factor VII, Factor X, or Factor XIII, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath. Compositions for administration to a subject include nucleic acid molecules which comprise an optimized nucleotide sequence of the disclosure encoding a FVIII clotting factor (for gene therapy applications) as well as FVIII polypeptide molecules.

In some embodiments, the hemostatic disorder is an inherited disorder. In one embodiment, the subject has hemophilia A. In other embodiments, the hemostatic disorder is the result of a deficiency in FVIII. In other embodiments, the hemostatic disorder can be the result of a defective FVIII clotting factor.

In another embodiment, the hemostatic disorder can be an acquired disorder. The acquired disorder can result from an underlying secondary disease or condition. The unrelated condition can be, as an example, but not as a limitation, cancer, an autoimmune disease, or pregnancy. The acquired disorder can result from old age or from medication to treat an underlying secondary disorder (e.g., cancer chemotherapy).

The disclosure also relates to methods of treating a subject that does not have a hemostatic disorder or a secondary disease or condition resulting in acquisition of a hemostatic disorder. The disclosure thus relates to a method of treating a subject in need of a general hemostatic agent comprising administering a therapeutically effective amount of the isolated nucleic acid molecule, vector, or FVIII polypeptide of the disclosure. For example, in one embodiment, the subject in need of a general hemostatic agent is undergoing, or is about to undergo, surgery. The isolated nucleic acid molecule, vector, or FVIII polypeptide of the disclosure can be administered prior to or after surgery as a prophylactic. The isolated nucleic acid molecule, vector, or FVIII polypeptide of the disclosure can be administered during or after surgery to control an acute bleeding episode. The surgery can include, but is not limited to, liver transplantation, liver resection, or stem cell transplantation.

In another embodiment, the isolated nucleic acid molecule, vector, or FVIII polypeptide of the disclosure can be used to treat a subject having an acute bleeding episode who does not have a hemostatic disorder. The acute bleeding episode can result from severe trauma, e.g., surgery, an automobile accident, wound, laceration gun shot, or any other traumatic event resulting in uncontrolled bleeding.

The isolated nucleic acid molecule, vector, or FVIII protein can be used to prophylactically treat a subject with a hemostatic disorder. The isolated nucleic acid molecule, vector, or FVIII protein can be used to treat an acute bleeding episode in a subject with a hemostatic disorder.

In another embodiment, expression of FVIII protein by administering the isolated nucleic acid molecule or vector of the disclosure does not induce an immune response in a subject. In some embodiments, the immune response comprises development of antibodies against FVIII. In some embodiments, the immune response comprises cytokine secretion. In some embodiments, the immune response comprises activation of B cells, T cells, or both B cells and T cells. In some embodiments, the immune response is an inhibitory immune response, wherein the immune response in the subject reduces the activity of the FVIII protein relative to the activity of the FVIII in a subject that has not developed an immune response. In certain embodiments, expression of FVIII protein by administering the isolated nucleic acid molecule or vector, of the disclosure prevents an inhibitory immune response against the FVIII protein or the FVIII protein expressed from the isolated nucleic acid molecule or the vector.

In some embodiments, an isolated nucleic acid molecule, vector, or FVIII protein composition of the disclosure is administered in combination with at least one other agent that promotes hemostasis. Said other agent that promotes hemostasis in a therapeutic with demonstrated clotting activity. As an example, but not as a limitation, the hemostatic agent can include Factor V, Factor VII, Factor IX, Factor X, Factor XI, Factor XII, Factor XIII, prothrombin, or fibrinogen or activated forms of any of the preceding. The clotting factor or hemostatic agent can also include anti-fibrinolytic drugs, e.g., epsilon-amino-caproic acid, tranexamic acid.

In one embodiment of the disclosure, the composition (e.g., the isolated nucleic acid molecule, vector, or FVIII polypeptide) is one in which the FVIII is present in activatable form when administered to a subject. Such an activatable molecule can be activated in vivo at the site of clotting after administration to a subject.

The isolated nucleic acid molecule, vector, or FVIII polypeptide can be administered intravenously, subcutaneously, intramuscularly, or via any mucosal surface, e.g., orally, sublingually, buccally, sublingually, nasally, rectally, vaginally or via pulmonary route. The FVIII protein can be implanted within or linked to a biopolymer solid support that allows for the slow release of the chimeric protein to the desired site.

For oral administration, the pharmaceutical composition can take the form of tablets or capsules prepared by conventional means. The composition can also be prepared as a liquid for example a syrup or a suspension. The liquid can include suspending agents (e.g. sorbitol syrup, cellulose derivatives or hydrogenated edible fats), emulsifying agents (lecithin or acacia), non-aqueous vehicles (e.g. almond oil, oily esters, ethyl alcohol, or fractionated vegetable oils), and preservatives (e.g. methyl or propyl-p-hydroxybenzoates or sorbic acid). The preparations can also include flavoring, coloring and sweetening agents. Alternatively, the composition can be presented as a dry product for constitution with water or another suitable vehicle.

For buccal and sublingual administration the composition can take the form of tablets, lozenges or fast dissolving films according to conventional protocols.

For administration by inhalation, the polypeptide having FVIII activity for use according to the present disclosure are conveniently delivered in the form of an aerosol spray from a pressurized pack or nebulizer (e.g., in PBS), with a suitable propellant, e.g., dichlorodifluoromethane, trichlorofluoromethane, dichlorotetrafluoromethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

In one embodiment, the route of administration of the isolated nucleic acid molecule, vector, or FVIII polypeptide is parenteral. The term parenteral as used herein includes intravenous, intraarterial, intraperitoneal, intramuscular, subcutaneous, rectal or vaginal administration. The intravenous form of parenteral administration is preferred. While all these forms of administration are clearly contemplated as being within the scope of the disclosure, a form for administration would be a solution for injection, in particular for intravenous or intraarterial injection or drip. Usually, a suitable pharmaceutical composition for injection can comprise a buffer (e.g. acetate, phosphate or citrate buffer), a surfactant (e.g. polysorbate), optionally a stabilizer agent (e.g. human albumin), etc. However, in other methods compatible with the teachings herein, the isolated nucleic acid molecule, vector, or FVIII polypeptide can be delivered directly to the site of the adverse cellular population thereby increasing the exposure of the diseased tissue to the therapeutic agent.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject disclosure, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a polypeptide by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations can be packaged and sold in the form of a kit. Such articles of manufacture will preferably have labels or package inserts indicating that the associated compositions are useful for treating a subject suffering from, or predisposed to clotting disorders.

The pharmaceutical composition can also be formulated for rectal administration as a suppository or retention enema, e.g., containing conventional suppository bases such as cocoa butter or other glycerides.

Effective doses of the compositions of the present disclosure, for the treatment of conditions vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages can be titrated using routine methods known to those of skill in the art to optimize safety and efficacy.

Dosages for administering a plasmid comprising a codon-optimized gene encoding polypeptides with Factor VIII (FVIII) activity, as described herein, or a polypeptide encoded by the codon-optimized gene can range from 1000 ug/kg to 0.1 ng/kg body weight. In one embodiment, the dosing range is 1 ug/kg to 100 ug/kg. Dosages for administering a lentiviral vector comprising a codon-optimized gene encoding polypeptides with Factor VIII (FVIII) activity, as described herein, can range from $10^3$ to $10^{15}$ TU/kg. Dosages for administering an AAV vector comprising a codon-optimized gene encoding polypeptides with Factor VIII (FVIII) activity, as described herein, can range from $10^5$ to $10^{18}$ VG/kg.

The isolated nucleic acid molecule, plasmid, vector, or FVIII polypeptide can be administered as a single dose or as multiple doses, wherein the multiple doses can be administered continuously or at specific timed intervals. In vitro assays can be employed to determine optimal dose ranges and/or schedules for administration. In vitro assays that measure clotting factor activity are known in the art. Additionally, effective doses can be extrapolated from dose-response curves obtained from animal models, e.g., a hemophiliac dog (Mount et al. 2002, *Blood* 99 (8): 2670).

Doses intermediate in the above ranges are also intended to be within the scope of the disclosure. Subjects can be administered such doses daily, on alternative days, weekly or according to any other schedule determined by empirical analysis. An exemplary treatment entails administration in multiple dosages over a prolonged period, for example, of at least six months. In some methods, two or more polypeptides can be administered simultaneously, in which case the dosage of each polypeptide administered falls within the ranges indicated.

The isolated nucleic acid molecule, vector, or FVIII polypeptides of the disclosure can be administered on multiple occasions. Intervals between single dosages can be daily, weekly, monthly or yearly. Intervals can also be irregular as indicated by measuring blood levels of modified polypeptide or antigen in the patient. Alternatively, polypeptides can be administered as a sustained release formulation, in which case less frequent administration is required. Dosage and frequency vary depending on the half-life of the polypeptide or polynucleotide in the patient.

The dosage and frequency of administration can vary depending on whether the treatment is prophylactic or therapeutic. In prophylactic applications, compositions containing the isolated nucleic acid molecule, vector, or FVIII polypeptide or a cocktail thereof are administered to a patient not already in the disease state to enhance the patient's resistance or minimize effects of disease. Such an amount is defined to be a "prophylactic effective dose." A relatively low dosage is administered at relatively infrequent intervals over a long period of time. Some patients continue to receive treatment for the rest of their lives.

The isolated nucleic acid molecule, vector, or FVIII polypeptides of the disclosure can optionally be administered in combination with other agents that are effective in treating the disorder or condition in need of treatment (e.g., prophylactic or therapeutic).

As used herein, the administration of isolated nucleic acid molecules, vectors, or FVIII polypeptides of the disclosure in conjunction or combination with an adjunct therapy means the sequential, simultaneous, coextensive, concurrent, concomitant or contemporaneous administration or application of the therapy and the disclosed polypeptides. Those skilled in the art will appreciate that the administration or application of the various components of the combined therapeutic regimen can be timed to enhance the overall effectiveness of the treatment. A skilled artisan (e.g., a physician) would be readily be able to discern effective combined therapeutic regimens without undue experimentation based on the selected adjunct therapy and the teachings of the instant specification.

It will further be appreciated that the isolated nucleic acid molecule, vector, or FVIII polypeptide of the instant disclosure can be used in conjunction or combination with an agent or agents (e.g., to provide a combined therapeutic regimen). Exemplary agents with which a polypeptide or polynucleotide of the disclosure can be combined include agents that represent the current standard of care for a particular disorder being treated. Such agents can be chemical or biologic in nature. The term "biologic" or "biologic agent" refers to any pharmaceutically active agent made from living organisms and/or their products which is intended for use as a therapeutic.

The amount of agent to be used in combination with the polynucleotides or polypeptides of the instant disclosure can vary by subject or can be administered according to what is known in the art. See, e.g., Bruce A Chabner et al., *Antineoplastic Agents*, in GOODMAN & GILMAN'S THE PHARMACOLOGICAL BASIS OF THERAPEUTICS 1233-1287 ((Joel G. Hardman et al., eds., 9$^{th}$ ed. 1996). In another embodiment, an amount of such an agent consistent with the standard of care is administered.

As previously discussed, the polynucleotides and polypeptides of the present disclosure, can be administered in a pharmaceutically effective amount for the in vivo treatment of clotting disorders. In this regard, it will be appreciated that the polypeptides or polynucleotides of the disclosure can be formulated to facilitate administration and promote stability of the active agent. Preferably, pharmaceutical compositions in accordance with the present disclosure comprise a pharmaceutically acceptable, non-toxic, sterile carrier such as physiological saline, non-toxic buffers, preservatives and the like. Of course, the pharmaceutical compositions of the present disclosure can be administered in single or multiple doses to provide for a pharmaceutically effective amount of the polypeptide.

A number of tests are available to assess the function of the coagulation system: activated partial thromboplastin time (aPTT) test, chromogenic assay, ROTEM® assay, prothrombin time (PT) test (also used to determine INR), fibrinogen testing (often by the Clauss method), platelet count, platelet function testing (often by PFA-100), TCT, bleeding time, mixing test (whether an abnormality corrects if the patient's plasma is mixed with normal plasma), coagulation factor assays, antiphosholipid antibodies, D-dimer, genetic tests (e.g., factor V Leiden, prothrombin mutation G20210A), dilute Russell's viper venom time (dRWT), miscellaneous platelet function tests, thromboelastography (TEG or Sonoclot), thromboelastometry (TEM®, e.g., ROTEM®), or euglobulin lysis time (ELT).

The aPTT test is a performance indicator measuring the efficacy of both the "intrinsic" (also referred to the contact activation pathway) and the common coagulation pathways. This test is commonly used to measure clotting activity of commercially available recombinant clotting factors, e.g., FVIII or FIX. It is used in conjunction with prothrombin time (PT), which measures the extrinsic pathway.

ROTEM® analysis provides information on the whole kinetics of haemostasis: clotting time, clot formation, clot stability and lysis. The different parameters in thromboelastometry are dependent on the activity of the plasmatic coagulation system, platelet function, fibrinolysis, or many factors which influence these interactions. This assay can provide a complete view of secondary haemostasis.

Gene Therapy

The disclosure provides a method of increasing expression of a polypeptide with FVIII activity in a subject comprising administering the isolated nucleic acid molecule of the disclosure to a subject in need thereof, wherein the expression of the polypeptide is increased relative to a reference nucleic acid molecule comprising SEQ ID NO: 16. The disclosure also provides a method of increasing expression of a polypeptide with FVIII activity in a subject comprising administering a vector of the disclosure to a subject in need thereof, wherein the expression of the polypeptide is increased relative to a vector comprising a reference nucleic acid molecule.

Somatic gene therapy has been explored as a possible treatment for hemophilia A. Gene therapy is a particularly appealing treatment for hemophilia because of its potential to cure the disease through continuous endogenous production of FVIII following a single administration of vector. *Haemophilia* A is well suited for a gene replacement approach because its clinical manifestations are entirely attributable to the lack of a single gene product (FVIII) that circulates in minute amounts (200 ng/ml) in the plasma.

A FVIII protein of the disclosure can be produced in vivo in a mammal, e.g., a human patient, using a gene therapy approach to treatment of a bleeding disease or disorder selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath would be therapeutically beneficial. In one embodiment, the bleeding disease or disorder is hemophilia. In another embodiment, the bleeding disease or disorder is hemophilia A. This involves administration of an optimized FVIII encoding nucleic acid operably linked to suitable expression control sequences. In certain embodiment, these sequences are incorporated into a viral vector. Suitable viral vectors for such gene therapy include adenoviral vectors, lentiviral vectors, baculoviral vectors, Epstein Barr viral vectors, papovaviral vectors, vaccinia viral vectors, herpes simplex viral vectors, and adeno associated virus (AAV) vectors. The viral vector can be a replication-defective viral vector. In other embodiments, an adenoviral vector has a deletion in its E1 gene or E3 gene. In other embodiments, the sequences are incorporated into a non-viral vector known to those skilled in the art.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference.

Having generally described this disclosure, a further understanding can be obtained by reference to the examples provided herein. These examples are for purposes of illustration only and are not intended to be limiting.

EXAMPLES

Example 1. Codon Optimization Strategy

Eight codon optimized BDD FVIII variants were created by controlling the codon usage bias, including coFVIII-3 (SEQ ID NO: 1; FIG. 1A), coFVIII-4 (SEQ ID NO: 2; FIG. 1B), coFVIII-5 (SEQ ID NO: 70; FIG. 1C), coFVIII-6 (SEQ ID NO: 71; FIG. 1D), coFVIII-52 (SEQ ID NO: 3; FIG. 1E), coFVIII-62 (SEQ ID NO: 4; FIG. 1F), coFVIII-25 (SEQ ID NO: 5; FIG. 1G), and coFVIII-26 (SEQ ID NO: 6; FIG. 1H). The online tool Eugene was used to facilitate codon optimization as previously described (See Gaspar et al., "EuGene: maximizing synthetic gene design for heterologous expression," Bioinformatics 28:2683-84 (2012)), and several codon usage parameters, such as codon adaptation index (CAI) and relative synonymous codon usage (RSCU), were monitored (Table 5). All variants were adjusted to CAI ≥83% and RSCU ≥1.63, while the parental B-domain deleted FVIII sequence, prior to optimization, has a CAI of 74% and an RSCU of 1.12 (Table 5).

FVIII variants with a higher CAI at the N-terminal half of the coding sequence and a lower CAI at the C-terminal half of the coding sequence (see FIGS. 2I and 2J). The third class includes coFVIII-25 (FIG. 2I) and coFVIII-26 (FIG. 2J).

Without being bound by any theory, it was speculated that a higher CAI might correlate with faster protein translation, and these three classes might represent different rates of protein synthesis from the start to finish. For example, translation of a region having a lower CAI might proceed slowly relative to translation of a region having a higher CAI. If so, translation of, e.g., the N-terminal half of coFVIII-52 of coFVIII-62, having a lower CAI, might initially proceed slowly followed by more rapid translation of the C-terminal half, having a higher CAI. This could be preferred for protein folding and post-translational modification during translation without slowing down the overall protein synthesis. The opposite effect might be seen for the coFVIII-25 and coFVIII-26 variants, which have a higher CAI at the N-terminal half and a lower CAI at the C-terminal half.

To ensure the stability of the mRNA, all the FVIII codon optimized variants were adjusted to avoid a number of sites, including cryptic splicing sites, premature polyA sites, RNA instability motifs (ARE), and repeat sequences, and to adjust the GC content (see Table 2).

TABLE 5

Codon Optimization Parameters

| | Parental BDD FVIII | coFVIII-3 | coFVIII-4 | coFVIII-5 | coFVIII-6 | coFVIII-52 | coFVIII-62 | coFVIII-25 | coFVIII-26 |
|---|---|---|---|---|---|---|---|---|---|
| Codon Adaptation Index (CAI; %) | 74 | 91 | 97 | 83 | 83 | 91 | 91 | 88 | 88 |
| Frequency of Optimal Codons (FOP) | 39 | 65 | 92 | 64 | 64 | 79 | 79 | 74 | 75 |
| GC Content (%) | 44.10 | 52.10 | 60.80 | 55.7 | 55.9% | 58.30 | 58.30 | 57.30 | 57.60 |
| Relative Synonymous Codon Usage (RSCU) | 1.12 | 2.32 | 2.72 | 1.63 | 1.63 | 2.22 | 2.19 | 2.04 | 2.58 |
| Codon Pair Bias | 0.19 | 0.43 | 0.04 | 0.11 | 0.11 | 0.27 | 0.27 | 0.23 | 0.48 |
| Effective number of codons | 54.2 | 25.6 | 22.8 | 39.7 | 39.1 | 30.9 | 31.4 | 34.1 | 26.7 |

In addition to the overall increase of the CAI, the eight variants were designed into three classes based on the distribution of CAI across the coding region, as illustrated in FIG. 2, relative to the non-optimized BDD FVIII sequence (FIG. 2A). The first class comprises BDD FVIII variants with an even distribution of the high CAI across the entire coding region (see FIGS. 2C-2F). The first class includes coFVIII-3 (FIG. 2C), coFVIII-4 (FIG. 2D), coFVIII-5 (FIG. 2E), coFVIII-6 (FIG. 2F), as well as the previously described coFVIII-1 (see International Publication No. WO 2014/127215 (SEQ ID NO: 1)) (FIG. 2B). The second class comprises BDD-FVIII variants with a lower CAI at the N-terminal half of the coding sequence and a higher CAI at the C-terminal half of the coding sequence (see FIGS. 2G and 2H). The second class includes coFVIII-52 (FIG. 2G) and coFVIII-62 (FIG. 2H). The third class comprises BDD Example 2. Cloning and Expression of coFVIII Variants from a pcDNA3 Plasmid Expression plasmids containing the various FVIII variants were designed for in vivo expression. The non-optimized BDD FVIII (FIG. 1I; SEQ ID NO: 16) and coFVIII-1 (FIG. 11Z; SEQ ID NO: 68) polynucleotides were cloned into a pcDNA3 backbone (Invitrogen), wherein the CMV promoter was replaced by an ET promoter (see FIG. 3). The resulting plasmids, FVIII-311 (BDD FVIII) and FVII-303 (coFVIII-1), drive the expression of non-optimized BDD FVIII and coFVIII-1, respectively.

In vivo expression of FVIII-311 and FVII-303 was evaluated in Hem A mice by hydrodynamic injection of 5 µg DNA/mouse of FVII-303 or FVIII-311. Plasma samples were collected at 24, 48, and 72 hours post-injection, and FVIII activity was determined by a FVIII specific chromogenic assay.

As shown in FIG. 4, the plasma FVIII activity of mice treated with FVII-311 (BDD FVIII; squares) was 74±43 mU/mL at 72 hours post-injection, whereas the plasma FVIII activity of mice treated with FVII-303 (coFVIII-1; circles) was 452±170 mU/mL at 72 hours post-injection (FIG. 4). This represents an approximately six-fold increase in the expression of coFVIII-1 relative to non-optimized BDD FVIII.

Example 3. Cloning and Expressing coFVIII Variants Using a Lentiviral Vector System To further assess the expression level of the codon optimized BDD FVIII variants, the coding sequences were cloned into lentiviral plasmids under the control of an ET promoter (see Amendola et al., "Coordinate dual-gene transgenesis by lentiviral vectors carrying synthetic bidirectional promoters," Nature Biol. 23:108-16 (2005); International Publication No. WO 2000/066759 A1). A plasmid map of pLV-coFVIII-52 is shown in FIG. 5; and plasmids containing non-optimized BDD FVIII (LV-2116), coFVIII-1 (LV-coFVIII-1), coFVIII-3 (LV-coFVIII-3), coFVIII-4 (LV-coFVIII-4), coFVIII-5 (LV-coFVIII-5), and coFVIII-6 (LV-coFVIII-6), coFVIII-62 (LV-coFVIII-62), coFVIII-25 (LV-coFVIII-25), and coFVIII-26 (LV-coFVIII-26) were constructed in the same manner, except that the coFVIII-52 fragment was replaced by each indicated coding sequence using the NheI and SaiI sites (Table 6).

TABLE 6

Expression Plasmids Coding for FVIII Variants

| Plasmid ID | Description |
| --- | --- |
| FVIII-303 (coFVIII-1) | coFVIII-1 under ET promoter in pcDNA3 |
| FVIII-311 (BDD FVIII) | Parental BDD-FVIII under ET promoter in pcDNA3 |
| LV-2116 (BDD FVIII) | Parental BDD-FVIII under ET promoter in lentiviral plasmid |
| LV-coFVIII-1 | coFVIII-1 under ET promoter in lentiviral plasmid |
| LV-coFVIII-3 | coFVIII-3 under ET promoter in lentiviral plasmid |
| LV-coFVIII-4 | coFVIII-4 under ET promoter in lentiviral plasmid |
| LV-coFVIII-5 | coFVIII-5 under ET promoter in lentiviral plasmid |
| LV-coFVIII-6 | coFVIII-6 under ET promoter in lentiviral plasmid |
| LV-coFVIII-52 | coFVIII-52 under ET promoter in lentiviral plasmid |
| LV-coFVIII-62 | coFVIII-62 under ET promoter in lentiviral plasmid |
| LV-coFVIII-25 | coFVIII-25 under ET promoter in lentiviral plasmid |
| LV-coFVIII-26 | coFVIII-26 under ET promoter in lentiviral plasmid |

The lentiviral codon optimized FVIII variants were evaluated in HemA mice by hydrodynamic injection at a dose of 5 µg DNA/mouse (FIGS. 6A, 6B) or 20 µg DNA/mouse (FIG. 6C). As shown in FIG. 6, each of coFVIII-3 (FIG. 6A; triangles), coFVIII-4 (FIG. 6A; inverted triangles), coFVIII-5 (FIG. 6A; diamonds), coFVIII-6 (FIG. 6A; open circles), coFVIII-25 (FIG. 6B; triangles), coFVIII-26 (FIG. 6B; inverted triangles), coFVIII-52 (FIG. 6C; squares), and coFVIII-62 (FIG. 6C; filled circles) exhibited higher FVIII activity than coFVIII-1 (FIG. 6A, circles; FIG. 6B, circles; and FIG. 6C, triangles). In particular, coFVIII-25 and coFVIII-26 exhibited a similar expression level at 72 hours post-injection, reaching about 3-fold higher activity than that of the coFVIII-1 (FIG. 6B), which translates into 24-fold higher FVIII activity compared to the non-optimized, parental BDD FVIII (see FIG. 4). Both coFVIII-52 (squares) and coFVIII-62 (filled circles) achieved even higher expression at 72 hours post-injection, exhibiting 6-fold and 4-fold greater expression, respectively, than coFVIII-1 (triangles), and 50-fold and 30-fold greater expression, respectively, than non-optimized, parental BDD FVIII (open circles) (FIG. 6C). These data indicate that the combination of a lower CAI at the N-terminal half of the coding sequence and a higher CAI at the C-terminal half of the coding sequence might be more beneficial for FVIII expression as compared to the reversed distribution of CAI.

Example 4: Long-Term Lentiviral Expression of Codon-Optimized FVIII Variants in HemA Mice Variants identified to drive high expression of FVIII in HemA mice at 72 hours post-hydrodynamic injection were evaluated for long term FVIII expression by lentiviral vectors mediated gene transfer. Lentiviral vectors were produced in 293T cells by transient transfection and concentrated by ultracentrifugation to about 5E9 TU/ml. The lentiviral vectors were then administered into 12-14 day old HemA mice by retro-orbital injection at a dose of 1E8 TU/mouse. At 21 days after lentiviral injection, the average plasma FVIII activity was about 0.04 IU/ml for mice injected with LV-2116 (BDD FVIII; FIG. 7). Each of coFVIII-1, coFVIII-5, coFVIII-52, coFVIII-6, and coFVIII-62 resulted in a higher circulating FVIII level at 21 days post-injection relative to the LV-2116 (non-optimized B domain deleted FVIII) control. In particular, coFVIII-1 and coFVIII-5 injection yielded a FVIII plasma activity levels of about 1.8 IU/mL, coFVIII-52 yielded a FVIII plasma activity level of about 4.9 IU/mL, coFVIII-6 yielded a FVIII plasma activity levels of about 4.6 IU/mL, and coFVIII-62 yielded a FVIII plasma activity level of about 2.5 IU/mL at 21 days post injection (FIG. 7). The FVIII plasma levels observed in mice injected with LV-coFVIII-6 and LV-coFVIII-52, 4.6 IU/ml and 4.9 IU/ml, respectively, are more than 100-fold higher than the plasma levels observed in mice injected with the LV-2116 (non-optimized BDD-FVIII) control.

Example 5. coFVIII-XTEN Fusion Constructs

The ability of XTEN to improve the steady state FVIII expression was tested. First, the coding sequence for an XTEN of 144 amino acids ("XTEN$_{144}$"; SEQ ID NO: 18) was inserted at nucleotide 1193 (or after the first 764 amino acids of the encoded polypeptide) of coFVIII-52 and coFVIII-1 to generate coFVIII-52-XTEN (FIG. 8A; SEQ ID NO: 19) and coFVIII-1-XTEN (FIG. 8B; SEQ ID NO: 20), respectively. The coFVIII-1-XTEN sequence was then cloned into a pcDNA3 backbone (Invitrogen) under the control of an ET promoter, as described above, to create the FVIII-306 expression plasmid; and the coFVIII-52-XTEN sequence was cloned into a lentiviral plasmid under the control of an ET promoter, as disclosed above, to create the pLV-coFVIII-52-XTEN (FIG. 9). FVIII-306 (coFVIII-1-XTEN) was administered to HemA mice at 5 µg DNA/mouse by hydrodynamic injection. As compared to FVIII-303 (coFVIII-1; FIG. 10A, small circles) and FVIII-311 (BDD FVIII; FIG. 10A, squares), fusion of XTEN$_{144}$ to coFVIII-1 (FVII-306; FIG. 10A, large circles) resulted in about 5-fold and 33-fold higher FVIII expression, respectively, in HemA mice at 72 hours post-injection. The effect of XTEN insertion on FVIII expression was also evaluated using lentiviral vector in HemA mice (FIG. 10B). LV-coFVIII-52-XTEN was administered to 12-14 day old HemA mice at 1E8 TU/mouse by retro orbital injection. As compared to LV-coFVIII52 and LV-2116 (BDD-FVIII), fusion of $XTEN_{144}$ to coFVIII-52 (FIG. 10B) resulted in about 4-fold and 450-fold higher FVIII expression, respectively, in HemA mice at 21 days post-injection.

Lentiviral vectors comprising each of coFVIII-3, coFVIII-4, coFVIII-5, coFVIII-6, coFVIII-62, coFVIII-25, and coFVIII-26 fused to $XTEN_{144}$ and fused to an ET promoter will be made as described above. The vectors will be tested for their expression of FVIII proteins.

Example 6. Expression of coFVIII Constructs

Codon optimized FVIII variants were cloned into lentiviral plasmids, as illustrated in FIG. 9, by standard molecular cloning techniques. Lentiviral vectors were then produced in HEK293 cells through transient transfection and isolated by ultracentrifugation.

FVIII lentiviral vectors were administered to 14-day-old HemA mouse pups by intravenous injection at a dose of 1.5E10 TU/kg LV-FVIII variant. FVIII plasma activity was measured at day 21 post LV-FVIII treatment, and vector copy number (VCN) per cell was measured in liver necropsy samples collected from LV-FVIII treated animals at day 150 post LV-FVIII treatment. While VCN values were similar in all animals regardless of the LV-FVIII variants administered (FIG. 12B), FVIII activity levels in animals treated with coFVIII variants were 30 to 100-fold higher than in animals treated with wtBDD-FVIII (FIGS. 12A and 12C; Table 7). These data indicate that FVIII codon optimization improves FVIII expression in a lentiviral vector setting.

TABLE 7

Relative expression of codon optimized FVIII constructs

| | LV-FVIII variants | | | | |
|---|---|---|---|---|---|
| | CoFVIII-1 | CoFVIII-3 | CoFVIII-4 | CoFVIII-5 | CoFVIII-6 |
| Fold-improvement of FVIII expression relative to LV-wtBDD-FVIII | 57 | 34 | 33 | 74 | 107 |

| | LV-FVIII variants | | | |
|---|---|---|---|---|
| | CoFVIII-52 | CoFVIII-62 | CoFVIII-25 | CoFVIII-26 |
| Fold-improvement of FVIII expression relative to LV-wtBDD-FVIII | 96 | 59 | 87 | 83 |

Example 7. FVIII Transgene Expression Mediated Immune Response in HemA Mice Following Lentiviral Treatment The LV-FVIII-treated mice of Example 6 were evaluated for long-term FVIII expression and anti-FVIII antibody formation. FVIII expression, as evidenced by FVIII plasma activity, varied among animals within the same treatment group (FIG. 13A). For example, three mice (designated 1, 2, and 3) treated with a lentiviral vector expressing the coFVIII-5 variant showed consistent FVIII expression over approximately 16 weeks, whereas three littermates (designated 4, 5, and 6), which were treated with the same lentiviral vector, showed sharp declines in FVIII plasma activity levels by about 10 weeks post treatment (FIG. 13A). The consistent FVIII plasma activity observed in mice 1, 2, and 3 correlated with non-detectable or very low levels of anti-FVIII antibodies (FIG. 13B; mice 1, 2, and 3). Conversely, the mice that exhibited sharp declines in FVIII plasma activity also exhibited increased levels of anti-FVIII antibodies (FIG. 13B; mice 4, 5, and 6). These data suggest that FVIII transgene expression induces anti-FVIII antibody formation in a subset of animals, and the resulting anti-FVIII antibodies eliminated transgenic FVIII protein from circulation.

The relationship between FVIII expression and anti-FVIII antibody formation was assessed. The LV-FVIII-treated mice of Example 6 were divided into two groups: mice that were anti-FVIII antibody negative and mice that were anti-FVIII antibody positive. As shown in FIG. 14, expression of transgenic FVIII at physiological levels does not induce an immune response to the transgenic FVIII (FIG. 14, circles) However, supra physiological levels of FVIII expression appears to induce anti-FVIII antibody formation, such that the higher the FVIII expression level, the higher the chance of anti-FVIII antibody induction. These data suggest that it may be beneficial to maintain physiological levels of FVIII expression in patients subjected to a FVIII gene therapy treatment.

To determine if FVIII expression induced immune response results in loss of transgene expressing liver cells, vector copy number (FIG. 15) and FVIII RNA transcription level (FIG. 16) were evaluated in liver necropsy samples from anti-FVIII antibody positive and negative mice. As shown in FIG. 15, the distribution of vector copy number was the same in anti-FVIII antibody positive and negative mice, indicating that cells with LV-FVIII integration were maintained despite the development of anti-FVIII antibody. This suggests that LV-FVIII mediated FVIII transgene expression dose not induce a Cytotoxic T Lymphocyte (CTL) response against FVIII expressing liver cells. To further confirm these results, FVIII RNA transcription was assessed by RNA in situ hybridization (FIGS. 16C and 16D). At the time of liver harvesting, mouse coFVIII-52-B had no detectable circulating FVIII and a high level of anti-FVIII antibodies (FIGS. 16A and 16B). However, the RNA transcription signal and the number of FVIII-RNA positive cells in liver tissue from the coFVIII-52-B mouse were comparable to the FVIII-52-A mouse, which had about 4 IU/ml of circulating FVIII at time of necropsy. Therefor FVIII expression did not induce CTL response in experimental HemA mice.

Example 8. FVIII Long-Term Expression in LV-FVIII Treated HemA Mouse Neonates

To assess the efficacy of using a lentiviral system for the treatment of pediatric HemA patients through targeting the liver, 2-day-old HemA mice were administered by temple vein injection about 1.5 E10 TU/kg of LV-coFVIII-52XTEN, LV-coFVIII6-XTEN, or a lentiviral vector expressing wtBDD-FVIII. Consistent long-term FVIII expression was observed for both variants and the control, demonstrating that the integrated FVIII expression cascade was maintained in the dividing liver cells of the treated mice (FIG. 17). These data suggest that LV-FVIII could potentially be used to treat both pediatric and adult HemA patients.

Example 9. Evaluation of LV-FVIII in HemA Dog Neonates

To further evaluate the efficacy of LV-FVIII in larger animal models, two one-week old HemA dog neonates (designated S3 and K4) were administered by intravenous injection 1.3×10$^9$ TU/kg LV-coFVIII-6-XTEN. This dose was more than 10-fold lower than the dose previously used in HemA mouse models. Following administration of the lentiviral vectors, plasma FVIII activity was monitored by one stage clotting assay (aPTT) (FIG. 18) and whole blood hemostasis was monitored by rotational thromboelastometry (ROTEM) assay (FIGS. 19A-19D). Before LV-FVIII treatment, the FVIII level for S3 was 0.7% of normal (FIG. 18). Post lentiviral vector treatment, the FVIII level of S3 increased to 79% and 103% of normal at day 7 and day 14, respectively (FIG. 18). For K4, the pre-administration FVIII level was 1.4% of normal (FIG. 18). After lentiviral vector treatment, the FVIII level increased to 22% and 25% of normal at day 6 and day 14, respectively (FIG. 18).

Correlated to the FVIII level, normalized ROTEM was observed for both animals at 2 weeks post treatment (FIGS. 19A-19C), demonstrating the therapeutic benefit mediated by LV-FVIII. The therapeutically beneficial FVIII expression level achieved by LV-FVIII in HemA dog, confirms the potential use of LV-FVIII for the treatment of Hemophilia A.

Example 10. Evaluation of LV-FVIII in HemA Mouse Neonates

Ex vivo gene therapy with lentiviral vectors (LV) for gene replacement has demonstrated clinical efficacy for multiple indications and with multi-year follow up in treated patients showing no evidence of tumorigenesis. Systemic delivery of LV-FIX mediates persistent FIX expression and is well tolerated in hemophilia animal models. The large packaging capacity, ability to sustain long-term transgene expression via gene integration, lack of pre-existing anti-LV antibodies (abs) in human populations and the encouraging in vivo profiles demonstrated in pre-clinical and clinical settings, make LV a promising vehicle for in vivo gene delivery, especially for gene candidates with large cDNA size such as FVIII.

To evaluate the potential use of LV-FVIII for the treatment of hemophilia A (HemA), codon optimized Human FVIII (hFVIII) variants placed under a hepatocyte-specific promoter were built into a LV system that contains multiple copies of microRNA-142 target sequences to minimize FVIII expression in antigen presenting cells and reduce the probability of inducing anti-FVIII antibodies. LV-hFVIII vectors were produced by transient-transfection of 293T cells, followed by 1000-fold concentration by ultra-centrifugation and evaluated in HemA mouse models. Post intravenous administration of LV-hFVIII, circulating hFVIII level was monitored by FVIII activity and antigen assays, LV transduction efficiency in the liver was assessed by measuring LV DNA copies via quantitative PCR and transgene RNA via In Situ Hybridization, anti-hFVIII antibodies were measured by total anti-hFVIII antibody ELISA.

Persistent FVIII expression was observed for all LV-hFVIII variants in HemA mice that were treated at the neonatal stage. At 1.5E10 transducing units/kg dose, LV encoding codon optimized hFVIII (LV-cohFVIII) resulted in 30 to 100-fold higher circulating FVIII than LV encoding wild type hFVIII (FIG. 12C), while the vector copy number in liver cells and percent of FVIII RNA positive cells were comparable in all tested groups (FIG. 12B). Combination of codon optimization with XTEN (LV-cohFVIII-XTEN), a non-structured hydrophilic poly-peptide that presumably improves the circulating half-life by increasing the hydrodynamic size of the payload, resulted in 30-50 IU/mL FVIII activity in plasma, representing 3,000 to 5,000% of normal circulating FVIII level (FIG. 12A, FIG. 17). Furthermore, anti-hFVIII abs were only detected in mice with supra physiological level of hFVIII (FIG. 14), but no cytotoxic T lymphocyte response against LV transduced cells was observed in anti-hFVIII antibody positive mice (FIGS. 15 and 16A-16D). Our result supports further development of LV-FVIII for in vivo gene therapy of hemophilia A.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

All patents and publications cited herein are incorporated by reference herein in their entirety.

What is claimed is:

1. An isolated nucleic acid molecule comprising a nucleotide sequence encoding a polypeptide with FVIII activity, wherein the nucleotide sequence comprises a nucleic acid sequence comprising nucleotides 58-2277 and 2320-4374 of SEQ ID NO: 71.

2. The isolated nucleic acid molecule of claim 1, wherein the nucleotide sequence further comprises a nucleic acid sequence encoding a signal peptide, wherein the nucleic acid sequence encoding a signal peptide comprises at least 90%, at least 95%, at least 96%, at least 97%, at least 98%, at least 99%, or 100% sequence identity to:
   (i) nucleotides 1 to 57 of SEQ ID NO: 1;
   (ii) nucleotides 1 to 57 of SEQ ID NO: 2;
   (iii) nucleotides 1 to 57 of SEQ ID NO: 3;
   (iv) nucleotides 1 to 57 of SEQ ID NO: 4;
   (v) nucleotides 1 to 57 of SEQ ID NO: 5;
   (vi) nucleotides 1 to 57 of SEQ ID NO: 6;
   (vii) nucleotides 1 to 57 of SEQ ID NO: 70;
   (viii) nucleotides 1 to 57 of SEQ ID NO: 71; or
   (ix) nucleotides 1 to 57 of SEQ ID NO: 68.

3. The isolated nucleic acid molecule of claim 1, wherein the nucleic acid molecule comprises one or more property selected from the group consisting of:
   (a) the human codon adaptation index of the nucleic acid molecule or a portion thereof is increased relative to SEQ ID NO: 16;
   (b) the frequency of optimal codons of the nucleotide sequence or a portion thereof is increased relative to SEQ ID NO:16;
   (c) the nucleotide sequence or a portion thereof contains a higher percentage of G/C nucleotides compared to the percentage of G/C nucleotides in SEQ ID NO: 16;
   (d) the relative synonymous codon usage of the nucleotide sequence or a portion thereof is increased relative to SEQ ID NO: 16;
   (e) the effective number of codons of the nucleotide sequence or a portion thereof is reduced relative SEQ ID NO: 16;
   (f) the nucleotide sequence contains fewer nuclear matrix attachment regions/autonomously replicating sequences (MARS/ARS) relative to SEQ ID NO: 16;
   (g) the nucleotide sequence contains fewer destabilizing elements relative to SEQ ID NO: 16; and
   (h) any combination thereof.

4. The isolated nucleic acid molecule of claim 1, wherein the FVIII polypeptide is a full length FVIII or a B domain deleted FVIII.

5. A vector comprising the nucleic acid molecule of claim 1.

6. A method of increasing expression of a polypeptide with FVIII activity in a mammalian subject comprising administering to said subject a vector comprising the isolated nucleic acid molecule of claim 1, wherein the expression of the polypeptide is increased relative to a reference nucleic acid molecule comprising SEQ ID NO: 16 or the vector comprising the reference nucleic acid molecule.

7. A method of treating hemophilia A in a mammalian subject comprising administering to said subject a vector comprising the nucleic acid molecule of claim 1.

8. An isolated nucleic acid molecule comprising a nucleotide sequence encoding a polypeptide with FVIII activity, wherein the nucleotide sequence comprises a nucleic acid sequence comprising SEQ ID NO: 72.

9. A vector comprising the nucleic acid molecule of claim 8.

10. The vector of claim 9, wherein the vector is a lentiviral vector.

11. A method of increasing expression of a polypeptide with FVIII activity in a mammalian subject comprising administering to said subject a vector comprising the isolated nucleic acid molecule of claim 8, wherein the expression of the polypeptide is increased relative to a reference nucleic acid molecule comprising SEQ ID NO: 16 or the vector comprising the reference nucleic acid molecule.

12. A method of treating hemophilia A in a mammalian subject comprising administering to said subject a vector comprising the nucleic acid molecule of claim 8.

13. A method of treating hemophilia A in a mammalian subject comprising administering to said subject the vector of claim 10.

14. The vector of claim 5, wherein the vector is a lentiviral vector.

15. A method of treating hemophilia A in a mammalian subject comprising administering to said subject the vector of claim 14.

* * * * *

UNITED STATES PATENT AND TRADEMARK OFFICE
CERTIFICATE OF CORRECTION

| | | |
|---|---|---|
| PATENT NO. | : 11,753,461 B2 | Page 1 of 1 |
| APPLICATION NO. | : 16/074729 | |
| DATED | : September 12, 2023 | |
| INVENTOR(S) | : Tan et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 768 days.

Signed and Sealed this
First Day of July, 2025

Coke Morgan Stewart
*Acting Director of the United States Patent and Trademark Office*

SEQUENCE LISTING

```
<160> NUMBER OF SEQ ID NOS: 103

<210> SEQ ID NO 1
<211> LENGTH: 4374
<212> TYPE: DNA
<213> ORGANISM: Artificial Sequence
<220> FEATURE:
<223> OTHER INFORMATION: coFVIII-5

<400> SEQUENCE: 1
```

```
atgcaaatcg aactgagcac ctgtttcttc ctctgcctgc tgagattctg tttctccgcg      60
acccgccgat actacctggg agcagtggag ctctcctggg attacatgca gagcgacctt     120
ggggagctgc ccgtggatgc caggttccct ccccgggtgc caaagtcgtt ccgttcaac      180
acctccgtgg tgtacaagaa aactctgttc gtggagttca ccgaccacct gttcaatatc     240
gccaagccca gacctccctg gatggggctg ttgggaccta ccatccaagc ggaggtgtac     300
gacactgtgg tcatcactct gaagaacatg gcctcgcatc ccgtgtccct gcacgccgtg     360
ggagtgtctt actggaaagc gtccgagggg gccgaatacg acgaccagac ctcgcagaga     420
gaaaaggaag atgacaaggt gttcccagga ggatcgcaca cctacgtgtg gcaagtgttg     480
aaggagaacg gcccaatggc ctccgacccg ctgtgcctga cctactcgta cctgtcccac     540
gtggacctcg tgaaggacct caactcggga ctgattggag ccctgctggt ctgcagggaa     600
ggctcactgg cgaaagaaaa gactcagacc ttgcacaagt tcattctgct gttcgctgtg     660
ttcgacgagg ggaagtcgtg gcacagcgag actaagaact ccctgatgca agatagagat     720
gccgcctccg cccgggcctg gcctaagatg cacaccgtga acggttacgt gaaccgctcc     780
ctccctggcc tgattggatg ccaccggaag tccgtgtact ggcacgtgat cgggatgggg     840
accacccccg aggtgcacag catcttcctg gaaggtcaca catttctcgt gcgcaaccac     900
cggcaggcct ccctggaaat cagccccatt accttcctca ctgcccagac tctgctgatg     960
gacctgggac agttcctgct gttctgccat atctcctccc ccaacatga cggaatggag    1020
gcatacgtga aggtcgattc ctgccctgag gaaccccagc tccgcatgaa gaacaatgag    1080
gaagccgagg actacgacga cgacctgacg gatagcgaga tggatgtggt ccggttcgat    1140
gacgataaca gcccttcctt catccaaatt cgctcggtgg caaagaagca ccccaagacc    1200
tgggtgcatt acattgcggc ggaagaagag gactgggatt atgccccgct tgtcctcgct    1260
cctgacgacc ggagctacaa gagccagtac ctgaacaacg gtccacagag gatcggtaga    1320
aagtacaaga aggtccgctt catggcctat accgacgaaa ccttcaaaac tagagaggcc    1380
atccaacacg aatccggcat cctgggcccg ctcttgtacg agaagtcgg cgacacccttt   1440
ctcattatct tcaagaacca ggcttcccgg ccgtacaaca tctatccgca tgggatcact    1500
gacgtgcgcc cactgtactc gcggcgcctg cccaagggtg tcaaacacct gaaggatttt    1560
ccgatccttc cgggagaaat cttcaagtac aagtggaccg tgaccgtgga agatggccca    1620
actaagtctg accctagatg cctcacccgc tactactcat ccttcgtcaa catggagcgc    1680
gacctggcca gcggactgat cggcccgctg ctgatttgct acaaggaatc agtgaccaa    1740
cggggaaacc agatcatgtc ggataagagg aacgtcatcc tcttctccgt gtttgacgaa    1800
aaccggtcgt ggtacctgac tgaaaacatc cagcggttcc tccccaaccc cgcgggcgtg    1860
cagctggaag atcctgagtt tcaggcatca acatcatgc actccattaa cggctacgtg    1920
ttcgattcgc tgcagctgag cgtgtgtctg cacgaagtgg cctactggta catcctgtcc    1980
attggtgccc agactgactt cctgtccgtg tttttctccg gctacacgtt caagcacaag    2040
atggtgtacg aggacacccct gaccctcttc cctttttccg gcgaaactgt gtttatgagc    2100
atggagaatc ccgcctgtg gatcttgggc tgccacaaca gcgacttccg taacagagga    2160
atgactgcgc tgctcaaggt gtccagctgc gacaagaaca ccggagacta ttatgaggac    2220
tcatacgagg acatctccgc ctacctcctg tccaagaata cgccattga acctcggagc    2280
ttcagccaga cccacccgt gcttaagaga catcaacggg agatcactag gaccaccctg    2340
cagtcagacc aggaggaaat cgactacgat gacaccatct cggtcgagat gaagaaggag    2400
```

```
gactttgaca tctacgacga agatgaaaac cagagcccga ggtcgttcca aaagaaaacc    2460
cgccactact ttattgctgc tgtcgagcgg ctgtgggact acggaatgtc gtcctcgccg    2520
cacgtgctcc gcaaccgagc ccagagcggc tcggtgccgc aattcaagaa ggtcgtgttc    2580
caggagttca ctgacgggag cttcactcag cctttgtacc ggggagaact caatgaacat    2640
ctcggcctcc tcggacctta catcagagca gaagtggaag ataacatcat ggtcactttc    2700
cgtaaccaag ccagccgccc gtactcgttc tactcctccc tcatttctta cgaagaggac    2760
cagcggcagg gcgcagaacc gcgcaagaac ttcgtgaagc ccaacgaaac caagacctac    2820
ttctggaaag tgcagcatca tatggccccg actaaggacg agtttgactg caaagcctgg    2880
gcctacttct ccgatgtgga cttggagaag gacgtccact ccggcctcat cggtcccctg    2940
ctcgtgtgcc ataccaatac cctgaacccc gcacacggtc gccaggtcac cgtgcaggag    3000
ttcgctctgt tcttcactat cttcgacgaa actaagtcct ggtacttcac cgagaacatg    3060
gagaggaact gcagagcccc ctgtaacatc cagatggagg acccgacgtt caaggaaaac    3120
taccggttcc acgccattaa cggatacatc atggatacgc tgccgggtct tgtgatggcc    3180
caggatcaac ggatcagatg gtacttattg tcgatgggca gcaacgagaa catccactct    3240
attcacttct ccggtcatgt gttcactgtg cggaagaagg aagagtacaa gatggccctg    3300
tacaaccttt atcccggagt gttcgaaact gtggaaatgc tgccgtcgaa ggccggcatt    3360
tggcgcgtgg agtgtttgat tggagaacat ctccatgcgg ggatgtcaac cctgttcctg    3420
gtgtatagca acaagtgcca gactccgctt gggatggcgt caggacacat tagggatttc    3480
cagatcactg cgtccggcca gtacggccaa tgggccccta agctggcccg cctgcattac    3540
tccggatcca ttaacgcctg gtcaaccaag gagccattct cctggatcaa ggtggacctt    3600
ctggccccca tgattatcca cggaattaag acccaggggg cccggcagaa gttctcctca    3660
ctgtacatca gccagttcat aatcatgtac tccctggacg gaaagaagtg gcaaacctac    3720 aggggggaaca gcaccggcac actgatggtc tttttcggaa atgtggactc ctccgggatt    3780
aagcataaca tcttcaaccc tccgattatc gctcggtaca ttagacttca ccctacccac    3840
tacagcattc gctccaccct gcggatggaa ctgatgggct cgatctgaa ctcgtgcagc    3900 atgccgttgg gaatggagtc caaagcaatt tccgacgcgc agatcaccgc ctcgtcctac    3960
tttaccaaca tgttcgccac gtggtcaccg tccaaggccc ggctgcacct ccagggaaga    4020
tccaacgcat ggcggccaca ggtcaacaac cctaaggagt ggctccaggt ggacttccag    4080
aaaaccatga aggtcaccgg agtcacaacc cagggagtga agtcgctgct gacttctatg    4140
tacgtcaagg agttcctgat ctccagcagc caggacgggc accagtggac cctgttcttc    4200
caaaatggaa aggtcaaggt gtttcagggc aatcaggatt cattcacccc ggtggtgaac    4260
tcccttgatc caccgctcct gacccgctac cttcgcatcc acccacagtc ctgggtgcac    4320
cagatcgcgc tgaggatgga ggtcctggga tgcgaagccc aggacctgta ctga          4374
```

<210> SEQ ID NO 2
<211> LENGTH: 4374
<212> TYPE: DNA
<213> ORGANISM: Artificial Sequence
<220> FEATURE:
<223> OTHER INFORMATION: coFVIII-4

<400> SEQUENCE: 2

```
atgcagatcg agctgagcac gtgcttcttc ctgtgcctgc tgaggttctg cttcagcgcc      60
```

```
accaggaggt actacctggg cgccgtggag ctgagctggg actacatgca gagcgacctg    120
ggcgagctgc ccgtggacgc caggttcccc cccagggtgc ccaagagctt cccttcaac     180 acgagcgtgg tgtacaagaa gaccctgttc gtggagttca ccgaccatct gttcaatatc    240
gccaagccca ggcccccctg gatggggctg ctggggccca cgatccaggc cgaggtgtac    300
gacaccgtgg tcatcaccct gaagaacatg gccagccacc ccgtgagcct gcacgccgtg    360
ggcgtgagct actggaaggc cagcgagggc gccgagtacg acgaccagac cagccagagg    420
gagaaggagg acgacaaggt gttccccggc ggcagccaca cctacgtgtg gcaggtgctg    480
aaggagaatg ggcccatggc cagcgacccc ctgtgcctga cctactctta cctgagccac    540
gtggatctgg tgaaggacct gaacagcggc ctgatcggcg ccctgctggt gtgcagggag    600
ggcagcctgg ccaaggagaa gacccagacc ctgcacaagt tcatcctgct gttcgccgtg    660
ttcgacgagg gcaagagctg gcacagcgag accaagaaca gcctgatgca ggataggagc    720
gccgccagcg ccagggcctg gcccaagatg cacaccgtga acggctacgt gaacaggtct    780
ctgcccggcc tgatcggctg ccacaggaag agcgtgtact ggcacgtgat cggcatgggg    840
accacccccg aggtgcacag catcttcctg gagggccaca cgttcctggt gaggaatcac    900
aggcaggcca gcctggagat cagcccgatc accttcctga ccgcccagac cctgctgatg    960
gacctggggc agttcctgct gttctgccat atcagctctc accagcacga cggcatggag   1020
gcctacgtga aggtggatag ctgccccgag gagccccagc tgaggatgaa gaacaacgag   1080
gaggccgagg actacgacga cgacctgacc gacagcgaga tggacgtggt gaggttcgac   1140
gacgacaata gcccgagctt catccagatc aggagcgtgg ccaagaagca ccccaagacc   1200
tgggtgcatt acatcgccgc cgaggaggag gattgggact acgccccct ggtgctggcc    1260 cccgacgaca ggtcttacaa gagccagtac ctgaacaacg ggccccagag gatcggcagg   1320
aagtacaaga aggtgaggtt catggcctac accgacgaga ccttcaagac cagggaggcg   1380
atccagcacg agagcgggat cctgggggcc ctgctgtacg cgaggtgggg cgacacgctg   1440
ctgatcatct tcaagaacca ggccagcagg ccgtacaata tctacccca cgggatcacc    1500 gacgtgaggc ccctgtactc taggaggctg cccaagggcg tgaagcacct gaaggacttc   1560
cccatcctgc ccggcgagat cttcaagtac aagtggaccg tgaccgtgga ggacgggccc   1620
acgaagagcg accccaggtg cctgaccagg tactacagcc ttttcgtgaa catggagagg   1680
gacctggcca gcggcctgat cgggcccctg ctgatctgct acaaggagag cgtggatcag   1740 agggggcaacc agatcatgag cgacaagagg aacgtgatcc tgttcagcgt gttcgacgag   1800
aataggtctt ggtacctgac cgagaatatc cagaggttcc tgcccaaccc cgccggcgtg   1860
cagctggagg atcccgagtt ccaggccagc aacatcatgc acagcatcaa cggctacgtg   1920
ttcgacagcc tgcagctgag cgtgtgcctg cacgaggtgg cctactggta catcctgagc   1980 atcgcgccc agaccgactt cctgagcgtg ttcttcagcg gctacacctt caagcacaag   2040
atggtgtacg aggataccct gaccctgttc cccttcagcg cgagaccgt gttcatgagc    2100 atggagaacc ccggcctgtg gatcctgggc tgccataact ccgacttcag gaataggggc   2160
atgaccgccc tgctgaaggt gagctcttgc gacaagaaca ccggcgacta ctacgaggat   2220
agctacgagg atatcagcgc ctacctgctg agcaagaaca acgccatcga gcccaggtct   2280
ttcagccaga accccccgt gctgaagagg caccagaggg agatcaccag gacgaccctg   2340
cagagcgacc aggaggagat cgactacgac gacacgatca gcgtggagat gaagaaggag   2400
gatttcgaca tctacgacga ggacgagaat cagagcccca ggtctttcca gaagaagacc   2460
```

```
aggcattact tcatcgccgc cgtggagagg ctgtgggact acggcatgag cagctctccc    2520
cacgtgctga ggaatagggc ccagagcggc agcgtgcccc agttcaagaa ggtggtgttc    2580
caggagttca ccgacggcag cttcacccag cccctgtaca ggggcgagct gaacgagcac    2640
ctgggcctgc tggggcccta catcagggcc gaggtggagg ataacatcat ggtgaccttc    2700
aggaatcagg ccagcaggcc ctatagcttc tatagctctc tgatcagcta cgaggaggat    2760
cagaggcagg gcgccgagcc caggaagaac ttcgtgaagc ccaacgagac caagacctac    2820
ttctggaagg tgcagcacca catggccccc acgaaggacg agttcgactg caaggcctgg    2880
gcctacttca gcgacgtgga tctggagaag acgtgcaca cggcctgat cgggcccctg    2940 ctggtgtgcc acaccaacac cctgaacccc gcccacggca ggcaggtgac cgtgcaggag    3000
ttcgccctgt tcttcaccat cttcgacgag accaagagct ggtacttcac cgagaatatg    3060
gagaggaatt gcagggcccc ctgcaatatc cagatggagg acccgacctt caaggagaat    3120
tacaggttcc acgccatcaa cggctacatc atggacacgc tgcccggcct ggtcatggcc    3180
caggatcaga ggatcaggtg gtatctgctg agcatgggga gcaacgagaa tatccacagc    3240
atccacttca gcggccacgt gttcaccgtg aggaagaagg aggagtacaa gatgcccctg    3300
tacaatctgt accccggcgt gttcgagacc gtggagatgc tgcccagcaa ggccgggatc    3360
tggagggtgg agtgcctgat cggcgagcac ctgcacgccg gcatgagcac gctgttcctg    3420
gtgtactcta acaagtgcca gacccccctg gggatggcca gcggccacat cagggacttc    3480
cagatcaccg ccagcggcca gtacggccag tgggcccca agctggccag gctgcactat    3540
tccggaagca tcaacgcctg gagcacgaag gagcccttca gctggatcaa ggtggatctg    3600 ctggcccca tgatcatcca cgggatcaag acccagggcg ccaggcagaa gttcagctct    3660
ctgtatatca gccagttcat catcatgtac tctctggacg gcaagaagtg gcagacctac    3720
aggggcaaca gcaccggcac gctgatggtg ttcttcggca acgtggactc tagcgggatc    3780
aagcacaata tcttcaaccc ccccatcatc gccaggtaca tcaggctgca ccccacccat    3840
tactctatca ggtctaccct gaggatggag ctgatgggct gcgacctgaa cagctgcagc    3900
atgcccctgg ggatggagag caaggccatc agcgacgccc agatcaccgc cagctcttac    3960
ttcaccaaca tgttcgccac ctggagcccg agcaaggcca ggctgcacct gcagggcagg    4020
tctaacgcct ggaggcccca ggtgaacaac cccaaggagt ggctgcaggt ggatttccag    4080
aagaccatga aggtgaccgg cgtgaccacg cagggcgtga gagcctgct gaccagcatg    4140 tacgtgaagg agttcctgat cagctctagc caggacggcc accagtggac cctgttcttc    4200
cagaacggca aggtgaaggt gttccagggc aaccaggata gcttcacccc cgtggtgaac    4260
agcctggacc ccccccctgct gaccaggtat ctgaggatcc accccagag ctgggtgcac    4320 cagatcgccc tgaggatgga ggtgctgggc tgcgaggccc aggatctgta ttga           4374
```

<210> SEQ ID NO 3
<211> LENGTH: 4374
<212> TYPE: DNA
<213> ORGANISM: Artificial Sequence
<220> FEATURE:
<223> OTHER INFORMATION: coFVIII-52

<400> SEQUENCE: 3

```
atgcaaatcg aactgagcac ctgtttcttc ctctgcctgc tgagattctg tttctccgcg     60
acccgccgat actacctggg agcagtggag ctctcctggg attacatgca gagcgacctt    120
```

-continued

```
ggggagctgc cgtggatgc caggttccct cccgggtgc caaagtcgtt tccgttcaac      180
acctccgtgg tgtacaagaa aactctgttc gtggagttca ccgaccacct gttcaatatc    240
gccaagccca gacctccctg gatggggctg ttgggaccta ccatccaagc ggaggtgtac    300
gacactgtgg tcatcactct gaagaacatg gcctcgcatc ccgtgtccct gcacgccgtg    360
ggagtgtctt actggaaagc gtccgagggg gccgaatacg acgaccagac ctcgcagaga    420
gaaaaggaag atgacaaggt gttcccagga ggatcgcaca cctacgtgtg gcaagtgttg    480
aaggagaacg gcccaatggc ctccgacccg ctgtgcctga cctactcgta cctgtcccac    540
gtggacctcg tgaaggacct caactcggga ctgattggag ccctgctggt ctgcagggaa    600
ggctcactgg cgaaagaaaa gactcagacc ttgcacaagt tcattctgct gttcgctgtg    660
ttcgacgagg ggaagtcgtg gcacagcgag actaagaact ccctgatgca agatagagat    720
gccgcctccg cccgggcctg gcctaagatg cacaccgtga acggttacgt gaaccgctcc    780
ctccctggcc tgattggatg ccaccggaag tccgtgtact ggcacgtgat cgggatgggg    840
accacccccg aggtgcacag catcttcctg gaaggtcaca catttctcgt gcgcaaccac    900
cggcaggcct ccctggaaat cagccccatt accttcctca ctgcccagac tctgctgatg    960
gacctgggac agttcctgct gttctgccat atctcctccc accaacatga cggaatggaa    1020
gcatacgtga aggtcgattc ctgccctgag gaaccccagc tccgcatgaa gaacaatgag    1080
gaagccgagg actacgacga cgacctgacg gatagcgaga tggatgtggt ccggttcgat    1140
gacgataaca gcccttcctt catccaaatt cgctcggtgg caaagaagca ccccaagacc    1200
tgggtgcatt acattgcggc ggaagaagag gactgggatt atgccccgct tgtcctcgct    1260
cctgacgacc ggagctacaa gagccagtac ctgaacaacg gtccacagag gatcggtaga    1320
aagtacaaga aggtccgctt catggcctat accgacgaaa ccttcaaaac tagagaggcc    1380
atccaacacg aatccggcat cctgggcccg ctcttgtacg agaagtcgg cgacacccctt    1440
ctcattatct tcaagaacca ggcttccgg ccgtacaaca tctatccgca tgggatcact    1500
gacgtgcgcc cactgtactc gcggcgcctg cccaagggtg tcaaacacct gaaggatttt    1560
ccgatccttc cgggagaaat cttcaagtac aagtggaccg tgaccgtgga agatggccca    1620
actaagtctg accctagatg cctcacccgc tactactcat ccttcgtcaa catggagcgc    1680
gacctggcca cgggactgat cggcccgctg ctgatttgct acaaggaatc agtgaccaa    1740
cggggaaaacc agatcatgtc ggataagagg aacgtcatcc tcttctccgt gtttgacgaa    1800
aaccggtcgt ggtacctgac cgagaacatc cagaggttcc tgcccaaccc tgctggggtg    1860
cagctggagg accccgagtt ccaggccagc aacatcatgc acagcatcaa tggctacgtg    1920
ttcgacagcc tgcagctgag cgtgtgcctg cacgaggtgg cctactggta catcctgagc    1980
atcggcgccc agaccgactt cctgagcgtg ttcttctctg gctacacctt caagcacaag    2040
atggtgtatg aggacaccct gaccctgttc cccttcagcg gggagactgt cttcatgagc    2100
atggagaacc ctggcctgtg gatcctgggc tgccacaaca cgcgacttcag gaacaggggc    2160
atgactgccc tgctgaaagt ctccagctgt gacaagaaca ccggggacta ctacgaggac    2220
agctacgagg acatcagcgc ctacctgctg agcaagaaca tgccatcga gcccaggagc    2280
ttctctcaga acccccagt gctgaagagg caccagaggg agatcaccag gaccaccctg    2340
cagtctgacc aggaggagat cgactatgat gacaccatca gcgtggagat gaagaaggag    2400
gacttcgaca tctacgacga ggacgagaac cagagcccca ggagcttcca gaagaagacc    2460
aggcactact tcattgctgc tgtggagagg ctgtgggact atggcatgtc cagcagcccc    2520
```

```
catgtgctga ggaacagggc ccagtctggc agcgtgcccc agttcaagaa agtcgtgttc      2580
caggagttca ccgacggcag cttcacccag cccctgtaca gggggagct gaacgagcac       2640 ctgggcctgc tgggccccta catcagggcc gaggtggagg acaacatcat ggtgaccttc      2700
aggaaccagg ccagcaggcc ctacagcttc tacagcagcc tgatcagcta cgaggaggac      2760
cagaggcagg gggctgagcc caggaagaac tttgtgaagc ccaatgaaac caagacctac      2820
ttctggaagg tgcagcacca catggccccc accaaggacg agttcgactg caaggcctgg      2880
gcctacttct ctgacgtgga cctggagaag gacgtgcact ctggcctgat tggcccctg       2940 ctggtgtgcc acaccaacac cctgaaccct gccatggca ggcaggtgac tgtgcaggag       3000
ttcgccctgt tcttcaccat cttcgatgaa accaagagct ggtacttcac tgagaacatg      3060
gagaggaact gcagggcccc ctgcaacatc cagatggagg accccacctt caaggagaac      3120
tacaggttcc atgccatcaa tggctacatc atggacaccc tgcctggcct ggtcatggcc      3180
caggaccaga ggatcaggtg gtatctgctg agcatgggca gcaacgagaa catccacagc      3240
atccacttct ctggccacgt gttcactgtg aggaagaagg aggagtacaa gatggcctg      3300 tacaacctgt accctgggt gttcgaaacc gtggagatgc tgcccagcaa ggccggcatc      3360
tggagggtgg agtgcctgat tggggagcac ctgcacgccg gcatgagcac cctgttcctg      3420
gtgtacagca caagtgcca gaccccctg ggcatggcct ctggccacat cagggacttc     3480
cagatcactg cctctggcca gtacggccag tgggccccca gctggccag gctgcactac      3540 tccggaagca tcaatgcctg gagcaccaag gagcccttca gctggatcaa agtgaccctg      3600
ctggccccca tgatcatcca cggcatcaag acccagggg ccaggcagaa gttctccagc      3660
ctgtacatca gccagttcat catcatgtac agcctggacg gcaagaagtg gcagacctac      3720
aggggcaaca gcaccggcac cctgatggtg ttcttcggca acgtggacag cagcggcatc      3780
aagcacaaca tcttcaaccc ccccatcatc gccagataca tcaggctgca ccccacccac      3840
tacagcatca ggagcaccct gaggatggag ctgatgggct gtgacctgaa cagctgcagc      3900
atgcccctgg gcatggagag caaggccatc tctgacgccc agatcactgc ctccagctac      3960
ttcaccaaca tgtttgccac ctggagcccc agcaaggca ggctgcacct gcagggcagg      4020
agcaatgcct ggaggcccca ggtcaacaac cccaaggagt ggctgcaggt ggacttccag      4080
aagaccatga aggtgactgg ggtgaccacc cagggggtga agagcctgct gaccagcatg      4140
tacgtgaagg agttcctgat ctccagcagc caggacggcc accagtggac cctgttcttc      4200
cagaatggca aggtgaaggt gttccagggc aaccaggaca gcttcacccc tgtggtcaac      4260
agcctggacc ccccctgct gaccagatac ctgaggatcc accccagag ctgggtgcac      4320 cagatcgccc tgaggatgga ggtgctgggc tgtgaggccc aggacctgta ctga           4374
```

<210> SEQ ID NO 4
<211> LENGTH: 4374
<212> TYPE: DNA
<213> ORGANISM: Artificial Sequence
<220> FEATURE:
<223> OTHER INFORMATION: coFVIII-62

<400> SEQUENCE: 4

```
atgcagattg agctgtccac ttgtttcttc ctgtgcctcc tgcgcttctg tttctccgcc       60
actcgccggt actaccttgg agccgtggag ctttcatggg actacatgca gagcgacctg      120
ggcgaactcc ccgtggatgc cagattcccc ccccgcgtgc caaagtcctt ccccttaac      180
```

-continued

```
acctccgtgg tgtacaagaa aaccctcttt gtcgagttca ctgaccacct gttcaacatc    240
gccaagccgc gcccaccttg gatgggcctc ctgggaccga ccattcaagc tgaagtgtac    300
gacaccgtgg tgatcaccct gaagaacatg gcgtcccacc ccgtgtccct gcatgcggtc    360
ggagtgtcct actggaaggc ctccgaagga gctgagtacg acgaccagac tagccagcgg    420
gaaaaggagg acgataaagt gttcccgggc ggctcgcata cttacgtgtg gcaagtcctg    480
aaggaaaacg gacctatggc atccgatcct ctgtgcctga cttactccta cctttcccat    540
gtggacctcg tgaaggacct gaacagcggg ctgattggtg cacttctcgt gtgccgcgaa    600
ggttcgctcg ctaaggaaaa gacccagacc ctccataagt tcatccttt gttcgctgtg     660 ttcgatgaag gaaagtcatg gcattccgaa actaagaact cgctgatgca ggaccgggat    720
gccgcctcag cccgcgcctg gcctaaaatg catacagtca acggatacgt gaatcggtca    780
ctgcccgggc tcatcggttg tcacagaaag tccgtgtact ggcacgtcat cggcatgggc    840
actacgcctg aagtgcactc catcttcctg gaagggcaca ccttcctcgt gcgcaaccac    900
cgccaggcct ctctggaaat ctccccgatt acctttctga ccgcccagac tctgctcatg    960
gacctggggc agttccttct cttctgccac atctccagcc atcagcacga cggaatggag   1020
gcctacgtga aggtggactc atgcccggaa gaacctcagt gcggatgaa gaacaacgag    1080 gaggccgagg actatgacga cgatttgact gactccgaga tggacgtcgt gcggttcgat   1140
gacgacaaca gccccagctt catccagatt cgcagcgtgg ccaagaagca ccccaaaacc   1200
tgggtgcact acatcgcggc cgaggaagaa gattgggact acgcccgtt ggtgctggca    1260 cccgatgacc ggtcgtacaa gtcccagtat ctgaacaatg tccgcagcg gattggcaga    1320 aagtacaaga agtgcggtt catggcgtac actgacgaaa cgtttaagac ccgggaggcc    1380
attcaacatg agagcggcat tctgggacca ctgctgtacg agaggtcgg cgataccctg   1440 ctcatcatct tcaaaaacca ggcctcccgg ccttacaaca tctaccctca cggaatcacc    1500
gacgtgcggc cactctactc gcggcgcctg ccgaagggcg tcaagcacct gaaagacttc   1560
cctatcctgc cgggcgaaat cttcaagtat aagtggaccg tcaccgtgga ggacgggccc   1620
accaagagcg atcctaggtg tctgactcgg tactactcca gcttcgtgaa catggaacgg   1680
gacctggcat cgggactcat tggaccgctg ctgatctgct acaaagagtc ggtggatcaa   1740
cgcggcaacc agatcatgtc cgacaagcgc aacgtgatcc tgttctccgt gtttgatgaa   1800
aacagatcct ggtacctgac cgagaacatc cagaggttcc tgcccaaccc tgctggggtg    1860
cagctggagg accccgagtt ccaggccagc aacatcatgc acagcatcaa tggctacgtg   1920
ttcgacagcc tgcagctgag cgtgtgcctg cacgaggtgg cctactggta catcctgagc   1980
atcggcgccc agaccgactt cctgagcgtg ttcttctctg gctacacctt caagcacaag   2040
atggtgtatg aggacaccct gaccctgttc cccttcagcg gggagactgt cttcatgagc   2100
atggagaacc ctggcctgtg gatcctgggc tgccacaaca gcgacttcag gaacaggggc   2160
atgactgccc tgctgaaagt ctccagctgt gacaagaaca ccggggacta ctacgaggac   2220
agctacgagg acatcagcgc ctacctgctg agcaagaaca tgccatcga gcccaggagc   2280 ttctctcaga ccccccagt gctgaagagg caccagaggg agatcaccag gaccaccctg   2340
cagtctgacc aggaggagat cgactatgat gacaccatca gcgtggagat gaagaaggag   2400
gacttcgaca tctacgacga ggacgagaac cagagcccca ggagcttcca gaagaagacc   2460
aggcactact tcattgctgc tgtggagagg ctgtgggact atggcatgtc cagcagcccc   2520
catgtgctga ggaacagggc ccagtctggc agcgtgcccc agttcaagaa agtcgtgttc   2580
```

| | | | |
|---|---|---|---|
| caggagttca | ccgacggcag | cttcacccag | cccctgtaca gagggagct gaacgagcac | 2640 |
| ctgggcctgc | tgggccccta | catcagggcc | gaggtggagg acaacatcat ggtgaccttc | 2700 |
| aggaaccagg | ccagcaggcc | ctacagcttc | tacagcagcc tgatcagcta cgaggaggac | 2760 |
| cagaggcagg | gggctgagcc | caggaagaac | tttgtgaagc ccaatgaaac caagacctac | 2820 |
| ttctggaagg | tgcagcacca | catggccccc | accaaggacg agttcgactg caaggcctgg | 2880 |
| gcctacttct | ctgacgtgga | cctggagaag | gacgtgcact ctggcctgat ggccccctg | 2940 |
| ctggtgtgcc | acaccaacac | cctgaaccct | gcccatggca ggcaggtgac tgtgcaggag | 3000 |
| ttcgccctgt | tcttcaccat | cttcgatgaa | accaagagct ggtacttcac tgagaacatg | 3060 |
| gagaggaact | gcagggcccc | ctgcaacatc | cagatggagg accccacctt caaggagaac | 3120 |
| tacaggttcc | atgccatcaa | tggctacatc | atggacaccc tgcctggcct ggtcatggcc | 3180 |
| caggaccaga | ggatcaggtg | gtatctgctg | agcatgggca gcaacgagaa catccacagc | 3240 |
| atccacttct | ctggccacgt | gttcactgtg | aggaagaagg aggagtacaa gatggccctg | 3300 |
| tacaacctgt | accctgggt  | gttcgaaacc | gtggagatgc tgcccagcaa ggccggcatc | 3360 |
| tggagggtgg | agtgcctgat | tggggagcac | ctgcacgccg gcatgagcac cctgttcctg | 3420 |
| gtgtacagca | acaagtgcca | gacccccctg | ggcatggcct ctggccacat cagggacttc | 3480 |
| cagatcactg | cctctggcca | gtacggccag | tgggcccca agctggccag gctgcactac | 3540 |
| tccggaagca | tcaatgcctg | gagcaccaag | gagcccttca gctggatcaa agtggacctg | 3600 |
| ctggccccca | tgatcatcca | cggcatcaag | acccagggg  ccaggcagaa gttctccagc | 3660 |
| ctgtacatca | gccagttcat | catcatgtac | agcctggacg gcaagaagtg gcagacctac | 3720 |
| aggggcaaca | gcaccggcac | cctgatggtg | ttcttcggca cgtggacag cagcggcatc | 3780 |
| aagcacaaca | tcttcaaccc | cccatcatc  | gccagataca tcaggctgca ccccacccac | 3840 |
| tacagcatca | ggagcaccct | gaggatggag | ctgatgggct gtgacctgaa cagctgcagc | 3900 |
| atgcccctgg | gcatggagag | caaggccatc | tctgacgccc agatcactgc ctccagctac | 3960 |
| ttcaccaaca | tgtttgccac | ctggagcccc | agcaaggcca ggctgcacct gcagggcagg | 4020 |
| agcaatgcct | ggaggcccca | ggtcaacaac | cccaaggagt ggctgcaggt ggacttccag | 4080 |
| aagaccatga | aggtgactgg | ggtgaccacc | caggggtga agagcctgct gaccagcatg | 4140 |
| tacgtgaagg | agttcctgat | ctccagcagc | caggacggcc accagtggac cctgttcttc | 4200 |
| cagaatggca | aggtgaaggt | gttccagggc | aaccaggaca gcttcacccc tgtggtcaac | 4260 |
| agcctggacc | ccccctgct  | gaccagatac | ctgaggatcc accccagag ctgggtgcac | 4320 |
| cagatcgccc | tgaggatgga | ggtgctgggc | tgtgaggccc aggacctgta ctga | 4374 |

<210> SEQ ID NO 5
<211> LENGTH: 4374
<212> TYPE: DNA
<213> ORGANISM: Artificial Sequence
<220> FEATURE:
<223> OTHER INFORMATION: coFVIII-25

<400> SEQUENCE: 5

| | | | |
|---|---|---|---|
| atgcagattg | agctgagcac | ctgcttcttc | ctgtgcctgc tgaggttctg cttctctgcc | 60 |
| accaggagat | actacctggg | cgccgtggag | ctgagctggg actacatgca gtctgacctg | 120 |
| ggcgagctgc | cagtggacgc | caggttcccc | ccagagtgc ccaagagctt cccccttcaac | 180 |
| accagcgtgg | tgtacaagaa | gaccctgttc | gtggagttca ctgaccacct gttcaacatc | 240 |

| | |
|---|---|
| gccaagccca ggccccctg atgggcctg ctgggcccca ccatccaggc cgaggtgtac | 300 |
| gacaccgtgg tcatcaccct gaagaacatg gccagccacc ccgtctccct gcacgccgtg | 360 |
| ggggtgagct actggaaggc ctctgagggc gccgagtacg acgaccagac cagccagagg | 420 |
| gagaaggagg acgacaaggt gttccctggg ggcagccaca cctacgtgtg gcaggtcctg | 480 |
| aaggagaacg gccccatggc ctctgacccc ctgtgcctga cctacagcta cctgagccac | 540 |
| gtggacctgg tgaaggacct gaactctggc ctgattgggg ccctgctggt gtgcagggag | 600 |
| ggcagcctgg ccaaggagaa gacccagacc ctgcacaagt tcatcctgct gttcgccgtg | 660 |
| ttcgacgagg gcaagagctg gcactctgaa accaagaaca gcctgatgca ggacagggac | 720 |
| gccgcctctg ccagggcctg gcccaagatg cacaccgtca acggctacgt caacaggagc | 780 |
| ctgcctggcc tgattggctg ccacaggaag agcgtgtact ggcatgtgat cggcatgggc | 840 |
| accacccctg aggtgcacag catcttcctg gagggccaca ccttcctggt caggaaccac | 900 |
| aggcaggcca gcctggagat cagccccatc accttcctga ccgcccagac cctgctgatg | 960 |
| gacctgggcc agttcctgct gttctgccac atctccagcc accagcacga cggcatggag | 1020 |
| gcctacgtga agtggacagc tgccctgag gagccccagc tgaggatgaa gaacaacgag | 1080 |
| gaggccgagg actatgatga cgacctgacc gacagcgaga tggacgtggt caggttcgac | 1140 |
| gacgacaaca gccccagctt catccagatc aggagcgtgg ccaagaagca ccccaagacc | 1200 |
| tgggtgcact acatcgctgc tgaggaggag gactgggact atgcccccct ggtgctggcc | 1260 |
| cctgatgaca ggagctacaa gagccagtac ctgaacaatg gcccccagag gattggcagg | 1320 |
| aagtacaaga agtcaggtt catggcctac actgatgaaa ccttcaagac cagggaggcc | 1380 |
| atccagcatg agtctggcat cctgggcccc ctgctgtacg ggaggtggg ggacaccctg | 1440 |
| ctgatcatct tcaagaacca ggccagcagg ccctacaaca tctaccccca tggcatcacc | 1500 |
| gacgtgaggc ccctgtacag caggaggctg cctaagggg tgaagcacct gaaagacttc | 1560 |
| cccatcctgc ctggggagat cttcaagtac aagtggactg tgactgtgga ggacggcccc | 1620 |
| accaagagcg accccaggtg cctgaccaga tactacagca gcttcgtcaa catggagagg | 1680 |
| gacctggcct ctggcctgat tggccccctg ctgatctgct acaaggagtc tgtggaccag | 1740 |
| aggggcaacc agatcatgag cgacaagagg aacgtgatcc tgttctctgt cttcgacgag | 1800 |
| aacaggagct ggtacctgac tgaaaacatc cagcggttcc tccccaaccc cgcgggcgtg | 1860 |
| cagctggaag atcctgagtt tcaggcatca acatcatgc actccattaa cggctacgtg | 1920 |
| ttcgattcgc tgcagctgag cgtgtgtctg cacgaagtgg cctactggta catcctgtcc | 1980 |
| attggtgccc agactgactt cctgtccgtg ttttttctccg gctacacgtt caagcacaag | 2040 |
| atggtgtacg aggacaccct gacctcttc cctttttccg gcgaaactgt gtttatgagc | 2100 |
| atggagaatc ccggcctgtg gatcttgggc tgccacaaca gcgacttccg taacagagga | 2160 |
| atgactgcgc tgctcaaggt gtccagctgc gacaagaaca ccggagacta ttatgaggac | 2220 |
| tcatacgagg acatctccgc ctacctcctg tccaagaata cgccattga acctcggagc | 2280 |
| ttcagccaga acccacccgt gcttaagaga catcaacggg agatcactag gaccaccctg | 2340 |
| cagtcagacc aggaggaaat cgactacgat gacaccatct cggtcgagat gaagaaggag | 2400 |
| gactttgaca tctacgacga agatgaaaac cagagcccga ggtcgttcca aaagaaaacc | 2460 |
| cgccactact ttattgctgc tgtcgagcgg ctgtgggact acggaatgtc gtcctcgccg | 2520 |
| cacgtgctcc gcaaccgagc ccagagcggc tcggtgccgc aattcaagaa ggtcgtgttc | 2580 |
| caggagttca ctgacgggag cttcactcag cctttgtacc ggggagaact caatgaacat | 2640 |

```
ctcggcctcc tcggacctta catcagagca gaagtggaag ataacatcat ggtcactttc    2700
cgtaaccaag ccagccgccc gtactcgttc tactcctccc tcatttctta cgaagaggac    2760
cagcggcagg gcgcagaacc gcgcaagaac ttcgtgaagc ccaacgaaac caagacctac    2820
ttctggaaag tgcagcatca tatggccccg actaaggacg agtttgactg caaagcctgg    2880
gcctacttct ccgatgtgga cttggagaag gacgtccact ccggcctcat cggtcccctg    2940
ctcgtgtgcc ataccaatac cctgaacccc gcacacggtc gccaggtcac cgtgcaggag    3000
ttcgctctgt tcttcactat cttcgacgaa actaagtcct ggtacttcac cgagaacatg    3060
gagaggaact gcagagcccc ctgtaacatc cagatggagg acccgacgtt caaggaaaac    3120
taccggttcc acgccattaa cggatacatc atggatacgc tgccgggtct tgtgatggcc    3180
caggatcaac ggatcagatg gtacttattg tcgatgggca gcaacgagaa catccactct    3240
attcacttct ccggtcatgt gttcactgtg cggaagaagg aagagtacaa gatggccctg    3300
tacaaccttt atcccggagt gttcgaaact gtggaaatgc tgccgtcgaa ggccggcatt    3360
tggcgcgtgg agtgtttgat tggagaacat ctccatgcgg ggatgtcaac cctgttcctg    3420
gtgtatagca acaagtgcca gactccgctt gggatggcgt caggacacat tagggatttc    3480
cagatcactg cgtccggcca gtacggccaa tgggcccctta agctggcccg cctgcattac    3540
tccggatcca ttaacgcctg gtcaaccaag gagccattct cctggatcaa ggtgaccttt    3600
ctggccccca tgattatcca cggaattaag acccaggggg cccggcagaa gttctcctca    3660
ctgtacatca gccagttcat aatcatgtac tccctggacg gaaagaagtg gcaaacctac    3720 aggggggaaca gcaccggcac actgatggtc tttttcggaa atgtggactc ctccgggatt    3780
aagcataaca tcttcaaccc tccgattatc gctcggtaca ttagacttca ccctacccac    3840
tacagcattc gctccaccct gcggatggaa ctgatgggct gcgatctgaa ctcgtgcagc    3900
atgccgttgg gaatggagtc caaagcaatt tccgacgcgc agatcaccgc ctcgtcctac    3960
tttaccaaca tgttcgccac gtggtcaccg tccaaggccc ggctgcacct ccagggaaga    4020
tccaacgcat ggcggccaca ggtcaacaac cctaaggagt ggctccaggt ggacttccag    4080
aaaaccatga aggtcaccgg agtcacaacc cagggagtga agtcgctgct gacttctatg    4140
tacgtcaagg agttcctgat ctccagcagc caggacgggc accagtggac cctgttcttc    4200
caaaatggaa aggtcaaggt gttcagggc aatcaggatt cattcacccc ggtggtgaac    4260
tcccttgatc caccccctcct gacccgctac cttcgcatcc acccacagtc ctgggtgcac    4320
cagatcgcgc tgaggatgga ggtcctggga tgcgaagccc aggacctgta ctga          4374
```

<210> SEQ ID NO 6
<211> LENGTH: 4374
<212> TYPE: DNA
<213> ORGANISM: Artificial Sequence
<220> FEATURE:
<223> OTHER INFORMATION: coFVIII-26

<400> SEQUENCE: 6

```
atgcagattg agctgagcac ctgcttcttc ctgtgcctgc tgaggttctg cttctctgcc      60
accaggagat actacctggg cgccgtggag ctgagctggg actacatgca gtctgacctg     120
ggcgagctgc cagtggacgc caggttcccc cccagagtgc caagagcttt cccctttcaac    180 accagcgtgg tgtacaagaa gaccctgttc gtggagttca ctgaccacct gttcaacatc     240
gccaagccca ggccccccctg gatgggcctg ctgggccccca ccatccaggc cgaggtgtac     300
```

```
gacaccgtgg tcatcaccct gaagaacatg gccagccacc ccgtctccct gcacgccgtg      360
ggggtgagct actggaaggc ctctgagggc gccgagtacg acgaccagac cagccagagg      420
gagaaggagg acgacaaggt gttccctggg ggcagccaca cctacgtgtg gcaggtcctg      480
aaggagaacg gccccatggc ctctgacccc ctgtgcctga cctacagcta cctgagccac      540
gtggacctgg tgaaggacct gaactctggc ctgattgggg ccctgctggt gtgcagggag      600
ggcagcctgg ccaaggagaa gacccagacc ctgcacaagt tcatcctgct gttcgccgtg      660
ttcgacgagg gcaagagctg gcactctgaa accaagaaca gcctgatgca ggacagggac      720
gccgcctctg ccagggcctg gcccaagatg cacaccgtca acggctacgt caacaggagc      780
ctgcctggcc tgattggctg ccacaggaag agcgtgtact ggcatgtgat cggcatgggc      840
accacccctg aggtgcacag catcttcctg gagggccaca ccttcctggt caggaaccac      900
aggcaggcca gcctggagat cagccccatc accttcctga ccgcccagac cctgctgatg      960
gacctgggcc agttcctgct gttctgccac atctccagcc accagcacga cggcatggag     1020
gcctacgtga agtggacagc tgccctgag gagcccagc tgaggatgaa gaacaacgag     1080
gaggccgagg actatgatga cgacctgacc gacagcgaga tggacgtggt caggttcgac     1140
gacgacaaca gccccagctt catccagatc aggagcgtgg ccaagaagca ccccaagacc     1200
tgggtgcact acatcgctgc tgaggaggag gactgggact atgccccct ggtgctggcc     1260
cctgatgaca ggagctacaa gagccagtac ctgaacaatg gccccagag gattggcagg     1320
aagtacaaga agtcaggtt catggcctac actgatgaaa ccttcaagac cagggaggcc     1380
atccagcatg agtctggcat cctgggcccc tgctgtacg ggaggtggg ggacaccctg     1440
ctgatcatct tcaagaacca ggccagcagg ccctacaaca tctaccccca tggcatcacc     1500
gacgtgaggc ccctgtacag caggaggctg cctaaggggg tgaagcacct gaaagacttc     1560
cccatcctgc ctggggagat cttcaagtac aagtggactg tgactgtgga ggacggcccc     1620
accaagagcg accccaggtg cctgaccaga tactacagca gcttcgtcaa catggagagg     1680
gacctggcct ctggcctgat tggccccctg ctgatctgct acaaggagtc tgtggaccag     1740
aggggcaacc agatcatgag cgacaagagg aacgtgatcc tgttctctgt cttcgacgag     1800
aacaggagct ggtacctcac tgaaaacatc cagaggttcc tcccaaaccc cgcaggagtg     1860
caactggagg accctgagtt tcaggcctcg aatatcatgc actcgattaa cggttacgtg     1920
ttcgactcgc tgcagctgag cgtgtgcctc catgaagtcg cttactggta cattctgtcc     1980
atcgcgccc agactgactt cctgagcgtg ttcttttccg gttacacctt taagcacaag     2040
atggtgtacg aagataccct gaccctgttc ccttcctccg gcgaaacggt gttcatgtcg     2100
atggagaacc cgggtctgtg gattctggga tgccacaaca gcgactttcg gaaccgcgga     2160
atgactgccc tgctgaaggt gtcctcatgc gacaagaaca ccggagacta ctacgaggac     2220
tcctacgagg atatctcagc ctacctcctg tccaagaaca acgcgatcga gccgcgcagc     2280
ttcagccaga acccgcctgt gctgaagagg caccagcgag aaattacccg gaccacctc     2340
caatcggatc aggaggaaat cgactacgac gacaccatct cggtggaaat gaagaaggaa     2400
gatttcgata tctacgacga ggacgaaaat cagtcccctc gctcattcca aaagaaaact     2460
agacactact ttatcgccgc ggtggaaaga ctgtgggact atggaatgtc atccagccct     2520
cacgtccttc ggaaccgggc ccagagcgga tcggtgcctc agttcaagaa agtggtgttc     2580
caggagttca ccgacggcag cttcacccag ccgctgtacc gggagaact gaacgaacac     2640
ctgggcctgc tcggtcccta catccgcgcg gaagtggagg ataacatcat ggtgaccttc     2700
```

```
cgtaaccaag catccagacc ttactccttc tattcctccc tgatctcata cgaggaggac    2760
cagcgccaag gcgccgagcc ccgcaagaac ttcgtcaagc ccaacgagac taagacctac    2820
ttctggaagg tccaacacca tatggccccg accaaggatg agtttgactg caaggcctgg    2880
gcctacttct ccgacgtgga ccttgagaag gatgtccatt ccggcctgat cgggccgctg    2940
ctcgtgtgtc acaccaacac cctgaaccca gcgcatggac gccaggtcac cgtccaggag    3000
tttgctctgt tcttcaccat ttttgacgaa actaagtcct ggtacttcac cgagaatatg    3060
gagcgaaact gtagagcgcc ctgcaatatc cagatggaag atccgacttt caaggagaac    3120
tatagattcc acgccatcaa cgggtacatc atggatactc tgccggggct ggtcatggcc    3180
caggatcaga ggattcggtg gtacttgctg tcaatgggat cgaacgaaaa cattcactcc    3240
attcacttct ccggtcacgt gttcactgtg cgcaagaagg aggagtacaa gatggcgctg    3300
tacaatctgt accccggggt gttcgaaact gtggagatgc tgccgtccaa ggccggcatc    3360
tggagagtgg agtgcctgat cggagagcac ctccacgcgg ggatgtccac cctcttcctg    3420
gtgtactcga ataagtgcca gacccccgctg gcatggcct cgggccacat cagagacttc    3480
cagatcacag caagcggaca atacggccaa tgggcgccga agctggcccg cttgcactac    3540
tccggatcga tcaacgcatg gtccaccaag gaaccgttct cgtggattaa ggtggacctc    3600
ctggccccta tgattatcca cggaattaag acccagggcg ccaggcagaa gttctcctcc    3660
ctgtacatct cgcaattcat catcatgtac agcctggacg ggaagaagtg gcagacttac    3720
agggaaaact ccaccggcac cctgatggtc ttttttcggca acgtggattc ctccggcatt    3780
aagcacaaca tcttcaaccc accgatcata gccagatata ttaggctcca ccccactcac    3840
tactcaatcc gctcaactct tcggatgaa ctcatggggt gcgacctgaa ctcctgctcc    3900
atgccgttgg ggatggaatc aaaggctatt agcgacgccc agatcaccgc gagctcctac    3960
ttcactaaca tgttcgccac ctggagcccc tccaaggcca ggctgcactt gcagggacgg    4020
tcaaatgcct ggcggccgca agtgaacaat ccgaaggaat ggcttcaagt ggatttccaa    4080
aagaccatga agtgaccgg agtcaccacc cagggagtga agtcccttct gacctcgatg    4140
tatgtgaagg agttcctgat tagcagcagc caggacgggc accagtggac cctgttcttc    4200
caaaacggaa aggtcaaggt gttccagggg aaccaggact cgttcacacc cgtggtgaac    4260
tccctggacc ccccactgct gacgcggtac ttgaggattc atcctcagtc ctgggtccat    4320
cagattgcat tgcgaatgga agtcctgggc tgcgaggccc aggacctgta ctga          4374
```

<210> SEQ ID NO 7
<211> LENGTH: 1734
<212> TYPE: DNA
<213> ORGANISM: Artificial Sequence
<220> FEATURE:
<223> OTHER INFORMATION: coFVIII-52-NT58

<400> SEQUENCE: 7

```
gcgacccgcc gatactacct gggagcagtg gagctctcct gggattacat gcagagcgac      60
cttggggagc tgcccgtgga tgccaggttc cctccccggg tgccaaagtc gtttccgttc     120
aacacctccg tggtgtacaa gaaaactctg ttcgtggagt tcaccgacca cctgttcaat     180
atcgccaagc ccagacctcc ctggatgggg ctgttgggac ctaccatcca gcggaggtg      240 tacgacactg tggtcatcac tctgaagaac atgcctcgc atcccgtgtc cctgcacgcc     300
gtgggagtgt cttactggaa agcgtccgag ggggccgaat acgacgacca gacctcgcag     360
```

| | |
|---|---|
| agagaaaagg aagatgacaa ggtgttccca ggaggatcgc acacctacgt gtggcaagtg | 420 |
| ttgaaggaga acggcccaat ggcctccgac ccgctgtgcc tgacctactc gtacctgtcc | 480 |
| cacgtggacc tcgtgaagga cctcaactcg ggactgattg gagccctgct ggtctgcagg | 540 |
| gaaggctcac tggcgaaaga aaagactcag accttgcaca agttcattct gctgttcgct | 600 |
| gtgttcgacg aggggaagtc gtggcacagc gagactaaga actccctgat gcaagataga | 660 |
| gatgccgcct ccgccgggc ctggcctaag atgcacaccg tgaacggtta cgtgaaccgc | 720 |
| tccctccctg gcctgattgg atgccaccgg aagtccgtgt actggcacgt gatcgggatg | 780 |
| gggaccaccc ccgaggtgca cagcatcttc ctggaaggtc acacatttct cgtgcgcaac | 840 |
| caccggcagg cctccctgga aatcagcccc attaccttcc tcactgccca gactctgctg | 900 |
| atggacctgg acagttcct gctgttctgc catatctcct cccaccaaca tgacggaatg | 960 |
| gaggcatacg tgaaggtcga ttcctgccct gaggaacccc agctccgcat gaagaacaat | 1020 |
| gaggaagccg aggactacga cgacgacctg acggatagcg agatggatgt ggtccggttc | 1080 |
| gatgacgata acagcccttc cttcatccaa attcgctcgg tggcaaagaa gcaccccaag | 1140 |
| acctgggtgc attacattgc ggcggaagaa gaggactggg attatgcccc gcttgtcctc | 1200 |
| gctcctgacg accggagcta caagagccag tacctgaaca acggtccaca gaggatcggt | 1260 |
| agaaagtaca gaaggtccg cttcatggcc tataccgacg aaaccttcaa aactagagag | 1320 |
| gccatccaac acgaatccgg catcctgggc ccgctcttgt acgagaagt cggcgacacc | 1380 |
| cttctcatta tcttcaagaa ccaggcttcc cggccgtaca acatctatcc gcatgggatc | 1440 |
| actgacgtgc gcccactgta ctcgcggcgc ctgcccaagg tgtcaaaca cctgaaggat | 1500 |
| tttccgatcc ttccgggaga aatcttcaag tacaagtgga ccgtgaccgt ggaagatggc | 1560 |
| ccaactaagt ctgaccctag atgcctcacc cgctactact catccttcgt caacatggag | 1620 |
| cgcgacctgg ccagcggact gatcggcccg ctgctgattt gctacaagga atcagtggac | 1680 |
| caacggggaa accagatcat gtcggataag aggaacgtca tcctcttctc cgtg | 1734 |

<210> SEQ ID NO 8
<211> LENGTH: 2583
<212> TYPE: DNA
<213> ORGANISM: Artificial Sequence
<220> FEATURE:
<223> OTHER INFORMATION: coFVIII-52-CT

<400> SEQUENCE: 8

| | |
|---|---|
| tttgacgaaa accggtcgtg gtacctgacc gagaacatcc agaggttcct gcccaaccct | 60 |
| gctggggtgc agctggagga cccccgagttc caggccagca acatcatgca cagcatcaat | 120 |
| ggctacgtgt tcgacagcct gcagctgagc gtgtgcctgc acgaggtggc ctactggtac | 180 |
| atcctgagca tcggcgccca gaccgacttc ctgagcgtgt tcttctctgg ctacaccttc | 240 |
| aagcacaaga tggtgtatga ggacaccctg accctgttcc ccttcagcgg ggagactgtc | 300 |
| ttcatgagca tggagaaccc tggcctgtgg atcctgggct gccacaacag cgacttcagg | 360 |
| aacaggggca tgactgccct gctgaaagtc tccagctgtg acaagaacac cggggactac | 420 |
| tacgaggaca gctacgagga catcagcgcc tacctgctga gcaagaacaa tgccatcgag | 480 |
| cccagggagct tctctcagaa ccccccagtg ctgaagaggc accagaggga tcaccagg | 540 |
| accacccctgc agtctgacca ggaggagatc gactatgatg acaccatcag cgtggagatg | 600 |
| aagaaggagg acttcgacat ctacgacgag gacgagaacc agagcccag gagcttccag | 660 |
| aagaagacca ggcactactt cattgctgct gtggagaggc tgtgggacta tggcatgtcc | 720 |

```
agcagccccc atgtgctgag aacagggcc cagtctggca gcgtgcccca gttcaagaaa      780
gtcgtgttcc aggagttcac cgacggcagc ttcacccagc ccctgtacag aggggagctg      840
aacgagcacc tgggcctgct gggccccctac atcagggccg aggtggagga caacatcatg     900
gtgaccttca ggaaccaggc cagcaggccc tacagcttct acagcagcct gatcagctac      960
gaggaggacc agaggcaggg ggctgagccc aggaagaact tgtgaagcc caatgaaacc     1020 aagacctact tctggaaggt gcagcaccac atggccccca ccaaggacga gttcgactgc    1080
aaggcctggg cctacttctc tgacgtggac ctggagaagg acgtgcactc tggcctgatt     1140
ggccccctgc tggtgtgcca caccaacacc ctgaaccctg ccatggcag caggtgact      1200 gtgcaggagt tcgccctgtt cttcaccatc ttcgatgaaa ccaagagctg gtacttcact    1260
gagaacatgg agaggaactg cagggccccc tgcaacatcc agatggagga ccccaccttc    1320
aaggagaact acaggttcca tgccatcaat ggctacatca tggacaccct gcctggcctg    1380
gtcatggccc aggaccagag gatcaggtgg tatctgctga gcatgggcag caacgagaac    1440
atccacagca tccacttctc tggccacgtg ttcactgtga ggaagaagga ggagtacaag    1500
atggccctgt acaacctgta ccctggggtg ttcgaaaccg tggagatgct gcccagcaag    1560
gccggcatct ggaggtgga gtgcctgatt ggggagcacc tgcacgccgg catgagcacc    1620
ctgttcctgg tgtacagcaa caagtgccag accccctgg gcatggcctc tggccacatc    1680
agggacttcc agatcactgc ctctggccag tacggccagt gggccccaa gctggccagg    1740 ctgcactact ccggaagcat caatgcctgg agcaccaagg agcccttcag ctggatcaaa    1800
gtggacctgc tggcccccat gatcatccac ggcatcaaga cccaggggc caggcagaag    1860 ttctccagcc tgtacatcag ccagttcatc atcatgtaca gcctgacgg caagaagtgg    1920 cagacctaca ggggcaacag caccggcacc ctgatggtgt tcttcggcaa cgtggacagc    1980
agcggcatca gcacaacat cttcaaccc cccatcatcg ccagatacat caggctgcac    2040
cccacccact acagcatcag gagcaccctg aggatggagc tgatgggctg tgacctgaac    2100
agctgcagca tgcccctggg catggagagc aaggccatct ctgacgccca gatcactgcc    2160
tccagctact tcaccaacat gtttgccacc tggagcccca gcaaggccag gctgcacctg    2220
cagggcagga gcaatgcctg gaggccccag gtcaacaacc caaggagtg gctgcaggtg    2280 gacttccaga gaccatgaa ggtgactggg gtgaccaccc aggggtgaa gagcctgctg    2340 accagcatgt acgtgaagga gttcctgatc tccagcagcc aggacggcca ccagtggacc    2400
ctgttcttcc agaatggcaa ggtgaaggtg ttcagggca accaggacag cttcacccct    2460
gtggtcaaca gcctggaccc ccccctgctg accagatacc tgaggatcca cccccagagc    2520
tgggtgcacc agatcgccct gaggatggag gtgctgggct gtgaggccca ggacctgtac    2580
tga                                                                   2583
```

<210> SEQ ID NO 9
<211> LENGTH: 1734
<212> TYPE: DNA
<213> ORGANISM: Artificial Sequence
<220> FEATURE:
<223> OTHER INFORMATION: coFVIII-62-NT58

<400> SEQUENCE: 9

```
gccactcgcc ggtactacct tggagccgtg gagctttcat ggactacat gcagagcgac       60 ctgggcgaac tccccgtgga tgccagattc ccccccgcg tgccaaagtc cttcccttt      120
```

| | |
|---|---:|
| aacacctccg tggtgtacaa gaaaaccctc tttgtcgagt tcactgacca cctgttcaac | 180 |
| atcgccaagc cgcgcccacc ttggatgggc ctcctgggac cgaccattca agctgaagtg | 240 |
| tacgacaccg tggtgatcac cctgaagaac atggcgtccc accccgtgtc cctgcatgcg | 300 |
| gtcggagtgt cctactggaa ggcctccgaa ggagctgagt acgacgacca gactagccag | 360 |
| cgggaaaagg aggacgataa agtgttcccg ggcggctcgc atacttacgt gtggcaagtc | 420 |
| ctgaaggaaa acggacctat ggcatccgat cctctgtgcc tgacttactc ctacctttcc | 480 |
| catgtggacc tcgtgaagga cctgaacagc gggctgattg gtgcacttct cgtgtgccgc | 540 |
| gaaggttcgc tcgctaagga aaagacccag accctccata agttcatcct tttgttcgct | 600 |
| gtgttcgatg aaggaaagtc atggcattcc gaaactaaga actcgctgat gcaggaccgg | 660 |
| gatgccgcct cagcccgcgc ctggcctaaa atgcatacag tcaacggata cgtgaatcgg | 720 |
| tcactgcccg ggctcatcgg ttgtcacaga agtccgtgt actggcacgt catcggcatg | 780 |
| ggcactacgc ctgaagtgca ctccatcttc ctggaagggc acaccttcct cgtgcgcaac | 840 |
| caccgccagg cctctctgga aatctccccg attaccttc tgaccgccca gactctgctc | 900 |
| atggacctgg ggcagttcct tctcttctgc cacatctcca gccatcagca cgacggaatg | 960 |
| gaggcctacg tgaaggtgga ctcatgcccg gaagaacctc agttgcggat gaagaacaac | 1020 |
| gaggaggccg aggactatga cgacgatttg actgactccg agatggacgt cgtgcggttc | 1080 |
| gatgacgaca acagccccag cttcatccag attcgcagcg tggccaagaa gcaccccaaa | 1140 |
| acctgggtgc actacatcgc ggccgaggaa gaagattggg actacgcccc gttggtgctg | 1200 |
| gcacccgatg accggtcgta caagtcccag tatctgaaca atggtccgca gcggattggc | 1260 |
| agaaagtaca gaaagtgcg gttcatggcg tacactgacg aaacgtttaa gacccgggag | 1320 |
| gccattcaac atgagagcgg cattctggga ccactgctgt acgagaggt cggcgatacc | 1380 |
| ctgctcatca tcttcaaaaa ccaggcctcc cggccttaca acatctaccc tcacggaatc | 1440 |
| accgacgtgc ggccactcta ctcgcggcgc ctgccaaagg cgtcaagca cctgaaagac | 1500 |
| ttccctatcc tgccgggcga aatcttcaag tataagtgga ccgtcaccgt ggaggacggg | 1560 |
| cccaccaaga gcgatcctag gtgtctgact cggtactact ccagcttcgt gaacatggaa | 1620 |
| cgggacctgg catcgggact cattggaccg ctgctgatct gctacaaaga gtcggtggat | 1680 |
| caacgcggca accagatcat gtccgacaag cgcaacgtga tcctgttctc cgtg | 1734 |

<210> SEQ ID NO 10
<211> LENGTH: 2583
<212> TYPE: DNA
<213> ORGANISM: Artificial Sequence
<220> FEATURE:
<223> OTHER INFORMATION: coFVIII-62-CT

<400> SEQUENCE: 10

| | |
|---|---:|
| tttgatgaaa acagatcctg gtacctgacc gagaacatcc agaggttcct gcccaaccct | 60 |
| gctggggtgc agctggagga cccccgagttc caggccagca catcatgca cagcatcaat | 120 |
| ggctacgtgt cgacagcct gcagctgagc gtgtgcctgc acgaggtggc ctactggtac | 180 |
| atcctgagca tcggcgccca gaccgacttc ctgagcgtgt tcttctctgg ctacaccttc | 240 |
| aagcacaaga tggtgtatga ggacaccctg accctgttcc ccttcagcgg ggagactgtc | 300 |
| ttcatgagca tggagaaccc tggcctgtgg atcctgggct gccacaacag cgacttcagg | 360 |
| aacaggggca tgactgccct gctgaaagtc tccagctgtg acaagaacac cggggactac | 420 |
| tacgaggaca gctacgagga catcagcgcc tacctgctga gcaagaacaa tgccatcgag | 480 |

```
cccaggagct tctctcagaa cccccagtg ctgaagaggc accagaggga gatcaccagg      540
accaccctgc agtctgacca ggaggagatc gactatgatg acaccatcag cgtggagatg      600
aagaaggagg acttcgacat ctacgacgag gacgagaacc agagcccag gagcttccag       660 aagaagacca ggcactactt cattgctgct gtgagaggc tgtgggacta tggcatgtcc       720
agcagccccc atgtgctgag gaacagggcc cagtctggca gcgtgcccca gttcaagaaa     780
gtcgtgttcc aggagttcac cgacggcagc ttcacccagc ccctgtacag aggggagctg     840
aacgagcacc tgggcctgct gggcccctac atcagggccg aggtggagga caacatcatg    900
gtgaccttca ggaaccaggc cagcaggccc tacagcttct acagcagcct gatcagctac     960
gaggaggacc agaggcaggg ggctgagccc aggaagaact tgtgaagcc caatgaaacc     1020 aagacctact tctggaaggt gcagcaccac atggccccca ccaaggacga gttcgactgc   1080
aaggcctggg cctacttctc tgacgtggac ctggagaagg acgtgcactc tggcctgatt    1140
ggccccctgc tggtgtgcca caccaacacc ctgaaccctg ccatggcag gcaggtgact    1200 gtgcaggagt tcgccctgtt cttcaccatc ttcgatgaaa ccaagagctg gtacttcact    1260
gagaacatgg agaggaactg cagggccccc tgcaacatcc agatggagga ccccaccttc    1320
aaggagaact acaggttcca tgccatcaat ggctacatca tggacaccct gcctggcctg    1380
gtcatggccc aggaccagag gatcaggtgg tatctgctga gcatgggcag caacgagaac    1440
atccacagca tccacttctc tggccacgtg ttcactgtga ggaagaagga ggagtacaag   1500
atggccctgt acaacctgta ccctgggggtg ttcgaaaccg tggagatgct gcccagcaag   1560
gccggcatct ggaggggtgga gtgcctgatt ggggagcacc tgcacgccgg catgagcacc   1620
ctgttcctgg tgtacagcaa caagtgccag acccccctgg gcatggcctc tggccacatc   1680
agggacttcc agatcactgc ctctggccag tacggccagt gggcccccaa gctggccagg   1740
ctgcactact ccggaagcat caatgcctgg agcaccaagg agcccttcag ctggatcaaa    1800
gtggacctgc tggcccccat gatcatccac ggcatcaaga cccaggggc caggcagaag    1860 ttctccagcc tgtacatcag ccagttcatc atcatgtaca gcctggacgg caagaagtgg    1920
cagacctaca ggggcaacag caccggcacc ctgatggtgt tcttcggcaa cgtggacagc    1980
agcggcatca gcacaacat cttcaacccc ccatcatcg ccagatacat caggctgcac       2040
cccacccact acagcatcag gagcaccctg aggatggagc tgatgggctg tgacctgaac    2100
agctgcagca tgcccctggg catggagagc aaggccatct ctgacgccca gatcactgcc    2160
tccagctact tcaccaacat gtttgccacc tggagcccca gcaaggccag gctgcacctg    2220
cagggcagga gcaatgcctg gaggccccag gtcaacaacc ccaaggagtg gctgcaggtg    2280
gacttccaga gaccatgaa ggtgactggg gtgaccaccc aggggggtgaa gagcctgctg    2340 accagcatgt acgtgaagga gttcctgatc tccagcagcc aggacggcca ccagtggacc    2400
ctgttcttcc agaatggcaa ggtgaaggtg ttccagggca accaggacag cttcacccct   2460
gtggtcaaca gcctggaccc cccctgctg accagatacc tgaggatcca cccccagagc    2520
tgggtgcacc agatcgccct gaggatggag gtgctgggct gtgaggccca ggacctgtac    2580
tga                                                                    2583
```

<210> SEQ ID NO 11
<211> LENGTH: 1734
<212> TYPE: DNA
<213> ORGANISM: Artificial Sequence
<220> FEATURE:

<223> OTHER INFORMATION: coFVIII-25-NT58

<400> SEQUENCE: 11

| | | | | | |
|---|---|---|---|---|---|
| gccaccagga | gatactacct | gggcgccgtg | gagctgagct | gggactacat | gcagtctgac | 60 |
| ctgggcgagc | tgccagtgga | cgccaggttc | cccccagag | tgcccaagag | cttccccttc | 120 |
| aacaccagcg | tggtgtacaa | gaagaccctg | ttcgtggagt | tcactgacca | cctgttcaac | 180 |
| atcgccaagc | ccaggcccc | ctggatgggc | ctgctgggcc | ccaccatcca | ggccgaggtg | 240 |
| tacgacaccg | tggtcatcac | cctgaagaac | atggccagcc | accccgtctc | cctgcacgcc | 300 |
| gtggggtga | gctactggaa | ggcctctgag | ggcgccgagt | acgacgacca | gaccagccag | 360 |
| agggagaagg | aggacgacaa | ggtgttccct | gggggcagcc | acacctacgt | gtggcaggtc | 420 |
| ctgaaggaga | acggcccat | ggcctctgac | ccctgtgcc | tgacctacag | ctacctgagc | 480 |
| cacgtggacc | tggtgaagga | cctgaactct | ggcctgattg | ggccctgct | ggtgtgcagg | 540 |
| gagggcagcc | tggccaagga | gaagacccag | accctgcaca | agttcatcct | gctgttcgcc | 600 |
| gtgttcgacg | agggcaagag | ctggcactct | gaaaccaaga | cagcctgat | gcaggacagg | 660 |
| gacgccgcct | ctgccagggc | ctggcccaag | atgcacaccg | tcaacggcta | cgtcaacagg | 720 |
| agcctgcctg | gcctgattgg | ctgccacagg | aagagcgtgt | actggcatgt | gatcggcatg | 780 |
| ggcaccaccc | tgaggtgca | cagcatcttc | ctggagggcc | acaccttcct | ggtcaggaac | 840 |
| cacaggcagg | ccagcctgga | gatcagcccc | atcaccttcc | tgaccgccca | gaccctgctg | 900 |
| atggacctgg | gccagttcct | gctgttctgc | cacatctcca | gccaccagca | cgacggcatg | 960 |
| gaggcctacg | tgaaagtgga | cagctgccct | gaggagcccc | agctgaggat | gaagaacaac | 1020 |
| gaggaggccg | aggactatga | tgacgacctg | accgacagcg | agatggacgt | ggtcaggttc | 1080 |
| gacgacgaca | acagccccag | cttcatccag | atcaggagct | ggccaagaa | gcaccccaag | 1140 |
| acctgggtgc | actacatcgc | tgctgaggag | gaggactggg | actatgcccc | cctggtgctg | 1200 |
| gccctgatg | acaggagcta | caagagccag | tacctgaaca | atggccccca | gaggattggc | 1260 |
| aggaagtaca | agaaagtcag | gttcatggcc | tacactgatg | aaaccttcaa | gaccagggag | 1320 |
| gccatccagc | atgagtctgg | catcctgggc | cccctgctgt | acggggaggt | ggggacacc | 1380 |
| ctgctgatca | tcttcaagaa | ccaggccagc | aggccctaca | acatctaccc | catggcatc | 1440 |
| accgacgtga | ggcccctgta | cagcaggagg | ctgcctaagg | gggtgaagca | cctgaaagac | 1500 |
| ttccccatcc | tgcctgggga | gatcttcaag | tacaagtgga | ctgtgactgt | ggaggacggc | 1560 |
| cccaccaaga | gcgaccccag | gtgcctgacc | agatactaca | gcagcttcgt | caacatggag | 1620 |
| agggacctgg | cctctggcct | gattggcccc | ctgctgatct | gctacaagga | gtctgtggac | 1680 |
| cagagggggca | accagatcat | gagcgacaag | aggaacgtga | tcctgttctc | tgtc | 1734 |

<210> SEQ ID NO 12
<211> LENGTH: 2583
<212> TYPE: DNA
<213> ORGANISM: Artificial Sequence
<220> FEATURE:
<223> OTHER INFORMATION: coFVIII-25-CT

<400> SEQUENCE: 12

| | | | | | |
|---|---|---|---|---|---|
| ttcgacgaga | acaggagctg | gtacctgact | gaaaacatcc | agcggttcct | ccccaacccc | 60 |
| gcgggcgtgc | agctggaaga | tcctgagttt | caggcatcaa | acatcatgca | ctccattaac | 120 |
| ggctacgtgt | tcgattcgct | gcagctgagc | gtgtgtctgc | acgaagtggc | ctactggtac | 180 |
| atcctgtcca | ttggtgccca | gactgacttc | ctgtccgtgt | ttttctccgg | ctacacgttc | 240 |

```
aagcacaaga tggtgtacga ggacaccctg accctcttcc cttttccgg cgaaactgtg    300 tttatgagca tggagaatcc cggcctgtgg atcttgggct gccacaacag cgacttccgt    360
aacagaggaa tgactgcgct gctcaaggtg tccagctgcg acaagaacac cggagactat    420
tatgaggact catacgagga catctccgcc tacctcctgt ccaagaataa cgccattgaa    480
cctcggagct tcagccagaa cccacccgtg cttaagagac atcaacggga gatcactagg    540 accacccctgc agtcagacca ggaggaaatc gactacgatg acaccatctc ggtcgagatg    600
aagaaggagg actttgacat ctacgacgaa gatgaaaacc agagcccgag gtcgttccaa    660
aagaaaaccc gccactactt tattgctgct gtcgagcggc tgtgggacta cggaatgtcg    720
tcctcgccgc acgtgctccg caaccgagcc cagagcggct cggtgccgca attcaagaag    780
gtcgtgttcc aggagttcac tgacgggagc ttcactcagc cttttgtaccg gggagaactc    840 aatgaacatc tcggcctcct cggaccttac atcagagcag aagtggaaga taacatcatg    900
gtcactttcc gtaaccaagc cagccgcccg tactcgttct actcctccct catttcttac    960
gaagaggacc agcggcaggg cgcagaaccg cgcaagaact tcgtgaagcc caacgaaacc   1020
aagacctact tctggaaagt gcagcatcat atggccccga ctaaggacga gtttgactgc   1080
aaagcctggg cctacttctc cgatgtggac ttggagaagg acgtccactc cggcctcatc   1140
ggtcccctgc tcgtgtgcca taccaatacc ctgaaccccg cacacggtcg ccaggtcacc   1200
gtgcaggagt tcgctctgtt cttcactatc ttcgacgaaa ctaagtcctg gtacttcacc   1260
gagaacatgg agaggaactg cagagccccc tgtaacatcc agatggagga cccgacgttc   1320
aaggaaaact accggttcca cgccattaac ggatacatca tggatacgct gccgggtctt   1380
gtgatggccc aggatcaacg gatcagatgg tacttattgt cgatgggcag caacgagaac   1440
atccactcta ttcacttctc cggtcatgtg ttcactgtgc ggaagaagga agagtacaag   1500
atggccctgt acaaccttta tcccggagtg ttcgaaactg tggaaatgct gccgtcgaag   1560
gccggcattt ggcgcgtgga gtgtttgatt ggagaacatc tccatgcggg gatgtcaacc   1620
ctgttcctgg tgtatagcaa caagtgccag actccgcttg ggatggcgtc aggacacatt   1680
agggatttcc agatcactgc gtccggccag tacgccaatg ggccccctaa gctggcccgc   1740
ctgcattact ccggatccat taacgcctgg tcaaccaagg agccattctc ctggatcaag   1800
gtggaccttc tggcccccat gattatccac ggaattaaga cccaggggc ccggcagaag   1860 ttctcctcac tgtacatcag ccagttcata atcatgtact ccctggacgg aaagaagtgg   1920
caaacctaca gggggaacag caccggcaca ctgatggtct ttttcggaaa tgtggactcc   1980
tccgggatta agcataacat cttcaaccct ccgattatcg ctcggtacat tagacttcac   2040
cctacccact acagcattcg ctccaccctg cggatggaac tgatgggctg cgatctgaac   2100
tcgtgcagca tgccgttggg aatggagtcc aaagcaattt ccgacgcgca gatcaccgcc   2160
tcgtcctact ttaccaacat gttcgccacg tggtcaccgt ccaaggcccg gctgcacctc   2220
cagggaagat ccaacgcatg gcggccacag gtcaacaacc ctaaggagtg gctccaggtg   2280
gacttccaga aaaccatgaa ggtcaccgga gtcacaaccc agggagtgaa gtcgctgctg   2340
acttctatgt acgtcaagga gttcctgatc tccagcagcc aggacgggca ccagtggacc   2400
ctgttcttcc aaaatggaaa ggtcaaggtg tttcagggca atcaggattc attccccccg   2460
gtggtgaact cccttgatcc acccctcctg accgctacc ttcgcatcca cccacagtcc   2520
tgggtgcacc agatcgcgct gaggatggag gtcctgggat gcgaagccca ggacctgtac   2580
``` tga                                                                    2583

<210> SEQ ID NO 13
<211> LENGTH: 1734
<212> TYPE: DNA
<213> ORGANISM: Artificial Sequence
<220> FEATURE:
<223> OTHER INFORMATION: coFVIII-26-NT58

<400> SEQUENCE: 13

```
gccaccagga gatactacct gggcgccgtg gagctgagct gggactacat gcagtctgac      60
ctgggcgagc tgccagtgga cgccaggttc ccccccagag tgcccaagag cttccccttc     120
aacaccagcg tggtgtacaa gaagaccctg ttcgtggagt tcactgacca cctgttcaac     180
atcgccaagc ccaggccccc ctggatgggc ctgctgggcc ccaccatcca ggccgaggtg     240
tacgacaccg tggtcatcac cctgaagaac atggccagcc accccgtctc cctgcacgcc     300
gtggggtga gctactggaa ggcctctgag ggcgccgagt acgacgacca gaccagccag     360
agggagaagg aggacgacaa ggtgttccct ggggcagcc acacctacgt gtggcaggtc     420
ctgaaggaga acggcccat ggcctctgac cccctgtgcc tgacctacag ctacctgagc     480
cacgtgacc tggtgaagga cctgaactct ggcctgattg gggccctgct ggtgtgcagg     540
gagggcagcc tggccaagga gaagacccag accctgcaca gttcatcct gctgttcgcc     600
gtgttcgacg agggcaagag ctggcactct gaaaccaaga cagcctgat gcaggacagg     660
gacgccgcct tgccagggc ctggcccaag atgcacaccg tcaacggcta cgtcaacagg     720
agcctgcctg gctgattgg ctgccacagg aagagcgtgt actggcatgt gatcggcatg     780
ggcaccaccc tgaggtgca cagcatcttc ctggagggcc acaccttcct ggtcaggaac     840
cacaggcagg ccagcctgga gatcagcccc atcaccttcc tgaccgccca gaccctgctg     900
atggacctgg gccagttcct gctgttctgc cacatctcca gccaccagca cgacggcatg     960
gaggcctacg tgaaagtgga cagctgccct gaggagcccc agctgaggat gaagaacaac    1020
gaggaggccg aggactatga tgacgacctg accgacagcg agatggacgt ggtcaggttc    1080
gacgacgaca cagcccag cttcatccag atcaggagct ggccaagaa caccccaag    1140
acctgggtgc actacatcgc tgctgaggag gaggactggg actatgcccc cctggtgctg    1200
gccctgatg acaggagcta caagagccag tacctgaaca atggccccca gaggattggc    1260
aggaagtaca agaaagtcag gttcatggcc tacactgatg aaaccttcaa gaccagggag    1320
gccatccagc atgagtctgg catcctgggc cccctgctgt acggggaggt ggggacacc    1380
ctgctgatca tcttcaagaa ccaggccagc aggccctaca acatctaccc ccatggcatc    1440
accgacgtga ggcccctgta cagcaggagg ctgcctaagg gggtgaagca cctgaaagac    1500
ttccccatcc tgcctgggga tcttcaag tacaagtgga ctgtgactgt ggaggacggc    1560
cccaccaaga gcgaccccag gtgcctgacc agatactaca gcagcttcgt caacatggag    1620
agggacctgg cctctggcct gattggcccc ctgctgatct gctacaagga gtctgtggac    1680
cagagggggca accagatcat gagcgacaag aggaacgtga tcctgttctc tgtc           1734
```

<210> SEQ ID NO 14
<211> LENGTH: 2583
<212> TYPE: DNA
<213> ORGANISM: Artificial Sequence
<220> FEATURE:
<223> OTHER INFORMATION: coFVIII-26-CT

<400> SEQUENCE: 14

```
ttcgacgaga acaggagctg gtacctcact gaaaacatcc agaggttcct cccaaacccc    60
gcaggagtgc aactggagga ccctgagttt caggcctcga atatcatgca ctcgattaac   120
ggttacgtgt tcgactcgct gcagctgagc gtgtgcctcc atgaagtcgc ttactggtac   180
attctgtcca tcgcgccca gactgacttc ctgagcgtgt tcttttccgg ttacacccttt   240 aagcacaaga tggtgtacga agatacccctg accctgttcc ctttctccgg cgaaacggtg   300
ttcatgtcga tggagaaccc gggtctgtgg attctgggat gccacaacag cgactttcgg   360
aaccgcggaa tgactgccct gctgaaggtg tcctcatgcg acaagaacac cggagactac   420
tacgaggact cctacgagga tatctcagcc tacctcctgt ccaagaacaa cgcgatcgag   480
ccgcgcagct tcagccagaa cccgcctgtg ctgaagaggc accagcgaga aattacccgg   540
accaccctcc aatcggatca ggaggaaatc gactacgacg acaccatctc ggtggaaatg   600
aagaaggaag atttcgatat ctacgacgag gacgaaaatc agtcccctcg ctcattccaa   660
aagaaaacta gacactactt tatcgccgcg gtggaaagac tgtgggacta tggaatgtca   720
tccagccctc acgtccttcg gaaccgggcc cagagcggat cggtgcctca gttcaagaaa   780
gtggtgttcc aggagttcac cgacggcagc ttcacccagc cgctgtaccg gggagaactg   840
aacgaacacc tgggcctgct cggtccctac atccgcgcgg aagtggagga taacatcatg   900
gtgaccttcc gtaaccaagc atccagacct tactccttct attcctccct gatctcatac   960
gaggaggacc agcgccaagg cgccgagccc cgcaagaact tcgtcaagcc caacgagact  1020
aagacctact tctggaaggt ccaacaccat atggccccga ccaaggatga gtttgactgc  1080
aaggcctggg cctacttctc cgacgtggac cttgagaagg atgtccattc cggcctgatc  1140
gggccgctgc tcgtgtgtca caccaacacc ctgaacccag cgcatggacg ccaggtcacc  1200
gtccaggagt ttgctctgtt cttcaccatt tttgacgaaa ctaagtcctg gtacttcacc  1260
gagaatatgg agcgaaactg tagagcgccc tgcaatatcc agatgaaga tccgactttc  1320 aaggagaact atagattcca cgccatcaac gggtacatca tggatactct gccggggctg  1380
gtcatggccc aggatcagag gattcggtgg tacttgctgt caatgggatc gaacgaaaac  1440
attcactcca ttcacttctc cggtcacgtg ttcactgtgc gcaagaagga ggagtacaag  1500
atggcgctgt acaatctgta ccccggggtg ttcgaaactg tggagatgct gccgtccaag  1560
gccggcatct ggagagtgga gtgcctgatc ggagagcacc tccacgcggg gatgtccacc  1620
ctcttcctgg tgtactcgaa taagtgccag accccgctgg gcatggcctc gggccacatc  1680
agagacttcc agatcacagc aagcggacaa tacggccaat gggcgccgaa gctggcccgc  1740
ttgcactact ccggatcgat caacgcatgg tccaccaagg aaccgttctc gtggattaag  1800
gtggacctcc tggcccctat gattatccac ggaattaaga cccagggcgc caggcagaag  1860
ttctcctccc tgtacatctc gcaattcatc atcatgtaca gcctggacgg gaagaagtgg  1920
cagacttaca ggggaaactc caccggcacc ctgatggtct ttttcggcaa cgtggattcc  1980
tccggcatta agcacaacat cttcaaccca ccgatcatag ccagatatat taggctccac  2040
cccactcact actcaatccg ctcaactctt cggatggaac tcatggggtg cgacctgaac  2100
tcctgctcca tgccgttggg gatggaatca aaggctatta gcgacgccca gatcaccgcg  2160
agctcctact tcactaacat gttcgccacc tggagcccct ccaaggccag gctgcacttg  2220
cagggacggt caaatgcctg gcggccgcaa gtgaacaatc cgaaggaatg gcttcaagtg  2280
gatttccaaa agaccatgaa agtgaccgga gtcaccaccc agggagtgaa gtcccttctg  2340
```

```
acctcgatgt atgtgaagga gttcctgatt agcagcagcc aggacgggca ccagtggacc   2400
ctgttcttcc aaaacggaaa ggtcaaggtg ttccagggga accaggactc gttcacaccc   2460
gtggtgaact ccctggaccc cccactgctg acgcggtact tgaggattca tcctcagtcc   2520
tgggtccatc agattgcatt gcgaatggaa gtcctgggct gcgaggccca ggacctgtac   2580
tga                                                                 2583
```

<210> SEQ ID NO 15
<211> LENGTH: 2332
<212> TYPE: PRT
<213> ORGANISM: Homo sapiens

<400> SEQUENCE: 15

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
```

-continued

```
                325                 330                 335
Met Lys Asn Asn Glu Glu Ala Glu Asp Tyr Asp Asp Leu Thr Asp
            340                 345                 350
Ser Glu Met Asp Val Val Arg Phe Asp Asp Asn Ser Pro Ser Phe
            355                 360                 365
Ile Gln Ile Arg Ser Val Ala Lys Lys His Pro Lys Thr Trp Val His
370                 375                 380
Tyr Ile Ala Ala Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Val Arg Phe Met Ala Tyr Thr
                420                 425                 430
Asp Glu Thr Phe Lys Thr Arg Glu Ala Ile Gln His Glu Ser Gly Ile
                435                 440                 445
Leu Gly Pro Leu Leu Tyr Gly Glu Val Gly Asp Thr Leu Leu Ile Ile
            450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
                500                 505                 510
Trp Thr Val Thr Val Glu Asp Gly Pro Thr Lys Ser Asp Pro Arg Cys
            515                 520                 525
Leu Thr Arg Tyr Tyr Ser Ser Phe Val Asn Met Glu Arg Asp Leu Ala
530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
            580                 585                 590
Arg Phe Leu Pro Asn Pro Ala Gly Val Gln Leu Glu Asp Pro Glu Phe
            595                 600                 605
Gln Ala Ser Asn Ile Met His Ser Ile Asn Gly Tyr Val Phe Asp Ser
610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Ser Gly Tyr
                645                 650                 655
Thr Phe Lys His Lys Met Val Tyr Glu Asp Thr Leu Thr Leu Phe Pro
                660                 665                 670
Phe Ser Gly Glu Thr Val Phe Met Ser Met Glu Asn Pro Gly Leu Trp
            675                 680                 685
Ile Leu Gly Cys His Asn Ser Asp Phe Arg Asn Arg Gly Met Thr Ala
            690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                725                 730                 735
Ile Glu Pro Arg Ser Phe Ser Gln Asn Ser Arg His Pro Ser Thr Arg
                740                 745                 750
```

```
Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
        835                 840                 845

Phe Thr Pro Glu Ser Gly Leu Gln Leu Arg Leu Asn Glu Lys Leu Gly
850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
        915                 920                 925

Leu Thr Glu Ser Gly Gly Pro Leu Ser Leu Ser Glu Glu Asn Asn Asp
930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
        995                 1000                1005

Thr Asn Arg Lys Thr His Ile Asp Gly Pro Ser Leu Leu Ile Glu
    1010                1015                1020

Asn Ser Pro Ser Val Trp Gln Asn Ile Leu Glu Ser Asp Thr Glu
    1025                1030                1035

Phe Lys Lys Val Thr Pro Leu Ile His Asp Arg Met Leu Met Asp
    1040                1045                1050

Lys Asn Ala Thr Ala Leu Arg Leu Asn His Met Ser Asn Lys Thr
    1055                1060                1065

Thr Ser Ser Lys Asn Met Glu Met Val Gln Gln Lys Lys Glu Gly
    1070                1075                1080

Pro Ile Pro Pro Asp Ala Gln Asn Pro Asp Met Ser Phe Phe Lys
    1085                1090                1095

Met Leu Phe Leu Pro Glu Ser Ala Arg Trp Ile Gln Arg Thr His
    1100                1105                1110

Gly Lys Asn Ser Leu Asn Ser Gly Gln Gly Pro Ser Pro Lys Gln
    1115                1120                1125

Leu Val Ser Leu Gly Pro Glu Lys Ser Val Glu Gly Gln Asn Phe
    1130                1135                1140

Leu Ser Glu Lys Asn Lys Val Val Val Gly Lys Gly Glu Phe Thr
    1145                1150                1155
```

```
Lys Asp Val Gly Leu Lys Glu Met Val Phe Pro Ser Ser Arg Asn
    1160                1165                1170
Leu Phe Leu Thr Asn Leu Asp Asn Leu His Glu Asn Asn Thr His
    1175                1180                1185
Asn Gln Glu Lys Lys Ile Gln Glu Glu Ile Glu Lys Lys Glu Thr
    1190                1195                1200
Leu Ile Gln Glu Asn Val Val Leu Pro Gln Ile His Thr Val Thr
    1205                1210                1215
Gly Thr Lys Asn Phe Met Lys Asn Leu Phe Leu Leu Ser Thr Arg
    1220                1225                1230
Gln Asn Val Glu Gly Ser Tyr Asp Gly Ala Tyr Ala Pro Val Leu
    1235                1240                1245
Gln Asp Phe Arg Ser Leu Asn Asp Ser Thr Asn Arg Thr Lys Lys
    1250                1255                1260
His Thr Ala His Phe Ser Lys Lys Gly Glu Glu Glu Asn Leu Glu
    1265                1270                1275
Gly Leu Gly Asn Gln Thr Lys Gln Ile Val Glu Lys Tyr Ala Cys
    1280                1285                1290
Thr Thr Arg Ile Ser Pro Asn Thr Ser Gln Gln Asn Phe Val Thr
    1295                1300                1305
Gln Arg Ser Lys Arg Ala Leu Lys Gln Phe Arg Leu Pro Leu Glu
    1310                1315                1320
Glu Thr Glu Leu Glu Lys Arg Ile Ile Val Asp Asp Thr Ser Thr
    1325                1330                1335
Gln Trp Ser Lys Asn Met Lys His Leu Thr Pro Ser Thr Leu Thr
    1340                1345                1350
Gln Ile Asp Tyr Asn Glu Lys Glu Lys Gly Ala Ile Thr Gln Ser
    1355                1360                1365
Pro Leu Ser Asp Cys Leu Thr Arg Ser His Ser Ile Pro Gln Ala
    1370                1375                1380
Asn Arg Ser Pro Leu Pro Ile Ala Lys Val Ser Ser Phe Pro Ser
    1385                1390                1395
Ile Arg Pro Ile Tyr Leu Thr Arg Val Leu Phe Gln Asp Asn Ser
    1400                1405                1410
Ser His Leu Pro Ala Ala Ser Tyr Arg Lys Lys Asp Ser Gly Val
    1415                1420                1425
Gln Glu Ser Ser His Phe Leu Gln Gly Ala Lys Lys Asn Asn Leu
    1430                1435                1440
Ser Leu Ala Ile Leu Thr Leu Glu Met Thr Gly Asp Gln Arg Glu
    1445                1450                1455
Val Gly Ser Leu Gly Thr Ser Ala Thr Asn Ser Val Thr Tyr Lys
    1460                1465                1470
Lys Val Glu Asn Thr Val Leu Pro Lys Pro Asp Leu Pro Lys Thr
    1475                1480                1485
Ser Gly Lys Val Glu Leu Leu Pro Lys Val His Ile Tyr Gln Lys
    1490                1495                1500
Asp Leu Phe Pro Thr Glu Thr Ser Asn Gly Ser Pro Gly His Leu
    1505                1510                1515
Asp Leu Val Glu Gly Ser Leu Leu Gln Gly Thr Glu Gly Ala Ile
    1520                1525                1530
Lys Trp Asn Glu Ala Asn Arg Pro Gly Lys Val Pro Phe Leu Arg
    1535                1540                1545
Val Ala Thr Glu Ser Ser Ala Lys Thr Pro Ser Lys Leu Leu Asp
```

```
                    1550                1555                1560
Pro Leu Ala Trp Asp Asn His Tyr Gly Thr Gln Ile Pro Lys Glu
                    1565                1570                1575
Glu Trp Lys Ser Gln Glu Lys Ser Pro Glu Lys Thr Ala Phe Lys
                    1580                1585                1590
Lys Lys Asp Thr Ile Leu Ser Leu Asn Ala Cys Glu Ser Asn His
                    1595                1600                1605
Ala Ile Ala Ala Ile Asn Glu Gly Gln Asn Lys Pro Glu Ile Glu
                    1610                1615                1620
Val Thr Trp Ala Lys Gln Gly Arg Thr Glu Arg Leu Cys Ser Gln
                    1625                1630                1635
Asn Pro Pro Val Leu Lys Arg His Gln Arg Glu Ile Thr Arg Thr
                    1640                1645                1650
Thr Leu Gln Ser Asp Gln Glu Ile Asp Tyr Asp Asp Thr Ile
                    1655                1660                1665
Ser Val Glu Met Lys Lys Glu Asp Phe Asp Ile Tyr Asp Glu Asp
                    1670                1675                1680
Glu Asn Gln Ser Pro Arg Ser Phe Gln Lys Lys Thr Arg His Tyr
                    1685                1690                1695
Phe Ile Ala Ala Val Glu Arg Leu Trp Asp Tyr Gly Met Ser Ser
                    1700                1705                1710
Ser Pro His Val Leu Arg Asn Arg Ala Gln Ser Gly Ser Val Pro
                    1715                1720                1725
Gln Phe Lys Lys Val Val Phe Gln Glu Phe Thr Asp Gly Ser Phe
                    1730                1735                1740
Thr Gln Pro Leu Tyr Arg Gly Glu Leu Asn Glu His Leu Gly Leu
                    1745                1750                1755
Leu Gly Pro Tyr Ile Arg Ala Glu Val Glu Asp Asn Ile Met Val
                    1760                1765                1770
Thr Phe Arg Asn Gln Ala Ser Arg Pro Tyr Ser Phe Tyr Ser Ser
                    1775                1780                1785
Leu Ile Ser Tyr Glu Glu Asp Gln Arg Gln Gly Ala Glu Pro Arg
                    1790                1795                1800
Lys Asn Phe Val Lys Pro Asn Glu Thr Lys Thr Tyr Phe Trp Lys
                    1805                1810                1815
Val Gln His His Met Ala Pro Thr Lys Asp Glu Phe Asp Cys Lys
                    1820                1825                1830
Ala Trp Ala Tyr Phe Ser Asp Val Asp Leu Glu Lys Asp Val His
                    1835                1840                1845
Ser Gly Leu Ile Gly Pro Leu Leu Val Cys His Thr Asn Thr Leu
                    1850                1855                1860
Asn Pro Ala His Gly Arg Gln Val Thr Val Gln Glu Phe Ala Leu
                    1865                1870                1875
Phe Phe Thr Ile Phe Asp Glu Thr Lys Ser Trp Tyr Phe Thr Glu
                    1880                1885                1890
Asn Met Glu Arg Asn Cys Arg Ala Pro Cys Asn Ile Gln Met Glu
                    1895                1900                1905
Asp Pro Thr Phe Lys Glu Asn Tyr Arg Phe His Ala Ile Asn Gly
                    1910                1915                1920
Tyr Ile Met Asp Thr Leu Pro Gly Leu Val Met Ala Gln Asp Gln
                    1925                1930                1935
Arg Ile Arg Trp Tyr Leu Leu Ser Met Gly Ser Asn Glu Asn Ile
                    1940                1945                1950
```

```
His Ser Ile His Phe Ser Gly His Val Phe Thr Val Arg Lys Lys
    1955            1960            1965

Glu Glu Tyr Lys Met Ala Leu Tyr Asn Leu Tyr Pro Gly Val Phe
    1970            1975            1980

Glu Thr Val Glu Met Leu Pro Ser Lys Ala Gly Ile Trp Arg Val
    1985            1990            1995

Glu Cys Leu Ile Gly Glu His Leu His Ala Gly Met Ser Thr Leu
    2000            2005            2010

Phe Leu Val Tyr Ser Asn Lys Cys Gln Thr Pro Leu Gly Met Ala
    2015            2020            2025

Ser Gly His Ile Arg Asp Phe Gln Ile Thr Ala Ser Gly Gln Tyr
    2030            2035            2040

Gly Gln Trp Ala Pro Lys Leu Ala Arg Leu His Tyr Ser Gly Ser
    2045            2050            2055

Ile Asn Ala Trp Ser Thr Lys Glu Pro Phe Ser Trp Ile Lys Val
    2060            2065            2070

Asp Leu Leu Ala Pro Met Ile Ile His Gly Ile Lys Thr Gln Gly
    2075            2080            2085

Ala Arg Gln Lys Phe Ser Ser Leu Tyr Ile Ser Gln Phe Ile Ile
    2090            2095            2100

Met Tyr Ser Leu Asp Gly Lys Lys Trp Gln Thr Tyr Arg Gly Asn
    2105            2110            2115

Ser Thr Gly Thr Leu Met Val Phe Phe Gly Asn Val Asp Ser Ser
    2120            2125            2130

Gly Ile Lys His Asn Ile Phe Asn Pro Pro Ile Ile Ala Arg Tyr
    2135            2140            2145

Ile Arg Leu His Pro Thr His Tyr Ser Ile Arg Ser Thr Leu Arg
    2150            2155            2160

Met Glu Leu Met Gly Cys Asp Leu Asn Ser Cys Ser Met Pro Leu
    2165            2170            2175

Gly Met Glu Ser Lys Ala Ile Ser Asp Ala Gln Ile Thr Ala Ser
    2180            2185            2190

Ser Tyr Phe Thr Asn Met Phe Ala Thr Trp Ser Pro Ser Lys Ala
    2195            2200            2205

Arg Leu His Leu Gln Gly Arg Ser Asn Ala Trp Arg Pro Gln Val
    2210            2215            2220

Asn Asn Pro Lys Glu Trp Leu Gln Val Asp Phe Gln Lys Thr Met
    2225            2230            2235

Lys Val Thr Gly Val Thr Thr Gln Gly Val Lys Ser Leu Leu Thr
    2240            2245            2250

Ser Met Tyr Val Lys Glu Phe Leu Ile Ser Ser Ser Gln Asp Gly
    2255            2260            2265

His Gln Trp Thr Leu Phe Phe Gln Asn Gly Lys Val Lys Val Phe
    2270            2275            2280

Gln Gly Asn Gln Asp Ser Phe Thr Pro Val Val Asn Ser Leu Asp
    2285            2290            2295

Pro Pro Leu Leu Thr Arg Tyr Leu Arg Ile His Pro Gln Ser Trp
    2300            2305            2310

Val His Gln Ile Ala Leu Arg Met Glu Val Leu Gly Cys Glu Ala
    2315            2320            2325

Gln Asp Leu Tyr
    2330
```

<210> SEQ ID NO 16
<211> LENGTH: 4371
<212> TYPE: DNA
<213> ORGANISM: Artificial Sequence
<220> FEATURE:
<223> OTHER INFORMATION: BDD-FVIII (non-optimized; "parental"),
      Nucleotide Sequence

<400> SEQUENCE: 16

| | | | | | |
|---|---|---|---|---|---|
| atgcaaatag | agctctccac | ctgcttcttt | ctgtgccttt | tgcgattctg | ctttagtgcc | 60 |
| accagaagat | actacctggg | tgcagtggaa | ctgtcatggg | actatatgca | aagtgatctc | 120 |
| ggtgagctgc | ctgtggacgc | aagatttcct | cctagagtgc | caaaatcttt | tccattcaac | 180 |
| acctcagtcg | tgtacaaaaa | gactctgttt | gtagaattca | cggatcacct | tttcaacatc | 240 |
| gctaagccaa | ggccaccctg | gatgggtctg | ctaggtccta | ccatccaggc | tgaggtttat | 300 |
| gatacagtgg | tcattacact | taagaacatg | gcttcccatc | ctgtcagtct | tcatgctgtt | 360 |
| ggtgtatcct | actggaaagc | ttctgaggga | gctgaatatg | atgatcagac | cagtcaaagg | 420 |
| gagaaagaag | atgataaagt | cttccctggt | ggaagccata | catatgtctg | gcaggtcctg | 480 |
| aaagagaatg | gtccaatggc | ctctgaccca | ctgtgcctta | cctactcata | tctttctcat | 540 |
| gtggacctgg | taaagactt | gaattcaggc | ctcattggag | ccctactagt | atgtagagaa | 600 |
| gggagtctgg | ccaaggaaaa | gacacagacc | ttgcacaaat | ttatactact | ttttgctgta | 660 |
| tttgatgaag | ggaaaagttg | gcactcagaa | acaaagaact | ccttgatgca | ggatagggat | 720 |
| gctgcatctg | ctcgggcctg | gcctaaaatg | cacacagtca | atggttatgt | aaacaggtct | 780 |
| ctgccaggtc | tgattggatg | ccacaggaaa | tcagtctatt | ggcatgtgat | tggaatgggc | 840 |
| accactcctg | aagtgcactc | aatattcctc | gaaggtcaca | catttcttgt | gaggaaccat | 900 |
| cgccaggcgt | ccttggaaat | ctcgccaata | actttcctta | ctgctcaaac | actcttgatg | 960 |
| gaccttggac | agtttctact | gttttgtcat | atctcttccc | accaacatga | tggcatggaa | 1020 |
| gcttatgtca | aagtagacag | ctgtccagag | gaaccccaac | tacgaatgaa | aaataatgaa | 1080 |
| gaagcggaag | actatgatga | tgatcttact | gattctgaaa | tggatgtggt | caggtttgat | 1140 |
| gatgacaact | ctccttcctt | tatccaaatt | cgctcagttg | ccaagaagca | tcctaaaact | 1200 |
| tgggtacatt | acattgctgc | tgaagaggag | gactgggact | atgctccctt | agtcctcgcc | 1260 |
| cccgatgaca | gaagttataa | aagtcaatat | ttgaacaatg | gccctcagcg | gattggtagg | 1320 |
| aagtacaaaa | aagtccgatt | tatggcatac | acagatgaaa | cctttaagac | tcgtgaagct | 1380 |
| attcagcatg | aatcaggaat | cttgggacct | ttactttatg | ggaagttgg | agacacactg | 1440 |
| ttgattatat | ttaagaatca | agcaagcaga | ccatataaca | tctaccctca | cggaatcact | 1500 |
| gatgtccgtc | ctttgtattc | aaggagatta | ccaaaaggtg | taaaacattt | gaaggatttt | 1560 |
| ccaattctgc | caggagaaat | attcaaatat | aaatggacag | tgactgtaga | agatgggcca | 1620 |
| actaaatcag | atcctcggtg | cctgacccgc | tattactcta | gtttcgttaa | tatggagaga | 1680 |
| gatctagctt | caggactcat | tggccctctc | ctcatctgct | acaaagaatc | tgtagatcaa | 1740 |
| agaggaaacc | agataatgtc | agacaagagg | aatgtcatcc | tgtttttctgt | atttgatgag | 1800 |
| aaccgaagct | ggtacctcac | agagaatata | caacgctttc | tccccaatcc | agctggagtg | 1860 |
| cagcttgagg | atccagagtt | ccaagcctcc | aacatcatgc | acagcatcaa | tggctatgtt | 1920 |
| tttgatagtt | tgcagttgtc | agtttgtttg | catgaggtgg | catactggta | cattctaagc | 1980 |
| attggagcac | agactgactt | cctttctgtc | ttcttctctg | gatatacctt | caaacacaaa | 2040 |

```
atggtctatg aagacacact caccctattc ccattctcag gagaaactgt cttcatgtcg    2100
atggaaaacc caggtctatg gattctgggg tgccacaact cagactttcg aacagaggc    2160
atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctctcaaa acccaccagt cttgaaacgc atcaacggg aaataactcg tactactctt    2340
cagtcagatc aagaggaaat tgactatgat gataccatat cagttgaaat gaagaaggaa    2400
gattttgaca tttatgatga ggatgaaaat cagagccccc gcagctttca aagaaaaca    2460
cgacactatt ttattgctgc agtggagagg ctctgggatt atgggatgag tagctcccca    2520
catgttctaa gaaacagggc tcagagtggc agtgtccctc agttcaagaa agttgttttc    2580
caggaattta ctgatggctc ctttactcag cccttatacc gtggagaact aaatgaacat    2640
ttgggactcc tggggccata tataagagca gaagttgaag ataatatcat ggtaactttc    2700
agaaatcagg cctctcgtcc ctattccttc tattctagcc ttatttctta tgaggaagat    2760
cagaggcaag gagcagaacc tagaaaaaac tttgtcaagc ctaatgaaac caaaacttac    2820
ttttggaaag tgcaacatca tatggcaccc actaaagatg agtttgactg caaagcctgg    2880
gcttatttct ctgatgttga cctggaaaaa gatgtgcact caggcctgat tggacccctt    2940
ctggtctgcc acactaacac actgaaccct gctcatggga gacaagtgac agtacaggaa    3000
tttgctctgt ttttcaccat ctttgatgag accaaaagct ggtacttcac tgaaaatatg    3060
gaaagaaact gcagggctcc ctgcaatatc cagatggaag atcccacttt taaagagaat    3120
tatcgcttcc atgcaatcaa tggctacata atggatacac tacctggctt agtaatggct    3180
caggatcaaa ggattcgatg gtatctgctc agcatgggca gcaatgaaaa catccattct    3240
attcatttca gtggacatgt gttcactgta cgaaaaaaag aggagtataa aatggcactg    3300
tacaatctct atccaggtgt ttttgagaca gtggaaatgt taccatccaa agctggaatt    3360
tggcgggtgg aatgccttat tggcgagcat ctacatgctg ggatgagcac actttttctg    3420
gtgtacagca ataagtgtca gactcccctg ggaatggctt ctggacacat tagagatttt    3480
cagattacag cttcaggaca atatggacag tgggccccaa agctggccag acttcattat    3540
tccggatcaa tcaatgcctg gagcaccaag gagcccttt cttggatcaa ggtggatctg    3600
ttggcaccaa tgattattca cggcatcaag acccagggtg cccgtcagaa gttctccagc    3660
ctctacatct ctcagtttat catcatgtat agtcttgatg ggaagaagtg gcagacttat    3720
cgaggaaatt ccactggaac cttaatggtc ttctttggca atgtggattc atctgggata    3780
aaacacaata tttttaaccc tccaattatt gctcgataca tccgtttgca cccaactcat    3840
tatagcattc gcagcactct tcgcatggag ttgatgggct gtgatttaaa tagttgcagc    3900
atgccattgg gaatggagag taaagcaata tcagatgcac agattactgc ttcatcctac    3960
tttaccaata tgtttgccac ctggtctcct tcaaaagctc gacttcacct ccaagggagg    4020
agtaatgcct ggagacctca ggtgaataat ccaaaagagt ggctgcaagt ggacttccag    4080
aagacaatga agtcacagg agtaactact cagggagtaa aatctctgct taccagcatg    4140
tatgtgaagg agttcctcat ctccagcagt caagatggcc atcagtggac tctcttttt    4200
cagaatggca aagtaaaggt ttttcaggga aatcaagact ccttcacacc tgtggtgaac    4260
tctctagacc caccgttact gactcgctac cttcgaattc accccagag ttgggtgcac    4320
cagattgccc tgaggatgga ggttctgggc tgcgaggcac aggacctcta c             4371
```

<210> SEQ ID NO 17
<211> LENGTH: 1438
<212> TYPE: PRT
<213> ORGANISM: Artificial Sequence
<220> FEATURE:
<223> OTHER INFORMATION: BDD-FVIII (non-optimized; "parental"), Amino Acid Sequence

<400> SEQUENCE: 17

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Leu Thr Asp
            340                 345                 350

Ser Glu Met Asp Val Val Arg Phe Asp Asp Asn Ser Pro Ser Phe
        355                 360                 365
```

```
Ile Gln Ile Arg Ser Val Ala Lys Lys His Pro Lys Thr Trp Val His
370                 375                 380
Tyr Ile Ala Ala Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Val Arg Phe Met Ala Tyr Thr
                420                 425                 430
Asp Glu Thr Phe Lys Thr Arg Glu Ala Ile Gln His Glu Ser Gly Ile
                435                 440                 445
Leu Gly Pro Leu Leu Tyr Gly Glu Val Gly Asp Thr Leu Leu Ile Ile
450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
                500                 505                 510
Trp Thr Val Thr Val Glu Asp Gly Pro Thr Lys Ser Asp Pro Arg Cys
                515                 520                 525
Leu Thr Arg Tyr Tyr Ser Ser Phe Val Asn Met Glu Arg Asp Leu Ala
530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
                580                 585                 590
Arg Phe Leu Pro Asn Pro Ala Gly Val Gln Leu Glu Asp Pro Glu Phe
                595                 600                 605
Gln Ala Ser Asn Ile Met His Ser Ile Asn Gly Tyr Val Phe Asp Ser
                610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
Thr Phe Lys His Lys Met Val Tyr Glu Asp Thr Leu Thr Leu Phe Pro
                660                 665                 670
Phe Ser Gly Glu Thr Val Phe Met Ser Met Glu Asn Pro Gly Leu Trp
                675                 680                 685
Ile Leu Gly Cys His Asn Ser Asp Phe Arg Asn Arg Gly Met Thr Ala
690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                725                 730                 735
Ile Glu Pro Arg Ser Phe Ser Gln Asn Pro Pro Val Leu Lys Arg His
                740                 745                 750
Gln Arg Glu Ile Thr Arg Thr Thr Leu Gln Ser Asp Gln Glu Glu Ile
                755                 760                 765
Asp Tyr Asp Asp Thr Ile Ser Val Glu Met Lys Lys Glu Asp Phe Asp
                770                 775                 780
Ile Tyr Asp Glu Asp Glu Asn Gln Ser Pro Arg Ser Phe Gln Lys Lys
```

-continued

```
            785                 790                 795                 800
      Thr Arg His Tyr Phe Ile Ala Ala Val Glu Arg Leu Trp Asp Tyr Gly
                          805                 810                 815
      Met Ser Ser Ser Pro His Val Leu Arg Asn Arg Ala Gln Ser Gly Ser
                          820                 825                 830
      Val Pro Gln Phe Lys Lys Val Phe Gln Glu Phe Thr Asp Gly Ser
                          835                 840                 845
      Phe Thr Gln Pro Leu Tyr Arg Gly Glu Leu Asn Glu His Leu Gly Leu
                          850                 855                 860
      Leu Gly Pro Tyr Ile Arg Ala Glu Val Glu Asp Asn Ile Met Val Thr
      865                 870                 875                 880
      Phe Arg Asn Gln Ala Ser Arg Pro Tyr Ser Phe Tyr Ser Ser Leu Ile
                          885                 890                 895
      Ser Tyr Glu Glu Asp Gln Arg Gln Gly Ala Glu Pro Arg Lys Asn Phe
                          900                 905                 910
      Val Lys Pro Asn Glu Thr Lys Thr Tyr Phe Trp Lys Val Gln His His
                          915                 920                 925
      Met Ala Pro Thr Lys Asp Glu Phe Asp Cys Lys Ala Trp Ala Tyr Phe
                          930                 935                 940
      Ser Asp Val Asp Leu Glu Lys Asp Val His Ser Gly Leu Ile Gly Pro
      945                 950                 955                 960
      Leu Leu Val Cys His Thr Asn Thr Leu Asn Pro Ala His Gly Arg Gln
                          965                 970                 975
      Val Thr Val Gln Glu Phe Ala Leu Phe Phe Thr Ile Phe Asp Glu Thr
                          980                 985                 990
      Lys Ser Trp Tyr Phe Thr Glu Asn  Met Glu Arg Asn Cys  Arg Ala Pro
                          995                 1000                1005
      Cys Asn  Ile Gln Met Glu Asp  Pro Thr Phe Lys Glu  Asn Tyr Arg
                          1010                1015                1020
      Phe His  Ala Ile Asn Gly Tyr  Ile Met Asp Thr Leu  Pro Gly Leu
                          1025                1030                1035
      Val Met  Ala Gln Asp Gln Arg  Ile Arg Trp Tyr Leu  Leu Ser Met
                          1040                1045                1050
      Gly Ser  Asn Glu Asn Ile His  Ser Ile His Phe Ser  Gly His Val
                          1055                1060                1065
      Phe Thr  Val Arg Lys Lys Glu  Glu Tyr Lys Met Ala  Leu Tyr Asn
                          1070                1075                1080
      Leu Tyr  Pro Gly Val Phe Glu  Thr Val Glu Met Leu  Pro Ser Lys
                          1085                1090                1095
      Ala Gly  Ile Trp Arg Val Glu  Cys Leu Ile Gly Glu  His Leu His
                          1100                1105                1110
      Ala Gly  Met Ser Thr Leu Phe  Leu Val Tyr Ser Asn  Lys Cys Gln
                          1115                1120                1125
      Thr Pro  Leu Gly Met Ala Ser  Gly His Ile Arg Asp  Phe Gln Ile
                          1130                1135                1140
      Thr Ala  Ser Gly Gln Tyr Gly  Gln Trp Ala Pro Lys  Leu Ala Arg
                          1145                1150                1155
      Leu His  Tyr Ser Gly Ser Ile  Asn Ala Trp Ser Thr  Lys Glu Pro
                          1160                1165                1170
      Phe Ser  Trp Ile Lys Val Asp  Leu Leu Ala Pro Met  Ile Ile His
                          1175                1180                1185
      Gly Ile  Lys Thr Gln Gly Ala  Arg Gln Lys Phe Ser  Ser Leu Tyr
                          1190                1195                1200
```

Ile Ser Gln Phe Ile Ile Met Tyr Ser Leu Asp Gly Lys Lys Trp
1205                1210                1215

Gln Thr Tyr Arg Gly Asn Ser Thr Gly Thr Leu Met Val Phe Phe
1220                1225                1230

Gly Asn Val Asp Ser Ser Gly Ile Lys His Asn Ile Phe Asn Pro
1235                1240                1245

Pro Ile Ile Ala Arg Tyr Ile Arg Leu His Pro Thr His Tyr Ser
1250                1255                1260

Ile Arg Ser Thr Leu Arg Met Glu Leu Met Gly Cys Asp Leu Asn
1265                1270                1275

Ser Cys Ser Met Pro Leu Gly Met Glu Ser Lys Ala Ile Ser Asp
1280                1285                1290

Ala Gln Ile Thr Ala Ser Ser Tyr Phe Thr Asn Met Phe Ala Thr
1295                1300                1305

Trp Ser Pro Ser Lys Ala Arg Leu His Leu Gln Gly Arg Ser Asn
1310                1315                1320

Ala Trp Arg Pro Gln Val Asn Asn Pro Lys Glu Trp Leu Gln Val
1325                1330                1335

Asp Phe Gln Lys Thr Met Lys Val Thr Gly Val Thr Thr Gln Gly
1340                1345                1350

Val Lys Ser Leu Leu Thr Ser Met Tyr Val Lys Glu Phe Leu Ile
1355                1360                1365

Ser Ser Ser Gln Asp Gly His Gln Trp Thr Leu Phe Phe Gln Asn
1370                1375                1380

Gly Lys Val Lys Val Phe Gln Gly Asn Gln Asp Ser Phe Thr Pro
1385                1390                1395

Val Val Asn Ser Leu Asp Pro Pro Leu Leu Thr Arg Tyr Leu Arg
1400                1405                1410

Ile His Pro Gln Ser Trp Val His Gln Ile Ala Leu Arg Met Glu
1415                1420                1425

Val Leu Gly Cys Glu Ala Gln Asp Leu Tyr
1430                1435

<210> SEQ ID NO 18
<211> LENGTH: 450
<212> TYPE: DNA
<213> ORGANISM: Artificial Sequence
<220> FEATURE:
<223> OTHER INFORMATION: XTEN nucleotide sequence

<400> SEQUENCE: 18
ggcgcgccaa catcagagag cgccacccct gaaagtggtc ccgggagcga gccagccaca      60
tctgggtcgg aaacgccagg cacaagtgag tctgcaactc ccgagtccgg acctggctcc     120
gagcctgcca ctagcggctc cgagactccg gaacttccg agagcgctac accagaaagc      180
ggacccggaa ccagtaccga acctagcgag ggctctgctc cggcagccc agccggctct      240 cctacatcca cggaggaggg cacttccgaa tccgccaccc cggagtcagg gccaggatct     300
gaacccgcta cctcaggcag tgagacgcca ggaacgagcg agtccgctac accggagagt     360
gggccaggga gccctgctgg atctcctacg tccactgagg aagggtcacc agcgggctcg     420
cccaccagca ctgaagaagg tgcctcgagc                                     450

<210> SEQ ID NO 19
<211> LENGTH: 4824
<212> TYPE: DNA

<213> ORGANISM: Artificial Sequence
<220> FEATURE:
<223> OTHER INFORMATION: coFVIII-52-XTEN

<400> SEQUENCE: 19

```
atgcaaatcg aactgagcac ctgtttcttc ctctgcctgc tgagattctg tttctccgcg      60
acccgccgat actacctggg agcagtggag ctctcctggg attacatgca gagcgacctt     120
ggggagctgc ccgtggatgc caggttccct ccccgggtgc aaagtcgtt tccgttcaac      180
acctccgtgg tgtacaagaa actctgttc gtggagttca ccgaccacct gttcaatatc     240
gccaagccca gacctccctg gatggggctg ttgggaccta ccatccaagc ggaggtgtac     300
gacactgtgg tcatcactct gaagaacatg gcctcgcatc ccgtgtccct gcacgccgtg     360
ggagtgtctt actggaaagc gtccgagggg gccgaatacg acgaccagac ctcgcagaga     420
gaaaaggaag atgacaaggt gttcccagga ggatcgcaca cctacgtgtg gcaagtgttg     480
aaggagaacg gcccaatggc ctccgacccg ctgtgcctga cctactcgta cctgtcccac     540
gtggacctcg tgaaggacct caactcggga ctgattggag ccctgctggt ctgcaggaa      600
ggctcactgg cgaaagaaaa gactcagacc ttgcacaagt tcattctgct gttcgctgtg     660
ttcgacgagg ggaagtcgtg gcacagcgag actaagaact ccctgatgca agatagagat     720
gccgcctccg cccgggcctg gcctaagatg cacaccgtga acggttacgt gaaccgctcc     780
ctccctggcc tgattggatg ccaccggaag tccgtgtact ggcacgtgat cgggatgggg     840
accacccccg aggtgcacag catcttcctg gaaggtcaca catttctcgt gcgcaaccac     900
cggcaggcct ccctggaaat cagccccatt accttcctca ctgcccagac tctgctgatg     960
gacctgggac agttcctgct gttctgccat atctcctccc accaacatga cggaatggag    1020
gcatacgtga aggtcgattc ctgccctgag gaacccagc tccgcatgaa gaacaatgag     1080
gaagccgagg actacgacga cgacctgacg gatagcgaga tggatgtggt ccggttcgat    1140
gacgataaca gccttccctt catccaaatt cgctcggtgg caagaagca ccccaagacc      1200
tgggtgcatt acattgcggc ggaagaagag gactgggatt atgccccgct gtcctcgct     1260
cctgacgacc ggagctacaa gagccagtac ctgaacaacg gtccacagag gatcggtaga    1320
aagtacaaga aggtccgctt catggcctat accgacgaaa ccttcaaaac tagagaggcc    1380
atccaacacg aatccggcat cctgggcccg ctcttgtacg agaagtcgg cgacacccctt    1440
ctcattatct tcaagaacca ggcttccgg ccgtacaaca tctatccgca tgggatcact     1500
gacgtgcgcc cactgtactc gcggcgcctg cccaagggtg tcaaacacct gaaggatttt    1560
ccgatccttc cgggagaaat cttcaagtac aagtggaccg tgaccgtgga agatggccca    1620
actaagtctg accctagatg cctcacccgc tactactcat ccttcgtcaa catggagcgc    1680
gacctggcca gcggactgat cggcccgctg ctgatttgct acaaggaatc agtggaccaa    1740
cggggaaacc agatcatgtc ggataagagg aacgtcatcc tcttctccgt gtttgacgaa    1800
aaccggtcgt ggtacctgac cgagaacatc cagaggttcc tgcccaaccc tgctggggtg    1860
cagctggagg accccgagtt ccaggccagc aacatcatgc acagcatcaa tggctacgtg    1920
ttcgacagcc tgcagctgag cgtgtgcctg cacgaggtgg cctactggta catcctgagc    1980
atcggcgccc agaccgactt cctgagcgtg ttcttctctg gctacacctt caagcacaag    2040
atggtgtatg aggacaccct gaccctgttc cccttcagcg gggagactgt cttcatgagc    2100
atggagaacc ctggcctgtg gatcctgggc tgccacaaca gcgacttcag gaacaggggc    2160
atgactgccc tgctgaaagt ctccagctgt gacaagaaca ccggggacta ctacgaggac    2220
```

```
agctacgagg acatcagcgc ctacctgctg agcaagaaca atgccatcga gcccaggagc   2280
ttctctcaga acggcgcgcc aacatcagag agcgccaccc ctgaaagtgg tcccgggagc   2340
gagccagcca catctgggtc ggaaacgcca ggcacaagtg agtctgcaac tcccgagtcc   2400
ggacctggct ccgagcctgc cactagcggc tccgagactc cgggaacttc cgagagcgct   2460
acaccagaaa gcggacccgg aaccagtacc gaacctagcg agggctctgc tccgggcagc   2520
ccagccggct ctcctacatc cacggaggag ggcacttccg aatccgccac cccggagtca   2580
gggccaggat ctgaacccgc tacctcaggc agtgagacgc caggaacgag cgagtccgct   2640
acaccggaga gtgggccagg gagccctgct ggatctccta cgtccactga ggaagggtca   2700
ccagcgggct cgcccaccag cactgaagaa ggtgcctcga gccccccagt gctgaagagg   2760
caccagaggg agatcaccag gaccaccctg cagtctgacc aggaggagat cgactatgat   2820
gacaccatca gcgtggagat gaagaaggag gacttcgaca tctacgacga ggacgagaac   2880
cagagcccca ggagcttcca gaagaagacc aggcactact tcattgctgc tgtggagagg   2940
ctgtgggact atggcatgtc cagcagcccc catgtgctga gaacagggc ccagtctggc   3000
agcgtgcccc agttcaagaa agtcgtgttc caggagttca ccgacggcag cttcacccag   3060
cccctgtaca gaggggagct gaacgagcac ctgggcctgc tgggcccta catcagggcc   3120
gaggtggagg acaacatcat ggtgaccttc aggaaccagg ccagcaggcc ctacagcttc   3180
tacagcagcc tgatcagcta cgaggaggac cagaggcagg gggctgagcc caggaagaac   3240
tttgtgaagc ccaatgaaac caagacctac ttctggaagg tgcagcacca catggccccc   3300
accaaggacg agttcgactg caaggcctgg gcctacttct ctgacgtgga cctggagaag   3360
gacgtgcact ctggcctgat tggcccctg ctggtgtgcc acaccaacac cctgaaccct   3420
gcccatggca ggcaggtgac tgtgcaggag ttcgccctgt tcttcaccat cttcgatgaa   3480
accaagagct ggtacttcac tgagaacatg gagaggaact gcagggcccc ctgcaacatc   3540
cagatggagg accccacctt caaggagaac tacaggttcc atgccatcaa tggctacatc   3600
atggacaccc tgcctggcct ggtcatggcc caggaccaga ggatcaggtg gtatctgctg   3660
agcatgggca gcaacgagaa catccacagc atccacttct ctggccacgt gttcactgtg   3720
aggaagaagg aggagtacaa gatggccctg tacaacctgt accctggggt gttcgaaacc   3780
gtggagatgc tgcccagcaa ggccggcatc tggaggtgg agtgcctgat tggggagcac   3840
ctgcacgccg gcatgagcac cctgttcctg gtgtacagca acaagtgcca gaccccctg    3900
ggcatggcct ctggccacat cagggacttc cagatcactg cctctggcca gtacggccag   3960
tgggccccca gctggccag gctgcactac tccggaagca tcaatgcctg gagcaccaag   4020
gagcccttca gctggatcaa agtggacctg ctggccccca tgatcatcca cggcatcaag   4080
acccaggggg ccaggcagaa gttctccagc ctgtacatca gccagttcat catcatgtac   4140
agcctggacg caagaagtg gcagacctac agggggcaaca gcaccggcac cctgatggtg   4200
ttcttcggca acgtggacag cagcggcatc aagcacaaca tcttcaaccc cccatcatc   4260
gccagataca tcaggctgca cccccaccac tacagcatca ggagcaccct gaggatggag   4320
ctgatgggct gtgacctgaa cagctgcagc atgcccctgg gcatggagag caaggccatc   4380
tctgacgccc agatcactgc ctccagctac ttcaccaaca tgtttgccac ctggagcccc   4440
agcaaggcca ggctgcacct gcagggcagg agcaatgcct ggaggccccca ggtcaacaac   4500
cccaaggagt ggctgcaggt ggacttccag aagaccatga aggtgactgg ggtgaccacc   4560
```

| | |
|---|---|
| caggggtga agagcctgct gaccagcatg tacgtgaagg agttcctgat ctccagcagc | 4620 |
| caggacggcc accagtggac cctgttcttc cagaatggca aggtgaaggt gttccagggc | 4680 |
| aaccaggaca gcttcacccc tgtggtcaac agcctggacc cccccctgct gaccagatac | 4740 |
| ctgaggatcc accccagag ctgggtgcac cagatcgccc tgaggatgga ggtgctgggc | 4800 |
| tgtgaggccc aggacctgta ctga | 4824 |

<210> SEQ ID NO 20
<211> LENGTH: 4824
<212> TYPE: DNA
<213> ORGANISM: Artificial Sequence
<220> FEATURE:
<223> OTHER INFORMATION: coFVIII-1-XTEN

<400> SEQUENCE: 20

| | |
|---|---|
| atgcagattg agctgtctac ttgctttttc ctgtgcctgc tgaggttttg cttttccgct | 60 |
| acacgaaggt attatctggg ggctgtggaa ctgtcttggg attacatgca gagtgacctg | 120 |
| ggagagctgc cagtggacgc aaggtttccc cctagagtcc ctaagtcatt cccccttcaac | 180 |
| actagcgtgg tctacaagaa aacactgttc gtggagttta ctgatcacct gttcaacatc | 240 |
| gcaaagccta ggccacccctg gatgggactg ctggggccaa caatccaggc cgaggtgtac | 300 |
| gacaccgtgg tcattacact taagaacatg gcctcacacc ccgtgagcct gcatgctgtg | 360 |
| ggcgtcagct actggaaggc ttccgaagga gcagagtatg acgatcagac ttcccagaga | 420 |
| gaaaagagg acgataaggt gtttcctggc ggatctcata cctacgtgtg gcaggtcctg | 480 |
| aaagagaatg gccctatggc ctccgaccct ctgtgcctga cctactctta tctgagtcac | 540 |
| gtggacctgg tcaaggatct gaacagcggc ctgatcggag ccctgctggt gtgcagggaa | 600 |
| ggaagcctgc taaggagaa acccagaca ctgcataagt tcattctgct gttcgccgtg | 660 |
| tttgacgaag ggaaatcatg gcacagcgag acaaagaata gtctgatgca ggacagggat | 720 |
| gccgcttcag ccagagcttg gcccaaaatg cacactgtga acggctacgt caatcgctca | 780 |
| ctgcctgggc tgatcggctg ccaccgaaag agcgtgtatt ggcatgtcat cgggatgggc | 840 |
| accacacctg aagtgcactc cattttcctg gagggacata cctttctggt ccgcaaccac | 900 |
| cgacaggctt ccctggagat ctctccaatt accttcctga cagcacagac tctgctgatg | 960 |
| gacctggggc agttcctgct gttttgccac atcagctccc caccagcatga tggcatggag | 1020 |
| gcttacgtga agtggactc ttgtcccgag gaacctcagc tgcggatgaa gaacaatgag | 1080 |
| gaagcagaag actatgacga tgacctgacc gactccagaga tggatgtggt ccgattcgat | 1140 |
| gacgataaca gcccctcctt tatccagatt agatctgtgg ccaagaaaca ccctaagaca | 1200 |
| tgggtccatt acatcgcagc cgaggaagag actgggatt atgcaccact ggtgctggca | 1260 |
| ccagacgatc gctcctacaa atctcagtat ctgaacaatg gccacagag gattggcaga | 1320 |
| aagtacaaga agtgcggtt catggcatat accgatgaga ccttcaagac tcgcgaagcc | 1380 |
| atccagcacg agagcggcat cctgggacca ctgctgtacg agaagtggg agacaccctg | 1440 |
| ctgatcattt tcaagaacca ggccagccgg ccttacaata tctatccaca tgggattaca | 1500 |
| gatgtgcgcc ctctgtacag caggagactg ccaaagggcg tcaaacacct gaaggacttc | 1560 |
| ccaatcctgc ccggagaaat cttcaagtac aagtggactg tcaccgtcga ggatggcccc | 1620 |
| actaagagcg accctcggtg cctgacccgc tactattcta gtttcgtgaa tatggaaaga | 1680 |
| gatctggcaa gcggactgat cggaccactg ctgatttgtt acaaagagag cgtggatcag | 1740 |
| agaggcaacc agatcatgtc cgacaagcgg aatgtgattc tgttcagtgt ctttgacgaa | 1800 |

```
aacaggtcat ggtacctgac cgagaacatc cagagattcc tgcctaatcc agctggggtg    1860
cagctggaag atcctgagtt tcaggcatct aacatcatgc atagtattaa tggctacgtg    1920
ttcgacagtt tgcagctgag cgtgtgcctg cacgaggtcg cttactggta tatcctgagc    1980
attggggcac agacagattt cctgagcgtg ttcttttccg gctacacttt taagcataaa    2040
atggtctatg aggacacact gactctgttc cccttcagcg gcgaaaccgt gtttatgagc    2100
atggagaatc ccgactgtg gattctgggg tgccacaaca gcgatttcag aaatcgcgga    2160
atgactgccc tgctgaaagt gtcaagctgt gacaagaaca ccggggacta ctatgaagat    2220
tcatacgagg acatcagcgc atatctgctg tccaaaaaca atgccattga accccggtct    2280
tttagtcaga atggcgcgcc aacatcagag agcgccaccc tgaaagtgg tcccgggagc     2340 gagccagcca catctgggtc ggaaacgcca ggcacaagtg agtctgcaac tcccgagtcc    2400
ggacctggct ccgagcctgc cactagcggc tccgagactc cgggaacttc cgagagcgct    2460
acaccagaaa gcggacccgg aaccagtacc gaacctagcg agggctctgc tccgggcagc    2520
ccagccggct ctcctacatc cacggaggag ggcacttccg aatccgccac cccggagtca    2580 gggcaggat ctgaacccgc tacctcaggc agtgagacgc caggaacgag cgagtccgct     2640
acaccggaga gtgggccagg gagccctgct ggatctccta cgtccactga ggaagggtca    2700
ccagcgggct cgcccaccag cactgaagaa ggtgcctcga gccctccagt gctgaagcgg    2760
caccagcgcg agatcacccg cactaccctg cagagtgatc aggaagagat cgactacgac    2820
gatacaattt ctgtggaaat gaagaaagag gacttcgata tctatgacga agatgagaac    2880
cagagtcctc gatcattcca gaagaaaacc aggcattact ttattgccgc agtggagcgg    2940
ctgtgggatt atggcatgtc ctctagtcct cacgtgctgc gaaatagggc ccagtcagga    3000
agcgtcccac agttcaagaa agtggtcttc caggagttta cagacgggtc ctttactcag    3060
ccactgtaca ggggcgaact gaacgagcac ctgggactgc tggggcccta tatcagagca    3120
gaagtggagg ataacattat ggtcaccttc agaaatcagg cctctcggcc ttacagtttt    3180
tattcaagcc tgatctctta cgaagaggac cagcgacagg gagctgaacc acgaaaaaac    3240
ttcgtgaagc ctaatgagac caaaacatac ttttggaagg tgcagcacca tatggcccca    3300
acaaaagacg agttcgattg caaggcatgg gcctattttt ctgacgtgga tctggagaag    3360
gacgtgcaca gtgcctgat tggcccactg ctggtgtgcc atactaacac cctgaatcca     3420
gcccacggcc ggcaggtcac tgtccaggag ttcgctctgt tctttaccat ctttgatgag    3480
acaaagagct ggtacttcac cgaaaacatg gagcgaaatt gcagggctcc atgtaacatt    3540
cagatggaag acccccacatt caaggagaac taccgctttc atgctatcaa tggatacatc    3600
atggatactc tgcccgggct ggtcatggca caggaccaga gaatccggtg gtatctgctg    3660
agcatgggca gcaacgagaa tatccactca attcatttca gcgggcacgt gtttactgtc    3720
aggaagaaag aagagtacaa gatggccctg tacaacctgt atcccggcgt gttcgaaacc    3780
gtcgagatgc tgcctagcaa ggccggaatc tggagagtgg aatgcctgat tggagagcac    3840
ctgcatgctg ggatgtctac cctgtttctg gtgtacagta ataagtgtca gacacccctg    3900
ggaatggcat ccgggcatat cagggatttc cagattaccg catctggaca gtacggacag    3960
tgggcaccta agctggctag actgcactat tccggatcta tcaacgcttg gtccacaaaa    4020
gagcctttct cttggattaa ggtggacctg ctggccccaa tgatcattca tggcatcaaa    4080
actcagggag ctcggcagaa gttctcctct ctgtacatct cacagtttat catcatgtac    4140
```

-continued

```
agcctggatg ggaagaaatg gcagacatac cgcggcaata gcacaggaac tctgatggtg    4200
ttctttggca acgtggacag cagcggaatc aagcacaaca ttttcaatcc ccctatcatt    4260
gctagataca tccggctgca cccaacccat tattctattc gaagtacact gaggatggaa    4320
ctgatgggat gcgatctgaa cagttgttca atgcccctgg ggatggagtc caaggcaatc    4380
tctgacgccc agattaccgc cagctcctac ttcactaata tgtttgctac ctggagccct    4440
tccaaagcaa gactgcacct gcaaggccgc agcaacgcat ggcgaccaca ggtgaacaat    4500
cccaaggagt ggttgcaggt cgattttcag aaaactatga aggtgaccgg ggtcacaact    4560
cagggcgtga aaagtctgct gacctcaatg tacgtcaagg agttcctgat ctctagttca    4620
caggacggac atcagtggac actgttcttt cagaacggga aggtgaaagt cttccagggc    4680
aatcaggatt cctttacacc tgtggtcaac agtctagacc ctccactgct gaccagatac    4740
ctgagaatcc accctcagtc ctgggtgcac cagattgccc tgagaatgga agtgctggga    4800
tgcgaggccc aggatctgta ctga                                           4824
```

```
<210> SEQ ID NO 21
<211> LENGTH: 6
<212> TYPE: DNA
<213> ORGANISM: Artificial Sequence
<220> FEATURE:
<223> OTHER INFORMATION: MAR/ARS

<400> SEQUENCE: 21 atattt                                                                    6

<210> SEQ ID NO 22
<211> LENGTH: 6
<212> TYPE: DNA
<213> ORGANISM: Artificial Sequence
<220> FEATURE:
<223> OTHER INFORMATION: MAR/ARS

<400> SEQUENCE: 22 aaatat                                                                    6

<210> SEQ ID NO 23
<211> LENGTH: 5
<212> TYPE: DNA
<213> ORGANISM: Artificial Sequence
<220> FEATURE:
<223> OTHER INFORMATION: destabilizing element

<400> SEQUENCE: 23 attta                                                                     5

<210> SEQ ID NO 24
<211> LENGTH: 5
<212> TYPE: DNA
<213> ORGANISM: Artificial Sequence
<220> FEATURE:
<223> OTHER INFORMATION: destabilizing element

<400> SEQUENCE: 24 taaat                                                                     5

<210> SEQ ID NO 25
<211> LENGTH: 6
<212> TYPE: DNA
<213> ORGANISM: Artificial Sequence
<220> FEATURE:
<223> OTHER INFORMATION: poly-T site
```

<400> SEQUENCE: 25 ttttttt                                                                     6

<210> SEQ ID NO 26
<211> LENGTH: 7
<212> TYPE: DNA
<213> ORGANISM: Artificial Sequence
<220> FEATURE:
<223> OTHER INFORMATION: poly-A site

<400> SEQUENCE: 26 aaaaaaa                                                                     7

<210> SEQ ID NO 27
<211> LENGTH: 6
<212> TYPE: DNA
<213> ORGANISM: Artificial Sequence
<220> FEATURE:
<223> OTHER INFORMATION: splice site

<400> SEQUENCE: 27 ggtgat                                                                      6

<210> SEQ ID NO 28
<211> LENGTH: 5
<212> TYPE: DNA
<213> ORGANISM: Artificial Sequence
<220> FEATURE:
<223> OTHER INFORMATION: TATA box

<400> SEQUENCE: 28 tataa                                                                       5

<210> SEQ ID NO 29
<211> LENGTH: 5
<212> TYPE: DNA
<213> ORGANISM: Artificial Sequence
<220> FEATURE:
<223> OTHER INFORMATION: TATA box

<400> SEQUENCE: 29 ttata                                                                       5

<210> SEQ ID NO 30
<211> LENGTH: 8
<212> TYPE: DNA
<213> ORGANISM: Artificial Sequence
<220> FEATURE:
<223> OTHER INFORMATION: AU rich sequence element

<400> SEQUENCE: 30 attttatt                                                                    8

<210> SEQ ID NO 31
<211> LENGTH: 8
<212> TYPE: DNA
<213> ORGANISM: Artificial Sequence
<220> FEATURE:
<223> OTHER INFORMATION: AU rich sequence element

<400> SEQUENCE: 31 attttaa                                                                     8

<210> SEQ ID NO 32

```
<211> LENGTH: 13
<212> TYPE: DNA
<213> ORGANISM: Artificial Sequence
<220> FEATURE:
<223> OTHER INFORMATION: kozak consensus sequence

<400> SEQUENCE: 32
gccgccacca tgc                                                            13

<210> SEQ ID NO 33
<211> LENGTH: 32
<212> TYPE: PRT
<213> ORGANISM: Artificial Sequence
<220> FEATURE:
<223> OTHER INFORMATION: CTP peptide

<400> SEQUENCE: 33

Asp Pro Arg Phe Gln Asp Ser Ser Ser Ser Lys Ala Pro Pro Pro Ser
1               5                   10                  15

Leu Pro Ser Pro Ser Arg Leu Pro Gly Pro Ser Asp Thr Pro Ile Leu
            20                  25                  30

<210> SEQ ID NO 34
<211> LENGTH: 28
<212> TYPE: PRT
<213> ORGANISM: Artificial Sequence
<220> FEATURE:
<223> OTHER INFORMATION: CTP peptide

<400> SEQUENCE: 34

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 35
<211> LENGTH: 11
<212> TYPE: PRT
<213> ORGANISM: Artificial Sequence
<220> FEATURE:
<223> OTHER INFORMATION: albumin-binding peptide core sequence

<400> SEQUENCE: 35

Asp Ile Cys Leu Pro Arg Trp Gly Cys Leu Trp
1               5                   10

<210> SEQ ID NO 36
<211> LENGTH: 20
<212> TYPE: PRT
<213> ORGANISM: Artificial Sequence
<220> FEATURE:
<223> OTHER INFORMATION: PAS sequence

<400> SEQUENCE: 36

Ala Ser Pro Ala Ala Pro Ala Pro Ala Ser Pro Ala Ala Pro Ala Pro
1               5                   10                  15

Ser Ala Pro Ala
            20

<210> SEQ ID NO 37
<211> LENGTH: 20
<212> TYPE: PRT
<213> ORGANISM: Artificial Sequence
<220> FEATURE:
<223> OTHER INFORMATION: PAS sequence
```

<400> SEQUENCE: 37

Ala Ala Pro Ala Ser Pro Ala Pro Ala Ala Pro Ser Ala Pro Ala Pro
1               5                   10                  15

Ala Ala Pro Ser
            20

<210> SEQ ID NO 38
<211> LENGTH: 20
<212> TYPE: PRT
<213> ORGANISM: Artificial Sequence
<220> FEATURE:
<223> OTHER INFORMATION: PAS sequence

<400> SEQUENCE: 38

Ala Pro Ser Ser Pro Ser Pro Ser Ala Pro Ser Ser Pro Ser Pro Ala
1               5                   10                  15

Ser Pro Ser Ser
            20

<210> SEQ ID NO 39
<211> LENGTH: 19
<212> TYPE: PRT
<213> ORGANISM: Artificial Sequence
<220> FEATURE:
<223> OTHER INFORMATION: PAS sequence

<400> SEQUENCE: 39

Ala Pro Ser Ser Pro Ser Pro Ser Ala Pro Ser Ser Pro Ser Pro Ala
1               5                   10                  15

Ser Pro Ser

<210> SEQ ID NO 40
<211> LENGTH: 20
<212> TYPE: PRT
<213> ORGANISM: Artificial Sequence
<220> FEATURE:
<223> OTHER INFORMATION: PAS sequence

<400> SEQUENCE: 40

Ser Ser Pro Ser Ala Pro Ser Pro Ser Ser Pro Ala Ser Pro Ser Pro
1               5                   10                  15

Ser Ser Pro Ala
            20

<210> SEQ ID NO 41
<211> LENGTH: 24
<212> TYPE: PRT
<213> ORGANISM: Artificial Sequence
<220> FEATURE:
<223> OTHER INFORMATION: PAS sequence

<400> SEQUENCE: 41

Ala Ala Ser Pro Ala Ala Pro Ser Ala Pro Pro Ala Ala Ala Ser Pro
1               5                   10                  15

Ala Ala Pro Ser Ala Pro Pro Ala
            20

<210> SEQ ID NO 42
<211> LENGTH: 20
<212> TYPE: PRT
<213> ORGANISM: Artificial Sequence
<220> FEATURE:
<223> OTHER INFORMATION: PAS sequence

```
<400> SEQUENCE: 42

Ala Ser Ala Ala Ala Pro Ala Ala Ser Ala Ala Ser Ala Pro
1               5                   10                  15

Ser Ala Ala Ala
            20

<210> SEQ ID NO 43
<211> LENGTH: 23
<212> TYPE: DNA
<213> ORGANISM: Artificial Sequence
<220> FEATURE:
<223> OTHER INFORMATION: miR142 target

<400> SEQUENCE: 43
tccataaagt aggaaacact aca                                           23

<210> SEQ ID NO 44
<211> LENGTH: 2332
<212> TYPE: PRT
<213> ORGANISM: Homo sapiens

<400> SEQUENCE: 44

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270
```

```
Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asn Ser Pro Ser Phe
    355                 360                 365

Ile Gln Ile Arg Ser Val Ala Lys Lys His Pro Lys Thr Trp Val His
370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
            450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
            610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
```

-continued

```
            690             695             700
Leu Leu Lys Val Ser Ser Cys Asp Lys Asn Thr Gly Asp Tyr Tyr Glu
705             710             715             720

Asp Ser Tyr Glu Asp Ile Ser Ala Tyr Leu Ser Lys Asn Asn Ala
            725             730             735

Ile Glu Pro Arg Ser Phe Ser Gln Asn Ser Arg His Pro Ser Thr Arg
            740             745             750

Gln Lys Gln Phe Asn Ala Thr Thr Ile Pro Glu Asn Asp Ile Glu Lys
        755             760             765

Thr Asp Pro Trp Phe Ala His Arg Thr Pro Met Pro Lys Ile Gln Asn
        770             775             780

Val Ser Ser Ser Asp Leu Leu Met Leu Leu Arg Gln Ser Pro Thr Pro
785             790             795             800

His Gly Leu Ser Leu Ser Asp Leu Gln Glu Ala Lys Tyr Glu Thr Phe
            805             810             815

Ser Asp Asp Pro Ser Pro Gly Ala Ile Asp Ser Asn Asn Ser Leu Ser
            820             825             830

Glu Met Thr His Phe Arg Pro Gln Leu His His Ser Gly Asp Met Val
        835             840             845

Phe Thr Pro Glu Ser Gly Leu Gln Leu Arg Leu Asn Glu Lys Leu Gly
850             855             860

Thr Thr Ala Ala Thr Glu Leu Lys Lys Leu Asp Phe Lys Val Ser Ser
865             870             875             880

Thr Ser Asn Asn Leu Ile Ser Thr Ile Pro Ser Asp Asn Leu Ala Ala
            885             890             895

Gly Thr Asp Asn Thr Ser Ser Leu Gly Pro Pro Ser Met Pro Val His
            900             905             910

Tyr Asp Ser Gln Leu Asp Thr Thr Leu Phe Gly Lys Lys Ser Ser Pro
        915             920             925

Leu Thr Glu Ser Gly Gly Pro Leu Ser Leu Ser Glu Glu Asn Asn Asp
930             935             940

Ser Lys Leu Leu Glu Ser Gly Leu Met Asn Ser Gln Glu Ser Ser Trp
945             950             955             960

Gly Lys Asn Val Ser Ser Thr Glu Ser Gly Arg Leu Phe Lys Gly Lys
            965             970             975

Arg Ala His Gly Pro Ala Leu Leu Thr Lys Asp Asn Ala Leu Phe Lys
            980             985             990

Val Ser Ile Ser Leu Leu Lys Thr Asn Lys Thr Ser Asn Asn Ser Ala
        995             1000            1005

Thr Asn Arg Lys Thr His Ile Asp Gly Pro Ser Leu Leu Ile Glu
        1010            1015            1020

Asn Ser Pro Ser Val Trp Gln Asn Ile Leu Glu Ser Asp Thr Glu
        1025            1030            1035

Phe Lys Lys Val Thr Pro Leu Ile His Asp Arg Met Leu Met Asp
        1040            1045            1050

Lys Asn Ala Thr Ala Leu Arg Leu Asn His Met Ser Asn Lys Thr
        1055            1060            1065

Thr Ser Ser Lys Asn Met Glu Met Val Gln Gln Lys Lys Glu Gly
        1070            1075            1080

Pro Ile Pro Pro Asp Ala Gln Asn Pro Asp Met Ser Phe Phe Lys
        1085            1090            1095

Met Leu Phe Leu Pro Glu Ser Ala Arg Trp Ile Gln Arg Thr His
        1100            1105            1110
```

```
Gly Lys Asn Ser Leu Asn Ser Gly Gln Gly Pro Ser Pro Lys Gln
    1115            1120                1125

Leu Val Ser Leu Gly Pro Glu Lys Ser Val Glu Gly Gln Asn Phe
    1130            1135                1140

Leu Ser Glu Lys Asn Lys Val Val Val Gly Lys Gly Glu Phe Thr
    1145            1150                1155

Lys Asp Val Gly Leu Lys Glu Met Val Phe Pro Ser Ser Arg Asn
    1160            1165                1170

Leu Phe Leu Thr Asn Leu Asp Asn Leu His Glu Asn Asn Thr His
    1175            1180                1185

Asn Gln Glu Lys Lys Ile Gln Glu Ile Glu Lys Lys Glu Thr
    1190            1195                1200

Leu Ile Gln Glu Asn Val Val Leu Pro Gln Ile His Thr Val Thr
    1205            1210                1215

Gly Thr Lys Asn Phe Met Lys Asn Leu Phe Leu Leu Ser Thr Arg
    1220            1225                1230

Gln Asn Val Glu Gly Ser Tyr Asp Gly Ala Tyr Ala Pro Val Leu
    1235            1240                1245

Gln Asp Phe Arg Ser Leu Asn Asp Ser Thr Asn Arg Thr Lys Lys
    1250            1255                1260

His Thr Ala His Phe Ser Lys Lys Gly Glu Glu Asn Leu Glu
    1265            1270                1275

Gly Leu Gly Asn Gln Thr Lys Gln Ile Val Glu Lys Tyr Ala Cys
    1280            1285                1290

Thr Thr Arg Ile Ser Pro Asn Thr Ser Gln Gln Asn Phe Val Thr
    1295            1300                1305

Gln Arg Ser Lys Arg Ala Leu Lys Gln Phe Arg Leu Pro Leu Glu
    1310            1315                1320

Glu Thr Glu Leu Glu Lys Arg Ile Ile Val Asp Asp Thr Ser Thr
    1325            1330                1335

Gln Trp Ser Lys Asn Met Lys His Leu Thr Pro Ser Thr Leu Thr
    1340            1345                1350

Gln Ile Asp Tyr Asn Glu Lys Glu Lys Gly Ala Ile Thr Gln Ser
    1355            1360                1365

Pro Leu Ser Asp Cys Leu Thr Arg Ser His Ser Ile Pro Gln Ala
    1370            1375                1380

Asn Arg Ser Pro Leu Pro Ile Ala Lys Val Ser Ser Phe Pro Ser
    1385            1390                1395

Ile Arg Pro Ile Tyr Leu Thr Arg Val Leu Phe Gln Asp Asn Ser
    1400            1405                1410

Ser His Leu Pro Ala Ala Ser Tyr Arg Lys Lys Asp Ser Gly Val
    1415            1420                1425

Gln Glu Ser Ser His Phe Leu Gln Gly Ala Lys Lys Asn Asn Leu
    1430            1435                1440

Ser Leu Ala Ile Leu Thr Leu Glu Met Thr Gly Asp Gln Arg Glu
    1445            1450                1455

Val Gly Ser Leu Gly Thr Ser Ala Thr Asn Ser Val Thr Tyr Lys
    1460            1465                1470

Lys Val Glu Asn Thr Val Leu Pro Lys Pro Asp Leu Pro Lys Thr
    1475            1480                1485

Ser Gly Lys Val Glu Leu Leu Pro Lys Val His Ile Tyr Gln Lys
    1490            1495                1500
```

```
Asp Leu Phe Pro Thr Glu Thr Ser Asn Gly Ser Pro Gly His Leu
    1505                1510                1515

Asp Leu Val Glu Gly Ser Leu Leu Gln Gly Thr Glu Gly Ala Ile
    1520                1525                1530

Lys Trp Asn Glu Ala Asn Arg Pro Gly Lys Val Pro Phe Leu Arg
    1535                1540                1545

Val Ala Thr Glu Ser Ser Ala Lys Thr Pro Ser Lys Leu Leu Asp
    1550                1555                1560

Pro Leu Ala Trp Asp Asn His Tyr Gly Thr Gln Ile Pro Lys Glu
    1565                1570                1575

Glu Trp Lys Ser Gln Glu Lys Ser Pro Glu Lys Thr Ala Phe Lys
    1580                1585                1590

Lys Lys Asp Thr Ile Leu Ser Leu Asn Ala Cys Glu Ser Asn His
    1595                1600                1605

Ala Ile Ala Ala Ile Asn Glu Gly Gln Asn Lys Pro Glu Ile Glu
    1610                1615                1620

Val Thr Trp Ala Lys Gln Gly Arg Thr Glu Arg Leu Cys Ser Gln
    1625                1630                1635

Asn Pro Pro Val Leu Lys Arg His Gln Arg Glu Ile Thr Arg Thr
    1640                1645                1650

Thr Leu Gln Ser Asp Gln Glu Glu Ile Asp Tyr Asp Asp Thr Ile
    1655                1660                1665

Ser Val Glu Met Lys Lys Glu Asp Phe Asp Ile Tyr Asp Glu Asp
    1670                1675                1680

Glu Asn Gln Ser Pro Arg Ser Phe Gln Lys Lys Thr Arg His Tyr
    1685                1690                1695

Phe Ile Ala Ala Val Glu Arg Leu Trp Asp Tyr Gly Met Ser Ser
    1700                1705                1710

Ser Pro His Val Leu Arg Asn Arg Ala Gln Ser Gly Ser Val Pro
    1715                1720                1725

Gln Phe Lys Lys Val Val Phe Gln Glu Phe Thr Asp Gly Ser Phe
    1730                1735                1740

Thr Gln Pro Leu Tyr Arg Gly Glu Leu Asn Glu His Leu Gly Leu
    1745                1750                1755

Leu Gly Pro Tyr Ile Arg Ala Glu Val Glu Asp Asn Ile Met Val
    1760                1765                1770

Thr Phe Arg Asn Gln Ala Ser Arg Pro Tyr Ser Phe Tyr Ser Ser
    1775                1780                1785

Leu Ile Ser Tyr Glu Glu Asp Gln Arg Gln Gly Ala Glu Pro Arg
    1790                1795                1800

Lys Asn Phe Val Lys Pro Asn Glu Thr Lys Thr Tyr Phe Trp Lys
    1805                1810                1815

Val Gln His His Met Ala Pro Thr Lys Asp Glu Phe Asp Cys Lys
    1820                1825                1830

Ala Trp Ala Tyr Phe Ser Asp Val Asp Leu Glu Lys Asp Val His
    1835                1840                1845

Ser Gly Leu Ile Gly Pro Leu Leu Val Cys His Thr Asn Thr Leu
    1850                1855                1860

Asn Pro Ala His Gly Arg Gln Val Thr Val Gln Glu Phe Ala Leu
    1865                1870                1875

Phe Phe Thr Ile Phe Asp Glu Thr Lys Ser Trp Tyr Phe Thr Glu
    1880                1885                1890

Asn Met Glu Arg Asn Cys Arg Ala Pro Cys Asn Ile Gln Met Glu
```

-continued

```
            1895                1900                1905
Asp Pro Thr Phe Lys Glu Asn Tyr Arg Phe His Ala Ile Asn Gly
        1910                1915                1920
Tyr Ile Met Asp Thr Leu Pro Gly Leu Val Met Ala Gln Asp Gln
        1925                1930                1935
Arg Ile Arg Trp Tyr Leu Leu Ser Met Gly Ser Asn Glu Asn Ile
        1940                1945                1950
His Ser Ile His Phe Ser Gly His Val Phe Thr Val Arg Lys Lys
        1955                1960                1965
Glu Glu Tyr Lys Met Ala Leu Tyr Asn Leu Tyr Pro Gly Val Phe
        1970                1975                1980
Glu Thr Val Glu Met Leu Pro Ser Lys Ala Gly Ile Trp Arg Val
        1985                1990                1995
Glu Cys Leu Ile Gly Glu His Leu His Ala Gly Met Ser Thr Leu
        2000                2005                2010
Phe Leu Val Tyr Ser Asn Lys Cys Gln Thr Pro Leu Gly Met Ala
        2015                2020                2025
Ser Gly His Ile Arg Asp Phe Gln Ile Thr Ala Ser Gly Gln Tyr
        2030                2035                2040
Gly Gln Trp Ala Pro Lys Leu Ala Arg Leu His Tyr Ser Gly Ser
        2045                2050                2055
Ile Asn Ala Trp Ser Thr Lys Glu Pro Phe Ser Trp Ile Lys Val
        2060                2065                2070
Asp Leu Leu Ala Pro Met Ile Ile His Gly Ile Lys Thr Gln Gly
        2075                2080                2085
Ala Arg Gln Lys Phe Ser Ser Leu Tyr Ile Ser Gln Phe Ile Ile
        2090                2095                2100
Met Tyr Ser Leu Asp Gly Lys Lys Trp Gln Thr Tyr Arg Gly Asn
        2105                2110                2115
Ser Thr Gly Thr Leu Met Val Phe Phe Gly Asn Val Asp Ser Ser
        2120                2125                2130
Gly Ile Lys His Asn Ile Phe Asn Pro Pro Ile Ile Ala Arg Tyr
        2135                2140                2145
Ile Arg Leu His Pro Thr His Tyr Ser Ile Arg Ser Thr Leu Arg
        2150                2155                2160
Met Glu Leu Met Gly Cys Asp Leu Asn Ser Cys Ser Met Pro Leu
        2165                2170                2175
Gly Met Glu Ser Lys Ala Ile Ser Asp Ala Gln Ile Thr Ala Ser
        2180                2185                2190
Ser Tyr Phe Thr Asn Met Phe Ala Thr Trp Ser Pro Ser Lys Ala
        2195                2200                2205
Arg Leu His Leu Gln Gly Arg Ser Asn Ala Trp Arg Pro Gln Val
        2210                2215                2220
Asn Asn Pro Lys Glu Trp Leu Gln Val Asp Phe Gln Lys Thr Met
        2225                2230                2235
Lys Val Thr Gly Val Thr Thr Gln Gly Val Lys Ser Leu Leu Thr
        2240                2245                2250
Ser Met Tyr Val Lys Glu Phe Leu Ile Ser Ser Ser Gln Asp Gly
        2255                2260                2265
His Gln Trp Thr Leu Phe Phe Gln Asn Gly Lys Val Lys Val Phe
        2270                2275                2280
Gln Gly Asn Gln Asp Ser Phe Thr Pro Val Val Asn Ser Leu Asp
        2285                2290                2295
```

```
Pro Pro Leu Leu Thr Arg Tyr Leu Arg Ile His Pro Gln Ser Trp
   2300                2305                2310

Val His Gln Ile Ala Leu Arg Met Glu Val Leu Gly Cys Glu Ala
   2315                2320                2325

Gln Asp Leu Tyr
   2330

<210> SEQ ID NO 45
<211> LENGTH: 4
<212> TYPE: PRT
<213> ORGANISM: Artificial Sequence
<220> FEATURE:
<223> OTHER INFORMATION: amino acids 233-236 of human IgG1

<400> SEQUENCE: 45

Glu Leu Leu Gly
1

<210> SEQ ID NO 46
<211> LENGTH: 42
<212> TYPE: PRT
<213> ORGANISM: Artificial Sequence
<220> FEATURE:
<223> OTHER INFORMATION: XTEN AE42-4, protein sequence

<400> SEQUENCE: 46

Gly Ala Pro Gly Ser Pro Ala Gly Ser Pro Thr Ser Thr Glu Glu Gly
1               5                   10                  15

Thr Ser Glu Ser Ala Thr Pro Glu Ser Gly Pro Gly Ser Glu Pro Ala
            20                  25                  30

Thr Ser Gly Ser Glu Thr Pro Ala Ser Ser
        35                  40

<210> SEQ ID NO 47
<211> LENGTH: 126
<212> TYPE: DNA
<213> ORGANISM: Artificial Sequence
<220> FEATURE:
<223> OTHER INFORMATION: XTEN AE42-4, DNA sequence

<400> SEQUENCE: 47
ggcgcgccag gttctcctgc tggctccccc acctcaacag aagagggac aagcgaaagc      60 gctacgcctg agagtggccc tggctctgag ccagccacct ccggctctga aacccctgcc    120
tcgagc                                                                126

<210> SEQ ID NO 48
<211> LENGTH: 144
<212> TYPE: PRT
<213> ORGANISM: Artificial Sequence
<220> FEATURE:
<223> OTHER INFORMATION: XTEN AE144-2A, protein sequence

<400> SEQUENCE: 48

Thr Ser Thr Glu Pro Ser Glu Gly Ser Ala Pro Gly Ser Pro Ala Gly
1               5                   10                  15

Ser Pro Thr Ser Thr Glu Glu Gly Thr Ser Thr Glu Pro Ser Glu Gly
            20                  25                  30

Ser Ala Pro Gly Thr Ser Thr Glu Pro Ser Glu Gly Ser Ala Pro Gly
        35                  40                  45

Thr Ser Glu Ser Ala Thr Pro Glu Ser Gly Pro Gly Ser Thr Thr Glu
    50                  55                  60
```

```
Pro Ser Glu Gly Ser Ala Pro Gly Thr Ser Glu Ser Ala Thr Pro Glu
 65                  70                  75                  80

Ser Gly Pro Gly Ser Glu Pro Ala Thr Ser Gly Ser Glu Thr Pro Gly
                 85                  90                  95

Thr Ser Thr Glu Pro Ser Glu Gly Ser Ala Pro Gly Thr Ser Thr Glu
            100                 105                 110

Pro Ser Glu Gly Ser Ala Pro Gly Thr Ser Glu Ser Ala Thr Pro Glu
        115                 120                 125

Ser Gly Pro Gly Thr Ser Glu Ser Ala Thr Pro Glu Ser Gly Pro Gly
    130                 135                 140
```

<210> SEQ ID NO 49
<211> LENGTH: 450
<212> TYPE: DNA
<213> ORGANISM: Artificial Sequence
<220> FEATURE:
<223> OTHER INFORMATION: XTEN AE144-2A, DNA sequence

<400> SEQUENCE: 49

```
ggcgcgccaa ccagtacgga gccgtccgag gggagcgcac caggaagccc ggctgggagc      60
ccgacttcta ccgaagaggg tacatctacc gaaccaagtg aaggttcagc accaggcacc     120
tcaacagaac cctctgaggg ctcggcgcct ggtacaagtg agtccgccac cccagaatcc     180
gggcctggga caagcacaga accttcggaa gggagtgccc ctggaacatc gaatcggca      240 accccagaat cagggccagg atctgagccc gcgacttcgg gctccgagac gcctgggaca     300
tccaccgagc cctccgaagg atcagcccca ggcaccagca cggagccctc tgagggaagc     360
gcacctggta ccagcgaaag cgcaactccc gaatcaggtc ccggtacgag cgagtcggcg     420
accccggaga gcgggccagg tgcctcgagc                                     450
```

<210> SEQ ID NO 50
<211> LENGTH: 144
<212> TYPE: PRT
<213> ORGANISM: Artificial Sequence
<220> FEATURE:
<223> OTHER INFORMATION: XTEN AE144-3B, protein sequence

<400> SEQUENCE: 50

```
Ser Pro Ala Gly Ser Pro Thr Ser Thr Glu Glu Gly Thr Ser Glu Ser
1               5                   10                  15

Ala Thr Pro Glu Ser Gly Pro Gly Ser Glu Pro Ala Thr Ser Gly Ser
            20                  25                  30

Glu Thr Pro Gly Thr Ser Glu Ser Ala Thr Pro Glu Ser Gly Pro Gly
        35                  40                  45

Thr Ser Thr Glu Pro Ser Glu Gly Ser Ala Pro Gly Thr Ser Thr Glu
    50                  55                  60

Pro Ser Glu Gly Ser Ala Pro Gly Thr Ser Thr Glu Pro Ser Glu Gly
65                  70                  75                  80

Ser Ala Pro Gly Thr Ser Thr Glu Pro Ser Glu Gly Ser Ala Pro Gly
                85                  90                  95

Thr Ser Thr Glu Pro Ser Glu Gly Ser Ala Pro Gly Thr Ser Thr Glu
            100                 105                 110

Pro Ser Glu Gly Ser Ala Pro Gly Ser Pro Ala Gly Ser Pro Thr Ser
        115                 120                 125

Thr Glu Glu Gly Thr Ser Thr Glu Pro Ser Glu Gly Ser Ala Pro Gly
    130                 135                 140
```

<210> SEQ ID NO 51
<211> LENGTH: 450
<212> TYPE: DNA
<213> ORGANISM: Artificial Sequence
<220> FEATURE:
<223> OTHER INFORMATION: XTEN AE144-3B, DNA sequence

<400> SEQUENCE: 51

```
ggcgcgccaa gtcccgctgg aagcccaact agcaccgaag aggggacctc agagtccgcc     60
accccgagt ccggccctgg ctctgagcct gccactagcg gctccgagac tcctggcaca    120
tccgaaagcg ctacacccga gagtggaccc ggcacctcta ccgagcccag tgagggctcc    180
gccccctggaa caagcaccga gcccagcgaa ggcagcgccc cagggacctc cacagagccc    240
agtgaaggca gtgctcctgg caccagcacc gaaccaagcg agggctctgc acccgggacc    300
tccaccgagc caagcgaagg ctctgcccct ggcacttcca ccgagcccag cgaaggcagc    360
gccccctggga ccccgctgg ctctcccacc agcactgagg agggcacatc taccgaacca    420
agtgaaggct ctgcaccagg tgcctcgagc                                      450
```

<210> SEQ ID NO 52
<211> LENGTH: 144
<212> TYPE: PRT
<213> ORGANISM: Artificial Sequence
<220> FEATURE:
<223> OTHER INFORMATION: XTEN AE144-4A, protein sequence

<400> SEQUENCE: 52

```
Thr Ser Glu Ser Ala Thr Pro Glu Ser Gly Pro Gly Ser Glu Pro Ala
1               5                   10                  15

Thr Ser Gly Ser Glu Thr Pro Gly Thr Ser Glu Ser Ala Thr Pro Glu
            20                  25                  30

Ser Gly Pro Gly Ser Glu Pro Ala Thr Ser Gly Ser Glu Thr Pro Gly
        35                  40                  45

Thr Ser Glu Ser Ala Thr Pro Glu Ser Gly Pro Gly Thr Ser Thr Glu
    50                  55                  60

Pro Ser Glu Gly Ser Ala Pro Gly Thr Ser Glu Ser Ala Thr Pro Glu
65                  70                  75                  80

Ser Gly Pro Gly Ser Pro Ala Gly Ser Pro Thr Ser Thr Glu Glu Gly
                85                  90                  95

Ser Pro Ala Gly Ser Pro Thr Ser Thr Glu Glu Gly Ser Pro Ala Gly
            100                 105                 110

Ser Pro Thr Ser Thr Glu Glu Gly Thr Ser Glu Ser Ala Thr Pro Glu
        115                 120                 125

Ser Gly Pro Gly Thr Ser Thr Glu Pro Ser Glu Gly Ser Ala Pro Gly
    130                 135                 140
```

<210> SEQ ID NO 53
<211> LENGTH: 450
<212> TYPE: DNA
<213> ORGANISM: Artificial Sequence
<220> FEATURE:
<223> OTHER INFORMATION: XTEN AE144-4A, DNA sequence

<400> SEQUENCE: 53

```
ggcgcgccaa cgtccgaaag tgctacccct gagtcaggcc ctggtagtga gcctgccaca     60
agcggaagcg aaactccggg gacctcagag tctgccactc ccgaatcggg gccaggctct    120
gaaccggcca cttcagggag cgaaacacca ggaacatcgg agagcgctac cccggagagc    180
```

```
gggccaggaa ctagtactga gcctagcgag ggaagtgcac ctggtacaag cgagtccgcc      240
acacccgagt ctggccctgg ctctccagcg ggctcaccca cgagcactga agagggctct      300
cccgctggca gcccaacgtc gacagaagaa ggatcaccag caggctcccc cacatcaaca      360
gaggagggta catcagaatc tgctactccc gagagtggac ccggtacctc cactgagccc      420 agcgaggga gtgcaccagg tgcctcgagc                                       450
```

<210> SEQ ID NO 54
<211> LENGTH: 144
<212> TYPE: PRT
<213> ORGANISM: Artificial Sequence
<220> FEATURE:
<223> OTHER INFORMATION: XTEN AE144-5A, protein sequence

<400> SEQUENCE: 54

```
Thr Ser Glu Ser Ala Thr Pro Glu Ser Gly Pro Gly Ser Glu Pro Ala
1               5                   10                  15

Thr Ser Gly Ser Glu Thr Pro Gly Thr Ser Glu Ser Ala Thr Pro Glu
            20                  25                  30

Ser Gly Pro Gly Ser Glu Pro Ala Thr Ser Gly Ser Glu Thr Pro Gly
        35                  40                  45

Thr Ser Glu Ser Ala Thr Pro Glu Ser Gly Pro Gly Thr Ser Thr Glu
    50                  55                  60

Pro Ser Glu Gly Ser Ala Pro Gly Ser Pro Ala Gly Ser Pro Thr Ser
65                  70                  75                  80

Thr Glu Glu Gly Thr Ser Glu Ser Ala Thr Pro Glu Ser Gly Pro Gly
                85                  90                  95

Ser Glu Pro Ala Thr Ser Gly Ser Glu Thr Pro Gly Thr Ser Glu Ser
            100                 105                 110

Ala Thr Pro Glu Ser Gly Pro Gly Ser Pro Ala Gly Ser Pro Thr Ser
        115                 120                 125

Thr Glu Glu Gly Ser Pro Ala Gly Ser Pro Thr Ser Thr Glu Glu Gly
    130                 135                 140
```

<210> SEQ ID NO 55
<211> LENGTH: 450
<212> TYPE: DNA
<213> ORGANISM: Artificial Sequence
<220> FEATURE:
<223> OTHER INFORMATION: XTEN AE144-5A, DNA sequence

<400> SEQUENCE: 55

```
ggcgcgccaa catcagagag cgccacccct gaaagtggtc ccgggagcga gccagccaca       60
tctgggtcgg aaacgccagg cacaagtgag tctgcaactc ccgagtccgg acctggctcc      120
gagcctgcca ctagcggctc cgagactccg ggaacttccg agagcgctac accagaaagc      180
ggacccggaa ccagtaccga acctagcgag ggctctgctc cgggcagccc agccggctct      240
cctacatcca cggaggaggg cacttccgaa tccgccaccc cggagtcagg gccaggatct      300
gaacccgcta cctcaggcag tgagacgcca ggaacgagcg agtccgctac accggagagt      360
gggccaggga gccctgctgg atctcctacg tccactgagg aagggtcacc agcgggctcg      420
cccaccagca ctgaagaagg tgcctcgagc                                      450
```

<210> SEQ ID NO 56
<211> LENGTH: 144
<212> TYPE: PRT
<213> ORGANISM: Artificial Sequence
<220> FEATURE:

<223> OTHER INFORMATION: XTEN AE144-6B, protein sequence

<400> SEQUENCE: 56

Thr Ser Thr Glu Pro Ser Glu Gly Ser Ala Pro Gly Thr Ser Glu Ser
1               5                   10                  15

Ala Thr Pro Glu Ser Gly Pro Gly Thr Ser Glu Ser Ala Thr Pro Glu
            20                  25                  30

Ser Gly Pro Gly Thr Ser Glu Ser Ala Thr Pro Glu Ser Gly Pro Gly
        35                  40                  45

Ser Glu Pro Ala Thr Ser Gly Ser Glu Thr Pro Gly Ser Glu Pro Ala
    50                  55                  60

Thr Ser Gly Ser Glu Thr Pro Gly Ser Pro Ala Gly Ser Pro Thr Ser
65                  70                  75                  80

Thr Glu Glu Gly Thr Ser Thr Glu Pro Ser Glu Gly Ser Ala Pro Gly
                85                  90                  95

Thr Ser Thr Glu Pro Ser Glu Gly Ser Ala Pro Gly Ser Glu Pro Ala
            100                 105                 110

Thr Ser Gly Ser Glu Thr Pro Gly Thr Ser Glu Ser Ala Thr Pro Glu
        115                 120                 125

Ser Gly Pro Gly Thr Ser Thr Glu Pro Ser Glu Gly Ser Ala Pro Gly
    130                 135                 140

<210> SEQ ID NO 57
<211> LENGTH: 450
<212> TYPE: DNA
<213> ORGANISM: Artificial Sequence
<220> FEATURE:
<223> OTHER INFORMATION: XTEN AE144-6B, DNA sequence

<400> SEQUENCE: 57
ggcgcgccaa catctaccga gccttccgaa ggctctgccc ctgggacctc agaatctgca      60
acccctgaaa gcggccctgg aacctccgaa agtgccactc ccgagagcgg cccaggggaca    120 agcgagtcag caaccccctga gtctggaccc ggcagcgagc ctgcaacctc tggctcagag    180
actcccggct cagaaccccgc tacctcaggc tccgagacac ccggctctcc tgctgggagt    240
cccacttcca ccgaggaagg aacatccact gagcctagtg agggctctgc ccctggaacc    300
agcacagagc caagtgaggg cagtgcacca ggatccgagc cagcaaccag cgggtccgag    360
actcccggga cctctgagtc tgccaccccca gagagcggac ccggcacttc aaccgagccc    420
tccgaaggat cagcaccagg tgcctcgagc                                      450

<210> SEQ ID NO 58
<211> LENGTH: 144
<212> TYPE: PRT
<213> ORGANISM: Artificial Sequence
<220> FEATURE:
<223> OTHER INFORMATION: XTEN AG144-1, protein sequence

<400> SEQUENCE: 58

Pro Gly Ser Ser Pro Ser Ala Ser Thr Gly Thr Gly Pro Gly Ser Ser
1               5                   10                  15

Pro Ser Ala Ser Thr Gly Thr Gly Pro Gly Thr Pro Gly Ser Gly Thr
            20                  25                  30

Ala Ser Ser Ser Pro Gly Ser Ser Thr Pro Ser Gly Ala Thr Gly Ser
        35                  40                  45

Pro Gly Ser Ser Pro Ser Ala Ser Thr Gly Thr Gly Pro Gly Ala Ser
    50                  55                  60

Pro Gly Thr Ser Ser Thr Gly Ser Pro Gly Thr Gly Ser Gly Thr
65                  70                  75                  80

Ala Ser Ser Pro Gly Ser Ser Thr Pro Ser Gly Ala Thr Gly Ser
                85                  90                  95

Pro Gly Thr Pro Gly Ser Gly Thr Ala Ser Ser Ser Pro Gly Ala Ser
            100                 105                 110

Pro Gly Thr Ser Ser Thr Gly Ser Pro Gly Ala Ser Pro Gly Thr Ser
            115                 120                 125

Ser Thr Gly Ser Pro Gly Thr Pro Gly Ser Gly Thr Ala Ser Ser Ser
        130                 135                 140

<210> SEQ ID NO 59
<211> LENGTH: 450
<212> TYPE: DNA
<213> ORGANISM: Artificial Sequence
<220> FEATURE:
<223> OTHER INFORMATION: XTEN AG144-1, DNA sequence

<400> SEQUENCE: 59
ggcgcgccac ccgggtcgtc cccgtcggcg tccaccggaa cagggccagg gtcatccccg      60
tcagcgtcga ctgggacggg acccgggaca cccggttcgg ggactgcatc ctcctcgcct    120
ggttcgtcca ccccgtcagg agccacgggt cgccgggaa gcagcccaag cgcatccact     180
ggtacagggc ctggggcttc accgggtact tcatccacgg ggtcaccggg aacgccgga     240 tcggggacgg cttcctcatc accaggatcg tcaacaccct cgggcgcaac gggcagcccc    300
ggaacccctg gttcgggtac ggcgtcgtcg agccccggtg cgagcccggg aacaagctcg    360
acaggatcgc ctggggcgtc accggcacg tcgagcacag gcagccccgg aacccctgga     420
tcgggaaccg cgtcgtcaag cgcctcgagc                                     450

<210> SEQ ID NO 60
<211> LENGTH: 144
<212> TYPE: PRT
<213> ORGANISM: Artificial Sequence
<220> FEATURE:
<223> OTHER INFORMATION: XTEN AG144-A, protein sequence

<400> SEQUENCE: 60

Gly Ala Ser Pro Gly Thr Ser Ser Thr Gly Ser Pro Gly Ser Ser Pro
1               5                   10                  15

Ser Ala Ser Thr Gly Thr Gly Pro Gly Ser Ser Pro Ser Ala Ser Thr
                20                  25                  30

Gly Thr Gly Pro Gly Thr Pro Gly Ser Gly Thr Ala Ser Ser Ser Pro
            35                  40                  45

Gly Ser Ser Thr Pro Ser Gly Ala Thr Gly Ser Pro Gly Ser Ser Pro
        50                  55                  60

Ser Ala Ser Thr Gly Thr Gly Pro Gly Ala Ser Pro Gly Thr Ser Ser
65                  70                  75                  80

Thr Gly Ser Pro Gly Thr Pro Gly Ser Gly Thr Ala Ser Ser Ser Pro
                85                  90                  95

Gly Ser Ser Thr Pro Ser Gly Ala Thr Gly Ser Pro Gly Thr Pro Gly
            100                 105                 110

Ser Gly Thr Ala Ser Ser Ser Pro Gly Ala Ser Pro Gly Thr Ser Ser
        115                 120                 125

Thr Gly Ser Pro Gly Ala Ser Pro Gly Thr Ser Ser Thr Gly Ser Pro
130                 135                 140

```
<210> SEQ ID NO 61
<211> LENGTH: 450
<212> TYPE: DNA
<213> ORGANISM: Artificial Sequence
<220> FEATURE:
<223> OTHER INFORMATION: XTEN AG144-A, DNA sequence

<400> SEQUENCE: 61
ggcgcgccag gtgcctcgcc gggaacatca tcaactggtt cacccgggtc atcccctcg      60 gcctcaaccg ggacgggtcc cggctcatcc cccagcgcca gcactggaac aggtcctggc    120
actcctggtt ccggtacggc atcgtcatcc ccgggaagct caacaccgtc cggagcgaca    180
ggatcacctg gctcgtcacc ttcggcgtca actggaacgg ggccaggggc ctcacccgga    240
acgtcctcga ctgggtcgcc tggtacgccg ggatcaggaa cggcctcatc ctcgcctggg    300
tcctcaacgc cctcgggtgc gactggttcg ccgggaactc ctggctcggg gacgcctcg     360 tcgtcgcctg gggcatcacc ggggacgagc tccacggggt ccctggagc gtcaccgggg    420 acctcctcga caggtagccc ggcctcgagc                                     450

<210> SEQ ID NO 62
<211> LENGTH: 144
<212> TYPE: PRT
<213> ORGANISM: Artificial Sequence
<220> FEATURE:
<223> OTHER INFORMATION: XTEN AG144-B, protein sequence

<400> SEQUENCE: 62

Gly Thr Pro Gly Ser Gly Thr Ala Ser Ser Pro Gly Ser Ser Thr
1               5                   10                  15

Pro Ser Gly Ala Thr Gly Ser Pro Gly Ala Ser Pro Gly Thr Ser Ser
                20                  25                  30

Thr Gly Ser Pro Gly Thr Pro Gly Ser Gly Thr Ala Ser Ser Ser Pro
            35                  40                  45

Gly Ser Ser Thr Pro Ser Gly Ala Thr Gly Ser Pro Gly Ser Ser Pro
        50                  55                  60

Ser Ala Ser Thr Gly Thr Gly Pro Gly Ser Ser Pro Ser Ala Ser Thr
65                  70                  75                  80

Gly Thr Gly Pro Gly Ser Ser Thr Pro Ser Gly Ala Thr Gly Ser Pro
                85                  90                  95

Gly Ser Ser Thr Pro Ser Gly Ala Thr Gly Ser Pro Gly Ala Ser Pro
            100                 105                 110

Gly Thr Ser Ser Thr Gly Ser Pro Gly Ala Ser Pro Gly Thr Ser Ser
        115                 120                 125

Thr Gly Ser Pro Gly Ala Ser Pro Gly Thr Ser Ser Thr Gly Ser Pro
130                 135                 140

<210> SEQ ID NO 63
<211> LENGTH: 450
<212> TYPE: DNA
<213> ORGANISM: Artificial Sequence
<220> FEATURE:
<223> OTHER INFORMATION: XTEN AG144-B, DNA sequence

<400> SEQUENCE: 63
ggcgcgccag gtacaccggg cagcggcacg gcttcgtcgt cacccggctc gtccacaccg     60
tcgggagcta cgggaagccc aggagcgtca ccgggaacgt cgtcaacggg gtcaccgggt   120
acgccaggta gcgcacggc cagcagctcg ccaggttcat cgaccccgtc gggagcgact    180
gggtcgcccg gatcaagccc gtcagcttcc actggaacag gacccgggtc gtcgccgtca   240
```

```
gcctcaacgg ggacaggacc tggttcatcg acgccgtcag gggcgacagg ctcgcccgga    300
tcgtcaacac cctcggggc aacggggagc cctggtgcgt cgcctggaac ctcatccacc    360
ggaagcccgg ggcctcgcc gggtacgagc tccacgggat cgcccggagc gtcccccgga    420
acttcaagca cagggagccc tgcctcgagc                                    450
```

<210> SEQ ID NO 64
<211> LENGTH: 144
<212> TYPE: PRT
<213> ORGANISM: Artificial Sequence
<220> FEATURE:
<223> OTHER INFORMATION: XTEN AG144-C, protein sequence

<400> SEQUENCE: 64

```
Gly Thr Pro Gly Ser Gly Thr Ala Ser Ser Pro Gly Ala Ser Pro
1               5                   10                  15

Gly Thr Ser Ser Thr Gly Ser Pro Gly Ala Ser Pro Gly Thr Ser Ser
                20                  25                  30

Thr Gly Ser Pro Gly Ala Ser Pro Gly Thr Ser Ser Thr Gly Ser Pro
            35                  40                  45

Gly Ser Ser Pro Ser Ala Ser Thr Gly Thr Gly Pro Gly Thr Pro Gly
        50                  55                  60

Ser Gly Thr Ala Ser Ser Pro Gly Ala Ser Pro Gly Thr Ser Ser
65                  70                  75                  80

Thr Gly Ser Pro Gly Ala Ser Pro Gly Thr Ser Ser Thr Gly Ser Pro
                85                  90                  95

Gly Ala Ser Pro Gly Thr Ser Ser Thr Gly Ser Pro Gly Ser Ser Thr
            100                 105                 110

Pro Ser Gly Ala Thr Gly Ser Pro Gly Ser Ser Thr Pro Ser Gly Ala
        115                 120                 125

Thr Gly Ser Pro Gly Ala Ser Pro Gly Thr Ser Ser Thr Gly Ser Pro
    130                 135                 140
```

<210> SEQ ID NO 65
<211> LENGTH: 450
<212> TYPE: DNA
<213> ORGANISM: Artificial Sequence
<220> FEATURE:
<223> OTHER INFORMATION: XTEN AG144-C, DNA sequence

<400> SEQUENCE: 65

```
ggcgcgccag gtacacccgg atcgggtaca gcgtcatcga gccccggtgc gtcacctggt    60
acgtcgagca cggggtcgcc aggggcgtcc cctgggacgt cctcaacagg ctcgcccggt    120
gcgtcacccg gcacgtcgtc cacggttca cctggtagct ccccttccgc gtccactggc    180
accgggcctg gaactccggg gagcggcaca gcagctcgt cgccgggagc atcgcctggg    240
acatcgagca ccgggtcgcc aggagcatcg cccggaacat ccagcacagg aagcccggc    300 gcgtcgcccg ggacatcaag cacaggttcc ccgggatcga gcacgccgtc cggagccact    360
ggatcaccag ggagctcgac accttccggc gcaacgggat cgcccggagc cagcccgggt    420
acgtcaagca ctggctcccc tgcctcgagc                                    450
```

<210> SEQ ID NO 66
<211> LENGTH: 144
<212> TYPE: PRT
<213> ORGANISM: Artificial Sequence
<220> FEATURE:
<223> OTHER INFORMATION: XTEN AG144-F, protein sequence

<400> SEQUENCE: 66

Gly Ser Ser Pro Ser Ala Ser Thr Gly Thr Gly Pro Gly Ser Ser Pro
1               5                   10                  15

Ser Ala Ser Thr Gly Thr Gly Pro Gly Ala Ser Pro Gly Thr Ser Ser
            20                  25                  30

Thr Gly Ser Pro Gly Ala Ser Pro Gly Thr Ser Thr Gly Ser Pro
        35                  40                  45

Gly Ser Ser Thr Pro Ser Gly Ala Thr Gly Ser Pro Gly Ser Ser Pro
    50                  55                  60

Ser Ala Ser Thr Gly Thr Gly Pro Gly Ala Ser Pro Gly Thr Ser Ser
65                  70                  75                  80

Thr Gly Ser Pro Gly Ser Ser Pro Ser Ala Ser Thr Gly Thr Gly Pro
            85                  90                  95

Gly Thr Pro Gly Ser Gly Thr Ala Ser Ser Ser Pro Gly Ser Ser Thr
            100                 105                 110

Pro Ser Gly Ala Thr Gly Ser Pro Gly Ser Ser Thr Pro Ser Gly Ala
        115                 120                 125

Thr Gly Ser Pro Gly Ala Ser Pro Gly Thr Ser Ser Thr Gly Ser Pro
    130                 135                 140

<210> SEQ ID NO 67
<211> LENGTH: 450
<212> TYPE: DNA
<213> ORGANISM: Artificial Sequence
<220> FEATURE:
<223> OTHER INFORMATION: XTEN AG144-F, DNA sequence

<400> SEQUENCE: 67

```
ggcgcgccag gctccagccc ctccgcgagc acgggaaccg gaccaggttc gtcaccctca      60
gcatcaacgg ggacgggacc gggggcgtca ccaggaacgt cctccaccgg ctcgccgggt     120
gcatcacccg gaacgtcatc gaccggatcg ccagggagct cgacgccatc aggcgcaaca     180
ggatcacctg gctcaagccc tagcgcgtca accggcacgg gtccgggtgc ctcccctggc     240
acgtccagca ccggatcacc cggatcgagc ccatccgcct caaccggaac cggaccggt     300
acaccagggt cgggaacagc ctcctcgtca ccaggctcct caaccccctc gggagccacg     360
ggttcgcccg gttcgtcaac gccttccgga gcaactggta gccccggagc atcgccagga     420
acttcgagca cggggtcgcc cgcctcgagc                                      450
```

<210> SEQ ID NO 68
<211> LENGTH: 4374
<212> TYPE: DNA
<213> ORGANISM: Artificial Sequence
<220> FEATURE:
<223> OTHER INFORMATION: coFVIII-1 DNA Sequence

<400> SEQUENCE: 68

```
atgcagattg agctgtctac ttgctttttc ctgtgcctgc tgaggttttg cttttccgct      60
acacgaaggt attatctggg ggctgtggaa ctgtcttggg attacatgca gagtgacctg     120
ggagagctgc cagtggacgc aaggtttccc cctagagtcc ctaagtcatt ccccttcaac     180
actagcgtgg tctacaagaa aacactgttc gtggagttta ctgatcacct gttcaacatc     240
gcaaagccta ggccaccctg gatgggactg ctggggccaa caatccaggc cgaggtgtac     300
gacaccgtgt tcattacact taagaacatg gcctcacacc ccgtgagcct gcatgctgtg     360
ggcgtcagct actggaaggc ttccgaagga gcagagtatg acgatcagac ttcccagaga     420
```

```
gaaaaagagg acgataaggt gtttcctggc ggatctcata cctacgtgtg gcaggtcctg    480
aaagagaatg gccctatggc ctccgaccct ctgtgcctga cctactctta tctgagtcac    540
gtggacctgg tcaaggatct gaacagcggc ctgatcggag ccctgctggt gtgcagggaa    600
ggaagcctgg ctaaggagaa acccagaca ctgcataagt tcattctgct gttcgccgtg    660
tttgacgaag ggaaatcatg gcacagcgag acaagaata gtctgatgca ggacagggat    720
gccgcttcag ccagagcttg gcccaaaatg cacactgtga acggctacgt caatcgctca    780
ctgcctgggc tgatcggctg ccaccgaaag agcgtgtatt ggcatgtcat cgggatgggc    840
accacacctg aagtgcactc catttcctg gagggacata cctttctggt ccgcaaccac    900
cgacaggctt ccctggagat ctctccaatt accttcctga cagcacagac tctgctgatg    960
gacctggggc agttcctgct gttttgccac atcagctccc accagcatga tggcatggag   1020
gcttacgtga agtggactc ttgtcccgag gaacctcagc tgcggatgaa gaacaatgag   1080
gaagcagaag actatgacga tgacctgacc gactccgaga tggatgtggt ccgattcgat   1140
gacgataaca gcccctcctt tatccagatt agatctgtgg ccaagaaaca ccctaagaca   1200
tgggtccatt acatcgcagc cgaggaagag gactgggatt atgcaccact ggtgctggca   1260
ccagacgatc gctcctacaa atctcagtat ctgaacaatg gccacagag gattggcaga   1320 aagtacaaga agtgcggtt catggcatat accgatgaga ccttcaagac tcgcgaagcc   1380
atccagcacg agagcggcat cctgggacca ctgctgtacg agaagtggg agacaccctg   1440 ctgatcattt tcaagaacca ggccagccgg cctacaata tctatccaca tgggattaca   1500
gatgtgcgcc ctctgtacag caggagactg ccaaggggcg tcaaacacct gaaggacttc   1560
ccaatcctgc ccggagaaat cttcaagtac aagtggactg tcaccgtcga ggatggcccc   1620
actaagagcg accctcggtg cctgacccgc tactattcta gtttcgtgaa tatggaaaga   1680
gatctggcaa gcggactgat cggaccactg ctgatttgtt acaaagagag cgtggatcag   1740
agaggcaacc agatcatgtc cgacaagcgg aatgtgattc tgttcagtgt cttgacgaa   1800 aacaggtcat ggtacctgac cgagaacatc cagagattcc tgcctaatcc agctggggtg   1860
cagctggaag atcctgagtt tcaggcatct aacatcatgc atagtattaa tggctacgtg   1920
ttcgacagtt tgcagctgag cgtgtgcctg cacgaggtcg cttactggta tatcctgagc   1980 attgggcac agacagattt cctgagcgtg ttcttttccg gctacacttt taagcataaa   2040
atggtctatg aggacacact gactctgttc cccttcagcg cgaaaccgt gtttatgagc   2100 atggagaatc ccgactgtg gattctgggg tgccacaaca gcgatttcag aaatcgcgga   2160
atgactgccc tgctgaaagt gtcaagctgt gacaagaaca ccggggacta ctatgaagat   2220
tcatacgagg acatcagcgc atatctgctg tccaaaaaca tgccattga ccccggtct   2280 tttagtcaga atcctccagt gctgaagagg caccagaggg agatcacccg cactaccctg   2340
cagagtgatc aggaagagat cgactacgac gatacaattt ctgtggaaat gaagaaagag   2400
gacttcgata tctatgacga agatgagaac cagagtcctc gatcattcca gaagaaaacc   2460
aggcattact ttattgccgc agtggagcgg ctgtgggatt atggcatgtc ctctagtcct   2520
cacgtgctgc gaaatagggc ccagtcagga agcgtcccac agttcaagaa agtggtcttc   2580
caggagttta cagacgggtc ctttactcag ccactgtaca ggggcgaact gaacgagcac   2640
ctgggactgc tggggcccta tatcagagca gaagtggagg ataacattat ggtcaccttc   2700
agaaatcagg cctctcggcc ttacagttt tattcaagcc tgatctctta cgaagaggac   2760
```

```
cagcgacagg gagctgaacc acgaaaaaac ttcgtgaagc ctaatgagac caaaacatac    2820
ttttggaagg tgcagcacca tatggcccca acaaaagacg agttcgattg caaggcatgg    2880
gcctattttt ctgacgtgga tctggagaag gacgtgcaca gtggcctgat tggcccactg    2940
ctggtgtgcc atactaacac cctgaatcca gcccacggcc ggcaggtcac tgtccaggag    3000
ttcgctctgt tctttaccat cttttgatgag acaaagagct ggtacttcac cgaaaacatg    3060
gagcgaaatt gcagggctcc atgtaacatt cagatggaag accccacatt caaggagaac    3120
taccgctttc atgctatcaa tggatacatc atggatactc tgcccgggct ggtcatggca    3180
caggaccaga gaatccggtg gtatctgctg agcatgggca gcaacgagaa tatccactca    3240
attcatttca gcgggcacgt gtttactgtc aggaagaaag aagagtacaa gatggccctg    3300
tacaacctgt atcccggcgt gttcgaaacc gtcgagatgc tgcctagcaa ggccggaatc    3360
tggagagtgg aatgcctgat tggagagcac ctgcatgctg ggatgtctac cctgtttctg    3420
gtgtacagta ataagtgtca gacacccctg ggaatggcat ccgggcatat cagggatttc    3480
cagattaccg catctggaca gtacggacag tgggcaccta agctggctag actgcactat    3540
tccggatcta tcaacgcttg gtccacaaaa gagcctttct cttggattaa ggtggacctg    3600
ctggccccaa tgatcattca tggcatcaaa actcagggag ctcggcagaa gttctcctct    3660
ctgtacatct cacagtttat catcatgtac agcctggatg ggaagaaatg cagacatac    3720 cgcggcaata gcacaggaac tctgatggtg ttctttggca acgtggacag cagcggaatc    3780
aagcacaaca ttttcaatcc ccctatcatt gctagataca tccggctgca cccaacccat    3840
tattctattc gaagtacact gaggatgaaa ctgatgggat gcgatctgaa cagttgttca    3900
atgcccctgg ggatggagtc caaggcaatc tctgacgccc agattaccgc cagctcctac    3960
ttcactaata tgtttgctac ctggagccct tccaaagcaa gactgcacct gcaaggccgc    4020
agcaacgcat ggcgaccaca ggtgaacaat cccaaggagt ggttgcaggt cgattttcag    4080
aaaactatga aggtgaccgg ggtcacaact caggcgtga aaagtctgct gacctcaatg    4140
tacgtcaagg agttcctgat ctctagttca caggacggac atcagtggac actgttctttt    4200 cagaacggga aggtgaaagt cttccagggc aatcaggatt cctttacacc tgtggtcaac    4260
agtctagacc ctccactgct gaccagatac ctgagaatcc accctcagtc ctgggtgcac    4320
cagattgccc tgagaatgga agtgctggga tgcgaggccc aggatctgta ctga          4374
```

<210> SEQ ID NO 69
<211> LENGTH: 577
<212> TYPE: DNA
<213> ORGANISM: Artificial Sequence
<220> FEATURE:
<223> OTHER INFORMATION: ET Promoter, DNA sequence

<400> SEQUENCE: 69

```
ctcgaggtca attcacgcga gttaataatt accagcgcgg gccaaataaa taatccgcga      60
ggggcaggtg acgtttgccc agcgcgcgct ggtaattatt aacctcgcga atattgattc     120
gaggccgcga ttgccgcaat cgcgaggggc aggtgacctt tgcccagcgc gcgttcgccc     180
cgccccggac ggtatcgata agcttaggag cttgggctgc aggtcgaggg cactgggagg     240
atgttgagta agatggaaaa ctactgatga cccttgcaga gacagagtat taggacatgt     300
ttgaacaggg gccgggcgat cagcaggtag ctctagagga tccccgtctg tctgcacatt     360
tcgtagagcg agtgttccga tactctaatc tccctaggaa aggttcatat ttgtgtaggt     420
tacttattct ccttttgttg actaagtcaa taatcagaat cagcaggttt ggagtcagct     480
```

| | |
|---|---|
| tggcagggat cagcagcctg ggttggaagg aggggggtata aaagcccctt caccaggaga | 540 |
| agccgtcaca cagatccaca agctcctgcc accatgg | 577 |

<210> SEQ ID NO 70
<211> LENGTH: 4374
<212> TYPE: DNA
<213> ORGANISM: Artificial Sequence
<220> FEATURE:
<223> OTHER INFORMATION: coFVIII-5

<400> SEQUENCE: 70

| | |
|---|---|
| atgcaaatcg aactgagcac ctgtttcttc ctctgcctgc tgagattctg tttctccgcg | 60 |
| acccgccgat actacctggg agcagtggag ctctcctggg attacatgca gagcgacctt | 120 |
| ggggagctgc ccgtggatgc caggttccct ccccgggtgc caaagtcgtt ccgttcaac | 180 |
| acctccgtgg tgtacaagaa actctgttc gtggagttca ccgaccacct gttcaatatc | 240 |
| gccaagccca acctccctg atggggctg ttgggaccta ccatccaagc ggaggtgtac | 300 |
| gacactgtgg tcatcactct gaagaacatg gcctcgcatc ccgtgtccct gcacgccgtg | 360 |
| ggagtgtctt actggaaagc gtccgagggg ccgaatacg acgaccagac ctcgcagaga | 420 |
| gaaaaggaag atgacaaggt gttcccagga ggatcgcaca cctacgtgtg caagtgttg | 480 |
| aaggagaacg gcccaatggc ctccgacccg ctgtgcctga cctactcgta cctgtcccac | 540 |
| gtggacctcg tgaaggacct caactcggga ctgattggag ccctgctggt ctgcagggaa | 600 |
| ggctcactgg cgaaagaaaa gactcagacc ttgcacaagt tcattctgct gttcgctgtg | 660 |
| ttcgacgagg ggaagtcgtg gcacagcgag actaagaact ccctgatgca agatagagat | 720 |
| gccgcctccg cccgggcctg gcctaagatg cacaccgtga acggttacgt gaaccgctcc | 780 |
| ctccctggcc tgattggatg ccaccggaag tccgtgtact ggcacgtgat cgggatgggg | 840 |
| accaccccg aggtgcacag catcttcctg gaaggtcaca catttctcgt gcgcaaccac | 900 |
| cggcaggcct ccctggaaat cagccccatt accttcctca ctgcccagac tctgctgatg | 960 |
| gacctgggac agttcctgct gttctgccat atctcctccc accaacatga cggaatggag | 1020 |
| gcatacgtga aggtcgattc ctgccctgag gaaccccagc tccgcatgaa gaacaatgag | 1080 |
| gaagccgagg actacgacga cgacctgacg gatagcgaga tggatgtggt ccggttcgat | 1140 |
| gacgataaca gccttccctt catccaaatt cgctcggtgg caaagaagca ccccaagacc | 1200 |
| tgggtgcatt acattgcggc ggaagaagag gactgggatt atgccccgct tgtcctcgct | 1260 |
| cctgacgacc ggagctacaa gagccagtac ctgaacaacg gtccacagag gatcggtaga | 1320 |
| aagtacaaga aggtccgctt catggcctat accgacgaaa ccttcaaaac tagagaggcc | 1380 |
| atccaacacg aatccggcat cctgggcccg ctcttgtacg agaagtcgg cgacacctt | 1440 |
| ctcattatct tcaagaacca ggcttcccgg ccgtacaaca tctatccgca tgggatcact | 1500 |
| gacgtgcgcc cactgtactc gcggcgcctg cccaagggtg tcaaacacct gaaggatttt | 1560 |
| ccgatccttc cgggagaaat cttcaagtac aagtggaccg tgaccgtgga agatggccca | 1620 |
| actaagtctg accctagatg cctcacccgc tactactcat ccttcgtcaa catggagcgc | 1680 |
| gacctggcca gcggactgat cggcccgctg ctgatttgct acaaggaatc agtggaccaa | 1740 |
| cggggaaacc agatcatgtc ggataagagg aacgtcatcc tcttctccgt gtttgacgaa | 1800 |
| aaccggtcgt ggtacctgac tgaaaacatc cagcggttcc tccccaaccc cgcgggcgtg | 1860 |
| cagctggaag atcctgagtt tcaggcatca aacatcatgc actccattaa cggctacgtg | 1920 |

```
ttcgattcgc tgcagctgag cgtgtgtctg cacgaagtgg cctactggta catcctgtcc    1980
attggtgccc agactgactt cctgtccgtg ttttttctccg gctacacgtt caagcacaag    2040
atggtgtacg aggacaccct gaccctcttc ccttttttccg gcgaaactgt gtttatgagc    2100
atggagaatc ccggcctgtg gatcttgggc tgccacaaca gcgacttccg taacagagga    2160
atgactgcgc tgctcaaggt gtccagctgc gacaagaaca ccggagacta ttatgaggac    2220
tcatacgagg acatctccgc ctacctcctg tccaagaata cgccattga acctcggagc    2280
ttcagccaga acccacccgt gcttaagaga catcaacggg agatcactag gaccacccg    2340
cagtcagacc aggaggaaat cgactacgat gacaccatct cggtcgagat gaagaaggag    2400
gactttgaca tctacgacga agatgaaaac cagagcccga ggtcgttcca aagaaaacc    2460
cgccactact ttattgctgc tgtcgagcgg ctgtgggact acggaatgtc gtcctcgccg    2520
cacgtgctcc gcaaccgagc ccagagcggc tcggtgccgc aattcaagaa ggtcgtgttc    2580
caggagttca ctgacgggag cttcactcag cctttgtacc ggggagaact caatgaacat    2640
ctcggcctcc tcggacctta catcagagca gaagtggaag ataacatcat ggtcactttc    2700
cgtaaccaag ccagccgccc gtactcgttc tactcctccc tcatttctta cgaagaggac    2760
cagcggcagg gcgcagaacc gcgcaagaac ttcgtgaagc ccaacgaaac caagacctac    2820
ttctggaaag tgcagcatca tatggccccg actaaggacg agtttgactg caaagcctgg    2880
gcctacttct ccgatgtgga cttggagaag gacgtccact ccggcctcat cggtcccctg    2940
ctcgtgtgcc ataccaatac cctgaacccc gcacacggtc gccaggtcac cgtgcaggag    3000
ttcgctctgt tcttcactat cttcgacgaa actaagtcct ggtacttcac cgagaacatg    3060
gagaggaact gcagagcccc ctgtaacatc cagatggagg acccgacgtt caaggaaaac    3120
taccggttcc acgccattaa cggatacatc atggatacgc tgccgggtct tgtgatggcc    3180
caggatcaac ggatcagatg gtacttattg tcgatgggca gcaacgagaa catccactct    3240
attcacttct ccggtcatgt gttcactgtg cggaagaagg aagagtacaa gatggccctg    3300
tacaaccttt atcccggagt gttcgaaact gtggaaatgc tgccgtcgaa ggccggcatt    3360
tggcgcgtgg agtgtttgat tggagaacat ctccatgcgg ggatgtcaac cctgttcctg    3420
gtgtatagca acaagtgcca gactccgctt gggatggcgt caggacacat tagggatttc    3480
cagatcactg cgtccggcca gtacggccaa tgggccccta agctggcccg cctgcattac    3540
tccggatcca ttaacgcctg gtcaaccaag gagccattct cctggatcaa ggtggacctt    3600
ctggccccca tgattatcca cggaattaag acccagggg cccggcagaa gttctcctca    3660
ctgtacatca gccagttcat aatcatgtac tccctggacg gaaagaagtg gcaaacctac    3720
agggggaaca gcaccggcac actgatggtc ttttttcggaa atgtggactc ctccgggatt    3780
aagcataaca tcttcaaccc tccgattatc gctcggtaca ttagacttca ccctacccac    3840
tacagcattc gctccaccct gcggatggaa ctgatgggct gcgatctgaa ctcgtgcagc    3900
atgccgttgg gaatggagtc caaagcaatt tccgacgcgc agatcaccgc ctcgtcctac    3960
tttaccaaca tgttcgccac gtggtcaccg tccaaggccc ggctgcacct ccagggaaga    4020
tccaacgcat ggcggccaca ggtcaacaac cctaaggagt ggctccaggt ggacttccag    4080
aaaaccatga aggtcaccgg agtcacaacc cagggagtga agtcgctgct gacttctatg    4140
tacgtcaagg agttcctgat ctccagcagc caggacgggc accagtggac cctgttcttc    4200
caaaatggaa aggtcaaggt gttttcaggc aatcaggatt cattcacccc ggtggtgaac    4260
tcccttgatc caccccctcct gacccgctac cttcgcatcc acccacagtc ctgggtgcac    4320
```
cagatcgcgc tgaggatgga ggtcctggga tgcgaagccc aggacctgta ctga      4374

<210> SEQ ID NO 71
<211> LENGTH: 4374
<212> TYPE: DNA
<213> ORGANISM: Artificial Sequence
<220> FEATURE:
<223> OTHER INFORMATION: coFVIII-6

<400> SEQUENCE: 71

| | |
|---|---|
| atgcagattg agctgtccac ttgtttcttc ctgtgcctcc tgcgcttctg tttctccgcc | 60 |
| actcgccggt actaccttgg agccgtggag ctttcatggg actacatgca gagcgacctg | 120 |
| ggcgaactcc ccgtggatgc cagattcccc cccgcgtgc caaagtcctt cccctttaac | 180 |
| acctccgtgg tgtacaagaa aaccctcttt gtcgagttca ctgaccacct gttcaacatc | 240 |
| gccaagccgc gcccaccttg gatgggcctc ctgggaccga ccattcaagc tgaagtgtac | 300 |
| gacaccgtgg tgatcaccct gaagaacatg gcgtcccacc ccgtgtccct gcatgcggtc | 360 |
| ggagtgtcct actggaaggc tccgaagga gctgagtacg acgaccagac tagccagcgg | 420 |
| gaaaaggagg acgataaagt gttcccgggc ggctcgcata cttacgtgtg caagtcctg | 480 |
| aaggaaaacg gacctatggc atccgatcct ctgtgcctga cttactccta cctttcccat | 540 |
| gtggacctcg tgaaggacct gaacagcggg ctgattggtg cacttctcgt gtgccgcgaa | 600 |
| ggttcgctcg ctaaggaaaa gacccagacc ctccataagt tcatccttt gttcgctgtg | 660 |
| ttcgatgaag gaaagtcatg gcattccgaa actaagaact cgctgatgca ggaccgggat | 720 |
| gccgcctcag cccgcgcctg gcctaaaatg catacagtca acggatacgt gaatcggtca | 780 |
| ctgcccgggc tcatcggttg tcacagaaag tccgtgtact ggcacgtcat cggcatgggc | 840 |
| actacgcctg aagtgcactc catcttcctg gaagggcaca ccttcctcgt gcgcaaccac | 900 |
| cgccaggcct ctctggaaat ctccccgatt accttctga ccgccagac tctgctcatg | 960 |
| gacctggggc agttccttct cttctgccac atctccagcc atcagcacga cggaatggag | 1020 |
| gcctacgtga aggtggactc atgcccggaa gaacctcagt gcggatgaa gaacaacgag | 1080 |
| gaggccgagg actatgacga cgatttgact gactccgaga tggacgtcgt gcggttcgat | 1140 |
| gacgacaaca gccccagctt catccagatt cgcagcgtgg ccaagaagca ccccaaaacc | 1200 |
| tgggtgcact acatcgcggc cgaggaagaa gattgggact acgccccgtt ggtgctggca | 1260 |
| cccgatgacc ggtcgtacaa gtcccagtat ctgaacaatg gtccgcagcg gattggcaga | 1320 |
| aagtacaaga aagtgcggtt catggcgtac actgacgaaa cgtttaagac ccgggaggcc | 1380 |
| attcaacatg agagcggcat tctgggacca ctgctgtacg agaggtcgg cgataccctg | 1440 |
| ctcatcatct tcaaaaacca ggcctccgg cttacaacaa tctaccctca cggaatcacc | 1500 |
| gacgtgcggc cactctactc gcggcgcctg ccgaagggcg tcaagcacct gaaagacttc | 1560 |
| cctatcctgc cgggcgaaat cttcaagtat aagtggaccg tcaccgtgga ggacgggccc | 1620 |
| accaagagcg atcctaggtg tctgactcgg tactactcca gcttcgtgaa catggaacgg | 1680 |
| gacctggcat cgggactcat tggaccgctg ctgatctgct acaaagagtc ggtggatcaa | 1740 |
| cgcggcaacc agatcatgtc cgacaagcgc aacgtgatcc tgttctccgt gtttgatgaa | 1800 |
| aacagatcct ggtacctcac tgaaaacatc cagaggttcc tcccaaaccc cgcaggagtg | 1860 |
| caactggagg accctgagtt tcaggcctcg aatatcatgc actcgattaa cggttacgtg | 1920 |
| ttcgactcgc tgcagctgag cgtgtgcctc catgaagtcg cttactggta cattctgtcc | 1980 |

```
atcggcgccc agactgactt cctgagcgtg ttcttttccg gttacacctt taagcacaag  2040
atggtgtacg aagataccct gaccctgttc cctttctccg gcgaaacggt gttcatgtcg  2100
atggagaacc cgggtctgtg gattctggga tgccacaaca gcgactttcg gaaccgcgga  2160
atgactgccc tgctgaaggt gtcctcatgc gacaagaaca ccggagacta ctacgaggac  2220
tcctacgagg atatctcagc ctacctcctg tccaagaaca cgcgatcga gccgcgcagc  2280 ttcagccaga cccgcctgt gctgaagagg caccagcgag aaattacccg gaccaccctc  2340
caatcggatc aggaggaaat cgactacgac gacaccatct cggtggaaat gaagaaggaa  2400
gatttcgata tctacgacga ggacgaaaat cagtcccctc gctcattcca aaagaaaact  2460
agacactact ttatcgccgc ggtggaaaga ctgtgggact atggaatgtc atccagccct  2520
cacgtccttc ggaaccgggc ccagagcgga tcggtgcctc agttcaagaa agtggtgttc  2580
caggagttca ccgacggcag cttcacccag ccgctgtacc ggggagaact gaacgaacac  2640
ctgggcctgc tcggtccta catccgcgcg gaagtggagg ataacatcat ggtgaccttc  2700
cgtaaccaag catccagacc ttactccttc tattcctccc tgatctcata cgaggaggac  2760
cagcgccaag gcgccgagcc cgcaagaac ttcgtcaagc ccaacgagac taagacctac  2820
ttctggaagg tccaacacca tatggccccg accaaggatg agtttgactg caaggcctgg  2880
gcctacttct ccgacgtgga ccttgagaag gatgtccatt ccggcctgat cgggccgctg  2940
ctcgtgtgtc acaccaacac cctgaaccca gcgcatggac gccaggtcac cgtccaggag  3000
tttgctctgt tcttcaccat ttttgacgaa actaagtcct ggtacttcac cgagaatatg  3060
gagcgaaact gtagagcgcc ctgcaatatc cagatgaaag atccgacttt caaggagaac  3120
tatagattcc acgccatcaa cgggtacatc atggatactc tgccggggct ggtcatggcc  3180
caggatcaga ggattcggtg gtacttgctg tcaatgggat cgaacgaaaa cattcactcc  3240
attcacttct ccggtcacgt gttcactgtg cgcaagaagg aggagtacaa gatggcgctg  3300
tacaatctgt acccccgggt gttcgaaact gtggagatgc tgccgtccaa ggccggcatc  3360
tggagagtgg agtgcctgat cggagagcac ctccacgcgg ggatgtccac cctcttcctg  3420
gtgtactcga ataagtgcca gaccccgctg ggcatggcct cgggccacat cagagacttc  3480
cagatcacag caagcggaca atacggccaa tgggcgccga agctggcccg cttgcactac  3540
tccggatcga tcaacgcatg gtccaccaag gaaccgttct cgtggattaa ggtgaccctc  3600
ctggccccta tgattatcca cggaattaag acccagggcg ccaggcagaa gttctcctcc  3660
ctgtacatct cgcaattcat catcatgtac agcctggacg ggaagaagtg gcagacttac  3720
aggggaaact ccaccggcac cctgatggtc ttttcggca acgtggattc ctccggcatt  3780
aagcacaaca tcttcaaccc accgatcata gccagatata ttaggctcca ccccactcac  3840
tactcaatcc gctcaactct tcggatggaa ctcatggggt gcgacctgaa ctcctgctcc  3900
atgccgttgg ggatggaatc aaaggctatt agcgacgccc agatcaccgc gagctcctac  3960
ttcactaaca tgttcgccac ctggagcccc tccaaggcca ggctgcactt gcagggacgg  4020
tcaaatgcct ggcggccgca agtgaacaat ccgaaggaat ggcttcaagt ggatttccaa  4080
aagaccatga agtgaccgg agtcaccacc caggagtga agtcccttct gacctcgatg  4140
tatgtgaagg agttcctgat tagcagcagc caggacgggc accagtggac cctgttcttc  4200
caaaacggaa aggtcaaggt gttccagggg aaccaggact cgttcacacc cgtggtgaac  4260
tccctggacc ccccactgct gacgcggtac ttgaggattc atcctcagtc ctgggtccat  4320
cagattgcat tgcgaatgga agtcctgggc tgcgaggccc aggacctgta ctga         4374
```

<210> SEQ ID NO 72
<211> LENGTH: 4824
<212> TYPE: DNA
<213> ORGANISM: Artificial Sequence
<220> FEATURE:
<223> OTHER INFORMATION: coFVIII-6-XTEN

<400> SEQUENCE: 72

```
atgcagattg agctgtccac ttgtttcttc ctgtgcctcc tgcgcttctg tttctccgcc      60
actcgccggt actaccttgg agccgtggag ctttcatggg actacatgca gagcgacctg     120
ggcgaactcc ccgtggatgc cagattcccc ccccgcgtgc caaagtcctt ccccttaac      180
acctccgtgg tgtacaagaa aaccctcttt gtcgagttca ctgaccacct gttcaacatc     240
gccaagccgc gcccaccttg gatgggcctc tgggaccga ccattcaagc tgaagtgtac      300
gacaccgtgg tgatcaccct gaagaacatg gcgtcccacc ccgtgtccct gcatgcggtc     360
ggagtgtcct actggaaggc ctccgaagga gctgagtacg acgaccagac tagccagcgg     420
gaaaaggagg acgataaagt gttcccgggc ggctcgcata cttacgtgtg caagtcctg     480
aaggaaaacg gacctatggc atccgatcct ctgtgcctga cttactccta cctttcccat     540
gtggacctcg tgaaggacct gaacagcggg ctgattggtg cacttctcgt gtgccgcgaa     600
ggttcgctcg ctaaggaaaa gacccagacc ctccataagt tcatccttt gttcgctgtg     660
ttcgatgaag gaaagtcatg gcattccgaa actaagaact cgctgatgca ggaccgggat     720
gccgcctcag cccgcgcctg gcctaaaatg catacagtca acggatacgt gaatcggtca     780
ctgcccgggc tcatcggttg tcacagaaag tccgtgtact ggcacgtcat cggcatgggc     840
actacgcctg aagtgcactc catcttcctg gaagggcaca ccttcctcgt gcgcaaccac     900
cgccaggcct ctctggaaat ctccccgatt acctttctga ccgcccagac tctgctcatg     960
gacctggggc agttccttct cttctgccac atctccagcc atcagcacga cggaatggag    1020
gcctacgtga aggtggactc atgcccggaa gaacctcagt tgcggatgaa gaacaacgag    1080
gaggccgagg actatgacga cgatttgact gactccgaga tggacgtcgt gcggttcgat    1140
gacgacaaca gccccagctt catccagatt cgcagcgtgg ccaagaagca ccccaaaacc    1200
tgggtgcact acatcgcggc cgaggaagaa gattgggact acgccccgtt ggtgctggca    1260
cccgatgacc ggtcgtacaa gtcccagtat ctgaacaatg gtccgcagcg gattggcaga    1320
aagtacaaga agtgcggtt catggcgtac actgacgaaa cgtttaagac ccgggaggcc    1380
attaacatgg agagcggcat tctgggacca ctgctgtacg agaggtcgg cgatacactg    1440
ctcatcatct tcaaaaacca ggcctccgg ccttacaaca tctaccctca cggaatcacc    1500
gacgtgcggc cactctactc gcggcgcctg ccgaagggcg tcaagcacct gaaagacttc    1560
cctatcctgc cgggcgaaat cttcaagtat aagtggaccg tcaccgtgga ggacgggccc    1620
accaagagcg atcctaggtg tctgactcgg tactactcca gcttcgtgaa catgaacgg    1680
gacctggcat cgggactcat ggaccgctg ctgatctgct acaaagagtc ggtggatcaa    1740
cgcggcaacc agatcatgtc cgacaagcgc aacgtgatcc tgttctccgt gtttgatgaa    1800
aacagatcct ggtacctcac tgaaaacatc cagaggttcc tcccaaaccc cgcaggagtg    1860
caactggagg accctgagtt tcaggcctcg aatatcatgc actcgattaa cggttacgtg    1920
ttcgactcgc tgcagctgag cgtgtgcctc catgaagtcg cttactggta cattctgtcc    1980
atcggcgccc agactgactt cctgagcgtg ttcttttccg gttacacctt taagcacaag    2040
```

```
atggtgtacg aagataccct gaccctgttc cctttctccg gcgaaacggt gttcatgtcg    2100
atggagaacc cgggtctgtg gattctggga tgccacaaca gcgactttcg gaaccgcgga    2160
atgactgccc tgctgaaggt gtcctcatgc gacaagaaca ccggagacta ctacgaggac    2220
tcctacgagg atatctcagc ctacctcctg tccaagaaca cgcgatcga gccgcgcagc     2280
ttcagccaga acggcgcgcc aacatcagag agcgccaccc ctgaaagtgg tcccgggagc    2340
gagccagcca catctgggtc ggaaacgcca ggcacaagtg agtctgcaac tcccgagtcc    2400
ggacctggct ccgagcctgc cactagcggc tccgagactc cgggaacttc cgagagcgct    2460
acaccagaaa gcggacccgg aaccagtacc gaacctagcg agggctctgc tccgggcagc    2520
ccagccggct ctcctacatc cacggaggag ggcacttccg aatccgccac cccggagtca    2580
gggccaggat ctgaacccgc tacctcaggc agtgagacgc caggaacgag cgagtccgct    2640
acaccggaga gtgggccagg gagccctgct ggatctccta cgtccactga ggaagggtca    2700
ccagcgggct cgcccaccag cactgaagaa ggtgcctcga gcccgcctgt gctgaagagg    2760
caccagcgag aaattacccg gaccaccctc caatcggatc aggaggaaat cgactacgac    2820
gacaccatct cggtggaaat gaagaaggaa gatttcgata tctacgacga ggacgaaaat    2880
cagtccccctc gctcattcca aaagaaaact agacactact ttatcgccgc ggtggaaaga    2940
ctgtgggact atggaatgtc atccagcccct cacgtccttc ggaaccgggc ccagagcgga    3000
tcggtgcctc agttcaagaa agtggtgttc caggagttca ccgacggcag cttcacccag    3060
ccgctgtacc ggggagaact gaacgaacac ctgggcctgc tcggtcccta catccgcgcg    3120
gaagtggagg ataacatcat ggtgaccttc cgtaaccaag catccagacc ttactccttc    3180
tattcctccc tgatctcata cgaggaggac cagcgccaag cgccgagcc ccgcaagaac     3240
ttcgtcaagc ccaacgagac taagacctac ttctggaagg tccaacacca tatggccccg    3300
accaaggatg agtttgactg caaggcctgg gcctacttct ccgacgtgga ccttgagaag    3360
gatgtccatt ccgcctgat cgggccgctg ctcgtgtgtc acaccaacac cctgaaccca     3420
gcgcatggac gccaggtcac cgtccaggag tttgctctgt tcttcaccat ttttgacgaa    3480
actaagtcct ggtacttcac cgagaatatg gagcgaaact gtagagcgcc ctgcaatatc    3540
cagatggaag atccgacttt caaggagaac tatagattcc acgccatcaa cgggtacatc    3600
atggatactc tgccggggct ggtcatggcc caggatcaga ggattcggtg gtacttgctg    3660
tcaatgggat cgaacgaaaa cattcactcc attcacttct ccggtcacgt gttcactgtg    3720
cgcaagaagg aggagtacaa gatggcgctg tacaatctgt accccggggt gttcgaaact    3780
gtggagatgc tgccgtccaa ggccggcatc tggagagtgg agtgcctgat cggagagcac    3840
ctccacgcgg ggatgtccac cctcttcctg gtgtactcga ataagtgcca gaccccgctg    3900
ggcatggcct cgggccacat cagagacttc cagatcacag caagcggaca atacggccaa    3960
tgggcgccga gctggcccg cttgcactac tccggatcga tcaacgcatg gtccaccaag    4020
gaaccgttct cgtggattaa ggtggacctc ctggccccta tgattatcca cggaattaag    4080
acccagggcg ccaggcagaa gttctcctcc ctgtacatct cgcaattcat catcatgtac    4140
agcctggacg ggaagaagtg gcagacttac aggggaaact ccaccggcac cctgatggtc    4200
tttttcggca acgtggattc ctccggcatt aagcacaaca tcttcaaccc accgatcata    4260
gccagatata ttaggctcca ccccactcac tactcaatcc gctcaactct tcggatggaa    4320
ctcatggggt gcgacctgaa ctcctgctcc atgccgttgg ggatggaatc aaaggctatt    4380
agcgacgccc agatcaccgc gagctcctac ttcactaaca tgttcgccac ctggagcccc    4440
```

```
tccaaggcca ggctgcactt gcagggacgg tcaaatgcct ggcggccgca agtgaacaat    4500
ccgaaggaat ggcttcaagt ggatttccaa aagaccatga aagtgaccgg agtcaccacc    4560
cagggagtga agtcccttct gacctcgatg tatgtgaagg agttcctgat tagcagcagc    4620
caggacgggc accagtggac cctgttcttc caaaacggaa aggtcaaggt gttccagggg    4680
aaccaggact cgttcacacc cgtggtgaac tccctggacc ccccactgct gacgcggtac    4740
ttgaggattc atcctcagtc ctgggtccat cagattgcat tgcgaatgga agtcctgggc    4800
tgcgaggccc aggacctgta ctga                                          4824
```

<210> SEQ ID NO 73
<211> LENGTH: 12
<212> TYPE: PRT
<213> ORGANISM: Artificial Sequence
<220> FEATURE:
<223> OTHER INFORMATION: AD motif

<400> SEQUENCE: 73

Gly Glu Ser Pro Gly Gly Ser Ser Gly Ser Glu Ser
1               5                   10

<210> SEQ ID NO 74
<211> LENGTH: 12
<212> TYPE: PRT
<213> ORGANISM: Artificial Sequence
<220> FEATURE:
<223> OTHER INFORMATION: AD motif

<400> SEQUENCE: 74

Gly Ser Glu Gly Ser Ser Gly Pro Gly Glu Ser Ser
1               5                   10

<210> SEQ ID NO 75
<211> LENGTH: 12
<212> TYPE: PRT
<213> ORGANISM: Artificial Sequence
<220> FEATURE:
<223> OTHER INFORMATION: AD motif

<400> SEQUENCE: 75

Gly Ser Ser Glu Ser Gly Ser Ser Glu Gly Gly Pro
1               5                   10

<210> SEQ ID NO 76
<211> LENGTH: 12
<212> TYPE: PRT
<213> ORGANISM: Artificial Sequence
<220> FEATURE:
<223> OTHER INFORMATION: AD motif

<400> SEQUENCE: 76

Gly Ser Gly Gly Glu Pro Ser Glu Ser Gly Ser Ser
1               5                   10

<210> SEQ ID NO 77
<211> LENGTH: 12
<212> TYPE: PRT
<213> ORGANISM: Artificial Sequence
<220> FEATURE:
<223> OTHER INFORMATION: AE, AM motif

<400> SEQUENCE: 77

Gly Ser Pro Ala Gly Ser Pro Thr Ser Thr Glu Glu
1               5                   10

<210> SEQ ID NO 78
<211> LENGTH: 12
<212> TYPE: PRT
<213> ORGANISM: Artificial Sequence
<220> FEATURE:
<223> OTHER INFORMATION: AE, AM, AQ motif

<400> SEQUENCE: 78

Gly Ser Glu Pro Ala Thr Ser Gly Ser Glu Thr Pro
1               5                   10

<210> SEQ ID NO 79
<211> LENGTH: 12
<212> TYPE: PRT
<213> ORGANISM: Artificial Sequence
<220> FEATURE:
<223> OTHER INFORMATION: AE, AM, AQ motif

<400> SEQUENCE: 79

Gly Thr Ser Glu Ser Ala Thr Pro Glu Ser Gly Pro
1               5                   10

<210> SEQ ID NO 80
<211> LENGTH: 12
<212> TYPE: PRT
<213> ORGANISM: Artificial Sequence
<220> FEATURE:
<223> OTHER INFORMATION: AE, AM, AQ motif

<400> SEQUENCE: 80

Gly Thr Ser Thr Glu Pro Ser Glu Gly Ser Ala Pro
1               5                   10

<210> SEQ ID NO 81
<211> LENGTH: 12
<212> TYPE: PRT
<213> ORGANISM: Artificial Sequence
<220> FEATURE:
<223> OTHER INFORMATION: AF, AM motif

<400> SEQUENCE: 81

Gly Ser Thr Ser Glu Ser Pro Ser Gly Thr Ala Pro
1               5                   10

<210> SEQ ID NO 82
<211> LENGTH: 12
<212> TYPE: PRT
<213> ORGANISM: Artificial Sequence
<220> FEATURE:
<223> OTHER INFORMATION: AF, AM motif

<400> SEQUENCE: 82

Gly Thr Ser Thr Pro Glu Ser Gly Ser Ala Ser Pro
1               5                   10

<210> SEQ ID NO 83
<211> LENGTH: 12
<212> TYPE: PRT
<213> ORGANISM: Artificial Sequence
<220> FEATURE:
<223> OTHER INFORMATION: AF, AM motif

<400> SEQUENCE: 83

Gly Thr Ser Pro Ser Gly Glu Ser Ser Thr Ala Pro
1               5                   10

```
<210> SEQ ID NO 84
<211> LENGTH: 12
<212> TYPE: PRT
<213> ORGANISM: Artificial Sequence
<220> FEATURE:
<223> OTHER INFORMATION: AF, AM motif

<400> SEQUENCE: 84

Gly Ser Thr Ser Ser Thr Ala Glu Ser Pro Gly Pro
1               5                   10

<210> SEQ ID NO 85
<211> LENGTH: 12
<212> TYPE: PRT
<213> ORGANISM: Artificial Sequence
<220> FEATURE:
<223> OTHER INFORMATION: AG, AM motif

<400> SEQUENCE: 85

Gly Thr Pro Gly Ser Gly Thr Ala Ser Ser Ser Pro
1               5                   10

<210> SEQ ID NO 86
<211> LENGTH: 12
<212> TYPE: PRT
<213> ORGANISM: Artificial Sequence
<220> FEATURE:
<223> OTHER INFORMATION: AG, AM motif

<400> SEQUENCE: 86

Gly Ser Ser Thr Pro Ser Gly Ala Thr Gly Ser Pro
1               5                   10

<210> SEQ ID NO 87
<211> LENGTH: 12
<212> TYPE: PRT
<213> ORGANISM: Artificial Sequence
<220> FEATURE:
<223> OTHER INFORMATION: AG, AM motif

<400> SEQUENCE: 87

Gly Ser Ser Pro Ser Ala Ser Thr Gly Thr Gly Pro
1               5                   10

<210> SEQ ID NO 88
<211> LENGTH: 12
<212> TYPE: PRT
<213> ORGANISM: Artificial Sequence
<220> FEATURE:
<223> OTHER INFORMATION: AG, AM motif

<400> SEQUENCE: 88

Gly Ala Ser Pro Gly Thr Ser Ser Thr Gly Ser Pro
1               5                   10

<210> SEQ ID NO 89
<211> LENGTH: 12
<212> TYPE: PRT
<213> ORGANISM: Artificial Sequence
<220> FEATURE:
<223> OTHER INFORMATION: AQ motif

<400> SEQUENCE: 89

Gly Glu Pro Ala Gly Ser Pro Thr Ser Thr Ser Glu
1               5                   10
```

```
<210> SEQ ID NO 90
<211> LENGTH: 12
<212> TYPE: PRT
<213> ORGANISM: Artificial Sequence
<220> FEATURE:
<223> OTHER INFORMATION: AQ motif

<400> SEQUENCE: 90

Gly Thr Gly Glu Pro Ser Ser Thr Pro Ala Ser Glu
1               5                   10

<210> SEQ ID NO 91
<211> LENGTH: 12
<212> TYPE: PRT
<213> ORGANISM: Artificial Sequence
<220> FEATURE:
<223> OTHER INFORMATION: AQ motif

<400> SEQUENCE: 91

Gly Ser Gly Pro Ser Thr Glu Ser Ala Pro Thr Glu
1               5                   10

<210> SEQ ID NO 92
<211> LENGTH: 12
<212> TYPE: PRT
<213> ORGANISM: Artificial Sequence
<220> FEATURE:
<223> OTHER INFORMATION: AQ motif

<400> SEQUENCE: 92

Gly Ser Glu Thr Pro Ser Gly Pro Ser Glu Thr Ala
1               5                   10

<210> SEQ ID NO 93
<211> LENGTH: 12
<212> TYPE: PRT
<213> ORGANISM: Artificial Sequence
<220> FEATURE:
<223> OTHER INFORMATION: AQ motif

<400> SEQUENCE: 93

Gly Pro Ser Glu Thr Ser Thr Ser Glu Pro Gly Ala
1               5                   10

<210> SEQ ID NO 94
<211> LENGTH: 12
<212> TYPE: PRT
<213> ORGANISM: Artificial Sequence
<220> FEATURE:
<223> OTHER INFORMATION: AQ motif

<400> SEQUENCE: 94

Gly Ser Pro Ser Glu Pro Thr Glu Gly Thr Ser Ala
1               5                   10

<210> SEQ ID NO 95
<211> LENGTH: 12
<212> TYPE: PRT
<213> ORGANISM: Artificial Sequence
<220> FEATURE:
<223> OTHER INFORMATION: BC motif

<400> SEQUENCE: 95

Gly Ser Gly Ala Ser Glu Pro Thr Ser Thr Glu Pro
1               5                   10

<210> SEQ ID NO 96
```

```
<211> LENGTH: 12
<212> TYPE: PRT
<213> ORGANISM: Artificial Sequence
<220> FEATURE:
<223> OTHER INFORMATION: BC motif

<400> SEQUENCE: 96

Gly Ser Glu Pro Ala Thr Ser Gly Thr Glu Pro Ser
1               5                   10

<210> SEQ ID NO 97
<211> LENGTH: 12
<212> TYPE: PRT
<213> ORGANISM: Artificial Sequence
<220> FEATURE:
<223> OTHER INFORMATION: BC motif

<400> SEQUENCE: 97

Gly Thr Ser Glu Pro Ser Thr Ser Glu Pro Gly Ala
1               5                   10

<210> SEQ ID NO 98
<211> LENGTH: 12
<212> TYPE: PRT
<213> ORGANISM: Artificial Sequence
<220> FEATURE:
<223> OTHER INFORMATION: BC motif

<400> SEQUENCE: 98

Gly Thr Ser Thr Glu Pro Ser Glu Pro Gly Ser Ala
1               5                   10

<210> SEQ ID NO 99
<211> LENGTH: 12
<212> TYPE: PRT
<213> ORGANISM: Artificial Sequence
<220> FEATURE:
<223> OTHER INFORMATION: BD motif

<400> SEQUENCE: 99

Gly Ser Thr Ala Gly Ser Glu Thr Ser Thr Glu Ala
1               5                   10

<210> SEQ ID NO 100
<211> LENGTH: 12
<212> TYPE: PRT
<213> ORGANISM: Artificial Sequence
<220> FEATURE:
<223> OTHER INFORMATION: BD motif

<400> SEQUENCE: 100

Gly Ser Glu Thr Ala Thr Ser Gly Ser Glu Thr Ala
1               5                   10

<210> SEQ ID NO 101
<211> LENGTH: 12
<212> TYPE: PRT
<213> ORGANISM: Artificial Sequence
<220> FEATURE:
<223> OTHER INFORMATION: BD motif

<400> SEQUENCE: 101

Gly Thr Ser Glu Ser Ala Thr Ser Glu Ser Gly Ala
1               5                   10

<210> SEQ ID NO 102
<211> LENGTH: 12
```

```
<212> TYPE: PRT
<213> ORGANISM: Artificial Sequence
<220> FEATURE:
<223> OTHER INFORMATION: BD motif

<400> SEQUENCE: 102

Gly Thr Ser Thr Glu Ala Ser Glu Gly Ser Ala Ser
1               5                   10

<210> SEQ ID NO 103
<211> LENGTH: 1607
<212> TYPE: PRT
<213> ORGANISM: Artificial Sequence
<220> FEATURE:
<223> OTHER INFORMATION: coFVIII-6-XTEN Protein Sequence

<400> SEQUENCE: 103

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
                100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
        130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320
```

```
Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
            405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
            485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
            565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
            645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
            725                 730                 735
```

-continued

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Gly Ala Pro Thr
            755                 760                 765

Ser Glu Ser Ala Thr Pro Glu Ser Gly Pro Gly Ser Glu Pro Ala Thr
            770                 775                 780

Ser Gly Ser Glu Thr Pro Gly Thr Ser Glu Ser Ala Thr Pro Glu Ser
785                 790                 795                 800

Gly Pro Gly Ser Glu Pro Ala Thr Ser Gly Ser Glu Thr Pro Gly Thr
            805                 810                 815

Ser Glu Ser Ala Thr Pro Glu Ser Gly Pro Gly Thr Ser Thr Glu Pro
            820                 825                 830

Ser Glu Gly Ser Ala Pro Gly Ser Pro Ala Gly Ser Pro Thr Ser Thr
            835                 840                 845

Glu Glu Gly Thr Ser Glu Ser Ala Thr Pro Glu Ser Gly Pro Gly Ser
            850                 855                 860

Glu Pro Ala Thr Ser Gly Ser Glu Thr Pro Gly Thr Ser Glu Ser Ala
865                 870                 875                 880

Thr Pro Glu Ser Gly Pro Gly Ser Pro Ala Gly Ser Pro Thr Ser Thr
            885                 890                 895

Glu Glu Gly Ser Pro Ala Gly Ser Pro Thr Ser Thr Glu Glu Gly Ala
            900                 905                 910

Ser Ser Pro Pro Val Leu Lys Arg His Gln Arg Glu Ile Thr Arg Thr
            915                 920                 925

Thr Leu Gln Ser Asp Gln Glu Glu Ile Asp Tyr Asp Asp Thr Ile Ser
930                 935                 940

Val Glu Met Lys Lys Glu Asp Phe Asp Ile Tyr Asp Glu Asp Glu Asn
945                 950                 955                 960

Gln Ser Pro Arg Ser Phe Gln Lys Lys Thr Arg His Tyr Phe Ile Ala
            965                 970                 975

Ala Val Glu Arg Leu Trp Asp Tyr Gly Met Ser Ser Ser Pro His Val
            980                 985                 990

Leu Arg Asn Arg Ala Gln Ser Gly Ser Val Pro Gln Phe Lys Lys Val
            995                 1000                1005

Val Phe Gln Glu Phe Thr Asp Gly Ser Phe Thr Gln Pro Leu Tyr
    1010                1015                1020

Arg Gly Glu Leu Asn Glu His Leu Gly Leu Leu Gly Pro Tyr Ile
    1025                1030                1035

Arg Ala Glu Val Glu Asp Asn Ile Met Val Thr Phe Arg Asn Gln
    1040                1045                1050

Ala Ser Arg Pro Tyr Ser Phe Tyr Ser Ser Leu Ile Ser Tyr Glu
    1055                1060                1065

Glu Asp Gln Arg Gln Gly Ala Glu Pro Arg Lys Asn Phe Val Lys
    1070                1075                1080

Pro Asn Glu Thr Lys Thr Tyr Phe Trp Lys Val Gln His His Met
    1085                1090                1095

Ala Pro Thr Lys Asp Glu Phe Asp Cys Lys Ala Trp Ala Tyr Phe
    1100                1105                1110

Ser Asp Val Asp Leu Glu Lys Asp Val His Ser Gly Leu Ile Gly
    1115                1120                1125

Pro Leu Leu Val Cys His Thr Asn Thr Leu Asn Pro Ala His Gly
    1130                1135                1140

Arg Gln Val Thr Val Gln Glu Phe Ala Leu Phe Phe Thr Ile Phe

```
            1145                1150                1155

Asp Glu Thr Lys Ser Trp Tyr Phe Thr Glu Asn Met Glu Arg Asn
            1160                1165                1170

Cys Arg Ala Pro Cys Asn Ile Gln Met Glu Asp Pro Thr Phe Lys
            1175                1180                1185

Glu Asn Tyr Arg Phe His Ala Ile Asn Gly Tyr Ile Met Asp Thr
            1190                1195                1200

Leu Pro Gly Leu Val Met Ala Gln Asp Gln Arg Ile Arg Trp Tyr
            1205                1210                1215

Leu Leu Ser Met Gly Ser Asn Glu Asn Ile His Ser Ile His Phe
            1220                1225                1230

Ser Gly His Val Phe Thr Val Arg Lys Lys Glu Glu Tyr Lys Met
            1235                1240                1245

Ala Leu Tyr Asn Leu Tyr Pro Gly Val Phe Glu Thr Val Glu Met
            1250                1255                1260

Leu Pro Ser Lys Ala Gly Ile Trp Arg Val Glu Cys Leu Ile Gly
            1265                1270                1275

Glu His Leu His Ala Gly Met Ser Thr Leu Phe Leu Val Tyr Ser
            1280                1285                1290

Asn Lys Cys Gln Thr Pro Leu Gly Met Ala Ser Gly His Ile Arg
            1295                1300                1305

Asp Phe Gln Ile Thr Ala Ser Gly Gln Tyr Gly Gln Trp Ala Pro
            1310                1315                1320

Lys Leu Ala Arg Leu His Tyr Ser Gly Ser Ile Asn Ala Trp Ser
            1325                1330                1335

Thr Lys Glu Pro Phe Ser Trp Ile Lys Val Asp Leu Leu Ala Pro
            1340                1345                1350

Met Ile Ile His Gly Ile Lys Thr Gln Gly Ala Arg Gln Lys Phe
            1355                1360                1365

Ser Ser Leu Tyr Ile Ser Gln Phe Ile Ile Met Tyr Ser Leu Asp
            1370                1375                1380

Gly Lys Lys Trp Gln Thr Tyr Arg Gly Asn Ser Thr Gly Thr Leu
            1385                1390                1395

Met Val Phe Phe Gly Asn Val Asp Ser Ser Gly Ile Lys His Asn
            1400                1405                1410

Ile Phe Asn Pro Pro Ile Ile Ala Arg Tyr Ile Arg Leu His Pro
            1415                1420                1425

Thr His Tyr Ser Ile Arg Ser Thr Leu Arg Met Glu Leu Met Gly
            1430                1435                1440

Cys Asp Leu Asn Ser Cys Ser Met Pro Leu Gly Met Glu Ser Lys
            1445                1450                1455

Ala Ile Ser Asp Ala Gln Ile Thr Ala Ser Ser Tyr Phe Thr Asn
            1460                1465                1470

Met Phe Ala Thr Trp Ser Pro Ser Lys Ala Arg Leu His Leu Gln
            1475                1480                1485

Gly Arg Ser Asn Ala Trp Arg Pro Gln Val Asn Asn Pro Lys Glu
            1490                1495                1500

Trp Leu Gln Val Asp Phe Gln Lys Thr Met Lys Val Thr Gly Val
            1505                1510                1515

Thr Thr Gln Gly Val Lys Ser Leu Leu Thr Ser Met Tyr Val Lys
            1520                1525                1530

Glu Phe Leu Ile Ser Ser Ser Gln Asp Gly His Gln Trp Thr Leu
            1535                1540                1545
```

```
Phe Phe Gln Asn Gly Lys Val Lys Val Phe Gln Gly Asn Gln Asp
    1550            1555            1560

Ser Phe Thr Pro Val Val Asn Ser Leu Asp Pro Pro Leu Leu Thr
    1565            1570            1575

Arg Tyr Leu Arg Ile His Pro Gln Ser Trp Val His Gln Ile Ala
    1580            1585            1590

Leu Arg Met Glu Val Leu Gly Cys Glu Ala Gln Asp Leu Tyr
    1595            1600            1605
```